(12) United States Patent
Richards et al.

(10) Patent No.: US 11,400,081 B2
(45) Date of Patent: Aug. 2, 2022

(54) COMPOUNDS

(71) Applicant: The University of Sheffield, Sheffield (GB)

(72) Inventors: Gareth Richards, Sheffield (GB); Timothy M. Skerry, Sheffield (GB); Joseph P. A. Harrity, Sheffield (GB); Jean-Olivier Zirimwabagabo, Sheffield (GB); Matthew J. Tozer, Sheffield (GB); Karl Richard Gibson, Sandwich (GB); Roderick Alan Porter, Sheffield (GB); Paul Matthew Blaney, Chapel-en-le-Frith (GB); Paul Alan Glossop, Sandwich (GB)

(73) Assignee: The University of Sheffield, Sheffield (GB)

( * ) Notice: Subject to any disclaimer, the term of this patent is extended or adjusted under 35 U.S.C. 154(b) by 155 days.

(21) Appl. No.: 16/613,828

(22) PCT Filed: May 16, 2018

(86) PCT No.: PCT/GB2018/051331
§ 371 (c)(1),
(2) Date: Nov. 15, 2019

(87) PCT Pub. No.: WO2018/211275
PCT Pub. Date: Nov. 22, 2018

(65) Prior Publication Data
US 2021/0113534 A1    Apr. 22, 2021

(30) Foreign Application Priority Data
May 17, 2017 (GB) ..................................... 1707938

(51) Int. Cl.
| | | |
|---|---|---|
| *C07D 471/10* | (2006.01) | |
| *A61K 31/438* | (2006.01) | |
| *A61K 31/437* | (2006.01) | |
| *A61K 31/4545* | (2006.01) | |
| *A61K 31/496* | (2006.01) | |
| *A61K 31/5377* | (2006.01) | |
| *A61K 45/06* | (2006.01) | |
| *C07D 471/20* | (2006.01) | |
| *C07D 519/00* | (2006.01) | |

(52) U.S. Cl.
CPC .......... *A61K 31/437* (2013.01); *A61K 31/438* (2013.01); *A61K 31/4545* (2013.01); *A61K 31/496* (2013.01); *A61K 31/5377* (2013.01); *A61K 45/06* (2013.01); *C07D 471/10* (2013.01); *C07D 471/20* (2013.01); *C07D 519/00* (2013.01)

(58) Field of Classification Search
CPC .. C07D 471/10; C07D 471/20; A61K 31/438; A61P 35/00
USPC ............................................ 546/18; 514/278
See application file for complete search history.

(56) References Cited

U.S. PATENT DOCUMENTS

| | | | |
|---|---|---|---|
| 7,989,624 B2 * | 8/2011 | Bell ..................... | C07D 471/04 546/18 |
| 2008/0249115 A1 | 10/2008 | Cuttitta et al. | |
| 2010/0240611 A1 | 9/2010 | Ronsheim et al. | |

FOREIGN PATENT DOCUMENTS

| | | |
|---|---|---|
| EP | 1794133 | 6/2007 |
| WO | WO-2004/092166 | 10/2004 |
| WO | WO-2006/031513 | 3/2006 |
| WO | WO-2006/041830 | 4/2006 |
| WO | WO-2007/016087 | 2/2007 |
| WO | WO-2007/020261 | 2/2007 |
| WO | WO-2007/028812 | 3/2007 |
| WO | WO-2007/036532 | 4/2007 |

(Continued)

OTHER PUBLICATIONS

U.S. Appl. No. 17/293,124, filed May 12, 2021 "Heterocyclic Spiro-Compounds as AM2 Receptor Inhibitors", 371 pages.
U.S. Appl. No. 17/293,157, filed May 12, 2021 "Heterocyclic Spiro-Compounds as AM2 Receptor Inhibitors", 219 pages.
Archbold et al., "Structural insights into RAMP modification of secretin family G protein-coupled receptors: implications for drug development," Trends in Pharmacological Sciences, 32(10), pp. 591-600 (2011).

(Continued)

*Primary Examiner* — Charanjit Aulakh
(74) *Attorney, Agent, or Firm* — Mintz, Levin, Cohn, Ferris, Glovsky and Popeo, P.C.

(57) ABSTRACT

Disclosed are compounds of the formula (I) and pharmaceutically acceptable salts thereof: (I) wherein $R^1$, $R^2$, $R^3$, $R^4$, $R^5$, $R^6$, $R^8$, $R^9$, X, $X_1$, $X_2$, $X_3$, $L^1$ and n are as defined herein. The compounds are inhibitors of adrenomedullin receptor subtype 2 ($AM_2$). Also disclosed are the compounds for use in the treatment of diseases modulated $AM_2$, including proliferative diseases such as cancer; pharmaceutical compositions comprising the compounds; methods for preparing the compounds; and intermediates useful in the preparation of the compounds.

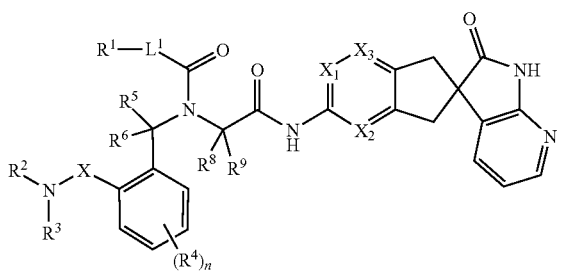

21 Claims, No Drawings

(56) References Cited

FOREIGN PATENT DOCUMENTS

| | | |
|---|---|---|
| WO | WO-2007/036533 | 4/2007 |
| WO | WO-2007/045672 | 4/2007 |
| WO | WO-2007/061676 | 5/2007 |
| WO | WO-2007/061677 | 5/2007 |
| WO | WO-2007/061692 | 5/2007 |
| WO | WO-2007/061694 | 5/2007 |
| WO | WO-2007/061695 | 5/2007 |
| WO | WO-2007/061696 | 5/2007 |
| WO | WO-2007/074130 | 7/2007 |
| WO | WO-2007/130860 | 11/2007 |
| WO | WO-2007/130927 | 11/2007 |
| WO | WO-2007/131020 | 11/2007 |
| WO | WO-2007/133491 | 11/2007 |
| WO | WO-2008/020902 | 2/2008 |
| WO | WO-2008/073251 | 6/2008 |
| WO | WO-2008/085317 | 7/2008 |
| WO | WO-2008/112159 | 9/2008 |
| WO | WO-2008/127584 | 10/2008 |
| WO | WO-2008/130512 | 10/2008 |
| WO | WO-2008/130524 | 10/2008 |
| WO | WO-2008/132453 | 11/2008 |
| WO | WO-2008/153849 | 12/2008 |
| WO | WO-2008/153852 | 12/2008 |
| WO | WO-2009/034028 | 3/2009 |
| WO | WO-2009/034029 | 3/2009 |
| WO | WO-2009/050232 | 4/2009 |
| WO | WO-2009/050234 | 4/2009 |
| WO | WO-2009/050235 | 4/2009 |
| WO | WO-2009/050237 | 4/2009 |
| WO | WO-2009/065919 | 5/2009 |
| WO | WO-2009/065921 | 5/2009 |
| WO | WO-2009/065922 | 5/2009 |
| WO | WO-2009/105348 | 8/2009 |
| WO | WO-2009/120652 | 10/2009 |
| WO | WO-2009/126530 | 10/2009 |
| WO | WO-2009/152010 | 12/2009 |
| WO | WO-2010/021864 | 2/2010 |
| WO | WO-2010/021919 | 2/2010 |
| WO | WO-2010/027927 | 3/2010 |
| WO | WO-2010/033421 | 3/2010 |
| WO | WO-2010/039673 | 4/2010 |
| WO | WO-2010/042356 | 4/2010 |
| WO | WO-2010/077752 | 7/2010 |
| WO | WO-2010/107605 | 9/2010 |
| WO | WO-2010/108103 | 9/2010 |
| WO | WO-2010/139717 | 12/2010 |
| WO | WO-2011/005731 | 1/2011 |
| WO | WO-2011/046997 | 4/2011 |
| WO | WO-2011/123232 | 10/2011 |
| WO | WO-2012/064910 | 5/2012 |
| WO | WO-2012/064911 | 5/2012 |
| WO | WO-2012/087777 | 6/2012 |
| WO | WO-2012/129013 | 9/2012 |
| WO | WO-2012/129014 | 9/2012 |
| WO | WO-2012/154354 | 11/2012 |
| WO | WO-2013/064508 | 5/2013 |
| WO | WO-2013/066360 | 5/2013 |
| WO | WO-2013/138418 | 9/2013 |
| WO | WO-2013/169563 | 11/2013 |
| WO | WO-2013/169565 | 11/2013 |
| WO | WO-2013/169567 | 11/2013 |
| WO | WO-2014/062548 | 4/2014 |
| WO | 2020/099882 A1 | 5/2020 |
| WO | 2020/099885 A1 | 5/2020 |

OTHER PUBLICATIONS

Avgoustou et al., "Discovery of a first-in-class potent small molecule antagonist against the Adrenomedullin-2 receptor," ACS Pharmacol. Transl. Sci., 40 pages (2020).
Banerjee and Kumar, "$C^{3'}$-endo-puckered pyrrolidine containing PNA has favorable geometry for RNA binding: Novel ethano locked PNA (ethano-PNA)," Bioorganic & Medicinal Chemistry, 21, pp. 4092-4101 (2013).
Bell et al., "Discovery of MK-3207: A Highly Potent, Orally Bioavailable CGRP Receptor Antagonist," ACS Medicinal Chemistry Letters, 1, pp. 24-29 (2010).
Bell, "Calcitonin Gene-Related Peptide Receptor Antagonists: New Therapeutic Agents for Migraine," Journal of Medicinal Chemistry, 57, pp. 7838-7858 (2014).
Berggren et al., "3-Aminopiperidine-Based Peptide Analogues as the First Selective Noncovalent Inhibitors of the Bacterial Cysteine Protease IdeS," Journal of Medical Chemistry, 55, pp. 2549-2560 (2012).
Booe et al., "Structural Basis for Receptor Activity-Modifying Protein-Dependent Selective Peptide Recognition by a G Protein-Coupled Receptor," Molecular Cell, 58, pp. 1040-1052 (2015).
Brekhman et al., "Receptor activity modifying protein-3 mediates the protumorigenic activity of lysyl oxidase-like protein-2," The FASEB Journal, 25, pp. 55-65 (2011).
ClinicalTrials.gov Identifier: NCT02456051, "Pancreatic Cancer Can be Detected by Adrenomedullin in New Onset Diabetes Patients (PaCANOD)," 5 pages (first posted May 28, 2015), found online at: https://clinicaltrials.gov/ct2/show/NCT02456051; last update posted Nov. 20, 2017.
ClinicalTrials.gov Identifier: NCT02828020, "Efficacy, Safety, and Tolerability Study of Oral Ubrogepant in the Acute Treatment of Migraine (Achieve I)," 8 pages (first posted Jul. 11, 2016), found online at: https://clinicaltrials.gov/ct2/show/NCT02828020; last update posted Jan. 3, 2019.
ClinicalTrials.gov Identifier: NCT03237845, "Safety and Efficacy in Adult Subjects With Acute Migraines," 8 pages (first posted Aug. 3, 2017), found online at: https://www.clinicaltrials.gov/ct2/show/NCT03237845; last update posted Aug. 28, 2019.
D'Angelo et al., "Adrenomedullin in pancreatic carcinoma: A case-control study of 22 patients," Integr. Cancer Sci. Therap., 3(2), pp. 390-392 (2016).
Doods et al., "Pharmacological profile of BIBN4096BS, the first selective small molecule CGRP antagonist," British Journal of Pharmacology, 129, pp. 420-423 (2000).
Edvinsson et al., "CGRP as the target of new migraine therapies—successful translation from bench to clinic," Nature Reviews Neurology 14, pp. 338-350 (2018).
Görgülü et al., "A Star of Connection Between Pancreatic Cancer and Diabetes: Adrenomedullin," JOP. J. Pancreas (Online), 16(5), pp. 408-412 (2015).
Hay and Pioszak, "Receptor Activity-Modifying Proteins (RAMPs): New Insights and Roles," Annual Review of Pharmacology and Toxicology, 56, pp. 469-487 (2016).
Hay et al. "Update on the pharmacology of calcitonin/CGRP family of peptides: IUPHAR Review 25," British Journal of Pharmacology, 175, pp. 3-17 (2018).
Hay et al., "Pharmacological Discrimination of Calcitonin Receptor: Receptor Activity-Modifying Protein Complexes," Mol. Pharmacol., 67(5), pp. 1655-1665 (2005).
Hay et al., "The Pharmacology of Adrenomedullin Receptors and Their Relationship to CGRP Receptors," J. Mol. Neuroscience, 22, pp. 105-113 (2004).
Hendrikse et al., "Identification of Small-Molecule Positive Modulators of Calcitonin-like Receptor-Based Receptors," ACS Pharmacology & Translational Science, 3, pp. 305-320 (2020).
Hewitt et al., "Randomized controlled trial of the CGRP receptor antagonist MK-3207 in the acute treatment of migraine," Cephalalgia, 31(6), pp. 712-722 (2011).
Hinson et al., "Adrenomedullin, a Multifunctional Regulatory Peptide," Endocrine Reviews, 21(2), pp. 138-167 (2000).
Ho et al., "Randomized controlled trial of the CGRP receptor antagonist telcagepant for migraine prevention," Neurology, 83, pp. 958-966 (2014).
Ho et al., "Randomized controlled trial of the CGRP receptor antagonist telcagepant for prevention of headache in women with perimenstrual migraine," Cephalalgia, 36(2), pp. 148-161 (2016).
International Search Report and Written Opinion for International Patent Application No. PCT/GB2018/051331, dated Jul. 9, 2018 (9 pages).

(56) References Cited

OTHER PUBLICATIONS

Ishikawa et al., "Adrenomedullin antagonist suppresses in-vivo growth of human pancreatic cancer cells in SCID mice by suppressing angiogenesis," Oncogene, 22, pp. 1238-1242 (2003).
Javeed et al., "Pancreatic Cancer-Derived Exosomes Cause Paraneoplastic β-cell Dysfunction," Clin. Cancer Res., 21(7), pp. 1722-1733 (2015).
Jiang et al., "Design, Synthesis, and Pharmacological Evaluation of Fused β-Homophenylalanine Derivatives as Potent DPP-4 Inhibitors," ACS Med. Chem. Lett., 6, pp. 602-606 (2015).
Kaafarani et al., "Targeting adrenomedullin receptors with systemic delivery of neutralizing antibodies inhibits tumor angiogenesis and suppresses growth of human tumor xenografts in mice," FASEB J., pp. 3424-3435 (2009).
Keleg et al., "Adrenomedullin is induced by hypoxia and enhances pancreatic cancer cell invasion," Int. J. Cancer, 121, pp. 21-32 (2007).
Kocemba et al., "The hypoxia target adrenomedullin is aberrantly expressed in multiple myeloma and promotes angiogenesis," Leukemia, 27, pp. 1729-1737 (2013).
Kunk et al., "From bench to bedside a comprehensive review of pancreatic cancer immunotherapy," Journal for ImmunoTherapy of Cancer, 4(14), 12 pages (2016).
Ma et al., "Recent Advancements in Pancreatic Cancer Immunotherapy," Cancer Research Frontiers, 2(2), pp. 252-276 (2016).
Moore et al., "Mapping the CGRP receptor ligand binding domain: Tryptophan-84 of RAMP1 is critical for agonist and antagonist binding," Biochemical and Biophysical Research Communications, 394, pp. 141-145 (2010).
Poyner et al., "International Union of Pharmacology. XXXII. The Mammalian Calcitonin Gene-Related Peptides, Adrenomedullin, Amylin, and Calcitonin Receptors," Pharmacol. Rev., 54(2), pp. 233-246 (2002).
Robinson et al., "Novel Peptide Antagonists of Adrenomedullin and Calcitonin Gene-Related Peptide Receptors: Identification, Pharmacological Characterization, and Interactions with Position 74 in Receptor Activity-Modifying Protein 1/3," The Journal of Pharmacology and Experimental Therapeutics, 331(2), pp. 513-521 (2009).
Salvatore et al., "Pharmacological Properties of MK-3207, a Potent and Orally Active Calcitonin Gene-Related Peptide Receptor Antagonist," The Journal of Pharmacology and Experimental Therapeutics, 333(1), pp. 152-160 (2010).
Tepper, "History and Review of anti-Calcitonin Gene-Related Peptide (CGRP) Therapies: From Translational Research to Treatment," Headache, 58, Suppl. 3, pp. 238-275 (2018).
Ter Haar et al., "Crystal Structure of the Ectodomain Complex of the CGRP Receptor, a Class-B GPCR, Reveals the Site of Drug Antagonism," Structure, 18, pp. 1083-1093 (2010).
Wood et al., "Novel CGRP receptor antagonists through a design strategy of target simplification with addition of molecular flexibility," Bioorganic & Medicinal Chemistry Letters, 19, pp. 5787-5790 (2009).
Wood et al., "Preparation of substituted dihydrospiro (imidazolidineindene) dione derivatives and analogs as CGRP receptor antagonists," CAS abstract accession No. 2008:1282079, 6 pages (2008).
Zudaire et al., "Adrenomedullin and cancer," Regulatory Peptides, 112, pp. 175-183 (2003).

Benyahia et al. (Feb. 28, 2017) "Stromal Fibroblasts Present in Breast Carcinomas Promote Tumor Growth and Angiogenesis Through Adrenomedullin Secretion", Oncotarget, 8(9):15744-15762.
Berenguer-Daizé et al. (Nov. 15, 2013) "Adrenomedullin Blockade Suppresses Growth of Human Hormone-Independent Prostate Tumor Xenograft in Mice", Clinical Cancer Research, 19(22):6138-6150.
Chen et al., Dec. 1, 2011, "Tumor-Associated Macrophages Promote Angiogenesis and Melanoma Growth via Adrenomedullin in a Paracrine and Autocrine Manner", Clinical Cancer Research, 17(23):7230-7239.
Drimal et al. (2006) "The Regulation of Human Adrenomedullin (AM) and Tumor Necrosis Factor Alpha (TNF-Alpha) Receptors on Human Epithelial Carcinoma (Hela) Cells. The Role of AM Secretion in Tumor Cell Sensitivity", Neoplasma, 53(2):144-149.
Fernandez-Sauze et al. (Mar. 1, 2004) "Effects of Adrenomedullin on Endothelial Cells in The multi step Process of Angiogenesis: Involvement CRLR/RAMP2 and CRLR/RAMP3 Receptors", International Journal of Cancer, 108(6):797-804.
Gao et al. (Sep. 27, 2016) "Adrenomedullin Blockade Suppresses Sunitinib-Resistant Renal Cell Carcinoma Growth by Targeting the ERK/MAPK Pathway", Oncotarget, 7(39):63374-63387.
Greillie et al. (Jan. 2016) "Functional Analysis of the Adrenomedullin Pathway in Malignant Pleural Mesothelioma.", Journal of Thoracic Oncology, 11(1):94-107.
Limuro et al. (Aug. 20, 2004) "Angiogenic Effects of Adrenomedullin in Ischemia and Tumor Growth", Circulation Research, 95(4):415-423.
Larráyoz et al. (Dec. 5, 2014) "Adrenomedullin and Tumour Microenvironment", Journal of Translational Medicine, 12:339.
Li et al. (Sep. 2014) "Silencing of Hypoxia Inducible Adrenomedullin Using RNA Interference Attenuates Hepatocellular Carcinoma Cell Growth In Vivo", Molecular Medicine Reports, 10(3):1295-1302.
Liddo et al. (Apr. 2016) "Adrenomedullin in the Growth Modulation and Differentiation of Acute Myeloid Leukemia Cells", International Journal of Oncology, 48(4):1659-1669.
Liu et al. (2013) "RNA Interference Targeting Adrenomedullin Induces Apoptosis and Reduces the Growth of Human Bladder Urothelial Cell Carcinoma", Medical Oncology, 30(3):616.
Nouguerède et al. (Apr. 2013) "Expression of Adrenomedullin in Human Colorectal Tumors and Its Role in Cell Growth and Invasion In Vitro and in Xenograft Growth In Vivo", Cancer Medicine, 2(2):196-207.
Ouafik et al. (Apr. 2002) "Neutralization of Adrenomedullin Inhibits the Growth of Human Glioblastoma Cell Lines In Vitro and Suppresses Tumor Xenograft Growth In Vivo", The American Journal of Pathology, 160(4):1279-1292.
Pang et al. (Jan. 29, 2013) "The Interaction of Adrenomedullin and Macrophages Induces Ovarian Cancer Cell Migration via Activation of RhoA Signaling Pathway", International Journal of Molecular Sciences, 14(2):2774-2787.
Portal-Nuñez et al. (Nov. 15, 2012) "Aryl Hydrocarbon Receptor-Induced Adrenomedullin Mediates Cigarette Smoke Carcinogenicity in Humans and Mice", Cancer Research, 72(22):5790-5800 (21 pages).
Vijay et al. (May 2005) "Adrenomedullin (22-52) Inhibits Growth of SAOS-2 Osteosarcoma Cell Line", Cellular and Molecular Biology 58: Signaling in Cancer, 3 pages.
Xu et al. (Aug. 23, 2016) "Adrenomedullin Promotes the Growth of Pancreatic Ductal Adenocarcinoma Through Recruitment of Myelomonocytic Cells", Oncotarget, 34(7):55043-55056.

* cited by examiner

COMPOUNDS

This application is a U.S. National Phase of International Application No. PCT/GB2018/051331, filed May 16, 2018, which claims the benefit of United Kingdom Application No. 1707938.5, filed May 17, 2016, the entire contents of which are incorporated herein by reference.

This invention relates to compounds which are $AM_2$ receptor inhibitors and to the use of the compounds as therapeutic agents in the treatment of conditions mediated by $AM_2$, for example in the treatment of proliferative disorders, including cancers such as pancreatic cancer. Also disclosed are pharmaceutical compositions comprising the compounds.

BACKGROUND

Adrenomedullin (AM) is a hormone with important physiological functions, including the regulation of blood pressure. However, AM is dysregulated in a number of diseases and is implicated in the development and progression of a wide range of cancers, for example pancreatic cancer (Adrenomedullin is induced by hypoxia and enhances pancreatic cancer cell invasion. Keleg S, Kayed H, Jiang X, Penzel R, Giese T, Büchler M W, Friess H, Kleeff J. Int. J. Cancer. 2007 Jul. 1; 121(1):21-32; Adrenomedullin and cancer. Zudaire E, Martínez A, Cuttitta F. Regulatory Peptides. 2003 Apr. 15; 112(1-3):175-183; Adrenomedullin, a Multifunctional Regulatory Peptide. Hinson J P, Kapas S, Smith D M. Endocrine reviews. 2000; 21(2):138-167).

There are two cell surface receptor complexes for adrenomedullin, adrenomedullin receptor subtype 1 ($AM_1$) and adrenomedullin receptor subtype 2 ($AM_2$). These receptors are heteromeric structures comprising a G-protein-coupled receptor (GPCR) and an accessory protein known as a Receptor Activity Modifying Protein (RAMP). More specifically the $AM_1$ receptor is formed as a complex of the calcitonin like receptor (CLR) and RAMP2. The $AM_2$ receptor is formed by CLR and RAMP3. The $AM_1$ receptor has a high degree of selectivity for AM over the calcitonin gene related peptide (CGRP). By contrast, the $AM_2$ receptor shows less specificity for AM, having appreciable affinity for βCGRP (Hay et al. J. Mol. Neuroscience 2004; 22(1-2):105-113). The CLR/RAMP1 receptor CGRP, is a high-affinity receptor for calcitonin gene related peptide (CGRP), but it also binds AM with lower affinity (Hay et al. Pharmacological discrimination of calcitonin receptor receptor activity-modifying protein complexes. Mol. Pharmacol. 2005; 67:1655-1665; Poyner et al. International Union of Pharmacology. XXXII. The mammalian calcitonin gene-related peptides, adrenomedullin, amylin, and calcitonin receptors. Pharmacol. Rev. 2002; 54:233-246).

Although $AM_1$ and $AM_2$ share the same GPCR, CLR, the effects of the two receptors are quite distinct. Adrenomedullin mediates important physiological functions through the $AM_1$ receptor, including regulation of blood pressure (Biological action of Adrenomedullin. Horio T & Yoshihara F. In: Nishikimi T. (eds); Adrenomedullin in Cardiovascular Disease. Springer, 2005, ISBN-10 0-387-25404-8: DOI.org/10.1007/0-387-25405-6_5).

In contrast, the $AM_2$ receptor is involved in numerous pro-tumourigenic actions through a number of different mechanisms including: stimulating cancer cell proliferation, protecting from stress induced apoptosis, promoting angiogenesis and increasing tumour invasiveness.

AM secreted by tumours leads to up-regulation of the $AM_2$ receptor in host tissues surrounding tumours. Host tissue expression of $AM_2$ is thought to be an important factor in the mechanism by which tumours promote angiogenesis and evade host defenses. This has been demonstrated in pancreatic tumours where $AM_2$ expression increases with tumour severity grade. Studies have shown that reduction in $AM_2$ expression either in tumours or in the host, or antagonism of the receptors with peptides or antibodies leads to reduction in cancer cell growth in-vitro and in-vivo (Ishikawa T et al. Adrenomedullin antagonist suppresses in-vivo growth of human pancreatic cancer cells in SCID mice by suppressing angiogenesis. Oncogene. 2003 Feb. 27; 22(8):1238-1242; Antolino et al. Pancreatic Cancer Can be Detected by Adrenomedullin in New Onset Diabetes Patients (PaCANOD). https://clinicaltrials.gov/ct2/show/NCT02456051; Antolino et al. Adrenomedullin in pancreatic carcinoma: A case-control study of 22 patients. Faculty of Medicine and Psychology, Sapienza University of Rome, Rome, Italy: DOI 10.15761/ICST.1000175).

Targeting of AM and its receptors have been shown to be efficacious in animal xenograft experiments. Local injection of the AM peptide antagonist (AM22-52) directly into tumours in a pancreatic cancer model, reduced tumour size significantly compared to controls (Adrenomedullin antagonist suppresses in-vivo growth of human pancreatic cancer cells in SCID mice by suppressing angiogenesis. Ishikawa T et al. Oncogene. 2003; 22:1238-1242: DOI 10.1038/sj.onc.1206207).

Pancreatic cells overexpressing AM, implanted into mice produced significantly larger tumours, and cells whose native AM expression was knocked down, had smaller tumours. Furthermore, metastasis in animals with AM knockdown cells were almost absent (Ishikawa T et al. 2003).

In human cancers, $AM_2$ receptors are upregulated in host tissues surrounding tumours. WO2008/132453 discloses a mouse monoclonal antibody to hRAMP3 reduced tumour volume in a mouse model, suggesting interference with the known mechanisms of action of AM in tumours.

In clinical trials, elevated levels of serum AM have been observed in pancreatic carcinoma patients compared to controls regardless of tumour stage, differentiation, operability and presence of diabetes (A Star of Connection Between Pancreatic Cancer and Diabetes: Adrenomedullin. Görgülü K et al. Journal of the Pancreas. 2015; 16(5):408-412). High serum AM is therefore generally regarded to be an indicator of poor prognosis in pancreatic cancer.

Elevated serum AM levels accompanied by atypical development of type 2 diabetes has also been shown to be predictive of early pancreatic cancer (Kaafarani I et al. Targeting adrenomedullin receptors with systemic delivery of neutralizing antibodies inhibits tumour angiogenesis and suppresses growth of human tumour xenografts in mice. FASEB J. 2009 Jun. 22: DOI:10.1096/fj.08-127852).

Accordingly, inhibition of the $AM_2$ receptor is an attractive target for the treatment of proliferative conditions such as cancer, for example in the treatment of pancreatic cancer. The $AM_2$ receptor may play a role in regulating cell proliferation and/or apoptosis and/or in mediating interactions with host tissues including cell migration and metastasis.

Pancreatic cancer is a devastating disease that kills most patients within 6 months of diagnosis. The one-year survival rate of less than 20% in pancreatic cancer is consistent with most patients being diagnosed at first presentation with advanced disease, at which point there is no effective life-extending therapy. Where diagnosis is early, surgical resection is the preferred treatment option and tumour resection is usually followed by chemotherapy (e.g. cytotoxic therapies, including gemcitabine or 5-fluorouracil and an EGF receptor tyrosine kinase inhibitor, erlotinib). However, due to difficulty in early diagnosis, the majority of the current therapies and management strategies focus on supportive chemotherapy with very limited expectation of life extension. Furthermore, pancreatic cancer is highly unusual from an immunological perspective meaning that current approaches to immuno-oncology therapies such as PDL-1 inhibitors are largely ineffective against pancreatic cancer (From bench to bedside a comprehensive review of pancreatic cancer immunotherapy. Kunk P R, Bauer T W, Slingluff C L, Rahma O E. Journal for ImmunoTherapy of Cancer. 2016; 4:14: DOI 10.1186/s40425-016-0119-z; Recent Advancements in Pancreatic Cancer Immunotherapy. Ma Y et al. Cancer Research Frontiers. 2016 May; 2(2):252-276: DOI 10.17980/2016.252). There is therefore a need for new treatments for pancreatic cancer.

Although certain peptide and antibody $AM_2$ receptor inhibitors are known such as $AM_{22-52}$ (Robinson et al. J. Pharmacology and Exp. Therapeutics. 2009; 331(2):513-521) there remains a need for new agents that are $AM_2$ receptor inhibitors. Suitably, an $AM_2$ inhibitor will be selective for the $AM_2$ receptor and in particular will exhibit little or no effects on the related $AM_1$ receptor. A selective $AM_2$ receptor is expected to provide a beneficial therapeutic effect, for example an anti-cancer effect, whilst having little or no effect on physiological effects mediated by the $AM_1$ receptor.

BRIEF SUMMARY OF THE DISCLOSURE

In accordance with the present invention there is provided a compound of formula (I), or a pharmaceutically acceptable salt thereof:

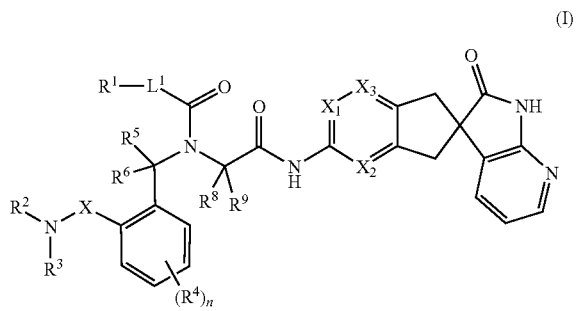

(I)

wherein
$X_1$ is N or $CR^7$;
$X_2$ and $X_3$ are each independently N or CH, provided that no more than one of $X_1$, $X_2$ and $X_3$ is N;
$L^1$ is a bond, —O—, or —N($R^{10}$)—;
$R^1$ is selected from: H, $C_{1-6}$ alkyl, $C_{2-6}$ alkenyl, $C_{2-6}$ alkynyl, $C_{1-6}$ haloalkyl, $C_{3-12}$ cycloalkyl, $C_{3-12}$ cycloalkyl-$C_{1-4}$ alkyl, $C_{3-12}$ cycloalkenyl, $C_{3-12}$ cycloalkenyl-$C_{1-4}$ alkyl, 4 to 12 membered heterocyclyl, 4 to 12 membered heterocyclyl-$C_{1-4}$ alkyl, $C_{6-10}$ aryl, $C_{6-10}$ aryl-$C_{1-4}$ alkyl, 5 to 10 membered heteroaryl, and 5 to 10 membered heteroaryl-$C_{1-4}$ alkyl;

and wherein $R^1$ is optionally substituted by one or more substituents independently selected from: halo, $C_{1-4}$ alkyl, —$C_{1-4}$ alkyl-$OR^{A1}$, —$C_{1-4}$ alkyl-$NR^{A1}R^{B1}$, —$C_{1-4}$ alkyl-C(O)$R^{A1}$, —$C_{1-4}$ alkyl-C(O)$NR^{A1}R^{B1}$, —$C_{1-4}$ alkyl-$NR^{A1}$C(O)$R^{B1}$, —$C_{1-4}$ alkyl-S(O)$_2NR^{A1}R^{B1}$, —$C_{1-4}$ alkyl-$NR^{A1}$S(O)$_2R^{B1}$, —$C_{1-4}$ alkyl-C(O)$OR^{A1}$, —$C_{1-4}$ alkyl-OC(O)$R^{A1}$, —$C_{1-4}$ alkyl-S(O)$_xR^{A1}$ (wherein x is 0, 1 or 2), $C_{1-4}$ haloalkyl, —$OR^{A1}$, —$NR^{A1}R^{B1}$, —$SR^{A1}$, —S(O)$R^{A1}$, —S(O)$_2R^{18}$, —C(O)$R^{18}$, —OC(O)$R^{A1}$, —C(O)$OR^{A1}$, —$NR^{A1}$C(O)$R^{18}$, —C(O)$NR^{A1}R^{18}$, —$NR^{A1}$SO$_2R^{B1}$, —SO$_2NR^{A1}R^{18}$, =O, —CN and $R^{17}$;

$R^{17}$ is independently selected from: $C_{3-6}$ cycloalkyl, $C_{3-6}$ cycloalkyl-$C_{1-4}$ alkyl, 4 to 7 membered heterocyclyl, 4 to 7 membered heterocyclyl-$C_{1-4}$ alkyl, phenyl, phenyl-$C_{1-4}$ alkyl, 5 to 10 membered heteroaryl, and 5 to 10 membered heteroaryl-$C_{1-4}$ alkyl;

$R^{18}$ is independently selected from H, $C_{1-6}$ alkyl, $C_{1-6}$ haloalkyl, $C_{3-6}$ cycloalkyl, $C_{3-6}$ cycloalkyl-$C_{1-4}$ alkyl, 4 to 7 membered heterocyclyl, 4 to 7 membered heterocyclyl-$C_{1-4}$ alkyl, $C_{6-10}$ aryl, $C_{6-10}$ aryl-$C_{1-4}$ alkyl, 5 to 10 membered heteroaryl, and 5 to 10 membered heteroaryl-$C_{1-4}$ alkyl, or any $NR^{A1}R^{18}$ group in $R^1$ forms a 4 to 7 membered heterocyclyl;

wherein $R^{17}$ and $R^{18}$ are each independently optionally substituted by one or more substituents independently selected from: halo, $C_{1-4}$ alkyl, $C_{1-4}$ haloalkyl, —$OR^{A6}$, —$NR^{A6}R^{B6}$, —S(O)$_xR^{A6}$ (wherein x is 0, 1 or 2), —C(O)$R^{A6}$, —OC(O)$R^{A6}$, —C(O)$OR^{A6}$, —$NR^{A6}$C(O)$R^{B6}$, —C(O)$NR^{A6}R^{B6}$, —$NR^{A6}$SO$_2R^{B6}$, —SO$_2NR^{A6}R^{B6}$, =O and —CN;

X is —(CR$^A$R$^B$)$_p$—;

$R^2$ and $R^3$ are each independently selected from: H, —C(=$NR^{A9}$)N($R^{A9}$)$_2$, —C(=$NR^{A9}$)$R^{A7}$, —C(=NCN)N($R^{A9}$)$_2$, $C_{1-6}$ alkyl, $C_{2-6}$ alkenyl, $C_{2-6}$ alkynyl, $C_{1-6}$ haloalkyl, —$OR^{A10}$, $C_{3-8}$ cycloalkyl, $C_{3-8}$ cycloalkyl-$C_{1-6}$ alkyl-, 4 to 7 membered heterocyclyl, 4 to 7 membered heterocyclyl-$C_{1-6}$ alkyl-, $C_{6-10}$ aryl-$C_{1-6}$ alkyl-, 5 to 10 membered heteroaryl-$C_{1-6}$ alkyl-, $C_{2-6}$ alkyl substituted by —$NR^{11}R^{12}$ and $C_{2-6}$ alkyl substituted by —$OR^{13}$, wherein $R^{11}$, $R^{12}$ and $R^{13}$ are independently selected from H, $C_{1-4}$ alkyl and $C_{1-4}$ haloalkyl, or $R^{11}$ and $R^{12}$ together with the nitrogen to which they are attached form a 4 to 6 membered heterocyclyl, $R^{A7}$ and each $R^{A9}$ is independently selected from H, $C_{1-6}$ alkyl, $C_{1-6}$ haloalkyl and $C_{3-8}$ cycloalkyl, or any —N($R^{A9}$)$_2$ within a substituent may form a 4 to 6 membered heterocyclyl;

and wherein $R^2$ and $R^3$ are independently optionally further substituted by one or more substituents independently selected from: halo, $C_{1-4}$ alkyl, $C_{1-4}$ haloalkyl, $C_{3-6}$ cycloalkyl, —$OR^{A2}$, —$NR^{A2}R^{B2}$, —S(O)$_xR^{A2}$ (wherein x is 0, 1 or 2), —C(O)$R^{A2}$, —OC(O)$R^{A2}$, —C(O)$OR^{A2}$, —$NR^{A2}$C(O)$R^{B2}$, —C(O)$NR^{A2}R^{B2}$, —$NR^{A2}$SO$_2R^{B2}$, —SO$_2NR^{A2}R^{B2}$, =O and —CN;

or $R^2$ and $R^3$ together with the nitrogen atom to which they are attached form a 4 to 7 membered heterocyclyl, or imidazolyl, wherein said 4 to 7 membered heterocyclyl or imidazolyl formed by $R^2$ and $R^3$ is optionally further substituted by one or more substituents selected from halo, $C_{1-4}$ alkyl, $C_{1-4}$ haloalkyl, $C_{3-6}$ cycloalkyl, —$OR^{A3}$, —$NR^{A3}R^{B3}$, —S(O)$_xR^{A3}$ (wherein x is 0, 1 or 2), —C(O)$R^{A3}$, —C(O)$OR^{A3}$, =O, —CN, $C_{1-8}$ alkyl substituted by —$NR^{A3}R^{B3}$ and $C_{1-6}$ alkyl substituted by —$OR^{A3}$;

or the group $R^2$N($R^3$)X— and the phenyl ring carbon atom adjacent to X together form a group of the formula:

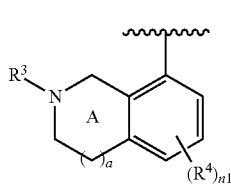

wherein

∿∿∿ indicates the point of attachment to the C(R$^5$R$^6$) group in formula (I); a is an integer 0, 1 or 2;

n1 is an integer 0, 1, 2 or 3 and, when present, R$^4$ is located on the phenyl ring; and wherein Ring A is optionally substituted by one or more substituents selected from halo, C$_{1-4}$ alkyl, C$_{1-4}$ haloalkyl, —OR$^{43}$, —NR$^{43}$R$^{B3}$ and =O;

or the group R$^2$N(R$^3$)X— and R$^6$ together with the atoms to which they are attached form a group of the formula:

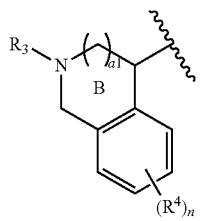

wherein

∿∿∿ indicates the point of attachment to the —N(C(O)L$^1$R$^1$)— group in formula (I);

a1 is an integer 0, 1 or 2;

when present, R$^4$ is located on the phenyl ring; and wherein Ring B is optionally substituted by one or more substituents selected from halo, C$_{1-4}$ alkyl and C$_{1-4}$ haloalkyl;

R$^4$ is independently selected from: halo, C$_{1-4}$ alkyl, C$_{1-4}$ haloalkyl, —OR$^{44}$, —NR$^{44}$R$^{B4}$, —S(O)$_x$R$^{44}$ (wherein x is 0, 1 or 2) and —CN;

R$^5$, R$^6$, R$^8$ and R$^9$ are independently selected from: H, C$_{1-6}$ alkyl and C$_{1-6}$ haloalkyl, wherein the C$_{1-6}$ alkyl is optionally substituted by —OR$^{45}$, —NR$^{45}$R$^{B5}$, —S(O)$_x$R$^{45}$ (wherein x is 0, 1 or 2), or R$^5$ and R$^6$ together with the carbon to which they are attached form a C$_{3-6}$ cycloalkyl or 4 to 7 membered heterocyclyl, or R$^8$ and R$^9$ together with the carbon to which they are attached form a C$_{3-6}$ cycloalkyl or 4 to 7 membered heterocyclyl;

R$^7$ is selected from: H, halo, C$_{1-6}$ alkyl and C$_{1-6}$ haloalkyl;

R$^A$ and R$^B$ are each independently selected from: H, halo, C$_{1-6}$ alkyl and C$_{1-6}$ haloalkyl, or R$^A$ and R$^B$ together with the carbon to which they are attached form a C$_{3-6}$ cycloalkyl or 4 to 7 membered heterocyclyl, or R$^A$ and R$^B$ attached to the same carbon atom in X form =NR$^{48}$ or =NOR$^{48}$;

R$^{10}$ is selected from: H, C$_{1-6}$ alkyl, C$_{1-6}$ haloalkyl and —OR$^{412}$;

R$^{41}$, R$^{B1}$, R$^{42}$, R$^{B2}$, R$^{43}$, R$^{B3}$, R$^{44}$, R$^{B4}$, R$^{45}$, R$^{B5}$, R$^{46}$, R$^{B6}$, R$^{48}$, R$^{410}$, and R$^{412}$ are each independently selected from: H, C$_{1-4}$ alkyl and C$_{1-4}$ haloalkyl, or wherein any —NR$^{41}$R$^{B1}$, —NR$^{42}$R$^{B2}$ or —NR$^{43}$R$^{B3}$ within a substituent may form a 4 to 6 membered heterocyclyl;

n is an integer selected from 0, 1, 2, 3 or 4; and p is an integer selected from 0, 1, 2 or 3.

Also provided is a pharmaceutical composition comprising a compound of the invention, or a pharmaceutically acceptable salt thereof, and a pharmaceutically acceptable excipient.

Also provided is a compound of the invention, or a pharmaceutically acceptable salt thereof, for use as a medicament. In some embodiments the compound of the invention, or a pharmaceutically acceptable salt thereof, is for use in the treatment of a disease or medical condition mediated by adrenomedullin receptor subtype 2 (AM$_2$) receptors.

Also provided is a method of treating a disease or medical condition mediated by AM$_2$ in a subject in need thereof, the method comprising administering to the subject an effective amount of a compound of the invention, or a pharmaceutically acceptable salt thereof.

In certain embodiments the compounds of the invention are for use in the treatment of proliferative diseases, for example cancer. In certain embodiments a compound of the invention is for use in the prevention or inhibition of cancer progression, for example by preventing or inhibiting cancer cell migration and/or preventing or inhibiting cancer metastasis.

Also provided is a compound of the invention for use in the treatment of a cancer in which AM and or AM$_2$ is implicated in development or progression of the cancer. For example in some embodiments a compound of the invention may be for use in the treatment of a cancer selected from: pancreatic, colorectal, breast and lung cancer. In a particular embodiment a compound of the invention is for use in the treatment of pancreatic cancer. In certain embodiments a compound of the invention is for use in the treatment of a patient with a cancer, for example pancreatic cancer, wherein the expression of AM, AM$_2$, CLR and/or RAMP3 in the patient is elevated compared to controls. For example, the patient may have elevated serum levels of AM, AM$_2$, CLR and/or RAMP3.

The compounds of the invention may be used alone or in combination with one or more anticancer agents and/or radiotherapy as described herein.

DETAILED DESCRIPTION

Definitions

Unless otherwise stated, the following terms used in the specification and claims have the following meanings set out below.

The terms "treating" or "treatment" refers to any indicia of success in the treatment or amelioration of a disease, pathology or condition, including any objective or subjective parameter such as abatement; remission; diminishing of symptoms or making the pathology or condition more tolerable to the patient; slowing in the rate of degeneration or decline; making the final point of degeneration less debilitating; improving a patient's physical or mental well-being. For example, certain methods herein treat cancer by decreasing a symptom of cancer. Symptoms of cancer would be known or may be determined by a person of ordinary skill in the art. The term "treating" and conjugations thereof, include prevention of a pathology, condition, or disease (e.g. preventing the development of one or more symptoms of a cancer associated with AM$_2$.

The term "associated" or "associated with" in the context of a substance or substance activity or function associated with a disease (e.g. cancer) means that the disease (e.g. cancer) is caused by (in whole or in part), or a symptom of the disease is caused by (in whole or in part) the substance or substance activity or function. For example, a symptom of a disease or condition associated with $AM_2$ receptor pathway activity may be a symptom that results (entirely or partially) from an increase in the level of activity of $AM_2$ protein pathway. As used herein, what is described as being associated with a disease, if a causative agent, could be a target for treatment of the disease. For example, a disease associated with an increase in the level of activity of $AM_2$, may be treated with an agent (e.g. compound as described herein) effective for decreasing the level of activity of $AM_2$.

As defined herein, the term "inhibition", "inhibit", "inhibiting" and the like in reference to a protein-inhibitor (e.g. antagonist) interaction means negatively affecting (e.g. decreasing) the level of activity or function of the protein (e.g. a component of the $AM_2$) protein pathway relative to the level of activity or function of the protein pathway in the absence of the inhibitor). In some embodiments inhibition refers to reduction of a disease or symptoms of disease (e.g. cancer associated with an increased level of activity of $AM_2$. In some embodiments, inhibition refers to a reduction in the level of activity of a signal transduction pathway or signalling pathway associated with $AM_2$. Thus, inhibition may include, at least in part, partially or totally blocking stimulation, decreasing, preventing, or delaying activation, or inactivating, desensitizing, or down-regulating signal transduction or enzymatic activity or the amount of a protein (e.g. the $AM_2$ receptor). Inhibition may include, at least in part, partially or totally decreasing stimulation, decreasing activation, or deactivating, desensitizing, or down-regulating signal transduction or enzymatic activity or the amount of a protein (e.g. a component of an $AM_2$ protein pathway) that may modulate the level of another protein or modulate cell survival, cell proliferation or cell motility relative to a non-disease control.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

The term "halo" or "halogen" refers to one of the halogens, group 17 of the periodic table. In particular the term refers to fluorine, chlorine, bromine and iodine. Preferably, the term refers to fluorine or chlorine.

The term $C_{m-n}$ refers to a group with m to n carbon atoms.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, iso-butyl, sec-butyl, tert-butyl, n-pentyl and n-hexyl. "$C_{1-4}$ alkyl" similarly refers to such groups containing up to 4 carbon atoms. Alkylene groups are divalent alkyl groups and may likewise be linear or branched and have two points of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_1$-$C_4$ alkoxy. Other substituents for the alkyl group may alternatively be used.

The term "$C_{1-6}$ haloalkyl", e.g. "$C_{1-4}$ haloalkyl", refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be a fluoroalkyl group, i.e. a hydrocarbon chain substituted with at least one fluorine atom.

The term "$C_{2-6}$ alkenyl" includes a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" includes a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{3-12}$ cycloalkyl" includes a saturated hydrocarbon ring system containing 3 to 12 carbon atoms. The cycloalkyl group may be monocyclic or a fused, bridged or spiro saturated hydrocarbon ring system. The term "$C_{3-6}$ cycloalkyl" includes a saturated hydrocarbon ring system containing 3, 4, 5 or 6 carbon atoms. For example, the $C_3$-$C_{12}$ cycoalkyl may be cyclopropyl, cyclobutyl, cyclopentyl, cyclohexyl, bicyclo[1.1.1]pentane, bicyclo[2.1.1] hexane, bicyclo[2.2.1]heptane (norbornane), bicyclo[2.2.2] octane or tricyclo[3.3.1.1]decane (adamantyl). For example, the "$C_3$-$C_6$ cycloalkyl" may be cyclopropyl, cyclobutyl, cyclopentyl, cyclohexyl, bicyclo[2.1.1]hexane or bicyclo [1.1.1]pentane. Suitably the "$C_3$-$C_6$ cycloalkyl" may be cyclopropyl, cyclobutyl, cyclopentyl or cyclohexyl.

The term "$C_{3-12}$ cycloalkenyl" includes a hydrocarbon ring system containing 3 to 12 carbon atoms and at least one double bond (e.g. 1 or 2 double bonds). The cycloalkenyl group may be monocyclic or a fused, bridged or spiro hydrocarbon ring system. For example, $C_{3-12}$ cycloalkenyl may be cyclobutenyl, cyclopentenyl, cyclohexenyl, The term "heterocyclyl", "heterocyclic" or "heterocycle" includes a non-aromatic saturated or partially saturated monocyclic or fused, bridged, or spiro bicyclic heterocyclic ring system. Monocyclic heterocyclic rings may contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles may contain from 7 to 12-member atoms in the ring. Bicyclic heterocyclic(s) rings may be fused, spiro, or bridged ring systems. The heterocyclyl group may be a 3-12, for example, a 3- to 7-membered non-aromatic monocyclic or bicyclic saturated or partially saturated group comprising 1, 2 or 3 heteroatoms independently selected from O, S and N in the ring system (in other words 1, 2 or 3 of the atoms forming the ring system are selected from O, S and N). By partially saturated it is meant that the ring may comprise one or two double bonds. This applies particularly to monocyclic rings with from 5 to 7 members. The double bond will typically be between two carbon atoms but may be between a carbon atom and a nitrogen atom. Bicyclic systems may be spiro-fused, i.e. where the rings are linked to each other through a single carbon atom; vicinally fused, i.e. where the rings are linked to each other through two adjacent carbon or nitrogen atoms; or they may be share a bridgehead, i.e. the rings are linked to each other through two non-adjacent carbon or nitrogen atoms (a bridged ring system). Examples of heterocyclic groups include cyclic ethers such as oxiranyl, oxetanyl, tetrahydrofuranyl, dioxanyl, and substituted cyclic ethers. Heterocycles comprising at least one nitrogen in a ring position include, for example, azetidinyl, pyrrolidinyl, piperidinyl, piperazinyl, morpholinyl, thiomorpholinyl, tetrahydrotriazinyl, tetrahydropyrazolyl, tetrahydropyridinyl, homopiperidinyl, homopiperazinyl, 2,5-diaza-bicyclo[2.2.] heptanyl and the like. Typical sulfur containing heterocycles include tetrahydrothienyl, dihydro-1,3-dithiol, tetrahydro-2H-thiopyran, and hexahydrothiepine. Other heterocycles include dihydro oxathiolyl, tetrahydro oxazolyl, tetrahydrooxadiazolyl, tetrahydrodioxazolyl, tetrahydrooxathiazolyl, hexahydrotriazinyl, tetrahydro oxazinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O), for example, 2 oxopyrrolidinyl, 2-oxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. For example, the term "piperidino" or "morpholino" refers to a piperidin-1-yl or morpholin-4-yl ring that is linked via the ring nitrogen.

The term "bridged ring systems" includes ring systems in which two rings share more than two atoms, see for example Advanced Organic Chemistry, by Jerry March, 4th Edition, Wiley Interscience, pages 131-133, 1992. Suitably the bridge is formed between two non-adjacent carbon or nitrogen atoms in the ring system. The bridge connecting the bridgehead atoms may be a bond or comprise one or more atoms. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane, and quinuclidine.

The term "spiro bi-cyclic ring systems" includes ring systems in which two ring systems share one common spiro carbon atom, i.e. the heterocyclic ring is linked to a further carbocyclic or heterocyclic ring through a single common spiro carbon atom. Examples of spiro ring systems include 3,8-diaza-bicyclo[3.2.1]octane, 2,5-diaza-bicyclo[2.2.]heptane, 6-azaspiro[3.4]octane, 2-oxa-6-azaspiro[3.4]octane, 2-azaspiro[3.3]heptane, 2-oxa-6-azaspiro[3.3]heptane, 6-oxa-2-azaspiro[3.4]octane, 2,7-diaza-spiro[4.4]nonane, 2-azaspiro[3.5]nonane, 2-oxa-7-azaspiro[3.5]nonane and 2-oxa-6-azaspiro[3.5]nonane.

"Heterocyclyl-$C_{m-n}$ alkyl" includes a heterocyclyl group covalently attached to a $C_{m-n}$ alkylene group, both of which are defined herein; and wherein the Heterocyclyl-$C_{m-n}$ alkyl group is linked to the remainder of the molecule via a carbon atom in the alkylene group. The groups "aryl-$C_{m-n}$ alkyl" "heteroaryl-$C_{m-n}$ alkyl" are defined in the same way.

"—$C_{m-n}$ alkyl substituted by —NRR" and "$C_{m-n}$ alkyl substituted by —OR" similarly refer to an —NRR or —OR group covalently attached to a $C_{m-n}$ alkylene group and wherein the group is linked to the remainder of the molecule via a carbon atom in the alkylene group.

The term "aromatic" when applied to a substituent as a whole includes a single ring or polycyclic ring system with 4n+2 electrons in a conjugated π system within the ring or ring system where all atoms contributing to the conjugated π system are in the same plane.

The term "aryl" includes an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π system where all atoms contributing to the conjugated π system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 1H-pyrazolo[4,3-d]-oxazolyl, 4H-imidazo[4,5-d]thiazolyl, pyrazino[2,3-d]pyridazinyl, imidazo[2,1-b]thiazolyl and imidazo[1,2-b][1,2,4]triazinyl. Examples of heteroaryl groups comprising at least one nitrogen in a ring position include pyrrolyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, indolyl, isoindolyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl and pteridinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five-membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six-membered heteroaryl groups include but are not limited to pyridyl, pyrazinyl, pyridazinyl, pyrimidinyl and triazinyl.

Particular examples of bicyclic heteroaryl groups containing a six-membered ring fused to a five-membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "optionally substituted" includes either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in " ".

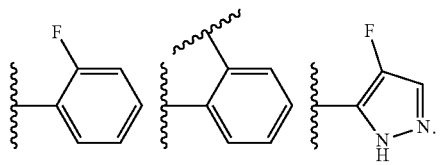

"Meta" substitution is a substitution patter where two substituents are on carbons one carbon removed from each other, i.e. with a single carbon atom between the substituted carbons. In other words there is a substituent on the second atom away from the atom with another substituent. For example the groups below are meta substituted.

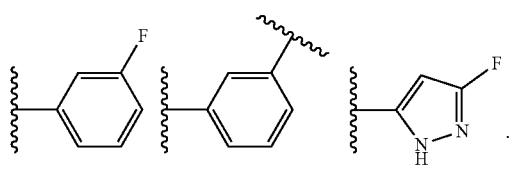

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted.

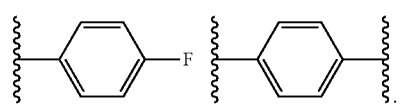

The phrase "compound of the invention" means those compounds which are disclosed herein, both generically and specifically. Accordingly compounds of the invention include compounds of the formulae (I), (II), (III), (IV), (V), (VI), (VII), (VIII), (VIIIa), (VIIIb), (IX), (IXa), (IXb), (X), (Xa), (Xb), (XI), (XIa), (XIb) and the compounds in the Examples.

A bond terminating in a " " represents that the bond is connected to another atom that is not shown in the structure. A bond terminating inside a cyclic structure and not terminating at an atom of the ring structure represents that the bond may be connected to any of the atoms in the ring structure where allowed by valency.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 585 and, for example, is 575 or less.

Suitable or preferred features of any compounds of the present invention may also be suitable features of any other aspect.

The invention contemplates pharmaceutically acceptable salts of the compounds of the invention. These may include the acid addition and base salts of the compounds. These may be acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:
(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereo centres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diasteroisomers or enantiomers as impurities. Hence a single stereoisomer does not necessarily have an enantiomeric excess (e.e.) or diastereomeric excess (d.e.) of 100% but could have an e.e. or d.e. of about at least 85%, for example at least 90%, at least 95% or at least 99%.

The compounds of this invention may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess $AM_2$ inhibitory activity.

Z/E (e.g. cis/trans) isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high-pressure liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{15}$O, $^{17}$O, $^{18}$O, $^{13}$N, $^{15}$N, $^{18}$F, $^{36}$Cl, $^{123}$I, $^{25}$I, $^{32}$P, $^{35}$S and the like. The radionuclide that is used will depend on the specific application of that radio-labelled derivative. For example, for in-vitro competition assays, $^3$H or $^{14}$C are often useful. For radio-imaging applications, $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

Isotopically-labelled compounds can generally be prepared by conventional techniques known to those skilled in the art or by processes analogous to those described using an appropriate isotopically-labelled reagent in place of the non-labelled reagent previously employed.

The selective replacement of hydrogen with deuterium in a compound may modulate the metabolism of the compound, the PK/PD properties of the compound and/or the toxicity of the compound. For example, deuteration may increase the half-life or reduce the clearance of the compound in-vivo. Deuteration may also inhibit the formation of toxic metabolites, thereby improving safety and tolerability. It is to be understood that the invention encompasses deuterated derivatives of compounds of formula (I). As used herein, the term deuterated derivative refers to compounds of the invention where in a particular position at least one hydrogen atom is replaced by deuterium. For example, one or more hydrogen atoms in a $C_{1-4}$-alkyl group may be replaced by deuterium to form a deuterated $C_{1-4}$-alkyl group. For example, $R^2$ may be a deuterated $C_{1-4}$-alkyl group, for example $CD_3$. In another example the group —X—NR$^2$R$^3$ is —CHD-NH(CD$_3$).

Certain compounds of the invention may exist in solvated as well as unsolvated forms such as, for example, hydrated forms. It is to be understood that the invention encompasses all such solvated forms that possess AM$_2$ inhibitory activity.

It is also to be understood that certain compounds of the invention may exhibit polymorphism, and that the invention encompasses all such forms that possess AM$_2$ inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

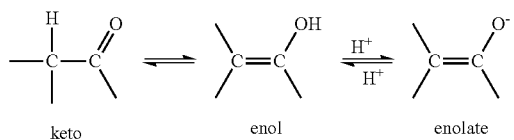

keto      enol      enolate

The in-vivo effects of a compound of the invention may be exerted in part by one or more metabolites that are formed within the human or animal body after administration of a compound of the invention.

It is further to be understood that a suitable pharmaceutically-acceptable pro-drug of a compound of the formula (I) also forms an aspect of the present invention. Accordingly, the compounds of the invention encompass pro-drug forms of the compounds and the compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in-vivo-cleavable ester derivatives that may be formed at a carboxy group or a hydroxy group in a compound of the invention and in-vivo-cleavable amide derivatives that may be formed at a carboxy group or an amino group in a compound of the invention.

Accordingly, the present invention includes those compounds of the invention as defined herein when made available by organic synthesis and when made available within the human or animal body by way of cleavage of a pro-drug thereof. Accordingly, the present invention includes those compounds of the formula (I) that are produced by organic synthetic means and also such compounds that are produced in the human or animal body by way of metabolism of a precursor compound, that is a compound of the formula (I) may be a synthetically-produced compound or a metabolically-produced compound.

A suitable pharmaceutically-acceptable pro-drug of a compound of the invention is one that is based on reasonable medical judgement as being suitable for administration to the human or animal body without undesirable pharmacological activities and without undue toxicity.

Various forms of pro-drug have been described, for example in the following documents:—
  a) *Methods in Enzymology*, Vol. 42, p. 309-396, edited by K. Widder, et al. (Academic Press, 1985);
  b) Design of Pro-drugs, edited by H. Bundgaard, (Elsevier, 1985);
  c) A Textbook of Drug Design and Development, edited by Krogsgaard-Larsen and H. Bundgaard, Chapter 5 "Design and Application of Pro-drugs", by H. Bundgaard p. 113-191 (1991);

d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the formula I that possesses a carboxy group is, for example, an in-vivo-cleavable ester thereof. An in-vivo-cleavable ester of a compound of the invention containing a carboxy group is, for example, a pharmaceutically-acceptable ester which is cleaved in the human or animal body to produce the parent acid. Suitable pharmaceutically-acceptable esters for carboxy include $C_{1-6}$ alkyl esters such as methyl, ethyl and tert-butyl, $C_{1-6}$ alkoxymethyl esters such as methoxymethyl esters, $C_{1-6}$ alkanoyloxymethyl esters such as pivaloyloxymethyl esters, 3-phthalidyl esters, $C_{3-8}$ cycloalkylcarbonyloxy-$C_{1-6}$ alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$ alkoxycarbonyloxy-$C_{1-6}$ alkyl esters such as methoxycarbonyloxymethyl and 1-methoxycarbonyloxyethyl esters.

A suitable pharmaceutically-acceptable pro-drug of a compound of the invention that possesses a hydroxy group is, for example, an in-vivo-cleavable ester or ether thereof. An in-vivo-cleavable ester or ether of a compound of the invention containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include $C_{1-10}$ alkanoyl groups such as acetyl, benzoyl, phenylacetyl and substituted benzoyl and phenylacetyl groups, $C_{1-10}$ alkoxycarbonyl groups such as ethoxycarbonyl, N,N—($C_{1-6}$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$ alkyl)piperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the invention that possesses a carboxy group is, for example, an in-vivo-cleavable amide thereof, for example an amide formed with an amine such as ammonia, a $C_{1-4}$ alkylamine such as methylamine, a ($C_{1-4}$ alkyl)$_2$amine such as dimethylamine, N-ethyl-N-methylamine or diethylamine, a $C_{1-4}$ alkoxy-$C_{2-4}$ alkylamine such as 2-methoxyethylamine, a phenyl-$C_{1-4}$ alkylamine such as benzylamine and amino acids such as glycine or an ester thereof.

A suitable pharmaceutically-acceptable pro-drug of a compound of the invention that possesses an amino group is, for example, an in-vivo-cleavable amide or carbamate derivative thereof. Suitable pharmaceutically-acceptable amides from an amino group include, for example an amide formed with $C_{1-10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$ alkyl)piperazin-1-ylmethyl. Suitable pharmaceutically-acceptable carbamates from an amino group include, for example acyloxyalkoxycarbonyl and benzyloxycarbonyl groups.

Compounds

The following paragraphs are applicable to the compounds of the invention.

In certain embodiments the compound of formula (I) is a compound according to formula (II), or a pharmaceutically acceptable salt thereof:

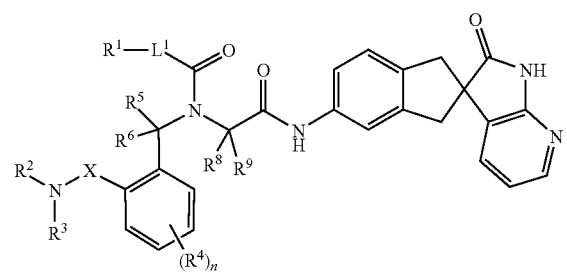

(II)

In certain embodiments the compound of formula (I) is a compound according to formula (III), or a pharmaceutically acceptable salt thereof:

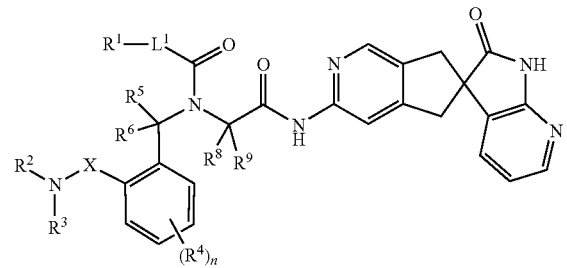

(III)

In certain embodiments the compound of formula (I) is a compound according to formula (IV), or a pharmaceutically acceptable salt thereof:

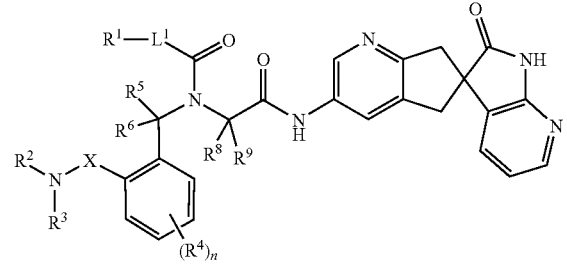

(IV)

In certain embodiments the compound of formula (I) is a compound according to formula (V), or a pharmaceutically acceptable salt thereof:

(V)

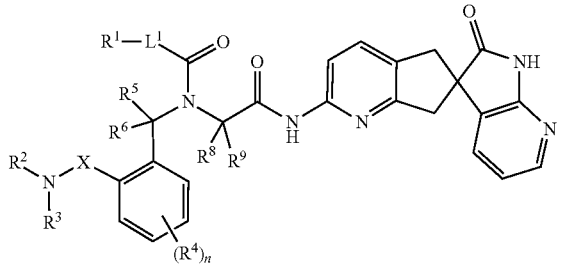

In certain embodiments the compound of formula (I) is a compound according to formula (VI), or a pharmaceutically acceptable salt thereof:

(VI)

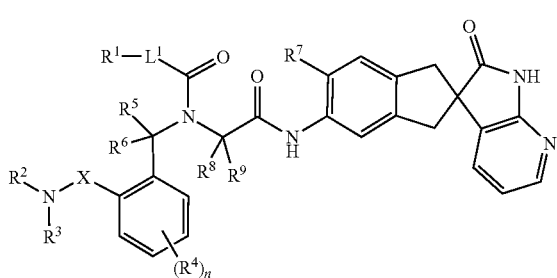

wherein $R^7$ has any of the values defined herein, provided that $R^7$ is not H. For example, $R^7$ is selected from: halo, $C_{1-4}$ alkyl and $C_{1-4}$ haloalkyl, for example $R^7$ is selected from: fluoro, methyl, ethyl or $CF_3$.

In certain embodiments in the compounds of formulae (I), (II), (III), (IV), (V) or (VI) $L^1$ is selected form a bond and —O—.

In certain embodiments in the compounds of formulae (I), (II), (III), (IV), (V) or (VI) $L^1$ is —N($R^{10}$)—.

In certain embodiments in the compounds of formulae (I), (II), (III), (IV), (V) or (VI) $L^1$ is selected from: —NH—, —N($C_{1-4}$ alkyl)-, —N(OH)— and —N(—O$C_{1-4}$ alkyl)-.

In certain embodiments in the compounds of formulae (I), (II), (III), (IV), (V) or (VI) $L^1$ is selected from: —NH— and —N($C_{1-4}$ alkyl)-.

In certain embodiments in the compounds of formulae (I), (II), (III), (IV), (V) or (VI) $L^1$ is —NH—.

In certain embodiments in the compounds of formulae (I), (II), (III), (IV), (V) or (VI) $L^1$ is —O—.

In certain embodiments in the compounds of formulae (I), (II), (III), (IV), (V) or (VI) $L^1$ is a bond.

In certain embodiments the compound of formula (I) is a compound of the formula (VII), or a pharmaceutically acceptable salt thereof:

(VII)

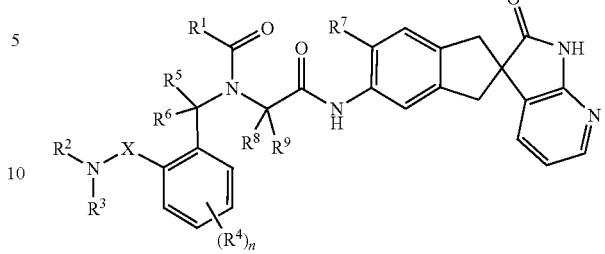

In certain embodiments in the compounds of formulae (I) or (VII) $R^7$ is selected from: H, halo, $C_{1-4}$ alkyl and $C_{1-4}$ haloalkyl. In certain embodiments $R^7$ is selected from halo, $C_{1-6}$ alkyl and $C_{1-6}$ haloalkyl. In certain embodiments $R^7$ is selected from: halo, $C_{1-4}$ alkyl and $C_{1-4}$ haloalkyl, for example $R^7$ is selected from: H, fluoro, methyl, ethyl or $CF_3$. In certain embodiments $R^7$ is F, methyl, ethyl or $CF_3$. In certain embodiments $R^7$ is selected from: halo and $C_{1-4}$ alkyl. In certain embodiments $R^7$ is selected from: H and $C_{1-4}$ alkyl. In certain embodiments $R^7$ is H. In certain embodiments $R^7$ is $C_{1-4}$ alkyl, for example methyl. In certain embodiments $R^7$ is halo, for example fluoro.

Particular compounds of the invention include, for example, compounds of formulae (I), (II), (III), (IV), (V), (VI) or (VII) or a pharmaceutically acceptable salt thereof, wherein, unless otherwise stated, each of $R^1$, $R^2$, $R^3$, $R^4$, $R^5$, $R^6$, $R^7$, $R^8$, $R^9$, $X_1$, $X_2$, $X_3$, $L^1$ and n has any of the meanings defined hereinbefore or in any of paragraphs (1) to (153) hereinafter:—

1. $R^8$ and $R^9$ are independently selected from H, $C_{1-4}$ alkyl, $C_{1-4}$ haloalkyl, —$C_{1-4}$ alkyl-$OR^A$, —$C_{1-4}$ alkyl-$NR^{A5}R^{B5}$ and —$C_{1-4}$ alkyl-$S(O)_xR^{A5}$, wherein x is 0, 1 or 2 and $R^{A5}$ and $R^{B5}$ are each independently selected from H and $C_{1-4}$ alkyl;
   or $R^8$ and $R^9$ together with the carbon to which they are attached form a $C_{3-6}$ cycloalkyl or 4 to 6 membered heterocyclyl, which heterocyclyl contains 1 or 2 heteroatoms selected from O, S and N.

2. $R^8$ and $R^9$ are independently selected from H, $C_{1-4}$ alkyl, $C_{1-4}$ haloalkyl, —$C_{1-4}$ alkyl-$OR^{A5}$, —$C_{1-4}$ alkyl-$NR^{A5}R^{B5}$ and —$C_{1-4}$ alkyl-$SR^{A5}$, wherein $R^{A5}$ is selected from H, methyl and ethyl;
   or $R^8$ and $R^9$ together with the carbon to which they are attached form a $C_{3-6}$ cycloalkyl or 4 to 6 membered heterocyclyl, which heterocyclyl contains 1 heteroatom selected from O, S and N.

3. $R^8$ and $R^9$ are independently selected from H, $C_{1-4}$ alkyl, —$C_{1-4}$ alkyl-$OR^{A5}$, $C_{1-4}$ alkyl-$NR^{A5}R^{B5}$ and —$C_{1-4}$ alkyl-$SR^{A5}$, wherein $R^{A5}$ and $R^{B5}$ are each independently selected from H, methyl and ethyl;
   or $R^8$ and $R^9$ together with the carbon to which they are attached form cyclopropyl, cyclobutyl or oxetanyl.

4. $R^8$ and $R^9$ are independently selected from H and $C_{1-3}$ alkyl, or
   $R^8$ and $R^9$ together with the carbon to which they are attached form cyclopropyl, cyclobutyl or oxetanyl.

5. $R^8$ is H and $R^9$ is selected from $C_{1-4}$ alkyl, $C_{1-4}$ haloalkyl, —$C_{1-4}$ alkyl-$OR^{A5}$, —$C_{1-4}$ alkyl-$NR^{A5}R^{B5}$ and —$C_{1-4}$ alkyl-$S(O)_xR^{A5}$, wherein x is 0, 1 or 2 and $R^{A5}$ and $R^B$ are each independently selected from H and $C_{1-4}$ alkyl;
   or $R^8$ and $R^9$ together with the carbon to which they are attached form a $C_{3-6}$ cycloalkyl or 4 to 6 membered heterocyclyl, which heterocyclyl contains 1 or 2 heteroatoms selected from O, S and N.
6. $R^8$ is H and $R^9$ is selected from H, $C_{1-4}$ alkyl, $C_{1-4}$ haloalkyl, —$C_{1-4}$ alkyl-$OR^{A5}$ and —$C_{1-4}$ alkyl-$SR^A$, wherein $R^{A5}$ is selected from H, methyl and ethyl;
or $R^8$ and $R^9$ together with the carbon to which they are attached form a $C_{3-6}$ cycloalkyl or 4 to 6 membered heterocyclyl, which heterocyclyl contains 1 or 2 heteroatoms selected from O, S and N.
7. $R^8$ is H and $R^9$ is selected from H and $C_{1-3}$ alkyl;
or $R^8$ and $R^9$ together with the carbon to which they are attached form cyclopropyl, cyclobutyl or oxetanyl.
8. $R^8$ is H and $R^9$ is $C_{1-3}$ alkyl, for example methyl.
9. $R^8$ and $R^9$ together with the carbon to which they are attached form a $C_{3-6}$ cycloalkyl, for example cyclopropyl or cyclobutyl.
10. $R^8$ and $R^9$ together with the carbon to which they are attached form a 4 or 5 membered heterocyclyl, which heterocyclyl contains 1 heteroatoms selected from 0, S and N, for example oxetanyl.
11. $R^8$ and $R^9$ are both $C_{1-4}$ alkyl, for example $R^8$ and $R^9$ are both methyl.
12. $R^8$ and $R^1$ are both H.
13. $R^5$ and R are independently selected from H, $C_{1-4}$ alkyl, $C_{1-4}$ haloalkyl, —$C_{1-4}$ alkyl-$OR^{A5}$, —$C_{1-4}$ alkyl-$NR^{A5}R^{B5}$ and —$C_{1-4}$ alkyl-S(O) $R^{A5}$, wherein x is 0, 1 or 2 and $R^{A5}$ and $R^{B5}$ are each independently selected from H and $C_{1-4}$ alkyl;
or $R^5$ and $R^6$ together with the carbon to which they are attached form a $C_{3-6}$ cycloalkyl or 4 to 6 membered heterocyclyl, which heterocyclyl contains 1 or 2 heteroatoms selected from O, S and N.
14. $R^5$ and $R^6$ are independently selected from H, $C_{1-4}$ alkyl and $C_{1-4}$ haloalkyl;
or $R^5$ and $R^6$ together with the carbon to which they are attached form cyclopropyl, cyclobutyl or oxetanyl.
15. $R^5$ and $R^6$ are independently selected from H and $C_{1-3}$ alkyl;
or $R^5$ and $R^6$ together with the carbon to which they are attached form cyclopropyl, cyclobutyl or oxetanyl.
16. $R^5$ is H and $R^6$ is selected from $C_{1-4}$ alkyl and $C_{1-4}$ haloalkyl;
or $R^5$ and $R^6$ together with the carbon to which they are attached form a $C_{3-6}$ cycloalkyl or 4 to 6 membered heterocyclyl, which heterocyclyl contains 1 or 2 heteroatoms selected from O, S and N.
17. $R^5$ is H and $R^6$ is selected from H and $C_{1-3}$ alkyl;
or $R^5$ and $R^6$ together with the carbon to which they are attached form a $C_{3-5}$ cycloalkyl or oxetanyl.
18. $R^5$ is H and $R^6$ is selected from H and $C_{1-3}$ alkyl, or $R^5$ and $R^6$ together with the carbon to which they are attached form cyclopropyl.
19. $R^5$ is H and $R^6$ is $C_{1-3}$ alkyl, for example $R^5$ is H and $R^6$ is methyl.
20. $R^5$ and $R^6$ are both $C_{1-3}$ alkyl, for example $R^5$ and $R^6$ are both methyl.
21. $R^5$ and $R^6$ together with the carbon to which they are attached form a $C_{3-6}$ cycloalkyl, for example cyclopropyl or cyclobutyl.
22. $R^5$ and $R^6$ together with the carbon to which they are attached form oxetanyl.
23. $R^5$ and $R^6$ are both H.
24. $R^4$ is independently selected from: halo, $C_{1-4}$ alkyl, $C_{1-4}$ haloalkyl, —$OR^{A4}$, —$NR^{A4}R^{B4}$, —$S(O)_xR^{A4}$, wherein x is 0, 1 or 2, and —CN.
25. $R^4$ is independently selected from: $C_{1-4}$ alkyl, —$OR^{A4}$ and —$NR^{A4}R^{B4}$.
26. $R^4$ is independently selected from: halo, $C_{1-4}$ alkyl, $C_{1-4}$ haloalkyl, —$OR^{A4}$, —$NR^{A4}R^{B4}$, —$S(O)_xR^{A4}$, wherein x is 0, 1 or 2, and —CN; and n is 1 or 2.
27. $R^4$ is independently selected from: halo, $C_{1-4}$ alkyl, $C_{1-4}$ haloalkyl, —$OR^{A4}$ and —$NR^{A4}R^{B4}$; and n is 1 or 2.
28. $R^4$ is independently selected from: halo, $C_{1-4}$ alkyl, $C_{1-4}$ haloalkyl, hydroxy, methoxy, ethoxy, amino, methylamino, ethylamino and dimethylamino; and n is 1 or 2.
29. $R^4$ is independently selected from: halo, $C_{1-4}$ alkyl and $C_{1-4}$ haloalkyl; and n is 1 or 2.
30. $R^4$ is independently selected from: $C_{1-4}$ alkyl and $C_{1-4}$ haloalkyl; and n is 1 or 2.
31. $R^4$ is independently selected from: $C_{1-4}$ alkyl and halo (e.g. fluoro); and n is 1 or 2.
32. $R^4$ is independently selected from: $C_{1-4}$ alkyl; and n is 1 or 2.
33. $R^4$ is independently halo, for example fluoro; and n is 1 or 2.
34. $R^4$ is fluoro and n is 1.
35. n is 0.
36. $R^2$ and $R^3$ are each independently selected from: H, —C(=NH)NH$_2$, —C(=NR$^{A9}$)NH$_2$, —C(=NH)NHR$^{A9}$, —C(=NH)N(R$^{A9}$)$_2$, —C(=NR$^{A9}$)NHR$^{A9}$, —C(=NR$^{A9}$)N(R$^{A9}$)$_2$, —C(=NH)R$^{A7}$, —C(=NR$^{A9}$)R$^{A7}$, —C(=NCN)NH$_2$, —C(=NCN)NHR$^{A9}$, —C(=NCN)N(R$^9$)$_2$, $C_{1-4}$ alkyl, $C_{2-6}$ alkenyl, $C_{2-6}$ alkynyl, $C_{1-4}$ haloalkyl, —$OR^{A10}$, $C_{3-8}$ cycloalkyl, $C_{3-8}$ cycloalkyl-$C_{1-3}$ alkyl-, 4 to 7 membered heterocyclyl, 4 to 7 membered heterocyclyl-$C_{1-3}$ alkyl-, phenyl-$C_{1-3}$ alkyl-, 5 or 6 membered heteroaryl-$C_{1-3}$ alkyl-, $C_{2-6}$ alkyl substituted by —$NR^{11}R^{12}$ and $C_{2-6}$ alkyl substituted by —$OR^{13}$, wherein $R^{11}$, $R^{12}$ and $R^{13}$ are independently selected from H, $C_{1-4}$ alkyl and $C_{1-4}$ haloalkyl, or $R^{11}$ and $R^{12}$ together with the nitrogen to which they are attached form a 4 to 6 membered heterocyclyl,
and wherein each $R^{A9}$ is independently $C_{1-6}$ alkyl;
and wherein $R^2$ and $R^3$ are independently optionally further substituted by one or more substituents independently selected from: halo, $C_{1-4}$ alkyl, $C_{1-4}$ haloalkyl, $C_{3-6}$ cycloalkyl, —$OR^{A2}$, —$NR^{A2}R^{B2}$, —$S(O)_xR^{A2}$, wherein x is 0, 1 or 2, —C(O)$R^{A2}$, —OC(O)$R^{A2}$, —C(O)$OR^{A2}$, —$NR^{A2}C(O)R^{B2}$, —C(O)$NR^{A2}R^{B2}$, —$NR^{A2}SO_2R^{B2}$, —$SO_2NR^{A2}R^{B2}$, =O and —CN; or $R^2$ and $R^3$ together with the nitrogen atom to which they are attached form a 4 to 7 membered heterocyclyl, wherein said 4 to 7 membered heterocyclyl formed by $R^2$ and $R^3$ is optionally further substituted by one or more substituents selected from halo, $C_{1-4}$ alkyl, $C_{1-4}$ haloalkyl, $C_{3-6}$ cycloalkyl, —$OR^{A3}$, —$NR^{A3}R^{B3}$, —$S(O)_xR^{A3}$, wherein x is 0, 1 or 2, =O, —CN, $C_{2-6}$ alkyl substituted by —$NR^{A3}R^{B3}$ and $C_{2-6}$ alkyl substituted by —$OR^{A3}$.
37. $R^2$ and $R^3$ are each independently selected from: H, $C_{1-6}$ alkyl, $C_{2-6}$ alkenyl, $C_{2-6}$ alkynyl, $C_{1-6}$ haloalkyl, $C_{3-8}$ cycloalkyl, $C_{3-8}$ cycloalkyl-$C_{1-3}$ alkyl-, 4 to 7 membered heterocyclyl, 4 to 7 membered heterocyclyl-$C_{1-3}$ alkyl-, phenyl-$C_{1-3}$ alkyl-, 5 or 6 membered heteroaryl-$C_{1-3}$ alkyl-, $C_{2-6}$ alkyl substituted by —$NR^{11}R^{12}$ and $C_{2-6}$ alkyl substituted by —$OR^{13}$, wherein $R^{11}$, $R^{12}$ and $R^{13}$ are independently selected from H, $C_{1-4}$ alkyl and $C_{1-4}$ haloalkyl, or $R^{11}$ and $R^{12}$ together with the nitrogen to which they are attached form a 4 to 6 membered heterocyclyl;
and wherein $R^2$ and $R^3$ are independently optionally further substituted by one or more substituents independently selected from: halo, $C_{1-4}$ alkyl, $C_{1-4}$ haloalkyl, $C_{3-6}$ cycloalkyl, —$OR^{A2}$, —$NR^{A2}R^{B2}$, —$S(O)_xR^{A2}$, wherein x is 0, 1 or 2, —C(O)$R^{A2}$, —OC(O)$R^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, =O and —CN; or R$^2$ and R$^3$ together with the nitrogen atom to which they are attached form a 4 to 7 membered heterocyclyl, wherein said 4 to 7 membered heterocyclyl formed by R$^2$ and R$^3$ is optionally further substituted by one or more substituents selected from halo, C$_{1-4}$ alkyl, C$_{1-4}$ haloalkyl, C$_{3-6}$ cycloalkyl, —OR$^{A3}$, —NR$^{A3}$R$^{B3}$, —S(O)$_x$R$^{A3}$, wherein x is 0, 1 or 2, =O, —CN, C$_{2-6}$ alkyl substituted by —NR$^{A3}$R$^{B3}$ and C$_{2-6}$ alkyl substituted by —OR$^{A3}$.

38. R$^2$ and R$^3$ are each independently selected from: H, C$_{1-6}$ alkyl, C$_{2-6}$ alkenyl, C$_{2-6}$ alkynyl, C$_{1-6}$ haloalkyl, C$_{3-6}$ cycloalkyl, C$_{3-6}$ cycloalkyl-C$_{1-3}$ alkyl-, 4 to 6 membered heterocyclyl, 4 to 6 membered heterocyclyl-C$_{1-3}$ alkyl-, phenyl-C$_{1-3}$ alkyl-, 5 or 6 membered heteroaryl-C$_{1-3}$ alkyl-, C$_{2-6}$ alkyl substituted by —NR$^{11}$R$^{12}$ and C$_{2-6}$ alkyl substituted by —OR$^{13}$, wherein R$^{11}$, R$^{12}$ and R$^{13}$ are independently selected from H, C$_{1-4}$ alkyl and C$_{1-4}$ haloalkyl, or R$^{11}$ and R$^{12}$ together with the nitrogen to which they are attached form a 4 to 6 membered heterocyclyl; and wherein R$^2$ and R$^3$ are independently optionally further substituted by one or more substituents independently selected from: halo, C$_{1-4}$ alkyl, C$_{1-4}$ haloalkyl, C$_{3-6}$ cycloalkyl, —OR$^{A2}$, —NR$^{A2}$R$^{B2}$, —S(O)$_x$R$^{A2}$, wherein x is 0, 1 or 2, —C(O)R$^{A2}$, —OC(O)R$^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, =O and —CN; or R$^2$ and R$^3$ together with the nitrogen atom to which they are attached form a 4 to 7 membered saturated heterocyclyl containing one ring nitrogen atom and optionally one additional ring nitrogen atom, and wherein said heterocyclyl is optionally substituted by one or more substituents selected from halo, C$_{1-4}$ alkyl, C$_{1-4}$ haloalkyl, C$_{3-6}$ cycloalkyl, —OR$^{A3}$, —NR$^{A3}$R$^{B3}$, —S(O)$_x$R$^{A3}$, wherein x is 0, 1 or 2, =O, —CN, C$_{2-6}$ alkyl substituted by —NR$^{A3}$R$^{B3}$ and C$_{2-6}$ alkyl substituted by —OR$^{A3}$.

39. R$^2$ and R$^3$ are each independently selected from: H, —C(=NH)NH$_2$, —C(=NR$^{A9}$)NH$_2$, —C(=NH)NHR$^{A9}$, —C(=NR$^{A9}$)NHR$^{A9}$, —C(=NH)R$^{A7}$, —C(=NR$^{A9}$)R$^{A7}$, —C(=NCN)NH$_2$, —C(=NCN)NHR$^{A9}$, C$_{1-6}$ alkyl, C$_{2-6}$ alkenyl, C$_{2-6}$ alkynyl, C$_{1-6}$ haloalkyl, C$_{3-6}$ cycloalkyl, C$_{3-6}$ cycloalkyl-C$_{1-3}$ alkyl-, 4 to 6 membered heterocyclyl, 4 to 6 membered heterocyclyl-C$_{1-3}$ alkyl-, phenyl-C$_{1-3}$ alkyl-, 5 or 6 membered heteroaryl-C$_{1-3}$ alkyl-, C$_2$. e alkyl substituted by —NR$^{11}$R$^{12}$ and C$_{2-6}$ alkyl substituted by —OR$^{13}$, wherein R$^{11}$, R$^{12}$ and R$^{13}$ are independently selected from H, C$_{1-4}$ alkyl and C$_{1-4}$ haloalkyl, or R$^{11}$ and R$^{12}$ together with the nitrogen to which they are attached form a 4 to 6 membered heterocyclyl, and wherein R$^{A7}$ and each R$^{A9}$ is independently C$_{1-4}$ alkyl; and wherein R$^2$ and R$^3$ are independently optionally further substituted by one or more substituents independently selected from: halo, C$_{1-4}$ alkyl, C$_{1-4}$ haloalkyl, —OR$^2$, —NR$^{A2}$R$^{B2}$, —S(O)$_x$R$^{A2}$, wherein x is 0, 1 or 2, —C(O)R$^{A2}$, —OC(O)R$^{A2}$, —C(O)OR$^{A2}$, —C(O)NR$^{A2}$R$^{B2}$, —SO$_2$NR$^{A2}$R$^{B2}$, =O and —CN.

40. R$^2$ and R$^3$ are each independently selected from: H, C$_{1-6}$ alkyl, C$_{2-6}$ alkenyl, C$_{2-6}$ alkynyl, C$_{1-6}$ haloalkyl, C$_{3-6}$ cycloalkyl, C$_{3-6}$ cycloalkyl-C$_{1-3}$ alkyl-, 4 to 6 membered heterocyclyl, 4 to 6 membered heterocyclyl-C$_{1-3}$ alkyl-, phenyl-C$_{1-3}$ alkyl-, 5 or 6 membered heteroaryl-C$_{1-3}$ alkyl-, C$_{2-6}$ alkyl substituted by —NR$^{11}$R$^{12}$ and C$_{2-6}$ alkyl substituted by —OR$^{13}$, wherein R$^{11}$, R$^{12}$ and R$^{13}$ are independently selected from H, C$_{1-4}$ alkyl and C$_{1-4}$ haloalkyl, or R$^{11}$ and R$^{12}$ together with the nitrogen to which they are attached form a 4 to 6 membered heterocyclyl; and wherein R$^2$ and R$^3$ are independently optionally further substituted by one or more substituents independently selected from: halo, C$_{1-4}$ alkyl, C$_{1-4}$ haloalkyl, —OR$^2$, —NR$^{A2}$R$^{B2}$, —S(O)$_x$R$^{A2}$, wherein x is 0, 1 or 2, —C(O)R$^{A2}$, —OC(O)R$^{A2}$, —C(O)OR$^{A2}$, —C(O)NR$^{A2}$R$^{B2}$, —SO$_2$NR$^{A2}$R$^{B2}$, =O and —CN.

41. R$^2$ and R$^3$ are each independently selected from: H, C$_{1-6}$ alkyl, C$_{2-6}$ alkenyl, C$_{1-6}$ haloalkyl, C$_{3-6}$ cycloalkyl, C$_{3-6}$ cycloalkyl-C$_{1-3}$ alkyl-, phenyl-C$_{1-3}$ alkyl-, imidazolyl-C$_{1-3}$ alkyl-, C$_{2-6}$ alkyl substituted by —NR$^{11}$R$^{12}$ and C$_{2-6}$ alkyl substituted by —OR$^{13}$, wherein R$^{11}$, R$^{12}$ and R$^{13}$ are independently selected from H, C$_{1-4}$ alkyl and C$_{1-4}$ haloalkyl, or R$^{11}$ and R$^{12}$ together with the nitrogen to which they are attached form a 4 to 6 membered heterocyclyl; and wherein R$^2$ and R$^3$ are independently optionally further substituted by one or more substituents independently selected from: halo, —CN, =O, C$_{1-4}$ alkyl, C$_{1-4}$ haloalkyl, —OR$^{A2}$ and —NR$^{A2}$R$^{B2}$.

42. R$^2$ and R$^3$ are each independently selected from: H, C$_{1-6}$ alkyl, C$_{1-6}$ haloalkyl, C$_{3-6}$ cycloalkyl, C$_{3-6}$ cycloalkyl-C$_{1-3}$ alkyl-, C$_{2-6}$ alkyl substituted by —NR$^{11}$R$^{12}$ and C$_{2-6}$ alkyl substituted by —OR$^{13}$, wherein R$^{11}$, R$^{12}$ and R$^{13}$ are independently selected from H, C$_{1-4}$ alkyl and C$_{1-4}$ haloalkyl, or R$^{11}$ and R$^{12}$ together with the nitrogen to which they are attached form a 4 to 6 membered heterocyclyl, wherein said heterocyclyl comprises one ring nitrogen and optionally further comprises one additional ring heteroatom selected from O, S and N (for example azetidinyl, pyrrolidinyl, piperidinyl, piperazinyl, morpholinyl or thiomorpholinyl); and wherein R$^2$ and R$^3$ are independently optionally further substituted by one or more substituents independently selected from: halo, —CN, =O, C$_{1-4}$ alkyl, C$_{1-4}$ haloalkyl, —OR$^{A2}$ and —NR$^{A2}$R$^{B2}$.

43. R$^2$ and R$^3$ are each independently selected from: H, —C(=NH)NH$_2$, —C(=NH)R$^{A7}$, —C(=NCN)NH$_2$, C$_{1-4}$ alkyl, C$_{1-4}$ fluoroalkyl, C$_{3-6}$ cycloalkyl, C$_{3-6}$ cycloalkyl-C$_{1-3}$ alkyl-, C$_{2-3}$ alkyl substituted by —NR$^{11}$R$^{12}$ and C$_{2-3}$ alkyl substituted by —OR$^{13}$, wherein R$^{11}$, R$^{12}$ and R$^{13}$ are independently selected from H, C$_{1-4}$ alkyl and C$_{1-4}$ haloalkyl and R$^{A7}$ is C$_{1-4}$ alkyl; or R$^2$ and R$^3$ together with the nitrogen atom to which they are attached form a heterocyclyl selected from azetidinyl, pyrrolidinyl, piperidinyl, piperazinyl, homopiperidinyl and homopiperazinyl, wherein the heterocyclyl formed by R$^2$ and R$^3$ is optionally substituted by one or more (for example 1, 2 or 3) substituents independently selected from: halo, =O, C$_{1-4}$ alkyl, C$_{1-4}$ haloalkyl and —NR$^{A2}$R$^{B2}$.

44. R$^2$ and R$^3$ are each independently selected from: H, C$_{1-4}$ alkyl, C$_{1-4}$ fluoroalkyl, C$_{3-6}$ cycloalkyl, C$_{3-6}$ cycloalkyl-C$_{1-3}$ alkyl-, C$_{2-3}$ alkyl substituted by —NR$^{11}$R$^{12}$ and C$_{2-3}$ alkyl substituted by —OR$^{13}$, wherein R$^{11}$, R$^{12}$ and R$^{13}$ are independently selected from H, C$_{1-4}$ alkyl and C$_{1-4}$ haloalkyl; or R$^2$ and R$^3$ together with the nitrogen atom to which they are attached form a heterocyclyl selected from azetidinyl, pyrrolidinyl, piperidinyl, piperazinyl, homopiperidinyl and homopiperazinyl, wherein the heterocyclyl formed by R$^2$ and R$^3$ is optionally substituted by one or more (for example 1, 2 or 3) substituents independently selected from: halo, =O, C$_{1-4}$ alkyl, C$_{1-4}$ haloalkyl and —NR$^{A2}$R$^{B2}$.

45. R$^2$ and R$^3$ are each independently selected from: H, C$_{1-4}$ alkyl, C$_{1-4}$ fluoroalkyl, C$_{3-6}$ cycloalkyl, C$_{3-6}$ cycloalkyl- C$_{1-3}$ alkyl-, C$_{2-3}$ alkyl substituted by —NR$^{11}$R$^{12}$ and C$_{2-3}$ alkyl substituted by —OR$^{13}$, wherein R$^{11}$, R$^{12}$ and R$^{13}$ are independently selected from H and C$_{1-4}$ alkyl.

46. R$^2$ and R$^3$ are each independently selected from: H, C$_{1-4}$ alkyl, C$_{2-4}$ alkenyl, C$_{1-4}$ haloalkyl, cyclopropyl, cyclobutyl, cyclopropyl-C$_{1-2}$ alkyl-, cyclobutyl-C$_{1-2}$ alkyl-, 2-hydroxyethyl, 2-methoxyethyl, 2-aminoethyl, 2-(methylamino)ethyl, 2-(dimethylamino)ethyl, 2-(ethylamino)ethyl, 2-(diethylamino)ethyl, 3-hydroxypropyl, 3-methoxypropyl, 3-aminopropyl, 3-(methylamino)propyl, 3-(dimethylamino)propyl, 3-(ethylamino)propyl, 3-(diethylamino)propyl, imidazolylmethyl-, imidazolylethyl-, benzyl and 2-phenylethyl;

or R$^2$ and R$^3$ together with the nitrogen atom to which they are attached form a heterocyclyl selected from azetidinyl, pyrrolidinyl, piperidinyl and piperazinyl, wherein the heterocyclyl formed by R$^2$ and R$^3$ is optionally substituted by one or more (for example 1, 2 or 3) substituents independently selected from: halo and C$_{1-4}$ alkyl.

47. R$^2$ and R$^3$ are each independently selected from: H, C$_{1-3}$ alkyl, C$_{1-3}$ fluoroalkyl, cyclopropyl, cyclobutyl, cyclopropyl-C$_{1-2}$ alkyl-, cyclobutyl-C$_{1-2}$ alkyl-, 2-hydroxyethyl, 2-methoxyethyl, 2-aminoethyl, 2-(methylamino)ethyl, 2-(dimethylamino)ethyl, 3-aminopropyl, 3-(methylamino)propyl and 3-(dimethylamino)propyl.

48. R$^2$ and R$^3$ together with the nitrogen atom to which they are attached form a saturated or partially saturated 4 to 7 membered heterocyclyl containing one ring nitrogen and optionally one or two additional ring heteroatoms selected from O, S and N, which heterocyclyl is optionally substituted by one or more (for example 1, 2 or 3) substituents independently selected from: halo, =O, C$_{1-4}$ alkyl, C$_{1-4}$ haloalkyl and —NR$^{A2}$R$^{B2}$.

49. R$^2$ and R$^3$ together with the nitrogen atom to which they are attached form a saturated or partially saturated 4 to 7 membered heterocyclyl containing one or two ring nitrogen atoms, which heterocyclyl is optionally substituted by one or more (for example 1, 2 or 3) substituents independently selected from: halo, =O, C$_{1-4}$ alkyl, C$_{1-4}$ haloalkyl and —NR$^{A2}$R$^{B2}$.

50. R$^2$ and R$^3$ together with the nitrogen atom to which they are attached form a saturated 4 to 6 membered heterocyclyl containing one or two ring nitrogen atoms, which heterocyclyl is optionally substituted by 1 or 2 substituents independently selected from: halo, and C$_{1-4}$ alkyl.

51. R$^2$ and R$^3$ together with the nitrogen atom to which they are attached form a heterocyclyl selected from azetidinyl, pyrrolidinyl, piperidinyl and piperazinyl, wherein the heterocyclyl formed by R$^2$ and R$^3$ is optionally substituted by one or more (for example 1, 2 or 3) substituents independently selected from: fluoro and C$_{1-4}$ alkyl.

52. R$^2$ and R$^3$ together with the nitrogen atom to which they are attached form a heterocyclyl selected from azetidinyl and pyrrolidinyl, wherein the heterocyclyl formed by R$^2$ and R$^3$ is optionally substituted by 1 substituent selected from: fluoro and C$_{1-3}$ alkyl.

53. R$^2$ and R$^3$ together with the nitrogen atom to which they are attached form an imidazolyl of the formula:

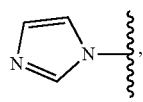

wherein the imidazolyl group is optionally substituted by one or two groups selected from: halo, C$_{1-4}$ alkyl and C$_{1-4}$ haloalkyl.

54. R$^2$ is H or C$_{1-4}$ alkyl and R$^3$ has any of the meaning set out in paragraphs 36 to 47.

55. R$^2$ is H.

56. R$^2$ and R$^3$ are both H.

57. R$^2$ is H or C$_{1-4}$ alkyl; and R$^3$ is selected from: H, —C(=NH)NH$_2$, —C(=NR$^{49}$)NH$_2$, —C(=NH)NHR$^{49}$, —C(=NH)N(R$^{49}$)$_2$, —C(=NR$^{49}$)NHR$^{49}$, —C(=NR$^{49}$)N(R$^{49}$)$_2$, —C(=NH)R$^{47}$, —C(=NR$^{49}$)R$^{47}$, —C(=NCN)NH$_2$, —C(=NCN)NHR$^{49}$, —C(=NCN)N(R$^{49}$)$_2$, C$_{1-4}$ alkyl, C$_{2-4}$ alkenyl, C$_{2-4}$ alkynyl, C$_{1-4}$ haloalkyl, —OR$^{41}$ 1, C$_{3-6}$ cycloalkyl, C$_{3-6}$ cycloalkyl-C$_{1-3}$ alkyl-, 4 to 7 membered heterocyclyl, 4 to 7 membered heterocyclyl-C$_{1-3}$ alkyl-, phenyl-C$_{1-3}$ alkyl-, 5 or 6 membered heteroaryl-C$_{1-3}$ alkyl-, C$_{2-4}$ alkyl substituted by —NR$^{11}$R$^{12}$ and C$_{2-4}$ alkyl substituted by —OR$^{13}$, wherein R$^{11}$, R$^{12}$ and R$^{13}$ are independently selected from: H, C$_{1-4}$ alkyl and C$_{1-4}$ haloalkyl, or R$^{11}$ and R$^{12}$ together with the nitrogen to which they are attached form a 4 to 6 membered heterocyclyl, and wherein each R$^{49}$ and R$^{47}$ is independently C$_{1-4}$ alkyl;
and wherein R$^3$ is optionally further substituted by one or more substituents (for example 1, 2 or 3) independently selected from: halo, C$_{1-4}$ alkyl, C$_{1-4}$ haloalkyl, C$_{3-6}$ cycloalkyl, —OR$^{A2}$, —NR$^{A2}$R$^{B2}$, —S(O)$_x$R$^{A2}$, wherein x is 0, 1 or 2, —C(O)R$^{A2}$, —OC(O)R$^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, =O and —CN.

58. R$^2$ is H and R$^3$ is selected from: H, C$_{1-4}$ alkyl, C$_{2-4}$ alkenyl, C$_{2-4}$ alkynyl, C$_{1-4}$ haloalkyl, C$_{3-6}$ cycloalkyl, C$_{3-6}$ cycloalkyl-C$_{1-3}$ alkyl-, 4 to 7 membered heterocyclyl, 4 to 7 membered heterocyclyl-C$_{1-3}$ alkyl-, phenyl-C$_{1-3}$ alkyl-, 5 or 6 membered heteroaryl-C$_{1-3}$ alkyl-, C$_{2-4}$ alkyl substituted by —NR$^{11}$R$^{12}$ and C$_{2-4}$ alkyl substituted by —OR$^{13}$, wherein R$^{11}$, R$^{12}$ and R$^{13}$ are independently selected from: H, C$_{1-4}$ alkyl and C$_{1-4}$ haloalkyl, or R$^{11}$ and R$^{12}$ together with the nitrogen to which they are attached form a 4 to 6 membered heterocyclyl;

and wherein R$^3$ is optionally further substituted by one or more substituents (for example 1, 2 or 3) independently selected from: halo, C$_{1-4}$ alkyl, C$_{1-4}$ haloalkyl, C$_{3-6}$ cycloalkyl, —OR$^{A2}$, —NR$^{A2}$R$^{B2}$, —S(O)$_x$R$^{A2}$, wherein x is 0, 1 or 2, —C(O)R$^2$, —OC(O)R$^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, =O and —CN.

59. R$^2$ is H and R$^3$ is selected from: C$_{1-4}$ alkyl, C$_{1-4}$ haloalkyl, C34 cycloalkyl, C34 cycloalkyl-C$_{1-3}$ alkyl-, 4 to 7 membered heterocyclyl, 4 to 7 membered heterocyclyl-C$_{1-3}$ alkyl-, phenyl-C$_{1-3}$ alkyl-, 5 or 6 membered heteroaryl-C$_{1-3}$ alkyl-, C$_{2-4}$ alkyl substituted by —NR$^{11}$R$^{12}$ and C$_{2-4}$ alkyl substituted by —OR$^{13}$, wherein R$^{11}$, R$^{12}$ and R$^{13}$ are independently selected from: H, C$_{1-4}$ alkyl and C$_{1-4}$ haloalkyl, or R$^{11}$ and R$^{12}$ together with the nitrogen to which they are attached form a 4 to 6 membered heterocyclyl;

and wherein R$^3$ is optionally further substituted by one or more substituents (for example 1, 2 or 3) independently selected from: halo, C$_{1-4}$ alkyl, C$_{1-4}$ haloalkyl, C$_{3-6}$ cycloalkyl, —OR$^{A2}$, —NR$^{A2}$R$^{B2}$, —S(O)$_x$R$^{A2}$, wherein x is 0, 1 or 2, —C(O)R$^{A2}$, —OC(O)R$^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, =O and —CN.

60. R$^2$ is H or C$_{1-4}$ alkyl and R$^3$ is selected from —C(=NH)NH$_2$, —C(=NR$^{49}$)NH$_2$, —C(=NH)NHR$^{49}$, —C(=NH)N($R^{A9}$)$_2$, —C(=N$R^{A9}$)NH$R^{A9}$, —C(=N$R^{A9}$)N($R^{A9}$)$_2$, —C(=NH)$R^{A7}$, —C(=N$R^{A9}$)$R^{A7}$, —C(=NCN)NH$_2$, —C(=NCN)NH$R^{A9}$, —C(=NCN)N($R^{A9}$)$_2$; wherein $R^{A7}$ and each $R^{A9}$ are independently selected from $C_{1-4}$ alkyl.

61. $R^2$ is H and $R^3$ is selected from —C(=NH)NH$_2$, —C(=NH)$R^{A7}$ and —C(=NCN)NH$_2$, wherein $R^{A7}$ is $C_{1-4}$ alkyl.

62. $R^2$ is H and $R^3$ is selected from: $C_{1-4}$ alkyl, $C_{1-4}$ fluoroalkyl, $C_{3-6}$ cycloalkyl, $C_{3-6}$ cycloalkyl-$C_{1-3}$ alkyl-, $C_{2-3}$ alkyl substituted by —N$R^{11}R^{12}$ and $C_{2-3}$ alkyl substituted by —O$R^{13}$, wherein $R^{11}$, $R^{12}$ and $R^{13}$ are independently selected from: H, $C_{1-4}$ alkyl and $C_{1-4}$ haloalkyl.

63. $R^2$ is H and $R^3$ is selected from: $C_{1-3}$ alkyl, $C_{1-3}$ fluoroalkyl, cyclopropyl, cyclobutyl, cyclopropyl-$C_{1-2}$ alkyl-, cyclobutyl-$C_{1-2}$ alkyl-, 2-hydroxyethyl, 2-methoxyethyl, 2-aminoethyl, 2-(methylamino)ethyl, 2-(dimethylamino)ethyl, 3-aminopropyl, 3-(methylamino)propyl and 3-(dimethylamino)propyl.

64. $R^2$ is H and $R^3$ is selected from: H, methyl, ethyl, isopropyl, 2-fluoroethyl, 2-hydroxyethyl, 2-methoxyethyl and 2-aminoethyl.

65. $R^2$ is H and $R^3$ is selected from: H and $C_{1-3}$ alkyl.

66. $R^2$ is H and $R^3$ is methyl or ethyl.

67. $R^2$ is H and $R^3$ is methyl.

68. $R^2$ is H and $R^3$ is selected from: $C_{3-6}$ cycloalkyl and $C_{3-6}$ cycloalkyl-$C_{1-3}$ alkyl, for example $R^3$ is selected from: cyclopropyl, cyclobutyl, cyclopropylmethyl and cyclobutylmethyl.

69. $R^2$ and $R^3$ are both $C_{1-3}$ alkyl, for example $R^2$ and $R^3$ are independently methyl or ethyl.

70. $R^2$ is H and $R^3$ is selected from: methyl, ethyl, isopropyl, 2-fluoroethyl, 2-methoxyethyl, 2-hydroxyethyl, cyclopropyl and cyclobutyl, or
$R^2$ and $R^3$ are both methyl, or
$R^2$ and $R^3$ together with the nitrogen to which they are attached form a heterocyclyl selected from: azetidinyl, pyrrolidinyl, piperidinyl and piperazinyl, which heterocyclyl is optionally substituted by one or two fluoro substituents, for example, wherein the heterocyclyl is optionally substituted by one fluoro substituent.

71. $R^2$ is H or methyl and $R^3$ is selected from: methyl, ethyl, isopropyl, 2-fluoroethyl, 2-methoxyethyl, 2-hydroxyethyl, cyclopropyl and —C(=NH)NH$_2$;
or
$R^2$ and $R^3$ together with the nitrogen to which they are attached form a heterocyclyl selected from: azetidinyl, pyrrolidinyl, which heterocyclyl is optionally substituted by one fluoro substituent.

72. $R^2$ is H or methyl and $R^3$ is selected from: methyl, ethyl, isopropyl, and cyclopropyl;
or
$R^2$ and $R^3$ together with the nitrogen to which they are attached form a heterocyclyl selected from: azetidinyl and pyrrolidinyl.

73. $R^2$ and $R^3$ together with the nitrogen to which they are attached form a heterocyclyl selected from: azetidinyl and fluoroazetidinyl (e.g. $R^2$ and $R^3$ together with the nitrogen to which they are attached form azetidinyl or 3-fluoroazetidinyl).

74. —N$R^2R^3$ is selected from —NH$_2$, —NH(Me), —NH(Et), —N(Me)$_2$, —NH(cyclopropyl), —NH(CH$_2$CH$_2$F), —NH(CH$_2$CH$_2$OH), —NH(CH$_2$CH$_2$OMe), azetidin-1-yl and pyrrolidin-1-yl; for example —N$R^2R^3$ is selected from: —NH$_2$, —NH(Me) —NH(Et), —NH(CH$_2$CH$_2$F), —NH(cyclopropyl) —NH(cyclobutyl) and azetidin-1-yl, (e.g. —N$R^2R^3$ is selected from —NH(Me) and azetidin-1-yl).

75. —N$R^2R^3$ is —NH(Me).

76. n is 0 and $R^2$ and $R^3$ have any of the meanings set out in paragraphs 36 to 75.

77. n is 0 and —N$R^2R^3$ is selected from —NH$_2$, —NH(Me), —NH(Et), —N(Me)$_2$, —NH(cyclopropyl), —NH(CH$_2$CH$_2$F), —NH(CH$_2$CH$_2$OH), —NH(CH$_2$CH$_2$OMe), azetidin-1-yl and pyrrolidin-1-yl.

78. n is 0 and —N$R^2R^3$ is —NH(Me).

79. p is 1 or 2.

80. p is 1.

81. p is 0.

82. p is 1 and $R^2$ and $R^3$ have any of the meanings set out in paragraphs 36 to 75.

83. p is 1 and —N$R^2R^3$ is selected from —NH$_2$, —NH(Me), —NH(Et), —N(Me)$_2$, —NH(cyclopropyl), —NH(CH$_2$CH$_2$F), —NH(CH$_2$CH$_2$OH), —NH(CH$_2$CH$_2$OMe), azetidin-1-yl and pyrrolidin-1-yl.

84. p is 1 and —N$R^2R^3$ is selected from —NH$_2$, —NH(Me), —NHC(=NH)NH$_2$ and —NHC(=NCN)NH$_2$.

85. p is 1 and —N$R^2R^3$ is-NH(Me).

86. p is 0 and $R^2$ and $R^3$ have any of the meanings set out in paragraphs 36 to 75.

87. p is 0 and —N$R^2R^3$ is selected from —NH$_2$, —N(Me)H, —NHC(=NH)NH$_2$ and —NHC(=NCN)NH$_2$.

88. X is selected from: —CH$_2$—, —CH$_2$CH$_2$—, —CH$R^A$—, *—CH$_2$CH$R^A$—, *—CH$R^A$CH$_2$—, —C$R^AR^B$—, *—CH$_2$C$R^AR^B$—, *—C$R^AR^B$CH$_2$—, —C(=N$R^{A8}$)—, —C(=NO$R^{A8}$)—, *—C(=N$R^{A8}$)CH$_2$—, *—C(=NO$R^{A8}$)CH$_2$— and ;

wherein $R^A$ and $R^B$ are each independently $C_{1-3}$ alkyl;
$R^{A8}$ is H or $C_{1-4}$ alkyl; and
* shows the point of attachment to N$R^2R^3$.

89. X is selected from: —CH$_2$—, —CH$_2$CH$_2$—, —CH$R^A$*—CH$_2$CH$R^A$—, *—CH$R^A$CH$_2$—, —C$R^AR^B$—, *—CH$_2$C$R^AR^B$—, *—C$R^AR^B$CH$_2$—, and ;

wherein $R^A$ and $R^B$ are each independently $C_{1-3}$ alkyl; and
* shows the point of attachment to N$R^2R^3$.

90. X is selected from: —CH$_2$—, —CH(CH$_3$)—, —CH$_2$CH$_2$—, and .

91. X is selected from: —C(=NR$^{A8}$)— and —C(=NOR$^{A8}$)—, wherein R$^{A8}$ is H or C$_{1-4}$ alkyl (for example X is —C(=NH)—, —C(=NMe)- or —C(=NOH)—).

92. X is selected from: —CH$_2$—, —CH(CH$_3$)— and —CH$_2$CH$_2$-.

93. X is selected from: —CH$_2$— and —CH(CH$_3$)—.

94. X is —CH$_2$CH$_2$-.

95. X is —CH$_2$-.

96. X is selected from: —C(=NR$^{A8}$)— and —C(=NOR$^{A8}$)—, wherein R$^{A8}$ is H or C$_{1-4}$ alkyl; R$^2$ is H or C$_{1-4}$ alkyl; and R$^3$ is H, C$_{1-4}$ alkyl, —OH or —OC$_{1-4}$alkyl, (for example X is —C(=NH)—or —C(=NMe)-; R$^2$ is H or C$_{1-4}$ alkyl; and R$^3$ is H, C$_{1-4}$ alkyl or —OH).

97. The group

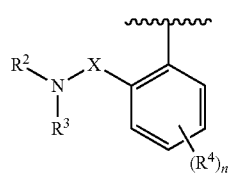

forms a group of the formula:

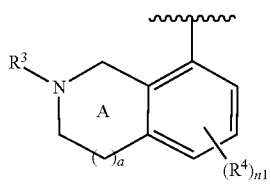

wherein a is an integer 0, 1 or 2;

n1 is an integer 0, 1, 2 or 3 and, when present, R$^4$ is located on the phenyl ring; and Ring A is optionally substituted by one or more (for example 1, 2 or 3) substituents selected from: halo, C$_{1-4}$ alkyl, C$_{1-4}$ haloalkyl and =O;

optionally R$^3$ is selected from: H, C$_{1-4}$ alkyl, C$_{2-4}$ alkenyl, C$_{1-4}$ fluoroalkyl, C34 cycloalkyl, C$_{3-6}$ cycloalkyl-C$_{1-3}$ alkyl-, C$_{2-3}$ alkyl substituted by —NR$^{11}$R$^{12}$ and C$_{2-3}$ alkyl substituted by —OR$^{13}$, wherein R$^{11}$, R$^{12}$ and R$^{13}$ are independently selected from: H, C$_{1-4}$ alkyl and C$_{1-4}$ haloalkyl; preferably R$^3$ is H or C$_{1-4}$ alkyl, more preferably R$^3$ is H;

optionally n1 is 1 and R$^4$ is halo, for example fluoro;

optionally n1 is 0.

98. The group

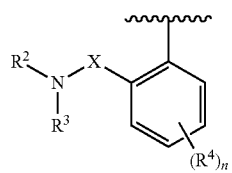

forms a group of the formula:

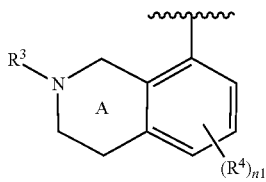

wherein:

n1 is an integer 0, 1 or 2 (for example n$_1$ is 0) and, when present, R$^4$ is located on the phenyl ring; and Ring A is optionally substituted by one or more (for example 1, 2 or 3) substituents selected from: halo, C$_{1-4}$ alkyl, C$_{1-4}$ haloalkyl and =O (preferably Ring A is unsubstituted);

optionally R$^3$ is selected from: H, C$_{1-4}$ alkyl, C$_{2-4}$ alkenyl, C$_{1-4}$ fluoroalkyl, C34 cycloalkyl, C$_{3-6}$ cycloalkyl-C$_{1-3}$ alkyl-, C$_{2-3}$ alkyl substituted by —NR$^{11}$R$^{12}$ and C$_{2-3}$ alkyl substituted by —OR$^{13}$, wherein R$^{11}$, R$^{12}$ and R$^{13}$ are independently selected from: H, C$_{1-4}$ alkyl and C$_{1-4}$ haloalkyl; preferably R$^3$ is H or C$_{1-4}$ alkyl, more preferably R$^3$ is H;

optionally n1 is 1 and R$^4$ is halo, for example fluoro;

optionally n1 is 0.

99. The group

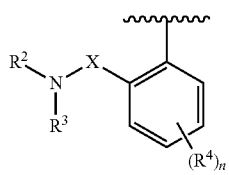

forms a group of the formula:

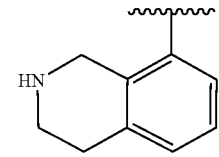 [SMILES: *c1cccc2c1CNCCCC2]

100. The group

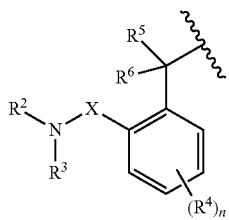

forms a group of the formula:

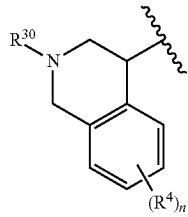

wherein
$n_2$ is an integer 0, 1 or 2 (e.g. n2 is 0) and, when present, $R^4$ is located on the phenyl ring; and
$R^{30}$ is selected from: H and $C_{1-4}$ alkyl; preferably $R^3$ is H or methyl, more preferably $R^3$ is H.

101. The group

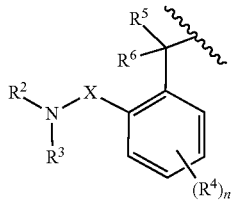

forms a group of the formula:

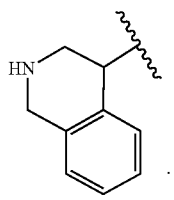

102. $R^1$ is selected from: H, $C_{1-6}$ alkyl, $C_{2-6}$ alkenyl, $C_{2-6}$ alkynyl, $C_{1-6}$ haloalkyl, Ca cycloalkyl, $C_{3-8}$ cycloalkyl-$C_{1-4}$ alkyl, 4 to 7 membered heterocyclyl, 4 to 7 membered heterocyclyl-$C_{1-4}$ alkyl, $C_{6-10}$ aryl, $C_{6-10}$ aryl-$C_{1-4}$ alkyl, 5 to 10 membered heteroaryl, and 5 to 10 membered heteroaryl-$C_{1-4}$ alkyl;
and wherein $R^1$ is optionally substituted by one or more substituents independently selected from: halo, $C_{1-4}$ alkyl, $C_{1-4}$ haloalkyl, —$OR^{A1}$, —$NR^{A1}R^{B1}$, —$S(O)_x R^{A1}$ (wherein x is 0, 1 or 2), —$C(O)R^{A1}$, —$OC(O)R^{A1}$, —$C(O)OR^{A1}$, —$NR^{A1}C(O)R^{B1}$, —$C(O)NR^{A1}R^{B1}$, —$NR^{A1}SO_2R^{B1}$, —$SO_2NR^{A1}R^{B1}$, =O, —CN and $R^{17}$;
$R^{17}$ is independently selected from: $C_{3-6}$ cycloalkyl, $C_{3-6}$ cycloalkyl-$C_{1-4}$ alkyl, 4 to 7 membered heterocyclyl, 4 to 7 membered heterocyclyl-$C_{1-4}$ alkyl, phenyl, phenyl-$C_{1-4}$ alkyl, 5 to 10 membered heteroaryl, and 5 to 10 membered heteroaryl-$C_{1-4}$ alkyl,
wherein $R^{17}$ is optionally substituted one or more substituents independently selected from: halo, $C_{1-4}$ alkyl, $C_{1-4}$ haloalkyl, —$OR^{A6}$, —$NR^{A6}R^{B6}$, —$S(O)_x R^{A6}$ (wherein x is 0, 1 or 2), —$C(O)R^{A6}$, —$OC(O)R^{A6}$, —$C(O)OR^{A6}$, —$NR^{A6}C(O)R^{B6}$, —$C(O)NR^{A6}R^{B6}$, —$NR^{A6}SO_2R^{B6}$, —$SO_2NR^{A6}R^{B6}$, =O and —CN.

103. $R^1$ is selected from: $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-4}$ alkyl, 4 to 7 membered heterocyclyl, 4 to 7 membered heterocyclyl-$C_{1-4}$ alkyl, phenyl, phenyl-$C_{1-4}$ alkyl, 5 to 10 membered heteroaryl, and 5 to 10 membered heteroaryl-$C_{1-4}$ alkyl;
and wherein $R^1$ is optionally substituted by one or more substituents independently selected from: halo, $C_{1-4}$ alkyl, $C_{1-4}$ haloalkyl, —$OR^{A1}$, —$NR^{A1}R^{B1}$, —$S(O)_x R^{A1}$ (wherein x is 0, 1 or 2), —$C(O)R^{A1}$, —$OC(O)R^{A1}$, —$C(O)OR^{A1}$, —$NR^{A1}C(O)R^{B1}$, —$C(O)NR^{A1}R^{B1}$, —$NR^{A1}SO_2R^{B1}$, —$SO_2NR^{A1}R^{B1}$, =O, —CN and $R^{17}$;
$R^{17}$ is independently selected from: $C_{3-6}$ cycloalkyl, 4 to 7 membered heterocyclyl, 4 to 7 membered heterocyclyl-$C_{1-3}$ alkyl, phenyl, phenyl-$C_{1-4}$ alkyl, 5 to 10 membered heteroaryl, and 5 to 10 membered heteroaryl-$C_{1-4}$ alkyl;
wherein $R^{17}$ is optionally substituted one or more substituents independently selected from: halo, $C_{1-4}$ alkyl, $C_{1-4}$ haloalkyl, —$OR^{A6}$, —$NR^{A6}R^{B6}$, —$S(O)_x R^{A6}$ (wherein x is 0, 1 or 2), —$C(O)R^{A6}$, —$OC(O)R^{A6}$, —$C(O)OR^{A6}$, —$NR^{A6}C(O)R^{A6}$, —$C(O)NR^{A6}R^{B6}$, —$NR^{A6}SO_2R^{B6}$, —$SO_2NR^{A6}R^{B6}$, =O and —CN.

104. $R^1$ is selected from: $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-4}$ alkyl, 4 to 6 membered heterocyclyl, 4 to 6 membered heterocyclyl-$C_{1-4}$ alkyl, phenyl, phenyl-$C_{1-4}$ alkyl, 5 to 6-membered heteroaryl, and 5 to 6-membered heteroaryl-$C_{1-4}$ alkyl;
and wherein $R^1$ is optionally substituted by one or more substituents independently selected from: halo, $C_{1-4}$ alkyl, $C_{1-4}$ haloalkyl, —$OR^{A1}$, —$NR^{A1}R^{B1}$, —$S(O)_x R^{A1}$ (wherein x is 0, 1 or 2), —$C(O)R^{A1}$, —$OC(O)R^{A1}$, —$C(O)OR^{A1}$, —$NR^{A1}C(O)R^{B1}$, —$C(O)NR^{A1}R^{B1}$, —$NR^{A1}SO_2R^{B1}$, —$SO_2NR^{A1}R^{B1}$, =O, —CN and $R^{17}$;
$R^{17}$ is independently selected from: 4 to 7 membered heterocyclyl, 4 to 7 membered heterocyclyl-$C_{1-3}$ alkyl, 5 to 10 membered heteroaryl, and 5 to 10 membered heteroaryl-$C_{1-3}$ alkyl; and wherein $R^{17}$ is optionally substituted one or more substituents independently selected from: halo, $C_{1-4}$ alkyl, $C_{1-4}$ haloalkyl, —$OR^{A6}$, —$NR^{A6}R^{B6}$ and =O.

105. $R^1$ is selected from: $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-4}$ alkyl, 4 to 6 membered heterocyclyl, 4 to 6 membered heterocyclyl-$C_{1-4}$ alkyl, phenyl, phenyl-$C_{1-4}$ alkyl, 5 or 6 membered heteroaryl and 5 or 6 membered heteroaryl-$C_{1-4}$ alkyl;
and wherein $R^1$ is optionally substituted by one or more substituents independently selected from: halo, $C_{1-4}$ alkyl, $C_{1-4}$ haloalkyl, —$OR^{A1}$, —$NR^{A1}R^{B1}$, —$S(O)_x R^{A1}$ (wherein x is 0, 1 or 2), —$C(O)R^{A1}$, —$OC(O)R^{A1}$, —$C(O)OR^{A1}$, —$NR^{A1}C(O)R^{B1}$, —$C(O)NR^{A1}R^{B1}$, —$NR^{A1}SO_2R^{B1}$, —$SO_2NR^{A1}R^{B1}$, =O, —CN and $R^{17}$;
$R^{17}$ is independently selected from: azetidinyl, pyrrolidinyl, piperidinyl, piperazinyl, morpholinyl, azetidinyl-$C_{1-3}$ alkyl, pyrrolidinyl-$C_{1-3}$ alkyl, piperidinyl-$C_{1-3}$ alkyl, piperazinyl-$C_{1-3}$ alkyl, morpholinyl-$C_{1-3}$ alkyl,

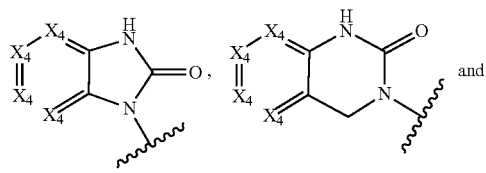

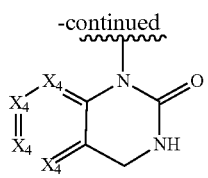

wherein each $X_4$ is independently CH or N, provided that no more than 2 $X_4$ groups are N; and wherein $R^{17}$ is optionally substituted one or more substituents independently selected from: halo, $C_{1-4}$ alkyl, $C_{1-4}$ haloalkyl and =O.

106. $R^1$ is selected from (i), (ii) and (iii) below:
(i) $C_{1-6}$ alkyl, $C_{1-6}$ haloalkyl, $C_{3-6}$ cycloalkyl, $C_{3-6}$ cycloalkyl-$C_{1-3}$ alkyl, 4 to 6 membered heterocyclyl, phenyl, phenyl-$C_{1-3}$ alkyl and 5 to 10 membered heteroaryl, each or which is optionally substituted by one or more substituents selected from: halo, $C_{1-4}$ alkyl, $C_{1-4}$ haloalkyl, —$OR^{A1}$, —$NR^{A1}R^{B1}$, —$S(O)_xR^{A1}$ (wherein x is 0, 1 or 2), =O and —CN;
(ii) phenyl, phenyl-$C_{1-3}$ alkyl, wherein the phenyl group is substituted by $R^{17}$, and $R^{17A}$ is selected from azetidinyl, pyrrolidinyl, piperidinyl, piperazinyl, azetidinyl-$C_{1-3}$ alkyl, pyrrolidinyl-$C_{1-3}$ alkyl, pipendinyl-$C_{1-3}$ alkyl, piperazinyl-$C_{1-3}$ alkyl, and wherein $R^{17}$ is optionally substituted by 1 or 2 substituents selected from halo, $C_{1-4}$ alkyl and =O; and
(iii)

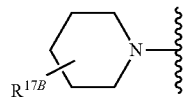

wherein $R^{17B}$ is selected from

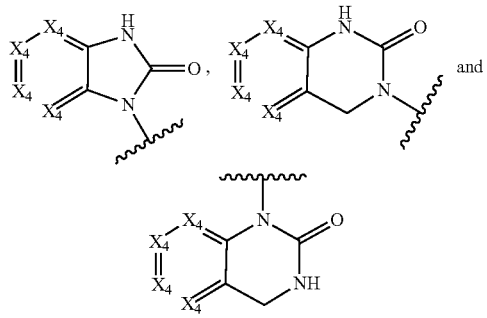

wherein each $X_4$ is independently CH or N, provided that no more than one of the $X_4$ groups are N; and wherein $R^{17B}$ is optionally substituted one or more substituents independently selected from: halo, $C_{1-4}$ alkyl, $C_{1-4}$ haloalkyl and =O.

107. $R^1$ is selected from (i), (ii) and (iii) below:
(i) $C_{1-6}$ alkyl, $C_{1-6}$ haloalkyl, $C_{3-6}$ cycloalkyl, $C_{3-6}$ cycloalkyl-$C_{1-3}$ alkyl, 4 to 6 membered heterocyclyl, 4 to 6 membered heterocyclyl-$C_{1-3}$ alkyl, phenyl, phenyl-$C_{1-3}$ alkyl, 5 or 6 membered heteroaryl and 5 or 6 membered heteroaryl-$C_{1-3}$ alkyl;
wherein the 4 to 6 membered heterocyclyl in (i) is selected from: azetidinyl, pyrrolidinyl, piperidinyl, piperazinyl, oxetanyl, tetrahydrofuranyl, pyranyl and morpholinyl;
wherein the 5 or 6 membered heteroaryl in (i) is selected from: furyl, pyrrolyl, thienyl, oxazolyl, isoxazolyl, imidazolyl, pyrazolyl, thiazolyl, isothiazolyl, pyridyl, pyridazinyl, pyrimidinyl and pyrazinyl;
and wherein each group listed in (i) is optionally substituted by one or more substituents selected from: halo, $C_{1-4}$ alkyl, $C_{1-4}$ haloalkyl, —$OR^{A1}$, —$NR^{A1}R^{B1}$, —$S(O)_xR^{A1}$ (wherein x is 0, 1 or 2), =O and —CN;
(ii) phenyl, phenyl-$C_{1-3}$ alkyl, wherein the phenyl group is substituted by $R^{17}$, and $R^{17A}$ is selected from azetidinyl, pyrrolidinyl, piperidinyl, piperazinyl, azetidinyl-$C_{1-3}$ alkyl, pyrrolidinyl-$C_{1-3}$ alkyl, pipendinyl-$C_{1-3}$ alkyl, piperazinyl-$C_{1-3}$ alkyl, and wherein $R^{17A}$ is optionally substituted by 1 or 2 substituents selected from halo, $C_{1-4}$ alkyl and =O; and
(iii)

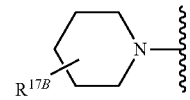

wherein $R^{17B}$ is selected from

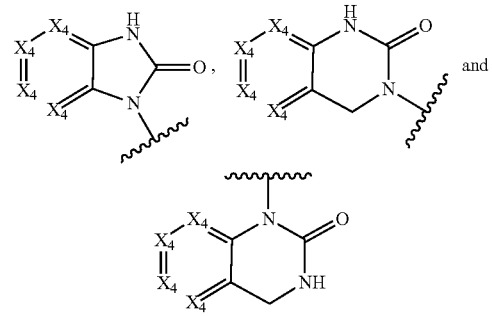

wherein each $X_4$ is independently CH or N, provided that no more than one of the $X_4$ groups are N; and wherein $R^{17}$ is optionally substituted one or more substituents independently selected from: halo, $C_{1-4}$ alkyl and $C_{1-4}$ haloalkyl.

108. $R^1$ is selected from: $C_{1-6}$ alkyl, $C_{1-6}$ haloalkyl, $C_{3-6}$ cycloalkyl, 4 to 7 membered heterocyclyl, phenyl and 5 to 10 membered heteroaryl;
and wherein $R^1$ is optionally substituted by one or more substituents selected from: halo, $C_{1-4}$ alkyl, $C_{1-4}$ haloalkyl, $C_{3-6}$ cycloalkyl, —$OR^{A1}$, —$NR^{A1}R^{B1}$, —$S(O)_xR^{A1}$ (wherein x is 0, 1 or 2), =O and —CN.

109. $R^1$ is selected from: $C_{1-4}$ alkyl, $C_{1-4}$ haloalkyl, $C_{3-6}$ cycloalkyl, 4 to 6 membered heterocyclyl, phenyl and 5 or 6 membered heteroaryl;
and wherein $R^1$ is optionally substituted by one or more substituents (for example 1, 2 or 3) selected from: halo, $C_{1-4}$ alkyl, $C_{1-4}$ haloalkyl, $C_{3-6}$ cycloalkyl, —$OR^{A1}$, —$NR^{A1}R^{B1}$, —$S(O)_xR^{A1}$ (wherein x is 0, 1 or 2), =O and —CN.

110. $R^1$ is selected from: $C_{1-4}$ alkyl and $C_{1-4}$ haloalkyl, wherein $R^1$ is optionally substituted by one or more substituents (for example 1, 2 or 3) selected from: halo, $C_{1-4}$ alkyl, —$OR^{A1}$, —$NR^{A1}R^{B1}$ and —$S(O)_xR^{A11}$.

111. $R^1$ is $C_{3-6}$ cycloalkyl optionally substituted by one or more (for example 1, 2 or 3) substituents selected from: halo, $C_{1-4}$ alkyl, $C_{1-4}$ haloalkyl, —$OR^{A1}$, —$NR^{A1}R^{B1}$ and =O.

112. $R^1$ is a 4 to 7 membered heterocyclyl, for example a saturated 4 to 7 membered heterocyclyl selected from: azetidinyl, oxetanyl, tetrahydrofuranyl, tetrahydropyranyl, pyrrolidinyl, piperidinyl, piperazinyl, morpholinyl, thiomorpholinyl, homopiperidinyl and homopiperazinyl, each of which is optionally substituted by one or more substituents (for example 1, 2 or 3) selected from: halo, $C_{1-4}$ alkyl, $C_{1-4}$ haloalkyl, —$OR^{A1}$, —$NR^{A1}R^{B1}$, and =O.

113. $R^1$ is selected from: phenyl or a 5 or 6-membered heteroaryl containing ring nitrogen and optionally 1, or 2 heteroatoms independently selected from: O, S and N, and wherein $R^1$ is optionally substituted by one or more substituents (for example 1, 2 or 3) selected from: halo, $C_{1-4}$ alkyl, $C_{1-4}$ haloalkyl, —$OR^{A1}$, —$NR^{A1}R^{B1}$, —$S(O)_x R^{A1}$ (wherein x is 0, 1 or 2) and —CN.

114. $R^1$ is selected from: phenyl, thiazolyl, pyridyl, pyrimidyl, pyrazinyl, indolyl and indazolyl, each of which is optionally substituted by one or more substituents (for example 1, 2 or 3) selected from: halo, $C_{1-4}$ alkyl, $C_{1-4}$ haloalkyl, —$OR^{A1}$, —$NR^{A1}R^{B1}$, —$S(O)_x R^{A1}$ (wherein x is 0, 1 or 2) and —CN.

115. $R^1$ is a group of the formula:

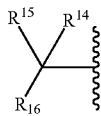

wherein
$R^{14}$, $R^{15}$ and $R^{16}$ are each independently selected from: halo, —$OR^{A1}$, —$NR^{A1}R^{B1}$, $C_{1-4}$ alkyl, $C_{2-4}$ alkenyl, $C_{2-4}$ alkynyl, $C_{1-4}$ haloalkyl, $C_{3-6}$ cycloalkyl, 4 to 7 membered heterocyclyl, 4 to 7 membered heterocyclyl-$C_{1-2}$ alkyl, phenyl, phenyl-$C_{1-2}$ alkyl, 5 or 6 membered heteroaryl, and 5 or 6 membered heteroaryl-$C_{1-2}$ alkyl;
or $R^{14}$ and $R^{15}$ together with the carbon atom to which they are attached form a $C_{3-6}$ cycloalkyl or 4 to 7 membered heterocyclyl;
and wherein the $C_{1-4}$ alkyl, $C_{2-4}$ alkenyl, $C_{2-4}$ alkynyl, $C_{1-4}$ haloalkyl, $C_{3-6}$ cycloalkyl, 4 to 7 membered heterocyclyl, 4 to 7 membered heterocyclyl-$C_{1-2}$ alkyl, phenyl, phenyl-$C_{1-2}$ alkyl, 5 or 6 membered heteroaryl, or 5 or 6 membered heteroaryl-$C_{1-2}$ alkyl groups represented by any of $R^{14}$, $R^{15}$ and $R^{16}$, or the $C_{3-6}$ cycloalkyl or 4 to 7 membered heterocyclyl formed by $R^{14}$ and $R^{15}$ together with the carbon atom to which they are attached, are each optionally substituted by one or more substituents selected from: halo, $C_{1-4}$ alkyl, $C_{1-4}$ haloalkyl, $C_3$ cycloalkyl, —$OR^{A1}$, —$NR^{A1}R^{B1}$, —$S(O)_x R^{A1}$ (wherein x is 0, 1 or 2), =O and —CN.

116. $R^1$ is a group of the formula:

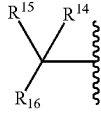

wherein $R^1$ is selected from halo, —$OR^{A1}$, —$NR^{A1}R^{B1}$, $C_{1-4}$ alkyl, $C_{2-4}$ alkenyl, $C_{2-4}$ alkynyl and $C_{1-4}$ haloalkyl;
$R^{14}$ and $R^{15}$ are each independently selected from halo, $C_{1-4}$ alkyl and $C_{1-4}$ haloalkyl;

or $R^{14}$ and $R^{15}$ together with the carbon atom to which they are attached form a $C_{3-6}$ cycloalkyl or 4 to 6 membered heterocyclyl containing one or two heteroatoms selected from O, S and N, wherein said cycloalkyl or heterocyclyl is optionally substituted by one or more (for example 1 or 2) substituents selected from halo, $C_{1-4}$ alkyl, $C_{1-4}$ haloalkyl, —$OR^{A1}$, —$NR^{A1}R^{B1}$, and =O.

117. $R^1$ is a group of the formula:

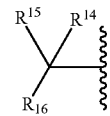

wherein $R^{16}$ is selected from halo, —$OR^{A1}$, $C_{1-4}$ alkyl and $C_{1-4}$ haloalkyl;
$R^{14}$ and $R^{15}$ are each independently selected from halo, $C_{1-4}$ alkyl and $C_{1-4}$ haloalkyl;
or $R^{14}$ and $R^{15}$ together with the carbon atom to which they are attached form cyclopropyl, cyclobutyl, cyclopentyl, cyclohexyl, oxetanyl, tetrahydrofuranyl, tetrahydropyranyl, azetidinyl, pyrrolidinyl or piperidinyl, each or which is optionally substituted by one or more (for example 1 or 2) substituents selected from halo, $C_{1-4}$ alkyl, $C_{1-4}$ haloalkyl, —$OR^{A1}$, —$NR^{A1}R^{B1}$, and =O.

118. 
$R^1$ is selected from

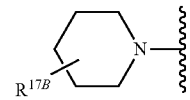

wherein $R^{17}$ is selected from

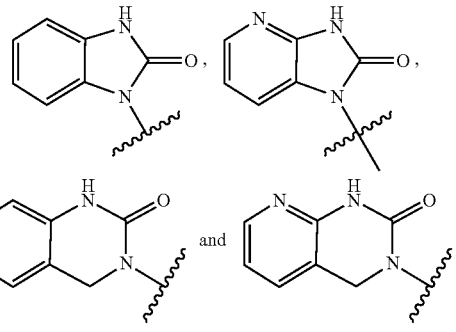

119. $R^1$ is selected from a 4 to 12 (e.g. a 4 to 7)-membered saturated or partially saturated heterocyclyl containing 1 ring nitrogen and optionally 1 or 2 additional ring heteroatoms selected from O, S and N,
wherein said heterocyclyl group is optionally substituted on the ring nitrogen by a group selected from: $C_{1-4}$ alkyl, —$C_{2-4}$ alkyl-$OR^{A1}$, —$C_{2-4}$ alkyl-$NR^{A1}R^{B1}$, —$C_{1-4}$ alkyl-$C(O)R^{A1}$, —$C_{1-4}$ alkyl-$C(O)NR^{A1}R^{B1}$, —$C_{1-4}$ alkyl-$NR^{A1}C(O)R^{B1}$, —$C_{1-4}$ alkyl-$S(O)_2 NR^{A1}R^{B1}$, —$C_{1-4}$ alkyl-$NR^{A1}S(O)_2 R^{B1}$, —$C_{1-4}$ alkyl-C (O)OR$^{A1}$, —C$_{1-4}$ alkyl-OC(O)R$^{A1}$, —C$_{1-4}$ alkyl-S(O)$_2$R$^{A1}$, C$_{1-4}$ haloalkyl, —S(O)$_2$R$^{18}$, —C(O)R$^{18}$, —C(O)OR$^{A1}$, —C(O)NR$^{A1}$R$^{18}$, —SO$_2$NR$^{A1}$R$^{18}$ and R$^{17}$;
and wherein said heterocyclyl group is optionally substituted on ring carbon atom(s) by one or more (e.g. 1 or 2) substituents selected from halo, C$_{1-4}$ alkyl, C$_{1-4}$ haloalkyl and =O.

120. R$^1$ is selected from a 4 to 12 (e.g. a 4 to 7)-membered saturated or partially saturated heterocyclyl containing 1 ring nitrogen and optionally 1 or 2 additional ring heteroatoms selected from O, S and N, and a 5-10 membered heteroaryl containing 1 ring nitrogen and optionally 1 or 2 additional ring heteroatoms selected from O, S and N; wherein R$^1$ is bonded to the group -L$^1$-C(O)— by a nitrogen in the heterocyclyl or heteroaryl group;
wherein said heterocyclyl is optionally substituted by one or more (e.g. 1 or 2) substituents independently selected from halo, C$_{1-4}$ alkyl, C$_{1-4}$ haloalkyl, —OR$^{A1}$, —NR$^{A1}$R$^{B1}$, —C(O)R$^{18}$, —C(O)OR$^{A1}$, —C(O)NR$^{A1}$R$^{B1}$, —S(O)$_2$R$^{A1}$ and =O; and
said heteroaryl is optionally substituted by one or more (e.g. 1 or 2) substituents independently selected from halo, C$_{1-4}$ alkyl, C$_{1-4}$ haloalkyl, —OR$^{A1}$, —NR$^{A1}$R$^{B1}$, —C(O)R$^{18}$, —C(O)OR$^{A1}$, —C(O)NR$^{A1}$R$^{B1}$ and —S(O)$_2$R$^1$.

121. R$^1$ is selected from azetidinyl, pyrrolidinyl, piperidinyl, piperazinyl, morpholinyl and thiomorpholinyl, wherein the ring nitrogen atom in the azetidinyl, pyrrolidinyl, piperidinyl, piperazinyl, morpholinyl or thiomorpholinyl is optionally substituted by a group selected from:
C$_{1-4}$ alkyl, —C$_{2-4}$ alkyl-OR$^{A1}$, —C$_{2-4}$ alkyl-NR$^{A1}$R$^{B1}$, —C$_{1-4}$ alkyl-C(O)R$^{A1}$, —C$_{1-4}$ alkyl-C(O)NR$^{A1}$R$^{B1}$, —C$_{1-4}$ alkyl-NR$^{A1}$C(O)R$^{B1}$, —C$_{1-4}$ alkyl-S(O)$_2$NR$^{A1}$R$^{B1}$, —C$_{1-4}$ alkyl-NR$^{A1}$S(O)$_2$R$^{B1}$, —C$_{1-4}$ alkyl-C(O)OR$^{A1}$, —C$_{1-4}$ alkyl-OC(O)R$^{A1}$, —C$_{1-4}$ alkyl-S(O)$_2$R$^{A1}$, C$_{1-4}$ haloalkyl, —S(O)$_2$R$^{18}$, —C(O)R$^{18}$, —C(O)OR$^{A1}$, —C(O)NR$^{A1}$R$^{18}$, —SO$_2$NR$^{A1}$R$^{18}$ and R$^{17}$.

122. R$^1$ is selected from azetidinyl, pyrrolidinyl, piperidinyl and piperazinyl, wherein said azetidinyl, pyrrolidinyl, piperidinyl or piperazinyl is bonded to the group -L$^1$-C(O)— by a ring carbon atom and wherein the ring nitrogen atom in the azetidinyl, pyrrolidinyl, piperidinyl or piperazinyl is optionally substituted by a group selected from:
C$_{1-4}$ alkyl, —C$_{2-4}$ alkyl-OR$^{A1}$, —C$_{2-4}$ alkyl-NR$^{A1}$R$^{B1}$, —C$_{1-4}$ alkyl-C(O)R$^{A1}$, —C$_{1-4}$ alkyl-C(O)NR$^{A1}$R$^{B1}$, —C$_{1-4}$ alkyl-NR$^{A1}$C(O)R$^{B1}$, —C$_{1-4}$ alkyl-S(O)$_2$NR$^{A1}$R$^{B1}$, —C$_{1-4}$ alkyl-NR$^{A1}$S(O)$_2$R$^{B1}$, —C$_{1-4}$ alkyl-C(O)OR$^{A1}$, —C$_{1-4}$ alkyl-OC(O)R$^{A1}$, —C$_{1-4}$ alkyl-S(O)$_2$R$^{A1}$, C$_{1-4}$ haloalkyl, —S(O)$_2$R$^{18A}$, —C(O)R$^{18A}$, —C(O)OR$^{A1}$, —C(O)NR$^{A1}$R$^{18A}$, —SO$_2$NR$^{A1}$R$^{18A}$ and R$^{17E}$;
R$^{17E}$ is selected from C$_{3-6}$ cycloalkyl, C$_{3-6}$ cycloalkyl-C$_{1-3}$ alkyl-, azetidinyl, pyrrolidinyl, piperidinyl, piperazinyl, morpholinyl, thiomorpholinyl, azetidinyl-C$_{1-3}$ alkyl-, pyrrolidinyl-C$_{1-6}$ alkyl-, piperidinyl-C$_{1-6}$ alkyl-, piperazinyl-C$_{1-6}$ alkyl-, morpholinyl-C$_{1-6}$ alkyl-, thiomorpholinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-6}$ alkyl-, pyridyl-C$_{1-3}$ alkyl-, pyrimidyl-C$_{1-6}$ alkyl-, pyrazinyl-C$_{1-3}$ alkyl- and pyridazinyl-C$_{1-6}$ alkyl-;
R$^{17E}$ is selected from C$_{1-4}$ alkyl, C$_{1-4}$ haloalkyl, C$_{3-6}$ cycloalkyl, C$_{3-6}$ cycloalkyl-C$_{1-3}$ alkyl, azetidinyl, pyrrolidinyl, piperidinyl, piperazinyl, morpholinyl, thiomorpholinyl, azetidinyl-C$_{1-6}$ alkyl-, pyrrolidinyl-C$_{1-6}$ alkyl-, piperidinyl-C$_{1-6}$ alkyl-, piperazinyl-C$_{1-6}$ alkyl-, morpholinyl-C$_{1-3}$ alkyl-, thiomorpholinyl-C$_{1-6}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-6}$ alkyl-, pyrimidyl-C$_{1-6}$ alkyl-, pyrazinyl-C$_{1-6}$ alkyl- and pyridazinyl-C$_1$. 3 alkyl-; and
wherein R$^{17E}$ and R$^{18A}$ are each independently optionally substituted one or more (e.g. 1 or 2) substituents independently selected from: halo, C$_{1-4}$ alkyl, C$_{1-4}$ haloalkyl, —OR$^{A6}$, —NR$^{A6}$R$^{B6}$, —S(O)$_x$R$^{A6}$ (wherein x is 0, 1 or 2), —C(O)R$^{A6}$, —OC(O)R$^{A6}$, —C(O)OR$^{A6}$, —NR$^{A6}$C(O)R$^{B6}$, —C(O)NR$^{A6}$R$^{B6}$, —NR$^{A6}$SO$_2$R$^{B6}$, —SO$_2$NR$^{A6}$R$^{B6}$, =O and —CN.

123. R$^1$ is selected from azetidinyl, pyrrolidinyl, piperidinyl and piperazinyl, wherein said azetidinyl, pyrrolidinyl, piperidinyl or piperazinyl is bonded to the group -L$^1$-C(O)— by a ring carbon atom and wherein the ring nitrogen atom in the azetidinyl, pyrrolidinyl, piperidinyl or piperazinyl is optionally substituted by a group selected from:
C$_{1-4}$ alkyl, C$_{1-4}$ haloalkyl, —C$_{2-4}$ alkyl-OR$^{A1}$, —C$_{2-4}$ alkyl-NR$^{A1}$R$^{B1}$, —C$_{1-4}$ alkyl-C(O)NR$^{A1}$R$^{B1}$, —C$_{1-4}$ alkyl-NR$^{A1}$C(O)R$^{B1}$, —C$_{1-4}$ alkyl-C(O)OR$^{A1}$, —C$_{1-4}$ alkyl-OC(O)R$^{A1}$, —S(O)$_2$R$^{18B}$, —C(O)R$^{18B}$, —C(O)NR$^{A1}$R$^{18B}$, and R$^{17F}$;
R$^{17F}$ is selected from C$_{3-6}$ cycloalkyl, C$_{3-6}$ cycloalkyl-C$_{1-3}$ alkyl-, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, morpholinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_1$. 3 alkyl-;
R$^{18B}$ is selected from C$_{1-4}$ alkyl, C$_{1-4}$ haloalkyl, C$_{3-6}$ cycloalkyl, C$_{3-6}$ cycloalkyl-C$_{1-3}$ alkyl, azetidinyl, pyrrolidinyl, piperidinyl, piperazinyl, morpholinyl, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_1$. 3 alkyl-;
wherein R$^{17F}$ and R$^{18B}$ are each independently optionally substituted one or more (e.g. 1 or 2) substituents independently selected from: halo, C$_{1-4}$ alkyl, C$_{1-4}$ haloalkyl, —OR$^{A6}$, —NR$^{A6}$R$^{B6}$, —C(O)R$^8$, —C(O)OR$^{A6}$ and —C(O)NR$^{A6}$R$^{B6}$.

124. R$^1$ is selected from azetidinyl, pyrrolidinyl, piperidinyl and piperazinyl, wherein said azetidinyl, pyrrolidinyl, piperidinyl or piperazinyl is bonded to the group -L$^1$-C(O)— by a ring carbon atom and wherein the ring nitrogen atom in the azetidinyl, pyrrolidinyl, piperidinyl or piperazinyl is optionally substituted by a group selected from:
C$_{1-4}$ alkyl, C$_{1-4}$ haloalkyl, —C$_{2-4}$ alkyl-OR$^{A1}$, —C$_{2-4}$ alkyl-NR$^{A1}$R$^{B1}$, —C$_{1-4}$ alkyl-C(O)NR$^{A1}$R$^{B1}$, —C$_{1-4}$ alkyl-C(O)OR$^{A1}$, —S(O)$_2$R$^{B1}$, —C(O)R$^{18B}$, —C(O)NR$^{A1}$R$^{B1}$, and R$^{17F}$;
R$^{17F}$ is selected from C$_{3-6}$ cycloalkyl, C$_{3-6}$ cycloalkyl-C$_{1-3}$ alkyl-, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, morpholinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_{1-3}$ alkyl-;
R$^{18B}$ is selected from C$_{1-4}$ alkyl, C$_{1-4}$ haloalkyl, C$_{3-6}$ cycloalkyl, C$_{3-6}$ cycloalkyl-C$_{1-3}$ alkyl, azetidinyl, pyrrolidinyl, piperidinyl, piperazinyl, morpholinyl, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_1$.$_3$ alkyl-;
wherein R$^{17F}$ and R$^{18B}$ are each independently optionally substituted one or more (e.g. 1 or 2) substituents independently selected from: halo, C$_{1-4}$ alkyl, C$_{1-4}$ haloalkyl, —OR$^{A6}$, —NR$^{A6}$R$^{B6}$, —C(O)R$^{A6}$, —C(O)OR$^{A6}$ and —C(O)NR$^{A6}$R$^{B6}$.

125. R$^1$ is a 4 to 7 membered saturated heterocyclyl containing one NH ring group and optionally 1 additional heteroatom selected from O, S and N (e.g. azetidinyl, pyrrolidinyl, piperidinyl, piperazinyl and morpholinyl), wherein the NH ring group in the 4 to 7 membered heterocyclyl is substituted by a group selected from: —S(O)$_2$R$^{B1}$, —C(O)R$^{18B}$ and —C(O)NR$^{A1}$R$^{B1}$;
R$^{18B}$ is selected from C$_{1-4}$ alkyl, C$_{1-4}$ haloalkyl, C$_{3-6}$ cycloalkyl, C$_{3-6}$ cycloalkyl-C$_{1-3}$ alkyl, azetidinyl, pyrrolidinyl, piperidinyl, piperazinyl, morpholinyl, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_{1-3}$ alkyl-;
wherein R$^{18B}$ is optionally substituted one or more (e.g. 1 or 2) substituents independently selected from: halo, C$_{1-4}$ alkyl, C$_{1-4}$ haloalkyl, —OR$^{A6}$, —NR$^{A6}$R$^{B6}$, —C(O)R$^{A6}$, —C(O)OR$^{A6}$ and —C(O)NR$^{A6}$R$^{B6}$.

126. R$^1$ is a 4 to 7 membered saturated heterocyclyl containing one NH ring group and optionally 1 additional heteroatom selected from O, S and N (e.g. azetidinyl, pyrrolidinyl, piperidinyl, piperazinyl or morpholinyl), wherein the NH ring group in the 4 to 7 membered heterocyclyl is substituted by a group selected from: C$_{1-4}$ alkyl, C$_{1-4}$ haloalkyl, —C$_{2-4}$ alkyl-OR$^{A1}$, —C$_{2-4}$ alkyl-NR$^{A1}$R$^{B1}$, —C$_{1-4}$ alkyl-C(O)NR$^{A1}$R$^{B1}$, —C$_{1-4}$ alkyl-C(O)OR$^{A1}$, and R$^{17G}$;
R$^{17G}$ is selected from C$_{3-6}$ cycloalkyl, C$_{3-6}$ cycloalkyl-C$_{1-3}$ alkyl-, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, morpholinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_{1-3}$ alkyl-
wherein R$^{17G}$ is optionally substituted one or more (e.g. 1 or 2) substituents independently selected from: halo, C$_{1-4}$ alkyl, C$_{1-4}$ haloalkyl, —OR$^{A6}$, —NR$^{A6}$R$^{B6}$, —C(O)R$^{A6}$, —C(O)OR$^{A6}$ and —C(O)NR$^{A6}$R$^{B6}$.

127. R$^1$ is selected from: phenyl and phenyl-C$_{1-3}$ alkyl, wherein the phenyl group is substituted by azetidinyl, pyrrolidinyl, piperidinyl, piperazinyl, azetidinyl-C$_{1-3}$ alkyl, pyrrolidinyl-C$_{1-3}$ alkyl, piperidinyl-C$_{1-3}$ alkyl or piperazinyl-C$_{1-3}$ alkyl.
R$^1$ is selected from cyclopropyl, cyclobutyl, cyclopentyl, cyclohexyl (wherein said cyclopropyl, cyclobutyl, cyclopentyl and cyclohexyl is independently optionally substituted with one or two R$^{102}$),

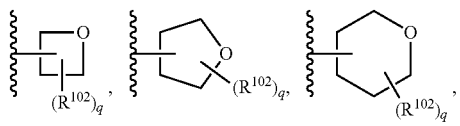

wherein
R$^{101}$ is independently selected from: H, C$_{1-4}$ alkyl, C$_{1-4}$ haloalkyl, —C$_{2-4}$ alkyl-OR$^{A1}$, —C$_{2-4}$ alkyl-NR$^{A1}$R$^{B1}$, —C$_{1-4}$ alkyl-C(O)NR$^{A1}$R$^{B1}$, —C$_{1-4}$ alkyl-NR$^{A1}$C(O)R$^{B1}$, —C$_{1-4}$ alkyl-C(O)OR$^{A1}$, —C$_{1-4}$ alkyl-OC(O)R$^{A1}$, —S(O)$_2$R$^{18B}$, —C(O)R$^{18B}$, —C(O)NR$^{A1}$R$^{B1}$, and R$^{17F}$;
R$^{17F}$ is selected from C$_{3-6}$ cycloalkyl, C$_{3-6}$ cycloalkyl-C$_{1-3}$ alkyl-, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, morpholinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_{1-3}$ alkyl-;
R$^{18B}$ is selected from C$_{1-4}$ alkyl, C$_{1-4}$ haloalkyl, C$_{3-6}$ cycloalkyl, C$_{3-6}$ cycloalkyl-C$_{1-3}$ alkyl, azetidinyl, pyrrolidinyl, piperidinyl, piperazinyl, morpholinyl, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_1$.$_3$ alkyl-;
wherein R$^{17F}$ and R$^{18B}$ are each independently optionally substituted one or more substituents independently selected from: halo, C$_{1-4}$ alkyl, C$_{1-4}$ haloalkyl, —OR$^{A6}$, —NR$^{A6}$R$^{B6}$, —C(O)R$^{A6}$, —C(O)OR$^{A6}$ and —C(O)NR$^{A6}$R$^{B6}$
(for example, R$^{101}$ is independently selected from: H, C$_{1-4}$ alkyl, C$_{1-4}$ haloalkyl, —SO$_2$R$^{A1}$, —C(O)R$^{A1}$, —C(O)NR$^{A1}$R$^{B1}$ and —SO$_2$NR$^{A1}$R$^{B1}$);
each R$^{102}$ is independently selected from halo, C$_{1-4}$ alkyl, C$_{1-4}$ haloalkyl, —OR$^{A1}$, —NR$^{A1}$R$^{B1}$ and =O; and
each q is in integer 0, 1 or 2.

128. R$^1$ is selected from phenyl, pyridyl and thiazolyl, wherein said phenyl, pyridyl and thiazolyl is optionally substituted by one or two groups selected from halo, C$_{1-4}$ alkyl, C$_{1-4}$ haloalkyl, —OR$^{A1}$, —NR$^{A1}$R$^{B1}$.

129. R¹ is selected from: methyl, ethyl, propyl, isopropyl, cyclopropyl-methyl-, cyclobutyl-methyl-, cyclopentyl-methyl-, cyclohexyl-methyl-

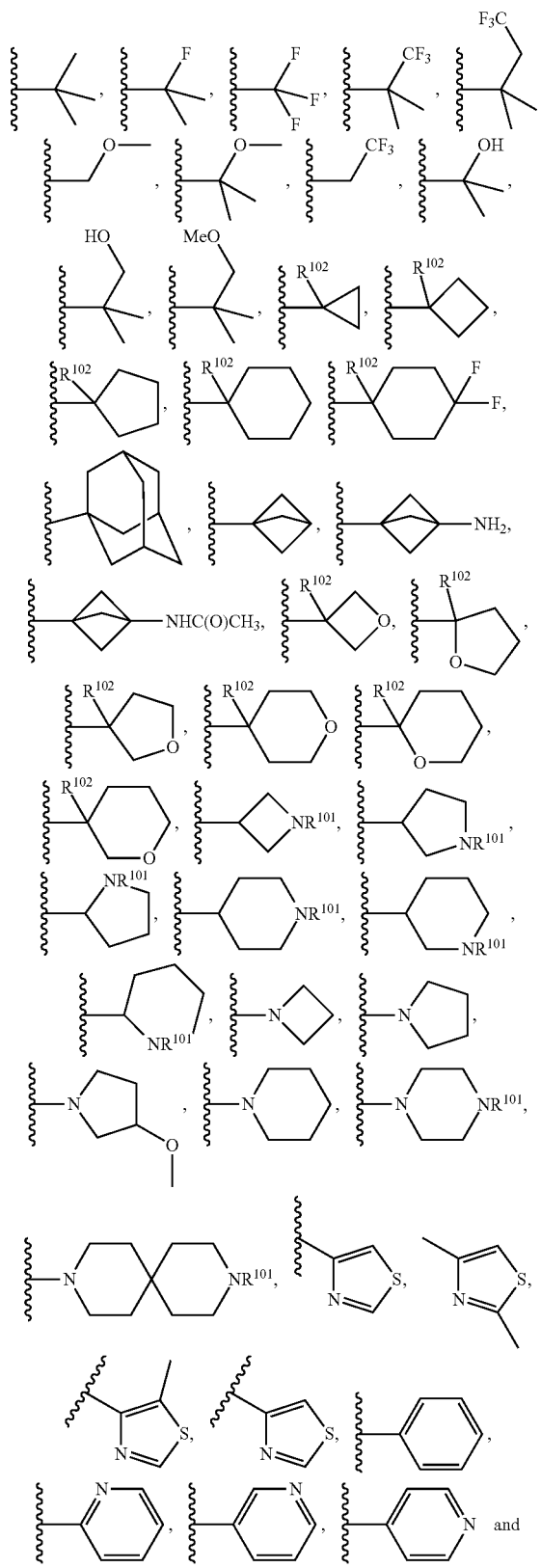

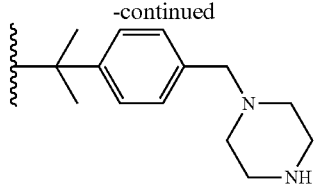

wherein
R¹⁰¹ is independently selected from: H, $C_{1-4}$ alkyl, $C_{1-4}$ haloalkyl, $-C_{2-4}$ alkyl-$OR^{A1}$, $-C_{2-4}$ alkyl-$NR^{A1}R^{B1}$, $-C_{1-4}$ alkyl-$C(O)NR^{A1}R^{B1}$, $-C_{1-4}$ alkyl-$NR^{A1}C(O)R^{B1}$, $-C_{1-4}$ alkyl-$C(O)OR^{A1}$, $-C_{1-4}$ alkyl-$OC(O)R^{A1}$, $-S(O)_2R^{18B}$, $-C(O)R^{18B}$, $-C(O)NR^{A1}R^{18B}$, and R¹⁷ᶠ is selected from $C_{3-6}$ cycloalkyl, $C_{3-6}$ cycloalkyl-$C_{1-3}$ alkyl-, azetidinyl-$C_{1-3}$ alkyl-, pyrrolidinyl-$C_{1-3}$ alkyl-, pipendinyl-$C_{1-3}$ alkyl-, piperazinyl-$C_{1-3}$ alkyl-, morpholinyl-$C_{1-3}$ alkyl-, phenyl, phenyl-$C_{1-3}$ alkyl-, pyrazolyl, pyridyl, pyrimidyl, pyrazinyl, pyridazinyl, pyrazolyl-$C_{1-3}$ alkyl-, pyridyl-$C_{1-3}$ alkyl-, pyrimidyl-$C_{1-3}$ alkyl-, pyrazinyl-$C_{1-3}$ alkyl- and pyridazinyl-$C_{1-3}$ alkyl-;

R¹⁸ᴮ is selected from $C_{1-4}$ alkyl, $C_{1-4}$ haloalkyl, $C_{3-6}$ cycloalkyl, $C_{3-6}$ cycloalkyl-$C_{1-3}$ alkyl, azetidinyl, pyrrolidinyl, piperidinyl, piperazinyl, morpholinyl, azetidinyl-$C_{1-3}$ alkyl-, pyrrolidinyl-$C_{1-3}$ alkyl-, piperidinyl-$C_{1-3}$ alkyl-, piperazinyl-$C_{1-3}$ alkyl-, phenyl, phenyl-$C_{1-3}$ alkyl-, pyrazolyl, pyridyl, pyrimidyl, pyrazinyl, pyridazinyl, pyrazolyl-$C_{1-3}$ alkyl-, pyridyl-$C_{1-3}$ alkyl-, pyrimidyl-$C_{1-3}$ alkyl-, pyrazinyl-$C_{1-3}$ alkyl- and pyridazinyl-$C_1$. 3 alkyl-;

wherein R¹⁷ᶠ and R¹⁸ᴮ are each independently optionally substituted one or more substituents independently selected from: halo, $C_{1-4}$ alkyl, $C_{1-4}$ haloalkyl, $-OR^{A6}$, $-NR^{A6}R^{B6}$, $-C(O)R^{A6}$, $-C(O)OR^{A6}$ and $-C(O)NR^{A6}R^{B6}$ (for example, R¹⁰¹ is selected from: H, $C_{1-4}$ alkyl, $-SO_2R^{A1}$, $-C(O)R^{A1}$, $-C(O)NR^{A1}R^{B1}$ and $-SO_2NR^{A1}R^{B1}$); and R¹⁰² is selected from H, $C_{1-3}$ alkyl and $C_{1-3}$ haloalkyl (e.g. R¹⁰² is H. e.g. R¹⁰² is $C_{1-3}$ alkyl. e.g. R¹⁰² is $-CF_3$).

130. R¹ is selected from: methyl, ethyl, propyl, isopropyl, isobutyl, cyclopropyl, cyclobutyl, cyclopentyl, cyclohexyl,

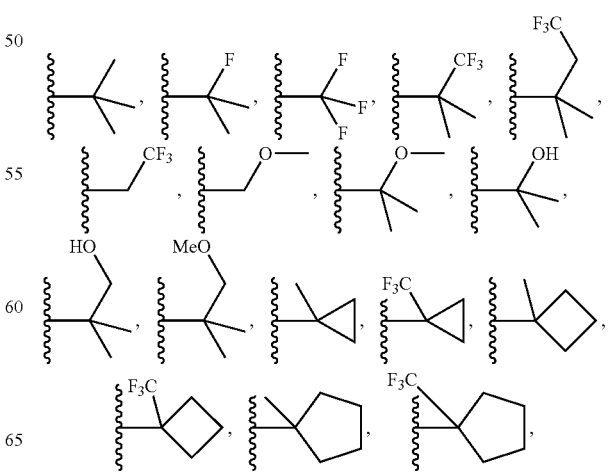

-continued
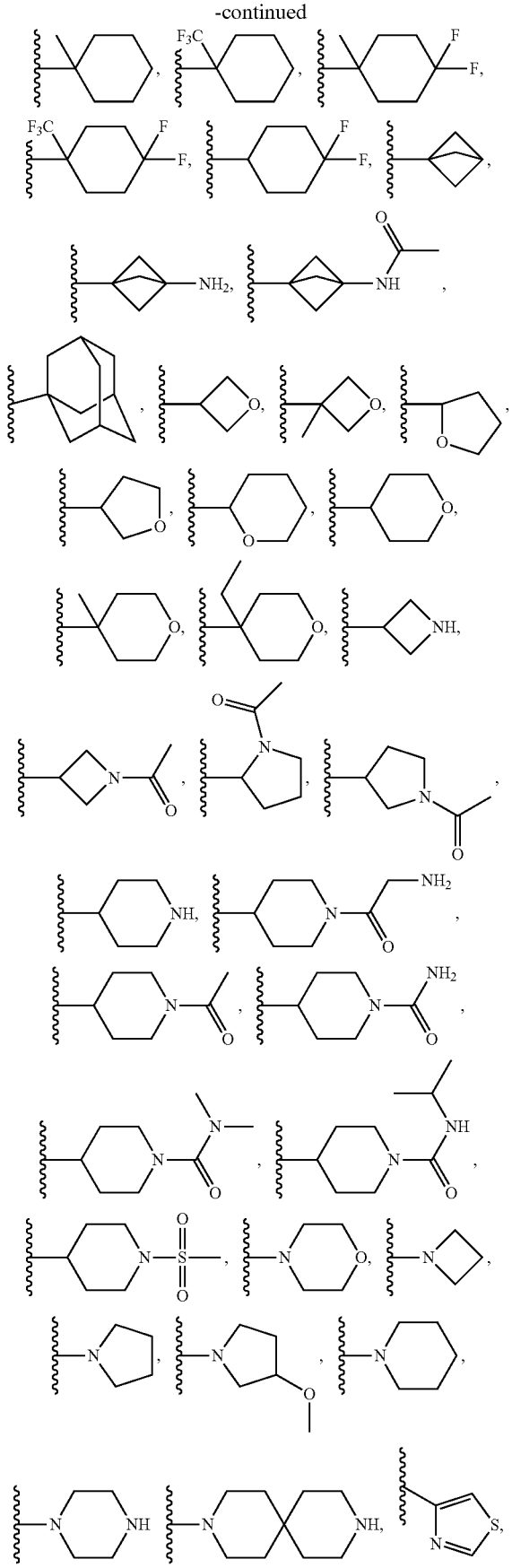
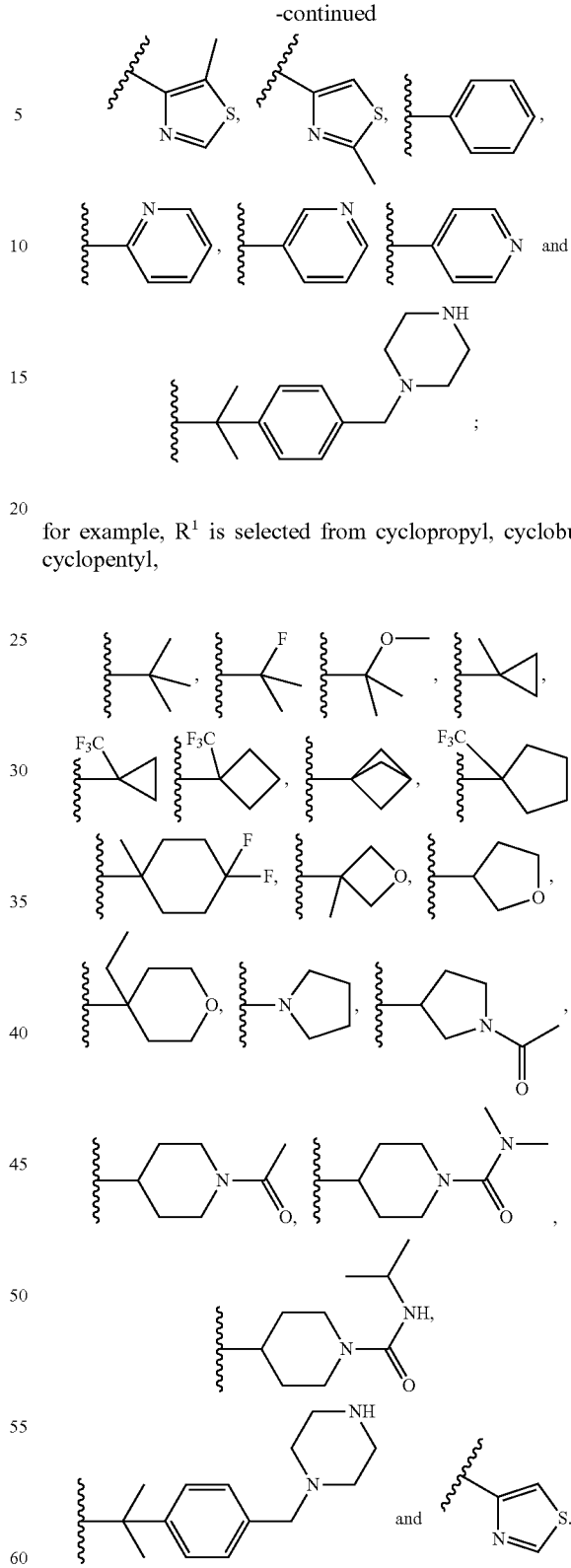
for example, R¹ is selected from cyclopropyl, cyclobutyl, cyclopentyl,
131. R¹ is selected from: methyl, ethyl, isopropyl, tert-butyl, hydroxymethyl, 2-hydroxyethyl, methoxymethyl, 2-methoxyethyl, cyclopropyl, cyclobutyl, cyclopentyl, oxetanyl, tetrahydrofuranyl, tetrahydropyranyl, phenyl, thiazolyl, pyridyl,

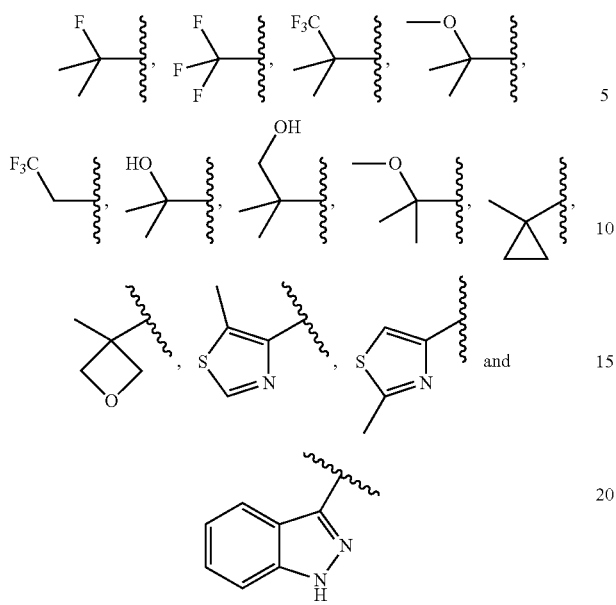

132. $R^1$ is selected from tert-butyl,

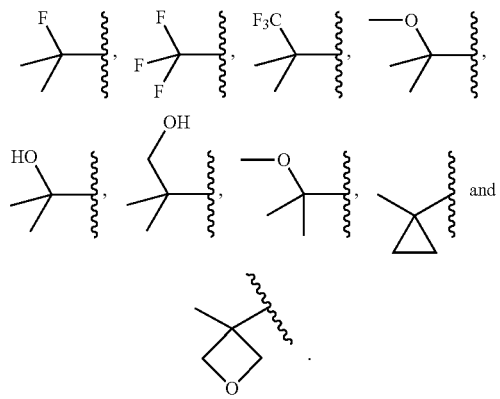

133. $R^1$ is selected from: cyclopropyl, cyclobutyl, cyclopentyl, oxetanyl, phenyl,

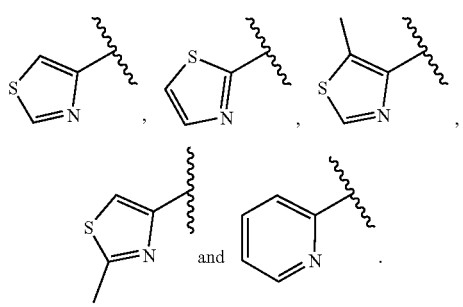

134. $R^1$ is selected from a 4 to 7 membered saturated or partially saturated heterocyclyl containing one or two ring oxygen atoms, for example oxetanyl, tetrahydrofuranyl, tetrahydropyranyl or dioxanyl.

135. $R^1$ is selected from:

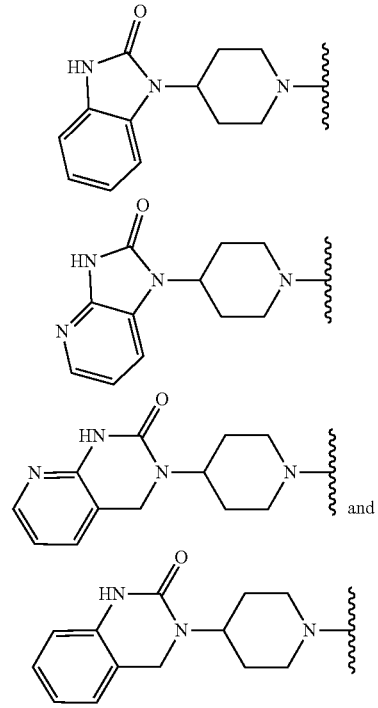

136. $R^1$ is selected from:

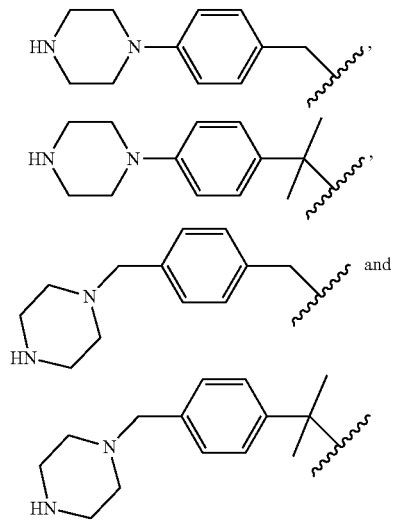

137. $R^1$ is selected from:

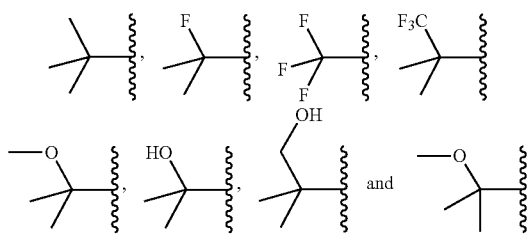

138. R$^1$ is selected from: cyclopropyl, cyclobutyl, cyclopentyl, cyclopropyl-methyl, cyclobutyl-methyl, and cyclopentyl-methyl (e.g R$^1$ is selected from: cyclopropyl, cyclobutyl and cyclopentyl).
139. R$^1$ is tert-butyl.
140. The group -L$^1$-C(O)— is bonded to a carbon atom in R$^1$.
141. L$^1$ is a bond and R$^1$ is attached to the carbonyl group by a carbon atom in R$^1$.
142. L$^1$ is a bond and R$^1$ is attached to the carbonyl group by a nitrogen atom in R$^1$.
143. L$^1$ is a bond and R$^1$ is as defined in any of 102 to 140 above.
144. L$^1$ is a bond and R$^1$ is 4 to 12 (e.g. a 4 to 7)-membered saturated or partially saturated heterocyclyl containing 1 ring nitrogen and optionally 1 or 2 additional ring heteroatoms selected from O, S and N, wherein said heterocyclyl is bonded to the carbonyl group by a ring nitrogen atom in the heterocyclyl, wherein said heterocyclyl is optionally substituted by one or more (e.g. 1 or 2) substituents selected from halo, C$_{1-4}$ alkyl, C$_{1-4}$ haloalkyl, —OR$^{A1}$, —NR$^{A1}$R$^{B1}$, —C(O)R$^{18}$, —C(O)OR$^{A1}$, —C(O)NR$^{A1}$R$^{B1}$ and —S(O)$_2$R$^{A1}$.
145. L$^1$ is a bond and R$^1$ is selected from:

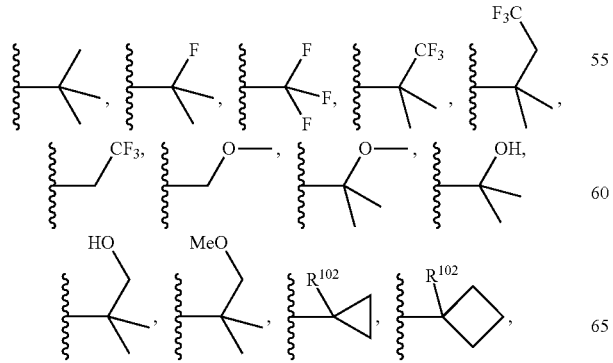

wherein R$^{101}$ is independently selected from: H, C$_{1-4}$ alkyl, C$_{1-4}$ haloalkyl, —SO$_2$R$^{A1}$, —C(O)R$^{A1}$, —C(O)NR$^{A1}$R$^{B1}$ and —SO$_2$NR$^{A1}$R$^{B1}$;
each R$^{102}$ is independently selected from halo, C$_{1-4}$ alkyl, C$_{1-4}$ haloalkyl, —OR$^{A1}$, —NR$^{A1}$R$^{B1}$ and =O; and
each q is in integer 0, 1 or 2
146. L$^1$ is —O— or —N(R$^{10}$)— and L$^1$ is bonded to a carbon atom in R$^1$.
147. L$^1$ is —O— or —N(R$^{10}$)— and L$^1$ is selected from: methyl, ethyl, propyl, isopropyl,

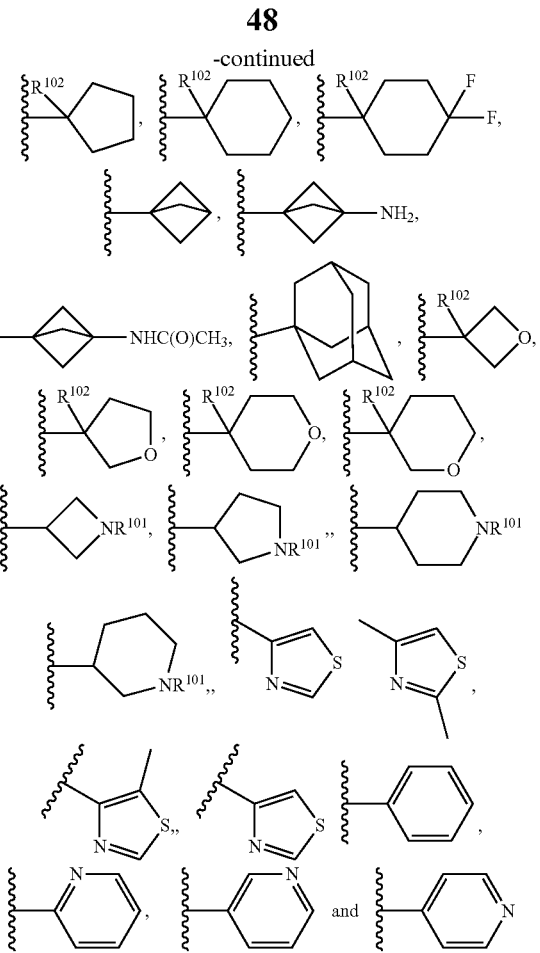

wherein
R$^{101}$ is independently selected from: H, C$_{1-4}$ alkyl, C$_{1-4}$ haloalkyl, —OR$^{A1}$, —C$_{2-4}$ alkyl-NR$^{A1}$R$^{B1}$, —C$_{1-4}$ alkyl-, —C(O)NR$^{A1}$R$^{B1}$, —C$_{1-4}$ alkyl-NR$^{A1}$C(O)R$^{B1}$, —C$_{1-4}$ alkyl-C(O)OR$^{A1}$, —C$_{1-4}$ alkyl-OC(O)R$^{A1}$, —S(O)$_2$R$^{18B}$, —C(O)R$^{18B}$, —C(O)NR$^{A1}$R$^{18B}$, and
R$^{17F}$ is selected from C$_{3-6}$ cycloalkyl, C$_{3-6}$ cycloalkyl-C$_{1-3}$ alkyl-, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, morpholinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_{1-3}$ alkyl-;
R$^{18B}$ is selected from C$_{1-4}$ alkyl, C$_{1-4}$ haloalkyl, C$_{3-6}$ cycloalkyl, C$_{3-6}$ cycloalkyl-C$_{1-3}$ alkyl, azetidinyl, pyrrolidinyl, piperidinyl, piperazinyl, morpholinyl, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_{1-3}$ alkyl-;
wherein R$^{17F}$ and R$^{18B}$ are each independently optionally substituted one or more substituents independently selected from: halo, C$_{1-4}$ alkyl, C$_{1-4}$ haloalkyl, —OR$^{A6}$, —NR$^{A6}$R$^{B6}$, —C(O)R$^{A6}$, —C(O)OR$^{A6}$ and —C(O)NR$^{A6}$R$^{B6}$
(for example, R$^{101}$ is selected from: H, C$_{1-4}$ alkyl, —SO$_2$R$^{A1}$, —C(O)R$^{A1}$, —C(O)NR$^{A1}$R$^{B1}$ and —SO$_2$NR$^{A1}$R$^{B1}$); and $R^{102}$ is selected from H, $C_{1-3}$ alkyl and $C_{1-3}$ haloalkyl (e.g. $R^{102}$ is H. e.g. $R^{102}$ is $C_{1-3}$ alkyl. e.g. $R^{102}$ is —$CF_3$).

148. The group of the formula:

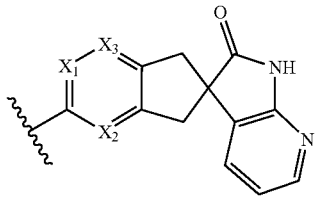

in the compounds of the formulae (I), (II), (III), (IV), (V), (VI) or (VII) is:

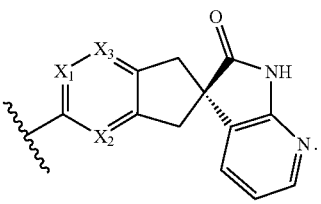

149. The group of the formula:

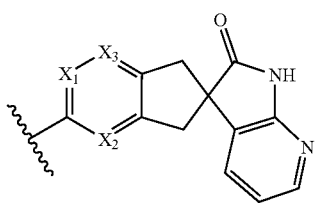

in the compounds of the formulae (I), (II), (III), (IV), (V), (VI) or (VII) is:

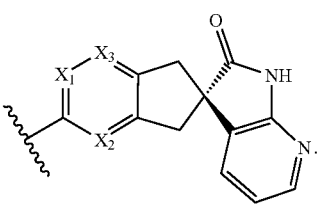

150.
151. The group of the formula:

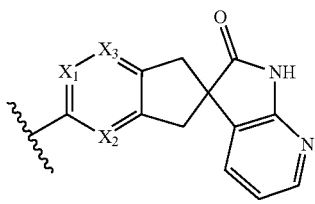

in the compounds of the formulae (I), (II), (III), (IV), (V), (VI) or (VII) is:

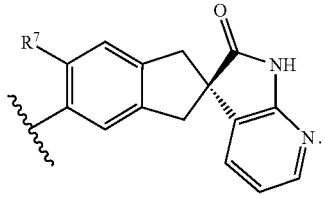

wherein $R^7$ has any of the values defined herein. For example, it may be that $R^7$ is hydrogen, halo or $C_{1-3}$ alkyl. It may be that $R^7$ is hydrogen. It may be that $R^7$ is $C_{1-3}$ alkyl, for example methyl. It may be that $R^7$ is halo, for example fluoro.

152. The group of the formula:

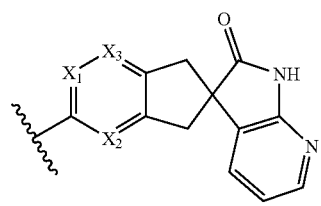

in the compounds of the formulae (I), (II), (III), (IV), (V), (VI) or (VII) is:

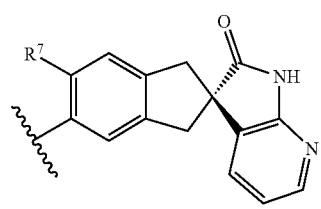

wherein $R^7$ has any of the values defined herein. For example, it may be that $R^7$ is hydrogen, halo or $C_{1-3}$ alkyl. It may be that $R^7$ is hydrogen. It may be that $R^7$ is $C_{1-3}$ alkyl, for example methyl. It may be that $R^7$ is halo, for example fluoro.

In certain embodiments in the compound of the formula (I), $X_2$ and $X_3$ are CH and $X_1$ is $CR^7$.

In certain embodiments in the compound of the formula (I), (II), (III) (IV), (V), (VI) or (VII):
X is selected from: —$CH_2$—, —$CH(CH_3)$—, —$CH_2CH_2$—, —C(=NOH)—,

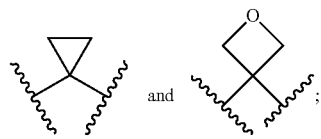 [SMILES: *C1(*)CC1 ; *C1(*)COC1]

$R^2$ is selected from: H, methyl and ethyl (for example $R^2$ is H, or $R^2$ is methyl);
$R^3$ is selected from: H, $C_{1-4}$ alkyl, $C_{1-4}$ fluoroalkyl, $C_{3-6}$ cycloalkyl (for example cyclopropyl or cyclobutyl), $C_{2-3}$ alkyl substituted by —$NR^{11}R^{12}$ and $C_{2-3}$ alkyl substituted by —$OR^{13}$, wherein $R^{11}$, $R^{12}$ and $R^{13}$ are independently selected from H and $C_{1-3}$ alkyl;
or $R^2$ and $R^3$ together with the nitrogen atom to which they are attached form a heterocyclyl selected from: azetidinyl, pyrrolidinyl, piperidinyl and piperazinyl, wherein the heterocyclyl formed by $R^2$ and $R^3$ is optionally substituted by fluoro (for example $R^2$ and $R^3$ together with the nitrogen atom to which they are attached form azetidinyl, 3-fluoroazetidinyl, pyrrolidinyl, piperidinyl or piperazinyl);

or the group

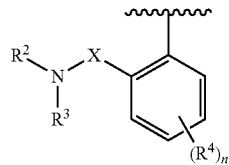

forms a group of the formula:

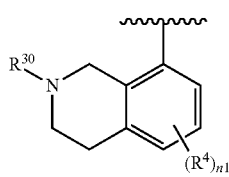

wherein $R^{30}$ is selected from: H and $C_{1-4}$ alkyl (for example $R^{30}$ is H, or $R^3$ is methyl);

n1 is an integer 0, 1, 2 or 3 and, when present, $R^4$ is located on the phenyl ring (for example n is 0);

$R^5$, $R^6$, $R^8$ and $R^9$ are each independently H or $C_{1-3}$ alkyl (for example H or methyl and particularly H).

In certain embodiments in the compound of the formula (I), (II), (III) (IV), (V), (VI) or (VII):

X is selected from: —$CH_2$—, —$CH(CH_3)$—, —$CH_2CH_2$— and —$C(=NOH)$—;

the group —$NR^2R^3$ is selected from: —$NH_2$, —NH(Me) —NH(Et), —$NH(CH_2CH_2OH)$, —$NH(CH_2CH_2OMe)$, —$NH(CH_2CH_2F)$, —NH(cyclopropyl), —NH(cyclobutyl), azetidin-1-yl, 3-fluoroazetidin-1-yl, pyrrolidin-1-yl, piperidin-1yl and piperazin-1-yl (e.g. —$NR^2R^3$ is selected from —NH(Me) and azetidin-1-yl, preferably —$NR^2R^3$ is —NH(Me));

or the group

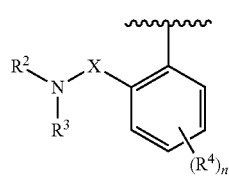

forms a group of the formula:

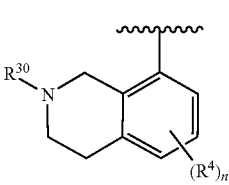

wherein $n_1$ is an integer 0, 1, 2 or 3 and, when present, $R^4$ is located on the phenyl ring (for example $n_1$ is 0);

or the group

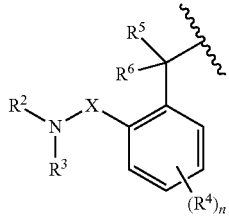

forms a group of the formula:

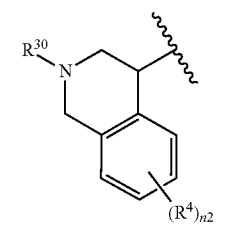

wherein $n_2$ is an integer 0, 1 or 2 (e.g. $n_2$ is 0) and, when present, $R^1$ is located on the phenyl ring;

$R^{30}$ is selected from: H and $C_{1-4}$ alkyl (for example $R^{30}$ is H, or $R^3$ is methyl);

$R^5$ and $R^6$ are H;

$R^8$ and $R^9$ are independently selected from: H and methyl (for example $R^8$ is H and $R^9$ is methyl; preferably both $R^8$ and $R^9$ are H);

$L^1$ is selected from a bond, —O—, and —NH— (preferably $L^1$ is a bond);

$R^4$ is selected from: $C_{1-4}$ alkyl and halo (e.g. fluoro); n is 0, 1 or 2; and $R^1$ is as defined in any one of paragraphs (102) to (140) above.

Preferably in this embodiment n is 0.

Preferably in this embodiment X is —$CH_2$—; the group —$NR^2R^3$ is —NH(Me); $L^1$ is a bond; and n is 0.

In certain embodiments in the compound of the formula (I), (II), (III) (IV), (V), (VI) or (VII):

X is selected from: —$CH_2$—, —$CH(CH_3)$— and —$CH_2CH_2$— (preferably X is —$CH_2$—);

the group —$NR^2R^3$ is selected from: —$NH_2$, —NH(Me) —NH(Et), —$NH(CH_2CH_2F)$, —NH(cyclopropyl) —NH(cyclobutyl) and azetidin-1-yl, (e.g. —$NR^2R^3$ is selected from —NH(Me) and azetidin-1-yl, preferably —$NR^2R^3$ is —NH(Me));

$R^5$ and $R^6$ are H;

$R^8$ and $R^9$ are independently selected from: H and methyl (for example $R^8$ is H and $R^9$ is methyl; preferably both $R^8$ and $R^9$ are H);

$L^1$ is a bond;

$R^4$ is halo (e.g. fluoro); n is 0 or 1 (preferably n is 0);

$X_2$ and $X_3$ are CH;
$X_1$ is N or $CR^7$ (preferably $X_1$ is CH);
$R^7$ is H or methyl;
and
$R^1$ is selected from cyclopropyl, cyclobutyl, cyclopentyl,

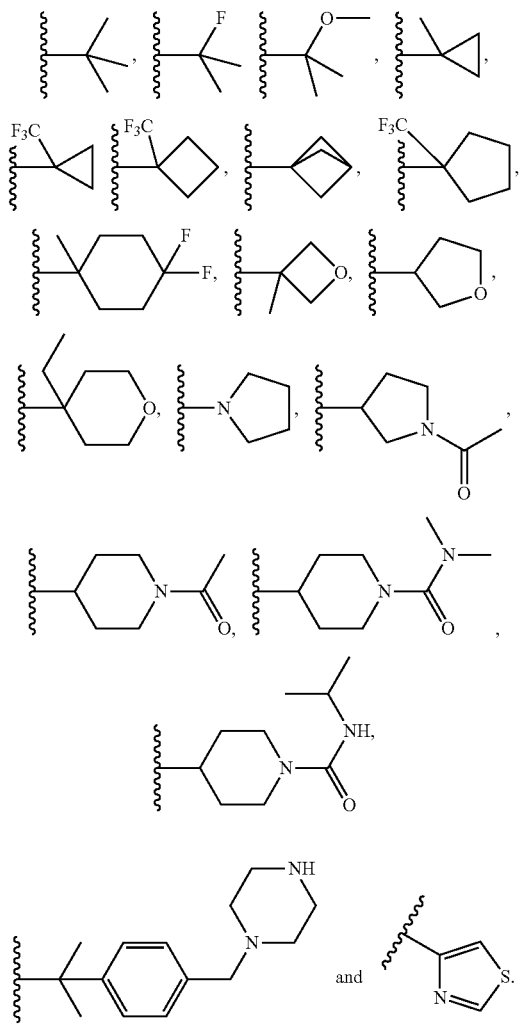

In an embodiment the compound of the formula (I) is a compound of the formula (VIII), (VIIIa) or (VIIIb), or a pharmaceutically acceptable salt thereof:

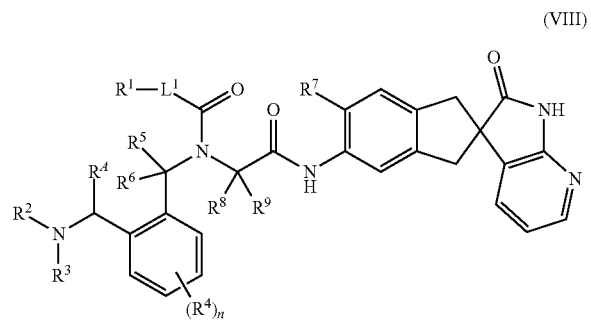

(VIII)

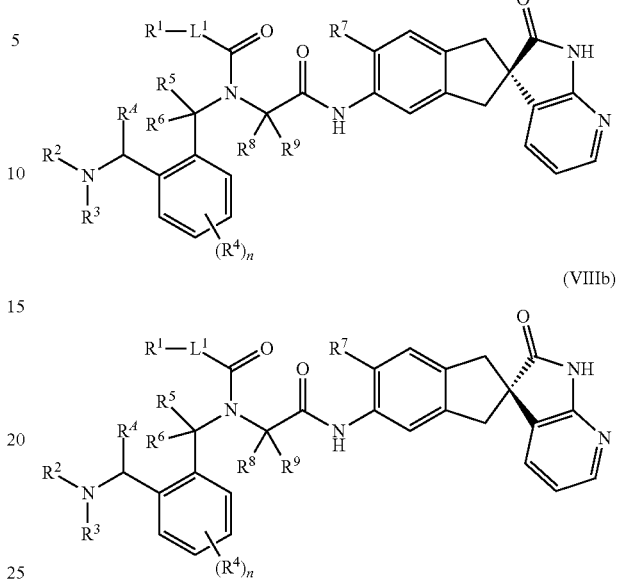

wherein
$R^4$ is H or $C_{1-3}$ alkyl;
$R^2$ is H or $C_{1-4}$ alkyl; and
$R^1$, $R^3$, $R^4$, $R^5$, $R^6$, $R^7$, $R^8$, $R^9$, $L^1$ and n have any of the meanings defined herein.

Preferably in this embodiment the compound is of the formula (VIIIa), or a pharmaceutically acceptable salt thereof.

In certain embodiments in a compound of the formula (VIII), (VIIIa) or (VIIIb): $R^2$ is H.

In certain embodiments in a compound of the formula (VIII), (VIIIa) or (VIIIb): $R^2$ is $C_{1-3}$ alkyl, for example methyl.

In certain embodiments in a compound of the formula (VIII), (VIIIa) or (VIIIb): $R^2$ is $C_{1-3}$ alkyl and $R^3$ is H.

In certain embodiments in a compound of the formula (VIII), (VIIIa) or (VIIIb): $R^2$ is $R^2$ is methyl and $R^3$ is H.

In certain embodiments in a compound of the formula (VIII), (VIIIa) or (VIIIb): $R^2$ is $C_{1-3}$ alkyl (for example $R^2$ is methyl) and $R^3$ is not H.

In certain embodiments in a compound of the formula (VIII), (VIIIa) or (VIIIb): $R^2$ and $R^3$ are independently $C_{1-3}$ alkyl (for example $R^2$ and $R^3$ are both methyl).

In certain embodiments in a compound of the formula (VIII), (VIIIa) or (VIIIb): the group $-NR^2R^3$ is azetidin-1-yl or pyrrolidin-1-yl.

In certain embodiments in a compound of the formula (VIII), (VIIIa) or (VIIIb): $R^4$ is $C_{1-3}$ alkyl (for example $R^4$ is methyl).

In certain embodiments in a compound of the formula (VIII), (VIIIa) or (VIIIb): $R^4$ is hydrogen.

In certain embodiments in a compound of the formula (VIII), (VIIIa) or (VIIIb): $R^7$ is $C_{1-3}$ alkyl (for example $R^7$ is methyl).

In certain embodiments in a compound of the formula (VIII), (VIIIa) or (VIIIb): $R^7$ is halo, for example fluoro or chloro, particularly fluoro.

In certain embodiments in a compound of the formula (VIII), (VIIIa) or (VIIIb): $R^7$ is hydrogen.

In certain embodiments in a compound of the formula (VIII), (VIIIa) or (VIIIb):
$R^4$ is H or methyl (for example $R^4$ is methyl);
$R^2$ is H or $C_{1-3}$ alkyl;
n is 0, 1 or 2 and $R^4$ is selected from: halo, $C_{1-4}$ alkyl and $C_{1-4}$ haloalkyl;
$L^1$ is a bond or —O—;
$R^1$ has any of the meaning defined herein (e.g. is as defined in relation to formula (I). e.g., as defined in any one of paragraphs (102) to (140) above);
$R^5$ and $R^6$ are each independently selected from: H, $C_{1-4}$ alkyl and $C_{1-4}$ haloalkyl;
or $R^5$ and $R^6$ together with the carbon to which they are attached form cyclopropyl, cyclobutyl or oxetanyl;
$R^8$ and $R^9$ are each independently selected from: H, $C_{1-4}$ alkyl, $C_{1-4}$ haloalkyl, —$C_{1-4}$ alkyl-$OR^{A5}$, —$C_{1-4}$ alkyl-$NR^{A5}R^{B5}$ and —$C_{1-4}$ alkyl-$SR^{A5}$, wherein $R^{A5}$ and $R^{B5}$ are each independently selected from: H, methyl and ethyl;
or $R^8$ and $R^9$ together with the carbon to which they are attached form cyclopropyl, cyclobutyl or oxetanyl;
$R^7$ is selected from: H, halo and $C_{1-4}$ alkyl (for example $R^7$ is halo or $C_{1-4}$ alkyl); and
$R^3$ is as defined in relation to formula (I).

In certain embodiments in a compound of the formula (VIII), (VIIIa) or (VIIIb):
$R^4$ is H or methyl (for example $R^4$ is methyl);
$R^2$ is H or methyl;
n is 0;
$L^1$ is a bond;
$R^1$ has any of the meanings defined herein (e.g. as defined in relation to formula (I). e.g as defined in any one of paragraphs (102) to (140) above);
$R^5$, $R^6$, $R^8$ and $R^9$ are H;
$R^7$ is H, fluoro or methyl (for example $R^7$ is fluoro or methyl); and
$R^3$ is as defined in relation to formula (I).

In certain embodiments in a compound of the formula (VIII), (VIIIa) or (VIIIb):
$R^4$ is H or methyl (for example $R^4$ is methyl);
n is 0;
$L^1$ is a bond;
$R^1$ has any of the meanings defined herein (e.g. as defined in relation to formula (I). e.g as defined in any one of paragraphs (102) to (140) above);
$R^5$, $R^6$, $R^8$ and $R^9$ are H;
$R^7$ is H, fluoro or methyl (for example $R^7$ is fluoro or methyl); and
the group —$NR^2R^3$ is selected from: —$NH_2$, —NH(Me) —NH(Et), —NH($CH_2CH_2OH$), —NH($CH_2CH_2OMe$), —NH($CH_2CH_2F$) —NH(cyclopropyl) —NH(cyclobutyl), azetidin-1-yl, 3-fluoroazetidin-1-yl, pyrrolidin-1-yl, piperidin-1yl and piperazin-1-yl (e.g. —$NR^2R^3$ is selected from —NH(Me) and azetidin-1-yl, preferably —$NR^2R^3$ is —NH(Me)).

In certain embodiments in a compound of the formula (VIII), (VIIIa) or (VIIIb):
$R^4$ is H or methyl (for example $R^4$ is methyl);
$R^2$ is H or methyl;
n is 0;
$L^1$ is —O—;
$R^1$ has any of the meanings defined herein (e.g. as defined in relation to formula (I). e.g as as defined in any one of paragraphs (102) to (140) above);
$R^7$ is selected from: H, fluoro and methyl (for example $R^7$ is fluoro or methyl); and
$R^3$ is as defined in relation to formula (I) (e.g. $R^3$ is methyl).

In certain embodiments in a compound of the formula (VIII), (VIIIa) or (VIIIb):
$R^4$ is H or methyl (for example $R^4$ is methyl);
n is 0;
$L^1$ is a bond or —O— (preferably $L^1$ is a bond);
$R^1$ is tert-butyl;
$R^2$ is H or $C_{1-3}$ alkyl;
$R^5$, $R^6$, $R^8$ and $R^9$ are H;
$R^7$ is selected from: H, fluoro and methyl (for example $R^7$ is fluoro or methyl); and
$R^3$ has any of the meanings defined herein (e.g. as defined in relation to formula (I); e.g. $R^3$ is $C_{1-3}$ alkyl).

In another embodiment the compound of the formula (I) is a compound of the formula (IX), (IXa) or (IXb), or a pharmaceutically acceptable salt thereof:

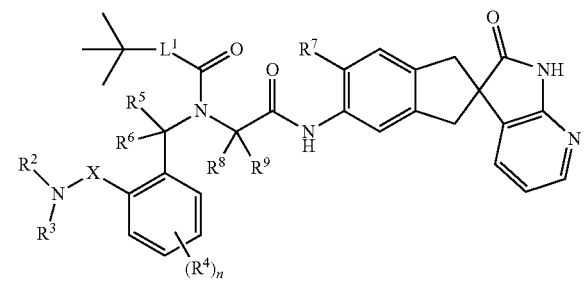

(IX)

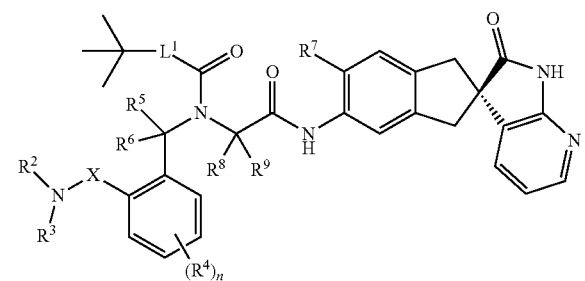

(IXa)

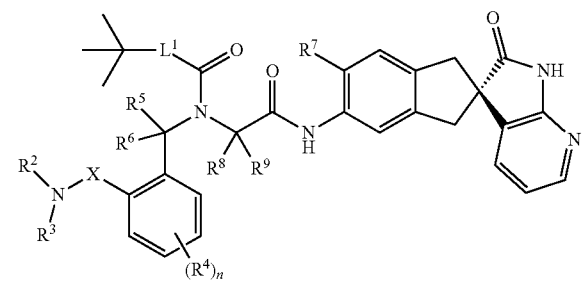

(IXb)

wherein
$R^2$, $R^3$, $R^4$, $R^5$, $R^6$, $R^7$, $R^8$, $R^9$, X, $L^1$ and n have any of the meanings defined herein.
Preferably in this embodiment the compound is a compound of the formula (IXa), or a pharmaceutically acceptable salt thereof.

In certain embodiments in a compound of the formula (IX), (IXa) or (IXb): $L^1$ is a bond.
In certain embodiments in a compound of the formula (IX), (IXa) or (IXb): $L^1$ is —O—
In certain embodiments in a compound of the formula (IX), (IXa) or (IXb): $L^1$ is —$N(R^{10})$—, wherein $R^{10}$ is H or $C_{1-4}$ alkyl (e.g. $L^1$ is —NH—).

In certain embodiments in a compound of the formula (IX), (IXa) or (IXb): $R^7$ is $C_{1-3}$ alkyl (for example $R^7$ is methyl).

In certain embodiments in a compound of the formula (IX), (IXa) or (IXb): $R^7$ is halo (for example $R^7$ is fluoro).

In certain embodiments in a compound of the formula (IX), (IXa) or (IXb): $R^7$ is hydrogen.

In certain embodiments in a compound of the formula (IX), (IXa) or (IXb):
n is 0, 1 or 2 and $R^4$ is selected from: halo, $C_{1-4}$ alkyl and $C_{1-4}$ haloalkyl;
$L^1$ is a bond or —O—;
X is selected from: —CH$_2$—, —CH(CH$_3$)—, —CH$_2$CH$_2$—,

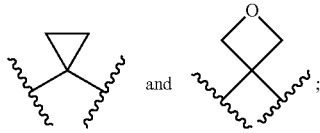 [SMILES: *C1(*)CC1 ; *C1(*)COC1]

$R^5$ and $R^6$ are each independently selected from: H, $C_{1-4}$ alkyl and $C_{1-4}$ haloalkyl;
  or $R^5$ and $R^6$ together with the carbon to which they are attached form cyclopropyl, cyclobutyl or oxetanyl;
$R^8$ and $R^9$ are each independently selected from: H, $C_{1-4}$ alkyl, $C_{1-4}$ haloalkyl, —$C_{1-4}$ alkyl-OR$^{A5}$, —$C_{1-4}$ alkyl-NR$^{A5}$R$^{B5}$ and —$C_{1-4}$ alkyl-SR$^{A5}$, wherein R$^{A5}$ and R$^{B5}$ are each independently selected from: H, methyl and ethyl;
  or $R^8$ and $R^9$ together with the carbon to which they are attached form cyclopropyl, cyclobutyl or oxetanyl;
$R^7$ is selected from: H, halo and $C_{1-4}$ alkyl; and
$R^2$ and $R^3$ have any of the meanings defined herein (e.g. as defined in relation to formula (I)).

In certain embodiments in a compound of the formula (IX), (IXa) or (IXb):
n is 0;
$L^1$ is a bond or —O—;
X is selected from: —CH$_2$—, —CH(CH$_3$)—, —CH$_2$CH$_2$—;
$R^5$, $R^6$, $R^8$ and $R^9$ are H;
$R^7$ is H or methyl;
$R^2$ is H or $C_{1-3}$ alkyl; and
$R^3$ has any of the meanings defined herein (e.g. as defined in relation to formula (I)).

In certain embodiments in a compound of the formula (IX), (IXa) or (IXb):
n is 0;
$L^1$ is a bond;
X is selected from: —CH$_2$—, —CH(CH$_3$)—, —CH$_2$CH$_2$—;
$R^5$ and $R^6$ are H;
$R^8$ and $R^9$ are H or methyl (e.g. $R^8$ and $R^9$ are both H; e.g. $R^8$ is H and $R^9$ is methyl);
$R^7$ is H, F or methyl; and
the group —NR$^2$R$^3$ is selected from —NH$_2$, —NH(Me), —NH(Et), —NH(CH$_2$CH$_2$OH), —NH(CH$_2$CH$_2$OMe), —NH(CH$_2$CH$_2$F) —NH(cyclopropyl) —NH(cyclobutyl), azetidin-1yl, 3-fluoroazetidin-1-yl, pyrrolidin-1-yl, piperidin-1yl and piperazin-1-yl (e.g. —NR$^2$R$^3$ is selected from —NH(Me) and azetidin-1-yl, preferably —NR$^2$R$^3$ is —NH(Me)).

In another embodiment the compound of the formula (I) is a compound of the formula (X), (Xa) or (Xb), or a pharmaceutically acceptable salt thereof:

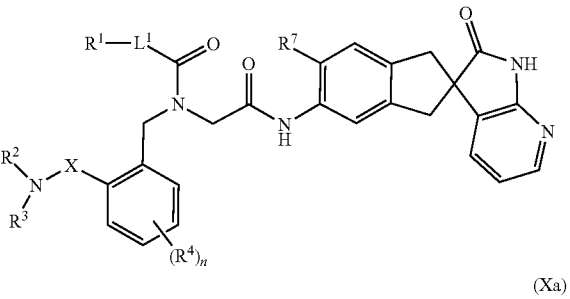

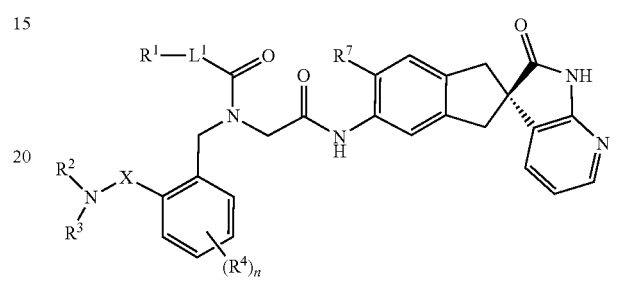

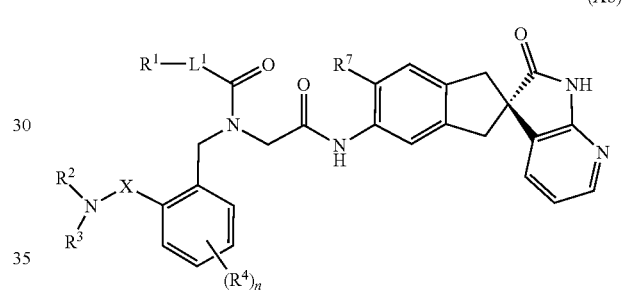

wherein
$R^2$, $R^3$, $R^4$, $R^7$, X, $L^1$ and n have any of the meanings defined herein (e.g. as defined in relation to the compound of formula (I)); and
$R^7$ is halo or $C_{1-4}$ alkyl (for example methyl).

Preferably in this embodiment the compound is a compound of the formula (Xa), or a pharmaceutically acceptable salt thereof.

In certain embodiments in a compound of the formula (X), (Xa) or (Xb) $R^7$ is halo, for example fluoro.

In certain embodiments in a compound of the formula (X), (Xa) or (Xb) $R^7$ is $C_{1-4}$ alkyl (for example methyl).

In certain embodiments in a compound of the formula (X), (Xa) or (Xb) $L^1$ is a bond.

In certain embodiments in a compound of the formula (X), (Xa) or (Xb) $L^1$ is —O—.

In certain embodiments in a compound of the formula (X), (Xa) or (Xb) $L^1$ is —NH—

In certain embodiments in a compound of the formula (X), (Xa) or (Xb) $R^1$ is as defined in any one of paragraphs (102) to (140) above.

In certain embodiments in a compound of the formula (X), (Xa) or (Xb):
$R^7$ is $C_{1-4}$ alkyl (for example methyl);
n is 0, 1 or 2 and $R^4$ is selected from: halo, $C_{1-4}$ alkyl and $C_{1-4}$ haloalkyl;

X is selected from: —CH$_2$—, —CH(CH$_3$)—, —CH$_2$CH$_2$—,

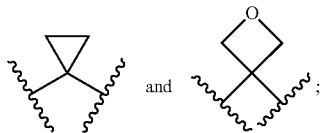 [SMILES: *C1(*)CC1 ; *C1(*)COC1]

L$^1$ is a bond or O;
R$^1$ is as defined in any one of paragraphs (102) to (140) above; and
R$^2$ and R$^3$ are as defined in relation to formula (I).

In certain embodiments in a compound of the formula (X), (Xa) or (Xb):
R$^7$ is C$_{1-4}$ alkyl (for example methyl) or halo (for example fluoro);
n is 0 or 1 and R$^4$ is selected from: halo, C$_{1-4}$ alkyl and C$_{1-4}$ haloalkyl;
X is selected from: —CH$_2$—, —CH(CH$_3$)— and —CH$_2$CH$_2$—;
L$^1$ is a bond or —O—;
R$^1$ is as defined in any one of paragraphs (102) to (140) above;
R$^2$ is H or C$_{1-3}$ alkyl; and
R$^3$ has any of the meanings defined herein (e.g. as defined in relation to formula (I)).

In certain embodiments in a compound of the formula (X), (Xa) or (Xb):
R$^7$ is C$_{1-4}$ alkyl (for example methyl) or halo (for example fluoro);
n is 0;
X is selected from: —CH$_2$—, —CH(CH$_3$)— and —CH$_2$CH$_2$—;
L$^1$ is a bond;
R$^1$ is as defined in any one of paragraphs (102) to (140) above; and
the group —NR$^2$R$^3$ is selected from: —NH$_2$, —NH(Me) —NH(Et), —NH(CH$_2$CH$_2$OH), —NH(CH$_2$CH$_2$OMe), —NH(CH$_2$CH$_2$F) —NH(cyclopropyl) —NH(cyclobutyl), azetidin-1-yl, 3-fluoroazetidin-1-yl, pyrrolidin-1-yl, piperidin-1yl and piperazin-1-yl (e.g. —NR$^2$R$^3$ is selected from —NH(Me) and azetidin-1-yl, preferably —NR$^2$R$^3$ is —NH(Me)).

In certain embodiments there is provided any of the embodiments of the formulae (VIII), (VIIIa), (VIIIb), (IX), (IXa), (IXb), (X), (Xa) and (Xb) described above, wherein R$^3$ may have any of the values defined herein, for example R$^3$ is as defined in any one of paragraphs (36) to (73).

In certain embodiments there is provided any of the embodiments of the formulae (VIII), (VIIIa), (VIIIb), (IX), (IXa), (IXb), (X), (Xa) and (Xb) described above, wherein R$^3$ may have any of the values defined herein, for example:
A. R$^3$ is selected from: H, C$_{1-4}$ alkyl, C$_{2-4}$ alkenyl, C$_{2-4}$ alkynyl, C$_{1-4}$ haloalkyl, C$_{3-6}$ cycloalkyl, C$_{3-6}$ cycloalkyl-C$_{1-3}$ alkyl-, 4 to 7 membered heterocyclyl, 4 to 7 membered heterocyclyl-C$_{1-3}$ alkyl-, phenyl-C$_{1-3}$ alkyl-, 5 or 6 membered heteroaryl-C$_{1-3}$ alkyl-, C$_{2-4}$ alkyl substituted by —NR$^{11}$R$^{12}$ and C$_{2-4}$ alkyl substituted by —OR$^{13}$, wherein R$^{11}$, R$^{12}$ and R$^{13}$ are independently selected from: H, C$_{1-4}$ alkyl and C$_{1-4}$ haloalkyl, or R$^{11}$ and R$^{12}$ together with the nitrogen to which they are attached form a 4 to 6 membered heterocyclyl;
and wherein R$^3$ is optionally further substituted by one or more substituents (for example 1, 2 or 3) independently selected from: halo, C$_{1-4}$ alkyl, C$_{1-4}$ haloalkyl, C$_{3-6}$ cycloalkyl, —OR$^{A2}$, —NR$^{A2}$R$^{B2}$, —S(O)$_x$R$^{A2}$, wherein x is 0, 1 or 2, —C(O)R$^{A2}$, —OC(O)R$^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, =O, —CN and —NO$_2$; or
B. R$^3$ is selected from: C$_{1-4}$ alkyl, C$_{2-4}$ alkenyl, C$_{1-4}$ fluoroalkyl, C$_{3-6}$ cycloalkyl, C$_{3-6}$ cycloalkyl-C$_{1-3}$ alkyl-, C$_{2-3}$ alkyl substituted by —NR$^{11}$R$^{12}$ and C$_{2-3}$ alkyl substituted by —OR$^{13}$, wherein R$^{11}$, R$^{12}$ and R$^{13}$ are independently selected from: H, C$_{1-4}$ alkyl and C$_{1-4}$ haloalkyl; or
C. R$^3$ is selected from: H, C$_{1-4}$ alkyl, C$_{1-4}$ fluoroalkyl, C$_{3-6}$ cycloalkyl (for example cyclopropyl or cyclobutyl), C$_{2-3}$ alkyl substituted by —NR$^{11}$R$^{12}$ and C$_{2-3}$ alkyl substituted by —OR$^{13}$, wherein R$^{11}$, R$^{12}$ and R$^{13}$ are independently selected from H and C$_{1-3}$ alkyl; or
D. R$^3$ is selected from: C$_{1-3}$ alkyl, C$_{1-3}$ fluoroalkyl, cyclopropyl, cyclobutyl, cyclopropyl-C$_{1-2}$ alkyl-, cyclobutyl-C$_{1-2}$ alkyl-, 2-hydroxyethyl, 2-methoxyethyl, 2-aminoethyl, 2-(methylamino)ethyl, 2-(dimethylamino)ethyl, 3-aminopropyl, 3-(methylamino)propyl and 3-(dimethylamino)propyl; or
E. R$^3$ is selected from: methyl, ethyl, isopropyl, 2-fluoroethyl, 2-methoxyethyl, 2-hydroxyethyl, cyclopropyl, cyclobutyl; or
F. R$^3$ is H; or
G. R$^2$ and R$^3$ together with the nitrogen atom to which they are attached form a heterocyclyl selected from: azetidinyl, pyrrolidinyl, piperidinyl and piperazinyl, wherein the heterocyclyl formed by R$^2$ and R$^3$ is optionally substituted by fluoro (for example R$^2$ and R$^3$ together with the nitrogen atom to which they are attached form azetidinyl, 3-fluoroazetidinyl, pyrrolidinyl, piperidinyl or piperazinyl);
H. the group

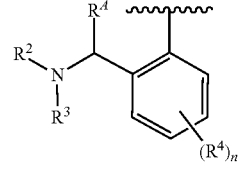

forms a group of the formula:

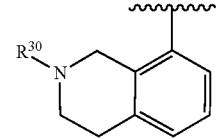

wherein
R$^{30}$ selected from: H and C$_{1-4}$ alkyl (for example R$^{30}$ is H, or R$^{30}$ is methyl);
I. R$^3$ is selected from —C(=NH)NH$_2$, —C(=NR$^{49}$)NH$_2$, —C(=NH)NHR$^{49}$, —C(=NH)N(R$^{49}$)$_2$, —C(=NR$^{49}$)NHR$^{49}$, —C(=NR$^{49}$)N(R$^{49}$)$_2$, —C(=NH)R$^{49}$, —C(=NR$^{49}$)R$^{49}$, —C(=NCN)NH$_2$, —C(=NCN)NHR$^{49}$, —C(=NCN)N(R$^{49}$)$_2$; wherein R$^{47}$ and each R$^{49}$ are independently selected from C$_{1-4}$ alkyl.

In further embodiments, it may be that in embodiments A to I described above that R$^2$ is selected from: H and C$_{1-4}$ alkyl. For example, R$^2$ may be H. For example, R$^2$ may be C$_{1-4}$ alkyl. For example R$^2$ is methyl or ethyl. For example R$^2$ is H or methyl.

In certain embodiments there is provided any of the embodiments of the formulae (I), (II), (III), (IV), (V), (VI), (VII), (VIII), (VIIIa), (VIIIb), (IX), (IXa), (IXb), (X), (Xa) and (Xb) described above, the group

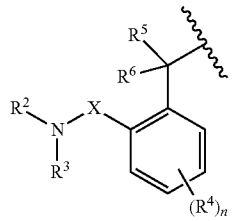

forms a group of the formula:

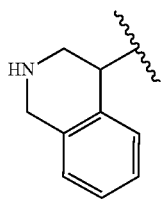

In certain embodiments there is provided any of the embodiments of the formulae (I), (II), (III), (IV), (V), (VI), (VII), (VIII), (VIIIa), (VIIIb), (X), (Xa) and (Xb) described above, wherein:
$L^1$ is a bond;
$R^1$ is selected from $C_{1-4}$alkyl, —$C_{1-4}$ alkyl-$OR^{41}$, wherein $R^{41}$ is H or $C_{1-3}$ alkyl, $C_{1-4}$ fluoroalkyl, $C_{3-8}$ cycloalkyl, oxetanyl, thiazolyl, wherein the $C_{3-5}$ cycloalkyl, oxetanyl, thiazolyl are each independently substituted by $C_{1-3}$ alkyl (for example methyl);
X is —$CH_2$— or —$CH(CH_3)$—;
$R^2$ is H or methyl;
$R^3$ is selected from: H, $C_{1-3}$ alkyl, fluoroethyl or cyclopropyl (for example H or $C_{1-3}$ alkyl); or
$R^2$ and $R^3$ together with the nitrogen to which they are attached form azetidinyl;
$R^4$ is fluoro and n is 0, or 1;
$R^5$ and $R^8$ are H;
$R^6$ and $R^9$ are independently selected from H and methyl; and
$R^7$ is H or methyl.

In another embodiment the compound of the formula (I) is a compound of the formula (XI), (XIa) or (XIb), or a pharmaceutically acceptable salt thereof:

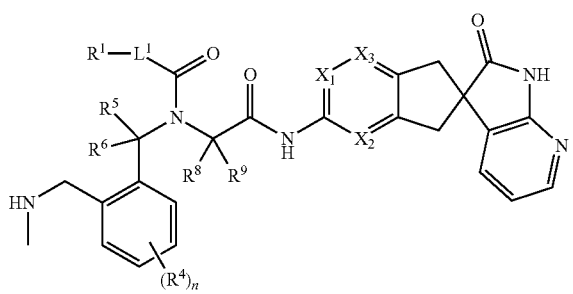

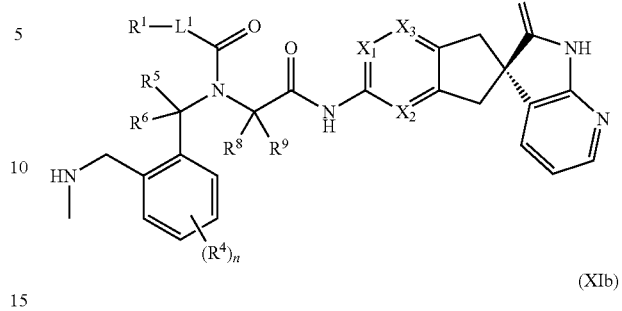

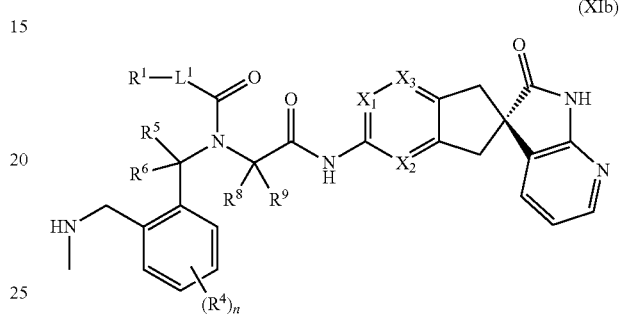

wherein:
$X_1, X_2, X_3, R^1, R^4, R^5, R^6, R^8, R^9, L^1$ and n have any of the meanings defined herein.

It may be that in a compound of the formula (XI), (XIa) or (XIb), $R^1$ is as defined in any one of paragraphs (102) to (140) above.

It may be that in a compound of the formula (XI), (XIa) or (XIb),
$X_1$ is N or $CR^7$;
$X_2$ and $X_3$ are each independently N or CH, provided that no more than one of $X_1$, $X_2$ and $X_3$ is N;
$R^7$ selected from H, halo and $C_{1-3}$ alkyl (e.g. $R^7$ is H, F or methyl);
$R^5$ and $R^6$ are H;
$R^8$ and $R^9$ are independently selected from: H and methyl (for example $R^8$ is H and $R^9$ is methyl; preferably both $R^8$ and $R^9$ are H);
$L^1$ is selected from a bond, —O—, and —NH— (preferably $L^1$ is a bond);
$R^4$ is selected from: $C_{1-4}$ alkyl and halo (e.g. fluoro); n is 0, 1 or 2; and
$R^1$ is as defined in any one of paragraphs (102) to (140) above.

Preferably in these embodiments the compound is a compound of the formula (XIa), or a pharmaceutically acceptable salt thereof.

Preferably in these embodiments n is 0.

Preferably in these embodiments $X_2$ and $X_3$ are CH and $X_1$ is $CR^7$.

Preferably in these embodiments $X_2$ and $X_3$ are CH, $X_1$ is $CR^7$ and is 0.

In another embodiment there is provided a compound selected from Table 1 or Table 2, or a pharmaceutically acceptable salt, or prodrug thereof:

TABLE 1
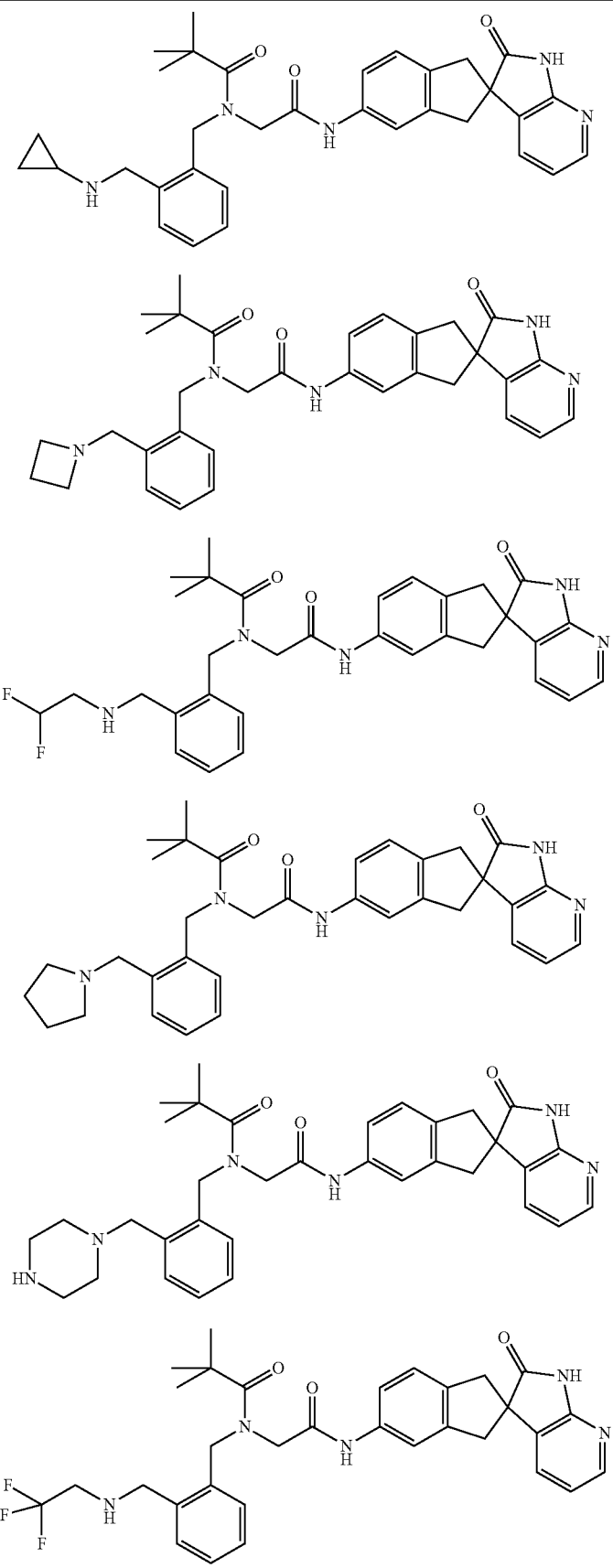

TABLE 1-continued
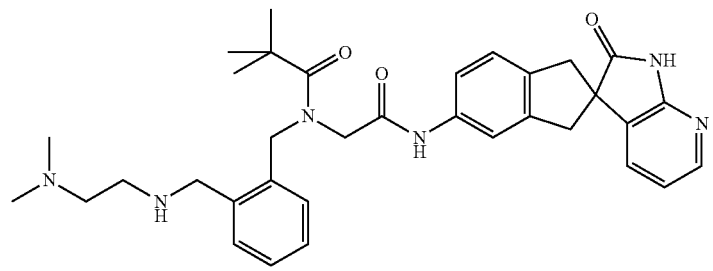 [SMILES: CN(C)CCNCc1ccccc1CN(CC(=O)Nc1ccc2c(c1)CC1(C2)C(=O)Nc2ncccc21)C(=O)C(C)(C)C]
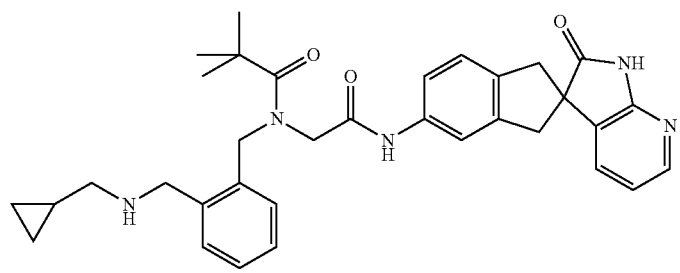 [SMILES: CC(C)(C)C(=O)N(CC(=O)Nc1ccc2c(c1)CC1(C2)C(=O)Nc2ncccc21)Cc1ccccc1CNCC1CC1]
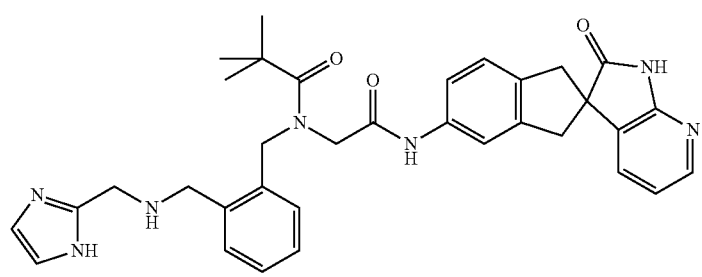 [SMILES: CC(C)(C)C(=O)N(CC(=O)Nc1ccc2c(c1)CC1(C2)C(=O)Nc2ncccc21)Cc1ccccc1CNCc1ncc[nH]1]
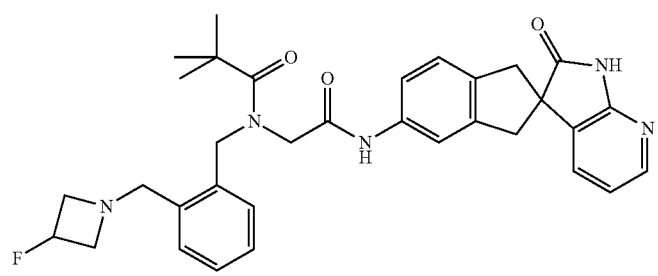 [SMILES: CC(C)(C)C(=O)N(CC(=O)Nc1ccc2c(c1)CC1(C2)C(=O)Nc2ncccc21)Cc1ccccc1CN1CC(F)C1]
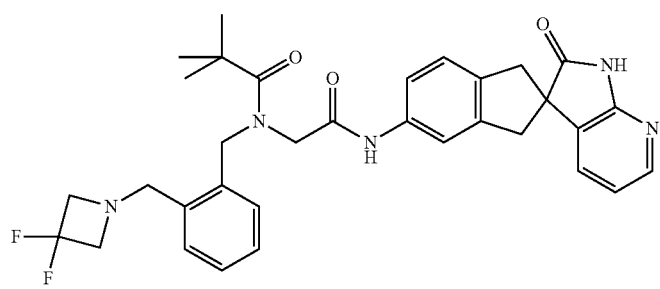 [SMILES: CC(C)(C)C(=O)N(CC(=O)Nc1ccc2c(c1)CC1(C2)C(=O)Nc2ncccc21)Cc1ccccc1CN1CC(F)(F)C1]

TABLE 1-continued
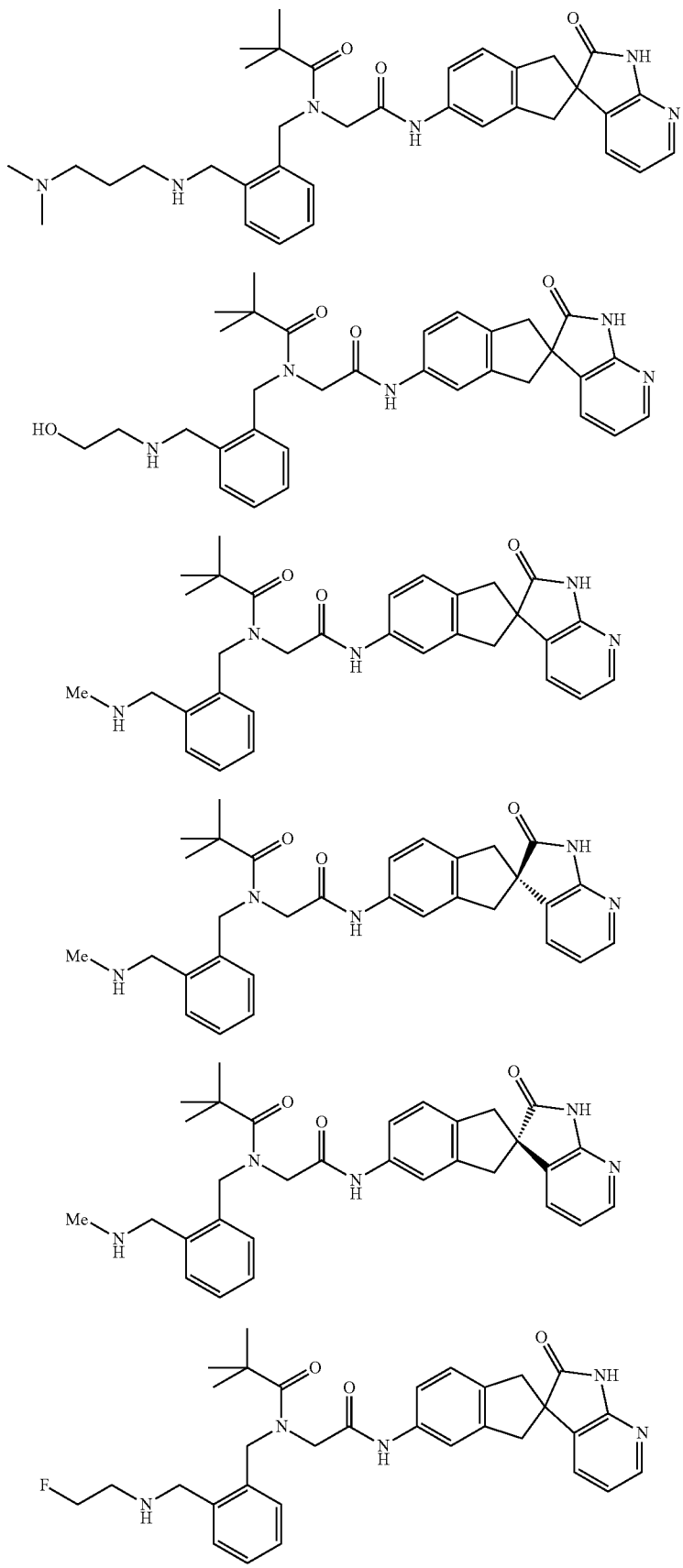

TABLE 1-continued
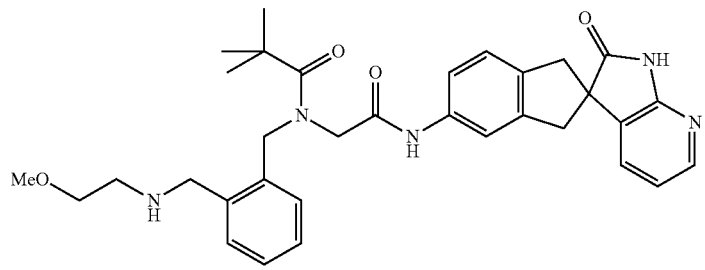 [SMILES: COCCNCc1ccccc1CN(CC(=O)Nc1ccc2c(c1)CC1(C2)C(=O)Nc2ncccc21)C(=O)C(C)(C)C]
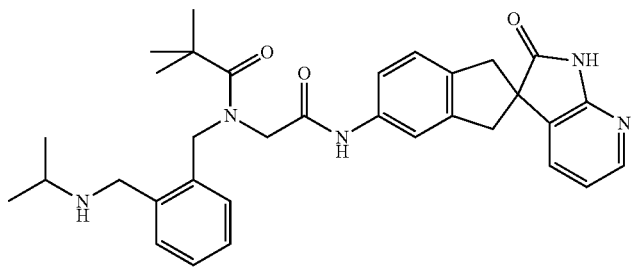 [SMILES: CC(C)NCc1ccccc1CN(CC(=O)Nc1ccc2c(c1)CC1(C2)C(=O)Nc2ncccc21)C(=O)C(C)(C)C]
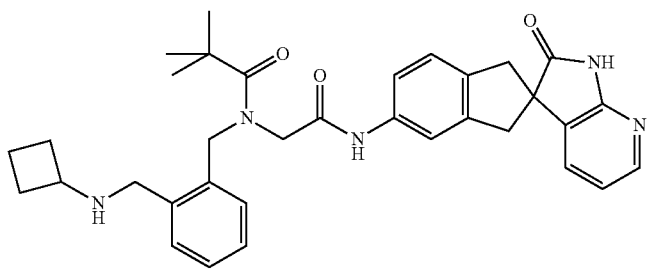 [SMILES: CC(C)(C)C(=O)N(CC(=O)Nc1ccc2c(c1)CC1(C2)C(=O)Nc2ncccc21)Cc1ccccc1CNC1CCC1]
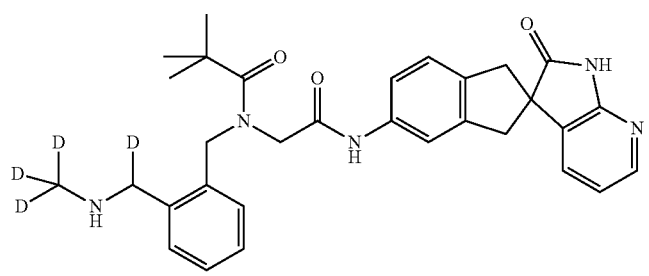 [SMILES: [2H]C(NC([2H])([2H])[2H])c1ccccc1CN(CC(=O)Nc1ccc2c(c1)CC1(C2)C(=O)Nc2ncccc21)C(=O)C(C)(C)C]
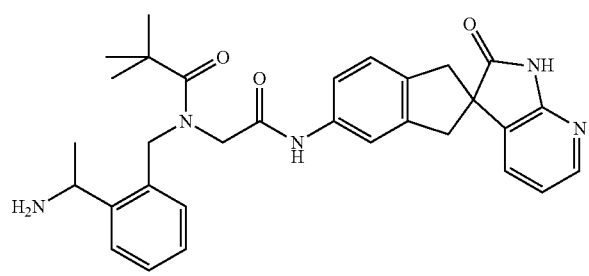 [SMILES: CC(N)c1ccccc1CN(CC(=O)Nc1ccc2c(c1)CC1(C2)C(=O)Nc2ncccc21)C(=O)C(C)(C)C]

TABLE 1-continued
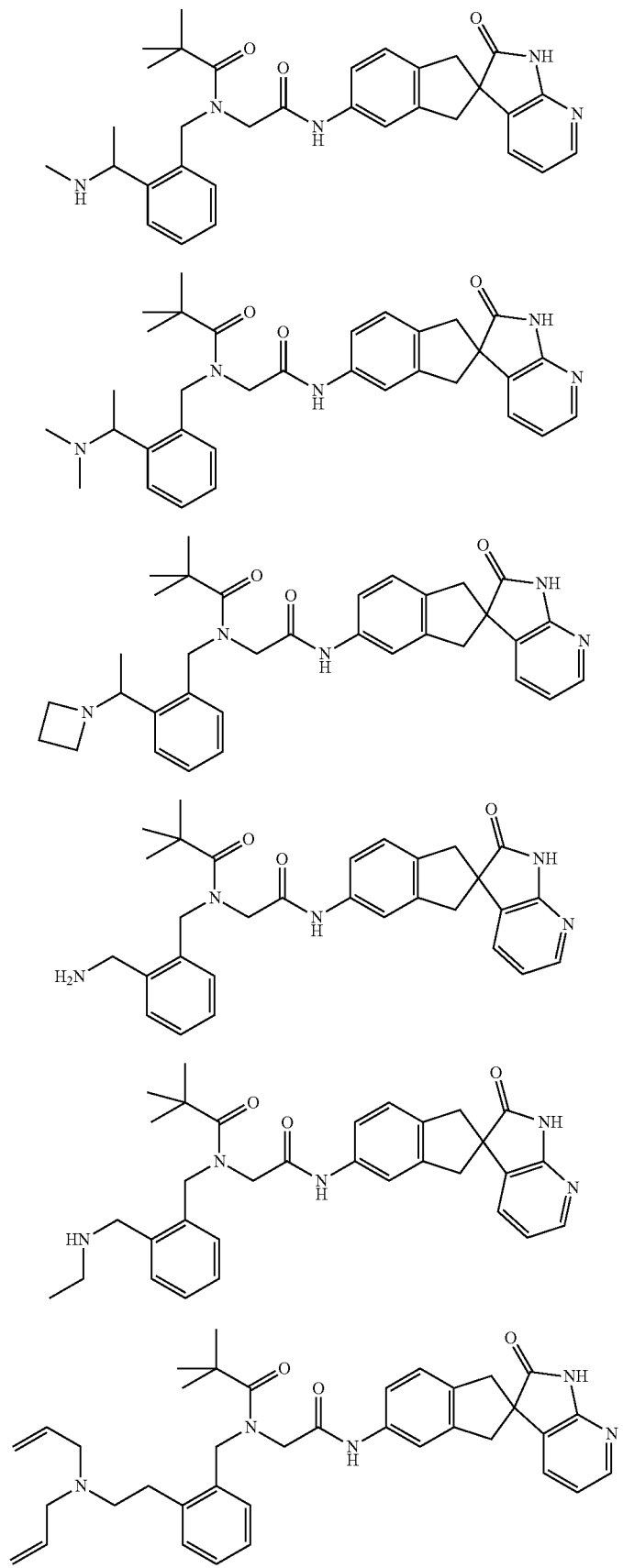

TABLE 1-continued
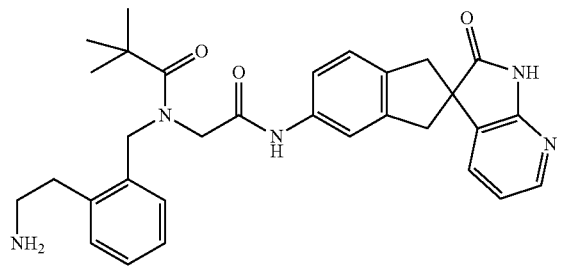 [SMILES: CC(C)(C)C(=O)N(CC(=O)Nc1ccc2c(c1)CC1(C2)C(=O)Nc2ncccc21)Cc1ccccc1CCN]
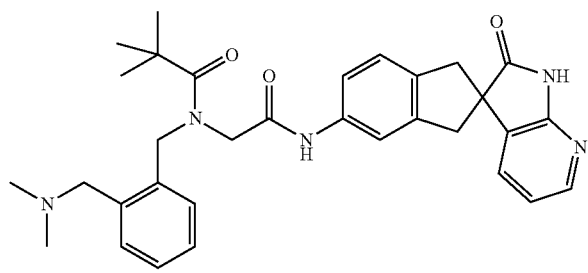 [SMILES: CN(C)Cc1ccccc1CN(CC(=O)Nc1ccc2c(c1)CC1(C2)C(=O)Nc2ncccc21)C(=O)C(C)(C)C]
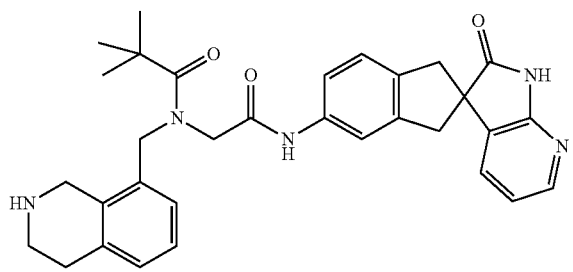 [SMILES: CC(C)(C)C(=O)N(CC(=O)Nc1ccc2c(c1)CC1(C2)C(=O)Nc2ncccc21)Cc1cccc2c1CNCC2]
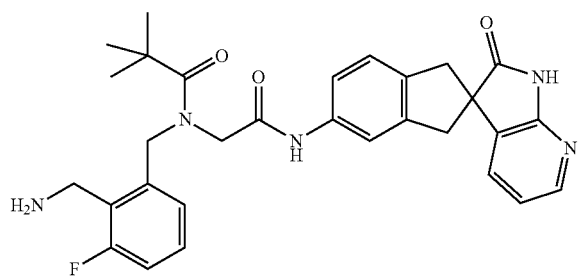 [SMILES: CC(C)(C)C(=O)N(CC(=O)Nc1ccc2c(c1)CC1(C2)C(=O)Nc2ncccc21)Cc1cccc(F)c1CN]
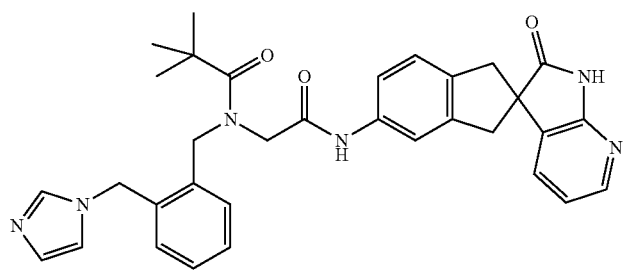 [SMILES: CC(C)(C)C(=O)N(CC(=O)Nc1ccc2c(c1)CC1(C2)C(=O)Nc2ncccc21)Cc1ccccc1Cn1ccnc1]

TABLE 1-continued
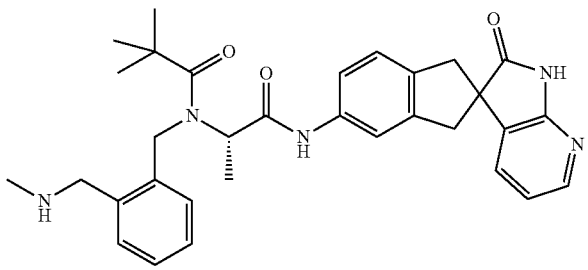 [SMILES: CNCc1ccccc1CN(C(=O)C(C)(C)C)[C@@H](C)C(=O)Nc1ccc2c(c1)CC1(C2)C(=O)Nc2ncccc21]
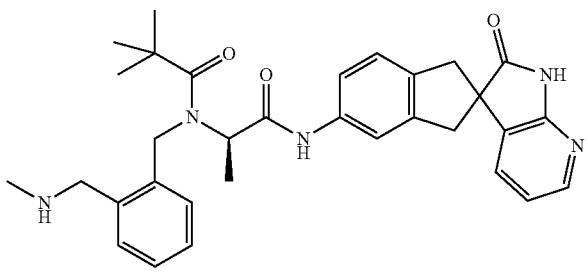 [SMILES: CNCc1ccccc1CN(C(=O)C(C)(C)C)[C@H](C)C(=O)Nc1ccc2c(c1)CC1(C2)C(=O)Nc2ncccc21]
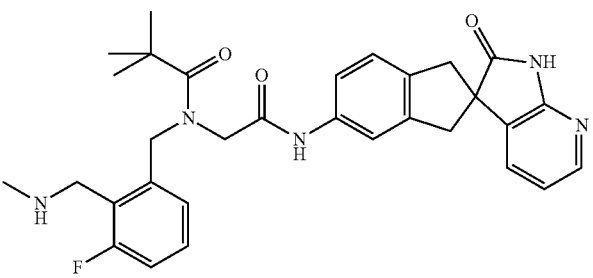 [SMILES: CNCc1c(F)cccc1CN(CC(=O)Nc1ccc2c(c1)CC1(C2)C(=O)Nc2ncccc21)C(=O)C(C)(C)C]
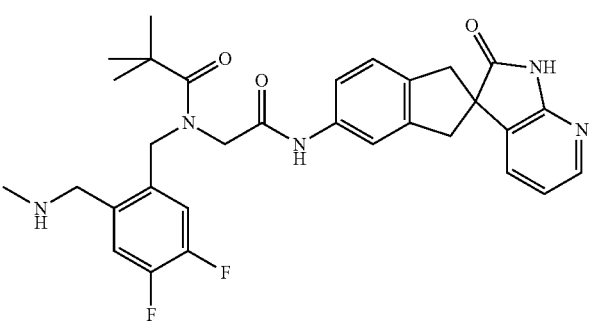 [SMILES: CNCc1cc(F)c(F)cc1CN(CC(=O)Nc1ccc2c(c1)CC1(C2)C(=O)Nc2ncccc21)C(=O)C(C)(C)C]
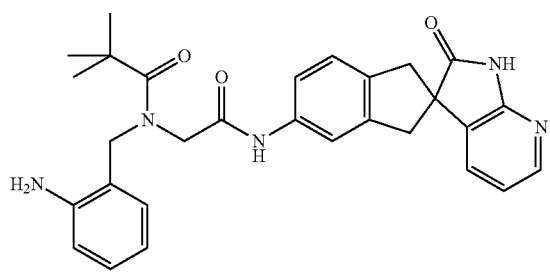 [SMILES: CC(C)(C)C(=O)N(CC(=O)Nc1ccc2c(c1)CC1(C2)C(=O)Nc2ncccc21)Cc1ccccc1N]

TABLE 1-continued
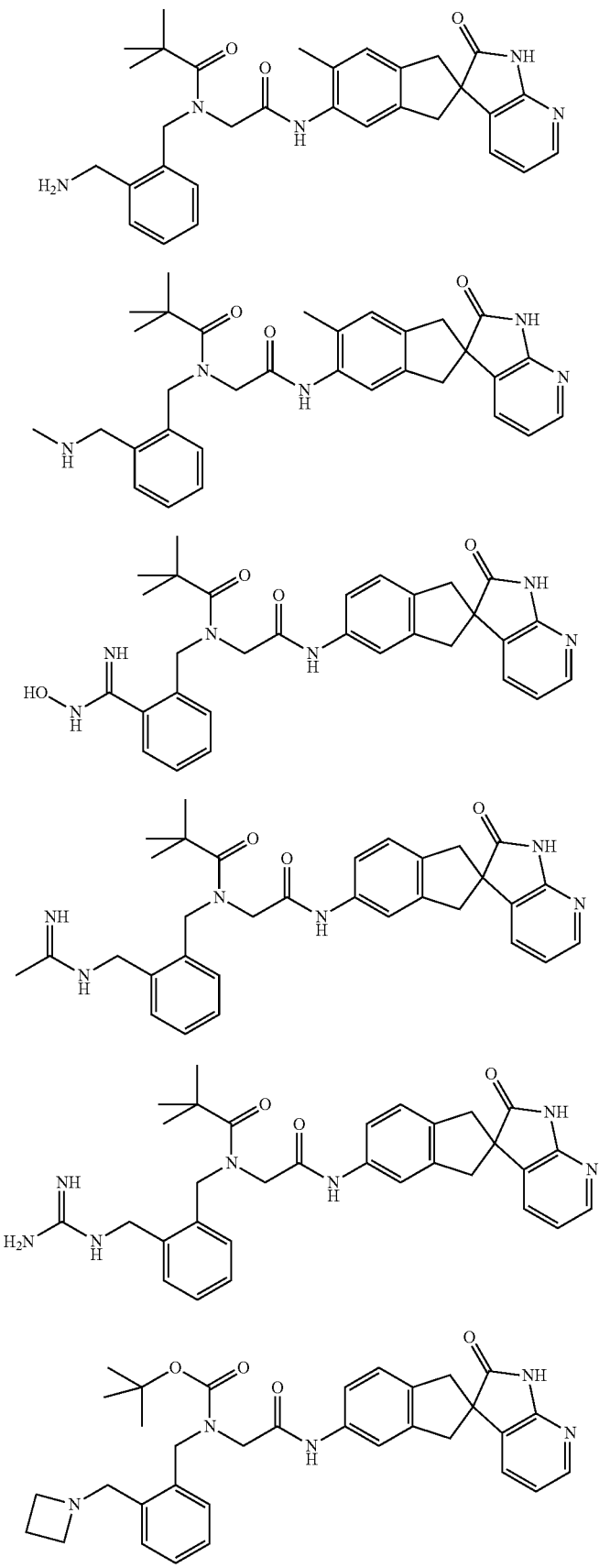

TABLE 1-continued
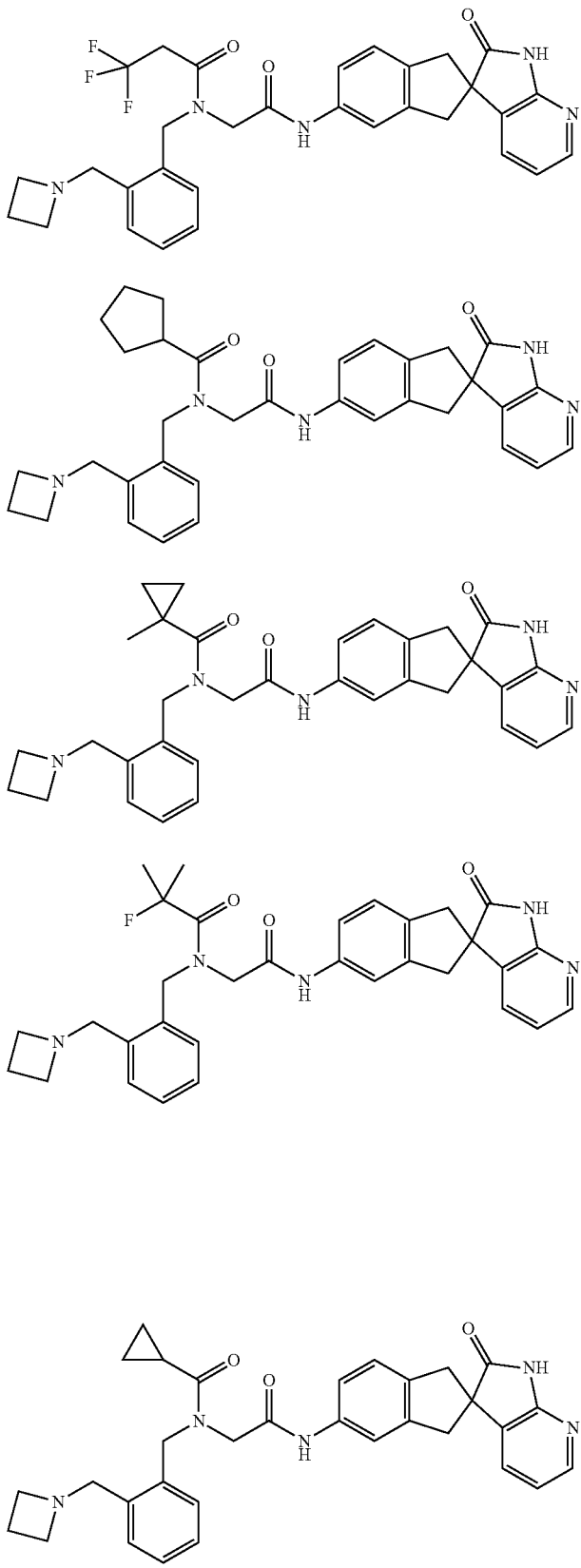

TABLE 1-continued
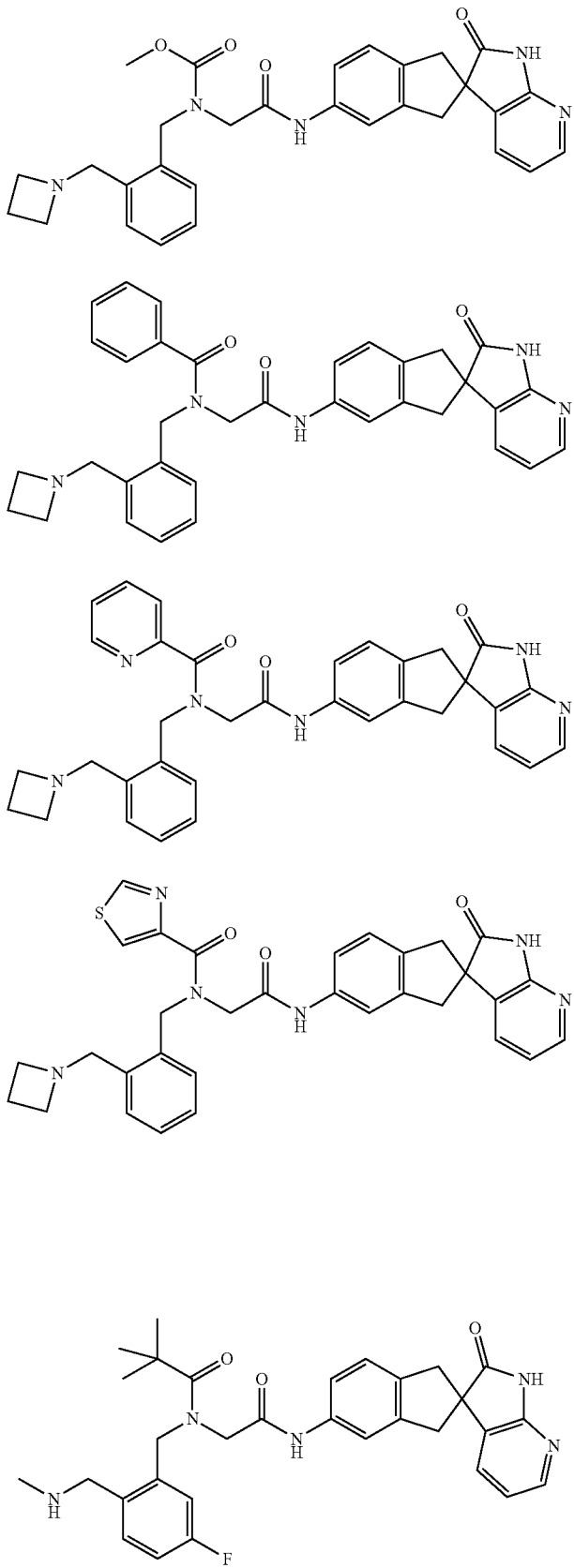

TABLE 1-continued
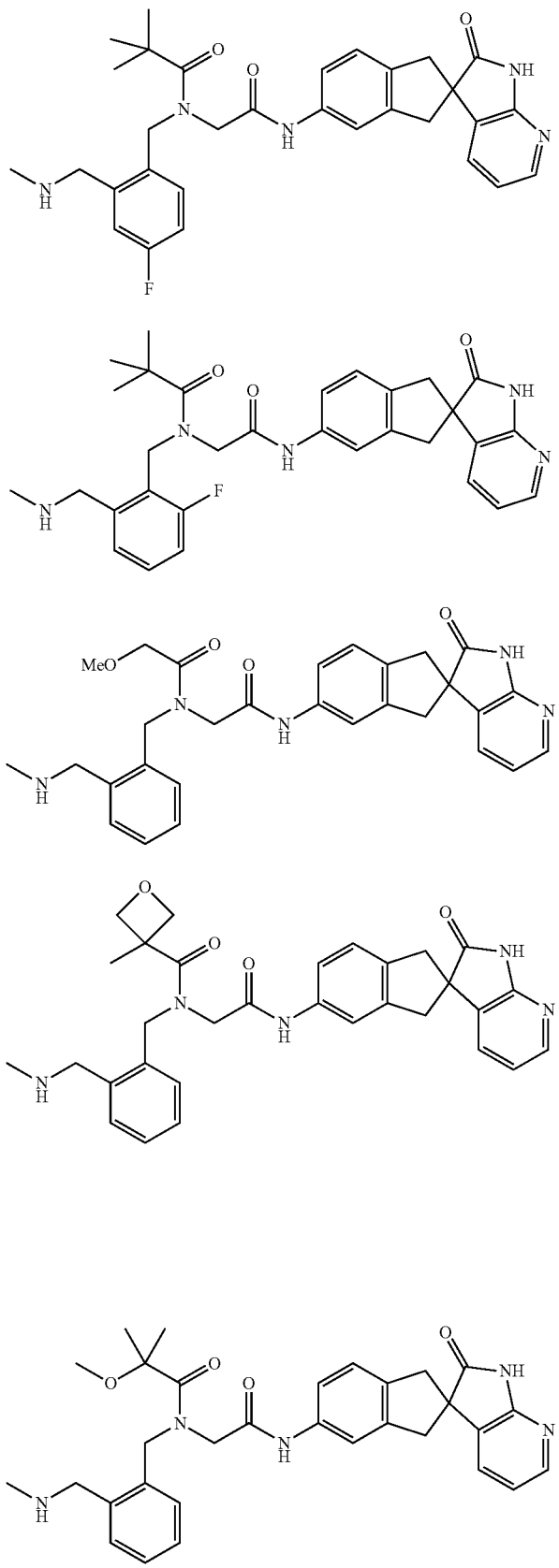

TABLE 1-continued
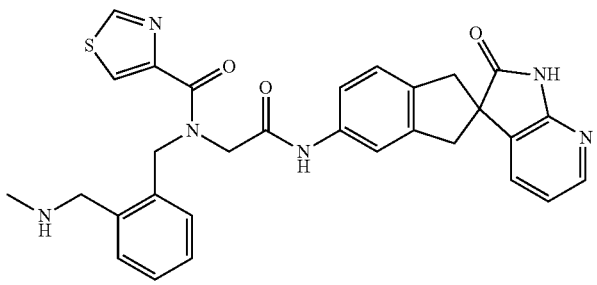 [SMILES: CNCc1ccccc1CN(CC(=O)Nc1ccc2c(c1)CC1(C2)C(=O)Nc2ncccc21)C(=O)c1cscn1]
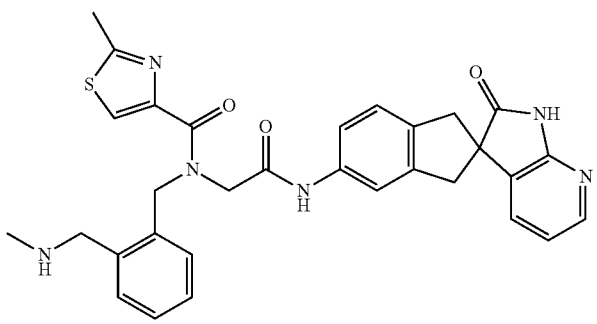 [SMILES: CNCc1ccccc1CN(CC(=O)Nc1ccc2c(c1)CC1(C2)C(=O)Nc2ncccc21)C(=O)c1csc(C)n1]
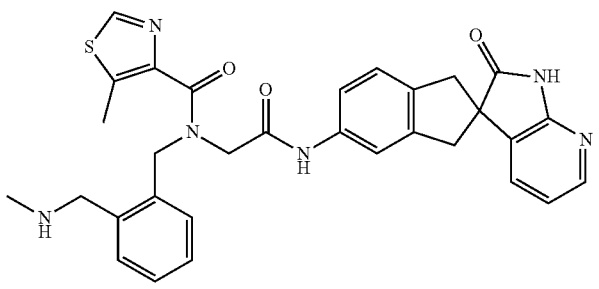 [SMILES: CNCc1ccccc1CN(CC(=O)Nc1ccc2c(c1)CC1(C2)C(=O)Nc2ncccc21)C(=O)c1ncsc1C]
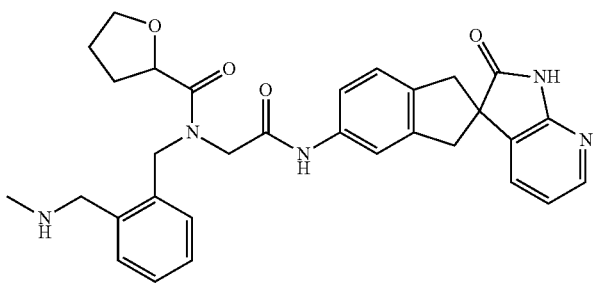 [SMILES: CNCc1ccccc1CN(CC(=O)Nc1ccc2c(c1)CC1(C2)C(=O)Nc2ncccc21)C(=O)C1CCCO1]
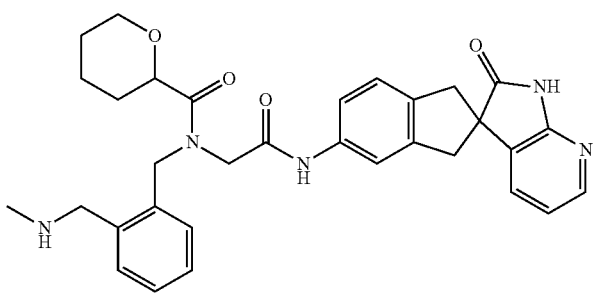 [SMILES: CNCc1ccccc1CN(CC(=O)Nc1ccc2c(c1)CC1(C2)C(=O)Nc2ncccc21)C(=O)C1CCCCO1]

TABLE 1-continued
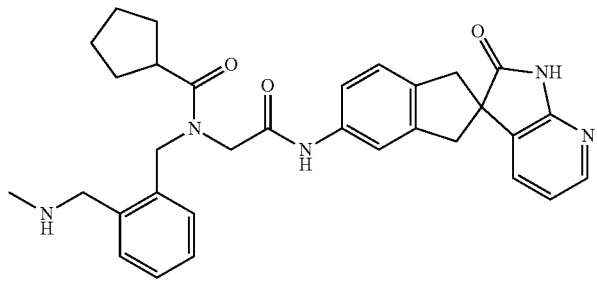 [SMILES: CNCc1ccccc1CN(CC(=O)Nc1ccc2c(c1)CC1(C2)C(=O)Nc2ncccc21)C(=O)C1CCCC1]
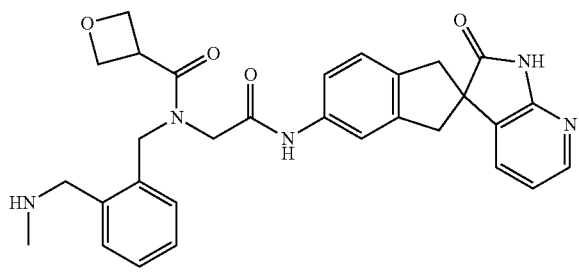 [SMILES: CNCc1ccccc1CN(CC(=O)Nc1ccc2c(c1)CC1(C2)C(=O)Nc2ncccc21)C(=O)C1COC1]
TABLE 2
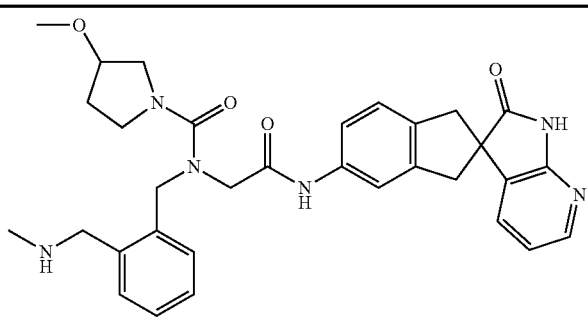
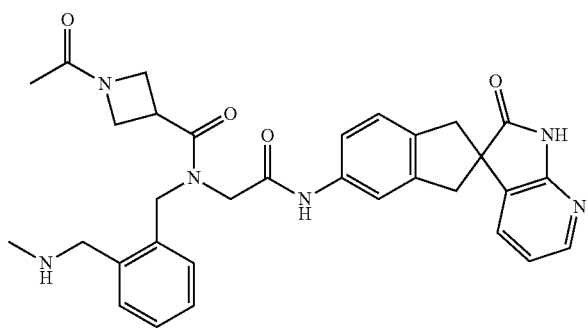 [SMILES: CNCc1ccccc1CN(CC(=O)Nc1ccc2c(c1)CC1(C2)C(=O)Nc2ncccc21)C(=O)C1CN(C(C)=O)C1]
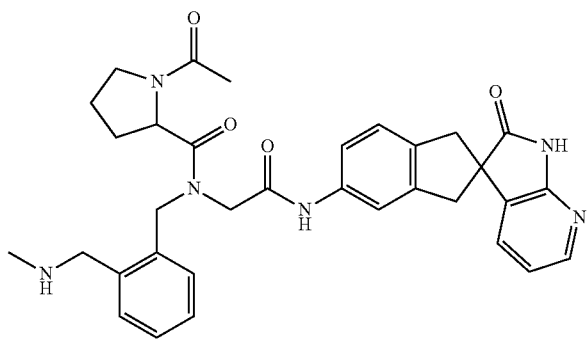 [SMILES: CNCc1ccccc1CN(CC(=O)Nc1ccc2c(c1)CC1(C2)C(=O)Nc2ncccc21)C(=O)C1CCCN1C(C)=O]

TABLE 2-continued
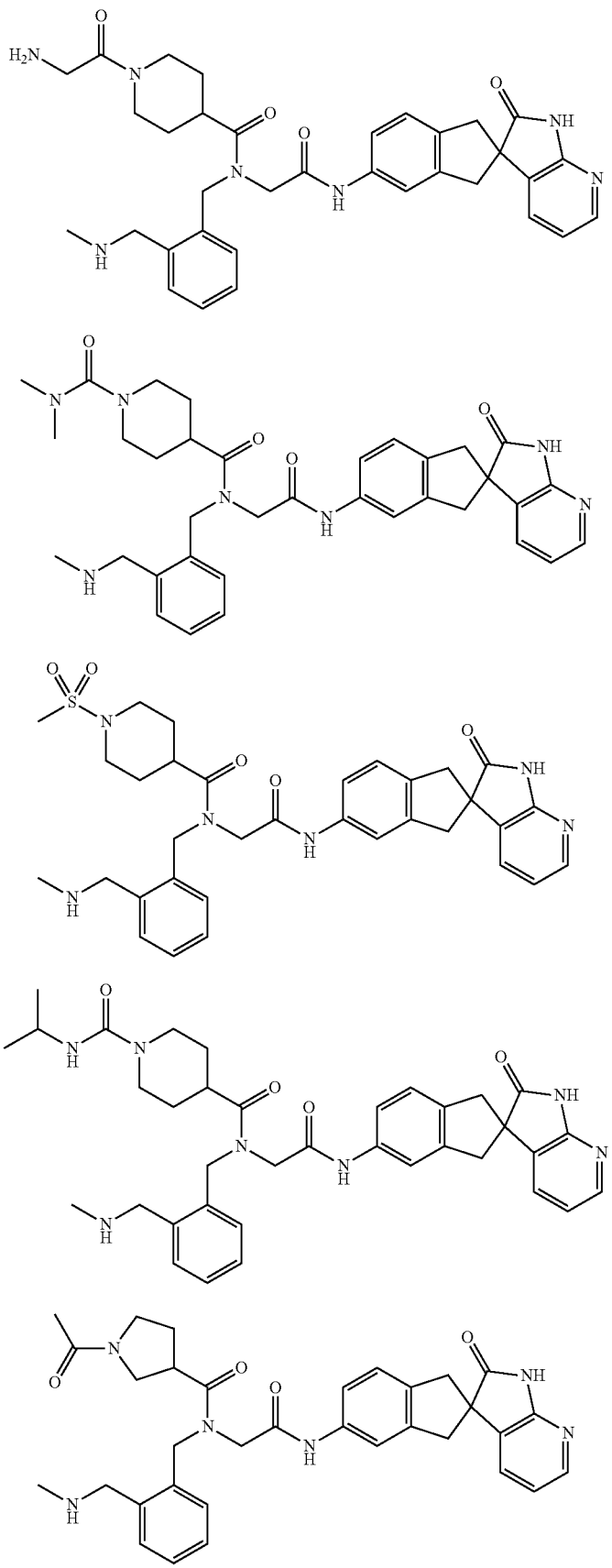

TABLE 2-continued
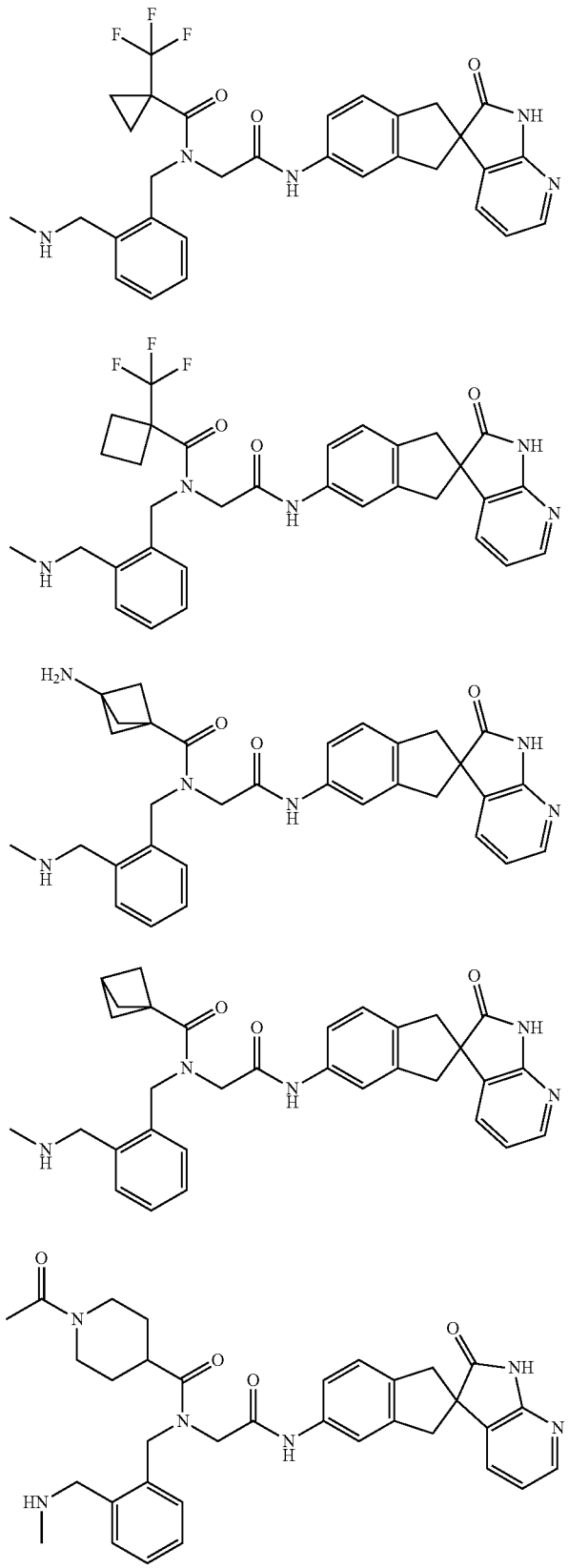

TABLE 2-continued
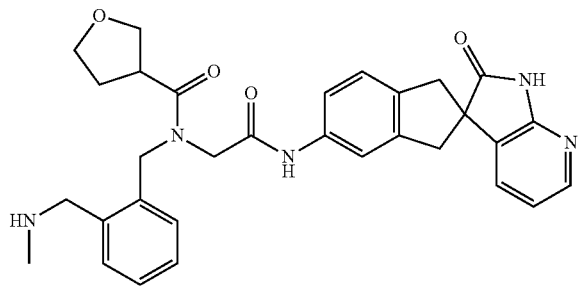 [SMILES: CNCc1ccccc1CN(CC(=O)Nc1ccc2c(c1)CC1(C2)C(=O)Nc2ncccc21)C(=O)C1CCOC1]
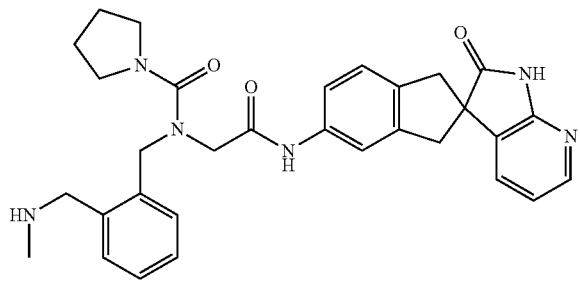 [SMILES: CNCc1ccccc1CN(CC(=O)Nc1ccc2c(c1)CC1(C2)C(=O)Nc2ncccc21)C(=O)N1CCCC1]
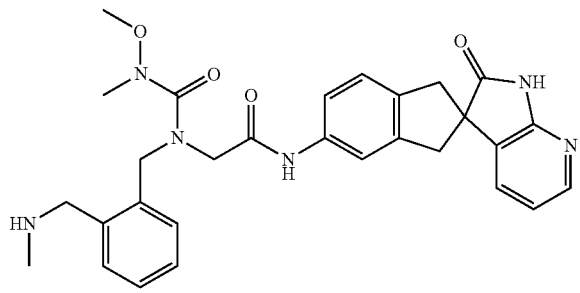 [SMILES: CNCc1ccccc1CN(CC(=O)Nc1ccc2c(c1)CC1(C2)C(=O)Nc2ncccc21)C(=O)N(C)OC]
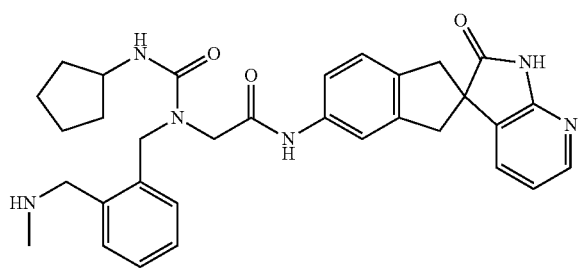 [SMILES: CNCc1ccccc1CN(CC(=O)Nc1ccc2c(c1)CC1(C2)C(=O)Nc2ncccc21)C(=O)NC1CCCC1]
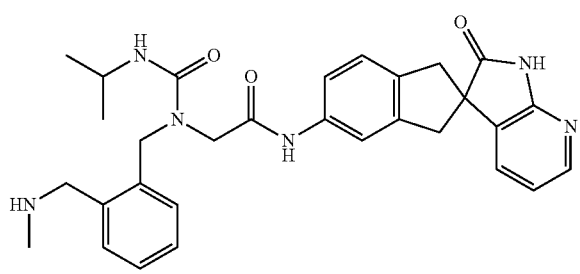 [SMILES: CNCc1ccccc1CN(CC(=O)Nc1ccc2c(c1)CC1(C2)C(=O)Nc2ncccc21)C(=O)NC(C)C]

TABLE 2-continued
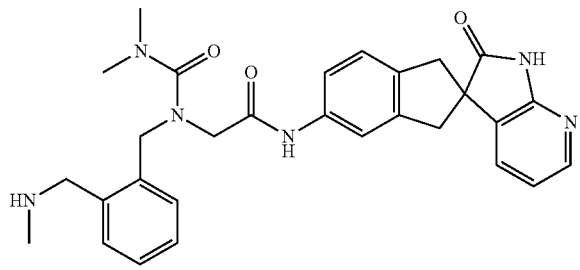 [SMILES: CNCc1ccccc1CN(CC(=O)Nc1ccc2c(c1)CC1(C2)C(=O)Nc2ncccc21)C(=O)N(C)C]
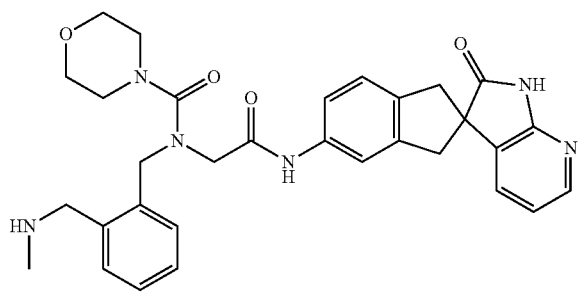
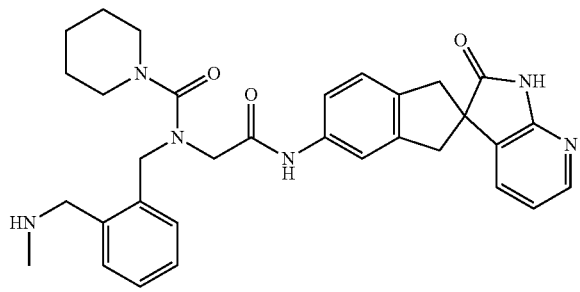 [SMILES: CNCc1ccccc1CN(CC(=O)Nc1ccc2c(c1)CC1(C2)C(=O)Nc2ncccc21)C(=O)N1CCOCC1]
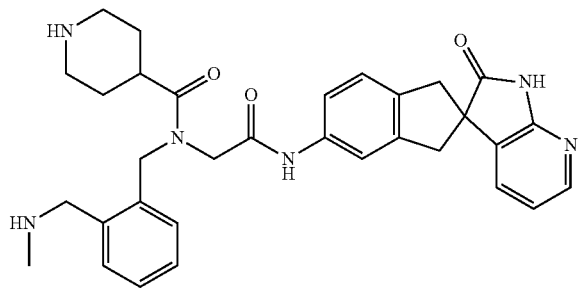 [SMILES: CNCc1ccccc1CN(CC(=O)Nc1ccc2c(c1)CC1(C2)C(=O)Nc2ncccc21)C(=O)C1CCNCC1]
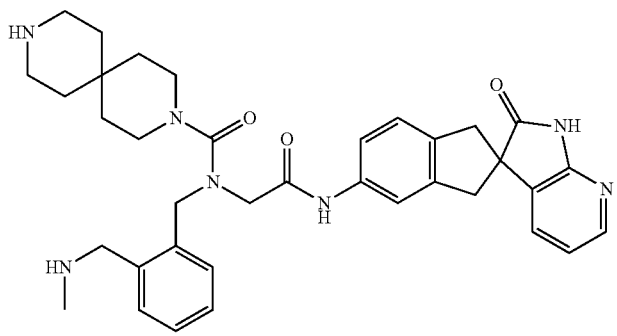 [SMILES: CNCc1ccccc1CN(CC(=O)Nc1ccc2c(c1)CC1(C2)C(=O)Nc2ncccc21)C(=O)N1CCC2(CCNCC2)CC1]

TABLE 2-continued
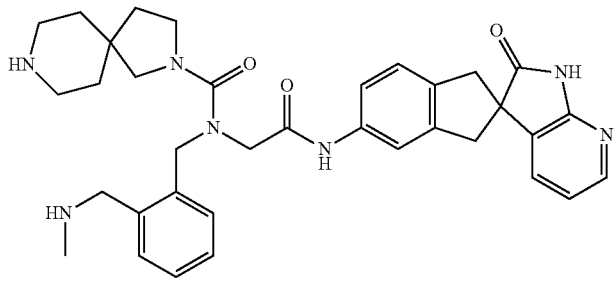 [SMILES: CNCc1ccccc1CN(CC(=O)Nc1ccc2c(c1)CC1(C2)C(=O)Nc2ncccc21)C(=O)N1CCC2(CCNCC2)C1]
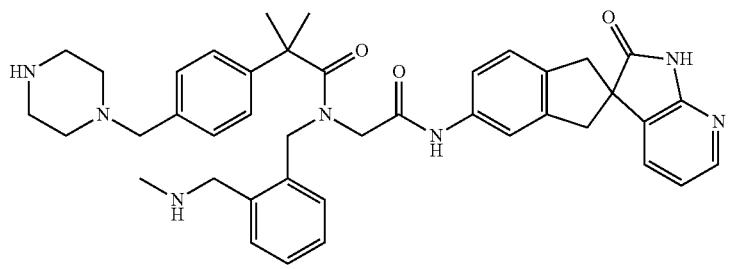 [SMILES: CNCc1ccccc1CN(CC(=O)Nc1ccc2c(c1)CC1(C2)C(=O)Nc2ncccc21)C(=O)C(C)(C)c1ccc(CN2CCNCC2)cc1]
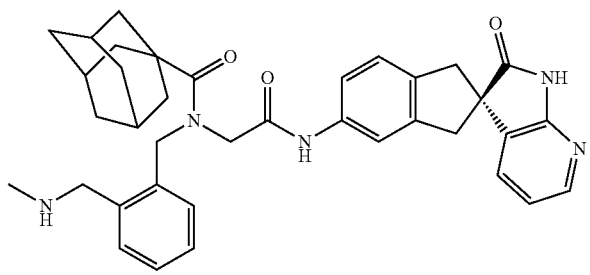 [SMILES: CNCc1ccccc1CN(CC(=O)Nc1ccc2c(c1)C[C@@]1(C2)C(=O)Nc2ncccc21)C(=O)C12CC3CC(CC(C3)C1)C2]
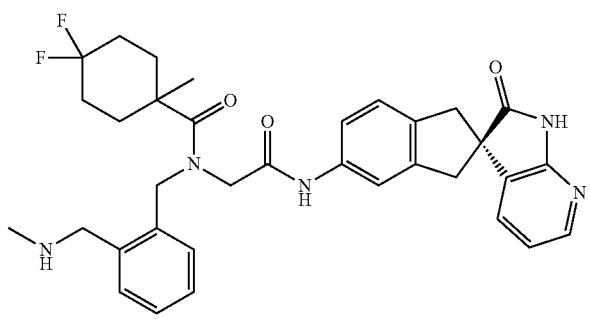 [SMILES: CNCc1ccccc1CN(CC(=O)Nc1ccc2c(c1)C[C@@]1(C2)C(=O)Nc2ncccc21)C(=O)C1(C)CCC(F)(F)CC1]
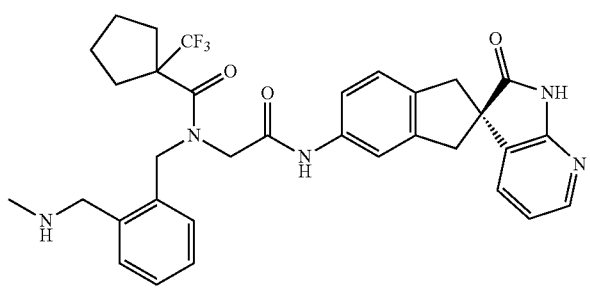 [SMILES: CNCc1ccccc1CN(CC(=O)Nc1ccc2c(c1)C[C@@]1(C2)C(=O)Nc2ncccc21)C(=O)C1(C(F)(F)F)CCCC1]

TABLE 2-continued
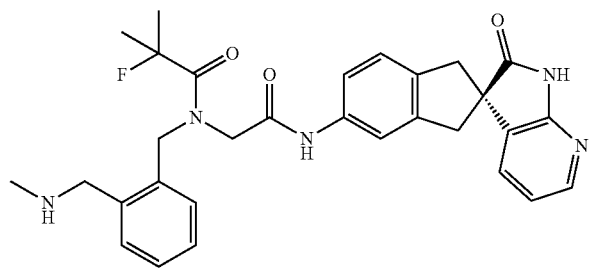 [SMILES: CNCc1ccccc1CN(CC(=O)Nc1ccc2c(c1)C[C@@]1(C2)C(=O)Nc2ncccc21)C(=O)C(C)(C)F]
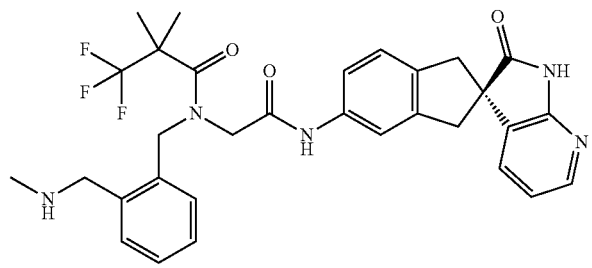 [SMILES: CNCc1ccccc1CN(CC(=O)Nc1ccc2c(c1)C[C@@]1(C2)C(=O)Nc2ncccc21)C(=O)C(C)(C)C(F)(F)F]
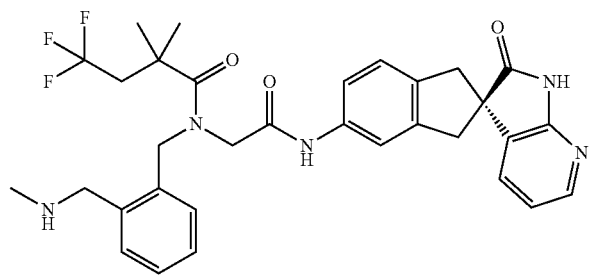 [SMILES: CNCc1ccccc1CN(CC(=O)Nc1ccc2c(c1)C[C@@]1(C2)C(=O)Nc2ncccc21)C(=O)C(C)(C)CC(F)(F)F]
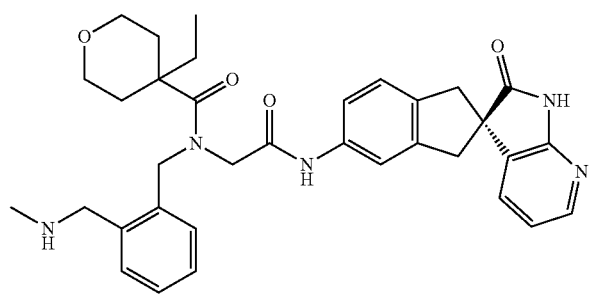 [SMILES: CCC1(C(=O)N(CC(=O)Nc2ccc3c(c2)C[C@@]2(C3)C(=O)Nc3ncccc32)Cc2ccccc2CNC)CCOCC1]
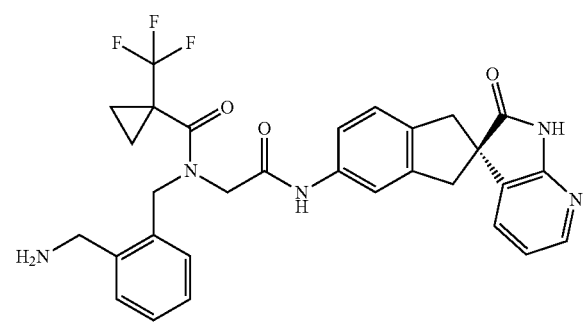 [SMILES: NCc1ccccc1CN(CC(=O)Nc1ccc2c(c1)C[C@@]1(C2)C(=O)Nc2ncccc21)C(=O)C1(C(F)(F)F)CC1]

TABLE 2-continued
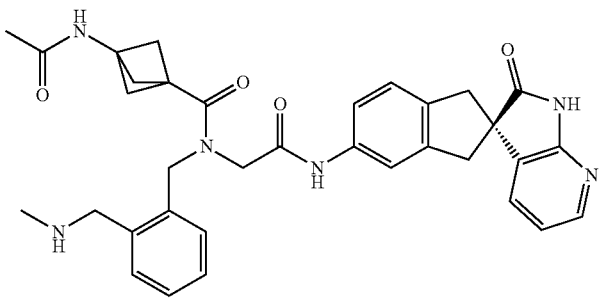 [SMILES: CNCc1ccccc1CN(CC(=O)Nc1ccc2c(c1)C[C@@]1(C2)C(=O)Nc2ncccc21)C(=O)C12CC(NC(C)=O)(C1)C2]
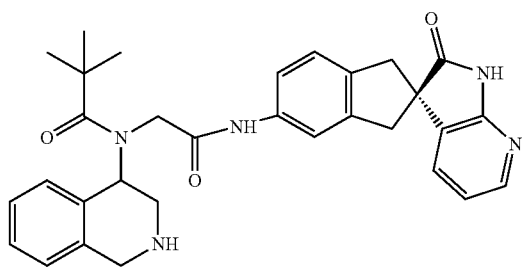 [SMILES: CC(C)(C)C(=O)N(CC(=O)Nc1ccc2c(c1)C[C@@]1(C2)C(=O)Nc2ncccc21)C1CNCc2ccccc21]
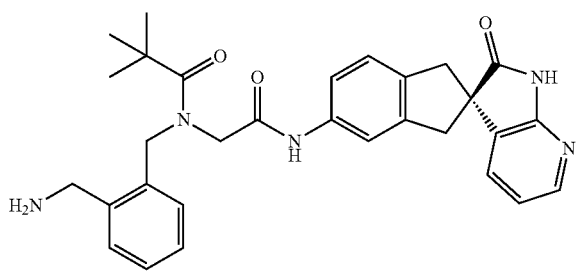 [SMILES: CC(C)(C)C(=O)N(CC(=O)Nc1ccc2c(c1)C[C@@]1(C2)C(=O)Nc2ncccc21)Cc1ccccc1CN]
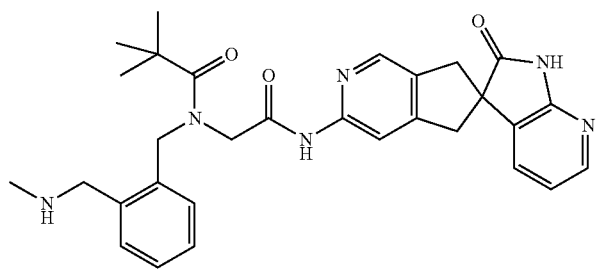 [SMILES: CNCc1ccccc1CN(CC(=O)Nc1cc2c(cn1)CC1(C2)C(=O)Nc2ncccc21)C(=O)C(C)(C)C]
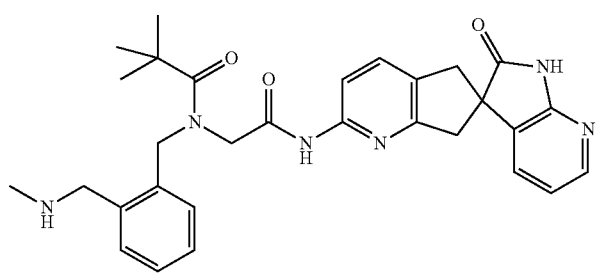 [SMILES: CNCc1ccccc1CN(CC(=O)Nc1ccc2c(n1)CC1(C2)C(=O)Nc2ncccc21)C(=O)C(C)(C)C]

TABLE 2-continued

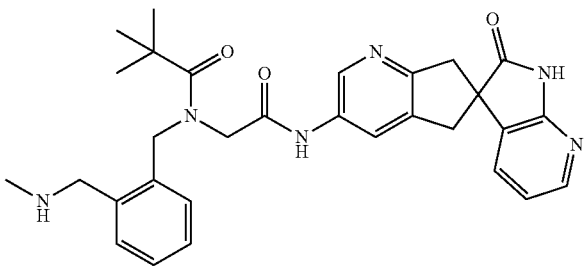 [SMILES: CNCc1ccccc1CN(CC(=O)Nc1cnc2c(c1)CC1(C2)C(=O)Nc2ncccc21)C(=O)C(C)(C)C]

or a pharmaceutically acceptable salt thereof.

Pharmaceutical Compositions

In accordance with another aspect, the present invention provides a pharmaceutical composition comprising a compound of the invention, or a pharmaceutically acceptable salt thereof, and a pharmaceutically acceptable excipient.

Conventional procedures for the selection and preparation of suitable pharmaceutical compositions are described in, for example, "Pharmaceuticals—The Science of Dosage Form Designs", M. E. Aulton, Churchill Livingstone, 1988.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intraperitoneal dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of a condition is an amount sufficient to symptomatically relieve in a warm-blooded animal, particularly a human the symptoms of the condition or to slow the progression of the condition.

The amount of active ingredient that is combined with one or more excipients to produce a single dosage form will necessarily vary depending upon the host treated and the particular route of administration. For example, a formulation intended for oral administration to humans will generally contain, for example, from 0.1 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, a daily dose selected from 0.1 mg/kg to 100 mg/kg, 1 mg/kg to 75 mg/kg, 1 mg/kg to 50 mg/kg, 1 mg/kg to 20 mg/kg or 5 mg/kg to 10 mg/kg body weight is received, given if required in divided doses. In general, lower doses will be administered when a parenteral route is employed. Thus, for example, for intravenous, subcutaneous, intramuscular or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Suitably the compound of the invention is administered orally, for example in the form of a tablet, or capsule dosage form. The daily dose administered orally may be, for example a total daily dose selected from 1 mg to 1000 mg, 5 mg to 1000 mg, 10 mg to 750 mg or 25 mg to 500 mg. Typically, unit dosage forms will contain about 0.5 mg to 0.5 g of a compound of this invention. In a particular embodiment the compound of the invention is administered parenterally, for example by intravenous administration. In another particular embodiment the compound of the invention is administered orally.

Therapeutic Uses and Applications

In accordance with another aspect, the present invention provides a compound of the invention, or a pharmaceutically acceptable salt thereof, for use as a medicament.

A further aspect of the invention provides a compound of the invention, or a pharmaceutically acceptable salt thereof, for use in the treatment of a disease or medical condition mediated by adrenomedullin receptor subtype 2 receptors ($AM_2$).

Also provided is the use of a compound of the invention, or a pharmaceutically acceptable salt therefor in the manufacture of a medicament for the treatment of a disease or medical condition mediated by $AM_2$.

Also provided is a method of treating a disease or medical condition mediated by $AM_2$ in a subject in need thereof, the method comprising administering to the subject an effective amount of a compound of the invention, or a pharmaceutically acceptable salt thereof.

In one embodiment the compound of the invention is not

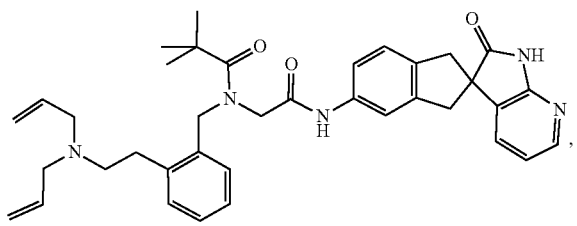 [SMILES: C=CCN(CC=C)CCc1ccccc1CN(CC(=O)Nc1ccc2c(c1)CC1(C2)C(=O)Nc2ncccc21)C(=O)C(C)(C)C]

In the following sections of the application reference is made to a compound of the invention, or a pharmaceutically acceptable salt thereof for use in the treatment of certain diseases or conditions. It is to be understood that any reference herein to a compound for a particular use is also intended to be a reference to (i) the use of the compound of the invention, or pharmaceutically acceptable salt thereof, in the manufacture of a medicament for the treatment of that disease or condition; and (ii) a method of treating the disease or condition in a subject, the method comprising administering to the subject a therapeutically effective amount of the compound of the invention, or pharmaceutically acceptable salt thereof.

The disease of medical condition mediated by $AM_2$ may be any of the diseases or medical conditions listed in this application, for example a proliferative disease, particularly cancer.

The subject to which the compound of the invention is administered may be a warm-blooded mammal, for example human or animal. In particular embodiments the subject or patient is a human. In other embodiments the subject is an animal, for example a rat, mouse, dog, cat, a primate or a horse.

The association of AM and the $AM_2$ receptor with diseases in humans and animals is set out in the Background of the Invention. This disclosure and the associated references provide further support for the therapeutic uses of the compounds of the invention. As such the supporting references linking AM, the $AM_2$ receptor and its inhibition also form part of the disclosure of the utility of the compounds of the invention in the treatment and prevention of the medical conditions described herein.

The role of $AM_2$ is has distinct roles in diseases such as cancer. Accordingly the inhibition of $AM_2$ may be advantageous. The $AM_2$ receptor is a complex formed by the GPCR, calcitonin-like receptor (CLR) and RAMP3. The related $AM_1$ receptor is formed by CLR and RAMP2 and mediates a number of important physiological functions including blood pressure. Accordingly it is preferred that a compound of the invention selectively inhibits $AM_2$ and has little or no effect on the function of $AM_1$.

RAMP1 and RAMP3 also interact with the calcitonin receptor (CTR) to form two functional amylin receptors (AMY receptors). CTR and RAMP1 form the $AMY_1$ receptor, whilst CTR and RAMP3 form the $AMY_3$ receptor. Amylin has important roles in glycaemic control, by virtue of its co-secretion with insulin in response to changes in blood glucose, and its specific functions to slow rises in serum glucose by slowing gastric emptying, slowing of release of digestive enzymes and bile, and increasing feelings of satiety to reduce or inhibit further food intake. It also reduces secretion of glucagon, thereby reducing the production of new glucose and its release into the bloodstream. Amylin is also known to stimulate bone formation by direct anabolic effects on osteoblasts. These functions are achieved by Amylin's actions on the amylin receptors. Of these, it is believed that the $AMY_1R$ and $AMY_3R$ are responsible for these homeostatic functions. The $AMY_2$ receptor (formed by CTR and RAMP2) is not known to have physiological functions of significance. Blockade of blood glucose control is not a desirable function, and in cancer patients, reductions in appetite and failure to maintain normal levels of blood glucose would be seen as undesirable effects in a drug. Accordingly, preferred compounds of the invention selectively inhibit $AM_2$ over $AMY_1$ and/or $AMY_3$. Particular compounds of the invention are expected to provide potent $AM_2$ antagonists suitable for therapeutic use, whilst having little or no antagonistic effects on the $AM_1$ receptor because of its important role in blood pressure regulation. Suitably compounds of the invention have little or no effect on the CTR/RAMP3 $AMY_3$ receptor that is involved in physiological regulation of energy metabolism.

In embodiments a compound of the invention is 10-fold, 50-fold or -100 fold more active against $AM_2$ compared to one or more of $AM_1$, $AMY_1$ and/or $AMY_3$. In certain embodiments the compound of the invention selectively inhibits $AM_2$ compared to $AM_1$ and/or $AMY_3$. For example, the $IC_{50}$ of a compound of the invention in the $AM_2$ cell-based assay described in the Examples is 10-fold, 50-fold or 100-fold lower than the $IC_{50}$ in one or more corresponding assay using cell lines which express $AM_1$, $AMY_1$ or $AMY_3$ receptors.

Suitably the compounds of the invention selectively inhibit the $AM_2$ receptor over other receptors to which AM binds, for example by exhibiting 5-fold, 10-fold, 50-fold or 100-fold selectivity for the $AM_2$ receptor over other receptors to which AM binds.

Proliferative Diseases

A further aspect of the invention provides a compound of the invention, or a pharmaceutically acceptable salt thereof, for use in the treatment of a proliferative disease. The proliferative disease may be malignant or non-malignant.

$AM_2$ is upregulated and plays a critical role in primary cancer and metastasis. Accordingly in an embodiment there is provided a compound of the invention for use in the treatment of cancer, which may be non-metastatic or metastatic. The cancer is suitably a solid tumour, however, a compound of the invention may also be useful in the treatment of a haematological ("liquid") cancers and effects associated with such cancers. There is evidence that haematological cancers express AM, and that its role in stimulating angiogenesis is important in disease progression (Kocemba K et al. The hypoxia target adrenomedullin is aberrantly expressed in multiple myeloma and promotes angiogenesis, Leukemia. 2013; 27:1729-1737: DOI 10.1038/leu.2013.76). Inhibiting $AM_2$ in the microenvironment of a tumour may be beneficial in preventing or inhibiting angiogenesis and disease progression associated with a cancer such as multiple myeloma.

Compounds of the invention may useful in the treatment and/or prevention of, for example:

Carcinoma, including for example tumours derived from stratified squamous epithelia (squamous cell carcinomas) and tumours arising within organs or glands (adenocarcinomas). Examples include breast, colon, lung, prostate, ovary, esophageal carcinoma (including, but not limited to, esophageal adenocarcinoma and squamous cell carcinoma), basal-like breast carcinoma, basal cell carcinoma (a form of skin cancer), squamous cell carcinoma (various tissues), head and neck carcinoma (including, but not limited to, squamous cell carcinomas), stomach carcinoma (including, but not limited to, stomach adenocarcinoma, gastrointestinal stromal tumour), signet ring cell carcinoma, bladder carcinoma (including transitional cell carcinoma (a malignant neoplasm of the bladder)), bronchogenic carcinoma, colorectal carcinoma (including, but not limited to, colon carcinoma and rectal carcinoma), anal carcinoma, gastric carcinoma, lung carcinoma (including but not limited to small cell carcinoma and non-small cell carcinoma of the lung, lung adenocarcinoma, squamous cell carcinoma, large cell carcinoma, bronchioloalveolar carcinoma, and mesothelioma), neuroendocrine tumours (including but not limited to carcinoids of the gastrointestinal tract, breast, and other organs), adrenocortical carcinoma, thyroid carcinoma, pancreatic carcinoma, breast carcinoma (including, but not limited to, ductal carcinoma, lobular carcinoma, inflammatory breast cancer, clear cell carcinoma, mucinous carcinoma), ovarian carcinoma (including, but not limited to, ovarian epithelial carcinoma or surface epithelial-stromal tumour including serous tumour, endometrioid tumour and mucinous cystadenocarcinoma, sex-cord-stromal tumour), liver and bile duct carcinoma (including, but not limited to, hepatocellular carcinoma, cholangiocarcinoma and hemangioma), prostate carcinoma, adenocarcinoma, brain tumours (including, but not limited to glioma, glioblastoma and medulloblastoma), germ cell tumours, sweat gland carcinoma, sebaceous gland carcinoma, papillary carcinoma, papillary adenocarcinoma, cystadenocarcinoma, kidney carcinoma (including, but not limited to, renal cell carcinoma, clear cell carcinoma and Wilm's tumour), medullary carcinoma, ductal carcinoma in situ or bile duct carcinoma, choriocarcinoma, seminoma, embryonal carcinoma, cervical carcinoma, uterine carcinoma (including, but not limited to, endometrial adenocarcinoma, uterine papillary serous carcinoma, uterine clear-cell carcinoma, uterine sarcomas and leiomyosarcomas, mixed mullerian tumours), testicular carcinoma, osteogenic carcinoma, epithelial carcinoma, sarcomatoid carcinoma, nasopharyngeal carcinoma, laryngeal carcinoma; oral and oropharyngeal squamous carcinoma;
Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and hemangioendothelioma (blood vessels); liposarcoma (adipose tissue); glioma and astrocytoma (neurogenic connective tissue found in the brain); myxosarcoma (primitive embryonic connective tissue); chordoma, endotheliosarcoma, lymphangiosarcoma, lymphangioendotheliosarcoma, synovioma, Ewing's sarcoma, mesenchymous and mixed mesodermal tumour (mixed connective tissue types) and other soft tissue sarcomas;
Solid tumours of the nervous system including medulloblastoma, craniopharyngioma, ependymoma, pinealoma, hemangioblastoma, acoustic neuroma, oligodendroglioma, meningioma, neuroblastoma and schwannoma;
Melanoma, uveal melanoma and retinoblastoma;
Myeloma and multiple myeloma;
Hematopoietic tumours, including: myelogenous and granulocytic leukemia (malignancy of the myeloid and granulocytic white blood cell series); lymphatic, lymphocytic, and lymphoblastic leukemia (malignancy of the lymphoid and lymphocytic blood cell series); polycythemia vera and erythremia (malignancy of various blood cell products, but with red cells predominating); myelofibrosis; and
Lymphomas, including: Hodgkin and Non-Hodgkin lymphomas.

In an embodiment a compound of the invention, or a pharmaceutically acceptable salt thereof is for use in the treatment of a solid tumour, for example any of the solid tumours listed above. In a particular embodiment a compound of the invention, or a pharmaceutically acceptable salt thereof is for use in the treatment of a cancer selected from: pancreatic, colorectal, breast, lung and bone cancer.

In another embodiment the compound of the invention, or a pharmaceutically acceptable salt thereof, is for use in the treatment of hormone dependent prostate cancer.

In another embodiment the compound of the invention, or a pharmaceutically acceptable salt thereof, is for use in the treatment of a breast cancer selected from Luminal A breast cancer (hormone-receptor positive (estrogen-receptor and/or progesterone-receptor positive), HER2 negative and low levels of the protein Ki-67); Luminal B breast cancer (hormone-receptor positive (estrogen-receptor and/or progesterone-receptor positive), and either HER2 positive or HER2 negative with high levels of Ki-67); triple negative breast cancer (i.e. the tumour is estrogen receptor-negative, progesterone receptor-negative and HER2-negative); HER2 positive breast cancer or normal-like breast cancer (classifications as defined in Table 1 of Dai et al. Am. J. Cancer Research. 2015; 5(10):2929-2943).

In an embodiment a compound of the invention, or a pharmaceutically acceptable salt thereof is for use in the treatment of a cancer selected from: pancreatic cancer, triple negative breast cancer (i.e. the tumour is estrogen receptor-negative, progesterone receptor-negative and HER2-negative), hormone refractory prostate cancer and non-small cell lung cancer.

In embodiments the compounds of the invention provide an anti-cancer effect on a cancer (for example any of the cancers disclosed herein) selected from one or more of an anti-proliferative effect, a pro-apoptotic effect, an anti-mitotic effect an anti-angiogenic effect, inhibition of cell migration, inhibition or prevention of tumour invasion and/or preventing or inhibiting metastasis.

Compounds of the invention may be used to prevent or inhibit the progression of a cancer. A compound of the invention may be for use in slowing, delaying or stopping cancer progression. The progress of a cancer is typically determined by assigning a stage to the cancer. Staging is typically carried out by assigning a number from I to IV to the cancer, with I being an isolated cancer and IV being an advanced stage of the disease where the cancer that has spread to other organs. The stage generally takes into account the size of a tumour, whether it has invaded adjacent organs, the number of lymph nodes it has spread to, and whether the cancer has metastasised. Preventing or inhibiting progression of the cancer is particularly important for preventing the spread of the cancer, for example the progression from Stage I to Stage II where the cancer spreads locally, or the progression from Stage III to Stage IV where the cancer metastasises to other organs.

It may be that a compound of the invention is for use in the treatment of a cancer wherein the cancer is a primary cancer, which may be a second primary cancer.

It may be that a compound of the invention is for use in the prevention or inhibition of occurrence of a second primary cancer.

It may be that a compound of the invention is for use in the treatment of a cancer wherein the cancer is refractory (resistant) to chemotherapy and/or radio therapy. The cancer may be resistant at the beginning of treatment or it may become resistant during treatment It may be that a compound of the invention is for use in the treatment of a cancer wherein the cancer is a recurrent cancer, which may be local, regional or distant. A recurrent cancer is a cancer which returns after initial treatment and after a period of time during which the cancer cannot be detected. The same cancer may return in the same tissue or in a different part of the body.

It may be that a compound of the invention is for use in the prevention or inhibition of recurrence of a cancer.

It may be that a compound of the invention is for use in the treatment of a cancer wherein the cancer is a metastatic or secondary cancer.

It may be that a compound of the invention is for use in the prevention or inhibition of cancer metastasis. The treatment of a metastatic cancer may be the same or different to the therapy previously used to treat the primary tumour. For example, in certain embodiments, a primary tumour may be surgically resected and a compound of the invention is for use in preventing the spread of cancer cells that may remain following surgery, or which may have already escaped the primary tumour. In other embodiments, the primary tumour may be treated using radiotherapy. In yet other embodiments, the primary tumour may be treated by chemotherapy. Combination therapies are commonly used to treat cancer to improve the treatment and, typically, maximise the length and depth of the remission. Any of the combination therapies disclosed herein may be used with a compound of the invention.

When the primary tumour has already metastasised and a secondary tumour has established, a compound of the invention may be used to treat the secondary tumour. This may involve both treatment of the secondary tumour and prevention of that secondary tumour metastasising. Reference to metastasis herein is intended to encompass metastasis of any of the tumours disclosed herein. Generally, the secondary tumour will be in a different tissue to that of the primary tumour. For example the secondary tumour may be a secondary tumour in bone. In a particular embodiment a compound of the invention is for use in the treatment of a secondary tumour in bone, for example for use in the treatment of a secondary bone tumour, wherein the primary tumour is a breast or prostate tumour.

Pancreatic Tumours

In an embodiment a compound of the invention, or a pharmaceutically acceptable salt thereof is for use in the treatment of a pancreatic tumour, especially a malignant pancreatic tumour. The term "pancreatic tumour" encompasses exocrine and endocrine tumours which may be benign or malignant. Exocrine tumours are the most prevalent forms of pancreatic cancer and account for about 95% of cases. Exocrine cancers include, for example ductal adenocarcinomas (PDAC), acinar cell carcinoma, papillary tumours (for example intraductal papillary-mucinous neoplasm (IPMN)), mucinous tumours (for example Mucinous cystadenocarcinoma), solid tumours and serous tumours. Pancreatic endocrine tumours are rare and develop as a result of abnormalities in islet cells within the pancreas. Examples of pancreatic endocrine tumours include gastrinoma (Zollinger-Ellison Syndrome), glucagonoma, insulinoma, somatostatinoma, VIPoma (Verner-Morrison Syndrome), nonfunctional islet cell tumour and multiple endocrine neoplasia type-1 (MEN1 also known as Wermer Syndrome). In a particular embodiment the compound is for use in the treatment of pancreatic cancer, particularly a pancreatic cancer selected from: pancreatic ductal adenocarcinoma, pancreatic adenocarcinoma, acinar cell carcinoma, intraductal papillary mucinous neoplasm with invasive carcinoma, mucinous cystic neoplasm with invasive carcinoma, islet cell carcinoma and neuroendocrine tumours. In another particular embodiment the pancreatic cancer is pancreatic adenocarcinoma.

It may be that the compound of the invention is for use in the treatment of pancreatic cancer in a patient wherein the tumour is resectable. In this embodiment a compound of the invention is administered to the patient as an adjunctive therapy following surgical resection of the tumour.

In some embodiments, the compounds of the invention are for use in the treatment of early stage pancreatic cancer. In some embodiments, the pancreatic cancer is late stage pancreatic cancer. In some embodiments, the pancreatic cancer is advanced pancreatic cancer. In some embodiments, the pancreatic cancer is locally advanced pancreatic cancer.

In some embodiments, the pancreatic cancer is recurrent pancreatic cancer. In some embodiments, the pancreatic cancer is non-metastatic pancreatic cancer. In some embodiments, the pancreatic cancer is metastatic pancreatic cancer. In some embodiments, the pancreatic cancer is a primary pancreatic cancer. In some embodiments, the primary pancreatic tumour has metastasized. In some embodiments, the pancreatic cancer has reoccurred after remission. In some embodiments, the pancreatic cancer is progressive pancreatic cancer. In some embodiments, the pancreatic cancer is pancreatic cancer in remission.

In some embodiments the treatment of pancreatic cancer is an adjuvant treatment. An adjuvant treatment may be one in which the patient has had a history of pancreatic cancer, and generally (but not necessarily) been responsive to a therapy, which includes, but is not limited to, surgical resection, radiotherapy and/or chemotherapy; however, because of their history of cancer, the patient is considered to be at risk of development of the disease. Treatment or administration in the adjuvant setting refers to a subsequent mode of treatment.

In some embodiments, the treatment of pancreatic cancer may be a neoadjuvant treatment. By "neo-adjuvant" is meant that a compound of the invention is for use in the treatment of the patient before a primary/definitive therapy for the pancreatic cancer. In some embodiments the compounds of the invention are for use in the treatment of pancreatic cancer in a patient, wherein the patient has not previously been treated for pancreatic cancer.

In some embodiments the compounds of the invention are for use in the treatment of pancreatic cancer in a patient who has previously been treated, or is being concurrently treated, for the pancreatic cancer. The prior or concurrent treatment may include a chemotherapy agent for example a treatment selected from: gemcitabine, gemcitabine with Nab-paclitaxel (Abraxane™); 5-fluorouracil (5-FU), capecitabine, the combination treatment FOLFIRINOX (leucovorin, 5-FU, irinotecan and oxaliplatin), a combination of oxaliplatin and 5-FU (also known as FOLFOX) and a combination of gemcitabine and capecitabine. In some embodiments, the prior treatment comprises gemcitabine and/or erlotinib. In some embodiments, the prior treatment comprises 5-FU.

In some embodiments a compound of the invention is for use in the second or third-line treatment of a patient with pancreatic cancer. For example, wherein the patient has been prior treated with a first and/or second therapy that has failed or substantially failed.

It may be that the compound of the invention is for use in the treatment of pancreatic cancer which is refractory to conventional chemotherapy, for example in the treatment of pancreatic cancer refractory to gemcitabine and/or 5FU.

In some embodiments a compound of the invention is used in combination with another anti-cancer agent in the treatment of pancreatic cancer. Any of the combination treatment disclosed herein may be used.

In embodiments the compounds of the invention are for use in the treatment of pancreatic cancer in a patient, wherein the patient has developed atypical type 2 diabetes.

Benign Proliferative Disease

A compound of the invention, or a pharmaceutically acceptable salt thereof the invention may be for use in the treatment of a benign proliferative disease. The benign disease may be a benign tumour, for example hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, moles, uterine fibroids, thyroid adenomas, adrenocortical adenomas or pituitary adenomas Patient Selection and Biomarkers Serum AM is up-regulated in a number of cancers, for example human pancreatic cancer. AM is also upregulated in tissue sections from pancreatic cancer patients, compared with normal tissue and pancreatitis. Additionally, the $AM_2$ receptor, or components thereof (i.e. CLR and/or RAMP3) are expressed in the majority of pancreatic tumours (Keleg et al. 2007). Pancreatic cancer patients have increased numbers of secreted exosomes containing AM. Evidence suggests these AM containing exosomes cause the paraneoplastic β-cell dysfunction that is frequently associated with the development of pancreatic cancer (Javeed et al 2015). Accordingly, a compound of the invention is expected to be beneficial in the treatment of a cancer, for example pancreatic cancer, wherein AM is upregulated in a biological sample compared to a reference sample. The biological sample may be, for example, a serum sample or a tissue sample, for example a tumour biopsy.

A compound of the invention is expected to be beneficial in the treatment of a cancer, for example pancreatic cancer, wherein $AM_2$ is upregulated in a biological sample compared to a reference sample. A compound of the invention is expected to be beneficial in the treatment of a cancer, for example pancreatic cancer, wherein components of $AM_2$; namely CLR and/or RAMP3 are upregulated in a biological sample compared to a reference sample, whether independently or in concert. The biological sample may be, for example, a serum sample or a tissue sample, for example a tumour biopsy. Additionally, in the case of RAMP3, expression of which is elevated in the healthy tissue surrounding tumours (Brekhman, V et al., The FASEB Journal. 2011; 25(1): 55-65), the tissue sample may be from healthy tissue immediately surrounding tumour tissue. This tissue may display no other signs of cancerous or pre-cancerous condition, other than elevation of RAMP3 expression relative to a reference sample.

Since elevated expression of AM, $AM_2$, CLR, and/or RAMP3 when compared with controls may be indicative of a cancer, particularly early-stage pancreatic cancer, patients can be subdivided into distinct, clinically useful groups based on their gene expression profiles. In particular, elevated expression of one or more of these biomarkers is predictive of therapeutic responsiveness to compounds of the invention. An ability to determine the patients which will respond well to treatment with compounds of the invention enables the appropriate treatment to be administered to each patient in an efficient manner, without the necessity for lengthy trial and error and the associated side effects of unnecessary, inappropriate or untimely treatment.

Accordingly, the invention provides a method of predicting or determining therapeutic responsiveness to treatment with compounds of the invention, comprising the steps of:

(a) analysing a biological sample obtained from a subject to determine the expression levels of one or more biomarkers, wherein the biomarkers are selected from AM and/or $AM_2$ and/or CLR and/or RAMP3; and (b) comparing the expression levels of the biomarkers determined in (a) with one or more reference values, wherein an increase in the expression levels of the one or more biomarkers in the sample(s) from the subject compared to the one or more reference values is indicative of therapeutic responsiveness to treatment with compounds of the invention and/or is indicative of the presence of a cancer, for example early-stage pancreatic cancer.

It will be appreciated that any of the biomarkers indicative of a cancer, for example early stage pancreatic cancer, that is AM and/or $AM_2$ and/or CLR and/or RAMP3 may be selected for analysis, whether independently or in combination, to determine therapeutic responsiveness to compounds of the invention.

Normally, the expression level of AM in a sample (for example a serum sample or a tumour sample) will be analysed and compared with one or more reference values. Preferably, the expression level of AM and/or $AM_2$ in a sample (for example a serum sample or a tumour sample) will be analysed and compared with one or more reference values. Preferably, the expression level of AM in a serum sample will be analysed and compared with one or more reference values.

Equally, the expression level of $AM_2$ receptor components, CLR or RAMP3 in a sample, (for example a tumour sample or circulating tumour cells) will be analysed and compared with one or more reference values. Additionally, circulating tumour cell free tumour DNA may be analysed in order to determine the presence of circulating tumour cell free tumour DNA coding for AM, $AM_2$, CLR or RAMP3, which may reveal or provide advance indication of potential expression of the one or more biomarkers.

An increase in the expression levels of the one or more biomarkers in the sample(s) from the subject compared to the one or more reference values is predictive of sensitivity to and/or therapeutic responsiveness to compounds of the invention. Preferably, an increase in the expression levels of AM in a serum sample from a subject compared to one or more reference values is predictive of sensitivity to and/or therapeutic responsiveness to compounds of the invention. Preferably, an increase in the expression levels of $AM_2$ in a serum sample from a subject compared to one or more reference values is predictive of sensitivity to and/or therapeutic responsiveness to compounds of the invention. More preferably, an increase in the expression levels of AM and $AM_2$ in a serum sample or a tumour sample from a subject compared to one or more reference values is predictive of sensitivity to and/or therapeutic responsiveness to compounds of the invention.

Biomarkers

Throughout, biomarkers in the biological sample(s) from the subject are said to be differentially expressed and indicative of for example, early stage pancreatic cancer, where their expression levels are significantly up-regulated compared with one or more reference values. Depending on the individual biomarker, early stage pancreatic cancer may be diagnosed in a biological sample by an increase in expression level, scaled in relation to sample mean and sample variance, relative to those of one or more control samples or one or more reference values. Clearly, variation in the sensitivity of individual biomarkers, subject and samples means that different levels of confidence are attached to each biomarker. Biomarkers of the invention may be said to be significantly up-regulated (or elevated) when after scaling of biomarker expression levels in relation to sample mean and sample variance, they exhibit a 2-fold change compared with one or more control samples or one or more reference values. Preferably, said biomarkers will exhibit a 3-fold change or more compared with one or more control samples or one or more reference values. More preferably biomarkers of the invention will exhibit a 4-fold change or more compared with one or more control samples or one or more reference values. That is to say, in the case of increased expression level (up-regulation relative to reference values), the biomarker level will be more than double that of the reference value or that observed in the one or more control samples. Preferably, the biomarker level will be more than 3 times the level of the one or more reference values or that in the one or more control samples. More preferably, the biomarker level will be more than 4 times the level of the one or more reference values or that in the one or more control samples.

Biomarker Reference Sequences

AM

As used herein "AM" designates "adrenomedullin". A reference sequence of full-length human AM mRNA transcript is available from the GenBank database under accession number NM_001124, version NM_001124.2.

$AM_2$

As used herein "$AM_2$" designates the "adrenomedullin receptor subtype 2". A reference sequence of full-length human $AM_2$ mRNA transcript is available from the GenBank database under accession number NM_001253845, version NM_001253845.1.

CLR

As used herein "CLR" designates the "calcitonin-like receptor". A reference sequence of full-length human CLR mRNA transcript variant 1 is available from the NCBI-GenBank database under accession number NM_005795, version NM_005795.5. A reference sequence of full-length human CLR mRNA transcript variant 2 is available from the GenBank database under accession number NM_214095, version NM_214095.1.

RAMP3

As used herein "RAMP3" designates the "receptor activity modifying protein 3". A reference sequence of full-length human RAMP3 mRNA transcript is available from the NCBI-GenBank database under accession number NM_005856, version NM_005856.2.

All accession and version numbers of the reference sequences of biomarkers disclosed herein were obtained from the NCBI-GenBank database (Flat File Release 218.0) available at https://www.ncbi.nlm.nih.gov/genbank/.

Reference Values

Throughout, the term "reference value" may refer to a pre-determined reference value, for instance specifying a confidence interval or threshold value for the diagnosis or prediction of the susceptibility of a subject to early stage pancreatic cancer. Preferably, "reference value" may refer to a pre-determined reference value, specifying a confidence interval or threshold value for the prediction of sensitivity to and/or therapeutic responsiveness to a compound of the invention. Alternatively, the reference value may be derived from the expression level of a corresponding biomarker or biomarkers in a 'control' biological sample, for example a positive (e.g. cancerous or known pre-cancerous) or negative (e.g. healthy) control. Furthermore, the reference value may be an 'internal' standard or range of internal standards, for example a known concentration of a protein, transcript, label or compound. Alternatively, the reference value may be an internal technical control for the calibration of expression values or to validate the quality of the sample or measurement techniques. This may involve a measurement of one or several transcripts within the sample which are known to be constitutively expressed or expressed at a known level. Accordingly, it would be routine for the skilled person to apply these known techniques alone or in combination in order to quantify the level of biomarker in a sample relative to standards or other transcripts or proteins or in order to validate the quality of the biological sample, the assay or statistical analysis.

Biological Samples

Typically, the biological sample of the invention will be selected from a serum sample, a tissue sample or a tumour tissue sample. Normally, the biological sample of the invention will be a serum sample. Elevated levels of AM and/or $AM_2$ expression may be detectable in the serum of a subject with early-stage pancreatic cancer. Elevated expression levels of AM and/or $AM_2$ and/or CLR and/or RAMP3 expression may be detectable in the cells of a tumour sample of a subject with a cancer, for example early-stage pancreatic cancer. These cells may be, for example derived from a biopsy of a tumour or may be circulating tumour cells. Similarly, circulating tumour cell free tumour DNA may usefully be analysed for the presence of DNA encoding any of the one or more biomarkers, in particular that of the $AM_2$ receptor components, CLR and/or RAMP3, which may indicate or foreshadow the potential expression of the one or more biomarkers. In the case of RAMP3 expression, elevated levels of RAMP3, indicative of a cancer, for example early-stage pancreatic cancer, may be detectable in a sample of tissue taken from the area surrounding tumour tissue of a subject with early-stage pancreatic cancer. Such tissue may be otherwise asymptomatic.

Suitably, methods of the invention may make use of a range of biological samples taken from a subject to determine the expression level of a biomarker selected from AM and/or $AM_2$ and/or CLR and/or RAMP3.

Elevated levels of AM and/or $AM_2$ expression in serum and/or tissue and/or tumour tissue samples when compared with one or more reference values or reference serum and/or tissue and/or tumour tissue samples is indicative of early-stage pancreatic cancer. Elevated levels of CLR and/or RAMP3 expression in tumour tissue samples when compared with one or more reference values or reference tumour tissue samples is indicative of early-stage pancreatic cancer. Elevated levels of AM and/or $AM_2$ and/or CLR and/or RAMP3 expression in a biological sample when compared with one or more reference values or reference biological samples may suitably be discerned at the transcript (mRNA) and/or protein level. Most conveniently, elevated levels of AM and/or $AM_2$ and/or CLR and/or RAMP3 expression in biological samples when compared with one or more reference values or control biological samples are detectable at the transcript (mRNA) level.

Suitably, the biomarkers are selected from the group consisting of biomarker protein; and nucleic acid molecule encoding the biomarker protein. It is preferred that the biomarker is a nucleic acid molecule, and particularly preferred that it is an mRNA molecule.

It is preferred that the levels of the biomarkers in the biological sample are investigated using specific binding partners. Suitably the binding partners may be selected from the group consisting of: complementary nucleic acids; aptamers; antibodies or antibody fragments. Suitable classes of binding partners for any given biomarker will be apparent to the skilled person.

Suitably, the levels of the biomarkers in the biological sample may be detected by direct assessment of binding between the target molecules and binding partners.

Conveniently, the levels of the biomarkers in the biological sample are detected using a reporter moiety attached to a binding partner. Preferably, the reporter moiety is selected from the group consisting of fluorophores; chromogenic substrates; and chromogenic enzymes.

Binding Partners

Expression levels of the biomarkers in a biological sample may be investigated using binding partners which bind or hybridize specifically to the biomarkers or a fragment thereof. In relation to the present invention the term 'binding partners' may include any ligands, which are capable of binding specifically to the relevant biomarker and/or nucleotide or peptide variants thereof with high affinity. Said ligands include, but are not limited to, nucleic acids (DNA or RNA), proteins, peptides, antibodies, antibody-conjugates, synthetic affinity probes, carbohydrates, lipids, artificial molecules or small organic molecules such as drugs. In certain embodiments the binding partners may be selected from the group comprising: complementary nucleic acids; aptamers; antibodies or antibody fragments. In the case of detecting mRNAs, nucleic acids represent highly suitable binding partners.

In the context of the invention, a binding partner which binds specifically to a biomarker should be taken as requiring that the binding partner should be capable of binding to at least one such biomarker in a manner that can be distinguished from non-specific binding to molecules that are not biomarkers. A suitable distinction may, for example, be based on distinguishable differences in the magnitude of such binding.

In preferred embodiments of the methods of the invention, the biomarker is a nucleic acid, preferably an mRNA molecule, and the binding partner is selected from the group comprising; complementary nucleic acids or aptamers.

Suitably, the binding partner may be a nucleic acid molecule (typically DNA, but it can be RNA) having a sequence which is complementary to the sequence the relevant mRNA or cDNA against which it is targeted. Such a nucleic acid is often referred to as a 'probe' (or a reporter or an oligo) and the complementary sequence to which it binds is often referred to as the 'target'. Probe-target hybridization is usually detected and quantified by detection of fluorophore-, silver-, or chemiluminescence-labelled targets to determine relative abundance of nucleic acid sequences in the target.

Probes can be from 25 to 1000 nucleotides in length. However, lengths of 30 to 100 nucleotides are preferred, and probes of around 50 nucleotides in length are commonly used with success in complete transcriptome analysis.

Whilst the determination of suitable probes can be difficult, e.g. in very complex arrays, there are many commercial sources of complete transcriptome arrays available, and it is routine to develop bespoke arrays to detect any given set of specific mRNAs using publicly available sequence information. Commercial sources of microarrays for transcriptome analysis include Illumina and Affymetrix.

It will be appreciated that effective nucleotide probe sequences may be routinely designed to any sequence region of the biomarker transcripts of AM (NM_001124.2), $AM_2$ (NM_001253845.1), CLR (CLR variant 1: NM_005795.5, CLR variant 2: NM_214095.1) or RAMP3 (NM_005856.2) or a variant thereof in order to specifically detect, and measure expression thereof. The person skilled in the art will appreciate that the effectiveness of the particular probes chosen will vary, amongst other things, according to the platform used to measure transcript abundance, the sequence region that the probe binds to and the hybridization conditions employed.

Alternatively, the biomarker may be a protein, and the binding partner may suitably be selected from the group comprising; antibodies, antibody-conjugates, antibody fragments or aptamers. Such a binding partner will be capable of specifically binding to an AM, $AM_2$, CLR or RAMP3 protein in order to detect and measure the expression thereof.

Polynucleotides encoding any of the specific binding partners of biomarkers of the invention recited above may be isolated and/or purified nucleic acid molecules and may be RNA or DNA molecules.

Throughout, the term "polynucleotide" as used herein refers to a deoxyribonucleotide or ribonucleotide polymer in single- or double-stranded form, or sense or anti-sense, and encompasses analogues of naturally occurring nucleotides that hybridize to nucleic acids in a manner similar to naturally occurring nucleotides. Such polynucleotides may be derived from *Homo sapiens*, or may be synthetic or may be derived from any other organism.

Commonly, polypeptide sequences and polynucleotides used as binding partners in the present invention may be isolated or purified. By "purified" is meant that they are substantially free from other cellular components or material, or culture medium. "Isolated" means that they may also be free of naturally occurring sequences which flank the native sequence, for example in the case of nucleic acid molecule, isolated may mean that it is free of 5' and 3' regulatory sequences.

In preferred embodiments of methods of the invention, the nucleic acid is mRNA. There are numerous suitable techniques known in the art for the quantitative measurement of mRNA transcript levels in a given biological sample. These techniques include but are not limited to; "Northern" RNA blotting, Real Time Polymerase Chain Reaction (RTPCR), Quantitative Polymerase Chain Reaction (qPCR), digital PCR (dPCR), multiplex PCR, Reverse Transcription Quantitative Polymerase Chain Reaction (RT-qPCR) or by high-throughput analysis such as hybridization microarray, Next Generation Sequencing (NGS) or by direct mRNA quantification, for example by "Nanopore" sequencing. Alternatively, "tag based" technologies may be used, which include but are not limited to Serial Analysis of Gene Expression (SAGE). Commonly, the levels of biomarker mRNA transcript in a given biological sample may be determined by hybridization to specific complementary nucleotide probes on a hybridization microarray or "chip", by Bead Array Microarray technology or by RNA-Seq where sequence data is matched to a reference genome or reference sequences.

In a preferred embodiment, where the nucleic acid is mRNA, the present invention provides a method of predicting or determining therapeutic responsiveness to treatment with compounds of the invention, wherein the levels of biomarker transcript(s) are determined by PCR. A variety of suitable PCR amplification-based technologies are well known in the art. PCR applications are routine in the art and the skilled person will be able to select appropriate polymerases, buffers, reporter moieties and reaction conditions. Preferably mRNA transcript abundance will be determined by qPCR, dPCR or multiplex PCR. Nucleotide primer sequences may routinely be designed to any sequence region of the biomarker transcripts of AM (NM_001124.2), $AM_2$ (NM_001253845.1), CLR (CLR variant 1: NM_005795.5, CLR variant 2: NM_214095.1) or RAMP3 (NM_005856.2) or a variant thereof, by methods which are well-known in the art. Consequently, the person skilled in the art will appreciate that effective primers can be designed to different regions of the transcript or cDNA of biomarkers selected from AM, $AM_2$, CLR or RAMP3, and that the effectiveness of the particular primers chosen will vary, amongst other things, according to the region selected, the platform used to measure transcript abundance, the biological sample and the hybridization conditions employed. It will therefore be appreciated that providing they allow specific amplification of the relevant cDNA, in principle primers targeting any region of the transcript may be used in accordance with the present invention. However, the person skilled in the art will recognise that in designing appropriate primer sequences to detect biomarker expression, it is required that the primer sequences be capable of binding selectively and specifically to the cDNA sequences of biomarkers corresponding to AM (NM_001124.2), $AM_2$ (NM_001253845.1), CLR (CLR variant 1: NM_005795.5, CLR variant 2: NM_214095.1) or RAMP3 (NM_005856.2) or fragments or variants thereof. Suitable binding partners are preferably nucleic acid primers adapted to bind specifically to the cDNA transcripts of biomarkers, as discussed above. Depending on the sample involved, preferably primers will be provided that specifically target either AM, $AM_2$, CLR or RAMP3.

Many different techniques known in the art are suitable for detecting binding of the target sequence and for high-throughput screening and analysis of protein interactions. According to the present invention, appropriate techniques include (either independently or in combination), but are not limited to; co-immunoprecipitation, bimolecular fluorescence complementation (BiFC), dual expression recombinase based (DERB) single vector system, affinity electrophoresis, pull-down assays, label transfer, yeast two-hybrid screens, phage display, in-vivo crosslinking, tandem affinity purification (TAP), ChIP assays, chemical cross-linking followed by high mass MALDI mass spectrometry, strep-protein interaction experiment (SPINE), quantitative immunoprecipitation combined with knock-down (QUICK), proximity ligation assay (PLA), bio-layer interferometry, dual polarisation interferometry (DPI), static light scattering (SLS), dynamic light scattering (DLS), surface plasmon resonance (SPR), fluorescence correlation spectroscopy, fluorescence resonance energy transfer (FRET), isothermal titration calorimetry (ITC), microscale thermophoresis (MST), chromatin immunoprecipitation assay, electrophoretic mobility shift assay, pull-down assay, microplate capture and detection assay, reporter assay, RNase protection assay, FISH/ISH co-localization, microarrays, microsphere arrays or silicon nanowire (SiNW)-based detection. Where biomarker protein levels are to be quantified, preferably the interactions between the binding partner and biomarker protein will be analysed using antibodies with a fluorescent reporter attached.

In certain embodiments of the invention, the expression level of a particular biomarker may be detected by direct assessment of binding of the biomarker to its binding partner. Suitable examples of such methods in accordance with this embodiment of the invention may utilise techniques such as electro-impedance spectroscopy (EIS) to directly assess binding of binding partners (e.g. antibodies) to target biomarkers (e.g. biomarker proteins).

In certain embodiments of the invention, the binding partner may be an antibody, antibody-conjugate or antibody fragment, and the detection of the target molecules utilises an immunological method. In certain embodiments of the methods or devices, the immunological method may be an enzyme-linked immunosorbent assay (ELISA) or utilise a lateral flow device.

A method of the invention may further comprise quantification of the amount of the target molecule indicative of expression of the biomarkers present in the biological sample from a subject. Suitable methods of the invention, in which the amount of the target molecule present has been quantified, and the volume of the patient sample is known, may further comprise determination of the concentration of the target molecules present in the patient sample which may be used as the basis of a qualitative assessment of the subject's condition, which may, in turn, be used to suggest a suitable course of treatment for the subject, for example, treatment with one or more of the compounds of the invention.

Reporter Moieties

In certain embodiments of the present invention the expression levels of the protein in a biological sample may be determined. In some instances, it may be possible to directly determine expression, e.g. as with GFP or by enzymatic action of the protein of interest (POI) to generate a detectable optical signal. However, in some instances it may be chosen to determine physical expression, e.g. by antibody probing, and rely on separate test to verify that physical expression is accompanied by the required function.

In certain embodiments of the invention, the expression levels of a particular biomarker will be detectable in a biological sample by a high-throughput screening method, for example, relying on detection of an optical signal, for instance using reporter moieties. For this purpose, it may be necessary for the specific binding partner to incorporate a tag, or be labelled with a removable tag, which permits detection of expression. Such a tag may be, for example, a fluorescence reporter molecule. Such a tag may provide a suitable marker for visualisation of biomarker expression since its expression can be simply and directly assayed by fluorescence measurement in-vitro or on an array. Alternatively, it may be an enzyme which can be used to generate an optical signal. Tags used for detection of expression may also be antigen peptide tags. Similarly, reporter moieties may be selected from the group consisting of fluorophores; chromogenic substrates; and chromogenic enzymes. Other kinds of label may be used to mark a nucleic acid binding partner including organic dye molecules, radiolabels and spin labels which may be small molecules.

Conveniently, the levels of a biomarker or several biomarkers may be quantified by measuring the specific hybridization of a complementary nucleotide probe to the biomarker of interest under high-stringency or very high-stringency conditions.

Conveniently, probe-biomarker hybridization may be detected and quantified by detection of fluorophore-, silver-, or chemiluminescence-labelled probes to determine relative abundance of biomarker nucleic acid sequences in the sample. Alternatively, levels of biomarker mRNA transcript abundance can be determined directly by RNA sequencing or nanopore sequencing technologies.

The methods of the invention may make use of molecules selected from the group consisting of: the biomarker protein; and nucleic acid encoding the biomarker protein.

Nucleotides and Hybridization Conditions

Throughout, the term "polynucleotide" as used herein refers to a deoxyribonucleotide or ribonucleotide polymer in single- or double-stranded form, or sense or anti-sense, and encompasses analogues of naturally occurring nucleotides that hybridize to nucleic acids in a manner similar to naturally occurring nucleotides.

The person skilled in the art would regard it as routine to design nucleotide probe sequences to any sequence region of the biomarker transcripts or cDNA sequences corresponding to AM (NM_001124.2), $AM_2$ (NM_001253845.1), CLR (CLR variant 1: NM_005795.5, CLR variant 2: NM_214095.1) or RAMP3 (NM_005856.2) or a fragment or variant thereof. This is also the case with nucleotide primers used where detection of expression levels is determined by PCR-based technology.

Of course the person skilled in the art will recognise that in designing appropriate probe sequences to detect biomarker expression, it is required that the probe sequences be capable of binding selectively and specifically to the transcripts or cDNA sequences of biomarkers corresponding to AM (NM_001124.2), $AM_2$ (NM_001253845.1), CLR (CLR variant 1: NM_005795.5, CLR variant 2: NM_214095.1) or RAMP3 (NM_005856.2) or fragments or variants thereof. The probe sequence will therefore be hybridizable to that nucleotide sequence, preferably under stringent conditions, more preferably very high stringency conditions. The term "stringent conditions" may be understood to describe a set of conditions for hybridization and washing and a variety of stringent hybridization conditions will be familiar to the skilled reader. Hybridization of a nucleic acid molecule occurs when two complementary nucleic acid molecules undergo an amount of hydrogen bonding to each other known as Watson-Crick base pairing. The stringency of hybridization can vary according to the environmental (i.e. chemical/physical/biological) conditions surrounding the nucleic acids, temperature, the nature of the hybridization method, and the composition and length of the nucleic acid molecules used. Calculations regarding hybridization conditions required for attaining particular degrees of stringency are discussed in Sambrook et al. (2001, *Molecular Cloning: A Laboratory Manual*, Cold Spring Harbor Laboratory Press, Cold Spring Harbor, N.Y.); and Tijssen (1993, *Laboratory Techniques in Biochemistry and Molecular Biology—Hybridization with Nucleic Acid Probes* Part I, Chapter 2, Elsevier, NY). The Tm is the temperature at which 50% of a given strand of a nucleic acid molecule is hybridized to its complementary strand.

In any of the references herein to hybridization conditions, the following are exemplary and not limiting:

Very High Stringency (allows sequences that share at least 90% identity to hybridize)
  Hybridization: 5×SSC at 65° C. for 16 hours
  Wash twice: 2×SSC at room temperature (RT) for 15 minutes each
  Wash twice: 0.5×SSC at 65° C. for 20 minutes each High Stringency (allows sequences that share at least 80% identity to hybridize)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each Low Stringency (allows sequences that share at least 50% identity to hybridize)
  Hybridization: 6×SSC at RT to 55° C. for 16-20 hours
  Wash at least twice: 2×-3×SSC at RT to 55° C. for 20-30 minutes each.

In a further aspect, the present invention relates to a method of treating or preventing cancer in a subject, said method comprising administering a therapeutically effective amount of an $AM_2$ inhibitor, for example a compound of the invention, to said subject, wherein said subject has a cancer associated with expression of AM and/or CLR and/or RAMP3. Without wishing to be bound by theory it is possible that expression of AM by a tumour may interact with $AM_2$ receptors in healthy tissue resulting in, for example metastasis and/or angiogenesis and progression of the cancer. Accordingly the expression of AM and/or CLR and/or RAMP3 may be in the tumour or in healthy tissues, for example in healthy tissues surrounding a tumour.

Optionally, the method may comprise determining the levels of AM and/or CLR and/or RAMP3 in a biological sample of said subject, and administering a compound of the invention to said subject when the level AM and/or CLR and/or RAMP3 is determined to be expressed or expressed at increased levels in the biological sample relative to one or more reference values.

In a further aspect, the present invention relates to a method of identifying a subject having increased likelihood of responsiveness or sensitivity to an $AM_2$ inhibitor, for example a compound of the invention, comprising determining the level of one or more of AM, CLR and RAMP3 in a biological sample of the subject;
wherein increased levels of AM, CLR and/or RAMP3 compared to one or more reference values indicates an increased likelihood of responsiveness or sensitivity to an $AM_2$ inhibitor in the subject.

Combination Therapies

The compounds of the invention may be used alone to provide a therapeutic effect The compounds of the invention may also be used in combination with one or more additional anti-cancer agent and/or radiotherapy.

Such chemotherapy may include one or more of the following categories of anti-cancer agents:

(i) antiproliferative/antineoplastic drugs and combinations thereof, such as alkylating agents (for example cis-platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5-fluorouracil and tegafur, raltitrexed, methotrexate, pemetrexed, cytosine arabinoside, floxuridine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, irinotecan, mitoxantrone and camptothecin); bleomcin, dactinomycin, daunorubicin, doxorubicin, epirubicin, idarubicin, ara-C, paclitaxel (Taxol™), nab paclitaxel (albumin-bound paclitaxel), docetaxel, mithramycin, deoxycoformycin, mitomycin-C, L-asparaginase, interferons (especially IFN-alpha), etoposide, teniposide, DNA-demethylating agents, (for example, azacitidine or decitabine); and histone de-acetylase (HDAC) inhibitors (for example vorinostat, MS-275, panobinostat, romidepsin, valproic acid, mocetinostat (MGCD0103) and pracinostat SB939);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-II, anastrazole, letrozole, capecitabine, reloxafme, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1l antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), afatinib, vandetanib, osimertinib and rociletinib) erbB2 tyrosine kinase inhibitors such as lapatinib) and antibodies to costimulatory molecules such as CTLA-4, 4-IBB and PD-I, or antibodies to cytokines (IL-10, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as famesyl transferase inhibitors, sorafenib, tipifamib and lonafamib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors, for example dalotuzumab; aurora kinase inhibitors and cyclin dependent kinase inhibitors such as CDK2 and/or CDK4 inhibitors; CCR2, CCR4 or CCR6 antagonists; RAF kinase inhibitors such as those described in WO2006043090, WO2009077766, WO2011092469 or WO2015075483; and Hedgehog inhibitors, for example vismodegib.

(v) antiangiogenic agents such as those which inhibit the effects of vascular endothelial growth factor, [for example the anti-vascular endothelial cell growth factor antibody bevacizumab (Avastin™)]; thalidomide; lenalidomide; and for example, a VEGF receptor tyrosine kinase inhibitor such as vandetanib, vatalanib, sunitinib, axitinib, pazopanib and cabozantinib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); toll-like receptor modulators for example TLR-7 or TLR-9 agonists; PD-1, PD-L1, PD-L2 and CTL4-A modulators (for example Nivolumab), antibodies and vaccines; other IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilumumab), CAR-T cell therapies; and (viii) cytotoxic agents for example fludaribine (fludara), cladribine, pentostatin (Nipent™);

(ix) targeted therapies, for example PI3K inhibitors, for example idelalisib and perifosine; SMAC (second mitochondriaderived activator of caspases) mimetics, also known as Inhibitor of Apoptosis Proteins (IAP) antagonists (IAP antagonists). These agents act to supress IAPs, for example XIAP, cIAP1 and cIAP2, and thereby re-establish cellular apoptotic pathways. Particular SMAC mimetics include Birinapant (TL32711, TetraLogic Pharmaceuticals), LCL161 (Novartis), AEG40730 (Aegera Therapeutics), SM-164 (University of Michigan), LBW242 (Novartis), ML101 (Sanford-Bumham Medical Research Institute), AT-406 (Ascenta Therapeutics/University of Michigan), GDC-0917 (Genentech), AEG35156 (Aegera Therapeutic), and HGS1029 (Human Genome Sciences); and agents which target ubiquitin proteasome system (UPS), for example, bortezomib, carfilzomib, marizomib (NPI-0052) and MLN9708; a CXCR4 antagonist, for example plerixafor or BL-8040;

(x) PARP inhibitors, for example niraparib (MK-4827), talazoparib (BMN-673), veliparib (ABT-888); olaparib, CEP 9722, and BGB-290

(xi) chimeric antigen receptors, anticancer vaccines and arginase inhibitors;

(xii) agents which degrade hyaluronan, for example the hyaluronidase enzyme PEGPH20

The additional anti-cancer agent may be a single agent or one or more of the additional agents listed herein.

Particular anti-cancer agents which may be used together with a compound of the invention include for example erlotinib, cabozantinib, bevacizumab, dalotuzumab, olaparib, PEGPH20, vismodegib, paclitaxel (including nab paclitaxel), gemcitabine, oxaliplatin, irinotecan, leucovorin and 5-fluorouracil. In some embodiments the additional anti-cancer agent selected from capecitabine, gemcitabine and 5-fluorouracil (5FU).

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

In some embodiments in which a combination treatment is used, the amount of the compound of the invention and the amount of the other pharmaceutically active agent(s) are, when combined, therapeutically effective to treat a targeted disorder in the patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound of the invention and an approved or otherwise published dosage range(s) of the other pharmaceutically active compound(s).

According to a further aspect of the invention there is provided a compound of the invention as defined hereinbefore and an additional anti-cancer agent as defined hereinbefore, for use in the conjoint treatment of cancer.

According to a further aspect of the invention there is provided a pharmaceutical product comprising a compound of the invention as defined hereinbefore and an additional anti-cancer agent as defined hereinbefore for the conjoint treatment of cancer.

According to a further aspect of the invention there is provided a method of treatment of a human or animal subject suffering from a cancer comprising administering to the subject a therapeutically effective amount of a compound of the invention, or a pharmaceutically acceptable salt thereof simultaneously, sequentially or separately with an additional anti-cancer agent as defined hereinbefore.

According to a further aspect of the invention there is provided a compound of the invention, or a pharmaceutically acceptable salt thereof for use simultaneously, sequentially or separately with an additional anti-cancer agent as defined hereinbefore, in the treatment of a cancer.

The compound of the invention may also be used be used in combination with radiotherapy. Suitable radiotherapy treatments include, for example X-ray therapy, proton beam therapy or electron beam therapies. Radiotherapy may also encompass the use of radionuclide agents, for example $^{131}$I, $^{32}$P, $^{90}$Y, $^{89}$Sr, $^{153}$Sm or $^{223}$Ra. Such radionuclide therapies are well known and commercially available.

According to a further aspect of the invention there is provided a compound of the invention, or a pharmaceutically acceptable salt thereof as defined hereinbefore for use in the treatment of cancer conjointly with radiotherapy.

According to a further aspect of the invention there is provided a method of treatment of a human or animal subject suffering from a cancer comprising administering to the subject a therapeutically effective amount of a compound of the invention, or a pharmaceutically acceptable salt thereof simultaneously, sequentially or separately with radiotherapy.

Biological Assays

The biological effects of the compounds may be assessed using one of more of the assays described herein in the Examples.

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl or trifluoroacetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively, an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, or sodium hydroxide, or ammonia. Alternatively, an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

General Synthetic Routes

The present invention further provides a process for the preparation of a compound of formula (I) or a pharmaceutically acceptable salt thereof as defined above which comprises reacting a compound of formula (XII), or a salt thereof:

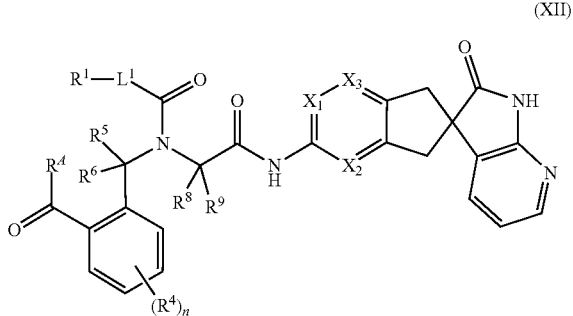

(XII)

wherein $R^1$, $R^A$, $R^4$, $R^5$, $R^6$, $R^8$, $R^9$, $L^1$, $X_1$, $X_2$, $X_3$ and n have any of the meanings defined herein, except that any functional group is protected if necessary, with a compound of the formula $NHR^2R^3$ or a salt thereof, wherein $R^2$ and $R^3$ have any of the meanings defined herein, except that any functional group is protected if necessary;

and optionally thereafter carrying out one or more of the following procedures:
converting a compound of formula (I) into another compound of formula (I)
removing any protecting groups
forming a pharmaceutically acceptable salt.

In one embodiment in the compound of formula (XII), $X_2$ and $X_3$ are CH; and $X_1$ is $CR^7$, wherein $R^7$ has any of the meanings defined herein, except that any functional group is protected if necessary.

The reaction is suitably carried out as a reductive amination of the aldehyde or ketone of the formula (XII). Suitably the reaction is carried out in the presence of a suitable reducing agent, for example sodium triacetoxyborohydride or sodium borohydride. The reaction is carried out in the presence of a suitable solvent, for example dichloromethane or methanol. When the compound of the formula $NHR^2R^3$ is used in the form of a salt, for example a hydrochloride salt the reaction is suitably performed in the presence of a base, for example a tertiary organic amine such as diisopropylethylamine. Optionally the reaction is performed in the presence of a suitable dehydrating agent, for example sodium or magnesium sulphate.

Compounds of the formula (XII) may be prepared as described in the Examples. Compounds of the formula are commercially available or can be prepared using well-known methods.

Compounds of the formula (I) wherein X is $CH_2$ and $R^2$ is H may also be prepared by reduction of the imine of the formula (XIII) or a salt thereof:

(XIII)

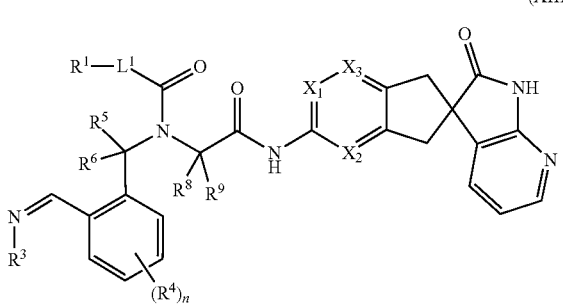

wherein $R^1$, $R^3$, $R^4$, $R^5$, $R^6$, $R^8$, $R^9$, $X_1$, $X_2$, $X_3$, $L^1$ and n have any of the meanings defined herein, except that any functional group is protected if necessary;

and optionally thereafter carrying out one or more of the following procedures:
converting a compound of formula (I) into another compound of formula (I)
removing any protecting groups
forming a pharmaceutically acceptable salt.

In one embodiment in the compound of formula (XIII), $X_2$ and $X_3$ are CH; and $X_1$ is $CR^7$, wherein $R^7$ has any of the meanings defined herein, except that any functional group is protected if necessary.

The reduction is performed in the presence of a suitable reducing agent, for example sodium borohydride. The reaction is suitably performed in the presence of a solvent, for example methanol.

The compound of the formula (XIII) may be prepared using methods analogous to those described in the Examples. For example, by reaction of an aldehyde of the formula (XIII) with a primary amine of the formula $NR^3H_2$.

Compounds of the formula (I) may also be prepared by coupling a compound of the formula (XIV), or a salt thereof:

(XIV)

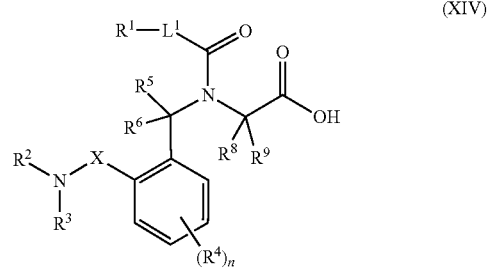

wherein $R^1$, $R^2$, $R^3$, $R^4$, $R^5$, $R^6$, $R^8$, $R^9$, $L^1$, X and n have any of the meanings defined herein, except that any functional group is protected if necessary (e.g. $R^2$ and/or $R^3$ may be an amino protecting group), with a compound of the formula (XV), or a salt thereof:

(XV)

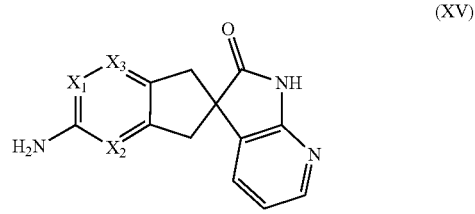

wherein $X_1$, $X_2$ and $X_3$ have any of the meanings defined herein, except that any functional group is protected if necessary;

and optionally thereafter carrying out one or more of the following procedures:
converting a compound of formula (I) into another compound of formula (I)
removing any protecting groups
forming a pharmaceutically acceptable salt.

In one embodiment in the compound of formula (XV), $X_2$ and $X_3$ are CH; and $X_1$ is $CR^7$, wherein $R^7$ has any of the meanings defined herein, except that any functional group is protected if necessary.

The reaction is carried out using well known methods for the coupling of acids with amines to form an amide. Representative methods are set out in the Example section herein. Compounds of the formulae (XIV) and (XV) may be prepared as described in the Examples.

The reaction above may be varied to provide intermediates which are subsequently transformed into a compound of the formula (I). For example, it is possible to carry out the reaction coupling an intermediate of the formula (XIVa), or a salt thereof:

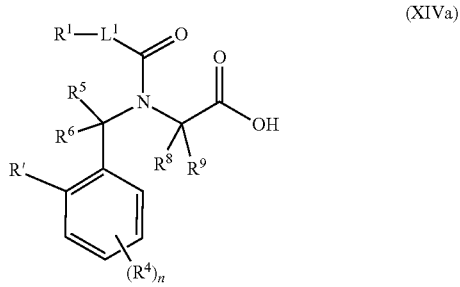

(XIVa)

wherein R' is halo, for example bromo, with the compound of the formula (XV). The resulting intermediate may then be converted to a compound of the formula (I) by for example conversion of the halo to a cyano group followed by reduction of the cyano group to an amine.

Compounds of the formula (I) may also be prepared by reacting a compound of the formula (XVI), or a salt thereof:

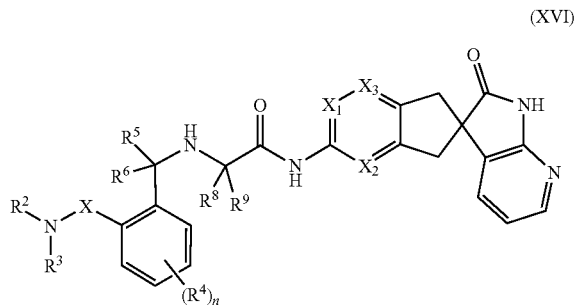

(XVI)

wherein $R^2$, $R^3$, $R^4$, $R^5$, $R^6$, $R^8$, $R^9$, X, $X_1$, $X_2$, $X_3$ and n have any of the meanings defined herein, except that any functional group is protected if necessary (e.g. $R^2$ and/or $R^3$ may be an amino protecting group), with a compound of the formula: $R^1L^1C(O)R''$, wherein $R^1$ and $L^1$ have any of the meanings defined herein and R'' is OH or halo (for example chloro), except that any functional group is protected if necessary.
and optionally thereafter carrying out one or more of the following procedures:
converting a compound of formula (I) into another compound of formula (I)
removing any protecting groups
forming a pharmaceutically acceptable salt.

In one embodiment in the compound of formula (XVI), $X_2$ and $X_3$ are CH; and $X_1$ is $CR^7$, wherein $R^7$ has any of the meanings defined herein, except that any functional group is protected if necessary.

The reaction is suitably performed in the presence of a solvent, for example a polar protic solvent such as N,N-dimethylformamide. The reaction is suitably performed in the presence of a base, for example an organic amine base such as N,N-diisopropylethylamine. Compounds of the formula (XI) may be prepared using analogous conditions to those described in the Examples. Compounds of the formula $R^1L^1C(O)R''$ are commercially available or can be prepared using well-known methods.

Compounds of the formula (I) wherein $R^2$ is H may be prepared by deprotecting a compound of the formula (XVII), or a salt thereof:

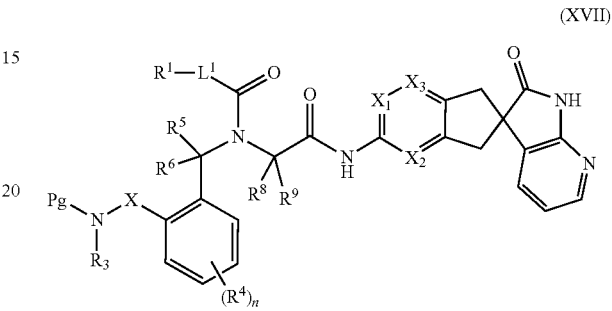

(XVII)

wherein $R^1$ $R^2$, $R^3$, $R^4$, $R^5$, $R^6$, $R^8$, $R^9$, X, $X_1$, $X_2$, $X_3$, $L^1$ and n have any of the meanings defined herein, except that any functional group is protected if necessary, and Pg is an amino protecting group.

Suitable amino protecting groups are well-known and include, for example, those disclosed herein such as tert-butoxycarbonyl (BOC), benzyloxycarbonyl (CBz), and 9-fluorenylmethoxycarbonyl (Fmoc), preferably BOC. The amino protecting group can be removed by conventional methods, for example treatment with a suitable acid or base.

Certain intermediates described herein are novel and form a further aspect of the invention. Accordingly, also provided is a compound of the formula (XII), (XIII), (XIV), (XIVa) (XV), (XVI) or (XVII), or a salt thereof.

In an embodiment there is provided a compound of the formula (XIV), or a salt thereof wherein X is —$(CR^AR^B)_{p1}$—, wherein p1 is an integer 1, 2 or 3, preferably 1. Suitably in this embodiment X is —$CH_2$—. Suitably in this embodiment $L^1$ a bond.

Suitably the salt of a compound of the formula (XII), (XIII), (XIV), (XIVa) (XV), (XVI) or (XVII) is a pharmaceutically acceptable salt thereof, however, it will be appreciated that other salts that are not pharmaceutically acceptable salts may be used in the manufacture of the compounds of the invention.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel- Crafts conditions; the introduction of an alkyl group using an alkyl halide and Lewis acid (such as aluminium trichloride) under Friedel-Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl.

When a pharmaceutically acceptable salt of a compound of the formula (I) is required, for example an acid or base addition salt, it may be obtained by, for example, reaction of the compound of formula (I) with a suitable acid or base using a conventional procedure as described above.

To facilitate isolation of a compound of the formula (I) during its preparation, the compound may be prepared in the form of a salt that is not a pharmaceutically acceptable salt. The resulting salt can then be modified by conventional techniques to give a pharmaceutically acceptable salt of the compound. Such salt modification techniques are well known and include, for example ion exchange techniques or re-precipitation of the compound from solution in the presence of a pharmaceutically acceptable counter ion as described above, for example by re-precipitation in the presence of a suitable pharmaceutically acceptable acid to give the required pharmaceutically acceptable acid addition salt of a compound of the formula (I).

EXAMPLES

Abbreviations

BINAP—2,2'-bis(diphenylphosphino)-1,1'-binaphthyl
Bn—benzyl
Boc—tert butoxycarbonyl
CPME—cyclopentyl methyl ether
CSH—charged surface hybrid
DCM—dichloromethane
DIPA—diisopropylamine
DIPEA—N,N-diisopropylethylamine
DMAc—dimethylacetamide
DMF—N,N-dimethylformamide
DMP—Dess-Martin periodinane (1,1,1-Tris(acetyloxy)-1,1-dihydro-1,2-benziodoxol-3-(1H)-one
DSC—differential scanning calorimetry
EDCl.HCl—1-ethyl-3-(3-dimethylaminopropyl)carbodiimide hydrochloride salt
HATU—1-[bis(dimethylamino)methylene]-1H-1,2,3-triazolo[4,5-b]pyridinium 3-oxide hexafluorophosphate
HOAt—1-hydroxy-7-azabenzotriazole
HPLC—high performance liquid chromatography
IPA—isopropanol
LCMS—liquid chromatography-mass spectrometry
LDA—lithium diisopropylamide
MDAP—mass-directed automated purification
MS—mass spectrometry
NBS—N-bromosuccinimide
NMM—N-methylmorpholine
NMR—nuclear magnetic resonance
PDA—photodiode array
pTSA—p-toluene sulfonic acid
QDA—Quadrupole Dalton
RT—room temperature
rt—retention time
SCX2—strong cation exchange 2 (SPE from Biotage)
SEM—trimethylsilylethoxymethyl
SPE—solid phase extraction
STMAd—succinic acid ethyl sulphide silica (SPE from Phosphonics)
TBAB—tetrabutylammonium bromide
TEA—triethylamine
TFA—trifluoroacetic acid
TFAA—trifluoroacetic anhydride
THF—tetrahydrofuran
UPLC—ultra performance liquid chromatography Analytical Methods The following methods apply to Examples 1-66, 70-74, 79-91, 103 and 104.

All UPLC-MS analyses were carried out using Waters Acquity UPLC-MS (quaternary pump flow 0.8 ml/min, Acquity autosampler, PDA and QDA).

Methods:

All basic methods run using XBridge C18 Column: XB C18 2.5 μm 2.1×50 mm

Short Basic: Run Time: 1.40 min; Solvents B) Acetonitrile C) 10 mM $NH_4HCO_3$ at pH10

Gradient 2-98% B with C in 1.2 min, hold at 98% B 2% C to 1.40 min @ 0.8 ml/min, 40° C.;

Long Basic: Run Time: 4.60 mins; Solvents B) acetonitrile C) 10 mM $NH_4HCO_3$ at pH10

Gradient 2-98% B with C in 4.0 min, hold at 98% B 2% C to 4.60 min @ 0.8 ml/min, 40° C.

All CSH methods are acidic methods using CSH C18 Column: CSH C18 1.7 μm 2.1×50 mm.

Short CSH: Run Time: 1.40 min; Solvents A) water B) acetonitrile D) 2% formic acid: the gradient runs with 5% D. Gradient: 2-95% B with A and 5% D in 1.2 min, hold at 95% B 5% D to 1.40 min @ 0.8 ml/min, 40° C.

Short CSH 2-50%: Run Time: 2.0 min; Solvents A) water B) acetonitrile D) 2% formic acid: the gradient runs with 5% D. Gradient 2-50% B with A and 5% D in 1.0 min, to 95% B with 5% D at 1.8 min, hold at 95% B 5% D to 2.0 min @ 0.8 ml/min, 40° C.

Short CSH 0-50%: Run Time: 1.40 min; Solvents: A) 0.1% formic acid, B) acetonitrile; Gradient 0-50% B in 0.80 min, 50-95% B to 1.20 min, hold @ 95% B to 1.40 min.

Long CSH: Run Time: 4.60 mins; Solvents A) water B) acetonitrile D) 2% formic acid: the gradient runs with 5% D. Gradient: 2-95% B with A and 5% D 4.0 min, hold at 95% B 5% D to 4.60 min @ 0.8 ml/min, 40° C.

HPLC-MS analyses were carried out using Waters Alliance 2695, flow 1 ml/min, (PDA, ZQ micromass).

Methods:

Long Basic: Run time: 3.1 min Solvents: A) Water 10 mM ammonium bicarbonate pH 10, B) MeCN; Gradient: 0-95% B with A to 2.0 min, hold at 95% B, 5% A to 3.10 min XBridge IS C18 2.5 μm 2.1×2.0 mm.

Long Basic, 11 min, 40%: Run time: 11 min; Solvents: 60% water pH 10 buffer 10 mM $NH_4HCO_3$, 40% acetonitrile, Isocratic, XBridge C18 Column: XB C18 5 μm 3×150 mm.

All NMR spectra were obtained using Jeol EXC300 MHz or EXC400 MHz NMR spectrometers running Delta software.

Exceptions to the above —Examples 38 (23L), 41 (230), 42 (23P), 43 (23 Q) were analysed using the following:

HPLC: Waters Alliance 2690, flow 1 ml/min, (Water 2487, UV visible detector); column: Thermo HyPurity C8, 250×4.6 mm, Gradient—5 to 95% acetonitrile/water 0.1% TFA over 20 mins, hold at 95%, 25 min run, RT.

MS: Agilent 6530 Q-ToF.

NMR: Bruker Advance III HD, advance operating at 400 MHz or Bruker Advance dpx operating at 400 MHz running Topspin software.

The following methods apply to Examples 67-69, 75-78 and 92-101. HPLC-MS analyses were carried out using SHIMADZU LCMS-2020; HPLC-MS (LC-20AB flow 0.8 ml/min, autosampler, PDA).

All acidic methods run using Kinetex@ 5 um EVO C18 30*2.1 mm and Chromolith@Flash RP-18E 25-2MM.

Short acidic: Run Time: 1.50 min; Solvents A) 0.0375% TFA in water (v/v) B) 0.01875% TFA in Acetonitrile (v/v). The gradient runs with 5% B. Gradient: 5-95% B with A 0.8 min, hold at 95% B to 1.20 min; 5% B at 1.21 min and hold at 5% B to 1.5 min @ 1.5 ml/min, 50° C.

Long acidic: Run Time: 4.00 min; Solvents A) 0.0375% TFA in water (v/v) B) 0.01875% TFA in Acetonitrile (v/v). The gradient runs with 5% B. Gradient: 5-95% B with A 3.00 min, hold at 95% B to 3.50 min; 5% B at 3.51 min and hold at 5% B to 4.00 min @ 0.8 ml/min, 50° C.

All NMR spectra were obtained using Bruker Avance 400 MHZ spectrometers running ACD/Spectrus Processor.

Synthesis of Intermediate A, B and C

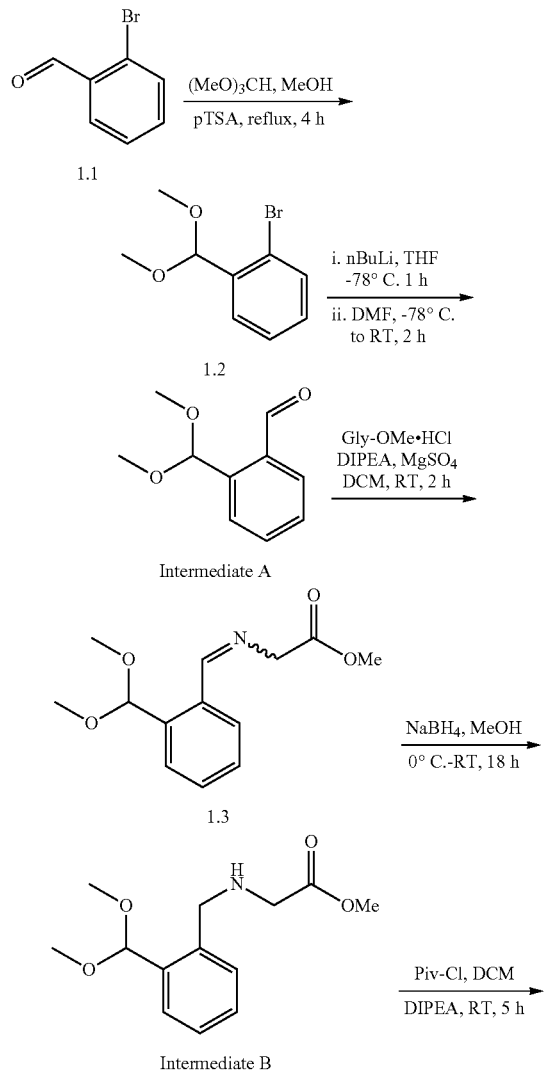

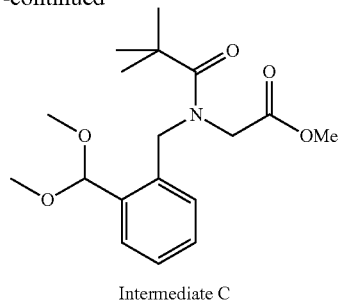

Intermediate C

1-Bromo-2-(dimethoxymethyl)benzene 1.2

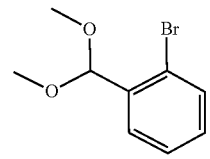

2-Bromobenzaldehyde 1.1 (3.15 g, 17.0 mmol) was dissolved in methanol (20 ml) and p-toluenesulfonic acid monohydrate (310 mg, 1.7 mmol) was added. The solution was warmed 20 to 50° C. then trimethyl orthoformate (10 ml) was added slowly down the condenser. The reaction was then heated to reflux for 4 h. The mixture was cooled on ice water then triethylamine (3 ml) was added. The volatiles were removed then the mixture diluted with diethyl ether and water. The aqueous layer was extracted twice with diethyl ether. The combined organic extracts were washed with brine, dried over sodium sulfate, filtered and the filtrate evaporated. The residue was purified via column chromatography (250 ml silica, 10-15% diethyl ether in hexane) to provide compound 1.2 (3.45 g, 88%) as a colourless oil.

$^1$H NMR (CDCl$_3$, 300 MHz) δ 3.39 (s, 6H), 5.56 (s, 1H), 7.20 (t, 1H), 7.33 (t, 1H), 7.57 (m, 2H).

2-(Dimethoxymethyl)benzaldehyde Intermediate A

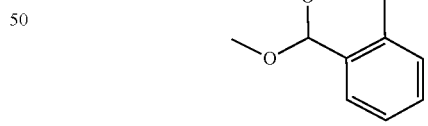

Compound 1.2 (3.60 g, 15.58 mmol) was dissolved in dry tetrahydrofuran (35 ml) under an argon atmosphere then cooled on dry ice/acetone. To this was added a solution of n-butyllithium (2.5 M in hexanes, 9.35 ml, 23.37 mmol) dropwise so that the internal temperature stayed below −60° C. (10 min addition). The reaction was stirred on dry ice/acetone for 70 min. To this was added N,N-dimethylformamide (2.43 ml, 31.16 mmol) in one portion. The mixture was stirred on dry ice/acetone for 60 min before being allowed to warm to RT over 1.5 h. Water was added then the mixture was extracted three times with diethyl ether. The combined organic extracts were washed with brine, dried over sodium sulfate, filtered and the filtrate evaporated to provide compound Intermediate A (2.92 g, quant.) as a straw-coloured oil; ¹H NMR (CDCl₃, 300 MHz) δ 3.39 (s, 6H), 5.87 (s, 1H), 7.49 (t, 1H), 7.59 (t, 1H), 7.66 (d, 1H), 7.91 (d, 1H), 10.43 (s, 1H)—contains trace THF and minor impurities. Used directly.

Methyl 2-((2-(dimethoxymethyl)benzylidene)amino)acetate
1.3

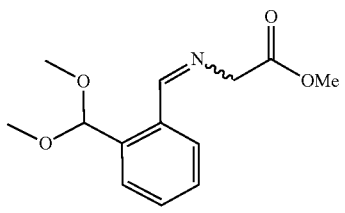 [SMILES: COC(=O)CN=Cc1ccccc1C(OC)OC]

Compound Intermediate A (3.60 g, ~15.58 mmol) was dissolved in dichloromethane (50 ml) under an argon atmosphere. N,N-Diisopropylethylamine (6.1 ml, 35 mmol) was added followed by methyl glycinate hydrochloride (3.92 g, 31.2 mmol) and magnesium sulfate (excess). The mixture was stirred at RT for 2 h. The mixture was filtered then the filtrate was washed with saturated sodium bicarbonate. The aqueous layer was extracted twice with dichloromethane. The combined organic extracts were washed with brine, dried over magnesium sulfate, filtered and the filtrate evaporated to provide compound 1.3 (4.78 g, quant.) as a pale yellow gum. Used directly. UPLC-MS (short basic) rt 0.70 (220 [M–OMe+H]⁺).

Methyl 2-((2-(dimethoxymethyl)benzyl)amino)acetate
Intermediate B

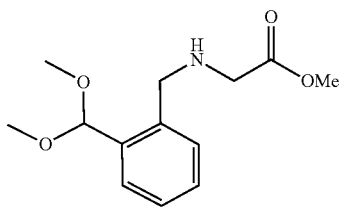 [SMILES: COC(=O)CNCc1ccccc1C(OC)OC]

Compound 1.3 (4.78 g, ~15.58 mmol) was dissolved in methanol (30 ml) under an argon atmosphere then cooled on ice/water. Sodium borohydride (297 mg, 7.8 mmol) was added portionwise (Note vigorous gas evolution). The mixture was stirred on ice/water for 10 min then allowed to warm to RT and reaction monitored followed by UPLC-MS. After 18 h, extra sodium borohydride (150 mg, 3.94 mmol) was added and reaction was complete after a further 20 min at RT. The mixture was poured into saturated sodium bicarbonate. The aqueous layer was extracted three times with ethyl acetate. The combined organic extracts were washed with water, brine, dried over magnesium sulfate, filtered and the filtrate evaporated to provide compound Intermediate B (4.04 g, quant.) as a pale straw-coloured gum. ¹H NMR (CDCl₃, 300 MHz) δ 3.34 (s, 6H), 3.44 (s, 2H), 3.73 (s, 3H), 3.89 (s, 2H), 5.62 (s, 1H), 7.33 (m, 3H), 7.57 (dd, 1H).— contains trace alkyl impurities. UPLC-MS (short basic): rt 0.68 (222 [M–OMe+H]⁺). Used directly.

Methyl 2-(N-(2-(dimethoxymethyl)benzyl)pivalamido)acetate
Intermediate C

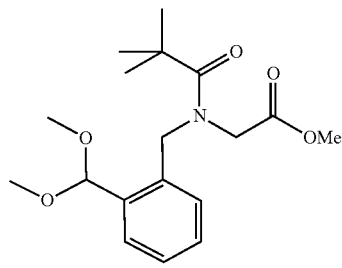 [SMILES: COC(=O)CN(Cc1ccccc1C(OC)OC)C(=O)C(C)(C)C]

Compound Intermediate B (4.04 g, ~15.58 mmol) was dissolved in dichloromethane (40 ml) under an argon atmosphere then N,N-diisopropylethylamine (5.45 ml, 31.2 mmol) was added. Trimethylacetyl chloride (1.91 ml, 15.6 mmol) was added dropwise—note after 0.4 ml added, reaction was noted to be warming—so the flask was cooled on ice/water and the addition continued. The mixture was stirred at RT for 4 h. after which the reaction was complete by UPLC-MS. The mixture was poured into saturated sodium bicarbonate. The aqueous layer was extracted three times with dichloromethane. The combined organic extracts were dried over magnesium sulfate, filtered and the filtrate evaporated. The residue was purified via column chromatography (300 ml silica, dichloromethane—gradient with ethyl acetate 0%-20%) to provide compound Intermediate C (4.32 g, 82%) as a colourless gum, which crystallised on standing. ¹H NMR (CDCl₃, 300 MHz) δ 1.29 (s, 9H), 3.32 (s, 6H), 3.72 (s, 3H), 3.93 (br s, 2H), 4.97 (br s, 2H), 5.33 (s, 1H), 7.21 (m, 1H), 7.31 (m, 2H), 7.52 (d, 1H). UPLC-MS (short basic): rt 0.84 (190 fragment).

Synthesis of Intermediate D and E

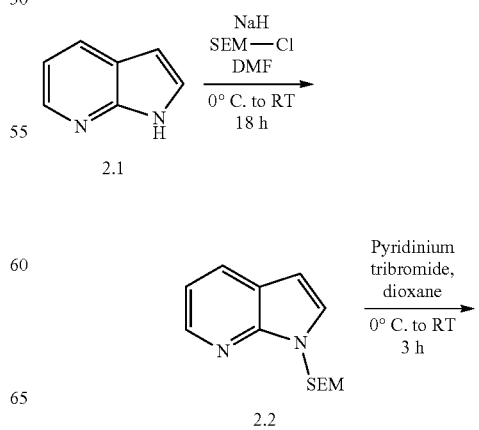

-continued

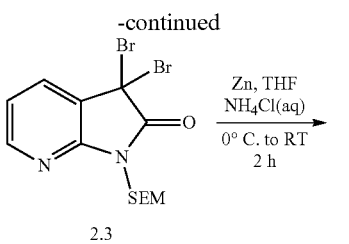
2.3

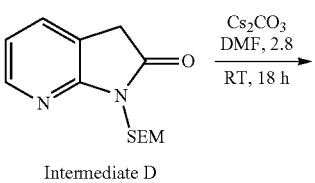
Intermediate D

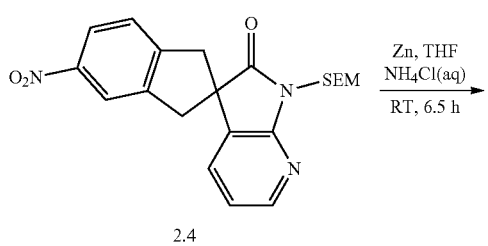
2.4

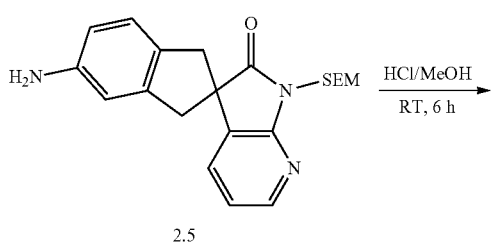
2.5

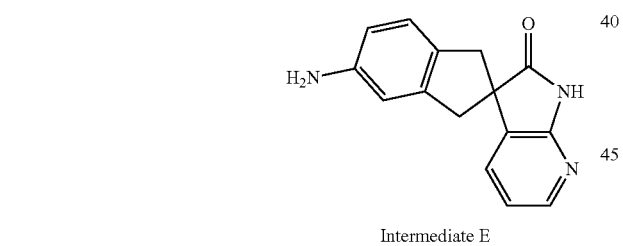
Intermediate E

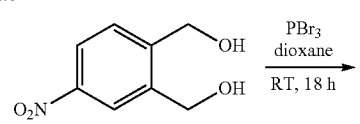
2.6

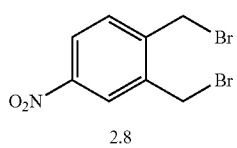
2.7

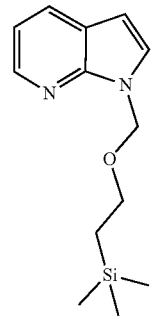 [SMILES: C[Si](C)(C)CCOCn1ccc2cccnc21]
2.8

1-((2-(Trimethylsilyl)ethoxy)methyl)-1H-pyrrolo[2,3-b]pyridine 2.2

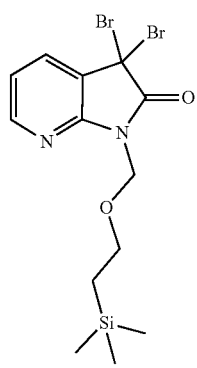 [SMILES: C[Si](C)(C)CCOCN1C(=O)C(Br)(Br)c2cccnc21]

A solution of 7-azaindole 2.1 (95 g, 804.2 mmol) in dimethylformamide (500 ml) was cooled to 0° C., and then sodium hydride (38.6 g, 964.9 mmol) was added in several small portions, maintaining internal temperature below 10° C. The suspension was stirred at 0-5° C. for 1 h. 2-(Trimethylsilyl)ethoxymethyl chloride (171 ml, 964.9 ml) was then added dropwise at 5-10° C. After addition was complete, the yellow suspension was then stirred at room temperature for 18 hours. The mixture was quenched by slow addition of water until effervescence ceased, then diluted up to a total of 1.5 L with further water. This mixture was extracted with ethyl acetate (2×1.5 L). The combined organic extracts were washed with water (2×1 L) and brine (2×1 L), then dried over magnesium sulfate and evaporated to provide compound 2.2 as an amber-coloured oil (199 g, 99% yield).

$^1$H NMR (CDCl$_3$, 300 MHz): δ −0.08 (s, 1H), 0.89 (m, 2H), 3.52 (m, 2H), 5.68 (s, 2H), 6.50 (dd, 1H), 7.08 (dd, 1H), 7.34 (d, 1H), 7.90 (dd, 1H), 8.33 (dd, 1H). UPLC (short basic, 1.30 min): rt 0.96 min, [M+H]$^+$ 249, purity 96%.

3,3-Dibromo-1-((2-(trimethylsilyl)ethoxy)methyl)-1H-pyrrolo[2,3-b]pyridin-2(3H)-one 2.3

A mechanically-stirred suspension of pyridinium tribromide (646 g, 2.02 mol) in 1,4-dioxane (900 ml) was cooled to 10-15° C. using an ice/water bath, and a solution of 2.2 (100 g, 403.2 mmol) in 1,4-dioxane (500 ml) was added dropwise (NOTE: no significant exotherm is observed, but the reaction is kept cool to minimise formation of polymeric by-products). After stirring for 2 hours at 10-15° C., the mixture was partitioned between water (1.5 L) and ethyl acetate (1.5 L). The ethyl acetate layer was collected, and washed with water (2×1 L), saturated aqueous sodium bicarbonate solution (1 L), sodium thiosulfate solution (1M solution, 1 L), and brine (2×1 L). The ethyl acetate layer was dried over magnesium sulfate and evaporated to provide compound 2.3 (144 g, 85% yield). $^1$H NMR (CDCl$_3$, 300 MHz): δ −0.03 (s, 9H), 0.97 (dd, 2H), 3.70 (dd, 2H), 5.32 (s, 2H), 7.15 (dd, 1H), 7.87 (dd, 1H), 8.30 (dd, 1H). UPLC-MS (short basic) rt 1.00 (421, 423, 425 [M+H]$^+$), 89% pure.

1-((2-(Trimethylsilyl)ethoxy)methyl)-1H-pyrrolo[2,3-b]pyridin-2(3H)-one Intermediate D

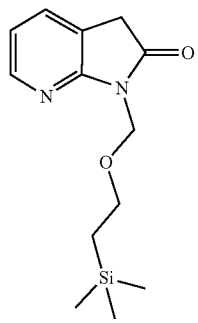 [SMILES: C[Si](C)(C)CCOCN1C(=O)Cc2cccnc21]

To a mechanically-stirred solution of 2.3 (144 g, 341 mmol) in tetrahydrofuran (2 L) was added saturated aqueous ammonium chloride solution (0.5 L). The suspension was cooled in an ice/salt/water bath to 5-10° C., and zinc powder (223 g, 3.41 mol) was then added portionwise. After half of the zinc had been added, the internal temperature peaked at 24° C., and no further significant exotherm was noted upon addition of the remaining zinc. After stirring for two hours at room temperature, the mixture was filtered through a pad of Celite, to remove excess Zn powder, washing with ethyl acetate (1 L). The filtrate was diluted with water (1.2 L), effecting precipitation of zinc bromide salts. This suspension was filtered through a further pad of Celite. The organic layer was separated from the filtrate, and washed with water (0.8 L) and brine (2×0.8 L), dried over magnesium sulfate, and evaporated to give a dark red oil.

This material was combined with a second batch (of 151 g of 2.3), and the combined crude material (201 g) was purified by dry-flash chromatography (0-30% ethyl acetate in heptane) to provide compound Intermediate D (110 g, 55% yield). $^1$H NMR (CDCl$_3$, 300 MHz): δ −0.03 (s, 9H), 0.98 (dd, 2H), 3.59 (s, 2H), 3.69 (dd, 2H), 5.25 (s, 2H), 6.97 (dd, 1H), 7.50 (dd, 1H), 8.22 (d, 1H). UPLC-MS (short basic) rt 0.85 (265 [M+H]$^+$), 88% pure.

(4-Nitro-1,2-phenylene)dimethanol 2.7

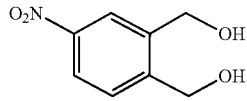 [SMILES: O=[N+]([O-])c1ccc(CO)c(CO)c1]

A mechanically-stirred solution of borane-tetrahydrofuran complex (1M in THF, 1.23 L, 1.23 mol) was cooled to 0° C. A solution of 4-nitrophthalic acid (100 g, 472 mmol) in tetrahydrofuran (1 L) was added dropwise over a period of ca. 45 minutes, maintaining the internal temperature below 10° C. The cooling bath was then removed, and the mixture stirred overnight at room temperature. The stirred mixture was then once again cooled to 0° C., and methanol added slowly to destroy excess borane (until effervescence was no longer observed). The mixture was concentrated to 25-30% volume, and then diluted to 1 L by addition of water. The mixture was adjusted to pH 10 by addition of 2M aqueous sodium hydroxide, and then extracted with ethyl acetate (5×1 L). The combined organic extracts were dried over magnesium sulfate, and evaporated to provide compound 2.7 (85.5 g, 98% yield). $^1$H NMR (CDCl$_3$, 300 MHz): δ 4.60 (m, 4H), 5.44 (q, 2H), 7.67 (d, 1H), 8.09 (dd, 1H), 8.23 (dd, 1H). UPLC-MS (short basic) rt 0.51 (182 [M−H]$^-$), 98% pure.

1,2-Bis(bromomethyl)-4-nitrobenzene 28

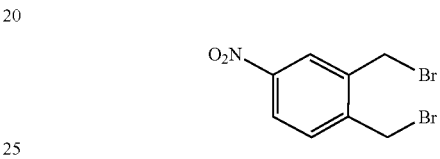

A suspension of the diol 2.7 (95.5 g, 521.6 mmol) in dioxane (2 L) was cooled to 0° C., and phosphorous tribromide (54 ml, 573.7 mmol) added dropwise. Cooling was then removed, and the mixture allowed to stir overnight at room temperature. The mixture was then poured carefully into a stirred 1.5 L solution of saturated sodium bicarbonate, and extracted with ethyl acetate (3×1 L). The organic extracts were dried over magnesium sulfate, and evaporated to provide compound 2.8 (153.9 g, 96% yield). $^1$H NMR (CDCl$_3$, 300 MHz): δ 4.66 (s, 2H), 4.67 (s, 2H), 7.56 (d, 1H), 8.16 (dd, 1H), 8.25 (d, 1H). UPLC-MS (short basic) rt 0.86 (no m/z), 98% pure.

5-Nitro-1'-((2-(trimethylsilyl)ethoxy)methyl)-1,3-dihydrospiro[indene-2,3'-pyrrolo[2,3-b]pyridin]-2'(1'H)-one 2.4

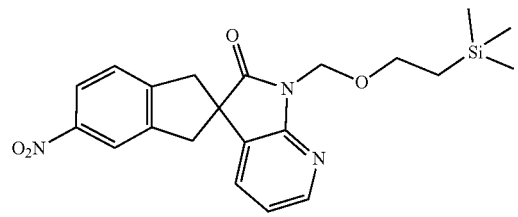

To a mechanically-stirred solution of Intermediate D (55 g, 208.3 mmol) in dimethylformamide (1.65 L) was added 2.8 (70.8 g, 229.1 mmol). Caesium carbonate (238 g, 729.1 mmol) was then added in one portion. This suspension was stirred for 16 hours at room temperature (or until reaction was complete), then filtered through a Celite pad, washing the filter cake with ethyl acetate (2 L). The filtrate was washed with water (3×1 L) and brine (1 L), then dried over magnesium sulfate and evaporated to a deep red oil (96 g). This was purified by dry flash chromatography (eluting with 9:1 heptane/ethyl acetate, followed by 17:3 heptane/ethyl acetate, 8:2 heptane/ethyl acetate, 3:1 heptane/ethyl acetate, 7:3 heptane/ethyl acetate, and 13:7 heptane/ethyl acetate) to give a yellow/orange powder (60.1 g), which was triturated with diethyl ether to afford compound 2.4 (45 g, 53% yield). An additional 54.5 g of 2.4 was obtained from the remaining 55 g of Intermediate D, giving a total of 99.5 g of 2.4 (58% yield). $^1$H NMR (CDCl$_3$, 300 MHz): δ −0.01 (s, 9H), 0.99 (dd, 2H), 3.18 (dd, 2H), 3.71 (m, 4H), 5.30 (s, 2H), 6.88 (dd, 2H), 7.08 (dd, 1H), 7.43 (d, 1H), 8.09 (m, 2H), 8.23 (dd, 1H). UPLC-MS (short basic) rt 0.99 (411 [M+H]$^+$), 97% pure.

5-Amino-1'-((2-(trimethylsilyl)ethoxy)methyl)-1,3-dihydrospiro[indene-2,3'-pyrrolo[2,3-b]pyridin]-2'(1'H)-one 2.5

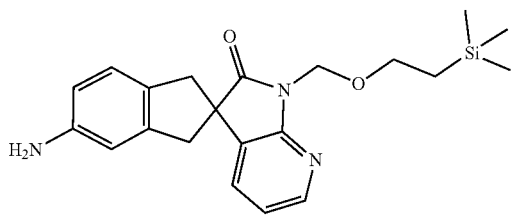 [SMILES: C[Si](C)(C)CCOCN1C(=O)C2(Cc3ccc([N+](=O)[O-])cc3C2)c2cccnc21]

To a mechanically-stirred solution of 2.4 (70 g, 170.3 mmol) in tetrahydrofuran (1.1 L) was added saturated ammonium chloride solution (300 ml), followed by zinc powder (111 g, 1.70 mol), added in three portions. Internal temperature rose initially from 22° C. to 33° C., then cooling slowly over 1 hr back to ambient temperature. LCMS analysis after 2.5 hrs indicated a mixture of product and hydroxylamine/nitroso intermediates. An additional 35 g zinc powder (3 eq) and 100 ml saturated ammonium chloride solution were added. After an additional 3.5 hrs, reduction was complete. The mixture was filtered through a pad of Celite, washing the filter cake with ethyl acetate (1 L). The filtrate was washed with water (3×1 L), dried over magnesium sulfate, and evaporated to a orange solid, which was triturated with diethyl ether to provide compound 2.5 as a pale yellow powder (48.8 g). Repurification of the trituration liquors by flash chromatography (eluting 1:1 heptane/ethyl acetate), and a further trituration with diethyl ether gave an additional 3 g of 2.5, giving a total of 51.9 g of 2.5 (80% yield). After processing all 99.5 g of 2.4, a total of 70.7 g of 2.5 was prepared (77% yield). $^1$H NMR (CDCl$_3$, 300 MHz): δ −0.02 (s, 9H), 0.98 (m, 2H), 2.91 (d, 2H), 3.56 (dd, 2H), 3.69 (m, 2H), 5.29 (s, 2H), 6.59 (m, 2H), 6.82 (dd, 1H), 7.02 (d, 1H), 7.09 (dd, 1H), 8.18 (dd, 1H). UPLC-MS (short basic) rt 0.92 (382 [M+H]$^+$), 95% pure.

5-Amino-1,3-dihydrospiro[indene-2,3'-pyrrolo[2,3-b]pyridin]-2'(1'H)-one Intermediate E

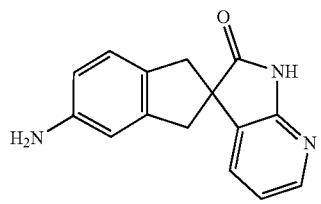 [SMILES: Nc1ccc2c(c1)CC1(C2)C(=O)Nc2ncccc21]

A solution of 2.5 (51.8 g, 135.9 mmol) in freshly-prepared hydrogen chloride in methanol [prepared to approximately 15% concentration (w/v)] was heated to reflux for 6 hours. Once reaction was complete, heating was stopped, and the solution allowed to cool to room temperature overnight. The mixture was concentrated in vacuo to a thick orange liquid, then diluted with 300 ml water, and the pH adjusted to 9 with saturated sodium carbonate solution. The aqueous mixture was extracted with dichloromethane (3×500 ml), and 9:1 dichloromethane/methanol (3×500 ml). The combined organics were dried over magnesium sulfate and evaporated to an orange solid, which was triturated with 2:1 dichloromethane/ethyl acetate (ca. 60 ml) to provide Intermediate E as a pale orange powder (21.5 g, 63% yield). 1H NMR (DMSO-d$_6$, 300 MHz): δ 2.84 (dd, 2H), 3.18 (dd, 2H), 4.94 (s, NH$_2$), 6.41 (m, 2H), 6.81 (dd, 1H), 6.86 (d, 1H), 7.08 (dd, 1H), 8.01 (dd, 1H), 11.03 (s, NH). UPLC-MS (short basic) rt 0.56 (252 [M+H]$^+$), 97% pure.

Synthesis of Intermediate F

SCHEME 3

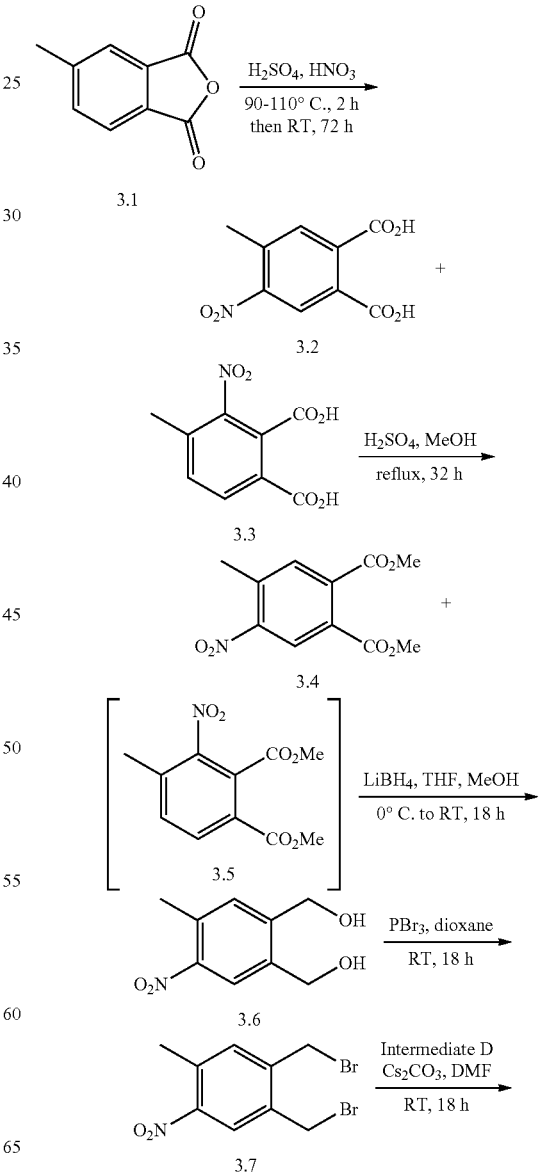

-continued

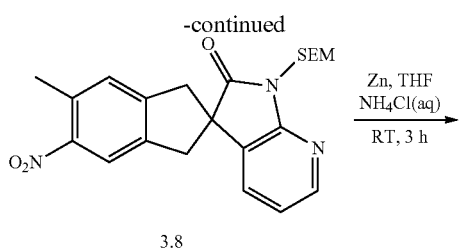

3.8

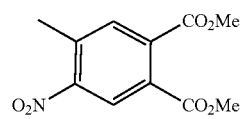

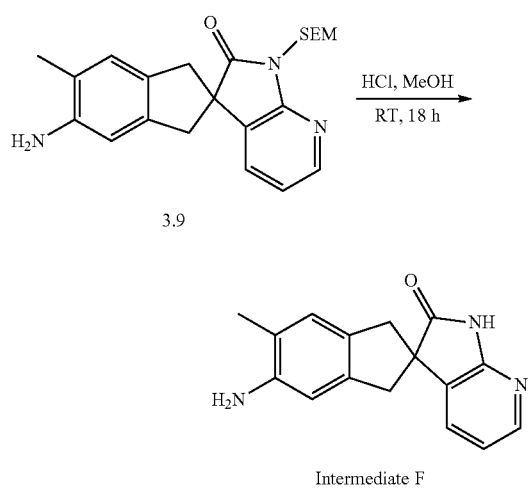

3.9

Intermediate F

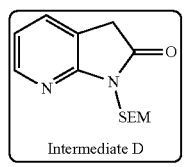

Intermediate D

4-Methyl-5-nitrophthalic Acid 3.2

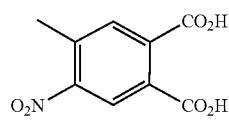

4-Methylphthalic anhydride (5.05 g, 31.1 mmol) was suspended in concentrated sulfuric acid (98%, 10.0 ml) then heated at 80° C. The heat was removed then to this was added a pre-combined mixture of fuming nitric acid (90%, 2.0 ml) and concentrated sulfuric acid (1.5 ml) dropwise, so that the temperature did not exceed 80° C., over 10 min. Once the addition was complete, heat was re-introduced to 80° C. and concentrated nitric acid (68%, 8.2 ml) was added in one portion then the mixture was stirred at 100° C. for 2 h then allowed to cool to RT. Water was added then the solids were filtered and washed with water. The filtered solids were dried to provide a 1:1 mixture of product 3.2 and regioisomer 3.3 (5.46 g, 78%) as a white powder. $^1$H NMR (DMSO-d$_6$, 400 MHz) δ 2.34 (s, 3H), 2.54 (s, 3H), 7.62 (d, 1H 3.3), 7.73 (s, 1H 3.2), 7.91 (d, 1H 3.3), 8.25 (s, 1H, 3.2) ~1:1 ratio. UPLC-MS (short acidic 0-50%) rt 0.72 (180 [M−CO$_2$H]$^−$), rt 0.82 (224, [M−H]$^−$). DSC analysis—exotherm at 220° C. therefore keep below 120° C.

Dimethyl 4-methyl-5-nitrophthalate 3.4

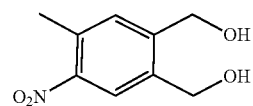

A mixture of compounds 3.2 and 3.3 (~1:1 6.23 g, 27.7 mmol) was dissolved in methanol (117 ml) then concentrated sulfuric acid (98%, 3.3 ml) was added and the mixture was heated to reflux for 8 h then cooled to RT for 8 h. The reaction was incomplete so was heated at reflux for a further 24 h. The mixture was concentrated to remove the methanol then partitioned between dichloromethane and saturated sodium bicarbonate. The aqueous layer was extracted twice with dichloromethane. The organic extracts were washed with water, dried over magnesium sulfate, filtered and the filtrate evaporated. The residue was crystallised from hot methanol, the crystals filtered and washed with a little methanol and solid dried. A second crop of crystals was recovered from the filtration liquors by recrystallising from hot methanol and the two batches of crystals combined and dried to provide pure product 3.4 (1.98 g, 28%) as a colourless crystalline solid. $^1$H NMR (CDCl$_3$, 400 MHz) δ 2.66 (s, 3H), 3.93 (s, 6H), 7.61 (s, 1H), 8.41 (s, 1H). HPLC-MS (long basic 11 min, 40%) rt 4.00 (254, [M+H]$^+$), 99% pure.

(4-Methyl-5-nitro-1,2-phenylene)dimethanol 3.6

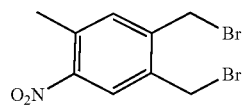

Compound 3.4 (1.76 mg, 6.95 mmol) was dissolved in dry tetrahydrofuran (41 ml) and methanol was added (0.56 ml) then cooled to 0° C. (ice/water). Lithium borohydride (0.38 g, 17.4 mmol) was added portionwise. The mixture turned purple then over time became yellow. The mixture was stirred at RT for 20 h. The mixture was poured into 20% aqueous citric acid then extracted three times with ethyl acetate. The organic extract was washed with saturated sodium bicarbonate, brine, dried over magnesium sulfate, filtered and the filtrate evaporated to provide product 3.6 (1.50 g, quant.) as a colourless solid. $^1$H NMR (CD$_3$OD, 300 MHz) δ 2.56 (s, 3H), 4.68 (d, 4H), 7.49 (s, 1H), 8.03 (s, 1H). UPLC-MS (short basic) rt 0.55 (196, [M−H]$^−$), 99% pure.

1,2-Bis(bromomethyl)-4-methyl-5-nitrobenzene 3.7

Compound 3.6 (1.66 g, 8.41 mmol) was suspended in dioxane (35 ml) then phosphorous tribromide (0.87 ml, 9.3 mmol) was added dropwise and the mixture was stirred at RT for 3 days. The mixture was then poured into saturated sodium bicarbonate, and extracted three times with ethyl acetate. The organic extracts were washed with brine, dried over magnesium sulfate, filtered and the filtrate evaporated to provide compound 3.7 (2.69 g, 99%) as a yellow solid. $^1$H NMR (CDCl$_3$, 400 MHz) δ 2.60 (s, 3H), 4.61 (d, 4H), 7.35 (s, 1H), 8.01 (s, 1H). UPLC-MS (short basic) rt 0.90 (no m/z), 96% pure.

5-Methyl-6-nitro-1'-((2-(trimethylsilyl)ethoxy)methyl)-1,3-dihydrospiro[indene-2,3'-pyrrolo[2,3-b]pyridin]-2'(1'H)-one 3.8

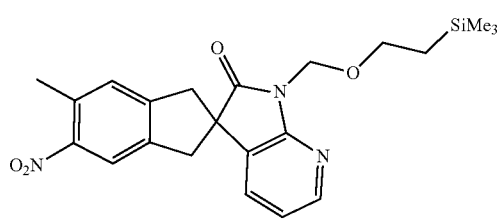 [SMILES: Cc1cc2c(cc1[N+](=O)[O-])CC1(C2)C(=O)N(COCC[Si](C)(C)C)c2ncccc21]

Compound 3.7 (2.69 g, 8.33 mmol) and Intermediate D (1.98 g, 7.49 mmol) were dissolved in N,N-dimethylformamide (53 ml). Caesium carbonate (8.94 g, 27.4 mmol) was added and the mixture stirred at RT for 18 h. The mixture was poured into water and extracted three times with ethyl acetate. The organic extract was washed with brine, dried over magnesium sulfate, filtered and the filtrate evaporated. The residue was purified via flash silica chromatography (1-17% EtOAc in heptane) to provide compound 3.8 (2.51 g, 79%) as an orange solid. $^1$H NMR (CDCl$_3$, 300 MHz) δ −0.01 (s, 9H), 1.00 (m, 2H), 2.62 (s, 3H), 3.10 (dd, 2H), 3.69 (m, 4H), 5.30 (s, 2H), 6.88 (dd, 1H), 7.10 (dd, 1H), 7.24 (s, 1H), 7.90 (s, 1H), 8.23 (dd, 1H). UPLC-MS (short basic) rt 1.02 (426 [M+H]$^+$), 95% pure 5-Amino-6-methyl-1'-((2-(trimethylsilyl)ethoxy)methyl)-1,3-dihydrospiro[indene-2,3'-pyrrolo[2,3-b]pyridin]-2'(1'H)-one 3.9

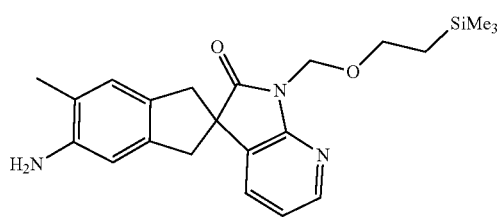

Compound 3.8 (2.51 g, 5.91 mmol) was suspended in tetrahydrofuran (40 ml) and saturated ammonium chloride (10 ml) then zinc powder (3.9 g, 59.1 mmol) was added and the mixture stirred at RT for 3 h. The mixture was filtered through Celite, washing with ethyl acetate. The filtrate was washed with water, brine, dried over magnesium sulfate, filtered and the filtrate evaporated to provide compound 3.9 (1.14 g, 49%) as a yellow solid. $^1$H NMR (CDCl$_3$, 300 MHz) δ −0.02 (s, 9H), 0.97 (m, 2H), 2.17 (s, 3H), 2.90 (d, 2H), 3.55 (dd, 2H), 3.69 (dd, 2H), 5.29 (s, 2H), 6.60 (s, 1H), 6.81 (dd, 1H), 6.94 (s, 1H), 7.10 (dd, 1H), 8.18 (dd, 1H). UPLC-MS (short basic) rt 0.95 (396 [M+H]$^+$), 86% pure.

5-Amino-6-methyl-1,3-dihydrospiro[indene-2,3'-pyrrolo[2,3-b]pyridin]-2'(1'H)-one Intermediate F

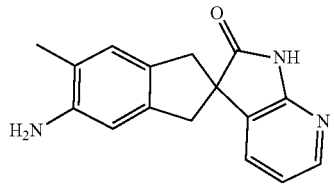 [SMILES: Cc1cc2c(cc1N)CC1(C2)C(=O)Nc2ncccc21]

Compound 3.9 (1.14 g, 2.88 mmol) was dissolved in freshly-prepared HCl in methanol [prepared to approximately 15% concentration (w/v), 100 ml] and stirred at RT for 18 h. UPLC-MS indicated incomplete reaction, so extra HCl in methanol (50 ml) was added and stirred at RT for 1.5 h then reflux for 4 h, then RT for 18 h. The mixture was concentrated, diluted with water, and the pH adjusted to 8 with solid sodium hydroxide. The aqueous was extracted twice with ethyl acetate. The organic extract was washed with brine, dried over magnesium sulfate, filtered and the filtrate evaporated. The residue was purified via flash silica chromatography (EtOAc) to provide Intermediate F (0.32 g, 28%) as a yellow solid. $^1$H NMR (DMSO-de, 400 MHz) δ 2.01 (s, 3H), 2.83 (dd, 2H), 3.17 (m, 2H), 4.68 (s, 2H), 6.49 (s, 1H), 6.80 (m, 2H), 7.05 (dd, 1H), 8.00 (dd, 1H), 11.0 (s, 1H). UPLC-MS (short basic) rt 0.95 (396 [M+H]$^+$), 86% pure.

Preparation of Intermediate G and H

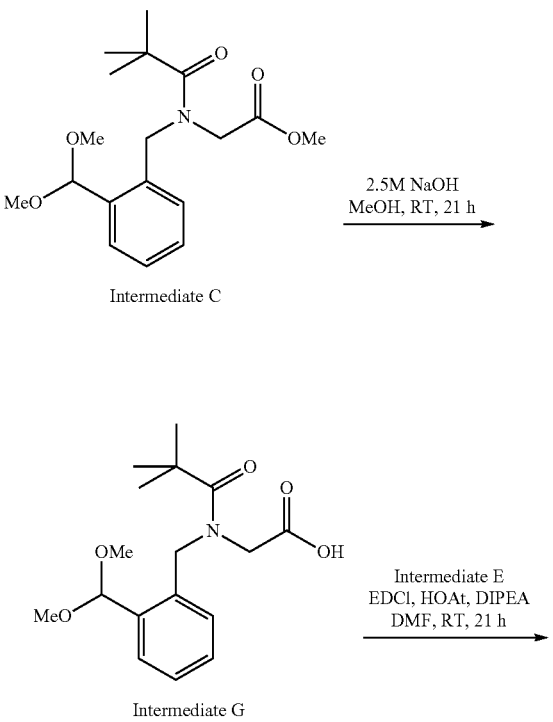

-continued

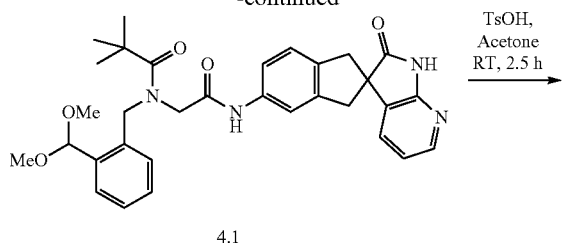

4.1

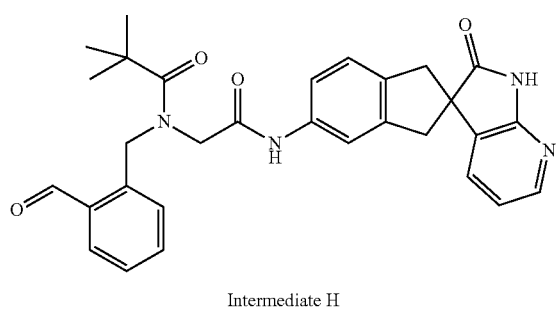

2-(N-(2-(Dimethoxymethyl)benzyl)pivalamido)acetic Acid Intermediate G

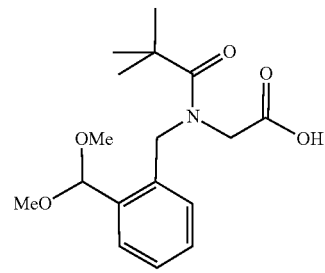 [SMILES: COC(OC)c1ccccc1CN(CC(=O)O)C(=O)C(C)(C)C]

Intermediate C (2.0 g, 5.93 mmol) was dissolved in methanol (25 ml) then 2.5M sodium hydroxide (4.8 ml, 12 mmol) was added. The mixture was stirred at 55° C. for 1.5 h, after which the reaction was complete by UPLC-MS. The mixture was allowed to cool to RT, most of the volatiles removed, then poured into water. The pH was adjusted very carefully to pH 4 with 2M hydrochloric acid. Once at pH 4, the aqueous was extracted with ethyl acetate. The aqueous was re-adjusted to pH 4 after each extraction (total 4 extractions, 6 ml 2M hydrochloric acid added). [NOTE: if the aqueous turns dark indigo/purple—immediately basify with 2.5M NaOH then start pH adjustment again]. The combined organic extracts were washed with brine, dried over sodium sulfate, filtered and evaporated carefully (30° C. water bath, not to dryness (NOTE: can be used in next step as ethyl acetate solution or DIPEA can be added before evaporation). Intermediate G which was used directly in the next step as the compound is not stable; UPLC-MS rt 0.51 (322 [M−H]⁻)

N-(2-(Dimethoxymethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 4.1

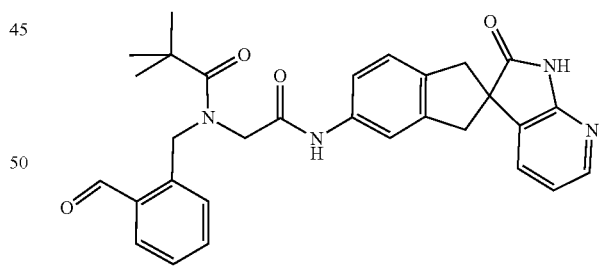

Intermediate G (~5.93 mmol) was dissolved in N,N-dimethylformamide (30 ml) under an argon atmosphere then N,N-diisopropylethylamine (2.9 ml, 16.3 mmol) was added. EDCl.HCl (1.24 g, 6.5 mmol) and HOAt (0.89 g, 6.5 mmol) were added followed by Intermediate E (1.4 g, 5.6 mmol). The mixture was stirred at RT for 18 h, after which reaction was complete by UPLC-MS. The mixture was poured into saturated sodium bicarbonate. The aqueous layer was extracted three times with ethyl acetate. The combined organic extracts were washed three times with water, dried over sodium sulfate, filtered and the filtrate evaporated. The residue was purified via column chromatography (300 ml silica, 4:1 ethyl acetate/heptanes—ethyl acetate) to provide compound 4.1 (2.48 g, 80%) as a colourless glass. $^1$H NMR (CDCl$_3$, 400 MHz) δ 1.31 (s, 9H), 3.01 (dd, 2H), 3.32 (s, 6H), 3.60 (dd, 2H), 4.10 (br s, 2H), 5.06 (br s, 2H), 5.37 (s, 1H), 6.81 (dd, 1H), 7.08 (dd, 1H), 7.18 (d, 2H), 7.22 (m, 1H), 7.32 (m, 2H), 7.54 (m, 2H), 8.12 (d, 1H), 8.62 (br s, 1H), 9.35 (br s, 1H). UPLC-MS (short basic) rt 0.80 (555 [M−H]⁻), 98% pure.

N-(2-Formylbenzyl)-N-(2-oxo-2-((2'-oxo-1,1',2',3-tetrahydrospiro[indene-2,3'-pyrrolo[2,3-b]pyridin]-5-yl)amino)ethyl)pivalamide Intermediate H Compound 4.1 (2.48 g, 4.46 mmol) was dissolved in acetone (100 ml) then p-toluene sulfonic acid monohydrate (860 mg, 4.9 mmol) was added. The mixture was stirred at RT. After 20 min, the colour turned green and UPLC-MS indicated reaction was complete. The mixture was poured into saturated sodium bicarbonate. The aqueous layer was extracted three times with ethyl acetate. The combined organic extracts were washed with brine, dried over sodium sulfate, filtered and the filtrate evaporated to provide Intermediate H (2.16 g, 95%) as a yellow solid. $^1$H NMR (CDCl$_3$, 300 MHz) δ 1.30 (s, 9H), 3.05 (dd, 2H), 3.60 (dd, 2H), 4.09 (br s, 2H), 5.36 (s, 2H), 6.82 (dd, 1H), 7.07 (dd, 1H), 7.20

(d, 1H), 7.30 (m, 1H), 7.34 (m, 1H), 7.55 (m, 2H), 7.63 (m, 1H), 8.12 (d, 1H), 8.63 (br s, 1H), 8.90 (br s, 1H), 10.11 (s, 1H). UPLC-MS (short basic) rt 0.74 (509 [M−H]⁻), 96% pure.

General Route A

SCHEME 5

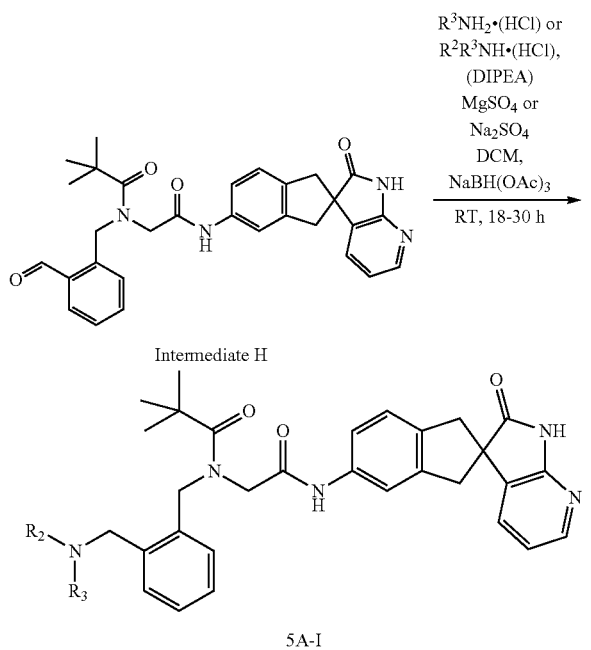

Intermediate H (30-40 mg, 0.059-0.078 mmol) was dissolved in dichloromethane (3 ml) and amine/amine hydrochloride added (0.12-0.18 mmol). N,N-Diisopropylethylamine (0.028-0.067 ml, 0.15-0.36 mmol) was added if an amine hydrochloride was used. Sodium or magnesium sulfate was added and the mixture stirred at room temperature and progress monitored by UPLC-MS. After 0.25-20 h sodium triacetoxyborohydride (20-29 mg, 0.094-0.136 mmol) was added and reaction stirred at room temperature, monitoring by UPLC-MS. Extra sodium triacetoxyborohydride (0.094 mmol) was added as required. Once complete, the reaction was poured into saturated sodium bicarbonate and extracted three times with dichloromethane. The combined organics were dried (sodium sulfate), filtered and evaporated.

Example 1: N-(2-(((Cyclopropylamino)methyl)benzyl)-N-(2-oxo-2-((2'-oxo-1,1',2',3-tetrahydrospiro[indene-2,3'-pyrrolo[2,3-b]pyridin-5-yl)amino)ethyl)pivalamide 5A

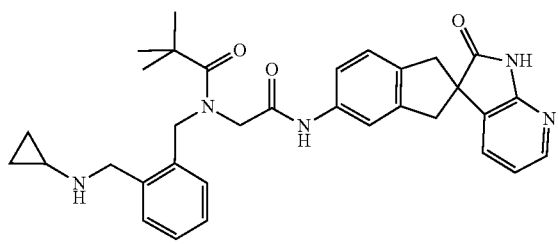 [SMILES: CC(C)(C)C(=O)N(CC(=O)Nc1ccc2c(c1)CC1(C2)C(=O)Nc2ncccc21)Cc1ccccc1CNC1CC1]

The title compound was synthesised according to General Route A from Intermediate H (30 mg, 0.059 mmol) using cyclopropylamine (8.3 μl, 0.12 mmol) premixed for 6 h, then worked up after 48 h and purified via SPE (2 g SiO₂ 0-12% MeOH in EtOAc) and trituration in diethyl ether to provide 5A (9 mg, 28%) as a colourless solid. ¹H NMR (CDCl₃, 300 MHz) δ 0.31 (m, 2H), 0.44 (m, 2H), 1.30 (s, 9H), 2.20 (m, 1H), 3.05 (dd, 2H), 3.61 (dd, 2H), 3.85 (s, 2H), 4.08 (br s, 2H), 5.05 (br s, 2H), 6.82 (dd, 1H), 7.10 (m, 2H), 7.31 (m, 5H), 7.55 (s, 1H), 8.11 (d, 1H), 8.20 (br s, 1H), 8.58 (br s, 1H). UPLC-MS rt 0.78 (552 [M+H]⁺), 95% pure.

Example 2: N-(2-(Azetidin-1-ylmethyl)benzyl)-N-(2-oxo-2-((2'-oxo-1,1',2',3-tetrahydrospiro[indene-2,3'-pyrrolo[2,3-b]pyridine]-5-yl)amino)ethyl)pivalamide 5B

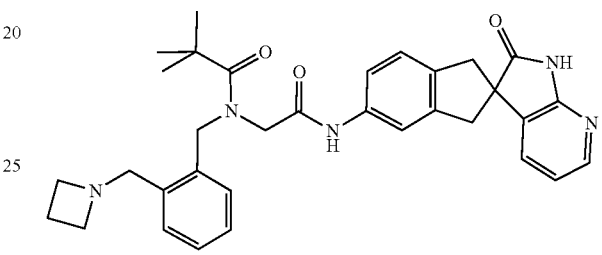

Synthesised according to General Route A from Intermediate H (30 mg, 0.059 mmol) using azetidine hydrochloride (11 mg, 0.12 mmol) premixed for 6 h, then worked up after 30 h and purified via SPE (2 g SiO₂ 0-10% MeOH in EtOAc then 10% MeOH in DCM) to provide 5B (21 mg, 65%) as a colourless glass. ¹H NMR (CDCl₃, 300 MHz) δ 1.33 (s, 9H), 2.02 (m, 2H), 3.05 (dd, 2H), 3.14 (br m, 4H), 3.60 (m, 4H), 4.12 (br s, 2H), 5.11 (br s, 2H), 6.81 (dd, 1H), 7.10 (m, 2H), 7.20 (m, 5H), 7.53 (br s, 1H), 8.11 (d, 1H), 8.68 (br d, 2H). UPLC-MS rt 0.78 (552 [M+H]⁺), 95% pure.

Example 3: N-(2-(((2,2-Difluoroethyl)amino)methyl)benzyl)-N-(2-oxo-2-((2'-oxo-1,1',2',3-tetrahydrospiro[indene-2,3'-pyrrolo[2,3-b]pyridine]-5-yl)amino)ethyl)pivalamide 5C

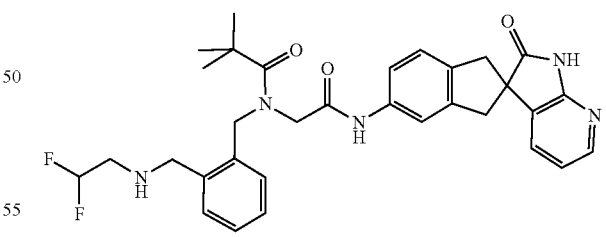

Synthesised according to General Route A from Intermediate H (30 mg, 0.059 mmol) using 2,2-difluoroethylamine (10 mg, 0.12 mmol) premixed for 22 h, then worked up after 30 h and purified via SPE (2 g SiO₂ EtOAc) to provide 5C (24 mg, 71%) as a colourless glass. H NMR (CDCl₃, 300 MHz) δ 1.30, 1.32 (2s, 9H), 3.02 (m, 4H), 3.60 (dd, 2H), 3.87 (s, 2H), 4.08 (br s, 2H), 5.11 (br s, 2H), 5.80 (tt, 1H), 6.82 (dd, 1H), 7.08 (d, 1H), 7.26 (m, 6H), 7.54 (m, 1H), 8.12 (d, 1H), 8.60 (br s, 2H). UPLC-MS rt 0.78 (576 [M+H]⁺), 98% pure.

Example 4: N-(2-Oxo-2-((2'-oxo-1,1',2',3-tetrahydrospiro[indene-2,3'-pyrrolo[2,3-b]pyridine]-5-yl)amino)ethyl)-N-(2-(pyrrolidin-1-ylmethyl)benzyl)pivalamide 5D

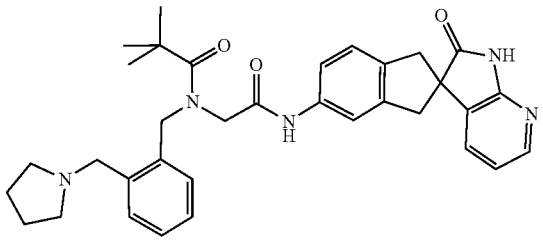 [SMILES: CC(C)(C)C(=O)N(CC(=O)Nc1ccc2c(c1)CC1(C2)C(=O)Nc2ncccc21)Cc1ccccc1CN1CCCC1]

Synthesised according to General Route A from Intermediate H (40 mg, 0.078 mmol) using pyrrolidine (15 µl, 0.18 mmol) premixed for 15 min, then worked up after 18 h and purified via SPE (2 g SiO$_2$ 0-10% MeOH in EtOAc then 10% MeOH in DCM) to provide 5D (26 mg, 59%) as a colourless solid. $^1$H NMR (CD$_3$OD, 300 MHz) δ 1.29 (s, 9H), 1.69 (m, 4H), 2.46 (m, 4H), 3.04 (dd, 2H), 3.50 (dd, 2H), 3.61 (s, 2H), 4.07 (br s, 2H), 5.18 (br s, 2H), 6.86 (dd, 1H), 7.10 (dd, 1H), 7.23 (m, 6H), 7.55 (s, 1H), 8.02 (d, 1H). UPLC-MS rt 0.89 (566 [M+H]$^+$), 99% pure.

Example 5: N-(2-Oxo-2-((2'-oxo-1,1',2',3-tetrahydrospiro[indene-2,3'-pyrrolo[2,3-b]pyridine]-5-yl amino)ethyl)-N-(2-(piperazin-1-ylmethyl)benzyl)pivalamide 5E

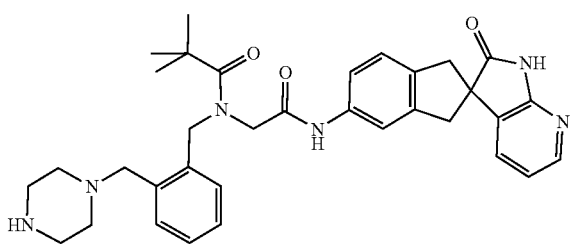 [SMILES: CC(C)(C)C(=O)N(CC(=O)Nc1ccc2c(c1)CC1(C2)C(=O)Nc2ncccc21)Cc1ccccc1CN1CCNCC1]

Synthesised according to General Route A using Intermediate H (30 mg, 0.059 mmol) and tert-butyl piperazine-1-carboxylate (10 mg, 0.12 mmol) premixed for 3 h, then worked up after 21 h and purified via SPE (2 g SiO$_2$ 0-5% MeOH in EtOAc). The Boc-protected intermediate (24 mg, 0.035 mmol) was deprotected by dissolving in dichloromethane (3 ml) and addition of trifluoroacetic acid (0.2 ml). After stirring at RT for 4 h, the reaction was poured into saturated sodium bicarbonate and extracted three times with dichloromethane. The combined organics were dried over sodium sulfate, filtered and evaporated. The residue was purified via SPE (2 g SiO$_2$, 0-10% MeOH in DCM) to provide 5E (12 mg, 35% 2 steps) as a colourless glass. $^1$H NMR (CD$_3$OD, 300 MHz) δ 1.31 (s, 9H), 2.44 (br s, 4H), 2.82 (br s, 4H), 3.06 (dd, 2H), 3.49 (m, 4H), 3.64 (m, 1H), 4.07 (br s, 2H), 5.19 (br s, 1H), 6.86 (dd, 1H), 7.13 (d, 1H), 7.20 (m, 4H), 7.33 (m, 2H), 7.55 (s, 1H), 8.02 (d, 1H). UPLC-MS rt 0.68 (581 [M+H]$^+$), 96% pure.

Example 6: N-(2-Oxo-2-((2'-oxo-1,1',2',3-tetrahydrospiro[indene-2,3'-pyrrolo[2,3-b]pyridine]-5-yl)amino)ethyl)-N-(2-(((2,2,2-trifluoroethyl)amino)methyl)benzyl)pivalamide 5F

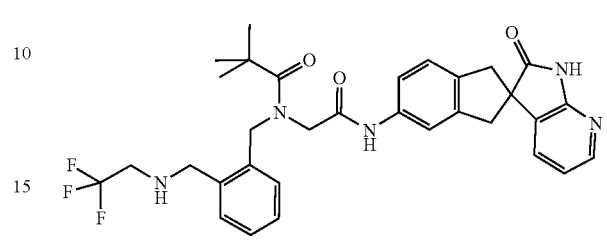

Synthesised according to General Route A from Intermediate H (30 mg, 0.059 mmol) using 2,2,2-trifluoroethylamine (9.5 µl, 0.12 mmol) premixed for 3 h, then worked up after 21 h and purified via SPE (2 g SiO$_2$ 0-5% MeOH in EtOAc) to provide 5F (9 mg, 26%) as a colourless solid. $^1$H NMR (CD$_3$OD, 300 MHz) δ 1.29 (s, 9H), 3.04 (dd, 2H), 3.18 (q, 1H), 3.50 (dd, 2H), 3.86 (s, 1H), 4.13 (m, 3H), 5.20 (br s, 3H), 6.86 (dd, 1H), 7.10 (dd, 1H), 7.30 (m, 6H), 7.77 and 8.66 (2s, 1H), 8.02 (d, 1H). UPLC-MS rt 0.81 (594 [M+H]$^+$), 93% pure.

Example 7: N-(2-(((2-(Dimethylamino)ethyl)amino)methyl)benzyl)-N-(2-oxo-2-((2'-oxo-1,1',2',3-tetrahydrospiro[indene-2,3'-pyrrolo[2,3-b]pyridine]-5-yl)amino)ethyl)pivalamide 5G

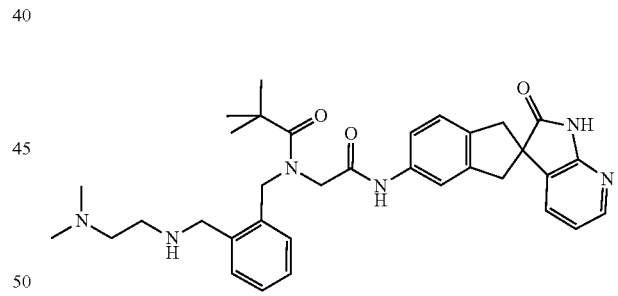

Synthesised according to General Route A from Intermediate H (30 mg, 0.059 mmol) using N,N-dimethylethylenediamine (13 µl, 0.12 mmol) premixed for 20 h, then worked up after 26 h and purified via SPE (2 g SiO$_2$ 0-10% MeOH in EtOAc then 10-20% MeOH in DCM) then triturated in diethyl ether, to provide 5G (18 mg, 53%) as a colourless solid. $^1$H NMR (CD$_3$OD, 400 MHz) δ 1.32 (s, 9H), 2.21 (s, 6H), 2.48 (t, 2H), 2.74 (t, 2H), 3.05 (dd, 2H), 3.50 (dd, 2H), 3.78 (s, 2H), 4.03 (br s, 2H), 5.02 (br s, 2H), 6.88 (dd, 1H), 7.12 (d, 1H), 7.28 (m, 6H), 7.54 (s, 1H), 8.03 (d, 1H). UPLC-MS rt 0.69 (583 [M+H]$^+$), 100% pure.

Example 8: N-(2-((((Cyclopropylmethyl)amino)methyl)benzyl)-N-(2-oxo-2-((2'-oxo-1,1',2',3-tetrahydrospiro[indene-2,3'-pyrrolo[2,3-b]pyridine]-5-yl)amino)ethyl)pivalamide 5H

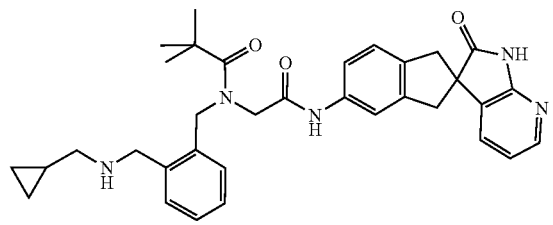 [SMILES: CC(C)(C)C(=O)N(CC(=O)Nc1ccc2c(c1)CC1(C2)C(=O)Nc2ncccc21)Cc1ccccc1CNCC1CC1]

Synthesised according to General Route A from Intermediate H (30 mg, 0.059 mmol) using (cyclopropylmethyl)amine (10 μl, 0.12 mmol) premixed for 20 h, then worked up after 26 h and purified via SPE (2 g SiO₂ 0-10% MeOH in EtOAc then 10-20% MeOH in DCM) then triturated in diethyl ether, to provide 5H (21 mg, 63%) as a colourless solid. $^1$H NMR (CD$_3$OD, 400 MHz) δ 0.21 (br s, 2H), 0.52 (br d, 2H), 1.00 (m, 1H), 1.30 (s, 9H), 2.63 (br m, 2H), 3.06 (dd, 2H), 3.50 (dd, 2H), 3.92 (br m, 2H), 4.22 (br s, 2H), 4.82 (m, 2H), 6.88 (dd, 1H), 7.12 (d, 1H), 7.30 (m, 6H), 7.52 (s, 1H), 8.03 (d, 1H). UPLC-MS rt 0.77 (566 [M+H]$^+$), 100% pure.

Example 9: N-(2-((((1H-Imidazol-2-yl)methyl)amino)methyl)benzyl)-N-(2-oxo-2-((2'-oxo-1,1',2',3-tetrahydrospiro[indene-2,3'-pyrrolo[2,3-b]pyridine]-5-yl)amino)ethyl)pivalamide 51

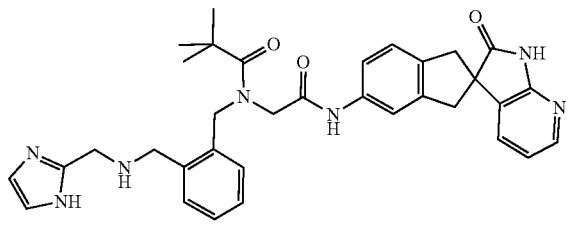 [SMILES: CC(C)(C)C(=O)N(CC(=O)Nc1ccc2c(c1)CC1(C2)C(=O)Nc2ncccc21)Cc1ccccc1CNCc1ncc[nH]1]

Synthesised according to General Route A from Intermediate H (30 mg, 0.059 mmol) using 2-methylaminoimidazole dihydrochloride (12 mg, 0.076 mmol) premixed for 3.5 h, then worked up after 21 h and purified via SPE (2 g STMAd MeOH, then NH₃ in MeOH, followed by 2 g SiO₂ 0-10% MeOH in EtOAc then 10% MeOH in DCM) to provide 51 (13 mg, 37%) as a pale yellow solid. $^1$H NMR (CD$_3$OD, 400 MHz) δ 1.29 (s, 9H), 3.04 (dd, 2H), 3.48 (dd, 2H), 3.63 (br d, 1H), 3.70 (br d, 1H), 3.78 (s, 2H), 3.90 (s, 2H), 4.97 (br s, 2H), 6.84 (dd, 1H), 6.98 (s, 2H), 7.09 (d, 1H), 7.20 (d, 1H), 7.26 (m, 5H), 7.52 (s, 1H), 8.03 (d, 1H). UPLC-MS rt 0.64 (592 [M+H]$^+$), 92% pure.

General Route B

SCHEME 6

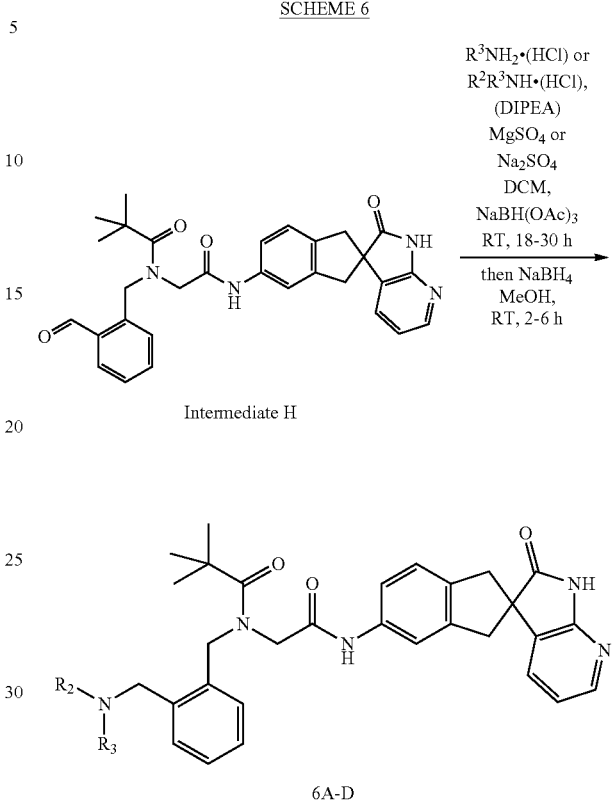

Intermediate H (30-40 mg, 0.059-0.078 mmol) was dissolved in dichloromethane (3 ml) and amine/amine hydrochloride added (0.12-0.18 mmol). N,N-Diisopropylethylamine (0.028-0.067 ml, 0.15-0.36 mmol) was added if amine hydrochloride was used. Sodium or magnesium sulfate was added and the mixture stirred at room temperature and progress monitored by UPLC-MS. After 0.25-1.5 h sodium triacetoxyborohydride (20-29 mg, 0.094-0.136 mmol) was added and reaction stirred at room temperature, monitoring by UPLC-MS. Extra sodium triacetoxyborohydride (0.094 mmol) added as required. Reactions had mixture of imine and amine by UPLC-MS. Reactions were poured into saturated sodium bicarbonate and extracted three times with dichloromethane. The combined organics were dried (sodium sulfate), filtered and evaporated. The crude residue was then dissolved in methanol and sodium borohydride (4 mg, 0.106 mmol) was added portionwise with gas evolution. The reactions were stirred at room temperature for 2-6 h. Once complete, the mixture was poured into saturated sodium bicarbonate and extracted three times with ethyl acetate. The organics were washed with brine, dried over sodium sulfate, filtered and evaporated.

Example 10: N-(2-((3-Fluoroazetidin-1-yl)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 8A

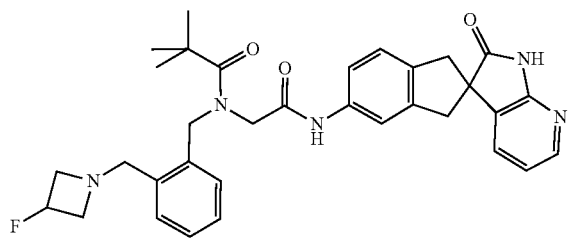 [SMILES: CC(C)(C)C(=O)N(CC(=O)Nc1ccc2c(c1)CC1(C2)C(=O)Nc2ncccc21)Cc1ccccc1CN1CC(F)C1]

Synthesised according to General Route B from Intermediate H (40 mg, 0.078 mmol) using 3-fluoroazetidine hydrochloride (20 mg, 0.18 mmol) premixed for 15 min, then worked up after 18 h. UPLC-MS showed 76% amine and 14% imine. Crude product was further reduced with sodium borohydride over 6 h and purified via SPE (2 g SiO$_2$ 50-100% EtOAc in DCM) to provide 6A (11 mg, 25%) as a colourless solid. $^1$H NMR (CD$_3$OD, 300 MHz) δ 1.31 (s, 9H), 3.03 (dd, 2H), 3.19 (m, 2H), 3.50 (m, 4H), 3.65 (m, 2H), 4.10 (br s, 2H), 4.99 (br s, 1H), 5.10 (br s, 2H), 6.58 (dd, 1H), 7.10 (dd, 1H), 7.25 (m, 6H), 7.55 (s, 1H), 8.02 (dd, 1H). UPLC-MS rt 0.79 (570 [M+H]$^+$), 94% pure.

Example 11: N-(2-((3,3-Difluoroazetidin-1-yl)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 8B

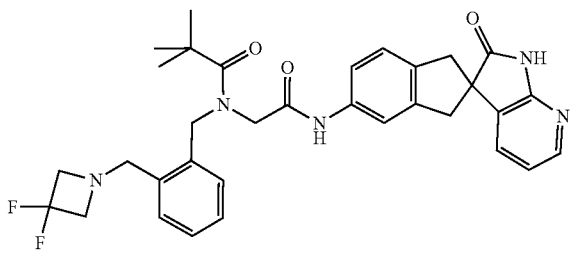 [SMILES: CC(C)(C)C(=O)N(CC(=O)Nc1ccc2c(c1)CC1(C2)C(=O)Nc2ncccc21)Cc1ccccc1CN1CC(F)(F)C1]

Synthesised according to General Route B from Intermediate H (40 mg, 0.078 mmol) using 3,3-difluoroazetidine hydrochloride (23 mg, 0.18 mmol) premixed for 15 min, then worked up after 18 h. UPLC-MS showed 33% amine and 37% imine. Crude product was further reduced with sodium borohydride over 6 h and purified via SPE (2 g SiO$_2$ 25-75% EtOAc in DCM) to provide 6B (9 mg, 20%) as a colourless solid. $^1$H NMR (CD$_3$OD, 300 MHz) δ 1.31 (s, 9H), 3.04 (dd, 2H), 3.50 (m, 6H), 3.74 (s, 2H), 4.09 (br s, 2H), 5.12 (br s, 2H), 6.86 (dd, 1H), 7.10 (d, 1H), 7.25 (m, 6H), 7.53 (s, 1H), 8.02 (d, 1H). UPLC-MS rt 0.83 (587 [M+H]$^+$), 83% pure.

Example 12: N-(2-(((3-(Dimethylamino)propyl)amino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 6C

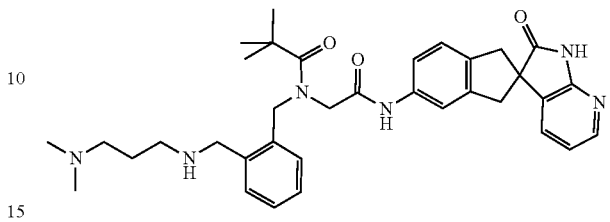

Synthesised according to General Route B from Intermediate H (30 mg, 0.059 mmol) using 3,3-dimethylaminopropylamine (15 µl, 0.12 mmol) premixed for 1.5 h, then worked up after 22 h. UPLC-MS showed 24% amine and 70% imine. Crude product was further reduced with sodium borohydride over 2 h and purified via SPE (2 g STMAd, MeOH then NH$_3$ in MeOH) to provide 6C (16 mg, 46%) as a colourless solid. $^1$H NMR (CD$_3$OD, 300 MHz) δ 1.32 (s, 9H), 1.71 (m, 2H), 2.17 (s, 6H), 2.37 (t, 2H), 2.62 (t, 2H), 3.05 (dd, 2H), 3.48 (dd, 2H), 3.76 (s, 2H), 4.10 (br s, 2H), 5.00 (br s, 2H), 6.86 (dd, 1H), 7.25 (m, 7H), 7.54 (s, 1H), 8.02 (d, 1H). UPLC-MS rt 0.69 (597 [M+H]$^+$), 76% pure.

Example 13: N-(2-(((2-Hydroxyethyl)amino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 6D

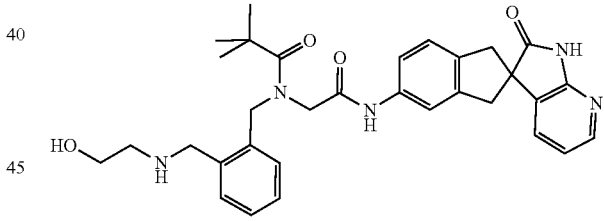

Synthesised according to General Route B from Intermediate H (30 mg, 0.059 mmol) using 2-ethanolamine (36 µl, 0.59 mmol) premixed for 15 min, then worked up after 18 h. UPLC-MS showed 76% imine. An additional step was carried out where reduction was attempted using sodium cyanoborohydride (3.2 mg 0.049 mmol) in methanol (2 ml) at RT for 18 h, but this still gave imine and a nitrile adduct of the imine. Crude product was further reduced with sodium borohydride over 1.5 h and purified via SPE (2 g SiO$_2$ 0-25% MeOH in EtOAc) to provide 6D (10 mg, 30%) as a colourless solid. $^1$H NMR (CDCl$_3$, 300 MHz) δ 1.34 (s, 9H), 2.85 (m, 2H), 3.05 (dd, 2H), 3.60 (dd, 2H), 3.68 (m, 2H), 3.87 (s, 2H), 4.10 (m, 2H), 5.10 (s, 2H), 6.81 (dd, 1H), 7.08 (dd, 1H), 7.21 (m, 3H), 7.30 (m, 3H), 7.50 (s, 1H), 8.10 (d, 1H), 8.74 (s, 1H). UPLC-MS rt 0.65 (556 [M+H]$^+$), 96% pure.

General Route C

SCHEME 7

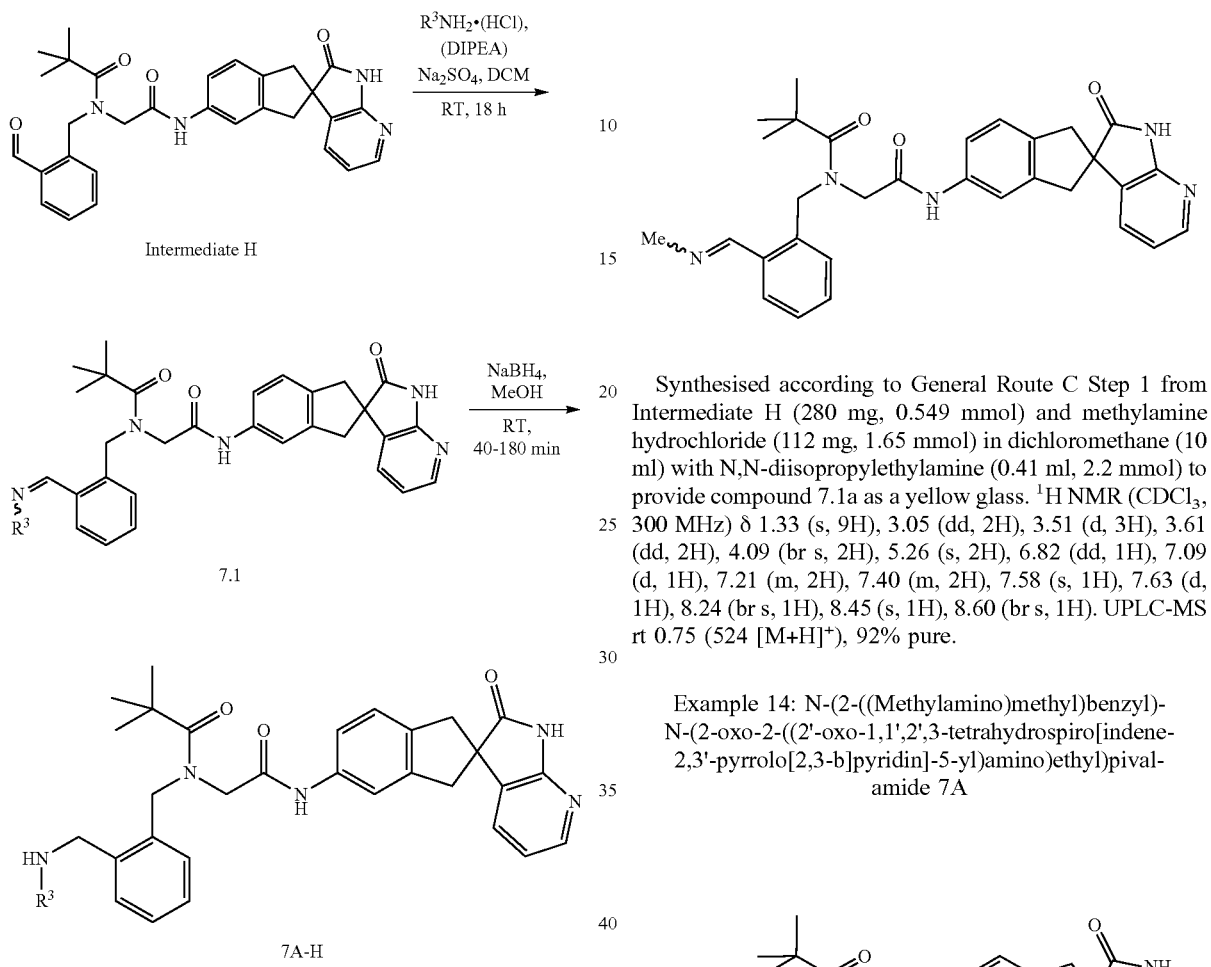

Step 1:

Intermediate H (40-280 mg, 0.078-0.549 mmol) was suspended in dichloromethane (2-10 ml) and amine/amine hydrochloride added (0.33-1.65 mmol). N,N-Diisopropylethylamine (88-410 μl, 0.47-2.2 mmol) was added if the amine hydrochloride was used. Sodium sulfate was added and the reaction stirred at RT for 18 h. The mixture was poured into saturated sodium bicarbonate and extracted three times with dichloromethane. The combined organic extracts were dried over sodium sulfate, filtered and the filtrate evaporated to provide compound 7.1 as a yellow glass.

Step 2:

Compound 7.1 (~0.078-0.549 mmol) was dissolved in methanol (2-10 ml) then sodium borohydride (4-31 mg, 0.108-0.823 mmol) was added portionwise (gas evolution). The mixture was stirred at RT for 40-180 min. UPLC-MS indicated the reaction was complete. The mixture was poured into saturated sodium bicarbonate and extracted three times with ethyl acetate. The combined organic extracts were washed with brine, dried over sodium sulfate, filtered and the filtrate evaporated.

N-(2-((Methylimino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7.1a Synthesised according to General Route C Step 1 from Intermediate H (280 mg, 0.549 mmol) and methylamine hydrochloride (112 mg, 1.65 mmol) in dichloromethane (10 ml) with N,N-diisopropylethylamine (0.41 ml, 2.2 mmol) to provide compound 7.1a as a yellow glass. $^1$H NMR (CDCl$_3$, 300 MHz) δ 1.33 (s, 9H), 3.05 (dd, 2H), 3.51 (d, 3H), 3.61 (dd, 2H), 4.09 (br s, 2H), 5.26 (s, 2H), 6.82 (dd, 1H), 7.09 (d, 1H), 7.21 (m, 2H), 7.40 (m, 2H), 7.58 (s, 1H), 7.63 (d, 1H), 8.24 (br s, 1H), 8.45 (s, 1H), 8.60 (br s, 1H). UPLC-MS rt 0.75 (524 [M+H]$^+$), 92% pure.

Example 14: N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7A

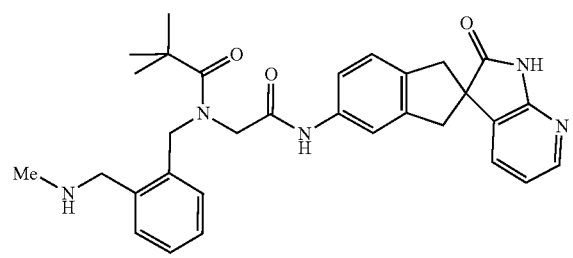 [SMILES: CNCc1ccccc1CN(CC(=O)Nc1ccc2c(c1)CC1(C2)C(=O)Nc2ncccc21)C(=O)C(C)(C)C]

Synthesised according to General Route C Step 2 from 7.1a (~0.549 mmol) and sodium borohydride (31 mg, 0.823 mmol) in methanol (10 ml) for 180 min then purified via flash silica chromatography (10% MeOH in EtOAc, then 10-20% MeOH in DCM, then 20% MeOH with NH$_3$ in DCM) to provide compound 7A (147 mg, 51%) as a colourless solid. $^1$H NMR (CDCl$_3$, 300 MHz) δ 1.32 (s, 9H), 2.48 (s, 3H), 3.02 (d, 2H), 3.58 (d, 2H), 3.84 (br s, 2H), 4.18 (br s, 2H), 5.02 (br s, 2H), 6.80 (dd, 1H), 7.07 (dd, 1H), 7.22 (d, 4H), 7.31 (m, 3H), 7.50 (s, 1H), 8.11 (d, 1H), 8.95 (br s, 1H). UPLC-MS rt 0.70 (526 [M+H]$^+$), 99% pure. A sample of compound 7A (49 mg, 0.093 mmol) was purified via chiral semi-preparative HPLC (Chiral IA, ID 20, 250 mm, 85% acetonitrile 15% methanol with 0.1% diethylamine, 18 ml/min) to provide 7A_S (16 mg, 33%) and 7A_R (13 mg, 26%) as Examples 15 and 16 below.

Example 15: (S)—N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7A_S

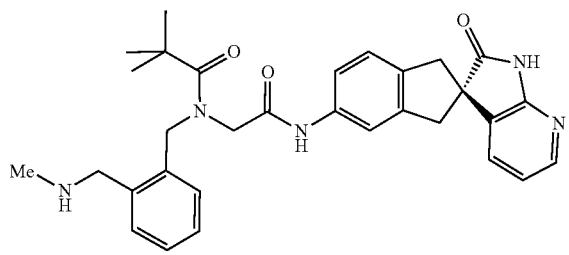 [SMILES: CNCc1ccccc1CN(CC(=O)Nc1ccc2c(c1)C[C@]1(C2)C(=O)Nc2ncccc21)C(=O)C(C)(C)C]

¹H NMR (CD₃OD, 300 MHz) δ 1.32 (s, 9H), 2.41 (s, 3H), 3.04 (dd, 2H), 3.50 (dd, 2H), 3.72 (s, 2H), 4.11 (br s, 2H), 4.96 (br s, 2H), 6.86 (dd, 1H), 7.11 (m, 1H), 7.20 (m, 2H), 7.30 (m, 4H), 7.52 (s, 1H), 8.03 (d, 1H). Chiral HPLC (IA, 90% acetonitrile, 10% methanol 0.1% diethylamine, 1 ml/min), 99.4% ee.

Example 16: (R)—N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7A_R

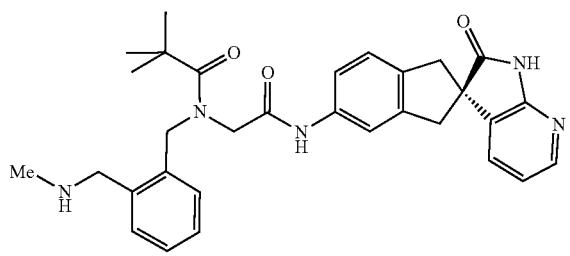 [SMILES: CNCc1ccccc1CN(CC(=O)Nc1ccc2c(c1)C[C@@]1(C2)C(=O)Nc2ncccc21)C(=O)C(C)(C)C]

¹H NMR (CD₃OD, 300 MHz) δ 1.32 (s, 9H), 2.41 (s, 3H), 3.04 (dd, 2H), 3.50 (dd, 2H), 3.72 (s, 2H), 4.11 (br s, 2H), 4.96 (br s, 2H), 6.86 (dd, 1H), 7.11 (m, 1H), 7.20 (m, 2H), 7.30 (m, 4H), 7.52 (s, 1H), 8.03 (d, 1H). Chiral HPLC (IA, 90% acetonitrile, 10% methanol 0.1% diethylamine, 1 ml/min), 98.1% ee.

N-(2-(((2-Fluoroethyl)imino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7.1b

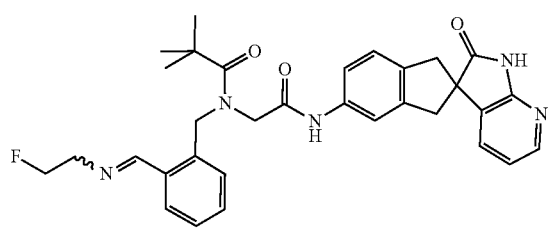 [SMILES: CC(C)(C)C(=O)N(CC(=O)Nc1ccc2c(c1)CC1(C2)C(=O)Nc2ncccc21)Cc1ccccc1C=NCCF]

Synthesised according to General Route C Step 1 from Intermediate H (40 mg, 0.078 mmol) and 2-fluoroethylamine hydrochloride (23.5 mg, 0.235 mmol) in dichloromethane (2 ml) with N,N-diisopropylethylamine (88 µl, 0.47 mmol) to provide compound 7.1b as a yellow glass. UPLC-MS rt 0.75 (556 [M+H]⁺), 75% pure.

Example 17: N-(2-(((2-Fluoroethyl)amino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7B

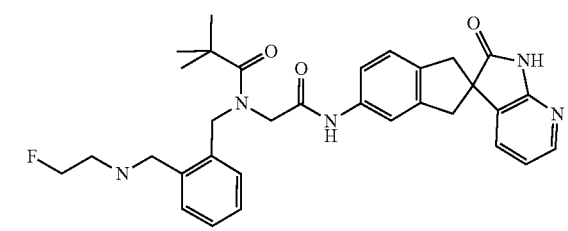 [SMILES: CC(C)(C)C(=O)N(CC(=O)Nc1ccc2c(c1)CC1(C2)C(=O)Nc2ncccc21)Cc1ccccc1CNCCF]

Synthesised according to General Route C Step 2 from 7.1b (~0.549 mmol) and sodium borohydride (4 mg, 0.106 mmol) in methanol (2 ml) for 40 min and purified via SPE (2 g SiO₂, 0-10% MeOH in EtOAc) to provide compound 7B (14 mg, 32%) as a colourless solid. ¹H NMR (CD₃OD, 300 MHz) δ 1.31 (s, 9H), 2.83 (t, 1H), 2.92 (t, 1H), 3.03 (dd, 2H), 3.49 (dd, 2H), 3.81 (d, 2H), 4.07 (br s, 2H), 4.39 (t, 1H), 4.56 (t, 1H), 5.07 (br s, 2H), 6.86 (dd, 1H), 7.11 (dd, 2H), 7.23 (m, 4H), 7.53 (s, 1H), 8.02 (dd, 1H). UPLC-MS rt 0.74 (558 [M+H]⁺), 93% pure.

N-(2-(((2-Methoxyethyl)imino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7.1c

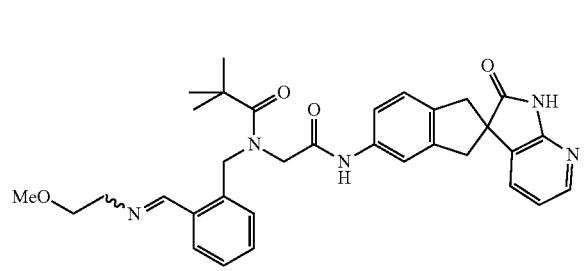 [SMILES: COCCN=Cc1ccccc1CN(CC(=O)Nc1ccc2c(c1)CC1(C2)C(=O)Nc2ncccc21)C(=O)C(C)(C)C]

Synthesised according to General Route C Step 1 from Intermediate H (40 mg, 0.078 mmol) and 2-methoxyethylamine (34 µl, 0.235 mmol) in dichloromethane (2 ml) to provide compound 7.1c as a yellow glass. UPLC-MS rt 0.74 (568 [M+H]⁺), 90% pure.

Example 18: N-(2-(((2-Methoxyethyl)amino) methyl)benzyl)-N-(2-oxo-2-((2'-oxo-1,1',2',3-tetra-hydrospiro[indene-2,3'-pyrrolo[2,3-b]pyridin]-5-yl) amino)ethyl)pivalamide 7C

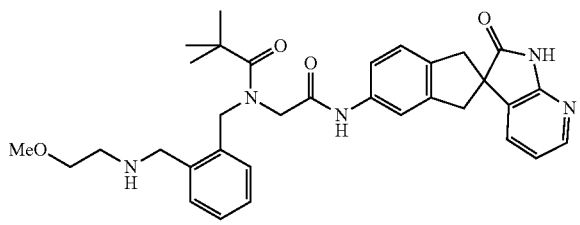 [SMILES: COCCNCc1ccccc1CN(CC(=O)Nc1ccc2c(c1)CC1(C2)C(=O)Nc2ncccc21)C(=O)C(C)(C)C]

Synthesised according to General Route C Step 2 from 7.1c (~0.549 mmol) and sodium borohydride (4 mg, 0.106 mmol) in methanol (2 ml) for 90 min and purified via SPE (2 g SiO$_2$, 0-10% MeOH in EtOAc) to provide compound 7C (24 mg, 54%) as a colourless solid. $^1$H NMR (CD$_3$OD, 300 MHz) δ 1.32 (s, 9H), 2.77 (t, 2H), 3.04 (dd, 2H), 3.30 (s, 3H), 3.49 (m, 4H), 3.79 (s, 2H), 4.10 (br s, 2H), 5.05 (br s, 2H), 6.87 (dd, 1H), 7.11 (d, 1H), 7.26 (m, 6H), 7.54 (s, 1H), 8.03 (d, 1H). UPLC-MS rt 0.74 (570 [M+H]$^+$), 99% pure.

N-(2-(((Isopropyl)imino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7.1d

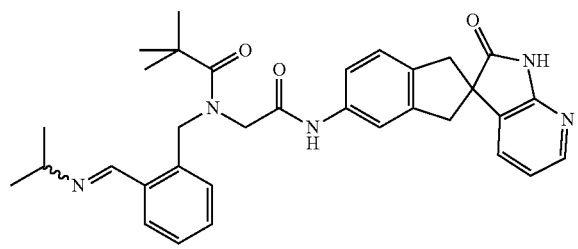 [SMILES: CC(C)N=Cc1ccccc1CN(CC(=O)Nc1ccc2c(c1)CC1(C2)C(=O)Nc2ncccc21)C(=O)C(C)(C)C]

Synthesised according to General Route C Step 1 from Intermediate H (50 mg, 0.098 mmol) and isopropylamine (42 μl, 0.49 mmol) in dichloromethane (2 ml) to provide compound 7.1d as a yellow glass. UPLC-MS rt 0.83 (552 [M+H]$^+$), 76% pure.

Example 19: N-(2-((Isopropylamino)methyl)benzyl)-N-(2-oxo-2-((2'-oxo-1,1',2',3-tetrahydrospiro [indene-2,3'-pyrrolo[2,3-b]pyridin]-5-yl)amino) ethyl)pivalamide 7D

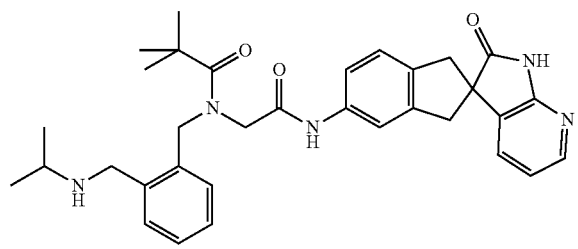

Synthesised according to General Route C Step 2 from 7.1d (~0.549 mmol) and sodium borohydride (4 mg, 0.106 mmol) in methanol (2 ml) for 60 min and purified via SPE (2 g SiO$_2$ 10% MeOH in EtOAc then 10-20% MeOH in DCM) to provide compound 7D (33 mg, 54%) as a colourless solid. $^1$H NMR (CDCl$_3$, 300 MHz) δ 1.09 (d, 6H), 1.32 (s, 9H), 2.86 (m, 1H), 3.03 (dd, 2H), 3.61 (dd, 2H), 3.79 (s, 2H), 4.12 (br s, 2H), 5.12 (br s, 2H), 6.81 (dd, 1H), 7.05 (dd, 1H), 7.19 (m, 4H), 7.30 (m, 2H), 7.54 (s, 1H), 8.11 (dd, 1H) 8.64 (s, 1H). UPLC-MS rt 0.79 (554 [M+H]$^+$), 97% pure.

N-(2-((((Cyclobutyl)imino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7.1e

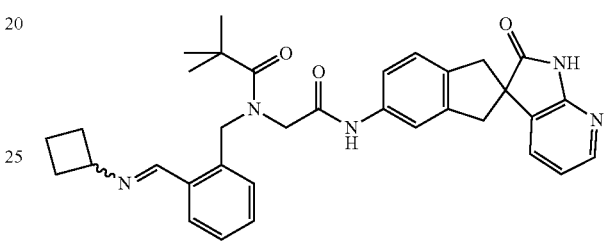

Synthesised according to General Route C Step 1 from Intermediate H (50 mg, 0.098 mmol) and cyclobutylamine (42 μl, 0.49 mmol) in dichloromethane (2 ml) to provide compound 7.1e as a yellow glass. UPLC-MS rt 0.85 (564 [M+H]$^+$), 87% pure.

Example 20: N-(2-((Cyclobutylamino)methyl)benzyl)-N-(2-oxo-2-((2'-oxo-1,1',2',3-tetrahydrospiro [indene-2,3'-pyrrolo[2,3-b]pyridin]-5-yl)amino) ethyl)pivalamide 7E

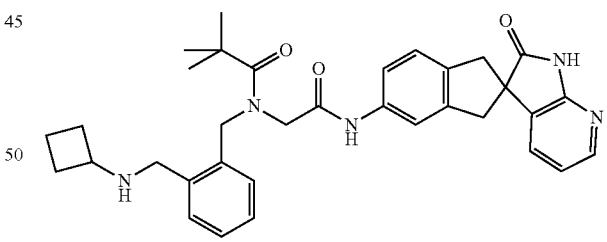

Synthesised according to General Route C Step 2 from 7.1e (~0.549 mmol) and sodium borohydride (4 mg, 0.106 mmol) in methanol (2 ml) for 60 min and purified via SPE (2 g SiO$_2$ 10% MeOH in EtOAc then 10-20% MeOH in DCM) to provide compound 7E (41 mg, 74%) as a colourless solid. $^1$H NMR (CDCl$_3$, 300 MHz) δ 1.32 (s, 9H), 1.70 (m, 4H), 2.19 (m, 2H), 3.03 (dd, 2H), 3.26 (m, 1H), 3.62 (dd, 2H), 3.72 (s, 2H), 4.12 (br s, 2H), 5.09 (br s, 2H), 6.82 (dd, 1H), 7.01 (dd, 1H), 7.20 (m, 4H), 7.30 (m, 2H), 7.51 (br s, 1H), 8.11 (dd, 1H) 8.68 (br s, 1H). UPLC-MS rt 0.81 (566 [M+H]$^+$), 96% pure.

161

N-(2-(($d_3$-Methylimino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7.1f

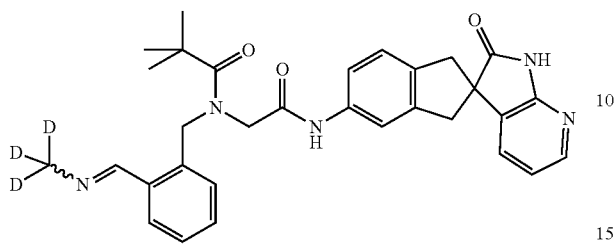

Synthesised according to General Route C Step 1 from Intermediate H (51 mg, 0.095 mmol), d3-methylamine hydrochloride (20 mg, 0.285 mmol) and N,N-diisopropylethylamine (88 µl, 0.47 mmol) in dichloromethane (3 ml) to provide compound 7.1f as a yellow glass. UPLC-MS rt 0.78 (527 [M+H]$^+$), 86% pure.

Example 21: N-(2-(($d_3$-Methylamino)-$d_1$-methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 7F


Synthesised according to General Route C Step 2 from 7.1f (~0.095 mmol) except using sodium borodeuteride (6.2 mg, 0.147 mmol) in $d_4$-methanol (2 ml) for 60 min and purified via SPE (2 g STMAd, MeOH then NH$_3$ in MeOH) to provide compound 7F (30 mg, 60%) as a colourless solid. $^1$H NMR (CD$_3$OD, 300 MHz) δ 1.32 (s, 9H), 3.05 (d, 2H), 3.50 (d, 2H), 3.70 (s, 1H), 4.11 (br s, 2H), 4.97 (br s, 2H), 6.86 (dd, 1H), 7.10 (dd, 1H), 7.20 (m, 2H), 7.28 (m, 2H), 7.33 (m, 2H), 7.52 (s, 1H), 8.02 (dd, 1H). UPLC-MS (CSH 2-50%) rt 0.59 (530 [M+H]$^+$), 98% pure.

Synthesis of Intermediate I

SCHEME 8

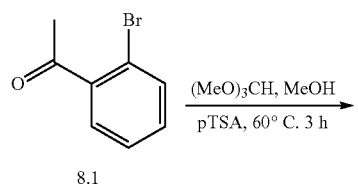

-continued

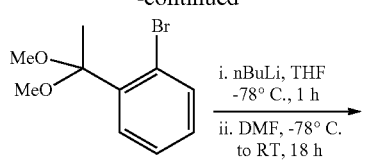

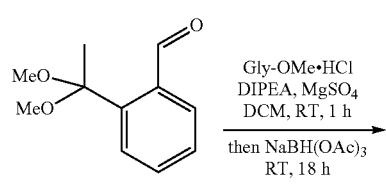

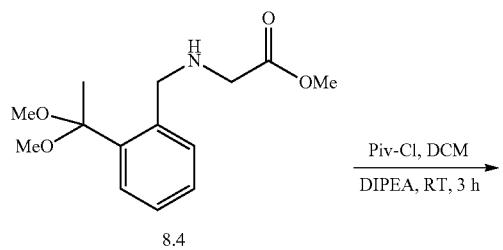

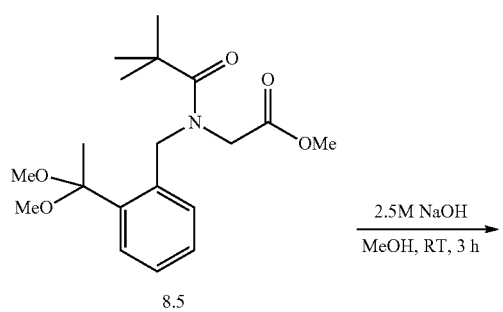

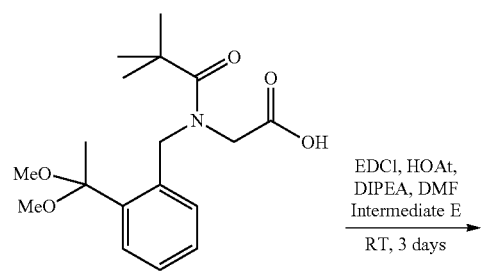

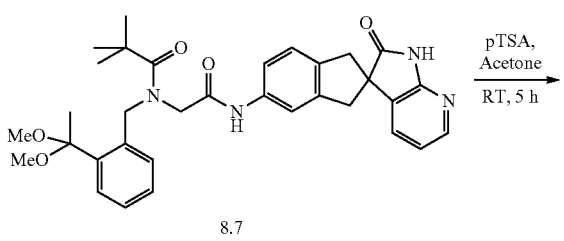

-continued

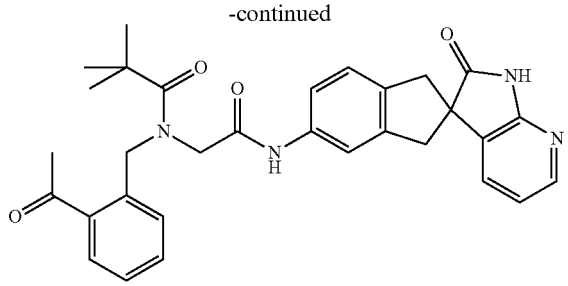

Intermediate I

1-Bromo-2-(1,1-dimethoxyethyl)benzene 8.2

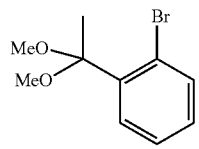

2-Bromoacetophenone 8.1 (876 mg, 4.4 mmol) was dissolved in methanol (6 ml) and p-toluenesulfonic acid monohydrate (84 mg, 0.44 mmol) and trimethyl orthoformate (10 ml) were added. The solution was warmed to 60° C. for 3 h. The mixture was cooled on ice water then triethylamine (1 ml) was added. The volatiles were removed then the mixture diluted with ethyl acetate and water. The aqueous layer was extracted twice with ethyl acetate. The combined organic extracts were washed with brine, dried over magnesium sulfate, filtered and the filtrate evaporated to provide compound 8.2 (1.03 g, 96%) as a colourless oil.

$^1$H NMR (CDCl$_3$, 300 MHz) δ 1.68 (s, 3H), 3.20 (s, 6H), 7.12 (td, 1H), 7.30 (td, 1H), 7.60 (dd, 1H), 7.79 (dd, 1H).

2-(1,1-Dimethoxyethyl)benzaldehyde 8.3

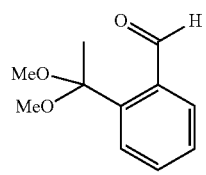

Compound 8.2 (830 mg, 3.39 mmol) was dissolved in dry tetrahydrofuran (10 ml) under an argon atmosphere then cooled on dry ice/acetone. To this was added a solution of n-butyllithium (2.04 ml, 5.09 mmol, 2.5 M in hexanes) dropwise so that the internal temperature stayed below −60° C. (10 min addition). The reaction was stirred on dry ice/acetone for 60 min. To this was added N,N-dimethylformamide (0.525 ml, 6.78 mmol) in one portion. The mixture was stirred on dry ice/acetone for 60 min before being allowed to warm to RT over 18 h. Water was added then the mixture was extracted three times with ethyl acetate. The combined organic extracts were washed with brine, dried over magnesium sulfate, filtered and the filtrate evaporated to provide compound 8.3 (634 mg, 96%) as a straw-coloured oil.

$^1$H NMR (CDCl$_3$, 300 MHz) δ 1.70 (s, 3H), 3.23 (s, 6H), 7.40 (t, 1H), 7.54 (dt, 1H), 7.64 (dd, 1H), 7.86 (dd, 1H), 10.64 (s, 1H).

Methyl 2-((2-(1,1-dimethoxyethyl)benzyl)amino)acetate 8.4

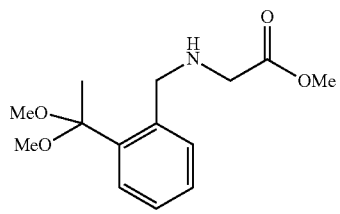 [SMILES: COC(=O)CNCc1ccccc1C(C)(OC)OC]

Compound 8.3 (634 mg, 3.26 mmol) was dissolved in dichloromethane (25 ml) under an argon atmosphere. N,N-Diisopropylethylamine (1.14 ml, 6.52 mmol) was added followed by methyl glycinate hydrochloride (777 mg, 6.19 mmol) and magnesium sulfate (excess). The mixture was stirred at RT for 1 h. Sodium triacetoxyborohydride (1.1 g, 5.2 mmol) was added and the mixture was stirred at RT for 18 h. The mixture was poured into water and the aqueous layer was extracted three times with dichloromethane. The combined organic extracts were washed with brine, dried over magnesium sulfate, filtered and the filtrate evaporated to provide compound 8.4 (717 g, 82%) as a pale straw-coloured gum. $^1$H NMR (CDCl$_3$, 300 MHz) δ 1.88 (s, 3H), 3.23 (s, 6H), 3.50 (s, 2H), 3.72 (s, 3H), 3.98 (s, 2H), 7.27 (m, 2H), 7.39 (m, 1H), 7.54 (m, 1H).

Methyl 2-(N-(2-(1,1-dimethoxyethyl)benzyl)pivalamido)acetate 8.5

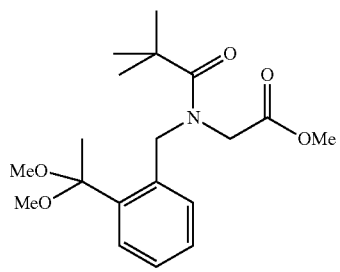 [SMILES: COC(=O)CN(Cc1ccccc1C(C)(OC)OC)C(=O)C(C)(C)C]

Compound 8.4 (685 mg, 2.56 mmol) was dissolved in dichloromethane (40 ml) under an argon atmosphere then N,N-diisopropylethylamine (1.34 ml, 7.68 mmol) was added. Trimethylacetyl chloride (0.38 ml, 3.07 mmol) was added dropwise. The mixture was stirred at RT for 3 h after which was complete by TLC. The mixture was poured into water and the aqueous layer was extracted three times with dichloromethane. The combined organic extracts were washed with brine, dried over magnesium sulfate, filtered and the filtrate evaporated to provide compound 8.5 (1.012 g, quant.) as a yellow gum. $^1$H NMR (CDCl$_3$, 300 MHz) δ 1.32 (s, 9H), 1.52 (s, 3H), 3.20 (s, 6H), 3.72 (s, 3H), 5.02 (br s, 2H), 7.27 (m, 3H), 7.60 (dd, 1H)-one signal collapsed, not visible.

2-(N-(2-(1,1-Dimethoxyethyl)benzyl)pivalamido) acetic Acid 8.6

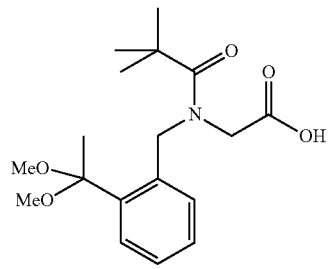 [SMILES: COC(C)(OC)c1ccccc1CN(CC(=O)O)C(=O)C(C)(C)C]

Compound 8.5 (500 mg, 1.40 mmol) was dissolved in methanol (5 ml) then 2.5M sodium hydroxide (0.84 ml, 2.1 mmol) was added. The mixture was stirred at RT for 3 h after which was complete by TLC. The mixture was diluted with water and the pH was adjusted very carefully to pH 4 with 10% potassium hydrogen sulfate. Once at pH 4, the aqueous was extracted twice with ethyl acetate. The combined organic extracts were washed with brine, dried over magnesium sulfate, filtered and evaporated carefully (30° C. water bath, not to dryness). Compound 8.6 was used directly in the next step as the compound is not stable.

N-(2-(1,1-Dimethoxyethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 8.7

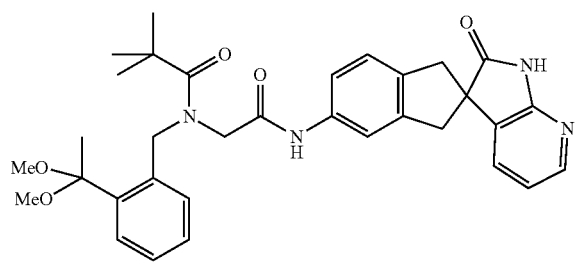 [SMILES: COC(C)(OC)c1ccccc1CN(CC(=O)Nc1ccc2c(c1)CC1(C2)C(=O)Nc2ncccc21)C(=O)C(C)(C)C]

Compound 8.6 (~1.40 mmol) was dissolved in N,N-dimethylformamide (15 ml) under an argon atmosphere then N,N-diisopropylethylamine (0.73 ml, 4.2 mmol) was added. EDCl.HCl (322 mg, 1.68 mmol) and HOAt (229 mg, 1.68 mmol) were added followed by Intermediate E (387 mg, 1.54 mmol). The mixture was stirred at RT for 3 days. The mixture was poured into saturated sodium bicarbonate. The aqueous layer was extracted three times with ethyl acetate. The combined organic extracts were washed three times with water, dried over sodium sulfate, filtered and the filtrate evaporated. The residue was purified via column chromatography (300 ml silica, 2:1 heptane/acetone) to provide compound 8.7 (247 mg, 31%) as a colourless glass. $^1$H NMR (CDCl$_3$, 300 MHz) δ 1.34 (s, 9H), 1.59 (s, 3H), 3.03 (m, 2H), 3.22 (s, 6H), 3.60 (m, 4H), 5.10 (br s, 2H), 6.61 (m, 1H), 6.68 (m, 1H), 7.05 (m, 2H), 7.18 (m, 1H), 7.28 (m, 1H), 7.32 (m, 2H), 8.05 (br s, 1H), 8.12 (m, 1H), 8.62 (br s, 1H).

N-(2-Acetylbenzyl)-N-(2-oxo-2-((2'-oxo-1,1',2',3-tetrahydrospiro[indene-2,3'-pyrrolo[2,3-b]pyridin]-5-yl)amino)ethyl)pivalamide Intermediate I

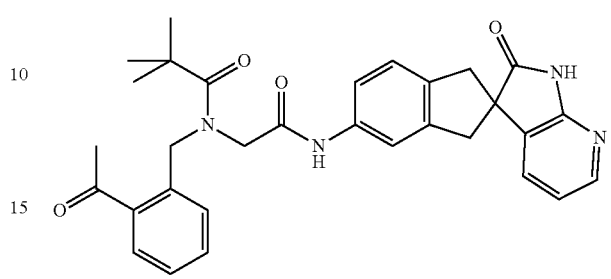

Compound 8.7 (247 mg, 0.43 mmol) was dissolved in acetone (15 ml) then p-toluene sulfonic acid monohydrate (89 mg, 0.47 mmol) was added. The mixture was stirred at RT for 4 h. Extra p-toluene sulfonic acid monohydrate (33 mg, 0.17 mmol) was added. No change after 1 h. The mixture was poured into saturated sodium bicarbonate. The aqueous layer was extracted three times with ethyl acetate. The combined organic extracts were washed with brine, dried over sodium sulfate, filtered and the filtrate evaporated to provide compound Intermediate I (89 mg, 39%) as a colourless solid. $^1$H NMR (CDCl$_3$, 300 MHz) δ 1.31 (s, 9H), 2.64 (s, 3H), 3.04 (dd, 2H), 3.63 (dd, 2H), 4.05 (s, 2H), 5.23 (s, 2H), 6.82 (dd, 1H), 7.07 (dd, 1H), 7.25 (m, 3H), 7.42 (t, 1H), 7.54 (m, 2H), 7.89 (d, 1H), 8.11 (dd, 1H), 8.63 (br s, 1H). UPLC-MS rt 0.75 (524 [M+H]$^+$), 90% pure.

SCHEME 9

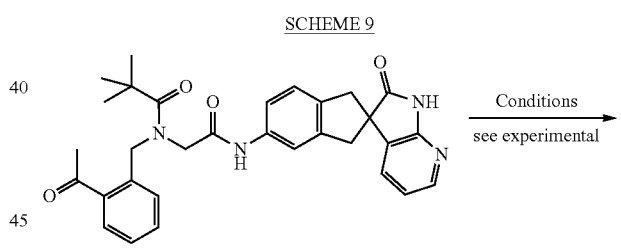

Intermediate I

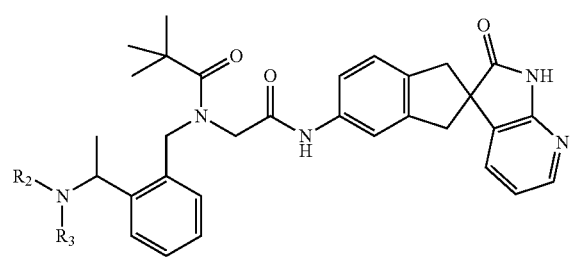

9A-D

Example 22: N-(2-(1-Aminoethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 9A

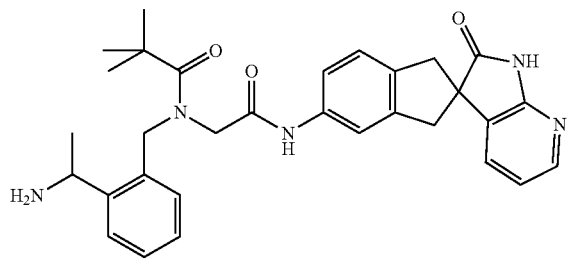

Intermediate I (83 mg, 0.17 mmol) was dissolved in methanol (3.5 ml) then ammonium acetate (131 mg, 1.7 mmol) and sodium cyanoborohydride (21 mg, 0.34 mmol) were added. The mixture was stirred at reflux for 18 h. Extra ammonium acetate (131 mg, 1.7 mmol) and sodium cyanoborohydride (21 mg, 0.34 mmol) were added and the mixture was stirred at 50° C. for 72 h. The mixture was poured into water and the aqueous layer was extracted with dichloromethane. The organic extract was evaporated and the residue purified via prep-HPLC (XBridge C18, ID 19 mm, length 150 mm, flow rate 20 ml/min: 40-60% MeCN in pH 10 [NH$_4$HCO$_3$ with NH$_4$OH] over 8 min) to provide compound 9B (15 mg, 17%) as a colourless solid. $^1$H NMR (CD$_3$OD, 300 MHz) δ 1.34 (m, 12H), 3.05 (dd, 2H), 3.49 (dd, 2H), 4.09 (br s, 2H), 4.29 (q, 1H), 4.96 (m, 2H), 6.86 (dt, 1H), 7.12 (m, 2H), 7.23 (m, 2H), 7.32 (t, 2H), 7.53 (m, 2H), 8.03 (d, 1H). UPLC-MS (long run) rt 1.86 (526 [M+H]$^+$), 99% pure.

Example 23: N-(2-(1-(Methylamino)ethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 9B

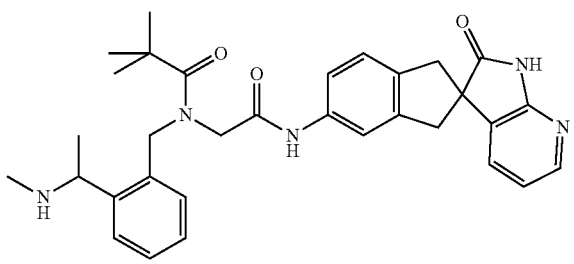 [SMILES: CNC(C)c1ccccc1CN(CC(=O)Nc1ccc2c(c1)CC1(C2)C(=O)Nc2ncccc21)C(=O)C(C)(C)C]

Intermediate I (42 mg, 0.08 mmol) was dissolved in methylamine in ethanol (2 ml, 33% solution, excess) then 4 Å molecular sieves were added. The mixture was stirred at RT for 22 h. UPLC-MS indicated 20% conversion so more methylamine in ethanol (0.5 ml, 33% solution) was added and stirred at RT for 24 h. UPLC-MS indicated 50% conversion so the reaction was decanted into saturated sodium bicarbonate and the aqueous layer was extracted three times with dichloromethane. The organic extract was dried over sodium sulfate, filtered and the filtrate evaporated. UPLC-MS (CSH) rt 0.46 (538 [M+H]$^+$). The crude residue was dissolved in methanol (2 ml) and sodium borohydride (5 mg, 0.132 mmol) was added under argon. After stirring for 1.5 h at RT, the mixture was poured into saturated sodium bicarbonate and the aqueous layer was extracted three times with dichloromethane. The organic extract was washed with brine dried over sodium sulfate, filtered and the filtrate evaporated. The residue was purified (2 g SiO$_2$ 0-10% MeOH in EtOAc then 10% MeOH in DCM followed by 500 mg SCX-2 MeOH to ammonia in MeOH) to provide compound 9A (6 mg, 14%) as a colourless solid. $^1$H NMR (CD$_3$OD, 300 MHz) δ 1.30 (m, 12H), 2.20 (s, 3H), 3.05 (dd, 2H), 3.50 (dd, 2H), 3.92 (q, 1H), 4.10 (br s, 2H), 4.98 (br d, 2H), 6.88 (dd, 1H), 7.20 (m, 6H), 7.50 (m, 2H), 8.03 (d, 1H). UPLC-MS (CSH) rt 0.47 (540 [M+H]$^+$), 96% pure.

Example 24: N-(2-(1-(Dimethylamino)ethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 9C

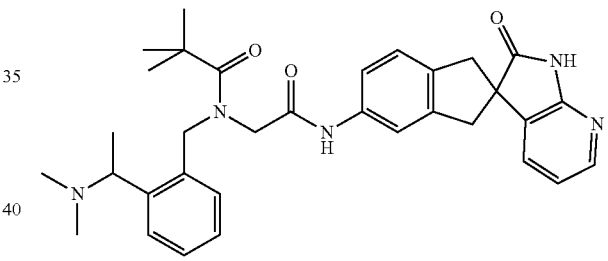

Intermediate I (43 mg, 0.082 mmol) was mixed with dimethylamine hydrochloride (20 mg, 0.246 mmol) and titanium isopropoxide (39 ml, 0.131 mmol). Initial mixing was not good so a small amount of dichloromethane was added (0.5 ml). The mixture was stirred at RT for 18 h. The volatiles were removed and methanol (0.75 ml) was added, followed by sodium borohydride (4 mg, 0.108 mmol) under argon. After stirring for 21 h at RT, the mixture was poured into saturated sodium bicarbonate and the aqueous layer was extracted three times with ethyl acetate. The organic extract was washed with brine dried over sodium sulfate, filtered and the filtrate evaporated. The residue was purified (2 g SiO$_2$ 0-10% MeOH in EtOAc, then 10% MeOH in DCM followed by 500 mg SCX-2 MeOH to ammonia in MeOH) to provide compound 9C (4 mg, 9%) as a colourless solid. $^1$H NMR (CDCl$_3$, 400 MHz) δ 1.28 (s, 9H), 1.32 (s, 3H), 2.17 (s, 6H), 3.03 (dd, 2H), 3.60 (m, 3H), 3.81 (br s, 1H), 4.36 (br s, 1H), 4.84 (br d, 1H), 5.46 (br s, 1H), 6.80 (dd, 1H), 7.07 (m, 2H), 7.19 (m, 2H), 7.27 (m, 1H), 7.40 (m, 1H), 7.56 (d, 1H), 8.11 (d, 1H), 8.69 (br s, 1H), 8.83 (br s, 1H). UPLC-MS (CSH) rt 0.81 (554 [M+H]$^+$), 100% pure.

Example 25: N-(2-(1-(Azetidin-1-yl)ethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 90

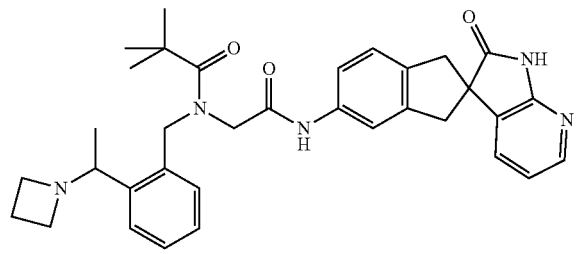 [SMILES: CC(c1ccccc1CN(CC(=O)Nc1ccc2c(c1)CC1(C2)C(=O)Nc2ncccc21)C(=O)C(C)(C)C)N1CCC1]

Intermediate I (43 mg, 0.082 mmol) was dissolved in dichloromethane (1.5 ml) then azetidine hydrochloride (23 mg, 0.246 mmol) was added followed by sodium triacetoxyborohydride (28 mg, 0.131 mmol) and sodium sulfate. The mixture was stirred at RT for 3 days. 2 drops of acetic acid were added then stirred at RT for 24 h. Extra sodium triacetoxyborohydride (28 mg, 0.131 mmol) was added and stirred at RT for 18 h. The mixture was poured into saturated sodium bicarbonate and the aqueous layer was extracted three times with dichloromethane. The organic extract was dried over sodium sulfate, filtered and the filtrate evaporated. The residue was purified (2 g $SiO_2$ 0-10% MeOH in EtOAc, then 10-15% MeOH in DCM then 15% ammonia and MeOH in DCM; followed by 500 mg SCX-2 MeOH to ammonia in MeOH) to provide compound 9D (15 mg, 32%) as a colourless solid.

$^1$H NMR ($CDCl_3$, 300 MHz) δ 1.17 (d, 3H), 1.34 (s, 9H), 2.02 (m, 2H), 3.04 (dd, 2H), 3.11 (m, 4H), 3.47 (m, 1H), 3.61 (m, 2H), 4.05 (br m, 2H), 5.08 (s, 2H), 6.81 (dd, 1H), 7.09 (t, 2H), 7.24 (m, 4H), 7.54 (m, 2H), 8.13 (d, 1H), 8.62 (br s, 1H), 9.56 (br s, 1H). UPLC-MS rt 0.77 (566 [M+H]$^+$), 98% pure.

Synthesis of Intermediate Acids A to M

Acid A

SCHEME 10

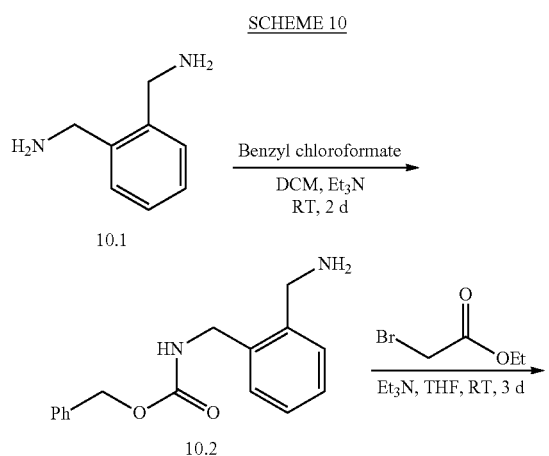

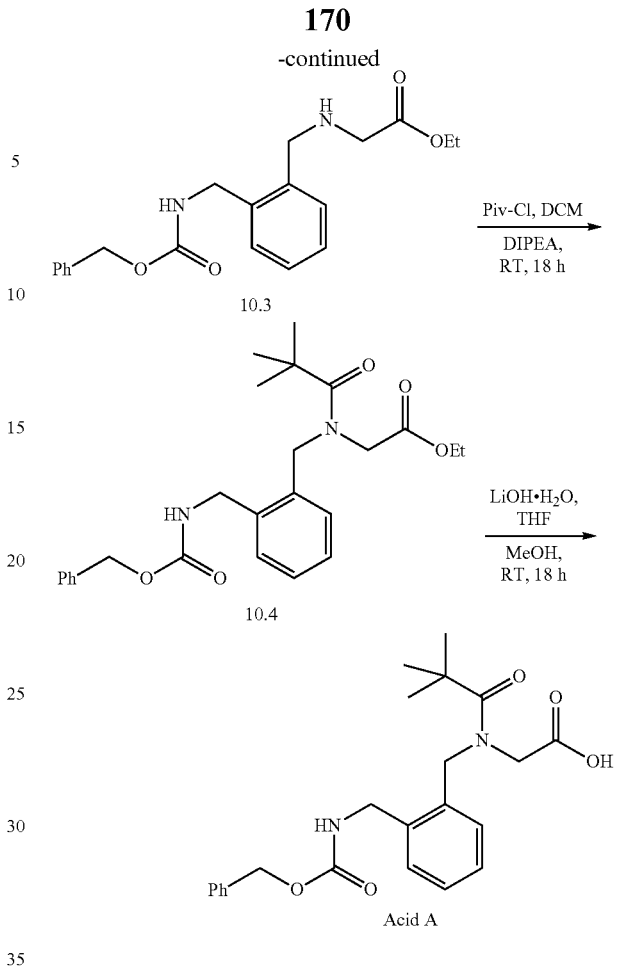

Benzyl 2-(aminomethyl)benzylcarbamate 10.2

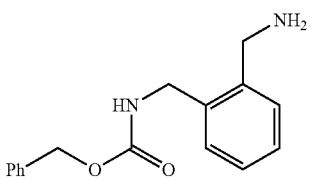 [SMILES: NCc1ccccc1CNC(=O)OCc1ccccc1]

o-Xylylenediamine 10.1 (1.04 g, 7.64 mmol) was dissolved in dry dichloromethane (50 ml) and triethylamine (1.0 ml, 7.2 mmol) was added. The solution was stirred at 5° C. (ice/water) then benzyl chloroformate (1.0 ml, 7.0 mmol) was added dropwise over 15 min as a solution in dry DCM (25 ml). The mixture was stirred at RT for 2 days. The volatiles were removed and the residue was partitioned between ethyl acetate and 2M sodium hydroxide. The organic layer was dried over magnesium sulfate, filtered and evaporated. The residue was purified via flash silica chromatography (0-10% MeOH in DCM, then 10% MeOH with ammonia in DCM) to provide compound 10.2 (0.706 g, 37%) as an orange oil. $^1$H NMR ($CDCl_3$, 300 MHz) δ 1.75 (br s, 2H), 3.93 (s, 2H), 4.42 (d, 2H), 5.09 (s, 2H), 6.88 (br s, 1H), 7.33 (m, 9H).

Ethyl 2-((2-((((benzyloxy)carbonyl)amino)methyl)benzyl)amino)acetate 10.3

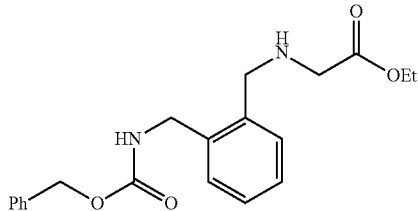 [SMILES: CCOC(=O)CNCc1ccccc1CNC(=O)OCc1ccccc1]

Compound 10.2 (353 mg, 1.31 mmol) was dissolved in dry tetrahydrofuran (3 ml) and triethylamine (0.36 ml, 2.6 mmol) was added. Ethyl bromoacetate (0.14 ml, 1.3 mmol) was added dropwise. The mixture was stirred at RT for 3 days. The reaction mixture was poured into water and extracted three times with ethyl acetate. The organic layer was washed with brine, dried over magnesium sulfate, filtered and evaporated. The residue was purified via flash silica chromatography (0-10% MeOH in DCM, then 10% MeOH with ammonia in DCM) to provide compound 10.3 (436 mg, 94%) as an orange oil. $^1$H NMR (CDCl$_3$, 300 MHz) δ 1.23 (t, 3H), 3.40 (s, 2H), 3.81 (s, 2H), 4.16 (q, 2H), 4.43 (d, 2H), 5.09 (s, 2H), 6.81 (m, 1H), 7.33 (m, 9H).

Ethyl 2-(N-(2-((((benzyloxy)carbonyl)amino)methyl)benzyl)pivalamido)acetate 10.4

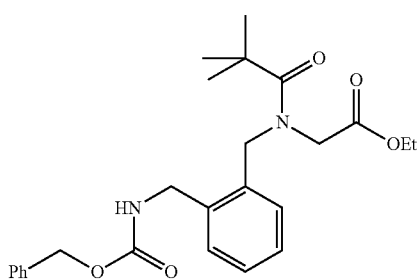 [SMILES: CCOC(=O)CN(Cc1ccccc1CNC(=O)OCc1ccccc1)C(=O)C(C)(C)C]

Compound 10.3 (436 mg, 1.22 mmol) was dissolved in dichloromethane (5 ml) under an argon atmosphere then N,N-diisopropylethylamine (0.64 ml, 3.7 mmol) was added. Trimethylacetyl chloride (0.18 ml, 1.46 mmol) was added dropwise then the mixture was stirred at RT for 18 h. The mixture was poured into water and the aqueous layer was extracted three times with dichloromethane. The combined organic extracts were washed with 20% aqueous citric acid, water, brine, dried over magnesium sulfate, filtered and the filtrate evaporated to provide compound 10.4 (588 mg, quant.) as a yellow oil. $^1$H NMR (CDCl$_3$, 300 MHz) δ 1.22 (t, 3H), 1.26 (s, 9H), 3.95 (br s, 2H), 4.16 (q, 2H), 4.35 (br d, 2H), 4.84 (br s, 2H), 5.12 (s, 2H), 7.12 (m, 1H), 7.28 (m, 9H).

2-(N-(2-((((Benzyloxy)carbonyl)amino)methyl)benzyl)pivalamido)acetic Acid Acid A

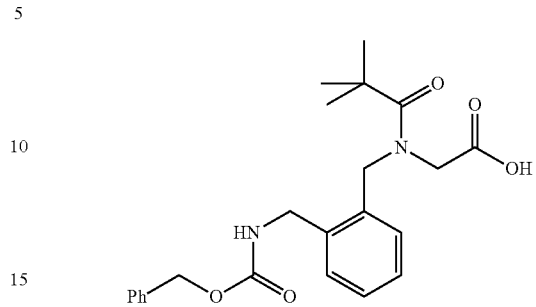

Compound 10.4 (285 mg, 0.65 mmol) was dissolved in 1:1 methanol/tetrahydrofuran (2 ml) then lithium hydroxide monohydrate (95 mg, 2.30 mmol) was added. The mixture was stirred at RT for 18 h. The volatiles were removed then the residue was dissolved in water and washed twice with ethyl acetate. The aqueous layer was acidified to pH 2 with 2M HCl then extracted twice with ethyl acetate. The organic extract was washed with brine, dried over magnesium sulfate, filtered, the filtrate evaporated then azeotroped twice with toluene to provide compound Acid A (199 mg, 75%) as an off-white solid. $^1$H NMR (CD$_3$OD, 300 MHz) δ 1.25 (br s, 9H), 3.88 (br s, 2H), 4.28 (br s, 2H), 4.89 (br s, 2H), 5.08 (s, 2H), 7.12 (m, 1H), 7.28 (m, 9H). UPLC-MS (short basic) rt 0.56 (413 [M+H]$^+$), 94% pure.

Acid B and Intermediate J

SCHEME 11

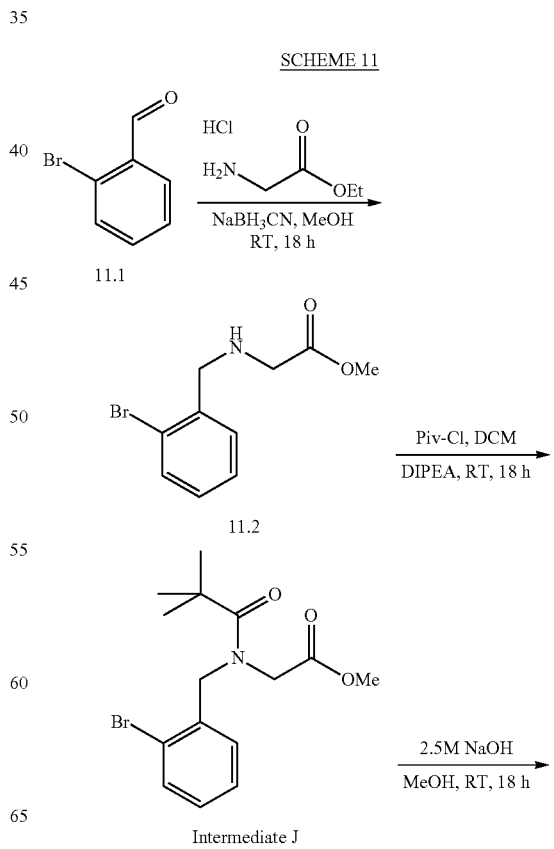

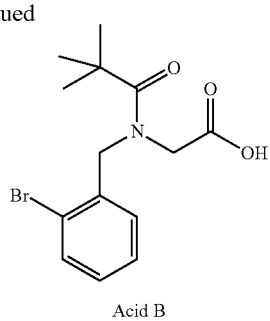

Acid B

Methyl 2-((2-bromobenzyl)amino)acetate 11.2

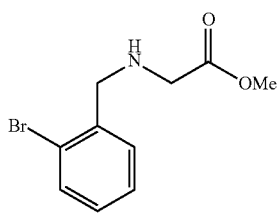 [SMILES: COC(=O)CNCc1ccccc1Br]

2-Bromobenzaldehyde 11.1 (16.8 g, 90.8 mmol) was dissolved in methanol (260 ml) and then methyl glycinate hydrochloride (34 g, 272.4 mmol) and sodium cyanoborohydride (8.6 g, 136.2 mmol) were added and the mixture was stirred at RT for 18 h. The reaction mixture was poured into aqueous sodium bicarbonate and extracted twice with dichloromethane. The organic extract was extracted three times with 2M HCl. The aqueous was basified with sodium carbonate then extracted three times with dichloromethane. This organic extract was dried over magnesium sulfate, filtered and evaporated to provide compound 11.2 (9.5 g, 41%) as an orange oil. $^1$H NMR (CDCl$_3$, 400 MHz) δ 3.44 (s, 2H), 3.71 (s, 3H), 3.89 (s, 2H), 7.12 (td, 1H), 7.28 (td, 1H), 7.38 (dd, 1H), 7.53 (dd, 1H). UPLC-MS (short basic) rt 0.73 (258, 260 [M+H]$^+$), 97% pure.

Methyl 2-(N-(2-bromobenzyl)pivalamido)acetate Intermediate J

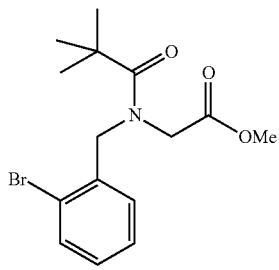 [SMILES: COC(=O)CN(Cc1ccccc1Br)C(=O)C(C)(C)C]

Compound 11.2 (9.5 g, 36.8 mmol) was dissolved in dichloromethane (200 ml) under an argon atmosphere then N,N-diisopropylethylamine (22.5 ml, 128.8 mmol) was added and the mixture stirred at 5° C. (ice/water). Trimethylacetyl chloride (4.6 ml, 36.8 mmol) was added dropwise then the mixture was stirred at RT for 18 h. The mixture was washed with 20% aqueous citric acid, saturated sodium bicarbonate, brine, dried over magnesium sulfate, filtered and the filtrate evaporated. The residue was purified via flash silica chromatography (9:1 to 1:1 heptane/EtOAc) to provide compound Intermediate J (11.8 g, 94%) as a yellow gum. $^1$H NMR (CDCl$_3$, 300 MHz) δ 1.28 (s, 9H), 3.73 (s, 3H), 3.95 (br s, 2H), 4.82 (s, 2H), 7.16 (m, 2H), 7.32 (t, 1H), 7.56 (d, 1H). UPLC-MS (short basic) rt 0.87 (342, 344 [M+H]$^+$), 99% pure.

2-(N-(2-Bromobenzyl)pivalamido)acetic Acid Acid B

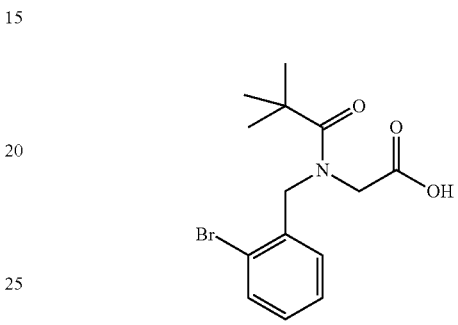

Compound Intermediate J (8.0 g, 23.38 mmol) was dissolved in methanol (60 ml) then 2.5M sodium hydroxide (12 ml, 30.0 mmol) was added and the mixture stirred at RT for 18 h. The mixture was diluted with water and dichloromethane. The aqueous was washed with dichloromethane then acidified to pH 4 with 20% aqueous citric acid. The aqueous layer was extracted three times with dichloromethane. This organic extract was dried over magnesium sulfate, filtered and the filtrate evaporated to provide compound Acid B (6.8 g, 89%) as an off-white solid. $^1$H NMR (CDCl$_3$, 300 MHz) δ 1.29 (s, 9H), 3.98 (br s, 2H), 4.83 (s, 2H), 7.16 (m, 2H), 7.33 (t, 1H), 7.57 (d, 1H). UPLC-MS (short basic) rt 0.51 (328, 330 [M+H]$^+$), 99% pure.

Acid C

SCHEME 12

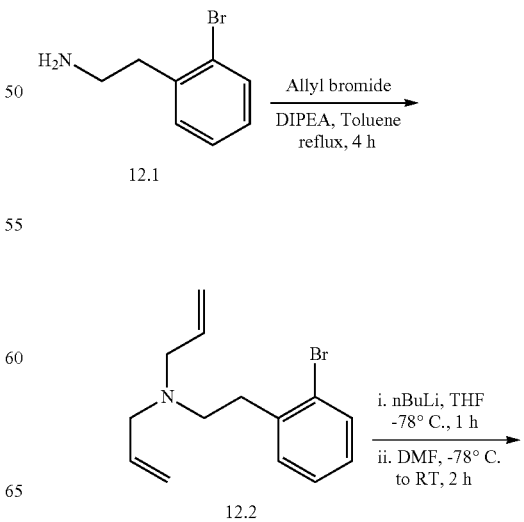

-continued

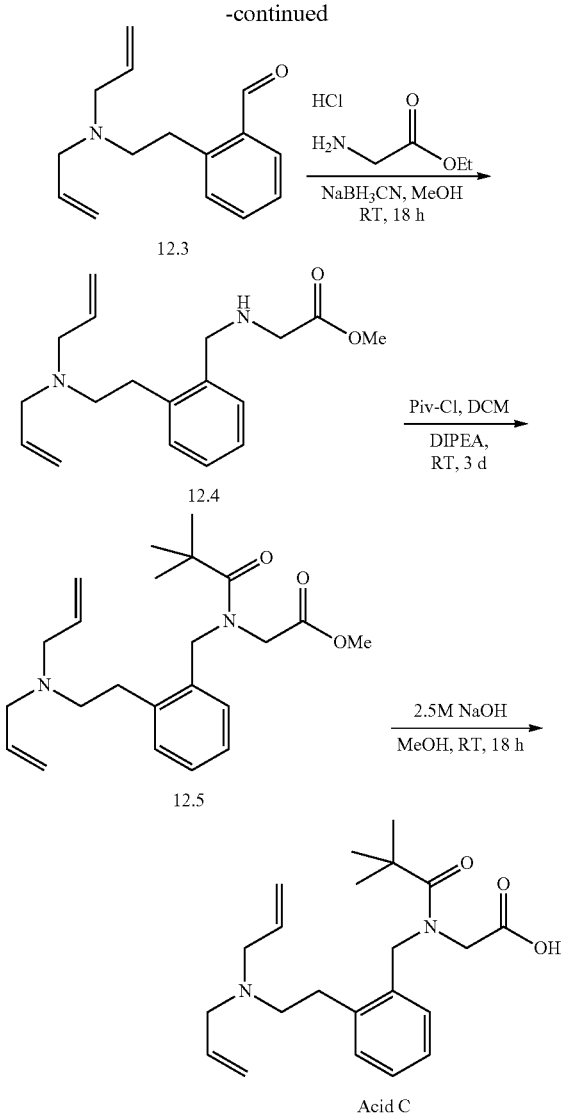

Acid C

N-Allyl-N-(2-bromophenethyl)prop-2-en-1-amine 12.2

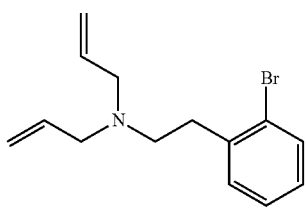 [SMILES: C=CCN(CC=C)CCc1ccccc1Br]

2-Bromophenethylamine 12.1 (2.63 g, 13.1 mmol) was dissolved in dry toluene (50 ml) and N,N-diisopropylethylamine (5.4 ml, 31.0 mmol) was added. Allyl bromide (10.8 ml, 125.0 mmol) was added dropwise then the mixture was stirred at reflux for 4 h then allowed to cool to RT for 18 h. The reaction mixture was filtered washing with toluene. The residue was partitioned between dichloromethane and water then the aqueous extracted twice with dichloromethane. The organic extracts were dried over magnesium sulfate, filtered and evaporated. The residue was purified via flash silica chromatography (9:1 to 7:3 heptane/EtOAc) to provide compound 12.2 (0.466 g, 13%) as a yellow oil. $^1$H NMR (CDCl$_3$, 300 MHz) δ 2.67 (m, 2H), 2.93 (m, 2H), 3.20 (m, 4H), 5.19 (m, 4H), 5.90 (m, 2H), 7.05 (m, 1H), 7.21 (m, 2H), 7.50 (d, 1H). UPLC-MS (short basic) rt 1.05 (280, 282 [M+H]$^+$), 98% pure.

2-(2-(Diallylamino)ethyl)benzaldehyde 12.3

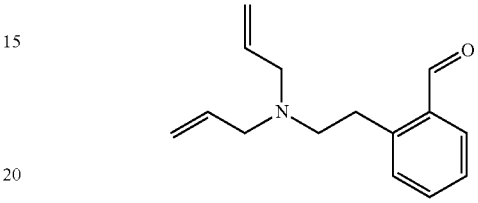

Compound 12.2 (157 mg, 0.56 mmol) was dissolved in dry tetrahydrofuran (2 ml) and cooled to −78° C. (dry ice, acetone). nButyllithium (2.5M in hexanes, 0.34 ml, 0.85 mmol) was added dropwise then the mixture was stirred at −78° C. for 1 h. Dry N,N-dimethylformamide (0.1 ml, 1.29 mmol) was added then stirring continued at −78° C. for 1 h before allowing to RT for 1 h. The reaction mixture was quenched with water then allowed to stir at RT for 18 h. The mixture was poured into water and extracted three times with ethyl acetate. The organic extracts were washed with brine, dried over magnesium sulfate, filtered and evaporated to provide compound 12.3 (116 mg, 90%) as an orange oil. $^1$H NMR (CDCl$_3$, 300 MHz) δ 3.00 (br m, 8H), 5.19 (m, 4H), 5.88 (m, 2H), 7.17 (t, 1H), 7.36 (t, 1H), 7.50 (dt, 1H), 7.82 (dd, 1H), 10.22 (s, 1H). UPLC-MS (short basic) rt 0.88 (230 [M+H]$^+$), 82% pure.

Methyl 2-((2-(2-(diallylamino)ethyl)benzyl)amino)acetate 12.4

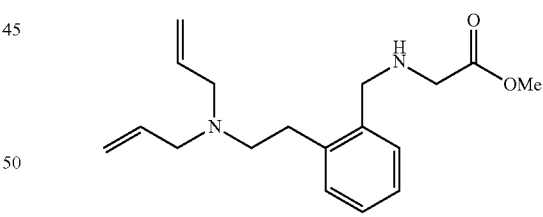

Compound 12.3 (116 mg, 0.516 mmol) was dissolved in methanol (2 ml) and then methyl glycinate hydrochloride (191 mg, 1.52 mmol) and sodium cyanoborohydride (55 mg, 0.88 mmol) were added and the mixture was stirred at RT for 18 h. The reaction mixture was poured into water and the pH adjusted to 4 with 2M HCl then washed twice with dichloromethane. The aqueous was basified with sodium carbonate then extracted twice with dichloromethane. This organic extract was dried over magnesium sulfate, filtered and evaporated to provide compound 12.4 (53 mg, 35%) as a colourless oil. $^1$H NMR (CDCl$_3$, 300 MHz) δ 2.73 (m, 4H), 3.18 (d, 4H), 3.44 (s, 2H), 3.74 (s, 3H), 3.79 (s, 2H), 5.18 (m, 4H), 5.88 (m, 2H), 7.21 (m, 4H). UPLC-MS (short basic) rt 0.84 (303 [M+H]$^+$), 80% pure.

Methyl 2-(N-(2-(2-(diallylamino)ethyl)benzyl)pivalamido)acetate 12.5

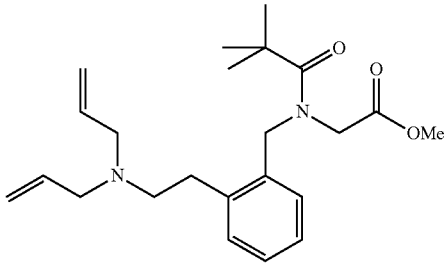 [SMILES: C=CCN(CC=C)CCc1ccccc1CN(CC(=O)OC)C(=O)C(C)(C)C]

Compound 12.4 (54 mg, 0.18 mmol) was dissolved in dichloromethane (1 ml) under an argon atmosphere then N,N-diisopropylethylamine (93 µl, 0.53 mmol) was added. Trimethylacetyl chloride (26 µl, 0.21 mmol) was added dropwise then the mixture was stirred at RT for 4 days. The mixture was poured into saturated sodium bicarbonate then extracted three times with dichloromethane. The organic extracts were evaporated to provide compound 12.5 (68 mg, 99%) as a colourless oil. UPLC-MS (short basic) rt 0.96 (387 [M+H]$^+$), 89% pure.

2-(N-(2-(2-(Diallylamino)ethyl)benzyl)pivalamido)acetic Acid Acid C

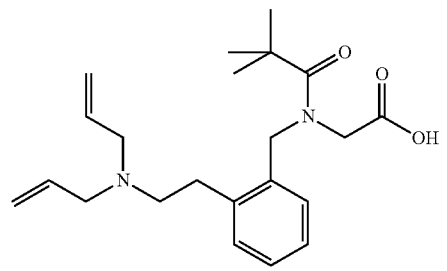 [SMILES: C=CCN(CC=C)CCc1ccccc1CN(CC(=O)O)C(=O)C(C)(C)C]

Compound 12.5 (68 mg, 0.176 mmol) was dissolved in methanol (1 ml) then 2.5M sodium hydroxide (0.22 ml, 0.55 mmol) was added and the mixture stirred at RT for 18 h. The volatiles were removed, the material diluted with water, and the pH adjusted to 5 with 2M HCl. This was then concentrated to dryness to provide compound Acid C (assume 0.176 mmol) as a glass. Used directly.

Acid D

SCHEME 13

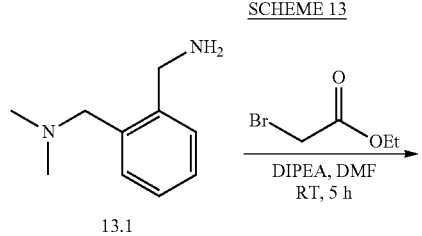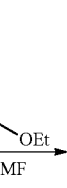

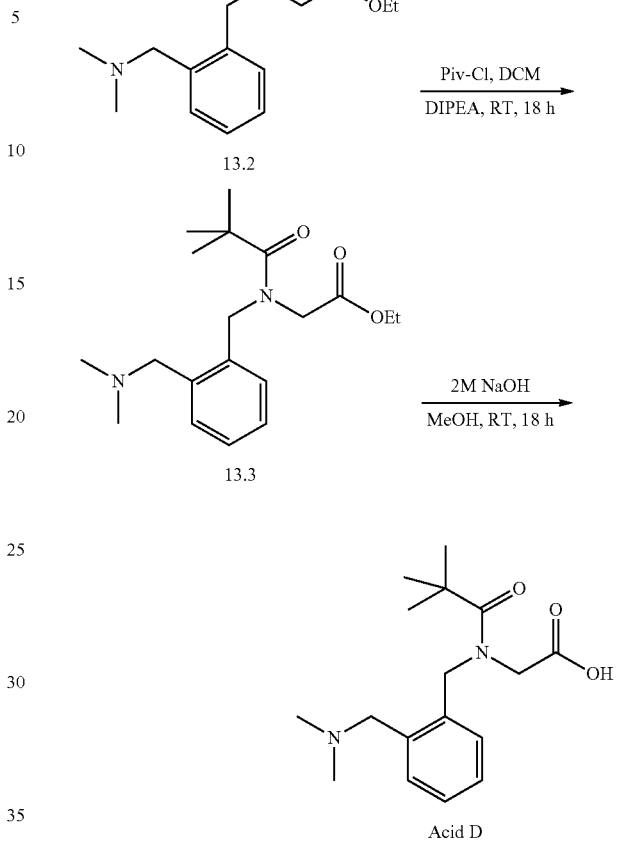

Acid D

Ethyl 2-((2-((dimethylamino)methyl)benzyl)amino)acetate 13.2

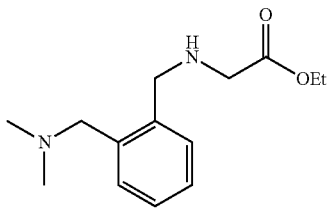 [SMILES: CCOC(=O)CNCc1ccccc1CN(C)C]

1-(2-Aminomethyl)phenyl-N,N-dimethylmethanamine dihydrochloride 13.1 (250 mg, 1.52 mmol) was dissolved in dry N,N-dimethylformamide (5 ml) and N,N-diisopropylethylamine (1.18 g, 9.13 mmol) was added. Ethyl bromoacetate (288 mg, 1.37 mmol) was added dropwise. The mixture was stirred at RT for 5 h. The reaction mixture was poured into water and extracted three times with ethyl acetate. The organic layer was washed twice with ammonium chloride, dried over sodium sulfate, filtered and evaporated to provide compound 13.2 (110 mg, 29%) as an orange oil. HPLC-MS (long basic) rt 1.66 (251 [M+H]$^+$). Used directly.

Ethyl 2-(N-(2-((dimethylamino)methyl)benzyl)pivalamido)acetate 13.3

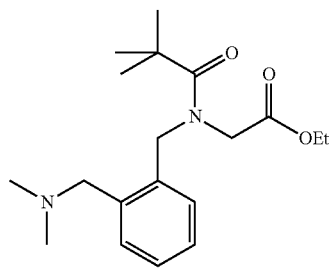 [SMILES: CCOC(=O)CN(Cc1ccccc1CN(C)C)C(=O)C(C)(C)C]

Compound 13.2 (110 mg, 0.439 mmol) was dissolved in dichloromethane (3 ml) under an argon atmosphere then N,N-diisopropylethylamine (113 mg, 0.87 mmol) was added. Trimethylacetyl chloride (79.5 mg, 0.669 mmol) was added dropwise then the mixture was stirred at RT for 3 days. The mixture was poured into saturated ammonium chloride then extracted three times with dichloromethane. The organic extracts were dried over sodium sulfate evaporated, filtered and the filtrate evaporated. The residue was purified via reverse phase chromatography (30 g C18 cartridge acetonitrile/pH 10 buffer with ammonium bicarbonate) to provide compound 13.3 (50 mg, 34%) as a colourless oil. UPLC-MS (short basic) rt 0.93 (335 [M+H]$^+$).

2-(N-(2-((Dimethylamino)methyl)benzyl)pivalamido)acetic Acid Acid D

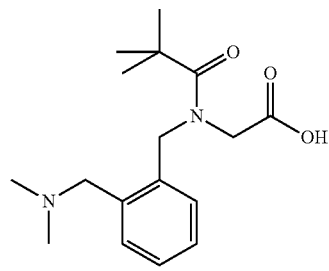 [SMILES: CN(C)Cc1ccccc1CN(CC(=O)O)C(=O)C(C)(C)C]

Compound 13.3 (50 mg, 0.149 mmol) was dissolved in methanol (4 ml) then 2M sodium hydroxide (0.22 ml, 0.45 mmol) was added and the mixture stirred at RT for 18 h. The reaction was quenched to pH 5 with 2M HCl then concentrated to dryness. This was purified via reverse phase chromatography (30 g C18 cartridge acetonitrile/pH 10 buffer with ammonium bicarbonate) to provide compound Acid D (40 mg, 88%) as a glass. UPLC-MS (short basic) rt 0.49 (307 [M+H]$^+$), 94% pure.

Acid E

SCHEME 14

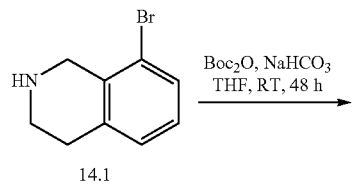

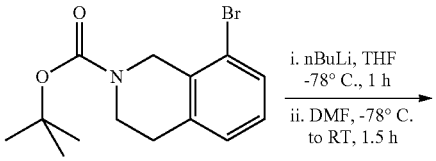

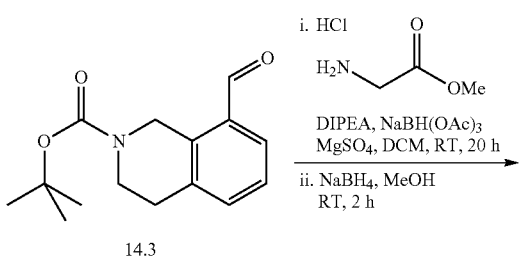

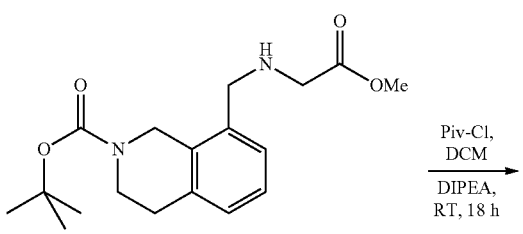

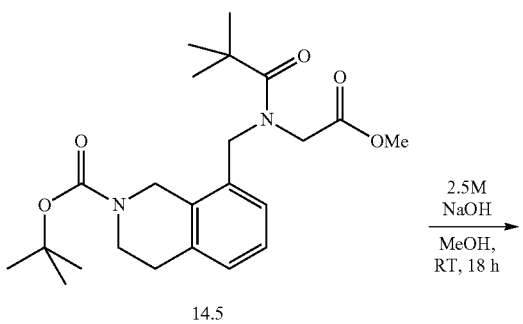

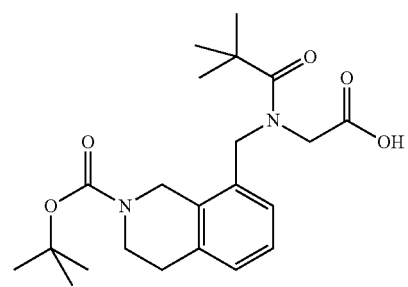

Acid E tert-Butyl 8-bromo-3,4-dihydroisoquinoline-2(1H)-carboxylate 14.2

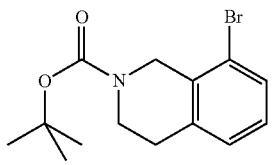 [SMILES: CC(C)(C)OC(=O)N1CCc2cccc(Br)c2C1]

8-Bromo-1,2,3,4-tetrahydroisoquinoline 14.1 (200 mg, 0.804 mmol) was suspended in tetrahydrofuran (4 ml) and saturated sodium bicarbonate (2 ml) then di-t-butyl dicarbonate (263 mg, 1.21 mmol) was added as a solution in THF (2 ml) and the mixture was stirred at RT for 42 h. The reaction mixture was poured into water and extracted three times with ethyl acetate. The organic extract was dried over sodium sulfate, filtered and evaporated. The residue was purified via flash silica chromatography (heptane/DCM 0-80%) to provide compound 14.2 (200 mg, 80%) as a colourless oil. $^1$H NMR (CDCl$_3$, 400 MHz) δ 1.30 (s, 9H), 2.82 (m, 2H), 3.63 (m, 2H), 4.60 (m, 2H), 7.05 (m, 2H), 7.39 (d, 1H). UPLC-MS (short basic) rt 1.01 (255, 257 [M−tBu+H]$^+$), 96% pure.

tert-Butyl 8-formyl-3,4-dihydroisoquinoline-2(1H)-carboxylate 14.3

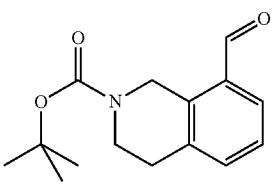 [SMILES: CC(C)(C)OC(=O)N1CCc2cccc(C=O)c2C1]

Compound 14.2 (200 mg, 0.64 mmol) was dissolved in dry tetrahydrofuran (10 ml) and cooled to −78° C. (dry ice, acetone). nButyllithium (2.4M in hexanes, 0.40 ml, 0.96 mmol) was added dropwise then the mixture was stirred at −78° C. for 1 h. Dry N,N-dimethylformamide (0.1 ml, 1.29 mmol) was added then stirring continued at −78° C. for 30 min before allowing to RT for 1 h. The reaction mixture was quenched with water then extracted three times with ethyl acetate. The organic extract was dried over sodium sulfate, filtered and evaporated. The residue was purified via flash silica chromatography (DCM/EtOAc 5%) to provide compound 14.3 (80 mg, 45%) as a colourless oil. $^1$H NMR (CDCl$_3$, 400 MHz) δ 1.35 (s, 9H), 2.90 (m, 2H), 3.65 (m, 2H), 5.02 (s, 2H), 7.36 (m, 2H), 7.67 (t, 1H), 10.13 (s, 1H). UPLC-MS (short basic) rt 0.85 (262 [M+H]$^+$), 95% pure.

tert-Butyl 8-(((2-methoxy-2-oxoethyl)amino)methyl)-3,4-dihydroisoquinoline-2(1H)-carboxylate 14.4

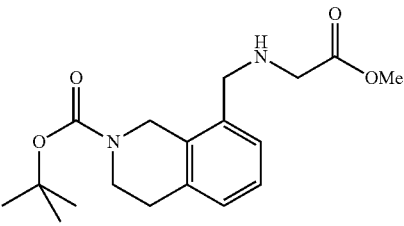 [SMILES: COC(=O)CNCc1cccc2c1CN(C(=O)OC(C)(C)C)CC2]

Compound 14.3 (80 mg, 0.306 mmol) was dissolved in dichloromethane (5 ml) then N,N-diisopropylethylamine (0.20 ml, 1.22 mmol) and glycine methyl ester hydrochloride (115 mg, 0.918 mmol) were added followed by magnesium sulfate. The mixture was stirred at RT for 4 h. Sodium triacetoxyborohydride (97 mg, 0.46 mmol) was added and stirring continued at RT for 72 h. The reaction mixture was poured into saturated sodium bicarbonate then extracted with dichloromethane. The organic extract was dried over sodium sulfate, filtered and evaporated. UPLC-MS indicated a 1:1 mixture of imine and amine. Repeating conditions with sodium triacetoxyborohydride in dichloromethane did not improve the ratio. The residue was dissolved in methanol (10 ml) cooled on ice/water then sodium borohydride (7 mg, 0.18 mmol) was added and the mixture and stirred at RT for 1.5 h. The mixture was diluted with ethyl acetate and washed with saturated sodium bicarbonate. The aqueous was extracted with ethyl acetate then the organic extracts were washed with water, dried over sodium sulfate, filtered and evaporated to provide compound 14.4 (150 mg, quant.) as a yellow oil. Used directly. UPLC-MS (short basic) rt 0.83 (335 [M+H]$^+$).

tert-Butyl 8-((N-(2-methoxy-2-oxoethyl)pivalamido)methyl)-3,4-dihydroisoquinoline-2(1H)-carboxylate 14.5

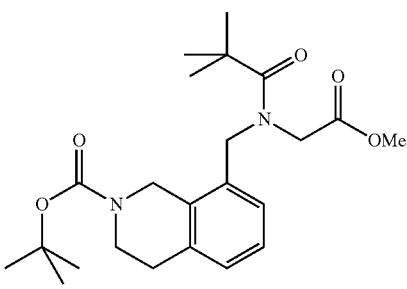 [SMILES: COC(=O)CN(Cc1cccc2c1CN(C(=O)OC(C)(C)C)CC2)C(=O)C(C)(C)C]

Compound 14.4 (148 mg, ~0.407 mmol) was dissolved in dichloromethane (3 ml) under an argon atmosphere then N,N-diisopropylethylamine (140 μl, 0.80 mmol) was added. Trimethylacetyl chloride (50 μl, 0.40 mmol) was added dropwise then the mixture was stirred at RT for 3 h. UPLC-MS indicated amine consumed. The mixture was poured into saturated sodium bicarbonate then extracted three times with dichloromethane. The organic extracts were dried over sodium sulfate, filtered and the filtrate evaporated. The residue was purified via flash silica SPE (5 g SiO$_2$ SPE, 15% EtOAc in DCM) to provide compound 14.5 (35 mg, 20%) as a colourless gum. UPLC-MS (short basic) rt 0.93 (419 [M+H]⁺), 80% pure.

2-(N-((2-(tert-Butoxycarbonyl)-1,2,3,4-tetrahydroisoquinolin-8-yl)methyl)pivalamido)-acetic acid Acid E

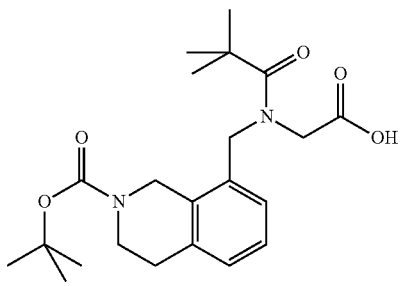 [SMILES: CC(C)(C)OC(=O)N1CCc2cccc(CN(CC(=O)O)C(=O)C(C)(C)C)c2C1]

Compound 14.5 (35 mg, 0.084 mmol) was dissolved in methanol (3 ml) then 2.5M sodium hydroxide (50 μl, 0.125 mmol) was added and the mixture stirred at RT for 18 h. UPLC-MS indicated incomplete hydrolysis so extra 2.5M sodium hydroxide (50 μl, 0.125 mmol) was added and the mixture stirred at RT for 72 h. The reaction was diluted with ethyl acetate and washed with saturated ammonium chloride. The aqueous was extracted twice with ethyl acetate. The organic extracts were dried over sodium sulfate, filtered and the filtrate evaporated to provide compound Acid E (~0.084 mmol) as a glass, which was used directly. UPLC-MS (short basic) rt 0.59 (405 [M+H]⁺).

Acid F

SCHEME 15

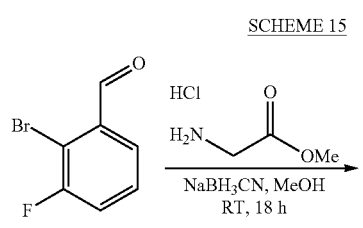

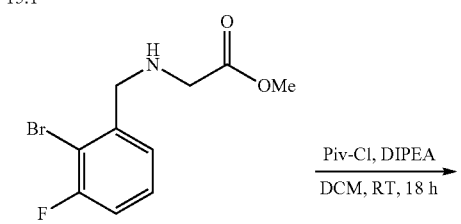

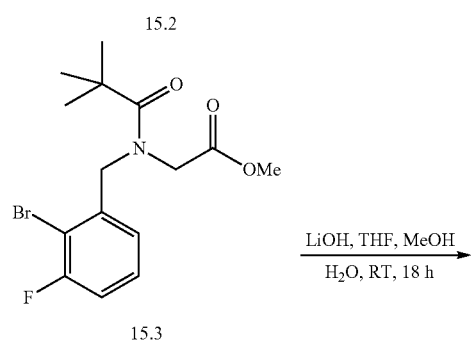

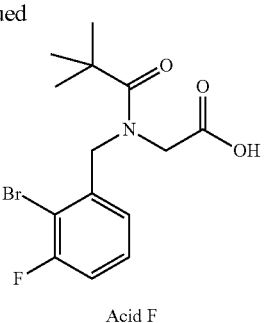

Acid F

Methyl 2-((2-bromo-3-fluorobenzyl)amino)acetate 15.2

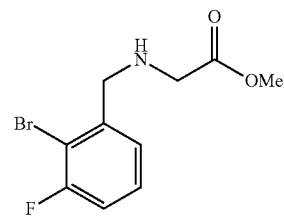 [SMILES: COC(=O)CNCc1cccc(F)c1Br]

2-Bromo-3-fluorobenzaldehyde 15.1 (1.05 g, 5.07 mmol) was dissolved in methanol (14 ml) and then methyl glycinate hydrochloride (1.88 g, 15.0 mmol) and sodium cyanoborohydride (0.50 g, 7.96 mmol) were added and the mixture was stirred at RT for 18 h. The reaction mixture was poured into water then pH adjusted to 4 with 2M HCl. This was washed with dichloromethane. The aqueous was adjusted to pH 8 with sodium carbonate then extracted three times with dichloromethane. This organic extract was dried over magnesium sulfate, filtered and evaporated to provide compound 15.2 (330 mg, 23%) as a yellow oil. ¹H NMR (CDCl₃, 300 MHz) δ 3.45 (s, 2H), 3.73 (s, 3H), 3.93 (s, 2H), 7.17 (m, 3H). UPLC-MS (short basic) rt 0.74 (276, 278 [M+H]⁺), 95% pure.

Methyl 2-(N-(2-bromo-3-fluorobenzyl)pivalamido)acetate 15.3

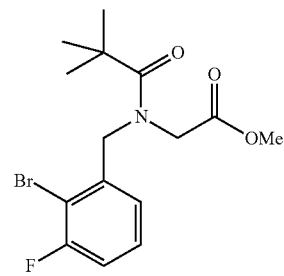 [SMILES: COC(=O)CN(Cc1cccc(F)c1Br)C(=O)C(C)(C)C]

Compound 15.2 (330 mg, 1.20 mmol) was dissolved in dichloromethane (3 ml) under an argon atmosphere then N,N-diisopropylethylamine (0.62 ml, 3.5 mmol) was added. Trimethylacetyl chloride (0.18 ml, 1.5 mmol) was added dropwise then the mixture was stirred at RT for 18 h. The mixture was poured into saturated sodium bicarbonate then extracted three times with ethyl acetate. The organic extracts were washed with water, 20% aqueous citric acid, brine, dried over magnesium sulfate, filtered and the filtrate evaporated. The residue was purified via flash silica chromatography (1:1 EtOAc/heptane) to provide compound 15.3 (310 mg, 72%) as a colourless solid. $^1$H NMR (CD$_3$OD, 300 MHz) δ 1.25 (s, 9H), 3.72 (s, 3H), 3.93 (br s, 2H), 4.80 (br s, 2H), 7.06 (m, 1H), 7.14 (t, 1H), 7.39 (m, 1H). UPLC-MS (short basic) rt 0.88 (360, 362 [M+H]$^+$), 90% pure.

2-(N-(2-Bromo-3-fluorobenzyl)pivalamido)acetic Acid Acid F

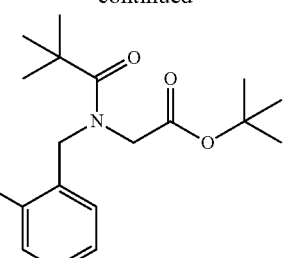

Compound 15.3 (310 mg, 0.86 mmol) was dissolved in THF (2 ml), methanol (2 ml) and water (2 ml) then lithium hydroxide monohydrate (109 mg, 2.59 mmol) was added and the mixture stirred at RT for 18 h. The volatiles were removed and the residue purified via flash silica chromatography (10-20% methanol in dichloromethane) to provide the crude product Acid F (238 mg, 80%) which was used directly. UPLC-MS (short basic) rt 0.52 (344 [M−H]−), 90% pure.

Acid G

SCHEME 16

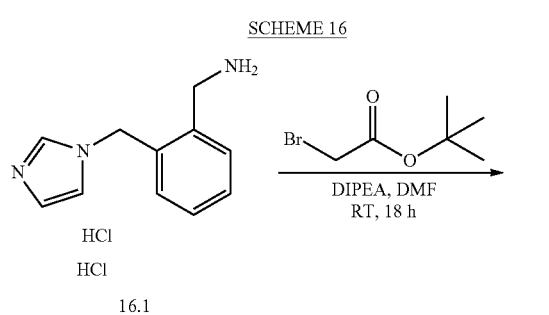

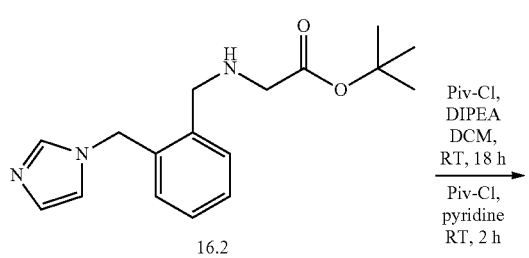

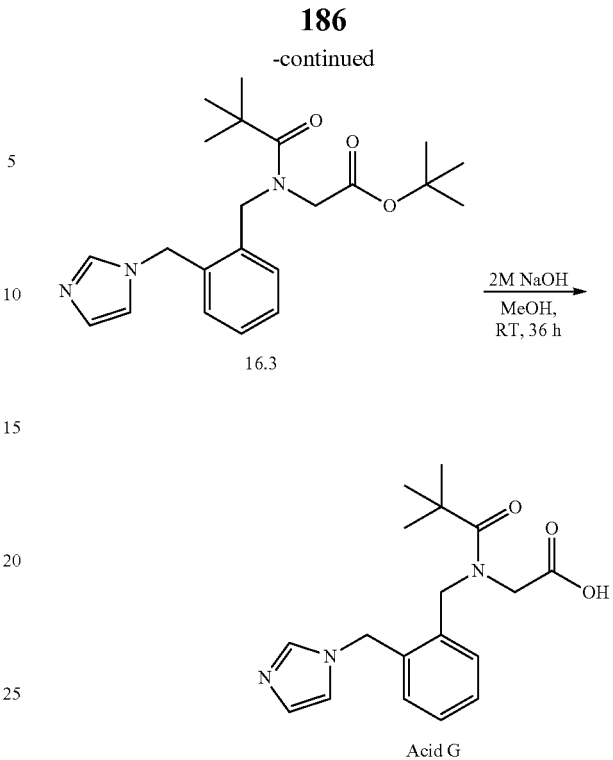

tert-Butyl 2-((2-((1H-imidazol-1-yl)methyl)benzyl)amino)acetate 16.2

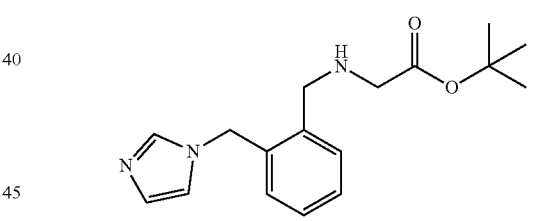

(2-((1H-Imidazol-1-yl)methyl)phenyl)methanamine dihydrochloride 16.1 (200 mg, 0.76 mmol) and N,N-diisopropylethylamine (596 mg, 4.61 mmol) were dissolved in dry N,N-dimethylformamide (5 ml). A solution of tert-butyl bromoacetate (135 mg, 0.69 mmol) in N,N-dimethylformamide (1 ml) was added slowly. The mixture was stirred at RT for 18 h. The reaction mixture was combined with another batch of material (0.192 mmol), quenched with saturated aqueous ammonium chloride solution and extracted three times with ethyl acetate. The organic extracts were dried over sodium sulfate, filtered and evaporated to provide compound 16.2 (100 mg, 22%) as a pale yellow solid. UPLC-MS (short basic) rt 0.58 (302 [M+H]$^+$). Used directly.

tert-Butyl 2-(N-(2-(((1H-imidazol-1-yl)methyl)benzyl)pivalamido)acetate 16.3

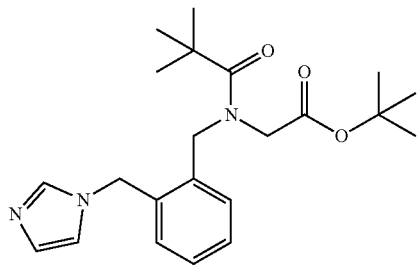 [SMILES: CC(C)(C)OC(=O)CN(Cc1ccccc1Cn1ccnc1)C(=O)C(C)(C)C]

Compound 16.2 (50 mg, 0.166 mmol) was dissolved in dichloromethane (3 ml) under an argon atmosphere then N,N-diisopropylethylamine (43 mg, 0.332 mmol) was added. Trimethylacetyl chloride (30 mg, 0.249 mmol) was added then the mixture was stirred at RT overnight. Further trimethylacetyl chloride (20 mg, 0.166 mmol) was added. UPLC indicated that the reaction was incomplete. The mixture was quenched with saturated aqueous ammonium chloride solution and extracted three times with dichloromethane. The organic extracts were dried over sodium sulfate, filtered and the filtrate evaporated. The residue was dissolved in pyridine (1 ml) and trimethylacetyl chloride (96 mg, 0.797 mmol) was added. The mixture was stirred at RT for 2 h then evaporated. The residue was dissolved in water and extracted three times with ethyl acetate. The organic extracts were dried over sodium sulfate, filtered, and the filtrate evaporated. The crude residue was purified via reverse phase chromatography (30 g C18 cartridge acetonitrile/pH 10 buffer with ammonium bicarbonate) to provide compound 16.3 (80 mg, 83%) as a white solid. UPLC-MS (long basic) rt 2.02 (386 [M+H]$^+$). Used directly.

2-(N-(2-((1H-Imidazol-1-yl)methyl)benzyl)pivalamido)acetic Acid Acid G

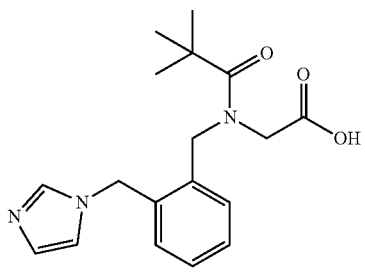 [SMILES: CC(C)(C)C(=O)N(CC(=O)O)Cc1ccccc1Cn1ccnc1]

Compound 16.3 (80 mg, 0.207 mmol) was dissolved in methanol (3 ml) then 2M sodium hydroxide (0.311 ml, 0.622 mmol) was added and the mixture stirred at RT for 2 days. The mixture was acidified to pH 5 with 2M aqueous HCl solution then extracted twice with ethyl acetate. The organic extracts were dried over sodium sulfate, evaporated, filtered and the filtrate evaporated to provide compound Acid G (40 mg, 59%) as a white solid. $^1$H NMR (CD$_3$OD, 300 MHz) δ 1.29 (s, 9H), 3.98 (s, 2H), 4.72 (s, 2H), 5.25 (s, 2H), 6.95 (m, 2H), 7.25 (m, 2H), 7.35 (m, 4H). UPLC-MS (short basic) rt 0.46 (330 [M+H]$^+$), 100% pure.

Acid H

SCHEME 17

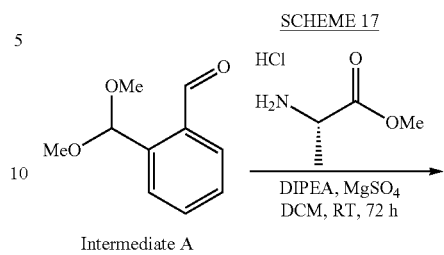

Intermediate A

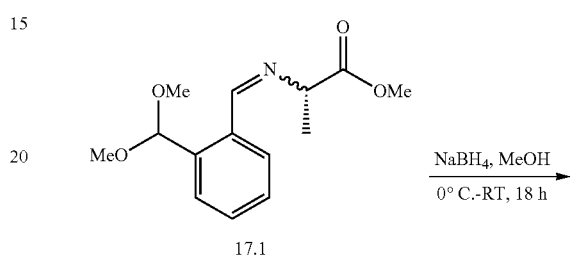

17.1

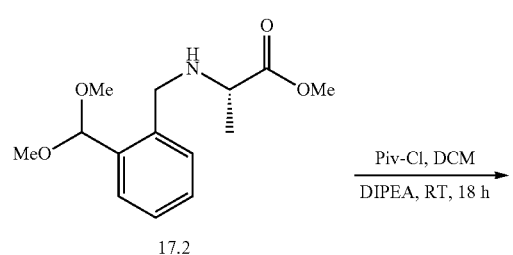

17.2

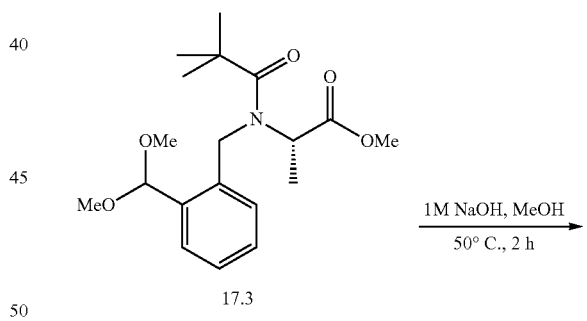

17.3

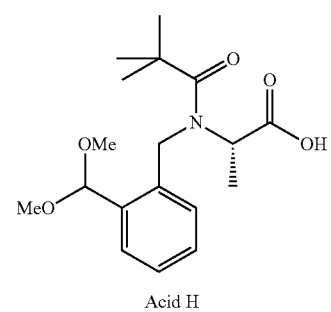

Acid H

(S, E/Z)-Methyl 2-((2-(dimethoxymethyl)benzylidene)amino)propanoate 17.1

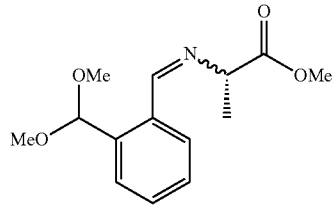 [SMILES: COC(=O)[C@H](C)N=Cc1ccccc1C(OC)OC]

L-Alanine methyl ester hydrochloride (250 mg, 1.79 mmol) was suspended in dichloromethane (8 ml) then N,N-diisopropylethylamine (1.25 ml, 7.16 mmol) was added. Intermediate A (0.5 g, 1.79 mmol) was added followed by magnesium sulfate (excess). The mixture was stirred at RT for 18 h. The mixture was filtered then the filtrate was washed twice with water. The aqueous layer was dried over magnesium sulfate, filtered, and the filtrate evaporated to provide compound 17.1 (assume 1.79 mmol) as a pale yellow gum. Used directly. $^1$H NMR (CDCl$_3$, 300 MHz) δ 1.53 (d, 3H), 3.31 (s, 3H), 3.33 (s, 3H), 3.75 (s, 3H), 4.18 (q, 1H), 5.66 (s, 1H), 7.39 (m, 2H), 7.55 (d, 1H), 8.01 (d, 1H), 8.77 (s, 1H). UPLC-MS (short basic) rt 0.81 (234 [M−OMe+H]$^+$).

(S)-Methyl 2-((2-(dimethoxymethyl)benzyl)amino)propanoate 17.2

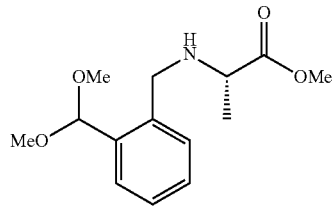 [SMILES: COC(=O)[C@H](C)NCc1ccccc1C(OC)OC]

Compound 17.1 (~1.79 mmol) was dissolved in methanol (10 ml) under an argon atmosphere then cooled on ice/water. Sodium borohydride (102 mg, 2.69 mmol) was added portionwise (Note: vigorous gas evolution) and the mixture was stirred at RT for 2 h. The mixture was poured into saturated sodium bicarbonate. The aqueous layer was extracted three times with dichloromethane. The combined organic extracts were dried over magnesium sulfate, filtered, and the filtrate evaporated. The residue was purified by normal phase chromatography (30 g SiO$_2$, Isolera, 5-20% IPA in heptane) to provide compound 17.2 (311 mg, 65%) as a pale straw-coloured gum. $^1$H NMR (CDCl$_3$, 300 MHz) δ 1.32 (d, 3H), 3.33 (s, 3H), 3.34 (s, 3H), 3.36 (s, 1H), 3.73 (s, 3H), 3.81 (dd, 2H), 5.63 (s, 1H), 7.28 (m, 2H), 7.34 (m, 1H), 7.57 (m, 1H). UPLC-MS (short basic) rt 0.79 (204 [M−2OMe+H]$^+$).

(S)-Methyl 2-(N-(2-(dimethoxymethyl)benzyl)pivalamido)propanoate 17.3

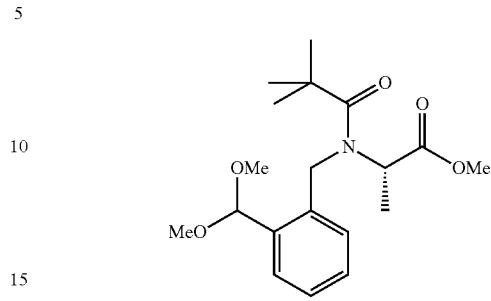

Compound 17.2 (311 mg, 1.16 mmol) was dissolved in dichloromethane (8 ml) under an argon atmosphere then N,N-diisopropylethylamine (0.61 ml, 3.49 mmol) was added. Trimethylacetyl chloride (0.14 ml, 1.16 mmol) was added then the reaction mixture was stirred at RT for 18 h. The mixture was diluted with dichloromethane and washed saturated sodium bicarbonate. The organic layer dried over magnesium sulfate, filtered and the filtrate evaporated. The residue was purified via normal phase chromatography (30 g Isolera, 5-30% EtOAc in heptane) to provide compound 17.3 (148 mg, 37%). $^1$H NMR (CDCl$_3$, 300 MHz) δ 1.26 (s, 9H), 1.41 (d, 3H), 3.31 (s, 3H), 3.33 (s, 3H), 3.65 (m, 1H), 3.71 (s, 3H), 4.79 (m, 1H), 5.06 (d, 1H), 5.36 (s, 1H), 7.50 (m, 4H). UPLC-MS (short basic) rt 0.98 (204 fragment), 90% pure.

(S)-2-(N-(2-(Dimethoxymethyl)benzyl)pivalamido) propanoic Acid Acid H

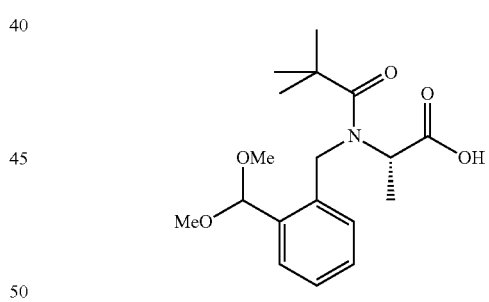

Compound 17.3 (148 mg, 0.422 mmol) was dissolved in methanol (4 ml) then 1M sodium hydroxide (0.85 ml, 0.85 mmol) was added and the reaction mixture stirred at 50° C. for 2 h. The mixture was concentrated to 0.5 volume then diluted with water and the pH adjusted to 4 by careful addition of 2M HCl. This was extracted with ethyl acetate. The aqueous was readjusted to pH 4 with 2M HCl and extracted again with ethyl acetate, repeating this pH adjustment one more time. The combined organic extracts were washed with brine, dried over magnesium sulfate and filtered. N,N-Diisopropylethylamine (0.2 ml) and N,N-dimethylformamide (2 ml) were added to the filtrate, and the filtrate was concentrated—but not evaporated to dryness so as to avoid compound decomposition—to provide Acid H, which was used directly (assume 0.422 mmol).

Acid I

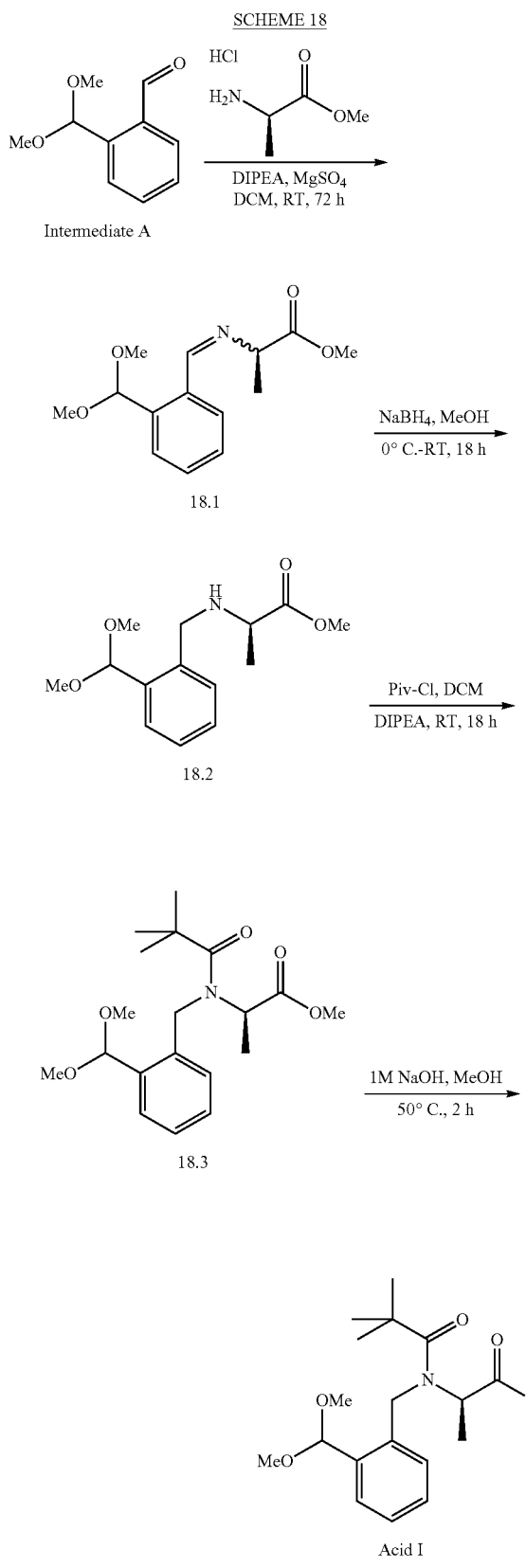

(R, E/Z)-Methyl 2-((2-(dimethoxymethyl)benzylidene)amino)propanoate 18.1

D-Alanine methyl ester hydrochloride (250 mg, 1.79 mmol) was suspended in dichloromethane (8 ml) then N,N-diisopropylethylamine (1.25 ml, 7.16 mmol) was added. Intermediate A (0.5 g, 1.79 mmol) was added followed by magnesium sulfate (excess). The mixture was stirred at RT for 72 h. The mixture was filtered then the filtrate was washed twice with water. The aqueous layer was dried over magnesium sulfate, filtered and the filtrate evaporated to provide compound 18.1 (assume 1.79 mmol) as a pale yellow gum. Used directly. $^1$H NMR (CDCl$_3$, 400 MHz) δ 1.52 (d, 3H), 3.30 (s, 3H), 3.34 (s, 3H), 3.75 (s, 3H), 4.18 (q, 1H), 5.65 (s, 1H), 7.39 (m, 2H), 7.55 (dd, 1H), 8.00 (dd, 1H), 8.76 (s, 1H). UPLC-MS (short basic) rt 0.79 (234 [M−OMe+H]$^+$).

(R)-Methyl 2-((2-(dimethoxymethyl)benzyl)amino)propanoate 18.2

Compound 18.1 (~1.79 mmol) was dissolved in methanol (10 ml) under an argon atmosphere then cooled on ice/water. Sodium borohydride (102 mg, 2.69 mmol) was added portionwise (Note: vigorous gas evolution). The mixture was stirred on ice/water for 10 min then stirred at RT for 18 h. The mixture was poured into saturated sodium bicarbonate. The aqueous layer was extracted three times with dichloromethane. The combined organic extracts were dried over magnesium sulfate, filtered, and the filtrate evaporated to provide compound 18.2 (480 mg, quant.) as a pale straw-coloured gum. $^1$H NMR (CDCl$_3$, 300 MHz) δ 1.32 (d, 3H), 3.33 (s, 3H), 3.34 (s, 3H), 3.36 (s, 2H), 3.73 (m, 4H), 5.63 (s, 1H), 7.40 (m, 4H). UPLC-MS (short basic) rt 0.76 (267 [M+H]$^+$).

(R)-Methyl 2-(N-(2-(dimethoxymethyl)benzyl)piva-lamido)propanoate 18.3

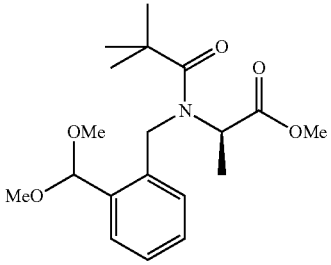 [SMILES: COC(=O)[C@@H](C)N(Cc1ccccc1C(OC)OC)C(=O)C(C)(C)C]

Compound 18.2 (478 mg, 1.79 mmol) was dissolved in dichloromethane (10 ml) under an argon atmosphere then N,N-diisopropylethylamine (0.93 ml, 5.37 mmol) was added. Trimethylacetyl chloride (0.22 ml, 1.79 mmol) was added then the reaction mixture was stirred at RT for 18 h. The mixture was diluted with dichloromethane and washed saturated sodium bicarbonate. The organic layer dried over magnesium sulfate, filtered and the filtrate evaporated. The residue was purified via flash silica chromatography (9:1 to 8:2 heptane/EtOAc) to provide compound 18.3 (189 mg, 30%). $^1$H NMR (CDCl$_3$, 400 MHz) δ 1.29 (s, 9H), 1.40 (d, 3H), 3.31 (s, 3H), 3.33 (s, 3H), 3.65 (m, 1H), 3.71 (s, 3H), 4.79 (m, 1H), 5.06 (d, 1H), 5.36 (s, 1H), 7.50 (m, 4H). UPLC-MS (short basic) rt 0.95 (320 [M−OMe+H]$^+$), 83% pure.

(R)-2-(N-(2-(Dimethoxymethyl)benzyl)pivalamido) propanoic Acid Acid I

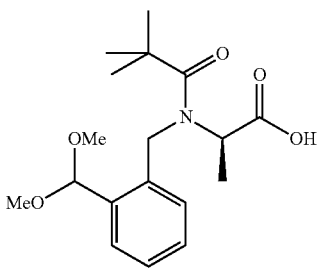 [SMILES: COC(OC)c1ccccc1CN(C(=O)C(C)(C)C)[C@H](C)C(=O)O]

Compound 18.3 (189 mg, 0.54 mmol) was dissolved in methanol (5 ml) then 1M sodium hydroxide (1.08 ml, 1.08 mmol) was added and the reaction mixture stirred at 50° C. for 2 h. The mixture was concentrated to 0.5 volume then diluted with water and the pH adjusted to 4 by careful addition of 2M HCl. This was extracted with ethyl acetate. The aqueous was readjusted to pH 4 with 2M HCl and extracted again with ethyl acetate, repeating this pH adjustment one more time. The combined organic extracts were washed with brine, dried over magnesium sulfate and filtered. N,N-Diisopropylethylamine (0.2 ml) and N,N-dimethylformamide (2 ml) were added to the filtrate then the filtrate evaporated, but not to dryness to avoid compound decomposition, to provide Acid I—used directly (assume 0.54 mmol).

Acid J

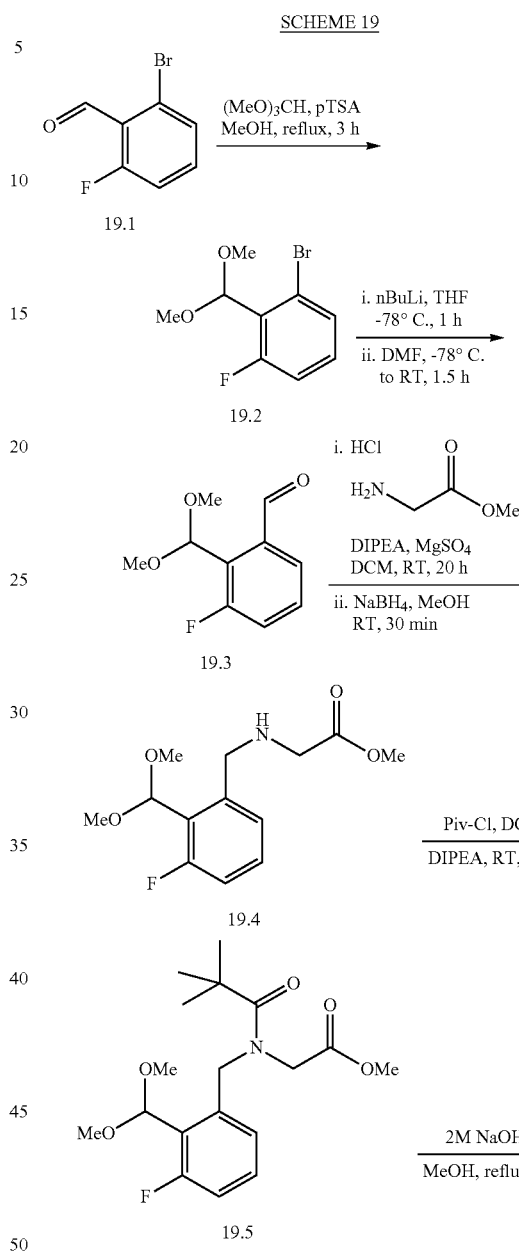

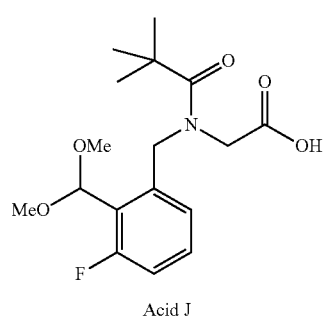

Acid J

1-Bromo-2-(dimethoxymethyl)-3-fluorobenzene 19.2

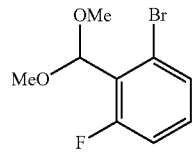

2-Bromo-6-fluorobenzaldehyde 19.1 (3 g, 14.8 mmol) was dissolved in methanol (20 ml) and p-toluenesulfonic acid monohydrate (270 mg, 1.48 mmol) and trimethyl orthoformate (10 ml) were added. The reaction was then heated to reflux for 3 h. The mixture was cooled on ice/water then triethylamine (3 ml) was added. The volatiles were removed then the mixture diluted with diethyl ether and water. The aqueous layer was extracted twice with diethyl ether. The combined organic extracts were washed with brine, dried over magnesium sulfate, filtered and the filtrate evaporated. The residue was purified via column chromatography (150 ml silica, 10% diethyl ether in hexane) to provide compound 19.2 (3.23 g, 88%) as a colourless oil. $^1$H NMR (CDCl$_3$, 300 MHz) δ 3.48 (s, 6H), 5.70 (s, 1H), 7.07 (dt, 1H), 7.15 (m, 1H), 7.35 (dd, 1H).

2-(Dimethoxymethyl)-3-fluorobenzaldehyde 19.3

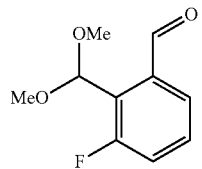 [SMILES: COC(OC)c1c(F)cccc1C=O]

Compound 19.2 (3.23 g, 13.02 mmol) was dissolved in dry tetrahydrofuran (30 ml) under an argon atmosphere then cooled on dry ice/acetone. To this was added a solution of n-butyllithium (2.5 M in hexanes, 5.73 ml, 14.33 mmol) dropwise so that the internal temperature stayed below −60° C. (10 min addition). The reaction was stirred on dry ice/acetone for 70 min. To this was added N,N-dimethylformamide (2.05 ml, 26.0 mmol) in one portion. The mixture was stirred on dry ice/acetone for 60 min before being allowed to warm to RT over 1.5 h. Water was added then the mixture was extracted three times with ethyl acetate. The combined organic extracts were washed with brine, dried over magnesium sulfate, filtered and the filtrate evaporated. The residue was purified via column chromatography (150 ml silica, 10% diethyl ether in hexane) to provide compound 19.3 (1.72 g, 67%) as a straw-coloured oil. $^1$H NMR (CDCl$_3$, 300 MHz) δ 3.48 (s, 6H), 5.70 (s, 1H), 7.26 (dt, 1H), 7.41 (m, 1H), 7.78 (d, 1H), 7.91 (d, 1H), 10.68 (s, 1H) Used directly.

Methyl 2-((2-(dimethoxymethyl)-3-fluorobenzyl)amino)acetate 19.4

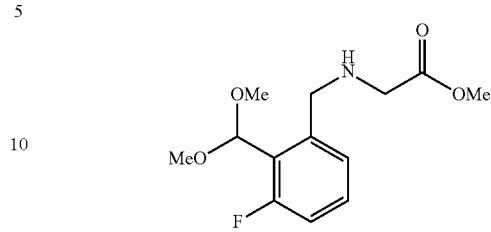

Compound 19.3 (1.0 g, 5.05 mmol) was dissolved in dichloromethane (30 ml) then N,N-diisopropylethylamine (2.5 ml, 13.8 mmol) and glycine methyl ester hydrochloride (577 mg, 4.6 mmol) were added followed by magnesium sulfate. The mixture was stirred at RT for 18 h. The mixture was filtered and the filtrate evaporated. The residue was dissolved in methanol (10 ml) then sodium borohydride (105 mg, 2.77 mmol) was added portionwise and stirred at RT for 30 min. The mixture was diluted with ethyl acetate and washed with saturated sodium bicarbonate. The aqueous was extracted twice with ethyl acetate then the organic extracts were washed with brine, dried over sodium sulfate, filtered and evaporated to provide compound 19.4 (1.26 g, 93%) as a yellow oil. $^1$H NMR (CDCl$_3$, 300 MHz) δ 2.46 (br s, 1H), 3.40 (s, 2H), 3.46 (s, 6H), 3.67 (s, 3H), 4.01 (s, 2H), 5.61 (s, 1H), 6.97 (t, 1H), 7.23 (m, 2H).

Methyl 2-(N-(2-(dimethoxymethyl)-3-fluorobenzyl) pivalamido)acetate 19.5

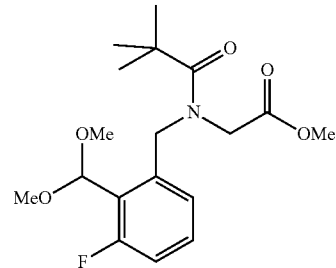 [SMILES: COC(=O)CN(Cc1cccc(F)c1C(OC)OC)C(=O)C(C)(C)C]

Compound 19.4 (1.26 g, 4.69 mmol) was dissolved in dichloromethane (20 ml) under an argon atmosphere then N,N-diisopropylethylamine (2.5 ml, 14.1 mmol) was added. Trimethylacetyl chloride (0.58 ml, 4.69 mmol) was added then the reaction mixture was stirred at RT for 30 min. The mixture was diluted with dichloromethane and washed saturated sodium bicarbonate. The organics were washed with brine, dried over magnesium sulfate, filtered and the filtrate evaporated. The residue was purified via flash silica chromatography (7:3 heptane/EtOAc) to provide compound 19.5 (1.27 mg, 76%) as a colourless solid. $^1$H NMR (CDCl$_3$, 300 MHz) δ 1.34 (s, 9H), 3.41 (s, 6H), 3.71 (s, 3H), 3.89 (s, 2H), 5.12 (s, 2H), 5.59 (s, 1H), 6.95 (t, 1H), 7.08 (d, 1H), 7.26 (m, 1H).

2-(N-(2-(Dimethoxymethyl)-3-fluorobenzyl)piva-lamido)acetic Acid Acid J

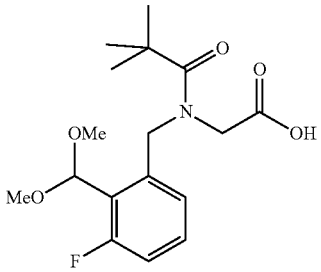 [SMILES: COC(OC)c1c(F)cccc1CN(CC(=O)O)C(=O)C(C)(C)C]

Compound 19.5 (1.27 g, 3.57 mmol) was dissolved in methanol (60 ml) then 2.5M sodium hydroxide (3.6 ml, 8.9 mmol) was added and the reaction mixture stirred at 50° C. for 1 h. The mixture was concentrated to 0.5 volume then diluted with water and the pH adjusted to 4 by careful addition of 2M HCl. This was extracted with ethyl acetate. The aqueous was readjusted to pH 4 with 2M HCl and extracted again with ethyl acetate, repeating this pH adjustment one more time. The combined organic extracts were washed with brine, dried over magnesium sulfate and filtered. N,N-Diisopropylethylamine (0.2 ml) and N,N-dimethylformamide (2 ml) were added to the filtrate then the filtrate evaporated, but not to dryness to avoid compound decomposition, to provide Acid J—used directly (assume 3.57 mmol).

Acid K

SCHEME 20

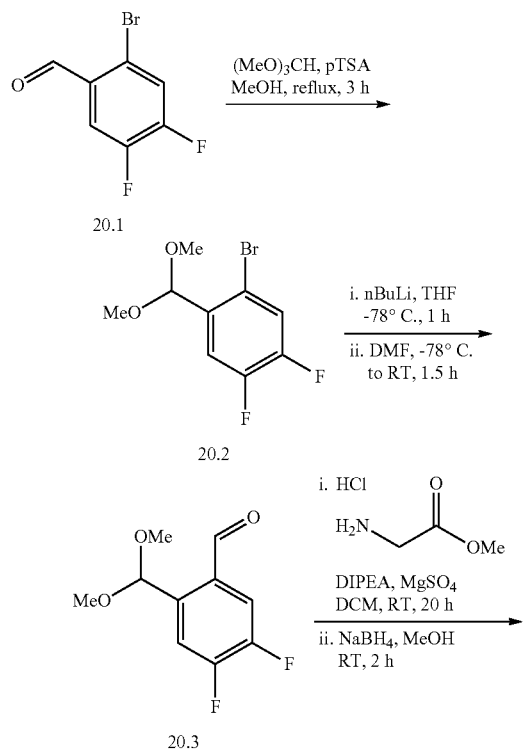

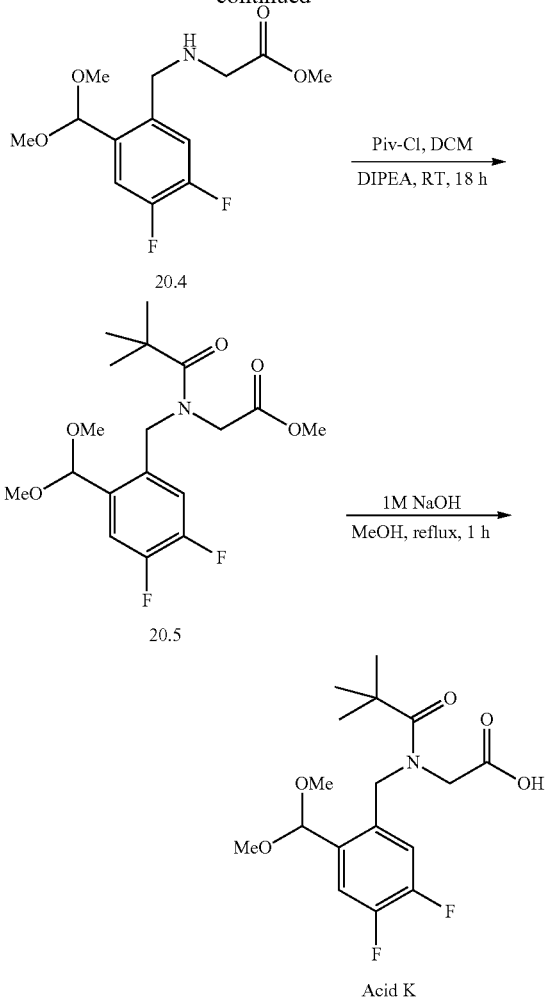

1-Bromo-2-(dimethoxymethyl)-4,5-difluorobenzene 20.2

2-Bromo-4,5-difluorobenzaldehyde 20.1 (1 g, 4.52 mmol) was dissolved in methanol (5 ml) and p-toluenesulfonic acid monohydrate (9 mg, 0.226 mmol) and trimethyl orthoformate (2 ml) were added. The reaction was then heated to reflux for 3 h. The mixture was cooled on ice water then the volatiles were removed. The mixture was diluted with diethyl ether and water. The aqueous layer was extracted twice with diethyl ether. The combined organic extracts were washed with brine, dried over magnesium sulfate, filtered and the filtrate evaporated. The residue was purified via column chromatography (150 ml silica, 5-20% diethyl ether in hexane) to provide compound 20.2 (1.1 g, 91%) as a colourless oil. ¹H NMR (CDCl₃, 300 MHz) δ 3.38 (s, 6H), 5.46 (s, 1H), 7.39 (dd, 1H), 7.46 (dd, 1H).

2-(Dimethoxymethyl)-4,5-difluorobenzaldehyde 20.3

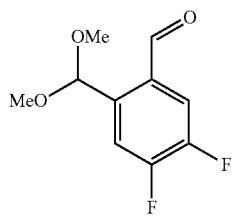 [SMILES: COC(OC)c1cc(F)c(F)cc1C=O]

Compound 20.2 (0.55 g, 2.06 mmol) was dissolved in dry tetrahydrofuran (6 ml) under an argon atmosphere then cooled on dry ice/acetone. To this was added a solution of n-butyllithium (2.5 M in hexanes, 1.24 ml, 3.09 mmol) dropwise so that the internal temperature stayed below −60° C. (10 min addition). The reaction was stirred on dry ice/acetone for 70 min. To this was added N,N-dimethylformamide (0.34 ml, 4.12 mmol) in one portion. The mixture was stirred on dry ice/acetone for 60 min before being allowed to warm to RT over 1.5 h. Water was added then the mixture was extracted three times with ethyl acetate. The combined organic extracts were washed with brine, dried over magnesium sulfate, filtered and the filtrate evaporated. The residue was purified via column chromatography (10-15% diethyl ether in hexane) to provide compound 20.3 (216 mg, 48%) as a straw-coloured oil.

¹H NMR (CDCl₃, 300 MHz) δ 3.40 (s, 6H), 5.88 (s, 1H), 7.37 (dd, 1H), 7.50 (ddd, 1H), 10.48 (s, 1H) Used directly.

Methyl 2-((2-(dimethoxymethyl)-4,5-difluorobenzyl)amino)acetate 20.4

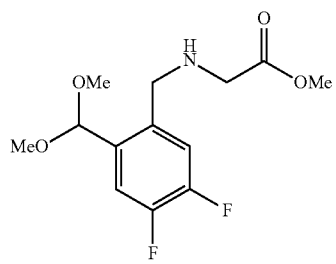 [SMILES: COC(=O)CNCc1cc(F)c(F)cc1C(OC)OC]

Compound 20.3 (216 mg, 1.00 mmol) was dissolved in dichloromethane (6 ml) then N,N-diisopropylethylamine (0.7 ml, 4.0 mmol) and glycine methyl ester hydrochloride (138 mg, 1.1 mmol) were added followed by magnesium sulfate. The mixture was stirred at RT for 18 h. The mixture was filtered, the filtrate washed with water, dried over magnesium sulfate and evaporated. The residue was dissolved in methanol (7 ml) then sodium borohydride (30 mg, 1.02 mmol) was added portionwise and stirred at RT for 2 h. The mixture was diluted with ethyl acetate and washed with saturated sodium bicarbonate. The aqueous was extracted twice with ethyl acetate then the organic extracts were washed with brine, dried over sodium sulfate, filtered and evaporated to provide compound 20.4 (145 mg, 59%) as a yellow oil.

¹H NMR (CDCl₃, 300 MHz) δ 3.34 (s, 6H), 3.44 (s, 2H), 3.73 (s, 3H), 3.89 (m, 2H), 5.57 (s, 1H), 7.08 (dd, 1H), 7.29 (m, 1H).

Methyl 2-(N-(2-(dimethoxymethyl)-4,5-difluorobenzyl)pivalamido)acetate 20.5

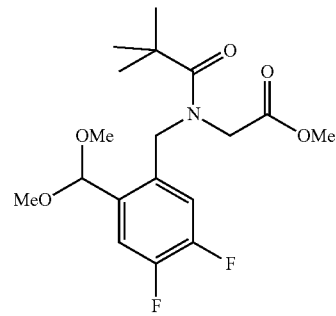 [SMILES: COC(=O)CN(Cc1cc(F)c(F)cc1C(OC)OC)C(=O)C(C)(C)C]

Compound 20.4 (145 mg, 0.50 mmol) was dissolved in dichloromethane (4 ml) under an argon atmosphere then N,N-diisopropylethylamine (0.27 ml, 1.51 mmol) was added. Trimethylacetyl chloride (62 μl, 0.50 mmol) was added then the reaction mixture was stirred at RT for 18 h. The mixture was diluted with dichloromethane and washed saturated sodium bicarbonate. The organics were washed with brine, dried over magnesium sulfate, filtered and the filtrate evaporated. The residue was purified via flash silica chromatography (19:1 heptane/IPA) to provide compound 20.5 (101 mg, 54%) as a yellow oil. ¹H NMR (CDCl₃, 300 MHz) δ 1.30 (s, 9H), 3.31 (s, 6H), 3.71 (s, 3H), 4.02 (br s, 2H), 4.90 (m, 2H), 5.44 (s, 1H), 7.10 (m, 1H), 7.34 (m, 1H).

2-(N-(2-(Dimethoxymethyl)-4,5-difluorobenzyl)pivalamido)acetic Acid Acid K

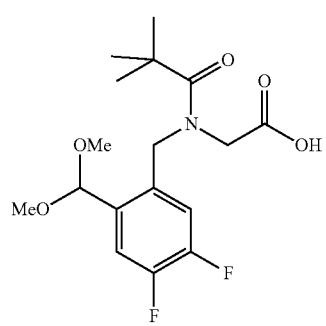 [SMILES: COC(OC)c1cc(F)c(F)cc1CN(CC(=O)O)C(=O)C(C)(C)C]

Compound 20.5 (101 mg, 0.27 mmol) was dissolved in methanol (3 ml) then 1M sodium hydroxide (0.33 ml, 0.33 mmol) was added and the reaction mixture stirred at 50° C. for 4 h then at RT for 18 h. The mixture was concentrated to 0.5 volume then diluted with water and the pH adjusted to 4 by careful addition of 2M HCl. This was extracted with ethyl acetate. The aqueous was readjusted to pH 4 with 2M HCl and extracted again with ethyl acetate, repeating this pH adjustment one more time. The combined organic extracts were washed with brine, dried over magnesium sulfate and filtered. N,N-Dimethylformamide (2 ml) was added to the filtrate then the filtrate evaporated, but not to dryness to avoid compound decomposition, to provide Acid K—used directly (assume 0.27 mmol).

Acid L

SCHEME 21

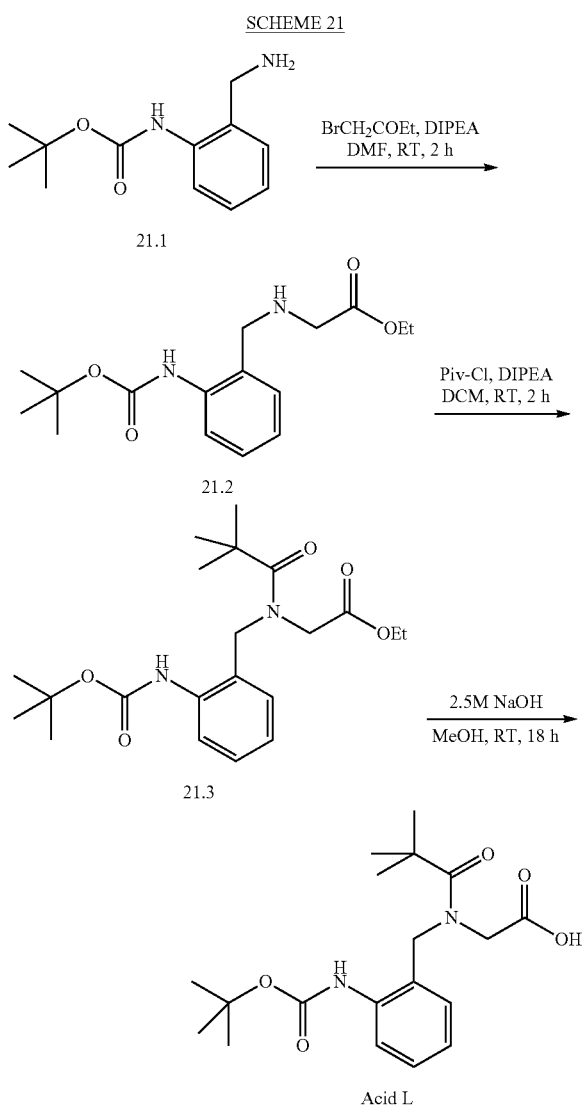

Ethyl 2-((2-((tert-butoxycarbonyl)amino)benzyl)amino)acetate 21.2

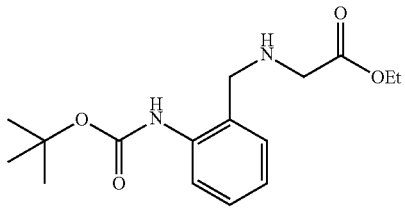 [SMILES: CCOC(=O)CNCc1ccccc1NC(=O)OC(C)(C)C]

t-Butyl-2-aminomethylphenylcarbamate 21.1 (100 mg, 0.45 mmol), ethyl bromoacetate (38 µl, 0.34 mmol) and N,N-diisopropylethylamine (157 µl, 0.90 mmol) were mixed in N,N-dimethylformamide (1 ml) and stirred at RT for 2 h after which the reaction was complete by UPLC-MS. The mixture was diluted with ethyl acetate and washed with water. The aqueous was extracted with ethyl acetate. The organics were washed with brine, dried over magnesium sulfate, filtered and the filtrate evaporated to provide compound 21.2 (119 mg, 86%) as a yellow gum. $^1$H NMR (CDCl$_3$, 300 MHz) δ 1.28 (t, 3H), 1.52 (s, 9H), 3.36 (s, 2H), 3.84 (s, 2H), 4.21 (q, 2H), 6.93 (dt, 1H), 7.06 (dd, 1H), 7.26 (m, 1H), 7.98 (brd, 1H), 9.14 (br s, 1H).

Ethyl 2-(N-(2-((tert-butoxycarbonyl)amino)benzyl)pivalamido)acetate 21.3

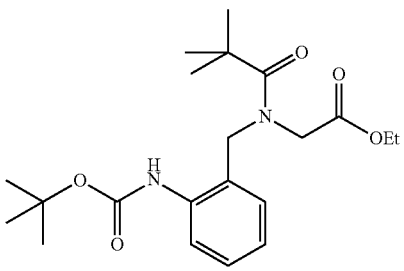 [SMILES: CCOC(=O)CN(Cc1ccccc1NC(=O)OC(C)(C)C)C(=O)C(C)(C)C]

Compound 21.2 (119 mg, 0.39 mmol) was dissolved in dichloromethane (5 ml) then N,N-diisopropylethylamine (204 µl, 1.17 mmol) and trimethylacetyl chloride (58 µl, 0.47 mmol) were added and the mixture stirred at RT for 2 h. UPLC-MS showed little reaction so further N,N-diisopropylethylamine (204 µl, 1.17 mmol) and trimethylacetyl chloride (58 µl, 0.47 mmol) were added. After an additional 2 h, UPLC-MS showed complete reaction. The mixture was poured into water and the aqueous extracted with dichloromethane. The organics were dried over magnesium sulfate, filtered and evaporated. The residue was purified via flash chromatography (4:1 heptane/ethyl acetate) to provide compound 21.3 (99 mg, 65%) as a colourless oil. $^1$H NMR (CDCl$_3$, 300 MHz) δ 1.28 (t, 3H), 1.30 (s, 9H), 1.51 (s, 9H), 4.00 (s, 2H), 4.18 (q, 2H), 4.72 (s, 2H), 7.04 (m, 2H), 7.27 (m, 1H), 7.99 (br s, 1H). UPLC-MS (short CSH 2-50%) rt 1.50 (415 [M+Na]$^+$), 95% pure.

2-(N-(2-((tert-Butoxycarbonyl)amino)benzyl)pivalamido)acetic Acid Acid L

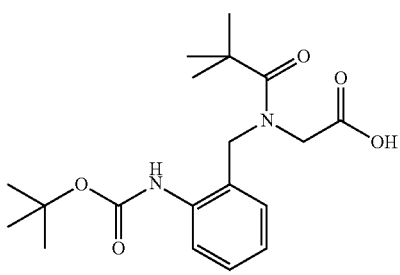 [SMILES: CC(C)(C)OC(=O)Nc1ccccc1CN(CC(=O)O)C(=O)C(C)(C)C]

Compound 21.3 (99 mg, 0.25 mmol) was dissolved in methanol (1.5 ml) and 2.5M sodium hydroxide (0.25 ml, 0.625 mmol)) was added and the mixture heated at reflux for 2 h. The mixture was poured into water and the pH was adjusted carefully to 4 by addition of 2M HCl and extracted with ethyl acetate. The aqueous pH was again adjusted to 4 and extracted with ethyl acetate. The organics were washed with brine, dried over magnesium sulfate, filtered and the filtrate evaporated to provide Acid L (80 mg, 88%) as a colourless solid. H NMR (CDCl₃, 300 MHz) δ 1.31 (s, 9H), 1.50 (s, 9H), 4.03 (s, 2H), 4.75 (s, 2H), 7.05 (m, 2H), 7.29 (m, 2H), 7.82 (br s, 1H). UPLC-MS (short CSH 2-50%) rt 1.28 (363 [M+Na]⁺), 95% pure.

Acid M

SCHEME 22

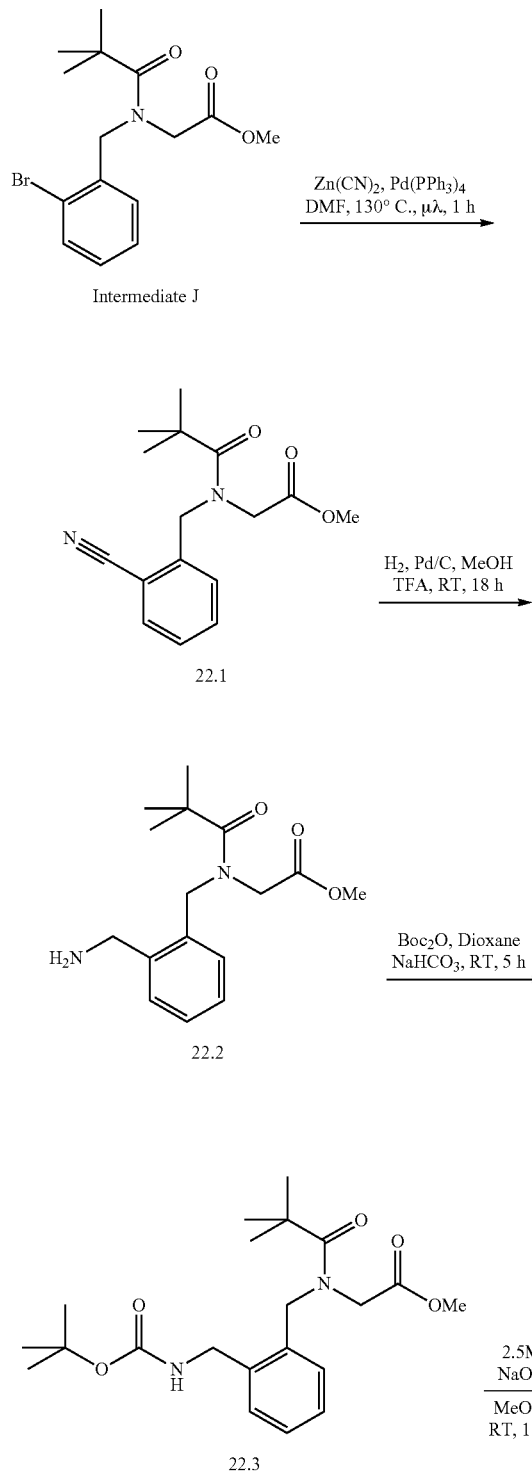

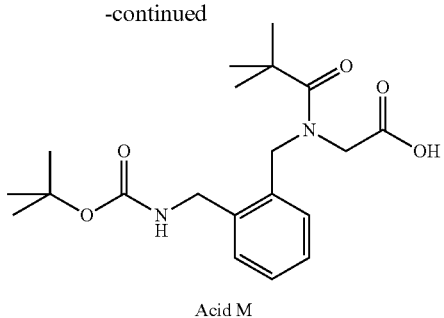

Acid M

Methyl 2-(N-(2-cyanobenzyl)pivalamido)acetate 22.1

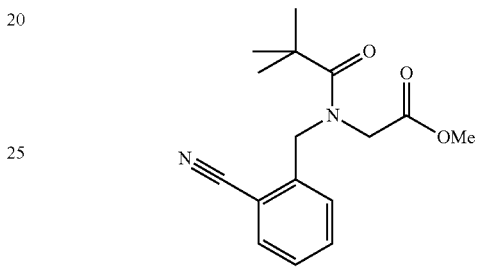

Intermediate J (500 mg, 1.46 mmol), zinc (II) cyanide (305 mg, 2.6 mmol) and tetrakis(triphenylphosphine)palladium(0) (335 mg, 0.29 mmol) were added to degassed dry N,N-dimethylformamide (10 ml) then heated at 130° C. under microwave irradiation for 1 h. The mixture was diluted with ethyl acetate and washed with water. The aqueous was extracted with ethyl acetate. The organics were washed with brine, dried over magnesium sulfate, filtered and the filtrate evaporated. The residue was purified via flash silica chromatography (0-20% acetone in heptane) to provide compound 22.1 (320 mg, 76%) as a yellow gum. ¹H NMR (CDCl₃, 300 MHz) δ 1.30 (s, 9H), 3.74 (s, 3H), 4.00 (br s, 2H), 4.96 (br s, 2H), 7.40 (m, 2H), 7.60 (t, 1H), 7.67 (d, 1H).

Methyl 2-(N-(2-(aminomethyl)benzyl)pivalamido)acetate 22.2

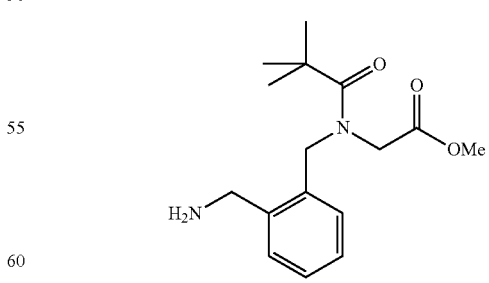

Compound 22.1 (320 mg, 1.1 mmol) was dissolved in methanol (14 ml) and trifluoroacetic acid (0.75 ml). Palladium on carbon (10% wet, 32 mg) was added, the vessel sealed and an atmosphere of hydrogen introduced at atmospheric pressure. The mixture was stirred at RT for 18 h. The reaction was filtered through Celite, washing with methanol and the filtrate evaporated. The residue was dissolved in ethyl acetate and washed with saturated sodium bicarbonate. The aqueous was extracted with ethyl acetate. The organics were washed with brine, dried over magnesium sulfate, filtered and the filtrate evaporated to provide compound 22.2 (132 mg, 41%) as a yellow gum. UPLC-MS (short CSH 2-50%) rt 0.45 (293 [M+H]$^+$).

Methyl 2-(N-(2-(((tert-butoxycarbonyl)amino)methyl)benzyl)pivalamido)acetate 22.3

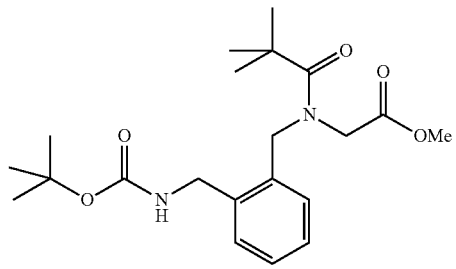 [SMILES: COC(=O)CN(Cc1ccccc1CNC(=O)OC(C)(C)C)C(=O)C(C)(C)C]

Compound 22.2 (341 mg, 1.2 mmol) was dissolved in 1,4-dioxane (10 ml) and saturated sodium bicarbonate (10 ml) was added followed by di-t-butyl dicarbonate (393 mg, 1.8 mmol). The mixture was stirred rapidly at RT for 5 h. The mixture was poured into ethyl acetate and water and the aqueous extracted with ethyl acetate. The organics were washed with brine, dried over magnesium sulfate, filtered and the filtrate evaporated. The residue was purified via flash chromatography (2:1 heptane/EtOAc) to provide compound 22.3 (300 mg, 64%) as a colourless oil. $^1$H NMR (CDCl$_3$, 300 MHz) δ 1.25 (s, 9H), 1.44 (s, 9H), 3.71 (s, 3H), 3.96 (br s, 2H), 4.29 (s, 2H), 4.86 (s, 2H), 7.26 (m, 4H). UPLC-MS (short CSH 2-50%) rt 1.21 (293 [M–Boc+H]$^+$).

2-(N-(2-(((tert-Butoxycarbonyl)amino)methyl)benzyl)pivalamido)acetic Acid Acid M

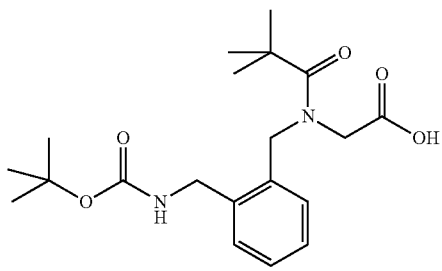 [SMILES: CC(C)(C)OC(=O)NCc1ccccc1CN(CC(=O)O)C(=O)C(C)(C)C]

Compound 22.3 (300 mg, 0.76 mmol) was dissolved in methanol (10 ml) and 2.5M sodium hydroxide (0.7 ml, 1.75 mmol)) was added and the mixture heated at reflux for 2 h then at RT for 18 h. The volatiles were removed then the residue dissolved in water. The pH was adjusted carefully to 4 by addition of 2M HCl and extracted with ethyl acetate. The aqueous pH was again adjusted to 4 and extracted with ethyl acetate (repeated 4 times). The organics were washed with brine, dried over magnesium sulfate, filtered and the filtrate evaporated, adding 2 ml of DMF, to provide Acid M as a yellow oil. Used directly.

General Route D

SCHEME 23

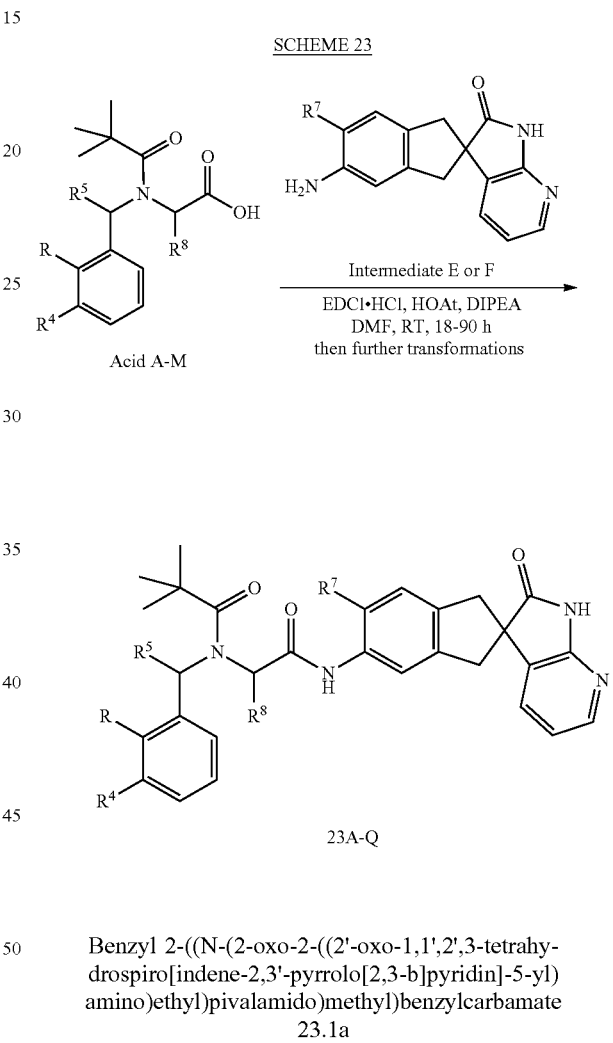

Benzyl 2-((N-(2-oxo-2-((2'-oxo-1,1',2',3-tetrahydrospiro[indene-2,3'-pyrrolo[2,3-b]pyridin]-5-yl)amino)ethyl)pivalamido)methyl)benzylcarbamate 23.1a

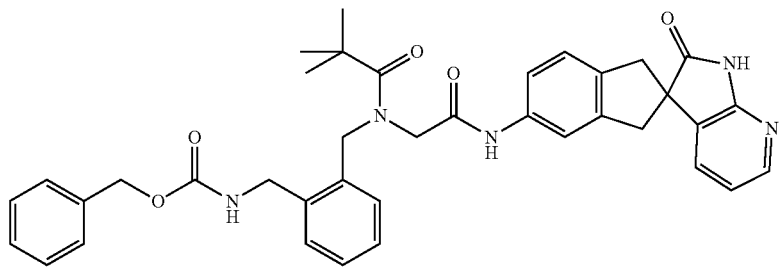 [SMILES: CC(C)(C)C(=O)N(CC(=O)Nc1ccc2c(c1)CC1(C2)C(=O)Nc2ncccc21)Cc1ccccc1CNC(=O)OCc1ccccc1]

Acid A (93 mg, 0.225 mmol), EDCl.HCl (52 mg, 0.271 mmol) and HOAt (45 mg, 0.330 mmol) were dissolved in dry N,N-dimethylformamide (2 ml). N,N-Diisopropylethylamine (0.10 ml, 0.60 mmol) and Intermediate E (50.5 mg, 0.20 mmol) were added and the mixture was stirred at RT for 18 h. The mixture was poured into saturated sodium bicarbonate and the aqueous layer was extracted twice with ethyl acetate. The organic extract was washed with water, 20% aqueous citric acid, water, brine, dried over magnesium sulfate, filtered and the filtrate evaporated. The residue was purified via flash silica chromatography (7:3 Heptane/EtOAc to EtOAc) to provide compound 23.1a (69 mg, 53%) as a colourless glass. $^1$H NMR (CD$_3$OD, 300 MHz) δ 1.29 (s, 9H), 2.81 (dd, 2H), 3.01 (dd, 2H), 3.45 (m, 2H), 4.06 (br s, 2H), 4.29 (m, 2H), 5.03 (s, 2H), 6.83 (dd, 1H), 7.08 (dd, 1H), 7.30 (m, 12H), 8.01 (dd, 1H). UPLC-MS (long basic) rt 2.40 (646 [M+H]$^+$), 97% pure.

Example 26: N-(2-(Aminomethyl)benzyl)-N-(2-oxo-2-((2'-oxo-1,1',2,3-tetrahydrospiro[indene-2,3'-pyrrolo[2,3-b]pyridin]-5-yl)amino)ethyl)pivalamide 23A

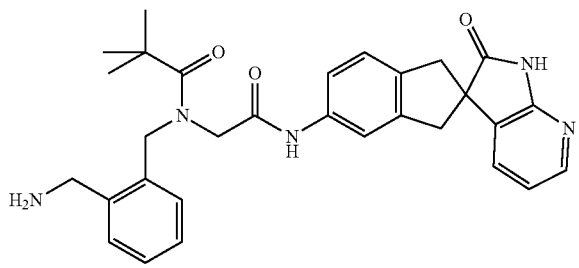 [SMILES: CC(C)(C)C(=O)N(CC(=O)Nc1ccc2c(c1)CC1(C2)C(=O)Nc2ncccc21)Cc1ccccc1CN]

Example 27: N-(2-((Ethylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 23B

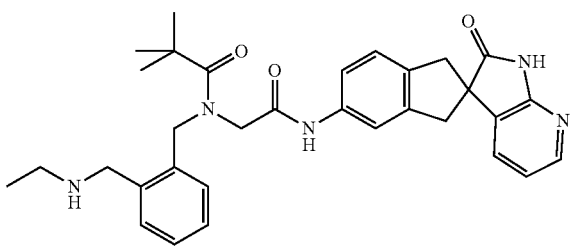 [SMILES: CCNCc1ccccc1CN(CC(=O)Nc1ccc2c(c1)CC1(C2)C(=O)Nc2ncccc21)C(=O)C(C)(C)C]

Compound 23.1a (46.5 mg, 0.072 mmol) was dissolved in absolute ethanol (2 ml) under an argon atmosphere. Palladium on carbon (5%, 13 mg) was added and hydrogen was introduced under balloon pressure. After stirring at RT for 2 h, UPLC-MS showed no progress so extra palladium on carbon (5%, 12 mg) was added and hydrogen reintroduced by balloon. The reaction was stirred at RT for 42 h. UPLC-MS analysis showed almost complete consumption of 23.1a, with two products formed. The mixture was filtered through Celite, washing with methanol, and the filtrate evaporated. The residue was purified via flash silica chromatography (0.5-7% ammonia and MeOH in EtOAc) to provide two compounds: (higher running spot) compound 23B (9.3 mg, 24%); and impure (lower running spot) compound 23A.

Impure 23A was purified (2 g STMAd SPE, MeOH then ammonia in MeOH) followed by trituration in ether then further purification (500 mg SiO$_2$ 5% ammonia and methanol in EtOAc) to provide compound 23A (2.0 mg, 5%)

Data for 23A $^1$H NMR (CD$_3$OD, 300 MHz) δ 1.32 (s, 9H), 3.05 (dd, 2H), 3.50 (dd, 2H), 3.83 (s, 2H), 4.13 (br s, 2H), 4.94 (br s, 2H), 6.87 (dd, 1H), 7.27 (m, 8H), 8.03 (dd, 1H). UPLC-MS (long basic) rt 1.77 (512 [M+H]$^+$), 95% pure.

Data for 23B $^1$H NMR (CD$_3$OD, 300 MHz) δ 1.11 (t, 3H), 1.32 (s, 9H), 2.66 (q, 2H), 3.04 (dd, 2H), 3.49 (dd, 2H), 3.75 (s, 2H), 4.13 (br s, 2H), 4.94 (br s, 2H), 6.86 (dd, 1H), 7.27 (m, 8H), 8.03 (dd, 1H). UPLC-MS (long basic) rt 2.07 (540 [M+H]$^+$), 90% pure.

Alternative Syntheses of 23A

N-(2-Bromobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 23.2a

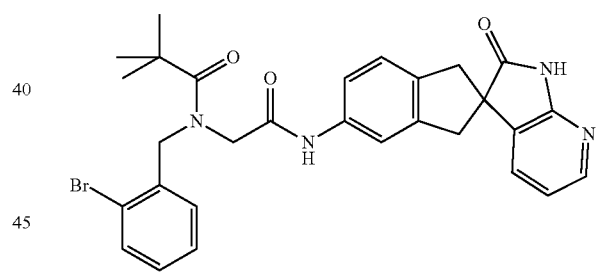

Acid B (3.11 g, 9.48 mmol), EDCl.HCl (2.5 g, 13.27 mmol) and HOAt (1.8 g, 13.27 mmol) were dissolved in dry N,N-dimethylformamide (60 ml). N,N-Diisopropylethylamine (5.0 ml, 28.44 mmol) and Intermediate E (2.38 g, 9.48 mmol) were added and the mixture was stirred at RT for 18 h. The mixture was diluted with ethyl acetate (250 ml) and washed with saturated sodium bicarbonate and three times with brine. The organic layer was dried over magnesium sulfate, filtered and the filtrate evaporated. The residue was purified via flash silica chromatography (0-100% EtOAc in DCM) to provide compound 23.2a (4.38 g, 83%) as a pale yellow solid. $^1$H NMR (CDCl$_3$, 300 MHz) δ 1.31 (s, 9H), 3.02 (dd, 2H), 3.61 (dd, 2H), 4.08 (s, 2H), 4.92 (s, 2H), 6.81 (dd, 1H), 7.06 (dd, 1H), 7.17 (m, 3H), 7.34 (t, 1H), 7.57 (m, 2H), 8.13 (dd, 1H), 8.49 (s, 1H), 9.29 (s, 1H). UPLC-MS (short basic) rt 0.84 (561, 563 [M+H]$^+$).

N-(2-Cyanobenzyl)-N-(2-oxo-2-((2'-oxo-1,1',2',3-tetrahydrospiro[indene-2,3'-pyrrolo[2,3-b]pyridin]-5-yl)amino)ethyl)pivalamide Intermediate K

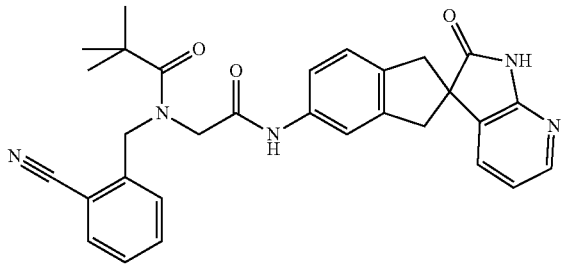 [SMILES: CC(C)(C)C(=O)N(CC(=O)Nc1ccc2c(c1)CC1(C2)C(=O)Nc2ncccc21)Cc1ccccc1C#N]

Compound 23.2a (4.40 g, 7.84 mmol) was dissolved in dry N,N-dimethylformamide (88 ml) and was degassed by bubbling argon through the solution. Zinc (II) cyanide (1.66 g, 14.12 mmol) and tetrakis(triphenylphosphine)palladium (0) (1.8 g, 1.57 mmol) were added and the mixture was stirred at 130° C. for 2 h. UPLC-MS indicated complete conversion. The heat was removed and stirred at RT for 18 h. The mixture was diluted with ethyl acetate (400 ml) and washed twice with saturated sodium bicarbonate and three times with brine. The organic layer was dried over magnesium sulfate, filtered and the filtrate evaporated. The residue was triturated with diethyl ether to provide Intermediate K (3.85 g, 96%) as an off-white solid. $^1$H NMR (DMSO-d6, 300 MHz) δ 1.20 (s, 9H), 3.04 (dd, 2H), 3.31 (dd, 2H), 4.22 (br s, 2H), 4.85 (br s, 2H), 6.83 (dd, 1H), 7.16 (t, 1H), 7.31 (d, 1H), 7.37 (m, 1H), 7.44 (t, 2H), 7.68 (t, 1H), 7.81 (d, 1H), 8.03 (dd, 1H), 9.98 (s, 1H), 11.06 (s, 1H). UPLC-MS (short basic) rt 0.72 (508 [M+H]$^+$).

Example 26: N-(2-(Aminomethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 23A

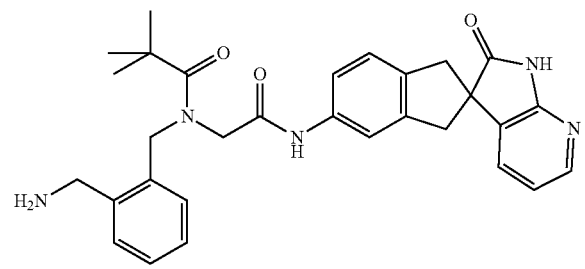 [SMILES: CC(C)(C)C(=O)N(CC(=O)Nc1ccc2c(c1)CC1(C2)C(=O)Nc2ncccc21)Cc1ccccc1CN]

Intermediate K (2.3 g, 4.53 mmol) was dissolved in 15% ammonia in methanol (180 ml) under an argon atmosphere in an autoclave. Raney nickel (250 mg, 0.45 mmol) was added and hydrogen was introduced to 500 psi. The vessel was stirred at 60° C. for 6 h then RT for 18 h. UPLC-MS showed 20% conversion so extra Raney nickel (400 mg, 0.72 mmol) was added and hydrogen was reintroduced to 500 psi. The vessel was stirred at 60° C. for 6.5 h. UPLC-MS analysis showed 58% conversion. The mixture was decanted (from the nickel solids) then filtered through celite, washing with 15% ammonia in methanol and the filtrate evaporated. The residue was dissolved in 15% ammonia in methanol (180 ml) under an argon atmosphere in an autoclave. Raney nickel (400 mg, 0.72 mmol) was added and hydrogen was reintroduced to 500 psi. The vessel was stirred at 50° C. for 6 h, then RT for 18 h, then 55° C. for 6 h, then RT for 42 h, then 55° C. for 8 h. The mixture was decanted (from the nickel solids) then filtered through Celite, washing with 15% ammonia in methanol and the filtrate evaporated. The residue was purified via flash silica chromatography (EtOAc then 5% MeOH in DCM, then 10-15% MeOH with ammonia in DCM) to provide compound 23A (240 mg, 10%) as a white powder, after freeze-drying from an aqueous solution. $^1$H NMR (CD$_3$OD, 300 MHz) δ 1.32 (s, 9H), 3.05 (dd, 2H), 3.50 (dd, 2H), 3.83 (s, 2H), 4.13 (br s, 2H), 4.94 (br s, 2H), 6.87 (dd, 1H), 7.27 (m, 8H), 8.03 (dd, 1H). UPLC-MS (long basic) rt 1.79 (512 [M+H]$^+$), 84% pure—contains 6% mono-N-methyl and 3% di-N-methyl by-products.

tert-Butyl 2-((N-(2-oxo-2-((2'-oxo-1,1',2',3-tetrahydrospiro[indene-2,3'-pyrrolo[2,3-b]pyridin]-5-yl)amino)ethyl)pivalamido)methyl)benzylcarbamate 23.4a

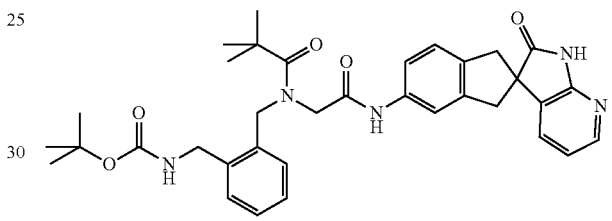

Acid M (~290 mg, ~0.765 mmol), EDCl.HCl (176 mg, 0.92 mmol) and HOAt (124 mg, 0.92 mmol) were dissolved in dry N,N-dimethylformamide (3 ml). N,N-Diisopropylethylamine (0.68 ml, 3.83 mmol) and Intermediate E (211 mg, 0.84 mmol) were added and the mixture was stirred at RT for 20 h. The mixture was diluted with ethyl acetate and washed with saturated sodium bicarbonate. The aqueous was extracted twice with ethyl acetate. The combined organics were washed three times with water then with brine, dried over magnesium sulfate, filtered and the filtrate evaporated. The residue was purified via flash silica chromatography (EtOAc) to provide compound 23.4a (228 mg, 48%) as a pale yellow solid. UPLC-MS (short basic) rt 0.91 (612 [M+H]$^+$), 90% pure.

Example 26: N-(2-(Aminomethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 23A

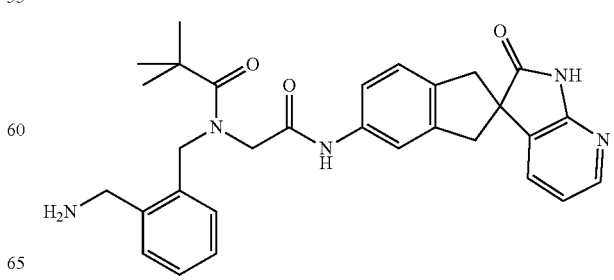

Compound 23.4a (228 mg, 0.37 mmol) was dissolved in dichloromethane (6 ml) and cooled on ice/water. Trifluoroacetic acid (0.3 ml) was added dropwise, stirred on ice/water for 15 min then at RT for 45 min. UPLC-MS suggested slow conversion. Extra trifluoroacetic acid (0.15 ml) was added and the reaction stirred for 55 min. The mixture was poured into saturated sodium bicarbonate and the aqueous layer was extracted three times with dichloromethane. The organic extract was dried over sodium sulfate, filtered and the filtrate evaporated to give 160 mg of material that was a 2:1 mixture of 23.4a and 23A. The aqueous was extracted with 10% methanol/ethyl acetate twice, the organics dried over magnesium sulfate, filtered and evaporated. The 160 mg mixed material was redissolved in dichloromethane (6 ml) and trifluoroacetic acid (0.45 ml) added and the mixture stirred at RT for 1 h. The reaction was worked up as above with the dichloromethane extracts kept apart from the 10% methanol/ethyl acetate extracts. The crude residues were purified via SPE (5 g $SiO_2$ 10-15% MeOH in DCM then 15% MeOH and ammonia in DCM) to provide compound 23A (96 mg, 51%) as a colourless glass. $^1$H NMR ($CD_3OD$, 300 MHz) δ 1.31 (s, 9H), 3.05 (dd, 2H), 3.50 (dd, 2H), 4.13 (br s, 2H), 4.35 (br s, 2H), 4.94 (br s, 2H), 6.87 (dd, 1H), 7.11 (d, 1H), 7.22 (d, 1H), 7.37 (m, 5H), 7.59 (s, 1H), 8.04 (dd, 1H). UPLC-MS (short CSH 2-50%) rt 0.65 (510 [M+H]$^+$), 99% pure.

Example 28: N-(2-(2-(Diallylamino)ethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 23.1c

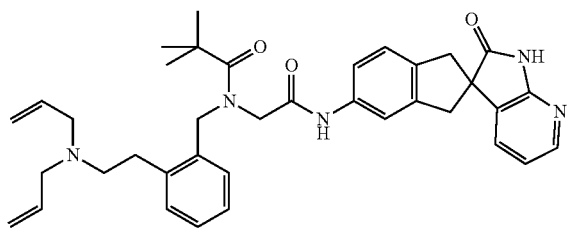 [SMILES: C=CCN(CC=C)CCc1ccccc1CN(CC(=O)Nc1ccc2c(c1)CC1(C2)C(=O)Nc2ncccc21)C(=O)C(C)(C)C]

Acid C (~0.176 mmol), EDCl.HCl (53 mg, 0.28 mmol) and HOAt (38 mg, 0.28 mmol) were dissolved in dry N,N-dimethylformamide (1 ml). N,N-Diisopropylethylamine (0.11 ml, 0.64 mmol) and Intermediate E (44.5 mg, 0.177 mmol) were added and the mixture was stirred at RT for 18 h. The mixture was poured into saturated sodium bicarbonate and extracted three times with ethyl acetate. The combined organic layers were washed with brine, dried over magnesium sulfate, filtered and the filtrate evaporated. The residue was purified via flash silica chromatography (EtOAc) to provide compound 23.1c (77 mg, 72%) as a pale yellow glass. $^1$H NMR ($CDCl_3$, 400 MHz) δ 1.32 (s, 9H), 2.69 (m, 4H), 3.05 (dd, 2H), 3.16 (d, 4H), 3.61 (dd, 2H), 4.02 (br s, 2H), 4.90 (s, 2H), 5.14 (m, 4H), 5.83 (m, 2H), 6.80 (dd, 1H), 7.15 (m, 7H), 7.56 (s, 1H), 8.15 (br s, 1H), 8.45 (s, 1H). UPLC-MS (long basic) rt 2.65 (606 [M+H]$^+$), 98% pure.

Example 29: N-(2-(2-Aminoethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 23C

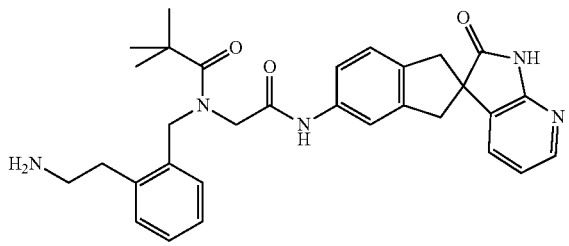 [SMILES: CC(C)(C)C(=O)N(CC(=O)Nc1ccc2c(c1)CC1(C2)C(=O)Nc2ncccc21)Cc1ccccc1CCN]

Compound 23.1c (77 mg, 0.127 mmol) and N,N'-dimethylbarbituric acid (125 mg, 0.801 mmol) were dissolved in dry degassed dichloromethane (2 ml) then degassed again. Tetrakis(triphenylphosphine)palladium(0) (11.4 mg, 0.010 mmol) was added and the mixture was stirred at 35° C. for 2 h, and at RT for 18 h. UPLC-MS analysis shows incomplete reaction. Tetrakis(triphenylphosphine)palladium(0) (13 mg, 0.011 mmol) was added and the mixture was stirred at 35° C. for 3.5 h. UPLC-MS still shows incomplete conversion. The mixture was diluted with dichloromethane and saturated sodium bicarbonate and layers separated. The aqueous was extracted with dichloromethane. The combined organic layers were dried over magnesium sulfate, filtered and the filtrate evaporated. The aqueous was back extracted twice with ethyl acetate, the combined organic layers were dried over magnesium sulfate, filtered and the filtrate evaporated. The extracted residues were combined and shown to contain monoallyl by-product. product was still in the aqueous layer. The aqueous was evaporated and purified using a Biotage Isolera (18 g, C18 Ultra cartridge, 60-80% acetonitrile/water with pH 10 buffer) to provide crude compound. This was further purified via MDAP (XBridge C18 19×150, 35-50% acetonitrile water with 0.1% ammonium hydroxide) to provide compound 23C (19.4 mg, 29%) as a pale-yellow glass. $^1$H NMR ($CDCl_3$, 300 MHz) δ 1.34 (s, 9H), 2.78 (dd, 2H), 3.00 (m, 4H), 3.60 (d, 2H), 4.05 (br s, 2H), 4.97 (br s, 2H), 6.80 (dd, 1H), 7.17 (m, 8H), 7.53 (s, 1H), 8.11 (dd, 1H), 8.62 (s, 1H). UPLC-MS (long basic) rt 1.79 (526 [M+H]$^+$), 94% pure.

Example 30: N-(2-((Dimethylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 23D

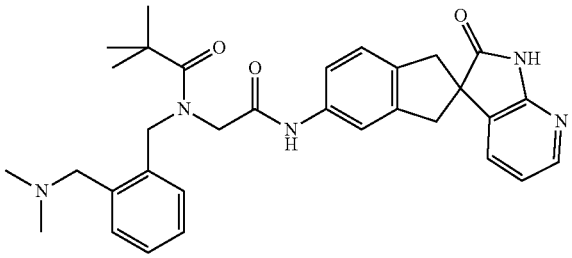 [SMILES: CN(C)Cc1ccccc1CN(CC(=O)Nc1ccc2c(c1)CC1(C2)C(=O)Nc2ncccc21)C(=O)C(C)(C)C]

Acid D (40 mg, 0.13 mmol), EDCl.HCl (38 mg, 0.19 mmol) and HOAt (27 mg, 0.19 mmol) were dissolved in dry N,N-dimethylformamide (3 ml). N,N-Diisopropylethylamine (101 mg, 0.78 mmol) and Intermediate E (40 mg, 0.16 mmol) were added and the mixture was stirred at RT for 18 h. The mixture was poured into saturated ammonium chloride and the aqueous layer was extracted twice with ethyl acetate. The organic extract was dried over sodium sulfate, filtered and the filtrate evaporated. The residue was purified via reverse phase chromatography (SP4 30 g C18 cartridge acetonitrile/pH 10 buffer with ammonium bicarbonate) to provide compound 23D (12 mg, 17%) as a colourless glass.
$^1$H NMR (CD$_3$OD, 300 MHz) δ 1.26 (s, 9H), 2.18 (s, 6H), 3.10 (m, 2H), 3.55 (m, 4H), 4.05 (br s, 2H), 5.10 (br s, 2H), 6.88 (d, 1H), 7.27 (m, 7H), 7.54 (s, 1H), 8.02 (d, 1H). HPLC-MS (long basic) rt 2.35 (540 [M+H]$^+$), 99% pure.

tert-Butyl 8-((N-(2-Oxo-2-((2'-oxo-1,1',2',3-tetrahydrospiro[indene-2,3'-pyrrolo[2,3-b]pyridin]-5-yl)amino)ethyl)pivalamido)methyl)-3,4-dihydroisoquinoline-2(1H)-carboxylate 23.1e

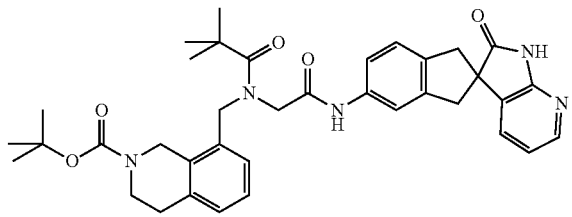 [SMILES: CC(C)(C)OC(=O)N1CCc2cccc(CN(CC(=O)Nc3ccc4c(c3)CC3(C4)C(=O)Nc4ncccc43)C(=O)C(C)(C)C)c2C1]

Acid E (35 mg, 0.084 mmol), EDCl.HCl (19 mg, 0.101 mmol) and HOAt (14 mg, 0.101 mmol) were dissolved in dry N,N-dimethylformamide (2 ml). N,N-Diisopropylethylamine (35 µl, 0.20 mmol) and Intermediate E (21 mg, 0.084 mmol) were added and the mixture was stirred at RT for 18 h. The mixture was poured into saturated sodium bicarbonate and the aqueous layer was extracted three times with ethyl acetate. The organic extract was washed three times with water, dried over sodium sulfate, filtered and the filtrate evaporated. The residue was purified via SPE (2 g SiO$_2$ EtOAc) to provide compound 23.1e (30 mg, 56%) as a colourless glass. UPLC-MS (short basic) rt 0.86 (638 [M+H]$^+$).

Example 31: N-(2-Oxo-2-((2'-oxo-1,1',2',3-tetrahydrospiro[indene-2,3'-pyrrolo[2,3-b]pyridin]-5-yl)amino)ethyl)-N-((1,2,3,4-tetrahydroisoquinolin-8-yl)methyl)pivalamide 23E

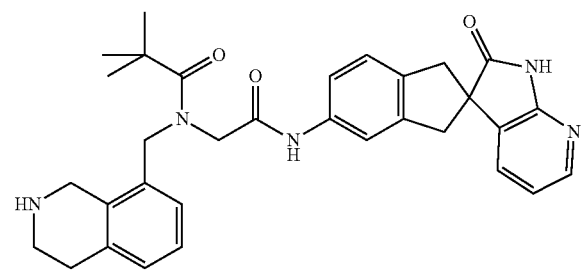 [SMILES: CC(C)(C)C(=O)N(CC(=O)Nc1ccc2c(c1)CC1(C2)C(=O)Nc2ncccc21)Cc1cccc2c1CNCC2]

Compound 23.1e (30 mg, 0.047 mmol) was dissolved in dichloromethane (3 ml). Trifluoroacetic acid (0.3 ml) was added and the solution was stirred at RT for 45 min. The mixture was poured into saturated sodium bicarbonate and the aqueous layer was extracted three times with dichloromethane. The organic extract dried over sodium sulfate, filtered and the filtrate evaporated. The residue was purified via SPE (2 g SiO$_2$ 10% MeOH in EtOAc then 10-20% MeOH in DCM) to provide compound 23E (12 mg, 48%) as a colourless glass.
$^1$H NMR (CD$_3$OD, 300 MHz) δ 1.31 (s, 9H), 2.89 (m, 2H), 3.06 (m, 4H), 3.50 (dd, 2H), 3.94 (s, 2H), 4.10 (br s, 2H), 4.74 (brs, 2H), 6.87 (d, 1H), 7.00 (d, 1H), 7.12 (m, 4H), 7.33 (d, 1H), 7.52 (s, 1H), 8.02 (dd, 1H). UPLC-MS (short basic) rt 0.66 (538 [M+H]$^+$), 99% pure.

N-(2-Bromo-3-fluorobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 23.1f

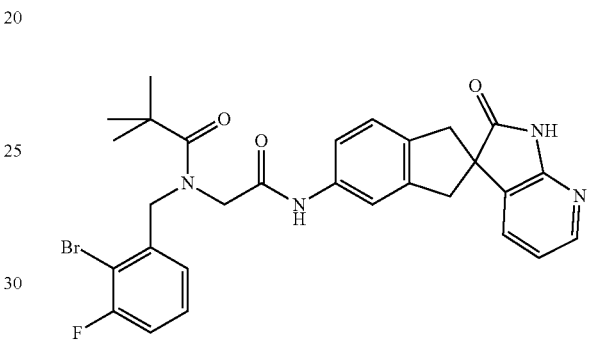

Acid F (45 mg, 0.13 mmol), Intermediate E (27 mg, 0.11 mmol) and HATU (54 mg, 0.14 mmol) were dissolved in dry N,N-dimethylformamide (1.5 ml). N-Methylmorpholine (0.1 ml, 9.3 mmol) was added and the mixture was stirred at RT for 30 min. The mixture was diluted with ethyl acetate then was washed three times with brine, dried over magnesium sulfate, filtered, and the filtrate evaporated. The residue was purified via reverse phase chromatography (30 g C18 cartridge, acetonitrile/pH 10 buffer with ammonium bicarbonate) to provide compound 23.1f (60 mg, 80%) as a colourless glass. $^1$H NMR (CD$_3$OD, 300 MHz) δ 1.30 (s, 9H), 2.97 (d, 2H), 3.55 (d, 2H), 4.08 (br s, 2H), 4.94 (br s, 2H), 6.80 (m, 1H), 6.96 (d, 1H), 7.10 (m, 3H), 7.30 (m, 2H), 7.54 (d, 1H), 8.65 (br s, 1H), 10.27 (br s, 1H). UPLC-MS (short basic) rt 0.84 (580, 582 [M+H]$^+$), 97% pure.

N-(2-Cyano-3-fluorobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 23.2f

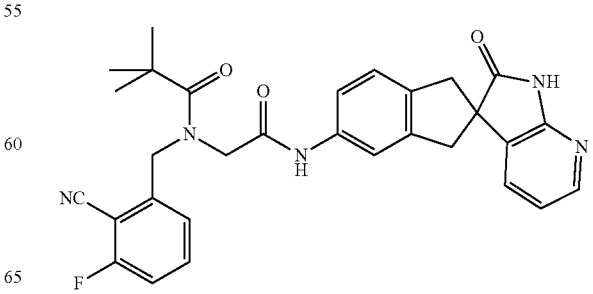

Compound 23.1f (50 mg, 0.08 mmol) was dissolved in dry N,N-dimethylformamide (2.5 ml) and was degassed by bubbling argon through the solution. Zinc (II) cyanide (13 mg, 0.11 mmol), tris(dibenzylideneacetone)dipalladium(0) (4.3 mg, 0.005 mmol) and 1,1'-bis(diphenylphosphino)ferrocene (5.3 mg, 0.01 mmol) were added and the mixture was stirred at 150° C. for 18 h. The mixture was diluted with ethyl acetate, filtered through Celite then the filtrate was washed three times with brine. The organic layer was evaporated and purified via reverse phase chromatography (30 g C18 cartridge, acetonitrile/pH 10 buffer with ammonium bicarbonate) to provide compound 23.2f (40 mg, 90%) as a colourless glass. UPLC-MS (short basic) rt 0.76 (526 [M+H]$^+$).

Example 32: N-(2-(Aminomethyl)-3-fluorobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 23F

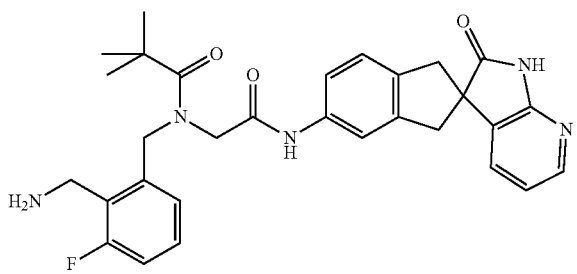 [SMILES: CC(C)(C)C(=O)N(CC(=O)Nc1ccc2c(c1)CC1(C2)C(=O)Nc2ncccc21)Cc1cccc(F)c1CN]

Compound 23.2f (10.4 mg, 0.02 mmol) was dissolved in methanol (1 ml) then cobalt (II) chloride (0.05 mg, 0.0005 mmol) was added and the mixture stirred at RT for 10 min. Sodium borohydride (1.5 mg, 0.04 mmol) was added portionwise over 10 min at RT then the mixture was stirred at RT for 3 h. The mixture was diluted with ethyl acetate, filtered through Celite and the filtrate evaporated. The residue was purified via reverse phase chromatography (30 g C18 cartridge acetonitrile/pH 10 buffer with ammonium bicarbonate) and then by SPE (SCX-2, 500 mg, MeOH then ammonia in MeOH) to provide compound 23F (6.7 mg, 64%) as a colourless glass. $^1$H NMR (CD$_3$OD, 400 MHz) δ 1.30 (s, 9H), 3.07 (d, 2H), 3.48 (dd, 2H), 4.23 (s, 2H), 4.40 (br s, 2H), 4.85 (br s, 2H), 6.87 (m, 1H), 7.13 (m, 1H), 7.21 (m, 4H), 7.33 (m, 1H), 7.44 (m, 1H), 7.50 (m, 1H), 8.04 (m, 1H). UPLC-MS (short basic) rt 0.68 (530 [M+H]$^+$), 97% pure.

Example 33: N-(2-((1H-Imidazol-1-yl)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 23G

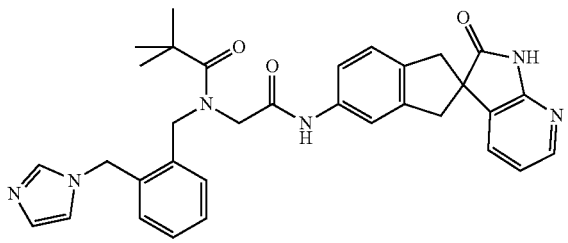 [SMILES: CC(C)(C)C(=O)N(CC(=O)Nc1ccc2c(c1)CC1(C2)C(=O)Nc2ncccc21)Cc1ccccc1Cn1ccnc1]

Acid G (40 mg, 0.121 mmol), EDCl.HCl (25 mg, 0.182 mmol) and HOAt (35 mg, 0.182 mmol) were dissolved in dry N,N-dimethylformamide (2 ml). N,N-Diisopropylethylamine (83 mg, 0.73 mmol) and Intermediate E (37 mg, 0.147 mmol) were added and the mixture was stirred at RT for 18 h. The mixture was poured into saturated ammonium chloride and the aqueous layer was extracted three times with ethyl acetate. The organic extract was washed three times with sodium bicarbonate, dried over sodium sulfate, filtered and the filtrate evaporated. The residue was purified via reverse phase chromatography (SP4 30 g C18 cartridge acetonitrile/pH 10 buffer with ammonium bicarbonate) to provide compound 23G (16 mg, 24%) as a colourless glass. $^1$H NMR (CD$_3$OD, 300 MHz) δ 1.20 (m, 9H), 3.00 (m, 2H), 4.00 (m, 4H), 4.80 (br s, 2H), 5.29 (s, 2H), 6.70-7.70 (m, 12H), 8.02 (d, 1H). UPLC-MS (long basic) rt 1.87 (563 [M+H]$^+$), 100% pure.

N-(2-(Dimethoxymethyl)benzyl)-N-((2S)-1-oxo-1-((2'-oxo-1,1',2',3-tetrahydrospiro[indene-2,3'-pyrrolo[2,3-b]pyridin]-5-yl)amino)propan-2-yl)pivalamide 23.1h

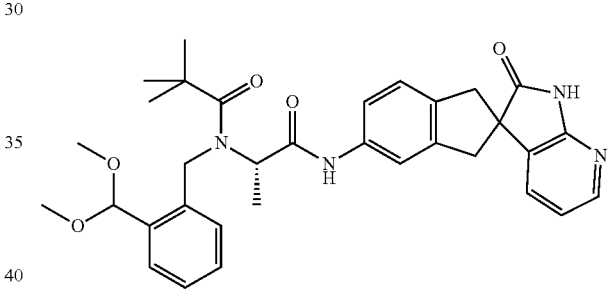

Acid H (~142 mg, assume 0.422 mmol), and Intermediate E (106 mg, 0.422 mmol) were dissolved in dry N,N-dimethylformamide (4 ml). N,N-Diisopropylethylamine (0.22 ml, 1.27 mmol) and HATU (192 mg, 0.506 mmol) were added and the mixture was stirred at 50° C. for 6 h then RT for 12 h. The mixture was poured into saturated sodium bicarbonate and extracted twice with ethyl acetate. The organic extract was washed three times with water then brine, dried over magnesium sulfate, filtered and the filtrate evaporated. The residue was purified using flash silica chromatography (10-30% IPA in heptane) and then again by normal phase (5 g SiO$_2$, Biotage Isolera, 50-80% EtOAc in heptane) to provide compound 23.1h (52 mg, 22%) as a yellow gum. $^1$H NMR (CDCl$_3$, 300 MHz) δ 1.32 (m, 12H), 3.05 (dd, 2H), 3.31 (s, 3H), 3.34 (s, 3H), 3.62 (dd, 2H), 4.74 (m, 2H), 4.97 (m, 1H), 5.38 (s, 1H), 6.80 (m, 1H), 7.06 (m, 1H), 7.18 (s, 1H), 7.29 (m, 4H), 7.52 (m, 1H), 7.85 (s, 1H), 8.10 (dd, 1H). UPLC-MS (short basic) rt 0.93 (569 [M−H]$^-$).

217

N-(2-Formylbenzyl)-N-((2S)-1-oxo-1-((2'-oxo-1,1', 2',3-tetrahydrospiro[indene-2,3'-pyrrolo[2,3-b]pyridin]-5-yl)amino)propan-2-yl)pivalamide 23.2h

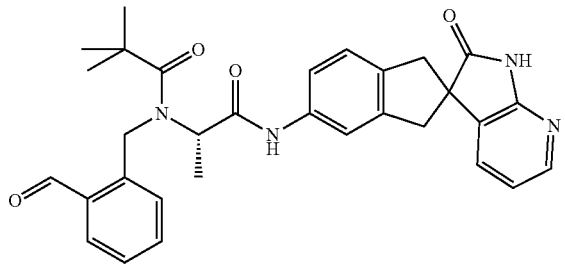 [SMILES: C[C@@H](C(=O)Nc1ccc2c(c1)CC1(C2)C(=O)Nc2ncccc21)N(Cc1ccccc1C=O)C(=O)C(C)(C)C]

Compound 23.1h (53 mg, 0.093 mmol) was dissolved in acetone (2 ml) then p-toluene sulfonic acid monohydrate (19 mg, 0.102 mmol) was added. The mixture was stirred at RT. After 35 min, UPLC-MS indicated the reaction was complete. The mixture was poured into saturated sodium bicarbonate. The aqueous layer was extracted twice with ethyl acetate. The combined organic extracts were dried over sodium sulfate, filtered and the filtrate evaporated to provide compound 23.2h (35 mg, 72%) as a yellow solid. Used directly.

$^1$H NMR (CDCl$_3$, 300 MHz) δ 1.32 (m, 12H), 3.05 (dd, 2H), 3.63 (dd, 2H), 4.74 (m, 2H), 5.15 (m, 1H), 6.82 (dd, 1H), 7.08 (m, 1H), 7.23 (m, 2H), 7.56 (m, 3H), 7.84 (d, 1H), 7.94 (s, 1H), 8.11 (dd, 1H), 10.11 (s, 1H). UPLC-MS rt 0.79 (525 [M+H]$^+$), 74% pure.

Example 34: N-(2-((Methylamino)methyl)benzyl)-N-((2S)-1-oxo-1-((2'-oxo-1,1',2',3-tetrahydrospiro[indene-2,3'-pyrrolo[2,3-b]pyridin]-5-yl)amino)propan-2-yl)pivalamide 23H

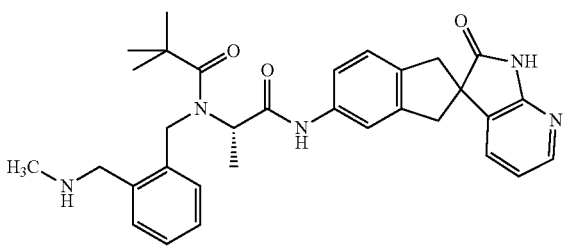 [SMILES: CNCc1ccccc1CN(C(=O)C(C)(C)C)[C@@H](C)C(=O)Nc1ccc2c(c1)CC1(C2)C(=O)Nc2ncccc21]

Compound 23.2h (35 mg, 0.067 mmol) was suspended in dichloromethane (3 ml) and methylamine hydrochloride (11 mg, 0.167 mmol) was added. N,N-Diisopropylethylamine (100 μl, 0.334 mmol) and magnesium sulfate were added and the reaction stirred at RT for 18 h. The mixture was poured into water and extracted three times with dichloromethane. The combined organic extracts were dried over sodium sulfate, filtered and the filtrate evaporated. UPLC-MS rt 0.83 (538 [M+H]$^+$). Used directly. The residue was dissolved in methanol (3 ml) then sodium borohydride (4 mg, 0.080 mmol) was added (gas evolution). The mixture was stirred at RT for 2 h. The mixture was poured into saturated sodium bicarbonate and extracted three times with dichloromethane. The combined organic extracts were washed with brine, dried over sodium sulfate, filtered, and the filtrate evaporated. The residue was purified via flash SPE (2 g SiO$_2$ EtOAc then 5-10% MeOH in DCM to 10% ammonia and MeOH in DCM) to provide compound 23H (8.4 mg, 23%) as a colourless glass. $^1$H NMR (CD$_3$OD, 400 MHz) δ 1.30 (s, 9H), 1.47 (m, 3H), 2.47 (s, 3H), 3.05 (m, 2H), 3.50 (dd, 2H), 3.84 (d, 2H), 4.70 (br s, 2H), 5.04 (m, 1H), 6.87 (ddd, 1H), 7.12 (d, 1H), 7.27 (m, 6H), 7.45 (d, 1H), 8.03 (d, 1H). UPLC-MS (long CSH) rt 1.17 (540 [M+H]$^+$), 95% pure.

N-(2-(Dimethoxymethyl)benzyl)-N-((2R)-1-oxo-1-((2'-oxo-1,1',2',3-tetrahydrospiro[indene-2,3'-pyrrolo[2,3-b]pyridin]-5-yl)amino)propan-2-yl)pivalamide 23.1I

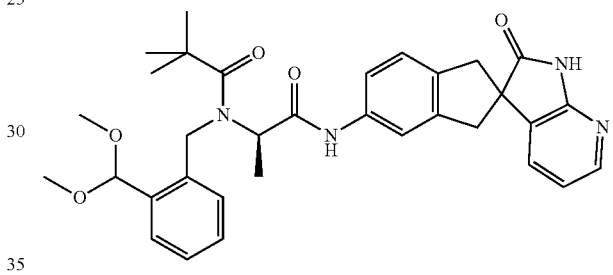

Acid I (~180 mg, assume 0.538 mmol), EDCl.HCl (124 mg, 0.646 mmol) and HOAt (88 mg, 0.646 mmol) were dissolved in dry N,N-dimethylformamide (4 ml). N,N-Diisopropylethylamine (280 μl, 1.61 mmol) and Intermediate E (135 mg, 0.538 mmol) were added and the mixture was stirred at RT for 18 h. The reaction was incomplete so extra EDCl.HCl (124 mg, 0.646 mmol), HOAt (88 mg, 0.646 mmol) and N,N-diisopropylethylamine (280 μl, 1.61 mmol) were added and the reaction stirred at 55° C. for 4 h. The mixture was diluted with ethyl acetate and washed with saturated sodium bicarbonate, three times with water then brine. The organic extract was dried over magnesium sulfate, filtered and the filtrate evaporated. The residue was purified using normal phase chromatography (Biotage Isolera 10 g SiO$_2$ cartridge 80-100% EtOAc in heptanes, then 5 g SiO$_2$ cartridge 10-30% IPA in heptane). The material still contained a minor impurity so was further purified via flash silica chromatography (80-100% EtOAc in heptane to provide compound 23.1I (19 mg, 6%) as a white solid. $^1$H NMR (CDCl$_3$, 300 MHz) δ 1.30 (s, 9H), 1.44 and 1.60 (m, rotamers, 3H), 3.02 (dd, 2H), 3.31 (s, 3H), 3.34 (s, 3H), 3.62 (dd, 2H), 4.74 (m, 1H), 4.97 (q, 2H), 5.38 (s, 1H), 6.80 (m, 1H), 7.06 (m, 1H), 7.18 (s, 2H), 7.29 (m, 2H), 7.49 (m, 2H), 8.13 (dd, 1H), 8.91 (s, 1H). UPLC-MS (short basic) rt 0.90 (571 [M+H]$^+$), 89% pure.

N-(2-Formylbenzyl)-N-((2R)-1-oxo-1-((2'-oxo-1,1', 2',3-tetrahydrospiro[indene-2,3'-pyrrolo[2,3-b]pyridin]-5-yl)amino)propan-2-yl)pivalamide 23.21

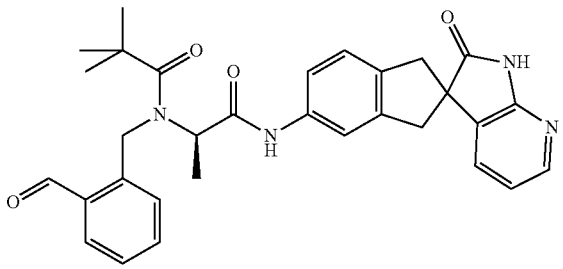 [SMILES: C[C@H](C(=O)Nc1ccc2c(c1)CC1(C2)C(=O)Nc2ncccc21)N(Cc1ccccc1C=O)C(=O)C(C)(C)C]

Compound 23.11 (19 mg, 0.033 mmol) was dissolved in acetone (1 ml) and p-toluene sulfonic acid monohydrate (7 mg, 0.036 mmol) was added. The mixture was stirred at RT. After 20 min, UPLC-MS indicated the reaction was complete. The mixture was poured into saturated sodium bicarbonate. The aqueous layer was extracted three times with ethyl acetate. The combined organic extracts were washed with brine, dried over sodium sulfate, filtered and the filtrate evaporated to provide compound 23.21 (10 mg, 95%) as a yellow solid. Used directly. UPLC-MS rt 0.80 (525 [M+H]+), 80% pure.

Example 35: N-(2-((Methylamino)methyl)benzyl)-N-((2R)-1-oxo-1-((2'-oxo-1,1',2',3-tetrahydrospiro[indene-2,3'-pyrrolo[2,3-b]pyridin]-5-yl)amino)propan-2-yl)pivalamide 231

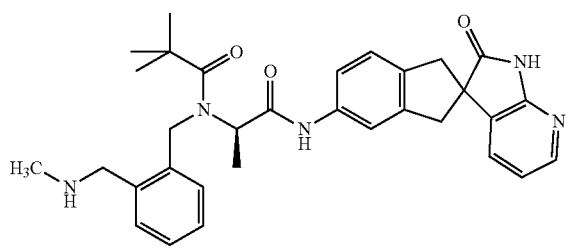 [SMILES: CNCc1ccccc1CN(C(=O)C(C)(C)C)[C@H](C)C(=O)Nc1ccc2c(c1)CC1(C2)C(=O)Nc2ncccc21]

Compound 23.21 (10 mg, 0.019 mmol) was suspended in dichloromethane (1 ml) and methylamine hydrochloride (3 mg, 0.048 mmol) was added. N,N-Diisopropylethylamine (17 µl, 0.095 mmol) and magnesium sulfate were added and the reaction stirred at RT for 18 h. The mixture was poured into water and extracted three times with dichloromethane. The combined organic extracts were dried over sodium sulfate, filtered and the filtrate evaporated. UPLC-MS rt 0.83 (538 [M+H]+). Used directly. The residue was dissolved in methanol (1 ml) and sodium borohydride (1 mg, 0.023 mmol) was added (gas evolution). The mixture was stirred at RT for 3 h. The mixture was poured into saturated sodium bicarbonate and extracted three times with dichloromethane. The combined organic extracts were washed with brine, dried over sodium sulfate, filtered and the filtrate evaporated. The residue was purified via SPE (2 g SiO$_2$ EtOAc then 5-10% MeOH in DCM to 10% ammonia and MeOH in DCM) to provide compound 231 (3 mg, 30%) as a colourless glass. $^1$H NMR (CD$_3$OD, 300 MHz) δ 1.37 (m, 12H), 2.47 (s, 3H), 3.05 (m, 2H), 3.49 (m, 3H), 3.82 (d, 2H), 4.85 (m, 1H), 5.13 (d, 1H), 6.87 (ddd, 1H), 7.12 (dd, 1H), 7.27 (m, 6H), 7.44 (d, 1H), 8.03 (dd, 1H). UPLC-MS (long basic) rt 2.25 (540 [M+H]+), 96% pure.

N-(2-(Dimethoxymethyl)-3-fluorobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 23.1j

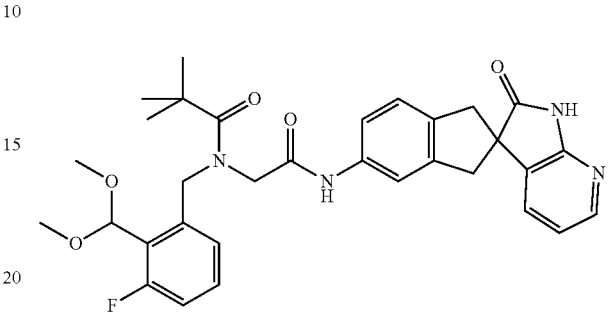

Acid J (~100 mg, assume 0.27 mmol), EDCl.HCl (63 mg, 0.33 mmol) and HOAt (45 mg, 0.33 mmol) were dissolved in dry N,N-dimethylformamide (3 ml). N,N-Diisopropylethylamine (106 mg, 0.80 mmol) and Intermediate E (76 mg, 0.30 mmol) were added and the mixture was stirred at RT for 18 h. The mixture was diluted with ethyl acetate and washed with saturated sodium bicarbonate, three times with water then brine. The organic extract was dried over magnesium sulfate, filtered and the filtrate evaporated. The residue was purified via flash chromatography (10 g SiO$_2$, 10-30% IPA in heptane) to provide compound 23.1j (145 mg, 93%) as a white solid. UPLC-MS (CSH 2-50%) rt 1.30 (573 [M+H]+), 90% pure.

N-(3-Fluoro-2-formylbenzyl)-N-(2-oxo-2-((2'-oxo-1, 1',2',3-tetrahydrospiro[indene-2,3'-pyrrolo[2,3-b] pyridin]-5-yl)amino)ethyl)pivalamide 23.2j

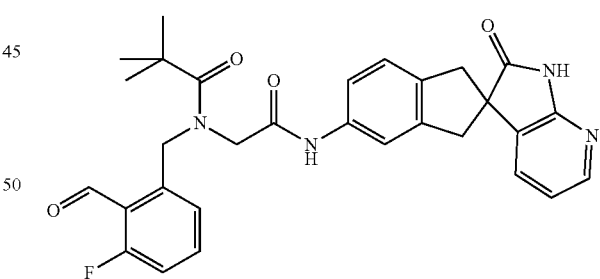

Compound 23.1j (145 mg, 0.25 mmol) was dissolved in acetone (5 ml) and p-toluene sulfonic acid monohydrate (53 mg, 0.275 mmol) was added. The mixture was stirred at RT for 30 min then 1 ml water added. After a further 5 min, UPLC-MS indicated the reaction was complete. The mixture was poured into saturated sodium bicarbonate. The aqueous layer was extracted three times with ethyl acetate. The combined organic extracts were washed with brine, dried over sodium sulfate, filtered and the filtrate evaporated to provide compound 23.2j (75 mg, 57%) as a yellow solid. Used directly. $^1$H NMR (CD$_3$OD, 300 MHz) δ 1.24 (s, 9H), 3.06 (dd, 2H), 3.49 (dd, 2H), 4.12 (br s, 2H), 5.28 (br s, 2H), 6.86 (t, 1H), 7.22 (m, 6H), 7.53 (s, 1H), 7.71 (m, 1H), 8.02 (d, 1H), 10.48 (s, 1H). UPLC-MS (CSH 2-95%) rt 0.87 (527 [M−H]⁻), 80% pure.

Example 36: N-(3-fluoro-2-((methylamino)methyl) benzyl)-N-(2-oxo-2-((2'-oxo-1,1',2',3-tetrahydrospiro [indene-2,3'-pyrrolo[2,3-b]pyridin]-5-yl)amino) ethyl)pivalamide 23J

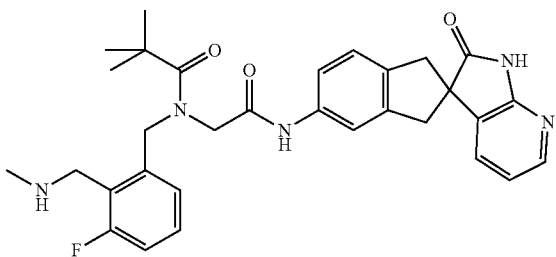 [SMILES: CNCc1c(F)cccc1CN(CC(=O)Nc1ccc2c(c1)CC1(C2)C(=O)Nc2ncccc21)C(=O)C(C)(C)C]

Compound 23.2j (75 mg, 0.142 mmol) was suspended in dichloromethane (10 ml) and methylamine hydrochloride (23 mg, 0.341 mmol) was added. N,N-Diisopropylethylamine (126 μl, 0.712 mmol) and magnesium sulfate were added and the reaction stirred at RT for 18 h. The mixture was filtered and the filtrate evaporated. UPLC-MS (short base) rt 0.86 (542 [M+H]⁺). Used directly. The residue was dissolved in methanol (5 ml) and sodium borohydride (15 mg, 0.526 mmol) was added. The mixture was stirred at RT for 30 min. The mixture was poured into saturated sodium bicarbonate and extracted three times with ethyl acetate. The combined organic extracts were washed with brine, dried over sodium sulfate, filtered and the filtrate evaporated. The residue was purified via flash chromatography (16 g SiO₂ 0-10% MeOH in EtOAc then) to provide compound 23J (54 mg, 68%) as a colourless glass. ¹H NMR (CD₃OD, 300 MHz) δ 1.31 (s, 9H), 2.40 (s, 3H), 3.04 (dd, 2H), 3.49 (dd, 3H), 3.80 (d, 2H), 4.15 (br s, 2H), 5.00 (br s, 2H), 6.88 (dd, 1H), 7.04 (m, 2H), 7.10 (d, 1H), 7.21 (d, 1H), 7.33 (m, 2H), 7.53 (s, 1H), 8.04 (d, 1H). UPLC-MS (long basic) rt 1.87 (544 [M+H]⁺), 97% pure.

N-(2-(Dimethoxymethyl)-4,5-difluorobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 23.1k

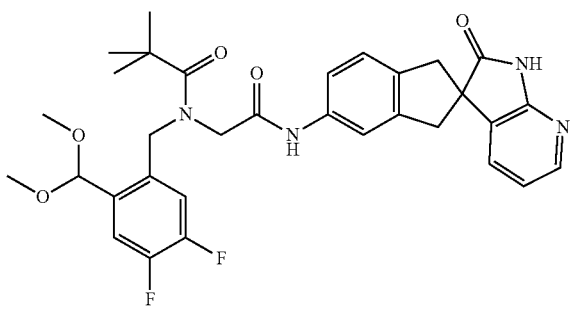 [SMILES: COC(OC)c1cc(F)c(F)cc1CN(CC(=O)Nc1ccc2c(c1)CC1(C2)C(=O)Nc2ncccc21)C(=O)C(C)(C)C]

Acid K (~98 mg, assume 0.27 mmol), EDCl.HCl (68 mg, 0.35 mmol) and HOAt (48 mg, 0.35 mmol) were dissolved in dry N,N-dimethylformamide (2.5 ml). N,N-Diisopropylethylamine (0.19 ml, 1.08 mmol) and Intermediate E (68 mg, 0.27 mmol) were added and the mixture was stirred at RT for 18 h. The mixture was warmed to 50° C. for 3 h then diluted with ethyl acetate and washed with saturated sodium bicarbonate, three times with water then brine. The organic extract was dried over magnesium sulfate, filtered and the filtrate evaporated. The residue was purified via flash chromatography (SiO₂, 7:3-8:2 EtOAc/heptane) to provide compound 23.1k (40 mg, 25%) as a white solid. ¹H NMR (CDCl₃, 400 MHz) δ 1.39 (s, 9H), 3.00 (m, 2H), 3.37 (s, 6H), 3.57 (m, 2H), 4.10 (m, 2H), 5.06 (s, 2H), 5.43 (s, 1H), 6.80 (dd, 1H), 7.04 (m, 2H), 7.20 (m, 2H), 7.42 (s, 1H), 8.13 (dd, 1H), 8.32 (s, 1H), 9.39 (s, 1H). UPLC-MS (long basic) rt 2.13 (593 [M+H]⁺), 72% pure.

N-(4,5-Difluoro-2-formylbenzyl)-N-(2-oxo-2-((2'-oxo-1,1',2',3-tetrahydrospiro[indene-2,3'-pyrrolo[2,3-b]pyridin]-5-yl)amino)ethyl)pivalamide 23.2k

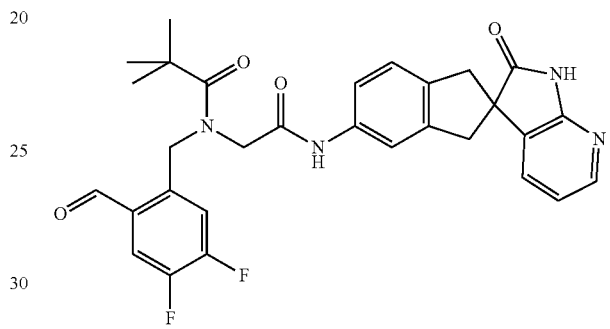

Compound 23.1k (40 mg, 0.068 mmol) was dissolved in acetone (1.5 ml) and p-toluene sulfonic acid monohydrate (14 mg, 0.074 mmol) was added. The mixture was stirred at RT for 1 h. UPLC-MS indicated reaction was complete. The mixture was poured into saturated sodium bicarbonate. The aqueous layer was extracted three times with ethyl acetate. The combined organic extracts were washed with brine, dried over sodium sulfate, filtered and the filtrate evaporated to provide compound 23.2k (34 mg, 92%) as a yellow solid. Used directly. ¹H NMR (CDCl₃, 300 MHz) δ 1.39 (s, 9H), 3.02 (dd, 2H), 3.61 (dd, 2H), 4.10 (br s, 2H), 5.31 (s, 2H), 6.81 (dd, 1H), 7.37 (m, 5H), 8.13 (dd, 1H), 8.31, 8.80 (2 s, 1H), 9.16 (s, 1H), 10.10 (s, 1H). UPLC-MS (short basic) rt 0.81 (547 [M+H]⁺).

Example 37: N-(4,5-difluoro-2-((methylamino) methyl)benzyl)-N-(2-oxo-2-((2'-oxo-1,1',2',3-tetrahydrospiro[indene-2,3'-pyrrolo[2,3-b]pyridin]-5-yl) amino)ethyl)pivalamide 23K

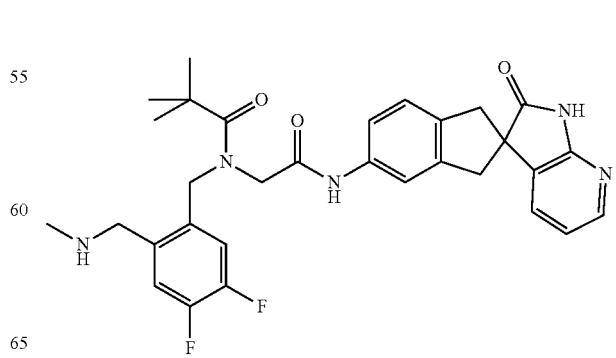

Compound 23.2k (34 mg, 0.062 mmol) was suspended in dichloromethane (2 ml) and methylamine hydrochloride (8.5 mg, 0.125 mmol) was added. N,N-Diisopropylethylamine (50 µl, 0.249 mmol) and magnesium sulfate were added and the reaction stirred at RT for 72 h. The mixture was filtered and the filtrate evaporated. The residue was dissolved in methanol (2 ml) and sodium borohydride (4 mg, 0.093 mmol) was added. The mixture was stirred at RT for 90 min. The mixture was poured into saturated sodium bicarbonate and extracted three times with ethyl acetate. The combined organic extracts were washed with brine, dried over sodium sulfate, filtered and the filtrate evaporated. The residue was purified via prep-HPLC (XBridge C18, ID 19 mm, length 150 mm, Flow Rate 20 ml/min: 40-45% MeCN in pH 10 [NH$_4$HCO$_3$ with NH$_4$OH] over 8 min) to provide compound 23K (3.8 mg, 11%) as a colourless glass. $^1$H NMR (CD$_3$OD, 400 MHz) δ 1.31 (s, 9H), 2.36 (s, 3H), 3.06 (dd, 2H), 3.50 (dd, 2H), 3.71 (s, 2H), 4.25 (m, 2H), 4.89 (br s, 2H), 6.87 (dd, 1H), 7.16 (m, 4H), 7.32 (d, 1H), 7.50 (s, 1H), 8.03 (dd, 1H). UPLC-MS (long basic 2-50%) rt 2.54 (562 [M+H]$^+$), 98% pure.

tert-Butyl (2-((N-(2-oxo-2-((2'-oxo-1,1',2',3-tetrahydrospiro[indene-2,3'-pyrrolo[2,3-b]pyridin]-5-yl)amino)ethyl)pivalamido)methyl)phenyl)carbamate 23.11

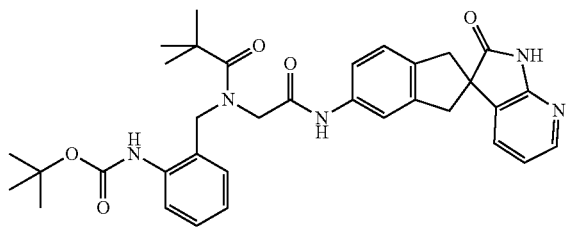 [SMILES: CC(C)(C)OC(=O)Nc1ccccc1CN(CC(=O)Nc1ccc2c(c1)CC1(C2)C(=O)Nc2ncccc21)C(=O)C(C)(C)C]

Acid L (80 mg, 0.22 mmol), EDCl.HCl (50 mg, 0.26 mmol) and HOAt (35 mg, 0.26 mmol) were dissolved in dry N,N-dimethylformamide (4 ml). N,N-Diisopropylethylamine (115 µl, 0.66 mmol) and Intermediate E (55 mg, 0.22 mmol) were added and the mixture was stirred at RT for 4 h. The mixture was diluted with ethyl acetate and washed with saturated sodium bicarbonate. The aqueous was extracted twice with ethyl acetate. The combined organics were washed with brine, dried over magnesium sulfate, filtered and the filtrate evaporated. The residue was purified via flash silica chromatography (1:1 heptane/acetone) to provide compound 23.11 (110 mg, 84%) as a colourless solid. $^1$H NMR (CDCl$_3$, 300 MHz) δ 1.36 (s, 9H), 1.51 (s, 9H), 3.04 (dd, 2H), 3.61 (dd, 2H), 4.06 (br s, 2H), 4.83 (s, 2H), 6.81 (dd, 1H), 7.06 (m, 2H), 7.17 (m, 3H), 7.30 (dt, 1H), 7.51 (s, 1H), 7.75 (br, s, 1H), 8.10 (m, 2H). UPLC-MS (short CSH 2-50%) rt 1.31 (498 [M−Boc+H]$^+$), 88% pure.

Example 38: N-(2-Aminobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 23L

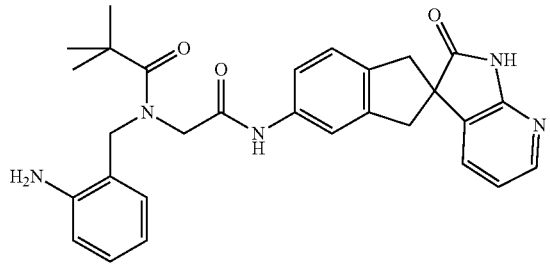 [SMILES: CC(C)(C)C(=O)N(CC(=O)Nc1ccc2c(c1)CC1(C2)C(=O)Nc2ncccc21)Cc1ccccc1N]

Compound 23.11 (20 mg, 0.033 mmol) was dissolved in dichloromethane (1 ml). Trifluoroacetic acid (0.05 ml) was added and the solution was stirred at RT for 7 h. The mixture was poured into water and the aqueous layer was extracted three times with dichloromethane. The organic extract dried over magnesium sulfate, filtered and the filtrate evaporated. The residue was purified via prep-HPLC (HP C18, ID 22 mm, length 150 mm, Flow Rate 16 ml/min: 5-50% MeCN/water/0.1% TFA over 20 min) to provide compound 23L (10.3 mg, 48%) as a colourless glass (TFA salt). $^1$H NMR (CD$_3$OD, 400 MHz) δ 1.34 (s, 9H), 3.09 (dd, 2H), 3.53 (dd, 2H), 4.17 (br s, 2H), 4.61 (br s, 1H), 4.75 (br s, 2H), 6.72 (m, 1H), 6.77 (m, 1H), 6.91 (m, 1H), 7.00 (m, 1H), 7.09 (m, 1H), 7.16 (m, 1H), 7.25 (m, 1H), 7.39 (m, 1H), 7.57 (br s, 1H), 8.07 (m, 1H). HPLC (25 min acidic) rt 12.28, 99% pure. MS 498 [M+H]$^+$ N-(2-Bromobenzyl)-N-(2-((5-methyl-2'-oxo-1,1',2',3-tetrahydrospiro[indene-2,3'-pyrrolo[2,3-b]pyridin]-6-yl)amino)-2-oxoethyl)pivalamide 23.1m

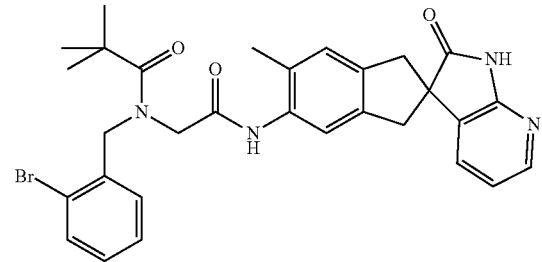 [SMILES: Cc1cc2c(cc1NC(=O)CN(Cc1ccccc1Br)C(=O)C(C)(C)C)CC1(C2)C(=O)Nc2ncccc21]

Acid B (131 mg, 0.40 mmol), EDCl.HCl (96 mg, 0.50 mmol) and HOAt (74 mg, 0.54 mmol) were dissolved in dry N,N-dimethylformamide (2.3 ml). N,N-Diisopropylethylamine (0.19 ml, 1.09 mmol) and Intermediate F (99 mg, 0.37 mmol) were added and the mixture was stirred at RT for 90 h. The mixture was poured into saturated sodium bicarbonate and extracted three times with ethyl acetate. The organic extract was washed with water, 20% aqueous citric acid, water, brine dried over magnesium sulfate, filtered, and the filtrate evaporated. The residue was purified via SPE (5 g SiO$_2$, EtOAc) to provide compound 23.1m (121 mg, 56%) as a pale yellow solid. UPLC-MS (short basic) rt 0.81 (575 [M+H]$^+$), 82%.

N-(2-Cyanobenzyl)-N-(2-((5-methyl-2'-oxo-1,1',2',3-tetrahydrospiro[indene-2,3'-pyrrolo[2,3-b]pyridin]-6-yl)amino)-2-oxoethyl)pivalamide 23.2m

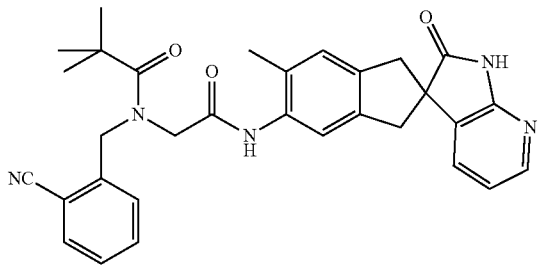

Compound 23.1m (100 mg, 0.17 mmol) was dissolved in dry N,N-dimethylformamide (3 ml) and was degassed by bubbling argon through the solution. Zinc (II) cyanide (36 mg, 0.31 mmol) and tetrakis(triphenylphosphine)palladium (0) (30 mg, 0.026 mmol) were added and the mixture was stirred at 120° C. under microwave irradiation for 1 h. UPLC-MS indicated incomplete conversion. Extra tetrakis (triphenylphosphine)palladium(0) (70 mg, 0.061 mmol) was added and the mixture was stirred at 120° C. under microwave irradiation for 1 h. UPLC-MS indicated complete conversion. The reaction was allowed to stand at RT for 3 days. The mixture was poured into saturated sodium bicarbonate and extracted with ethyl acetate. The organic extract was washed twice with brine, dried over magnesium sulfate, filtered and the filtrate evaporated. The residue was purified via SPE (5 g SiO$_2$ 0-50% EtOAc in DCM) to provide compound 23.2m (40 mg, 44%) as a pale yellow solid. $^1$H NMR (CDCl$_3$, 300 MHz) δ 1.35 (s, 9H), 2.27 (s, 3H), 3.01 (t, 2H), 3.58 (dd, 2H), 4.14 (s, 2H), 5.09 (br s, 2H), 6.80 (dd, 1H), 7.10 (m, 1H), 7.36 (d, 1H), 7.42 (t, 1H), 7.61 (t, 1H), 7.70 (d, 1H), 7.79 (s, 1H), 8.12 (d, 1H), 8.30 (br s, 1H), 9.39 (br s, 1H). UPLC-MS (long basic 20-70%) rt 1.87 (522 [M+H]$^+$), 94% pure.

Example 39: N-(2-(Aminomethyl)benzyl)-N-(2-((5-methyl-2'-oxo-1,1',2,3-tetrahydrospiro[indene-2,3'-pyrrolo[2,3-b]pyridin]-6-yl)amino)-2-oxoethyl)pivalamide 23M

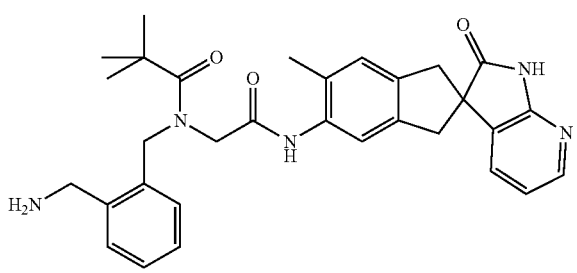 [SMILES: Cc1cc2c(cc1NC(=O)CN(Cc1ccccc1CN)C(=O)C(C)(C)C)CC1(C2)C(=O)Nc2ncccc21]

Compound 23.2m (40 mg, 0.078 mmol) was suspended in methanol (2 ml) and trifluoroacetic acid (0.2 ml) under an argon atmosphere. Palladium on carbon (10%, 15 mg) was added and hydrogen was introduced under balloon pressure. After stirring at RT for 6 h, UPLC-MS showed slow progress so extra palladium on carbon (10%, 15 mg) was added and hydrogen reintroduced at 200 psi and stirred at RT for 18 h.

UPLC-MS analysis showed incomplete conversion so hydrogen was reintroduced at 800 psi and the mixture stirred at RT for 24 h. The mixture was filtered through Celite, washing with methanol and the filtrate evaporated. The residue was purified via SPE (2 g SiO$_2$, 0-10% MeOH in EtOAc then 10% MeOH in DCM) to provide compound 23M (16 mg, 39%) as a colourless glass. $^1$H NMR (CD$_3$OD, 300 MHz) δ 1.32 (s, 9H), 2.20 (s, 3H), 3.01 (m, 2H), 3.47 (d, 2H), 4.22 (s, 2H), 4.47 (br s, 2H), 4.82 (br s, 2H), 6.86 (dd, 1H), 7.14 (m, 3H), 7.41 (m, 4H), 8.03 (dd, 1H). UPLC-MS (short basic) rt 0.67 (526 [M+H]$^+$), 98% pure.

N-(2-(Dimethoxymethyl)benzyl)-N-(2-((5-methyl-2'-oxo-1,1',2',3-tetrahydrospiro[indene-2,3'-pyrrolo[2,3-b]pyridin]-6-yl)amino)-2-oxoethyl)pivalamide 23.1n

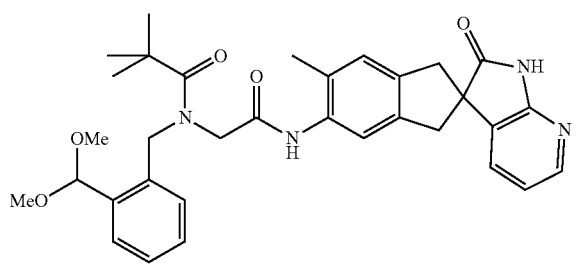 [SMILES: COC(OC)c1ccccc1CN(CC(=O)Nc1cc2c(cc1C)CC1(C2)C(=O)Nc2ncccc21)C(=O)C(C)(C)C]

Intermediate G (78 mg, 0.23 mmol), EDCl.HCl (47 mg, 0.245 mmol) and HOAt (33 mg, 0.245 mmol) were dissolved in dry N,N-dimethylformamide (3 ml). N,N-Diisopropylethylamine (134 µl, 0.754 mmol) and Intermediate F (50 mg, 0.19 mmol) were added and the mixture was stirred at RT for 18 h. UPLC-MS indicated incomplete conversion so extra EDCl.HCl (47 mg, 0.245 mmol), HOAt (33 mg, 0.245 mmol) and N,N-diisopropylethylamine (67 µl, 0.38 mmol) were added and stirring continued at RT for 24 h. The mixture was poured into saturated sodium bicarbonate and extracted with ethyl acetate. The organic extract was washed twice with water, dried over magnesium sulfate, filtered and the filtrate evaporated. The residue was purified via flash silica chromatography (80% EtOAc in heptane) to provide compound 23.1n (68 mg, 63%) as a pale yellow solid. UPLC-MS (short basic) rt 0.85 (569 [M-H]$^-$), 78% pure.

N-(2-Formylbenzyl)-N-(2-((5-methyl-2'-oxo-1,1',2',3-tetrahydrospiro[indene-2,3'-pyrrolo[2,3-b]pyridin]-6-yl)amino)-2-oxoethyl)pivalamide 23.2n

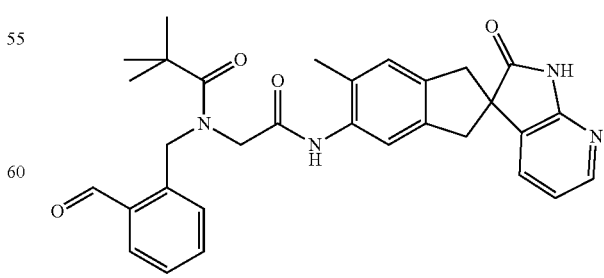

Compound 23.1n (68 mg, 0.12 mmol) was dissolved in acetone (2 ml), then p-toluene sulfonic acid monohydrate (25 mg, 0.13 mmol) was added and the mixture was stirred at RT for 30 min. A blue colour developed. The mixture was poured into saturated sodium bicarbonate. The aqueous layer was extracted twice with dichloromethane. The combined organic extracts were dried over sodium sulfate, filtered and the filtrate evaporated to provide compound 23.2n (56 mg, 89%) as a colourless glass. UPLC-MS (short basic) rt 0.75 (523 [M–H]$^-$), 70% pure.

N-(2-((5-Methyl-2'-oxo-1,1',2',3-tetrahydrospiro [indene-2,3'-pyrrolo[2,3-b]pyridin]-6-yl)amino)-2-oxoethyl)-N-(2-((methylimino)methyl)benzyl)pivalamide 23.3n

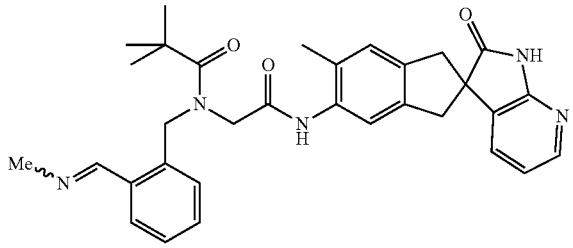

Compound 23.2n (56 mg, 0.107 mmol) was suspended in dichloromethane (2 ml) and methylamine hydrochloride was added (14.5 mg, 0.214 mmol). N,N-Diisopropylethylamine (76 μl, 0.43 mmol) and magnesium sulfate were added and the mixture stirred at RT for 76 h. The mixture was filtered and the filtrate evaporated. The residue was dissolved in dichloromethane and washed with saturated sodium bicarbonate, water, dried over magnesium sulfate, filtered, and the filtrate evaporated to provide compound 23.3n (55 mg, 96%) as a yellow glass. Used directly. UPLC-MS (short basic) rt 0.75 (538 [M+H]$^+$).

Example 40: N-(2-((5-Methyl-2'-oxo-1,1',2',3-tetrahydrospiro[indene-2,3'-pyrrolo[2,3-b]pyridin]-6-yl)amino)-2-oxoethyl)-N-(2-((methylamino)methyl)benzyl)pivalamide 23N

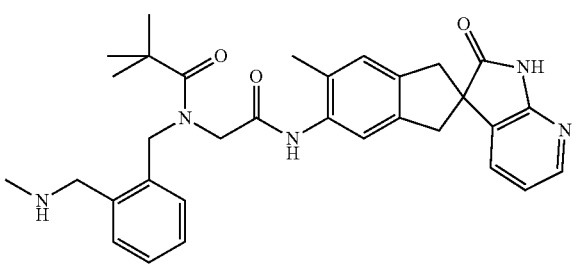 [SMILES: CNCc1ccccc1CN(CC(=O)Nc1cc2c(cc1C)CC1(C2)C(=O)Nc2ncccc21)C(=O)C(C)(C)C]

Compound 23.3n (55 mg, 0.102 mmol) was dissolved in methanol (2 ml), cooled at 0° C. (ice/water) then sodium borohydride (7.8 mg, 0.204 mmol) was added portionwise (gas evolution). The mixture was stirred at RT for 2 h. UPLC-MS indicated the reaction was complete. The mixture was poured into saturated sodium bicarbonate and extracted with dichloromethane. The organic extract was washed with water, dried over magnesium sulfate, filtered and the filtrate evaporated. The residue was purified via flash silica chromatography (0-10% MeOH in DCM) then the material triturated in 5% methanol in diethyl ether to provide product 23N (9.5 mg, 17%) as a colourless glass. $^1$H NMR (CD$_3$OD, 300 MHz) δ 1.32 (s, 9H), 2.19 (s, 3H), 2.70 (s, 3H), 3.05 (d, 2H), 3.45 (d, 2H), 4.20 (s, 2H), 4.47 (br s, 2H), 4.80 (s, 2H), 6.85 (dd, 1H), 7.14 (m, 3H), 7.41 (m, 4H), 8.03 (dd, 1H). UPLC-MS (long basic) rt 1.91 (540 [M+H]$^+$), 96% pure.

Example 41: N-(2-(N-Hydroxycarbamimidoyl)benzyl)-N-(2-oxo-2-((2'-oxo-1,1',2',3-tetrahydrospiro [indene-2,3'-pyrrolo[2,3-b]pyridin]-5-yl)amino) ethyl)pivalamide 230

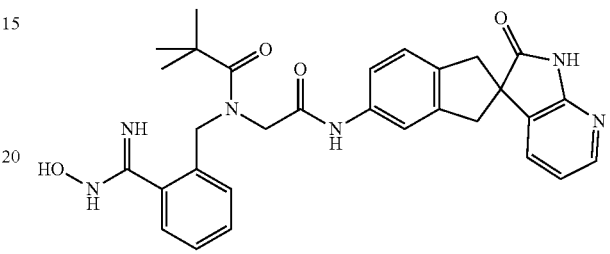

Intermediate K (11 mg, 0.022 mmol), hydroxylamine (50% in water, 73 mg, 2.2 mmol) and triethylamine (331 mg, 3.3 mmol) in ethanol (1.2 ml) was heated at 70° C. under microwave irradiation for 3 h. Methanol was added and the mixture was purified directly by prep-HPLC (HP C18, ID 22 mm, length 150 mm, flow 16 ml/min: 5-50% MeCN water/acetonitrile over 20 min) to provide the desired compound 230 (10 mg, 85%) as a colourless glass. $^1$H NMR (CD$_3$OD, 400 MHz) δ 1.36 (s, 9H), 3.09 (dd, 2H), 3.53 (dd, 2H), 4.14 (br s, 2H), 4.64 (br s, 1H), 5.01 (br s, 2H), 6.90 (dd, 1H), 7.15 (dd, 1H), 7.24 (m, 1H), 7.41 (m, 3H), 7.49 (m, 1H), 7.55 (m, 2H), 8.08 (dd, 1H). HPLC: 99% pure. MS: 541 [M+H]$^+$.

Example 42: N-(2-(Acetimidamidomethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 23P

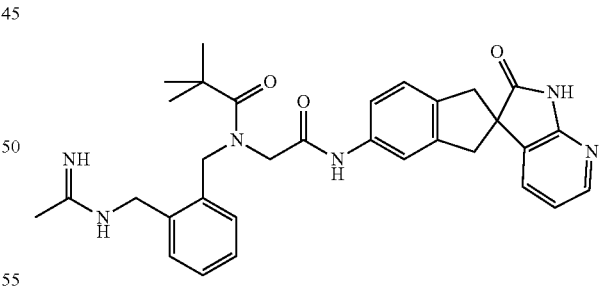

Compound 23A (5 mg, 0.01 mmol) and acetonitrile (8.2 mg, 0.2 mmol) were dissolved in toluene (0.7 ml) then dimethylaluminium chloride (0.01 ml, 0.08 mmol) was added and the mixture was heated at 140° C. under microwave irradiation for 1 h. The mixture was quenched by the addition of three drops of water, diluted with ethyl acetate and filtered through Celite, washing with ethyl acetate. The filtrate was evaporated then purified directly by prep-HPLC (HP C18, ID 22 mm, length 150 mm, flow 16 ml/min: 5-55% MeCN water/acetonitrile 0.1% TFA over 20 min) to provide the desired compound 23P (1.9 mg, 35%) as a colourless glass (TFA salt). $^1$H NMR (CD$_3$OD, 400 MHz) δ 1.36 (s, 9H), 2.28 (s, 3H), 3.10 (dd, 2H), 3.51 (dd, 2H), 4.31 (br s, 2H), 4.53 (br s, 2H), 4.85 (br s, 2H), 6.92 (dd, 1H), 7.17 (dd, 1H), 7.25 (d, 1H), 7.38 (m, 5H), 7.53 (br s, 1H), 8.08 (d, 1H). HPLC: 97% pure. MS: 553 [M+H]+.

Example 43: N-(2-(Guanidinomethyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 23Q

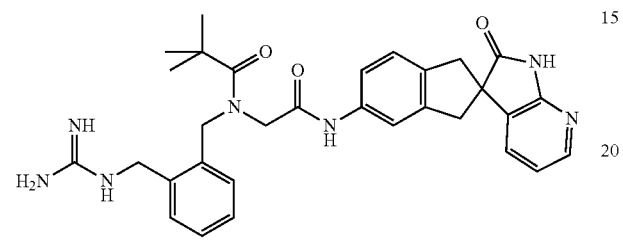

Compound 23A (15 mg, 0.03 mmol) and 4-benzyl-3,5-dimethyl-1H-pyrazole-1-carboximidamide hydrochloride (prepared according to *Tetrahedron Letts*, 2002, p1401; 30 mg, 0.117 mmol) and triethylamine (15 mg, 0.15 mmol) were added to tetrahydrofuran (0.3 ml) and acetonitrile (0.3 ml) and the mixture was heated at 90° C. under microwave irradiation for 1 h. The mixture was diluted with methanol then purified directly by prep-HPLC (HP C18, ID 22 mm, length 150 mm, flow 16 ml/min: 5-45% MeCN water/acetonitrile 0.1% TFA over 20 min) to provide the desired compound 23Q (8.9 mg, 55%) as a colourless glass (TFA salt). $^1$H NMR (CD$_3$OD, 400 MHz) δ 1.36 (s, 9H), 3.10 (dd, 2H), 3.52 (dd, 2H), 4.29 (br s, 2H), 4.48 (m, 2H), 4.85 (br s, 2H), 6.93 (dd, 1H), 7.19 (dd, 1H), 7.24 (d, 1H), 7.36 (m, 5H), 7.52 (br s, 1H), 7.87 (m, 1H), 8.07 (dd, 1H). HPLC: 98% pure. MS: 554 [M+H]$^+$.

General Route E

Synthesis of Intermediate L

SCHEME 24

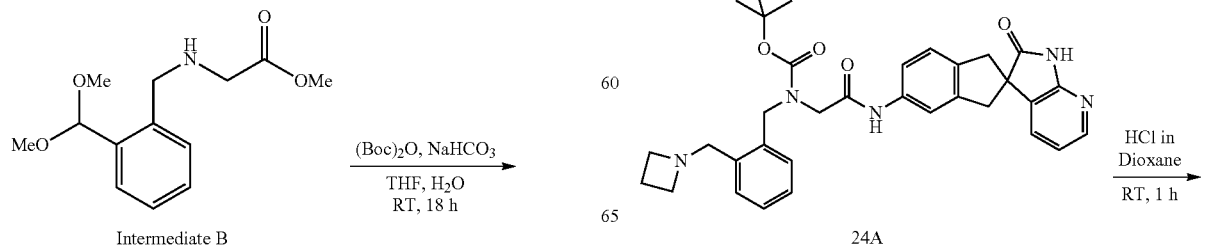

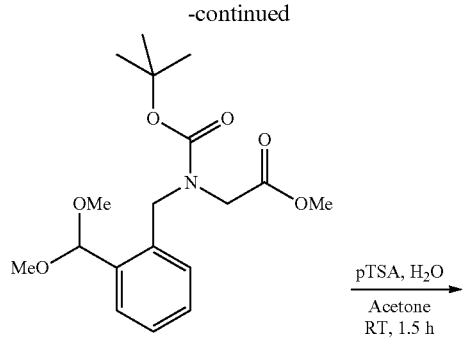

24.1

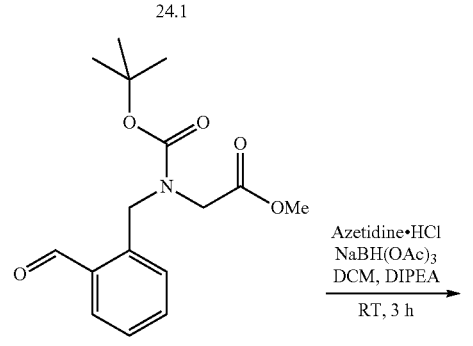

24.2

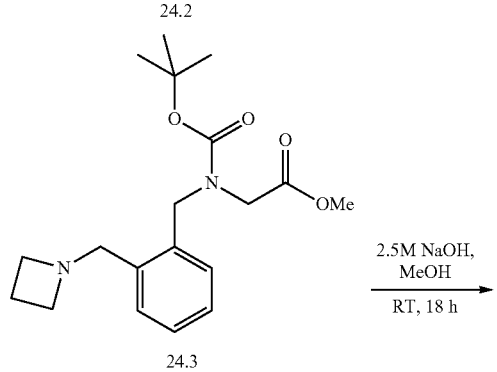

24.3

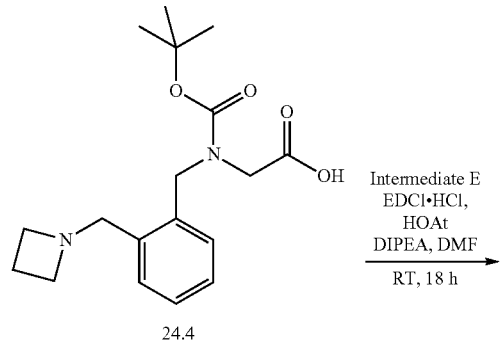

24.4

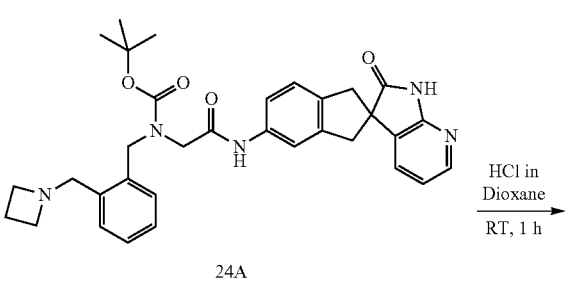

24A

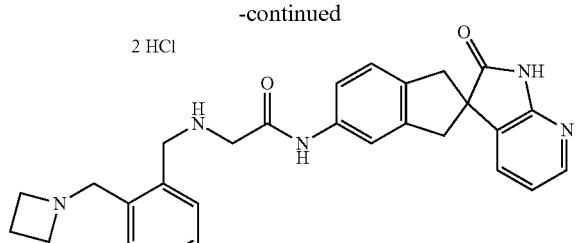

Intermediate L

Methyl 2-((tert-butoxycarbonyl)(2-(dimethoxymethyl)benzyl)amino)acetate 24.1

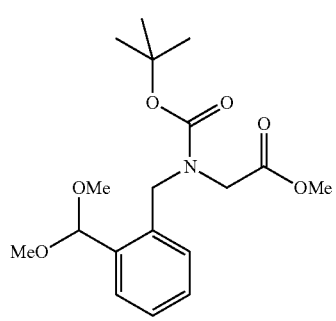 [SMILES: COC(=O)CN(Cc1ccccc1C(OC)OC)C(=O)OC(C)(C)C]

Intermediate B (3.19 g, 12.6 mmol) was dissolved in tetrahydrofuran (20 ml) and saturated sodium bicarbonate solution (10 ml) was added. To this was added di-t-butyl dicarbonate (3.03 g, 13.9 mmol) and the mixture was stirred at RT for 18 h. The mixture was poured into ethyl acetate and the aqueous extracted twice with ethyl acetate. The organic extract was washed with brine, dried over sodium sulfate, filtered, and the filtrate evaporated. The residue was purified via flash silica chromatography (10% EtOAc in heptane with 1% Et₃N) to provide compound 24.1 (2.48 g, 56%) as a yellow oil. ¹H NMR (CDCl₃, 300 MHz) δ 1.45 (s, 9H), 3.29 (d, 6H), 3.69 (s, 3H), 3.76 (s, 1H), 3.90 (s, 1H), 4.66 (d, 2H), 5.40 (s, 1H), 7.27 (m, 3H), 7.51 (d, 1H). UPLC-MS (short basic) rt 0.89 (190 [M−2OMe-Boc+H]⁺), 90% pure.

Methyl 2-((tert-butoxycarbonyl)(2-formylbenzyl)amino)acetate 24.2

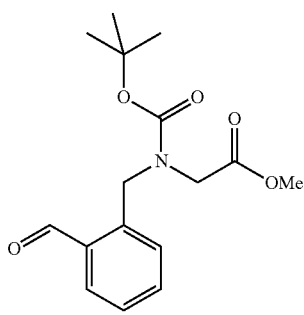 [SMILES: COC(=O)CN(Cc1ccccc1C=O)C(=O)OC(C)(C)C]

Compound 24.1 (2.48 g, 7.0 mmol) was dissolved in acetone (30 ml) and p-toluenesulfonic acid monohydrate (1.46 g, 7.7 mmol) was added. The mixture was stirred at RT for 1.5 h, then poured into saturated sodium bicarbonate. The aqueous layer was extracted five times with ethyl acetate. The organic extract was washed with brine, dried over sodium sulfate, filtered and the filtrate evaporated to provide compound 24.2 (2.14 g, 99%) as a red oil.
¹H NMR (CDCl₃, 300 MHz) δ 1.40 (s, 9H), 3.70 (s, 3H), 3.84 (s, 1H), 3.97 (s, 1H), 4.97 (d, 2H), 7.47 (m, 2H), 7.55 (m, 1H), 7.84 (d, 1H). UPLC-MS (short basic) rt 0.82 (190 fragment).

Methyl 2-((2-(azetidin-1-ylmethyl)benzyl)(tert-butoxycarbonyl)amino)acetate 24.3

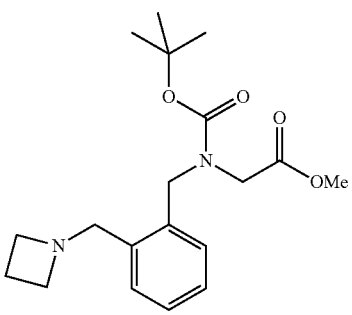 [SMILES: COC(=O)CN(Cc1ccccc1CN1CCC1)C(=O)OC(C)(C)C]

Compound 24.2 (762 mg, 2.48 mmol) was dissolved in dichloromethane (40 ml) and azetidine hydrochloride was added (696 mg, 7.44 mmol) followed by N,N-diisopropylethylamine (1.6 g, 12.4 mmol), sodium sulfate (1.05 g) and sodium triacetoxyborohydride (789 mg, 3.72 mmol). The reaction was stirred at RT for 3 h. The mixture was poured into saturated sodium bicarbonate and extracted three times with dichloromethane. The organic extract was dried over sodium sulfate, filtered, and the filtrate evaporated. The residue was purified via flash silica chromatography (20% EtOAc in heptane with 1% Et₃N) to provide compound 24.3 (597 mg, 69%) as a colourless oil.
¹H NMR (CDCl₃, 300 MHz) δ 1.47 (s, 9H), 2.03 (quin, 2H), 3.14 (t, 4H), 3.52 (d, 2H), 3.71 (s, 3H), 3.81 (s, 1H), 3.92 (s, 1H), 4.64 (d, 2H), 7.21 (m, 4H). UPLC-MS (short basic) rt 0.89 (349 [M+H]⁺), 94% pure.

2-((2-(Azetidin-1-ylmethyl)benzyl)(tert-butoxycarbonyl)amino)acetic Acid 24.4

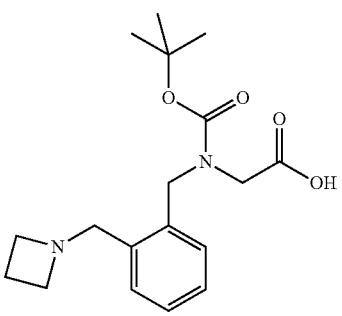 [SMILES: CC(C)(C)OC(=O)N(CC(=O)O)Cc1ccccc1CN1CCC1]

Compound 24.3 (567 mg, 1.63 mmol) was dissolved in methanol, then 2.5M sodium hydroxide (5.2 ml, 13.03 mmol) was added and the reaction mixture stirred at RT for 18 h. The volatiles were removed and 1M HCl (13 ml) added to neutralise the mixture. The volatiles were removed and azeotroped twice with toluene to provide compound 24.4 (assume 1.63 mmol) as a colourless solid. Used directly. UPLC-MS (short basic) rt 0.51 (333 [M–H]$^-$), 97% pure.

Example 44: tert-Butyl 2-(azetidin-1-ylmethyl)benzyl(2-oxo-2-((2'-oxo-1,1',2',3-tetrahydrospiro[indene-2,3'-pyrrolo[2,3-b]pyridin]-5-yl)amino)ethyl)carbamate 24A

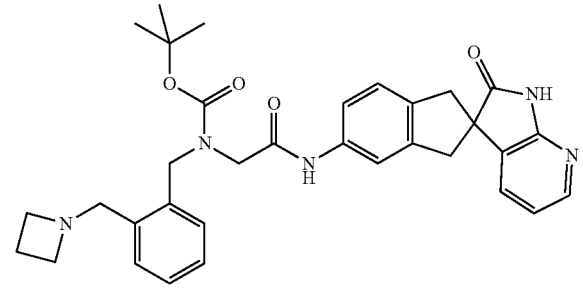 [SMILES: CC(C)(C)OC(=O)N(CC(=O)Nc1ccc2c(c1)CC1(C2)C(=O)Nc2ncccc21)Cc1ccccc1CN1CCC1]

Compound 24.4 (~1.63 mmol) was dissolved in N,N-dimethylformamide (10 ml) under an argon atmosphere, and N,N-diisopropylethylamine (1.7 ml, 9.78 mmol) was added. EDCl.HCl (376 mg, 1.95 mmol) and HOAt (267 mg, 1.95 mmol) were added followed by Intermediate E (409 mg, 1.63 mmol). The mixture was stirred at RT for 18 h, after which time reaction was complete by UPLC-MS. The mixture was poured into saturated sodium bicarbonate. The aqueous layer was extracted twice with ethyl acetate. The combined organic extracts were washed three times with water, then brine, dried over sodium sulfate, filtered and the filtrate evaporated. The residue was purified via column chromatography (300 ml silica, 9:1 EtOAc/MeOH to 9:1 DCM/MeOH then 9:1 DCM/MeOH with ammonia) to provide compound 24A (631 mg, 68%) as a colourless glass. $^1$H NMR (CD$_3$OD, 400 MHz) δ 1.47 (s, 9H), 2.09 (m, 2H), 3.06 (dd, 2H), 3.32 (m, 4H), 3.50 (dd, 2H), 3.71 (m, 2H), 3.92 (br s, 2H), 4.68 (s, 2H), 6.86 (dd, 1H), 7.13 (dd, 1H), 7.27 (m, 6H), 7.80 (s, 1H), 8.03 (dd, 1H). UPLC-MS (long CSH) rt 1.26 (568 [M+H]$^+$), 95% pure.

2-((2-(Azetidin-1-ylmethyl)benzyl)amino)-N-(2'-oxo-1,1',2',3-tetrahydrospiro[indene-2,3'-pyrrolo[2,3-b]pyridin]-5-yl)acetamide dihydrochloride Intermediate L

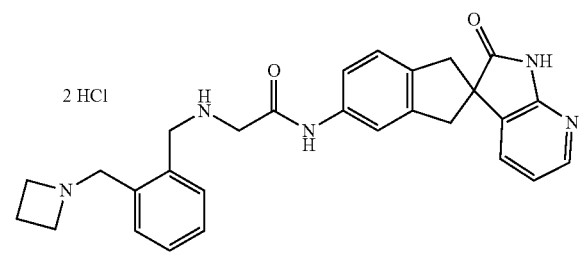 [SMILES: O=C(CNCc1ccccc1CN1CCC1)Nc1ccc2c(c1)CC1(C2)C(=O)Nc2ncccc21]

Compound 24A (199 mg, 0.35 mmol) was dissolved in 1,4-dioxane (5 ml) then 4M HCl in dioxane (4 ml, 16 mmol) was added and the mixture stirred at RT for 1 h, after which the reaction was complete by UPLC-MS. The mixture was diluted with diethyl ether then the solid was isolated by decanting off the liquor. The solid was washed three times with diethyl ether and dried to provide compound Intermediate L (192 mg, quant.) as a colourless solid.
$^1$H NMR (CD$_3$OD, 300 MHz) δ 2.47 (m, 1H), 2.59 (m, 1H), 3.06 (dd, 2H), 3.32 (m, 2H), 3.57 (dd, 2H), 4.21 (m, 2H), 4.32 (m, 2H), 4.53 (s, 2H), 4.70 (s, 2H), 7.27 (m, 2H), 7.49 (d, 1H), 7.62 (m, 6H), 8.12 (dd, 1H). UPLC-MS (long CSH) rt 0.68 (468 [M+H]$^+$), 95% pure.

Synthesis of Compounds 25A-I

SCHEME 25

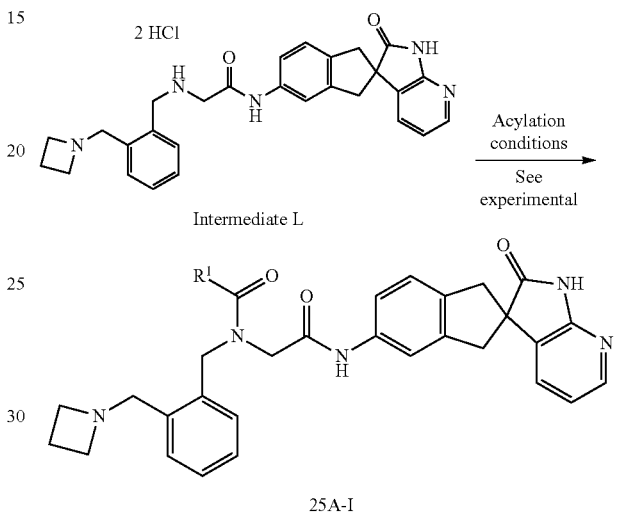

Example 45: N-(2-(Azetidin-1-ylmethyl)benzyl)-3,3,3-trifluoro-N-(2-oxo-2-((2'-oxo-1,1',2',3-tetrahydrospiro[indene-2,3'-pyrrolo[2,3-b]pyridin]-5-yl)amino)ethyl)propanamide 25A

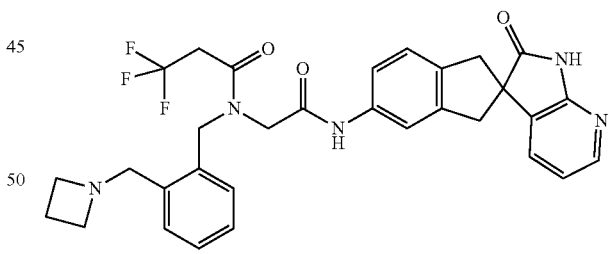

Intermediate L (25 mg, 0.046 mmol) was added to a solution of 3,3,3-trifluoropropionic acid (6.5 mg, 0.051 mmol), EDCl.HCl (11.4 mg, 0.06 mmol) and HOAt (8.2 mg, 0.06 mmol) in N,N-dimethylformamide (5 ml) under an argon atmosphere, then N,N-diisopropylethylamine (30 mg, 0.231 mmol) was added. The mixture was stirred at RT for 18 h, after which time the reaction was complete by UPLC-MS. The mixture was poured into saturated sodium bicarbonate. The aqueous layer was extracted twice with ethyl acetate. The combined organic extracts were washed twice with water, then brine, dried over sodium sulfate, filtered, and the filtrate evaporated. The residue was purified via flash silica chromatography (10-15% MeOH in EtOAc) and then crystallised from 1:20 methanol/diethyl ether to provide compound 25A (6.1 mg, 23%) as a white solid. ¹H NMR (CD₃OD, 400 MHz) δ 2.08 (m, 2H), 3.05 (dd, 2H), 3.24 (m, 2H), 3.33 (m, 1H), 3.54 (m, 5H), 4.17 (s, 2H), 4.77 (br d, 2H), 4.82 (m, 2H), 6.85 (dd, 1H), 7.11 (m, 1H), 7.26 (m, 6H), 7.45 (br d, 1H), 8.04 (d, 1H). UPLC-MS (long CSH) rt 1.03 (578 [M+H]⁺), 98% pure.

Example 46: N-(2-(Azetidin-1-ylmethyl)benzyl)-N-(2-oxo-2-((2'-oxo-1,1',2',3-tetrahydrospiro[indene-2,3'-pyrrolo[2,3-b]pyridin]-5-yl)amino)ethyl)cyclopentanecarboxamide 25B

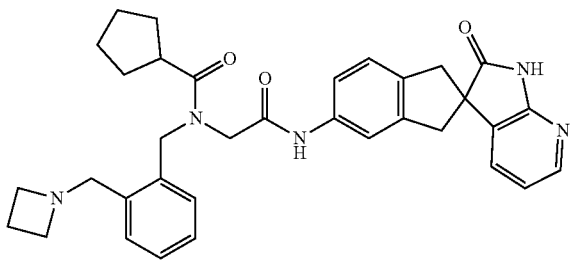 [SMILES: O=C(CN(Cc1ccccc1CN1CCC1)C(=O)C1CCCC1)Nc1ccc2c(c1)CC1(C2)C(=O)Nc2ncccc21]

Intermediate L (27 mg, 0.05 mmol) was added to a solution of cyclopentane carboxylic acid (6.3 mg, 0.055 mmol), EDCl.HCl (13.3 mg, 0.07 mmol) and HOAt (9.6 mg, 0.07 mmol) in dichloromethane (4 ml) under an argon atmosphere, then N,N-diisopropylethylamine (33 mg, 0.25 mmol) was added. The mixture was stirred at RT for 3 days, after which time reaction was complete by UPLC-MS. The mixture was poured into saturated sodium bicarbonate. The aqueous layer was extracted twice with dichloromethane. The combined organic extracts were washed with water, then brine, dried over sodium sulfate, filtered, and the filtrate evaporated. The residue was purified via flash silica chromatography (0-5% MeOH in EtOAc, then 5% MeOH in DCM, then 5% MeOH with ammonia in DCM) to provide crude compound, containing some alkyl impurity. This was purified by dissolving in acetonitrile and washing with heptane. The acetonitrile layer was evaporated. This was further purified via SPE (STMAd 2 g MeOH then ammonia in MeOH, then SCX-2 2 g MeOH then ammonia in MeOH) to provide compound 25B (2.0 mg, 7%) as a white solid. ¹H NMR (CD₃OD, 300 MHz) δ 1.60 (m, 2H), 1.80 (m, 8H), 2.10 (m, 1H), 2.26 (m, 1H), 3.05 (m, 2H), 3.30 (m, 2H), 3.50 (m, 2H), 3.68 (m, 2H), 4.12 (s, 1H), 4.30 (s, 1H), 4.80 (m, 1H), 4.95 (m, 2H), 6.85 (dd, 1H), 7.12 (dd, 1H), 7.30 (m, 6H), 7.49 (m, 1H), 8.03 (dd, 1H). UPLC-MS (long CSH) rt 1.18 (564 [M+H]⁺), 94% pure.

Example 47: N-(2-(Azetidin-1-ylmethyl)benzyl)-1-methyl-N-(2-oxo-2-((2'-oxo-1,1',2',3-tetrahydrospiro[indene-2,3'-pyrrolo[2,3-b]pyridin]-5-yl)amino)ethyl)-cyclopropanecarboxamide 25C

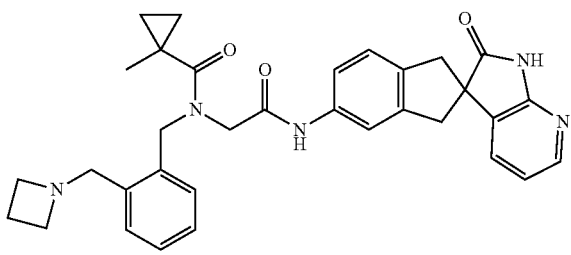 [SMILES: CC1(C(=O)N(CC(=O)Nc2ccc3c(c2)CC2(C3)C(=O)Nc3ncccc32)Cc2ccccc2CN2CCC2)CC1]

Intermediate L (35 mg, 0.065 mmol) was added to a solution of 1-methylcyclopropane carboxylic acid (7 mg, 0.072 mmol), EDCl.HCl (16 mg, 0.085 mmol) and HOAt (12 mg, 0.085 mmol) in N,N-dimethylformamide (1 ml) under an argon atmosphere, then N,N-diisopropylethylamine (57 µl, 0.33 mmol) was added. The mixture was stirred at RT for 3 h, after which time the reaction was complete by UPLC-MS. The mixture was poured into saturated sodium bicarbonate. The aqueous layer was extracted twice with ethyl acetate. The combined organic extracts were washed twice with brine, dried over magnesium sulfate, filtered and the filtrate evaporated. The residue was purified via flash silica chromatography (20% MeOH in EtOAc) and repurified via flash silica chromatography (10% ammonia and MeOH in DCM) to provide compound 25C (1 mg, 3%) as a colourless glass. ¹H NMR (CD₃OD, 300 MHz) δ 0.65 (m, 2H), 0.98 (m, 1H), 1.02 (m, 2H), 1.35 (s, 3H), 2.03 (m, 2H), 3.05 (m, 2H), 3.50 (m, 4H), 3.70 (br s, 2H), 4.00 (br s, 1H), 4.40 (br s, 2H), 5.02 (br s, 2H), 6.85 (dd, 1H), 7.11 (m, 1H), 7.26 (m, 6H), 7.45 (br d, 1H), 8.04 (d, 1H). UPLC-MS (long CSH) rt 1.01 (550 [M+H]⁺), 96% pure.

Example 48: N-(2-(Azetidin-1-ylmethyl)benzyl)-2-fluoro-2-methyl-N-(2-oxo-2-((2'-oxo-1,1',2',3-tetrahydrospiro[indene-2,3'-pyrrolo[2,3-b]pyridin]-5-yl)amino)ethyl)propanamide 25D

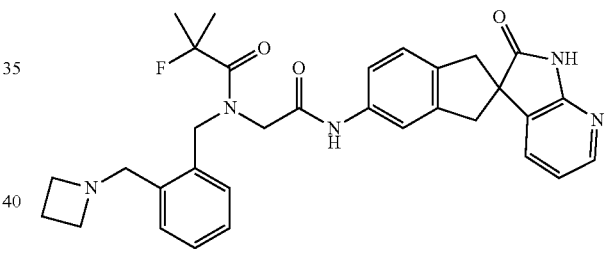

Intermediate L (35 mg, 0.065 mmol) was added to a solution of 2-fluoroisobutyric acid (7.6 mg, 0.072 mmol), EDCl.HCl (16 mg, 0.085 mmol) and HOAt (12 mg, 0.085 mmol) in N,N-dimethylformamide (1 ml) under an argon atmosphere, then N,N-diisopropylethylamine (57 µl, 0.33 mmol) was added. The mixture was stirred at RT for 3 h, after which time the reaction was complete by UPLC-MS. The mixture was poured into saturated sodium bicarbonate. The aqueous layer was extracted twice with ethyl acetate. The combined organic extracts were washed twice with brine, dried over magnesium sulfate, filtered, and the filtrate evaporated. The residue was purified via flash silica chromatography (20% MeOH in EtOAc) and repurified via flash silica chromatography (10% ammonia and MeOH in DCM) to provide compound 25D (3.9 mg, 11%) as a colourless glass. ¹H NMR (CD₃OD, 300 MHz) δ 1.28 (s, 2H), 1.64 (s, 3H), 1.72 (s, 3H), 2.05 (br s, 2H), 3.06 (dd, 2H), 3.50 (dd, 2H), 3.65 (s, 3H), 4.03 (br s, 1H), 4.36 (br s, 1H), 5.07 (br s, 1H), 6.85 (dd, 1H), 7.11 (m, 1H), 7.26 (m, 6H), 7.45 (br d, 1H), 8.04 (d, 1H). UPLC-MS (long CSH) rt 1.06 (556 [M+H]⁺), 92% pure.

Example 49: N-(2-(Azetidin-1-ylmethyl)benzyl)-N-(2-oxo-2-((2'-oxo-1,1',2',3-tetrahydrospiro[indene-2,3'-pyrrolo[2,3-b]pyridin]-5-yl)amino)ethyl)cyclopropanecarboxamide 25E

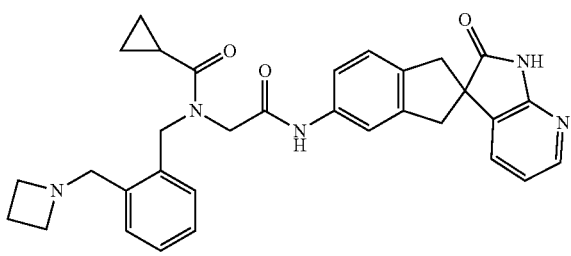 [SMILES: O=C(CN(Cc1ccccc1CN1CCC1)C(=O)C1CC1)Nc1ccc2c(c1)CC1(C2)C(=O)Nc2ncccc21]

Intermediate L (45 mg, 0.083 mmol) was added to a solution of cyclopropane carboxylic acid (7.7 mg, 0.09 mmol), EDCl.HCl (20.6 mg, 0.11 mmol) and HOAt (15 mg, 0.11 mmol) in N,N-dimethylformamide (3 ml) under an argon atmosphere, then N,N-diisopropylethylamine (73 µl, 0.41 mmol) was added. The mixture was stirred at RT for 72 h, after which time reaction was complete by UPLC-MS. The mixture was poured into saturated sodium bicarbonate. The aqueous layer was extracted twice with ethyl acetate. The combined organic extracts were washed twice with brine, dried over magnesium sulfate, filtered, and the filtrate evaporated. The residue was purified via flash silica chromatography (5-10% MeOH in EtOAc then 10% MeOH/NH$_4$OH in EtOAc) then triturated in diethyl ether to provide compound 25E (26 mg, 58%) as a colourless glass. $^1$H NMR (CD$_3$OD, 300 MHz) δ 0.85 (m, 2H), 0.99 (m, 2H), 1.72 (s, 3H), 2.05 (br s, 2H), 3.06 (dd, 2H), 3.50 (dd, 2H), 3.65 (s, 3H), 4.03 (br s, 1H), 4.36 (br s, 1H), 5.07 (br s, 1H), 6.85 (dd, 1H), 7.11 (m, 1H), 7.26 (m, 6H), 7.45 (br d, 1H), 8.04 (d, 1H). UPLC-MS (long CSH) rt 0.96 (536 [M+H]$^+$), 94% pure.

Example 50: Methyl 2-(azetidin-1-ylmethyl)benzyl (2-oxo-2-((2'-oxo-1,1',2',3-tetrahydrospiro[indene-2,3'-pyrrolo[2,3-b]pyridin]-5-yl)amino)ethyl)carbamate 25F

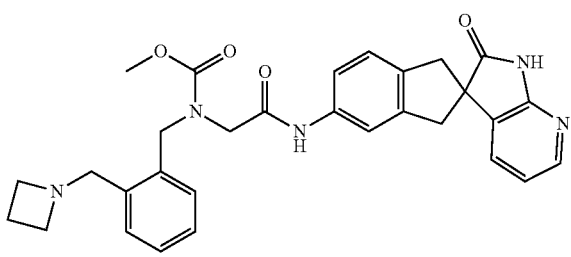 [SMILES: COC(=O)N(CC(=O)Nc1ccc2c(c1)CC1(C2)C(=O)Nc2ncccc21)Cc1ccccc1CN1CCC1]

Intermediate L (34 mg, 0.059 mmol) was stirred vigorously in dichloromethane (2 ml) and saturated sodium bicarbonate (1 ml) then methyl chloroformate (5.5 ml, 0.07 mmol) was added dropwise and the mixture was stirred at RT for 18 h. The mixture was diluted with dichloromethane and washed with saturated sodium bicarbonate. The aqueous was extracted twice with dichloromethane. The organic extracts were dried over sodium sulfate, filtered and the filtrate evaporated. The residue was purified via SPE (2 g SiO$_2$ 0-10% MeOH in EtOAc to 10% MeOH with ammonia in EtOAc) to provide compound 25F (2 mg, 6%) as a colourless glass. $^1$H NMR (CD$_3$OD, 300 MHz) δ 2.23 (m, 2H), 3.05 (m, 2H), 3.49 (dd, 2H), 3.60 (m, 4H), 3.78 (s, 3H), 4.00 (m, 4H), 4.72 (s, 2H), 6.87 (dd, 1H), 7.12 (m, 1H), 7.20 (m, 1H), 7.30 (m, 5H), 7.43 (s, 1H), 8.02 (d, 1H). UPLC-MS (CSH 2-50%) rt 0.55 (526 [M+H]$^+$), 100% pure.

Example 51: N-(2-(Azetidin-1-ylmethyl)benzyl)-N-(2-oxo-2-((2'-oxo-1,1',2',3-tetrahydrospiro[indene-2,3'-pyrrolo[2,3-b]pyridin]-5-yl)amino)ethyl)benzamide 25G

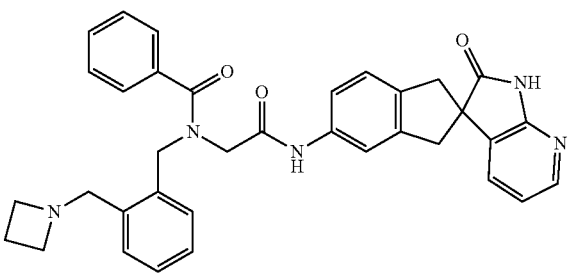 [SMILES: O=C(CN(Cc1ccccc1CN1CCC1)C(=O)c1ccccc1)Nc1ccc2c(c1)CC1(C2)C(=O)Nc2ncccc21]

Intermediate L (35 mg, 0.065 mmol) was added to a solution of benzoic acid (8.1 mg, 0.068 mmol), EDCl.HCl (15 mg, 0.078 mmol) and HOAt (11 mg, 0.078 mmol) in N,N-dimethylformamide (2 ml) under an argon atmosphere, then N,N-diisopropylethylamine (68 µl, 0.39 mmol) was added. The mixture was stirred at RT for 18 h, after which time the reaction was complete by UPLC-MS. The mixture was poured into saturated sodium bicarbonate. The aqueous layer was extracted twice with ethyl acetate. The combined organic extracts were washed three times with water, dried over magnesium sulfate, filtered, and the filtrate evaporated. The residue was purified via flash silica chromatography (0-6% MeOH with ammonia in EtOAc) then triturated in diethyl ether with 5% methanol to provide compound 25G (3 mg, 9%) as a colourless glass. $^1$H NMR (CD$_3$OD, 300 MHz) δ 1.92 (m, 1H), 2.07 (m, 1H), 3.07 (m, 4H), 3.37 (m, 2H), 3.58 (m, 3H), 3.78 (s, 1H), 3.99 (s, 1H), 4.24 (s, 1H), 4.80 (s, 1H), 4.99 (s, 1H), 6.88 (dd, 1H), 7.11 (m, 1H), 7.39 (m, 12H), 8.02 (d, 1H). UPLC-MS (long basic) rt 1.46 (572 [M+H]$^+$), 90% pure.

Example 52: N-(2-(Azetidin-1-ylmethyl)benzyl)-N-(2-oxo-2-((2'-oxo-1,1',2,3-tetrahydrospiro[indene-2,3'-pyrrolo[2,3-b]pyridin]-5-yl)amino)ethyl)picolinamide 25H

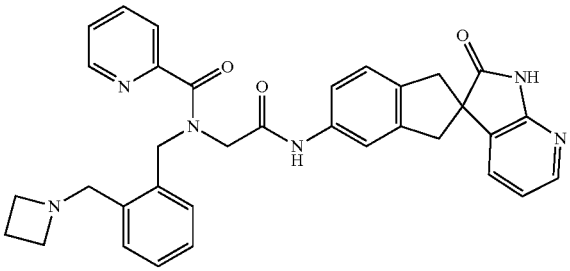 [SMILES: O=C(CN(Cc1ccccc1CN1CCC1)C(=O)c1ccccn1)Nc1ccc2c(c1)CC1(C2)C(=O)Nc2ncccc21]

Intermediate L (35 mg, 0.065 mmol) was added to a solution of 2-picolinic acid (8.0 mg, 0.068 mmol), EDCl.HCl (15 mg, 0.078 mmol) and HOAt (11 mg, 0.078 mmol) in N,N-dimethylformamide (2 ml) under an argon atmosphere, then N,N-diisopropylethylamine (68 µl, 0.39 mmol) was added. The mixture was stirred at RT for 18 h, after which time the reaction was complete by UPLC-MS. The mixture was poured into saturated sodium bicarbonate. The aqueous layer was extracted twice with ethyl acetate. The combined organic extracts were washed three times with water, dried over magnesium sulfate, filtered, and the filtrate evaporated. The residue was purified via flash silica chromatography (0-6% MeOH with ammonia in EtOAc) then azeotroped three times with toluene to provide compound 25H (4.1 mg, 12%) as a colourless glass. $^1$H NMR (CD$_3$OD, 300 MHz) δ 2.00 (m, 2H), 3.07 (m, 3H), 3.27 (s, 1H), 3.50 (m, 3H), 3.72 (s, 1H), 4.23 (s, 2H), 4.89 (s, 2H), 5.00 (s, 2H), 6.88 (dd, 1H), 7.10 (m, 1H), 7.39 (m, 8H), 7.78 (m, 1H), 7.93 (dt, 1H), 8.04 (dd, 1H), 8.57 (m, 1H). UPLC-MS (long basic) rt 1.76 (573 [M+H]$^+$), 93% pure.

Example 53: N-(2-(Azetidin-1-ylmethyl)benzyl)-N-(2-oxo-2-((2'-oxo-1,1',2',3-tetrahydrospiro[indene-2,3'-pyrrolo[2,3-b]pyridin]-5-yl)amino)ethyl)thiazole-4-carboxamide 25I

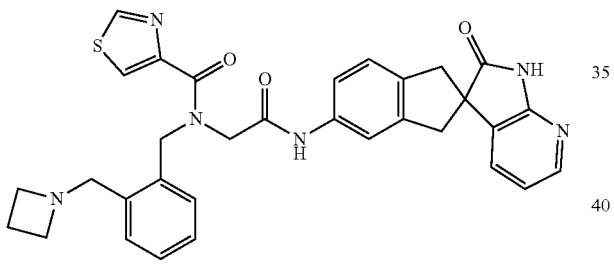

Intermediate L (35 mg, 0.065 mmol) was added to a solution of thiazole-4-carboxylic acid (8.0 mg, 0.061 mmol), EDCl.HCl (15 mg, 0.078 mmol) and HOAt (11 mg, 0.078 mmol) in N,N-dimethylformamide (2 ml) under an argon atmosphere, then N,N-diisopropylethylamine (70 µl, 0.39 mmol) was added. The mixture was stirred at RT for 18 h, after which time the reaction was complete by UPLC-MS. The mixture was poured into saturated sodium bicarbonate. The aqueous layer was extracted twice with ethyl acetate. The combined organic extracts were washed three times with water, dried over magnesium sulfate, filtered, and the filtrate evaporated. The residue was purified via SPE (2 g SiO$_2$ 5% MeOH in EtOAc then 5% MeOH with ammonia in EtOAc) then triturated in diethyl ether to provide compound 25I (3.1 mg, 8%) as a colourless glass. $^1$H NMR (CD$_3$OD, 300 MHz) δ 2.00 (m, 2H), 3.03 (d, 2H), 3.22 (m, 4H), 3.51 (m, 4H), 4.21 (s, 1H), 4.51 (s, 1H), 4.99 (s, 1H), 5.20 (s, 1H), 6.86 (dd, 1H), 7.10 (d, 1H), 7.41 (m, 7H), 8.03 (dd, 1H), 8.23 (m, 1H), 9.00 (d, 1H). UPLC-MS (long basic) rt 1.74 (579 [M+H]$^+$), 92% pure.

Synthesis of Intermediate M

SCHEME 26

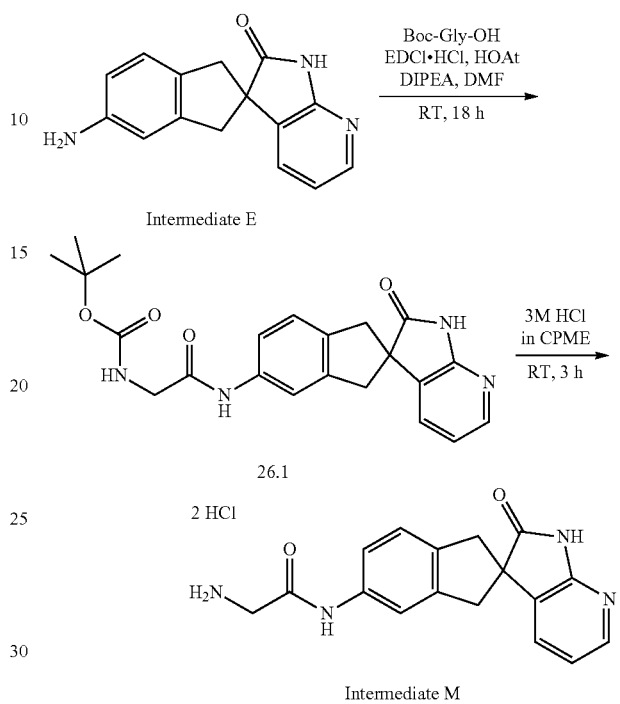

tert-Butyl (2-oxo-2-((2'-oxo-1,1',2',3-tetrahydrospiro[indene-2,3'-pyrrolo[2,3-b]pyridine]-5-yl)amino)ethyl)carbamate 26.1

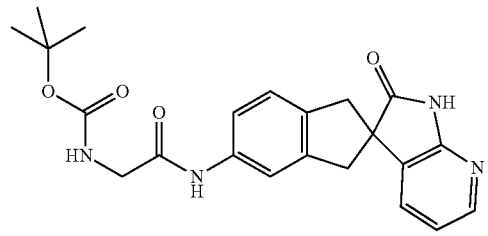 [SMILES: CC(C)(C)OC(=O)NCC(=O)Nc1ccc2c(c1)CC1(C2)C(=O)Nc2ncccc21]

N,N-Diisopropylethylamine (6.24 ml, 35.8 mmol) was added was added to a solution of Boc-Glycine-OH (2.4 g, 13.7 mmol), EDCl.HCl (2.52 g, 13.2 mmol) and HOAt (1.8 g, 13.2 mmol) in N,N-dimethylformamide (25 ml) under an argon atmosphere. Intermediate E (3.0 g, 11.9 mmol) was added, washing in with N,N-dimethylformamide (10 ml). The mixture was stirred at RT for 18 h, after which time the reaction was complete by UPLC-MS. The mixture was poured into saturated sodium bicarbonate. The aqueous layer was extracted three times with ethyl acetate. The combined organic extracts were washed with three times with water, 20% aqueous citric acid, 3 times with water, dried over magnesium sulfate, filtered, and the filtrate evaporated to provide compound 26.1 (4.84 mg, 99%) as a pale yellow glass.

$^1$H NMR (CD$_3$OD, 300 MHz) δ 1.45 (s, 9H), 3.06 (dd, 2H), 3.50 (dd, 2H), 3.84 (br s, 2H), 6.87 (dd, 1H), 7.12 (d,

1H), 7.22 (d, 1H), 7.38 (d, 1H), 7.55 (s, 1H), 8.02 (dd, 1H). UPLC-MS (CSH 2-50%) rt 0.93 (409 [M+H]$^+$).

2-Amino-N-(2'-oxo-1,1',2',3-tetrahydrospiro[indene-2,3'-pyrrolo[2,3-b]pyridine]-5-yl)acetamide dihydrochloride Intermediate M

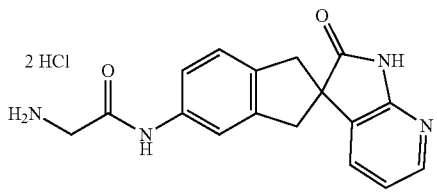 [SMILES: NCC(=O)Nc1ccc2c(c1)CC1(C2)C(=O)Nc2ncccc21]

Compound 26.1 (4.84 ml, 11.9 mmol) was triturated in 3M HCl in cyclopentyl methyl ether (20 ml, 60 mmol) until a flowing suspension was obtained. The mixture was stirred at RT for 3 h after which the reaction was complete by UPLC-MS. The solid was isolated by decanting the solvent, then washing and decanting three times with diethyl ether. The solid was dried to provide Intermediate M (4.62 mg, quant.) as a beige powder. UPLC-MS (short basic) rt 0.43 (309 [M+H]$^+$), 93% pure.

Synthesis of Aldehyde Intermediates N-P

SCHEME 27

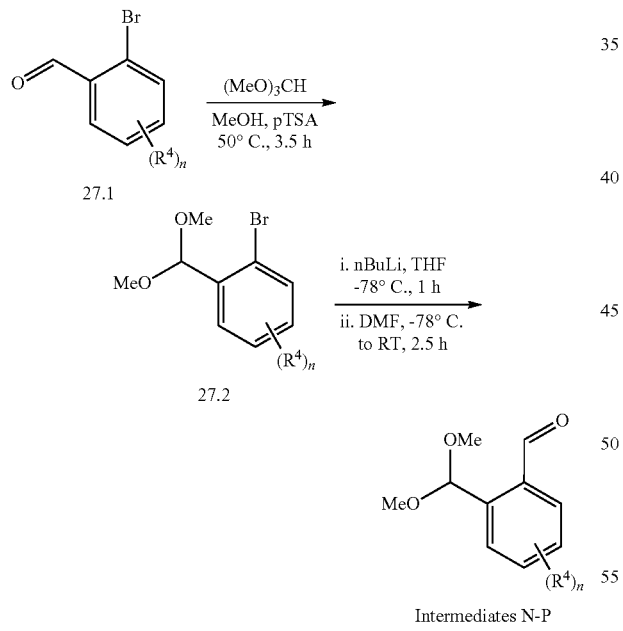

Synthesis of Aldehyde Intermediates N-P

Bromobenzaldehyde 27.1 (3.0 g, 14.78 mmol) was dissolved in methanol (20 ml) then trimethyl orthoformate (10 ml) and p-toluenesulfonic acid monohydrate (270 mg, 1.48 mmol) were added. The solution was warmed to 50° C. for 3.5 h. The mixture was cooled on ice/water, then triethylamine (3 ml) was added. The volatiles were removed, and the mixture diluted with diethyl ether and water. The aqueous layer was extracted twice with diethyl ether. The combined organic extracts were washed with brine, dried over sodium sulfate, filtered, and the filtrate evaporated. The residue was purified via column chromatography (250 ml silica, 10-15% diethyl ether in hexane) to provide compound 27.2 as a colourless oil.

27.2 (1 g, 4.02 mmol) was dissolved in tetrahydrofuran (15 ml) and cooled on dry ice/acetone, under argon. N-Butyllithium (2.5 M in hexane, 2.4 ml, 6.02 mmol) was added dropwise then stirred on dry ice/acetone for 1 h. N,N-Dimethylformamide (0.63 mmol) was added in one portion and stirring continued for 1 h before allowing to RT for 1.5 h. The reaction was poured into water and extracted three times with diethyl ether. The organic layer was washed with brine, dried over magnesium sulfate, filtered and evaporated. The oil obtained was purified via flash silica chromatography if necessary (diethyl ether in hexane) to provide Intermediates N-P.

2-(Dimethoxymethyl)-5-fluorobenzaldehyde Intermediate N

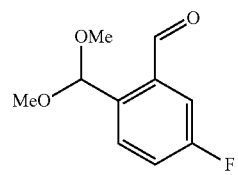 [SMILES: COC(OC)c1ccc(F)cc1C=O]

General method from 2-bromo-4-fluorobenzaldehyde to provide 27.2n (3.7 g, quant.) $^1$H NMR (CDCl$_3$, 300 MHz) δ 3.37 (s, 6H), 5.51 (s, 1H), 7.03 (dt, 1H), 7.30 (dd, 1H), 7.57 (dd, 1H).

27.1n converted to Intermediate N (0.45 g, 57%) after purification (10-15% hexane in diethyl ether). $^1$H NMR (CDCl$_3$, 300 MHz) δ 3.38 (s, 6H), 5.78 (s, 1H), 7.26 (dt, 1H), 7.63 (m, 2H), 10.43 (s, 1H). UPLC (short basic): rt 0.78 (167 [M+H]$^+$) 94% pure.

2-(Dimethoxymethyl)-4-fluorobenzaldehyde Intermediate O

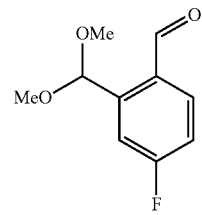

General method from 2-bromo-5-fluorobenzaldehyde to provide 27.2o (4.8 g, quant)$^1$H NMR (CDCl$_3$, 300 MHz) δ 3.38 (s, 6H), 5.50 (s, 1H), 6.93 (dt, 1H), 7.35 (dd, 1H), 7.50 (dd, 1H).

27.2o converted to Intermediate O (0.55 g, 69%) after purification (20% hexane in diethyl ether). $^1$H NMR (CDCl$_3$, 300 MHz) δ 3.39 (s, 6H), 5.92 (s, 1H), 7.16 (dt, 1H), 7.41 (dd, 1H), 7.95 (dd, 1H), 10.33 (s, 1H).

2-(Dimethoxymethyl)-6-fluorobenzaldehyde Intermediate P

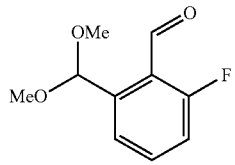

General method from 2-bromo-3-fluorobenzaldehyde to provide 27.2p (3.54 g, 96%) $^1$H NMR (CDCl$_3$, 300 MHz) δ 3.39 (s, 6H), 5.56 (s, 1H), 7.11 (dt, 1H), 7.31 (m, 1H), 7.39 (d, 1H).

27.2p converted to Intermediate P (0.79 g, 99%), no purification needed. $^1$H NMR (CDCl$_3$, 300 MHz) δ 3.42 (s, 6H), 5.99 (s, 1H), 7.16 (m, 1H), 7.56 (m, 2H), 10.51 (s, 1H).

General Synthesis of Intermediates Q-T

SCHEME 28

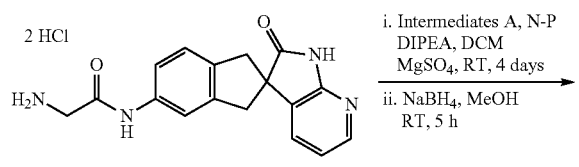

Intermediate M

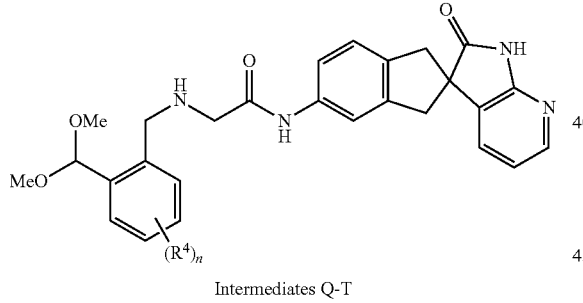

Intermediates Q-T

Intermediate M (385-480 mg, 1.01-1.27 mmol) was suspended in dichloromethane (10-14 ml) then N,N-diisopropylethylamine (0.8-0.98 ml, 4.54-5.8 mmol) was added to give a solution. After 5 min, Intermediate A, N, O or P was added followed by magnesium sulfate (excess). The mixture was stirred at RT for 1 to 5 days, heating to 50° C. if the reaction was incomplete. The mixture was filtered and washed with dichloromethane, and the filtrate evaporated. The crude mixture was dissolved in methanol (8-10 ml) and sodium borohydride (46-77 mg, 1.21-2.03 mmol) was added portionwise over 5 min then stirred at RT for 1 h. Extra sodium borohydride (50 mg, 0.66-1.32 mmol) was added if needed and stirred at RT for 1-3 h. The mixture was poured into water and extracted three times with ethyl acetate. The organic extract was washed with brine, dried over sodium sulfate, filtered, and the filtrate evaporated. The residue was purified via flash silica chromatography to provide compound Intermediates Q-T. Used directly.

2-((2-(Dimethoxymethyl)-5-fluorobenzyl)amino)-N-(2'-oxo-1,1',2,3-tetrahydrospiro[indene-2,3'-pyrrolo[2,3-b]pyridin]-5-yl)acetamide Intermediate Q

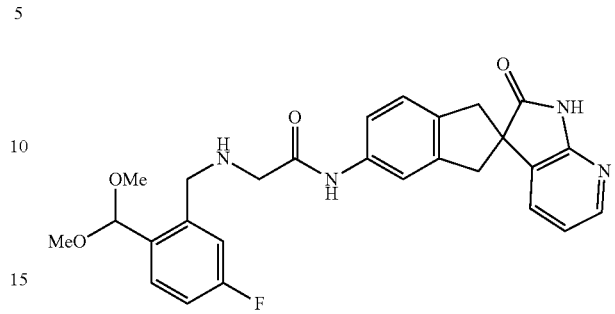

Synthesised as described in SCHEME 28 using Intermediate N (0.2 g, 1.01 mmol), Intermediate M (385 mg, 1.01 mmol), N,N-diisopropylethylamine (0.8 ml, 4.5 mmol) in dichloromethane (10 ml) at RT for 3 days. The imine was reduced using sodium borohydride (46 mg, 1.21 mmol) in methanol (10 ml) for 2.5 h. Purified by flash silica chromatography (Isolera, SiO$_2$ 10-30% IPA in heptane) to provide Intermediate Q (120 mg, 24%) as a colourless glass. $^1$H NMR (CD$_3$OD, 300 MHz) δ 3.05 (dd, 2H), 3.33 (s, 6H), 3.44 (s, 2H), 3.61 (dd, 2H), 3.91 (s, 2H), 5.52 (s, 1H), 6.80 (dd, 1H), 7.00 (td, 1H), 7.09 (m, 2H), 7.21 (d, 1H), 7.39 (d, 1H), 7.56 (dd, 1H), 7.69 (s, 1H), 8.13 (dd, 1H). UPLC-MS (Short Basic) rt 0.78 (489 [M–H]$^-$), 88% pure.

2-((2-(Dimethoxymethyl)-4-fluorobenzyl)amino)-N-(2'-oxo-1,1',2',3-tetrahydrospiro[indene-2,3'-pyrrolo[2,3-b]pyridin]-5-yl)acetamide Intermediate R

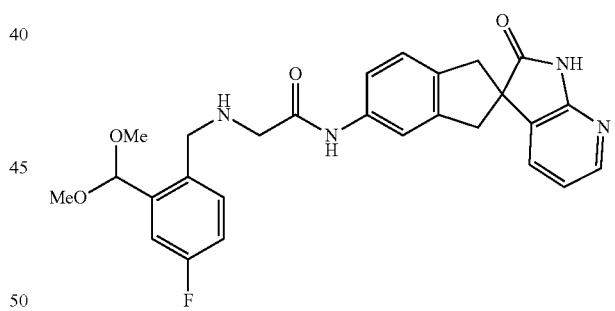

Synthesised as described in SCHEME 28 using aldehyde Intermediate 0 (277 mg, 1.4 mmol), Intermediate M (0.48 g, 1.27 mmol), N,N-diisopropylethylamine (0.98 ml, 5.8 mmol) in dichloromethane (14 ml) at RT for 2 days then 50° C. for 6 h. The imine was reduced using sodium borohydride (77 mg, 2.03 mmol) in methanol (8 ml) for 40 min, extra sodium borohydride was added (50 mg, 1.32 mmol) for 1 h. Purified by flash silica chromatography (5-10% MeOH in EtOAc) to provide Intermediate R (125 mg, 20%) as a colourless glass.

$^1$H NMR (CDCl$_3$, 300 MHz) δ 3.02 (dd, 2H), 3.34 (s, 6H), 3.42 (s, 2H), 3.64 (dd, 2H), 3.87 (s, 2H), 5.59 (s, 1H), 6.80 (dd, 1H), 7.06 (m, 1H), 7.30 (m, 4H), 7.71 (s, 1H), 7.84 (br s, 1H), 8.11 (dd, 1H), 9.43 (s, 1H). UPLC-MS (Short Basic) rt 0.78 (489 [M–H]$^-$), 89% pure.

2-((2-(Dimethoxymethyl)-6-fluorobenzyl)amino)-N-(2'-oxo-1,1',2',3-tetrahydrospiro[indene-2,3'-pyrrolo[2,3-b]pyridin]-5-yl)acetamide Intermediate S

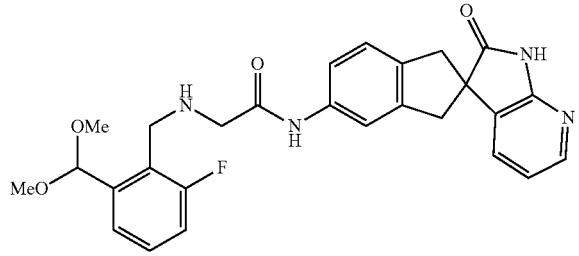 [SMILES: COC(OC)c1cccc(F)c1CNCC(=O)Nc1ccc2c(c1)CC1(C2)C(=O)Nc2ncccc21]

Synthesised as described in SCHEME 28 using aldehyde Intermediate P (277 mg, 1.4 mmol), Intermediate M (0.48 g, 1.27 mmol), N,N-diisopropylethylamine (0.98 ml, 5.8 mmol) in dichloromethane (14 ml) at RT for 2 days. The imine was reduced using sodium borohydride (77 mg, 2.03 mmol) in methanol (8 ml) for 1.5 h. Purified by flash silica chromatography (1.5-10% MeOH in EtOAc) to provide Intermediate S (210 mg, 34%) as a colourless glass. $^1$H NMR (CD$_3$OD, 300 MHz) δ 3.04 (dd, 2H), 3.34 (s, 6H), 3.40 (s, 2H), 3.49 (dd, 2H), 3.96 (s, 2H), 5.59 (s, 1H), 6.85 (dd, 1H), 7.12 (m, 2H), 7.21 (d, 1H), 7.33 (m, 3H), 7.57 (s, 1H), 8.02 (dd, 1H). UPLC-MS (CSH 2-95%) rt 0.40 (427 [M−2OMe+H]$^-$), 90% pure.

2-((2-(Dimethoxymethyl)benzyl)amino)-N-(2'-oxo-1,1',2',3-tetrahydrospiro[indene-2,3'-pyrrolo[2,3-b]pyridin]-5-yl)acetamide Intermediate T

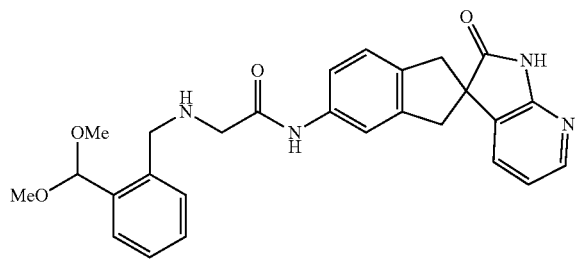 [SMILES: COC(OC)c1ccccc1CNCC(=O)Nc1ccc2c(c1)CC1(C2)C(=O)Nc2ncccc21]

Synthesised as described in SCHEME 28 using Intermediate A (Scheme 1, 252 mg, 1.4 mmol), Intermediate M (484 mg, 1.27 mmol), N,N-diisopropylethylamine (0.88 ml, 5.08 mmol) in dichloromethane (15 ml) for 2 days at RT then 3 days at reflux. The imine was reduced using sodium borohydride (48 mg, 1.27 mmol) in methanol (10 ml) with extra sodium borohydride added at 1 h (25 mg) and 2 h (30 mg) and reacted for total of 5 h. Purified by flash silica chromatography (0-12.5% MeOH in EtOAc) to provide Intermediate T (275 mg, 46%) as a colourless glass. $^1$H NMR (CD$_3$OD, 400 MHz) δ 3.05 (dd, 2H), 3.34 (s, 6H), 3.51 (dd, 2H), 3.92 (s, 2H), 4.91 (s, 2H), 5.62 (s, 1H), 6.86 (dd, 1H), 7.14 (d, 1H), 7.30 (d, 5H), 7.55 (s, 2H), 8.04 (d, 1H). UPLC-MS (CSH 2-50%) rt 0.57 (409 [M−2MeO+H]$^+$), 87% pure.

Alternative—Mesylate Route to Intermediate T

SCHEME 29

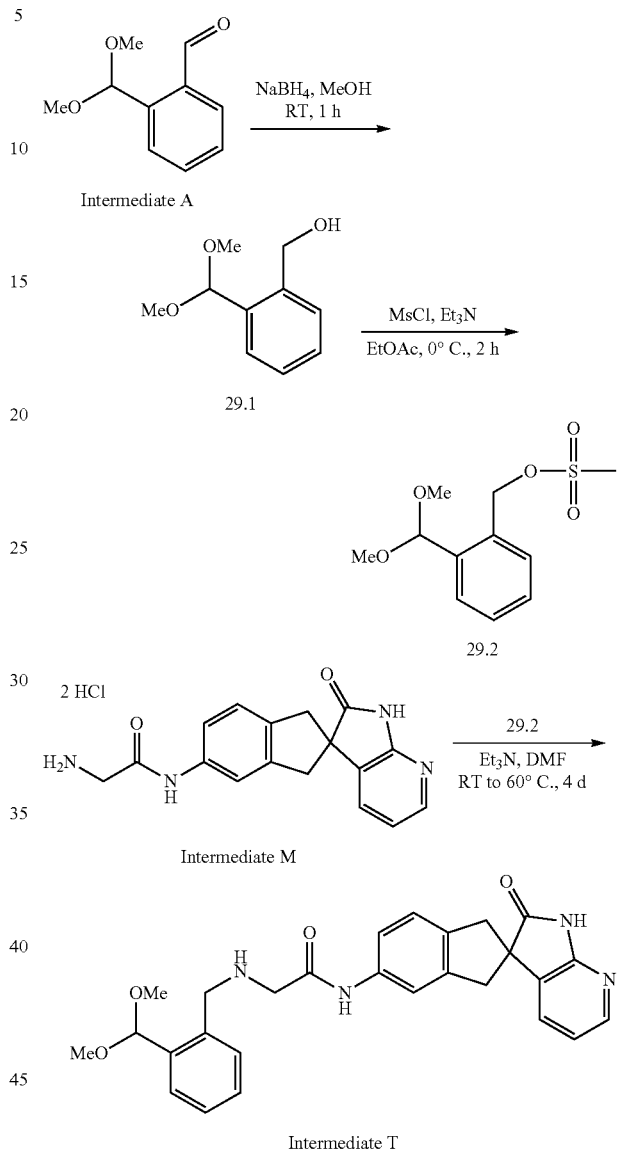

(2-(Dimethoxymethyl)phenyl)methanol 29.1

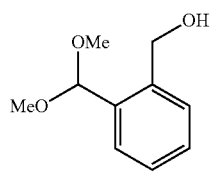 [SMILES: COC(OC)c1ccccc1CO]

Intermediate A (1 g, 5.55 mmol) was dissolved in methanol (30 ml) under argon and cooled on ice/water. Sodium borohydride (231 mg, 6.10 mmol) was added portionwise over 15 min then stirring continued on ice/water for 10 min before allowing to RT for 1 h. Acetic acid (1 ml) was added then the reaction poured into saturated sodium bicarbonate and extracted twice with diethyl ether. The organic layer was washed with saturated sodium bicarbonate, water, dried over magnesium sulfate, filtered and the filtrate evaporated. The residue was purified via flash silica chromatography (50-100% DCM in hexane) to provide compound 29.1 (480 mg, 48%) as a colourless oil. $^1$H NMR (CDCl$_3$, 300 MHz) δ 3.06 (t, 1H), 3.37 (s, 6H), 4.71 (d, 2H), 5.51 (s, 1H), 7.35 (m, 3H), 7.52 (dd, 1H).

2-(Dimethoxymethyl)benzyl Methanesulfonate 29.2

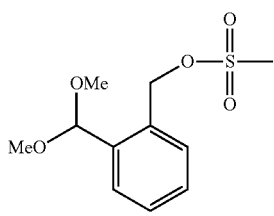 [SMILES: COC(OC)c1ccccc1COS(C)(=O)=O]

Compound 29.1 (240 mg, 1.45 mmol) was dissolved in ethyl acetate (5 ml) under argon, triethylamine (0.37 ml, 2.64 mmol) was added, and cooled on ice/water. Methanesulfonyl chloride (112 µl, 1.45 mmol) was added dropwise then stirring continued on ice/water for 2 h. The reaction was filtered through celite washing with ethyl acetate. The filtrate was washed with saturated sodium bicarbonate, brine, dried over magnesium sulfate, filtered and the filtrate evaporated. The residue was purified via flash silica chromatography (50-100% DCM in hexane) to provide compound 29.2 (340 mg, 99%) as a colourless oil. $^1$H NMR (CDCl$_3$, 400 MHz) δ 2.96 (s, 3H), 3.34 (s, 6H), 5.43 (s, 2H), 5.48 (s, 1H), 7.39 (m, 2H), 7.48 (m, 1H), 7.58 (m, 1H).

2-((2-(Dimethoxymethyl)benzyl)amino)-N-(2'-oxo-1,1',2',3'-tetrahydrospiro[indene-2,3'-pyrrolo[2,3-b]pyridin]-5-yl)acetamide Intermediate T

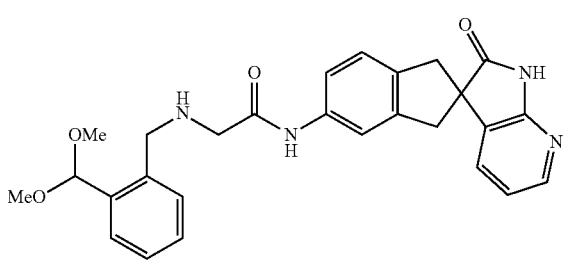 [SMILES: COC(OC)c1ccccc1CNCC(=O)Nc1ccc2c(c1)CC1(C2)C(=O)Nc2ncccc21]

Intermediate M (570 mg, 1.50 mmol) was dissolved in N,N-dimethylformamide (10 ml) and triethylamine (0.84 ml) then 29.2 (390 mg, 1.50 mmol) was added. The mixture was stirred at RT for 24 h then heated at 60° C. for 16 h before allowing to stand for 2 days. The mixture was poured into saturated sodium bicarbonate and the solid that formed was filtered and washed with water and dried to give crude product. The filtrate was extracted three times with ethyl acetate then the organics washed three times with brine, dried over magnesium sulfate, filtered and evaporated to provide compound Intermediate T (90 mg). The crude solid was further purified by flash silica chromatography (0-4% MeOH in DCM) to provide compound Intermediate T (100 mg)—combined yield 27%. UPLC-MS (short basic) 0.75 (471, [M−H]$^-$), 85% pure.

General Route F

SCHEME 30

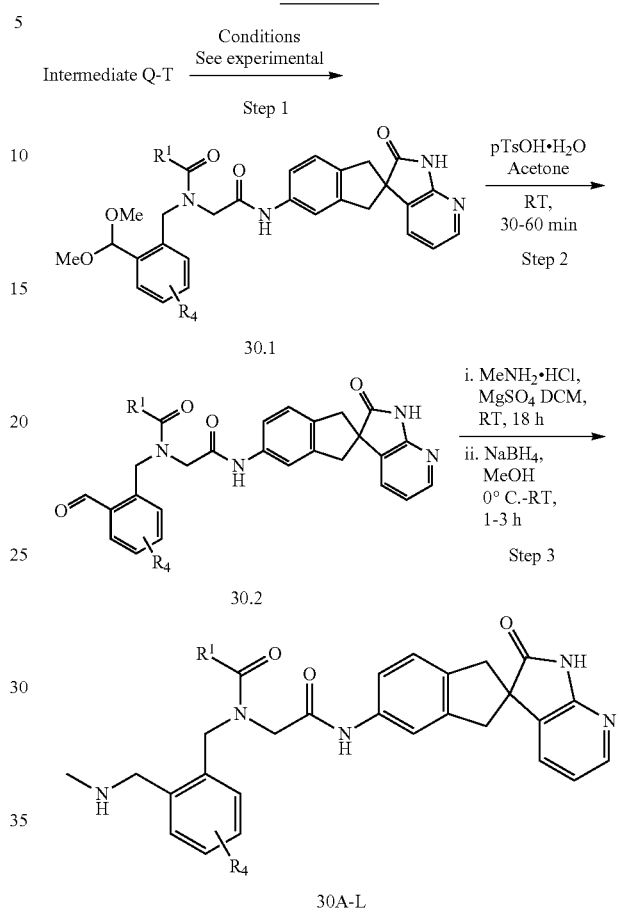

Step 1
A: Acid Chloride

Intermediate Q, R, S or T (0.16-0.25 mmol) was dissolved in dichloromethane (3-10 ml) under an argon atmosphere then N,N-diisopropylethylamine (0.06-0.13 ml, 0.35-0.74 mmol) was added. Acid chloride R$^1$C(O)Cl (0.13-0.24 mmol) was added and the mixture was stirred at RT for 18 h, after which time reaction was complete by UPLC-MS. The mixture was poured into saturated sodium bicarbonate. The aqueous layer was extracted three times with dichloromethane. The combined organic extracts were dried over magnesium sulfate, filtered, and the filtrate evaporated. The residue was purified via flash silica chromatography to provide compounds 30.1.

B: Carboxylic Acid

Intermediate Q, R, S or T (0.106-0.116 mmol) was dissolved in N,N-dimethylformamide (3-4 ml), followed by addition of N,N-diisopropylethylamine (56-61 µl, 0.32-0.35 mmol), carboxylic acid X'COOH (0.116-0.128 mmol) EDCl.HCl (26-30 mg, 0.137-0.151 mmol) and HOAt (19-20.5 mg, 0.137-0.151 mmol). The reaction was stirred at RT or 80° C. for 18 h depending on the acid. The mixture was diluted with ethyl acetate and washed with saturated sodium bicarbonate, three times with water, dried over sodium sulfate, filtered and evaporated. The crude residues were purified via flash silica chromatography to provide compounds 30.1.

Step 2

Compound 30.1 (0.04-0.125 mmol) was dissolved in acetone (1.5-3 ml) then p-toluene sulfonic acid monohydrate (8-26 mg, 0.04-0.14 mmol) was added. The mixture was stirred at RT for 30-60 min then poured into saturated sodium bicarbonate. The aqueous layer was extracted three times with ethyl acetate. The combined organic extracts were washed with brine, dried over sodium sulfate, filtered and the filtrate evaporated to provide compound 30.2.

Step 3

Compound 30.2 (0.04-0.104 mmol) was dissolved in dichloromethane (3-5 ml) and N,N-diisopropylethylamine (46-100 µl, 0.26-0.52 mmol), methylamine hydrochloride (10-18 mg, 0.15-0.26 mmol) and magnesium sulfate was added and the mixture stirred at room temperature for 18 h. The mixture was filtered, washing with DCM. The filtrate was washed with water, dried over magnesium sulfate, filtered and evaporated. The residue was dissolved in methanol then sodium borohydride (2.7-5 mg, 0.073-0.125 mmol) was added (at 0° C. or RT) and reaction stirred at RT for 1-3 h, monitoring by UPLC-MS. Once complete, the reaction was poured into saturated sodium bicarbonate and extracted three times with ethyl acetate or dichloromethane. The combined organics were dried (sodium sulfate), filtered and evaporated. See specific examples for purification methods.

N-(2-(Dimethoxymethyl)-5-fluorobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 30.1a

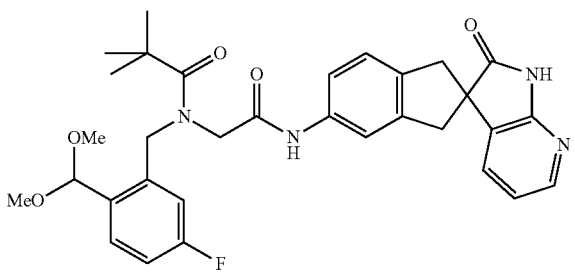 [SMILES: COC(OC)c1ccc(F)cc1CN(CC(=O)Nc1ccc2c(c1)CC1(C2)C(=O)Nc2ncccc21)C(=O)C(C)(C)C]

Synthesised according to General Route F (step 1 A) from Intermediate Q (125 mg, 0.25 mmol) in dichloromethane (3 ml) with N,N-diisopropylethylamine (0.13 ml, 0.74 mmol), pivaloyl chloride (30 µl, 0.24 mmol) and purified via flash silica chromatography (5 g SiO$_2$ SPE, 10-30% IPA in heptane) to provide compound 30.1a (72 mg, 52%) as a colourless glass. $^1$H NMR (CDCl$_3$, 300 MHz) δ 1.31 (s, 9H), 3.03 (dd, 2H), 3.32 (s, 6H), 3.61 (dd, 2H), 4.05 (s, 2H), 4.70 (s, 2H), 5.34 (s, 1H), 6.81 (dd, 1H), 6.89 (dd, 1H), 6.98 (td, 1H), 7.06 (dd, 1H), 7.19 (t, 1H), 7.36 (t, 1H), 7.54 (m, 2H), 8.12 (dd, 1H), 8.56 (br s, 1H), 9.13 (br s, 1H). UPLC-MS (CSH) rt 0.85 (575 [M+H]$^+$), 87% pure.

N-(5-Fluoro-2-formylbenzyl)-N-(2-oxo-2-((2'-oxo-1,1',2',3-tetrahydrospiro[indene-2,3'-pyrrolo[2,3-b]pyridin]-5-yl)amino)ethyl)pivalamide 30.2a

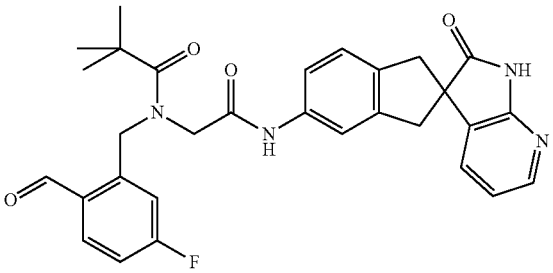 [SMILES: CC(C)(C)C(=O)N(CC(=O)Nc1ccc2c(c1)CC1(C2)C(=O)Nc2ncccc21)Cc1cc(F)ccc1C=O]

Synthesised according to General Route F (step 2) from 30.1a (72 mg, 0.125 mmol), p-toluene sulfonic acid monohydrate (26 mg, 0.14 mmol) in acetone (3 ml) to provide compound 30.2a (55 mg, 83%) as a colourless glass. $^1$H NMR (CDCl$_3$, 300 MHz) δ 1.30 (s, 9H), 3.02 (dd, 2H), 3.61 (dd, 2H), 4.08 (m, 2H), 5.36 (s, 2H), 6.81 (dd, 1H), 7.07 (dd, 2H), 7.22 (m, 2H), 7.36 (d, 1H), 7.54 (s, 1H), 7.90 (dd, 1H), 8.13 (dd, 1H), 8.57 (s, 1H), 9.27 (s, 1H), 10.06 (s, 1H). UPLC-MS (short basic) rt 0.76 (529 [M+H]$^+$), 78% pure.

Example 54: N-(5-Fluoro-2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 30A

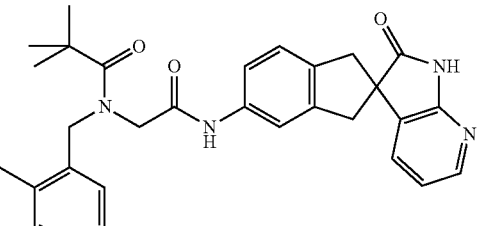

Synthesised according to General Route F (step 3) from 30.2a (55 mg, 0.104 mmol), methylamine hydrochloride (18 mg, 0.26 mmol), N,N-diisopropylethylamine (0.1 ml, 0.52 mmol) in dichloromethane (3 ml) to provide intermediate imine UPLC-MS (short basic) rt 0.84 (542 [M+H]$^+$), which was reduced with sodium borohydride (5 mg, 0.125 mmol) in methanol (2 ml) at RT for 2 h. Purified via prep-HPLC (XBridge C18, ID 19 mm, length 150 mm, Flow Rate 20 ml/min: 40-45% MeCN in pH 10 [NH$_4$HCO$_3$ with NH$_4$OH] over 8 min) then flash silica chromatography (EtOAc to 10% MeOH in DCM to 10% MeOH with ammonia in DCM) to provide compound 30A (8.5 mg, 15%) as a colourless glass. $^1$H NMR (CD$_3$OD, 300 MHz) δ 1.32 (s, 9H), 2.41 (s, 3H), 3.05 (dd, 2H), 3.49 (dd, 2H), 3.71 (s, 2H), 4.13 (br s, 2H), 4.96 (br s, 2H), 6.86 (dd, 1H), 6.98 (m, 2H), 7.11 (dd, 1H), 7.21 (d, 1H), 7.34 (m, 2H), 7.53 (s, 1H), 8.03 (dd, 1H). UPLC-MS (long CSH) rt 1.12 (544 [M+H]$^+$), 99% pure.

N-(2-(Dimethoxymethyl)-4-fluorobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 30.1b

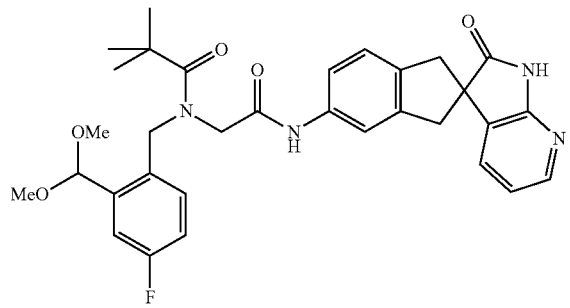 [SMILES: COC(OC)c1cc(F)ccc1CN(CC(=O)Nc1ccc2c(c1)CC1(C2)C(=O)Nc2ncccc21)C(=O)C(C)(C)C]

Synthesised according to General Route F (step 1 A) from Intermediate R (62.5 mg, 0.13 mmol) in dichloromethane (2 ml) with N,N-diisopropylethylamine (67 µl, 0.38 mmol), pivaloyl chloride (16 µl, 0.13 mmol) and purified via flash silica chromatography (5 g SiO$_2$ SPE, 0-30% IPA in heptane) to provide compound 30.1b (49 mg, 67%) as a colourless glass. $^1$H NMR (CDCl$_3$, 300 MHz) δ 1.31 (s, 9H), 3.04 (dd, 2H), 3.33 (s, 6H), 3.62 (dd, 2H), 4.05 (s, 2H), 4.98 (s, 2H), 5.39 (s, 1H), 6.82 (dd, 1H), 7.10 (m, 4H), 7.32 (dd, 1H), 7.54 (s, 1H), 7.88 (s, 1H), 8.11 (dd, 1H). UPLC-MS (short basic) rt 0.89 (573 [M−H]$^-$), 94% pure.

N-(4-Fluoro-2-formylbenzyl)-N-(2-oxo-2-((2'-oxo-1,1',2',3-tetrahydrospiro[indene-2,3'-pyrrolo[2,3-b]pyridin]-5-yl)amino)ethyl)pivalamide 30.2b

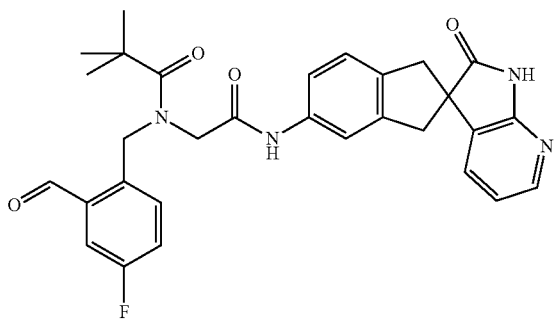 [SMILES: CC(C)(C)C(=O)N(CC(=O)Nc1ccc2c(c1)CC1(C2)C(=O)Nc2ncccc21)Cc1ccc(F)cc1C=O]

Synthesised according to General Route F (step 2) from 30.1b (49 mg, 0.085 mmol), p-toluene sulfonic acid monohydrate (17 mg, 0.094 mmol) in acetone (2 ml) to provide compound 30.2b (43 mg, 95%) as a colourless glass. $^1$H NMR (CDCl$_3$, 300 MHz) δ 1.30 (s, 9H), 3.03 (dd, 2H), 3.32 (s, 2H), 3.62 (dd, 2H), 4.06 (m, 2H), 6.81 (dd, 1H), 7.07 (dd, 1H), 7.18 (m, 2H), 7.32 (m, 2H), 7.53 (s, 1H), 7.58 (dd, 1H), 8.13 (dd, 1H), 8.56 (s, 1H), 9.25 (s, 1H), 10.08 (s, 1H). UPLC-MS (short basic) rt 0.80 (529 [M+H]$^+$), 78% pure.

Example 55: N-(4-Fluoro-2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 30B

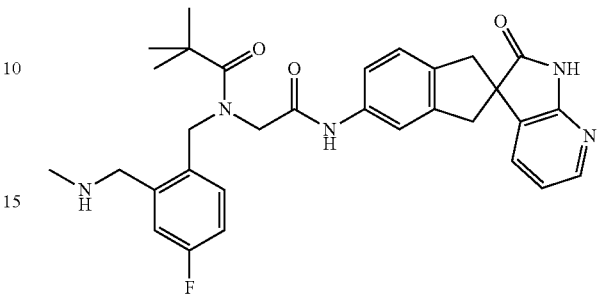

Synthesised according to General Route F (step 3) from 30.2b (43 mg, 0.081 mmol), methylamine hydrochloride (14 mg, 0.203 mmol), N,N-diisopropylethylamine (0.07 ml, 0.41 mmol) in dichloromethane (3 ml) to provide intermediate imine UPLC-MS (short basic) rt 0.82 (542 [M+H]$^+$), which was reduced with sodium borohydride (4 mg, 0.102 mmol) in methanol (2 ml) at RT for 1 h. Purified via prep-HPLC (XBridge C18, ID 19 mm, length 150 mm, Flow Rate 20 ml/min: 30-70% MeCN in pH 10 [NH$_4$HCO$_3$ with NH$_4$OH] over 8 min) to provide compound 30B (13 mg, 28%) as a colourless glass. $^1$H NMR (CD$_3$OD, 300 MHz) δ 1.32 (s, 9H), 2.41 (s, 3H), 3.05 (dd, 2H), 3.50 (dd, 2H), 3.71 (s, 2H), 4.13 (br s, 2H), 4.90 (br s, 2H), 6.86 (dd, 1H), 7.02 (td, 1H), 7.12 (m, 2H), 7.21 (m, 1H), 7.34 (m, 2H), 7.53 (s, 1H), 8.03 (dd, 1H). UPLC-MS (long CSH) rt 1.10 (544 [M+H]$^+$), 96% pure.

N-(2-(Dimethoxymethyl)-6-fluorobenzyl)-N-(2-oxo-2-((2'-oxo-1,1',2',3-tetrahydrospiro[indene-2,3'-pyrrolo[2,3-b]pyridin]-5-yl)amino)ethyl)pivalamide 30.1c

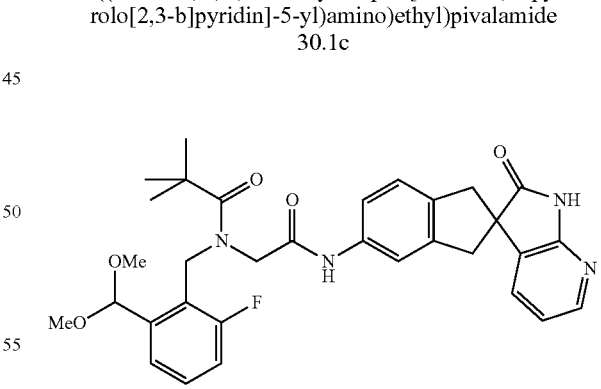

Synthesised according to General Route F (step 1 A) from Intermediate S (50 mg, 0.10 mmol) in dichloromethane (2 ml) with N,N-diisopropylethylamine (54 µl, 0.30 mmol), pivaloyl chloride (14 µl, 0.11 mmol) and purified via flash silica chromatography (5 g SiO$_2$ SPE, 20-100% EtOAc in heptane to 10% MeOH in EtOAc) to provide compound 30.1c (53 mg, 92%) as a colourless glass. UPLC-MS (short basic) rt 0.77 (573 [M−H]$^-$).

253

N-(2-Fluoro-6-formylbenzyl)-N-(2-oxo-2-((2'-oxo-1,1',2',3-tetrahydrospiro[indene-2,3'-pyrrolo[2,3-b]pyridin]-5-yl)amino)ethyl)pivalamide 30.2c

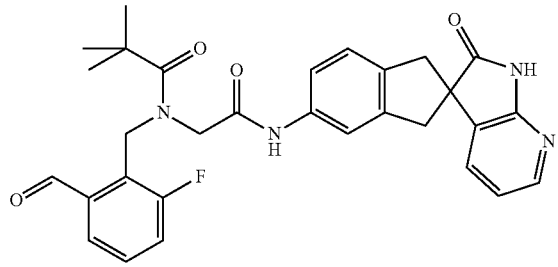 [SMILES: CC(C)(C)C(=O)N(CC(=O)Nc1ccc2c(c1)CC1(C2)C(=O)Nc2ncccc21)Cc1c(F)cccc1C=O]

Synthesised according to General Route F (step 2) from 30.1c (53 mg, 0.092 mmol), p-toluene sulfonic acid monohydrate (18 mg, 0.094 mmol) in acetone (3 ml) to provide compound 30.2c (35 mg, 95%) as a colourless glass. $^1$H NMR (CD$_3$OD, 300 MHz) δ 1.27 (s, 9H), 3.08 (dd, 2H), 3.30 (dd, 2H), 4.30 (m, 2H), 5.14 (m, 2H), 6.88 (m, 1H), 7.29 (m, 6H), 7.73 (d, 1H), 8.04 (d, 1H), 10.28 (s, 1H). UPLC-MS (CSH 2-50%) rt 1.08 (529 [M+H]$^+$), 92% pure.

Example 56: N-(2-Fluoro-6-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pivalamide 30C

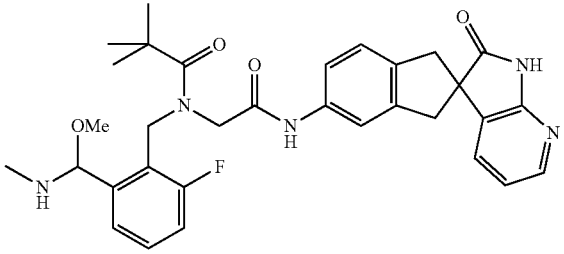 [SMILES: CNC(OC)c1cccc(F)c1CN(CC(=O)Nc1ccc2c(c1)CC1(C2)C(=O)Nc2ncccc21)C(=O)C(C)(C)C]

Synthesised according to General Route F (step 3) from 30.2c (35 mg, 0.066 mmol), methylamine hydrochloride (11 mg, 0.165 mmol), N,N-diisopropylethylamine (0.06 ml, 0.33 mmol) in dichloromethane (15 ml) to provide intermediate imine UPLC-MS (short basic) rt 0.77 (542 [M+H]$^+$), which was reduced with sodium borohydride (4 mg, 0.102 mmol) in methanol (10 ml) at RT for 1 h. Purified via flash chromatography (5-10% MeOH in EtOAc to 10% MeOH with ammonia in EtOAc) to provide compound 30C (10 mg, 28%) as a colourless solid. $^1$H NMR (CD$_3$OD, 300 MHz) δ 1.28 (s, 9H), 2.58 (s, 3H), 3.09 (dd, 2H), 3.49 (dd, 2H), 4.05 (s, 2H), 4.41 (br s, 2H), 4.81 (br s, 2H), 6.85 (dd, 1H), 7.12 (m, 2H), 7.23 (m, 2H), 7.33 (m, 2H), 7.49 (s, 1H), 8.03 (dd, 1H). UPLC-MS (long CSH) rt 1.16 (544 [M+H]$^+$), 95% pure.

254

N-(2-(Dimethoxymethyl)benzyl)-2-methoxy-N-(2-oxo-2-((2'-oxo-1,1',2',3-tetrahydrospiro[indene-2,3'-pyrrolo[2,3-b]pyridine]-5-yl)amino)ethyl)acetamide 30.1 d

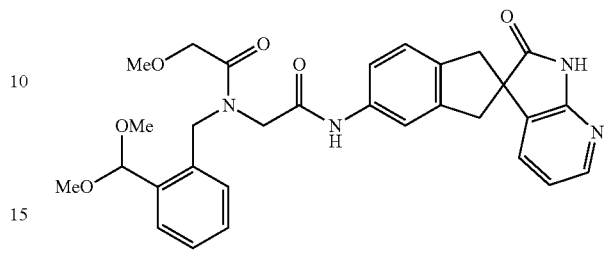

Synthesised according to General Route F (step 1 A) from Intermediate T (55 mg, 0.116 mmol) in dichloromethane (10 ml) with N,N-diisopropylethylamine (61 μl, 0.349 mmol), methoxyacetyl chloride (13.8 mg, 0.123 mmol) and purified via flash silica chromatography (20% heptane in 80% EtOAc, then 0-2% MeOH in EtOAc) to provide compound 30.1 d (50 mg, 87%) as a colourless glass. UPLC-MS (short basic) rt 0.68 (543 [M−H]$^−$), 81% pure.

N-(2-Formylbenzyl)-2-methoxy-N-(2-oxo-2-((2'-oxo-1,1',2',3-tetrahydrospiro[indene-2,3'-pyrrolo[2,3-b]pyridine]-5-yl)amino)ethyl)acetamide 30.2 d

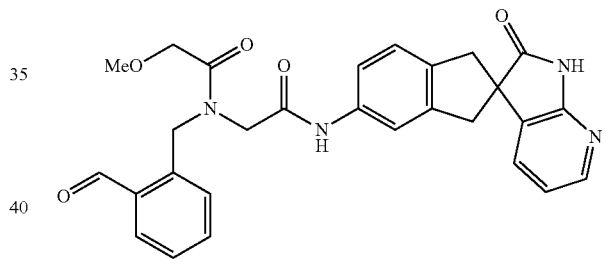

Synthesised according to General Route F (step 2) from 30.1 d (50 mg, 0.092 mmol), p-toluene sulfonic acid monohydrate (19.2 mg, 0.01 mmol) in acetone (2 ml) to provide compound 30.2 d (50 mg, quant.) as a yellow solid. UPLC-MS (short basic) rt 0.60 (499 [M+H]$^+$).

Example 57: 2-Methoxy-N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)acetamide 30D

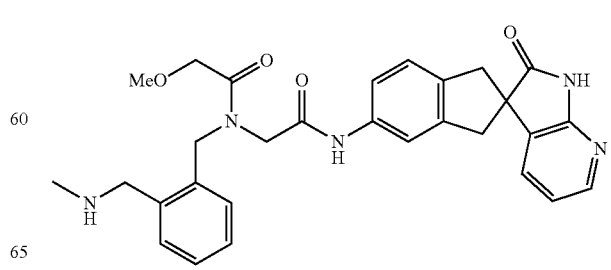

Synthesised according to General Route F (step 3) from 30.2 d (50 mg, 0.092 mmol), methylamine hydrochloride (13.5 mg, 0.20 mmol), N,N-diisopropylethylamine (51 mg, 0.40 mmol) in dichloromethane (4 ml) to provide intermediate imine UPLC-MS (short basic) rt 0.62 (512 [M+H]$^+$), which was reduced with sodium borohydride (7.4 mg, 0.195 mmol) in methanol (4 ml) at RT for 2 h. Purified via SPE (2 g STMAd, MeOH then ammonia in MeOH) to provide compound 30D (4.2 mg, 9%) as a colourless solid. $^1$H NMR (CD$_3$OD, 400 MHz) δ 2.80 (s, 2H), 3.04 (d, 2H), 3.43 (s, 3H), 3.46 (d, 2H), 4.23 (s, 1H), 4.30 (s, 4H), 4.82 (s, 2H), 6.87 (dd, 1H), 7.10 (d, 1H), 7.15 (s, 2H), 7.42 (m, 5H), 8.05 (d, 1H). UPLC-MS (long basic) rt 1.35 (514 [M+H]$^+$), 99% pure.

N-(2-(Dimethoxymethyl)benzyl)-3-methyl-N-(2-oxo-2-((2'-oxo-1,1',2',3-tetrahydrospiro[indene-2,3'-pyrrolo[2,3-b]pyridin]-5-yl)amino)ethyl)oxetane-3-carboxamide 30.1e

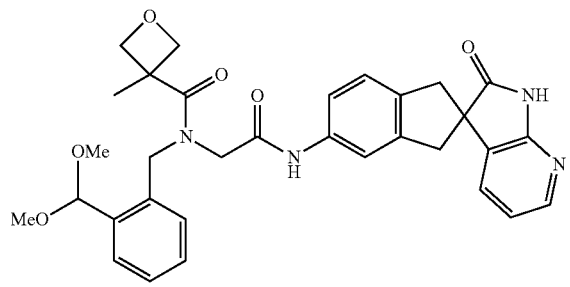 [SMILES: COC(OC)c1ccccc1CN(CC(=O)Nc1ccc2c(c1)CC1(C2)C(=O)Nc2ncccc21)C(=O)C1(C)COC1]

Synthesised according to General Route F (step 1 B) from Intermediate T (55 mg, 0.116 mmol) in N,N-dimethylformamide (4 ml) with N,N-diisopropylethylamine (61 μl, 0.349 mmol), 3-methyl-oxetane-3-carboxylic acid (15 mg, 0.128 mmol), EDCl.HCl (29 mg, 0.151 mmol), HOAt (20.5 mg, 0.151 mmol) and purified via flash silica chromatography (50-100% EtOAc) to provide compound 30.1e (21 mg, 31%) as a colourless glass. UPLC-MS (short basic) rt 0.71 (570 [M−H]$^−$), 80% pure.

N-(2-Formylbenzyl)-3-methyl-N-(2-oxo-2-((2'-oxo-1,1',2',3-tetrahydrospiro[indene-2,3'-pyrrolo[2,3-b]pyridin]-5-yl)amino)ethyl)oxetane-3-carboxamide 30.2e

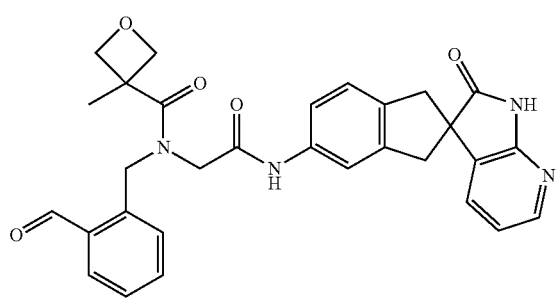 [SMILES: CC1(C(=O)N(CC(=O)Nc2ccc3c(c2)CC2(C3)C(=O)Nc3ncccc32)Cc2ccccc2C=O)COC1]

Synthesised according to General Route F (step 2) from 30.1e (21 mg, 0.037 mmol), p-toluene sulfonic acid monohydrate (7.7 mg, 0.040 mmol) in acetone (1.5 ml) to provide compound 30.2e (19 mg, quant.) as a yellow solid. UPLC-MS (short basic) rt 0.62 (525 [M+H]$^+$).

Example 58: 3-Methyl-N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)oxetane-3-carboxamide 30E

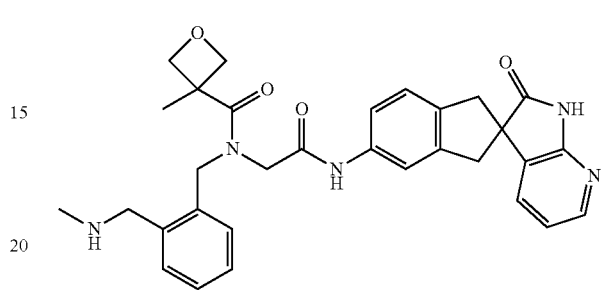

Synthesised according to General Route F (step 3) from 30.2e (19 mg, 0.037 mmol), methylamine hydrochloride (10 mg, 0.15 mmol), N,N-diisopropylethylamine (46 μl, 0.26 mmol) in dichloromethane (3 ml) to provide intermediate imine UPLC-MS (short basic) rt 0.64 (538 [M+H]$^+$), which was reduced with sodium borohydride (2.7 mg, 0.073 mmol) in methanol (2 ml) at RT for 3 h. Purified via flash silica chromatography (0-4% MeOH with ammonia in DCM) to provide compound 30E (3.7 mg, 18%) as a colourless solid. $^1$H NMR (CD$_3$OD, 300 MHz) δ 1.75 (s, 1H), 1.76 (s, 1H), 2.38 (s, 3H), 3.06 (m, 2H), 3.50 (m, 2H), 3.70 (m, 3H), 4.04 (s, 1H), 4.35 (d, 2H), 4.50 (s, 1H), 4.81 (d, 2H), 5.04 (t, 2H), 6.87 (m, 1H), 7.25 (m, 7H), 7.52 (d, 1H), 8.05 (d, 1H). UPLC-MS (long basic) rt 1.45 (540 [M+H]$^+$), 96% pure.

N-(2-(Dimethoxymethyl)benzyl)-2-methoxy-2-methyl-N-(2-oxo-2-((2'-oxo-1,1',2',3-tetrahydrospiro[indene-2,3'-pyrrolo[2,3-b]pyridin]-5-yl)amino)ethyl)propanamide 30.1f

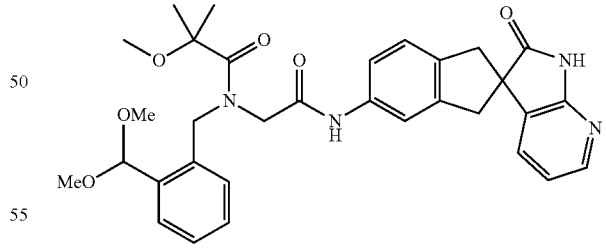

Synthesised according to General Route F (step 1 B) from Intermediate T (55 mg, 0.116 mmol) in N,N-dimethylformamide (4 ml) with N,N-diisopropylethylamine (61 μl, 0.349 mmol), 2-methoxy-2-methylpropanoic acid (15 mg, 0.128 mmol), EDCl.HCl (29 mg, 0.151 mmol), HOAt (20.5 mg, 0.151 mmol) and purified via flash silica chromatography (50-100% EtOAc in heptane) to provide compound 30.1f (25 mg, 37%) as a colourless glass. UPLC-MS (short basic) rt 0.81 (571 [M−H]$^−$), 70% pure.

257

N-(2-Formylbenzyl)-2-methoxy-2-methyl-N-(2-oxo-2-((2'-oxo-1',1',2',3-tetrahydrospiro[indene-2,3'-pyrrolo[2,3-b]pyridin]-5-yl)amino)ethyl)propanamide 30.2f

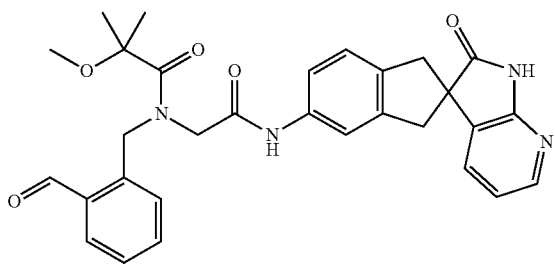 [SMILES: COC(C)(C)C(=O)N(CC(=O)Nc1ccc2c(c1)CC1(C2)C(=O)Nc2ncccc21)Cc1ccccc1C=O]

Synthesised according to General Route F (step 2) from 30.1f (25 mg, 0.044 mmol), p-toluene sulfonic acid monohydrate (9 mg, 0.048 mmol) in acetone (1.5 ml) to provide compound 30.2f (23 mg, quant.) as a yellow solid. UPLC-MS (short basic) rt 0.73 (527 [M+H]$^+$).

Example 59: 2-Methoxy-2-methyl-N-(2-((methylamino)methyl)benzyl)-N-(2-oxo-2-((2'-oxo-1',1',2',3-tetrahydrospiro[indene-2,3'-pyrrolo[2,3-b]pyridin]-5-yl)amino)ethyl)propanamide 30F

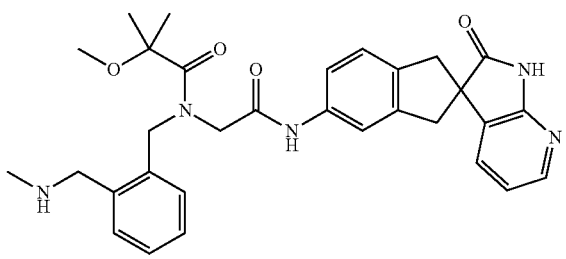 [SMILES: CNCc1ccccc1CN(CC(=O)Nc1ccc2c(c1)CC1(C2)C(=O)Nc2ncccc21)C(=O)C(C)(C)OC]

Synthesised according to General Route F (step 3) from 30.2f (23 mg, 0.044 mmol), methylamine hydrochloride (12 mg, 0.17 mmol), N,N-diisopropylethylamine (54 µl, 0.30 mmol) in dichloromethane (3 ml) to provide intermediate imine UPLC-MS (short basic) rt 0.74 (540 [M+H]$^+$), which was reduced with sodium borohydride (3.3 mg, 0.087 mmol) in methanol (2 ml) at RT for 3 h. Purified via flash silica chromatography (0-4% MeOH with ammonia in DCM) then trituration in ether to provide compound 30F (5.3 mg, 22%) as a colourless solid. $^1$H NMR (CD$_3$OD, 300 MHz) δ 1.47 (d, 6H), 2.40 (d, 3H), 3.06 (m, 2H), 3.28 (d, 3H), 3.49 (dd, 2H), 3.71 (s, 2H), 4.05 (s, 1H), 4.62 (s, 1H), 4.82 (s, 1H), 5.34 (s, 1H), 6.87 (t, 1H), 7.10 (t, 1H), 7.27 (m, 6H), 7.36 (d, 2H), 7.52 (s, 1H), 8.05 (d, 1H). UPLC-MS (long basic) rt 1.66 (542 [M+H]$^+$), 91% pure.

258

N-(2-(Dimethoxymethyl)benzyl)-N-(2-oxo-2-((2'-oxo-1',1',2',3-tetrahydrospiro[indene-2,3'-pyrrolo[2,3-b]pyridin]-5-yl)amino)ethyl)thiazole-4-carboxamide 30.1g

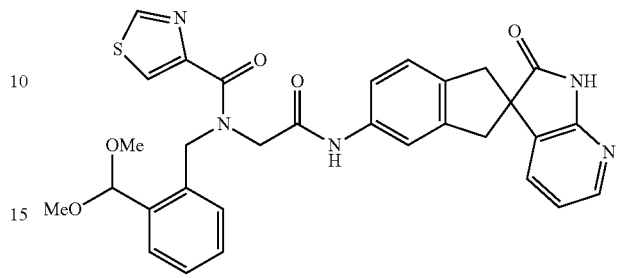

Synthesised according to General Route F (step 1 B) from Intermediate T (55 mg, 0.116 mmol) in N,N-dimethylformamide (4 ml) with N,N-diisopropylethylamine (61 µl, 0.349 mmol), 1,3-thiazole-4-carboxylic acid (16.5 mg, 0.128 mmol), EDCl.HCl (29 mg, 0.151 mmol), HOAt (20.5 mg, 0.151 mmol) and purified via flash silica chromatography (50-100% EtOAc in heptane) to provide compound 30.1g (50 mg, 82%) as a colourless glass. UPLC-MS (short basic) rt 0.73 (582 [M−H]$^−$), 67% pure.

N-(2-Formylbenzyl)-N-(2-oxo-2-((2'-oxo-1',1',2',3-tetrahydrospiro[indene-2,3'-pyrrolo[2,3-b]pyridin]-5-yl)amino)ethyl)thiazole-4-carboxamide 30.2g

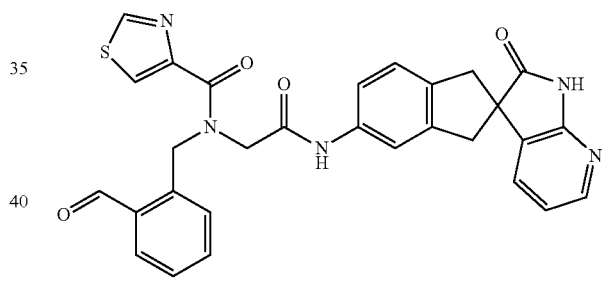

Synthesised according to General Route F (step 2) from 30.1g (50 mg, 0.086 mmol), p-toluene sulfonic acid monohydrate (18 mg, 0.094 mmol) in acetone (2 ml) to provide compound 30.2g (50 mg, quant.) as a yellow solid. UPLC-MS (short basic) rt 0.65 (538 [M+H]$^+$).

Example 60: N-(2-((Methylamino)methyl)benzyl)-N-(2-oxo-2-((2'-oxo-1',1',2',3-tetrahydrospiro[indene-2,3'-pyrrolo[2,3-b]pyridin]-5-yl)amino)ethyl)thiazole-4-carboxamide 30G

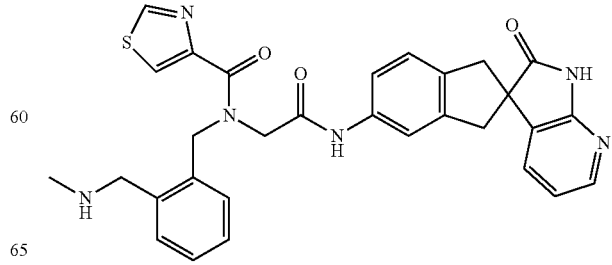

Synthesised according to General Route F (step 3) from 30.2g (50 mg, 0.086 mmol), methylamine hydrochloride (12.5 mg, 0.18 mmol), N,N-diisopropylethylamine (48 mg, 0.37 mmol) in dichloromethane (4 ml) to provide intermediate imine UPLC-MS (short basic) rt 0.66 (551 [M+H]⁺), which was reduced with sodium borohydride (7 mg, 0.18 mmol) in methanol (3 ml) at RT for 2 h. Purified via SPE (STMAd 2 g, MeOH then MeOH with ammonia) to provide compound 30G (5.3 mg, 22%) as a colourless solid. ¹H NMR (CD₃OD, 300 MHz) δ 2.40 (m, 3H), 2.95 (s, 1H), 3.08 (m, 1H), 3.52 (d, 2H), 3.78 (m, 2H), 4.20+4.58 (2 s, 2H rotamers), 5.00+5.22 (2 s, 2H rotamers), 6.87 (t, 1H), 7.12 (d, 1H), 7.23 (d, 2H), 7.30 (m, 3H), 7.40 (m, 2H), 8.05 (d, 1H), 8.25 (s, 1H), 8.98 (d, 1H). UPLC-MS (long basic) rt 1.49 (553[M+H]⁺).

N-(2-(Dimethoxymethyl)benzyl)-2-methyl-N-(2-oxo-2-((2'-oxo-1,1',2',3-tetrahydrospiro[indene-2,3'-pyrrolo[2,3-b]pyridin]-5-yl)amino)ethyl)thiazole-4-carboxamide 30.1h

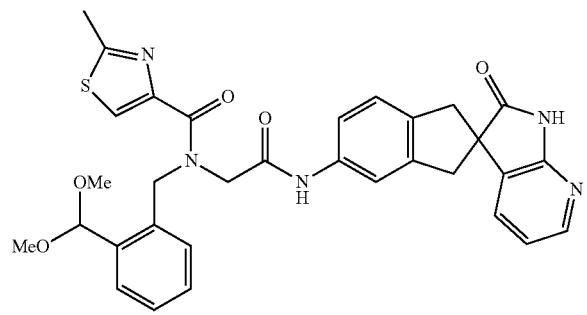 [SMILES: COC(OC)c1ccccc1CN(CC(=O)Nc1ccc2c(c1)CC1(C2)C(=O)Nc2ncccc21)C(=O)c1csc(C)n1]

Synthesised according to General Route F (step 1 B) from Intermediate T (50 mg, 0.106 mmol) in N,N-dimethylformamide (3 ml) with N,N-diisopropylethylamine (56 μl, 0.32 mmol), 2-methyl-1,3-thiazole-4-carboxylic acid (16.5 mg, 0.116 mmol), EDCl.HCl (26 mg, 0.137 mmol), HOAt (19 mg, 0.137 mmol) and purified via flash silica chromatography (50-100% EtOAc in heptane then 2% MeOH in EtOAc) to provide compound 30.1h (55 mg, 87%) as a colourless glass. UPLC-MS (short basic) rt 0.78 (596 [M−H]⁻), 94% pure.

N-(2-Formylbenzyl)-2-methyl-N-(2-oxo-2-((2'-oxo-1,1',2',3-tetrahydrospiro[indene-2,3'-pyrrolo[2,3-b]pyridin]-5-yl)amino)ethyl)thiazole-4-carboxamide 30.2h

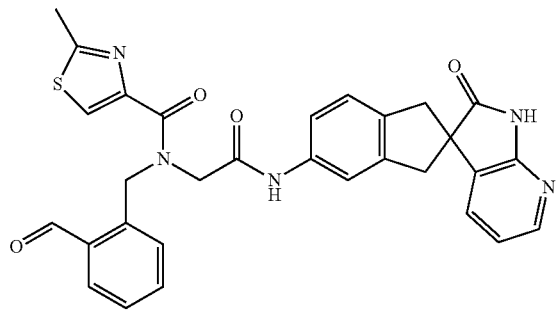 [SMILES: Cc1nc(C(=O)N(CC(=O)Nc2ccc3c(c2)CC2(C3)C(=O)Nc3ncccc32)Cc2ccccc2C=O)cs1]

Synthesised according to General Route F (step 2) from 30.1h (55 mg, 0.092 mmol), p-toluene sulfonic acid monohydrate (19 mg, 0.101 mmol) in acetone (3 ml) with water (0.5 ml) added after 30 min, complete at 1 h, to provide compound 30.2h (51 mg, quant.) as a yellow solid. UPLC-MS (CSH 2-50%) rt 0.97 (552 [M+H]⁺), 89% pure.

Example 61: 2-Methyl-N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)thiazole-4-carboxamide 30H

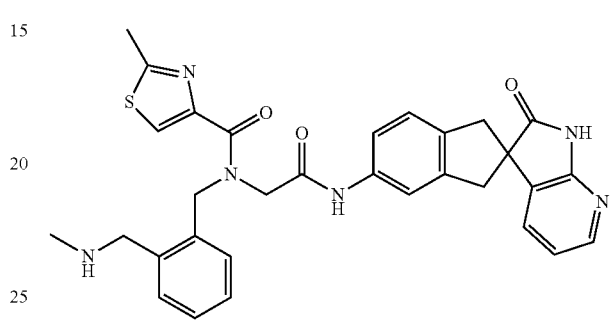

Synthesised according to General Route F (step 3) from 30.2h (51 mg, 0.092 mmol), methylamine hydrochloride (12.5 mg, 0.18 mmol), N,N-diisopropylethylamine (65 μl, 0.37 mmol) in dichloromethane (5 ml) to provide intermediate imine UPLC-MS (short basic) rt 0.73 (565 [M+H]⁺), which was reduced with sodium borohydride (7 mg, 0.18 mmol) in methanol (3 ml) at RT for 3 h. Purified via flash silica chromatography (0-8% MeOH with ammonia in DCM) then triturated in 1:1 diethyl ether/heptane with 2% methanol to provide compound 30H (3.7 mg, 7%) as a colourless solid. ¹H NMR (CD₃OD, 300 MHz) δ 2.52 (s, 3H), 2.70 (s, 3H), 3.02 (s, 1H), 3.07 (s, 1H), 3.50 (dd, 2H), 4.07 (m, 2H), 4.40 (m, 2H), 5.07 (m, 2H), 6.85 (t, 1H), 7.10 (d, 1H), 7.23 (m, 2H), 7.37 (m, 3H), 7.44 (m, 2H), 8.05 (m, 2H). UPLC-MS (long basic) rt 1.32 (567 [M+H]⁺), 92% pure.

N-(2-(Dimethoxymethyl)benzyl)-5-methyl-N-(2-oxo-2-((2'-oxo-1,1',2',3-tetrahydrospiro[indene-2,3'-pyrrolo[2,3-b]pyridin]-5-yl)amino)ethyl)thiazole-4-carboxamide 30.1i

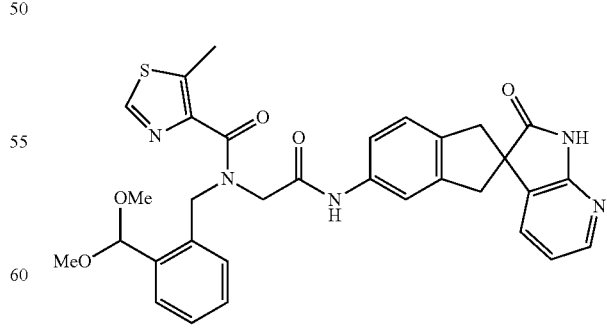

Synthesised according to General Route F (step 1 B) from Intermediate T (50 mg, 0.106 mmol) in N,N-dimethylformamide (3 ml) with N,N-diisopropylethylamine (56 μl, 0.32 mmol), 5-methyl-1,3-thiazole-4-carboxylic acid (16.5 mg, 0.116 mmol), EDCl.HCl (26 mg, 0.137 mmol), HOAt (19 mg, 0.137 mmol) and purified via flash silica chromatography (50-100% EtOAc in heptane then 2% MeOH in EtOAc) to provide compound 30.1i (50 mg, 63%) as a colourless glass. UPLC-MS (short basic) rt 0.77 (596 [M−H]−), 91% pure.

N-(2-Formylbenzyl)-5-methyl-N-(2-oxo-2-((2'-oxo-1,1',2',3-tetrahydrospiro[indene-2,3'-pyrrolo[2,3-b]pyridin]-5-yl)amino)ethyl)thiazole-4-carboxamide 30.2i

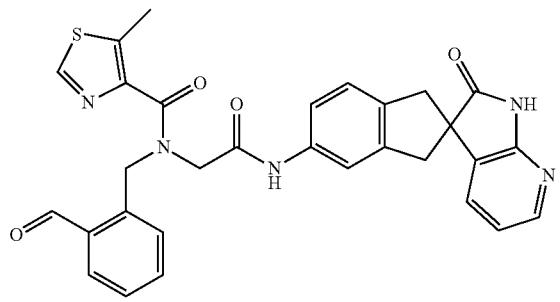 [SMILES: Cc1scnc1C(=O)N(CC(=O)Nc1ccc2c(c1)CC1(C2)C(=O)Nc2ncccc21)Cc1ccccc1C=O]

Synthesised according to General Route F (step 2) from 30.1i (50 mg, 0.084 mmol), p-toluene sulfonic acid monohydrate (17.5 mg, 0.092 mmol) in acetone (3 ml) with water (0.5 ml) added after 30 min, complete at 1 h, to provide compound 30.2i (46 mg, quant.) as a yellow solid. UPLC-MS (CSH 2-50%) rt 0.96 (552 [M+H]+), 91% pure.

Example 62: 5-Methyl-N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)thiazole-4-carboxamide 30l

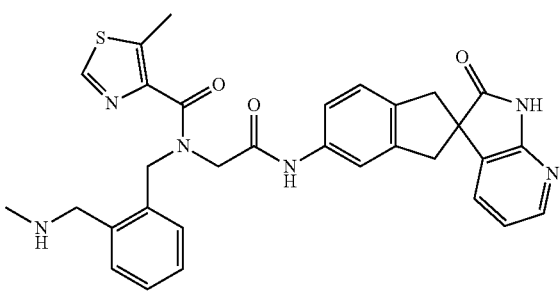 [SMILES: CNCc1ccccc1CN(CC(=O)Nc1ccc2c(c1)CC1(C2)C(=O)Nc2ncccc21)C(=O)c1ncsc1C]

Synthesised according to General Route F (step 3) from 30.2i (46 mg, 0.084 mmol), methylamine hydrochloride (11 mg, 0.16 mmol), N,N-diisopropylethylamine (59 µl, 0.34 mmol) in dichloromethane (5 ml) to provide intermediate imine UPLC-MS (short basic) rt 0.72 (565 [M+H]+), which was reduced with sodium borohydride (6.3 mg, 0.165 mmol) in methanol (3 ml) at RT for 3 h. Purified via flash silica chromatography (0-6% MeOH with ammonia in DCM) then triturated in 1:1 diethyl ether/heptane with 2% methanol to provide compound 30l (5.9 mg, 12%) as a colourless solid. 1H NMR (CD3OD, 300 MHz) δ 2.45 (m, 3H), 2.62 (s, 3H), 3.02 (s, 1H), 3.07 (s, 1H), 3.50 (dd, 2H), 3.80 (m, 2H), 4.20 (s, 2H), 4.92 (m, 2H), 6.85 (t, 1H), 7.10 (d, 1H), 7.19 (s, 2H), 7.30 (m, 3H), 7.40 (s, 2H), 8.03 (d, 1H), 8.76 (s, 1H). UPLC-MS (long basic) rt 1.28 (567 [M+H]+), 92% pure.

N-(2-(Dimethoxymethyl)benzyl)-N-(2-oxo-2-((2'-oxo-1,1',2',3-tetrahydrospiro[indene-2,3'-pyrrolo[2,3-b]pyridin]-5-yl)amino)ethyl)tetrahydrofuran-2-carboxamide 30.1j

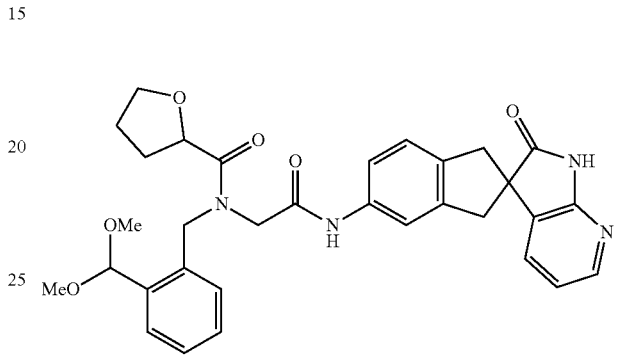

Synthesised according to General Route F (step 1 B) from Intermediate T (45 mg, 0.095 mmol) in N,N-dimethylformamide (3 ml) with N,N-diisopropylethylamine (68 µl, 0.381 mmol), 2-tetrahydrofuroic acid (13.2 mg, 0.114 mmol), EDCl.HCl (24 mg, 0.123 mmol), HOAt (17 mg, 0.123 mmol) and purified via flash silica chromatography (EtOAc) to provide compound 30.1j (30 mg, 55%) as a colourless glass. UPLC-MS (short basic) rt 0.74 (569 [M−H]−), 88% pure.

N-(2-Formylbenzyl)-N-(2-oxo-2-((2'-oxo-1,1',2',3-tetrahydrospiro[indene-2,3'-pyrrolo[2,3-b]pyridin]-5-yl)amino)ethyl)tetrahydrofuran-2-carboxamide 30.2j

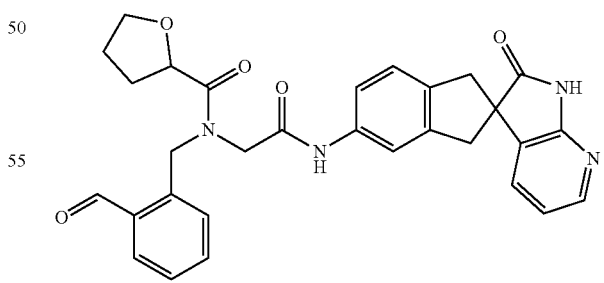

Synthesised according to General Route F (step 2) from 30.1j (30 mg, 0.052 mmol), p-toluene sulfonic acid monohydrate (10 mg, 0.052 mmol) in acetone (2 ml) to provide compound 30.2j (27 mg, 99%) as a yellow solid. UPLC-MS (short basic) rt 0.65 (525 [M+H]+).

Example 63: N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)tetrahydrofuran-2-carboxamide 30J

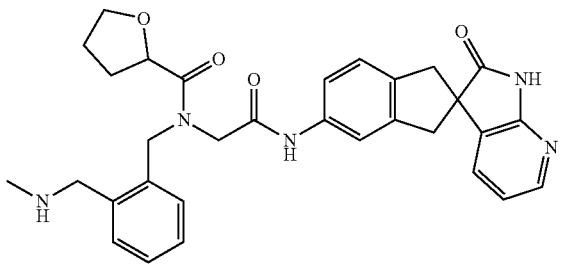 [SMILES: CNCc1ccccc1CN(CC(=O)Nc1ccc2c(c1)CC1(C2)C(=O)Nc2ncccc21)C(=O)C1CCCO1]

Synthesised according to General Route F (step 3) from 30.2j (27 mg, 0.051 mmol), methylamine hydrochloride (7 mg, 0.10 mmol), N,N-diisopropylethylamine (37 µl, 0.205 mmol) in dichloromethane (4 ml) to provide intermediate imine UPLC-MS (short basic) rt 0.74 (538 [M+H]$^+$), which was reduced with sodium borohydride (3.8 mg, 0.102 mmol) in methanol (4 ml) at RT for 3 h. Purified via flash silica chromatography (0-5% MeOH with ammonia in DCM) and SPE (STMAd, 2 g, MeOH then ammonia in MeOH) to provide compound 30J (1.5 mg, 5%) as a colourless solid. $^1$H NMR (CD$_3$OD, 300 MHz) δ 1.96 (m, 2H), 2.20 (m, 2H), 2.55 (2 s, 3H, rotamer), 3.05 (d, 2H), 3.49 (m, 2H), 3.86 (m, 2H), 3.99 (m, 1H), 4.25 (d, 2H), 4.60 (m, 2H), 5.00 (m, 1H), 6.85 (t, 1H), 7.10 (d, 1H), 7.20 (s, 1H), 7.31 (m, 5H), 7.65 (d, 1H), 8.02 (d, 1H). UPLC-MS (long acidic CSH) rt 0.89 (540 [M+H]$^+$), 86% pure.

N-(2-(Dimethoxymethyl)benzyl)-N-(2-oxo-2-((2'-oxo-1,1',2',3-tetrahydrospiro[indene-2,3'-pyrrolo[2,3-b]pyridin]-5-yl)amino)ethyl)tetrahydro-2H-pyran-2-carboxamide 30.1k

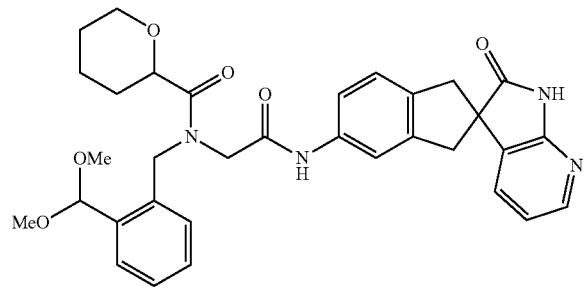 [SMILES: COC(OC)c1ccccc1CN(CC(=O)Nc1ccc2c(c1)CC1(C2)C(=O)Nc2ncccc21)C(=O)C1CCCCO1]

Synthesised according to General Route F (step 1 B) from Intermediate T (45 mg, 0.095 mmol) in N,N-dimethylformamide (3 ml) with N,N-diisopropylethylamine (68 µl, 0.381 mmol), tetrahydro-2H-pyran-2-carboxylic acid (14.8 mg, 0.114 mmol), EDCl.HCl (24 mg, 0.123 mmol), HOAt (17 mg, 0.123 mmol) and purified via flash silica chromatography (4:1 EtOAc/heptane to 100% EtOAc) to provide compound 30.1k (30 mg, 55%) as a colourless glass. UPLC-MS (short basic) rt 0.80 (583 [M–H]$^-$), 88% pure.

N-(2-Formylbenzyl)-N-(2-oxo-2-((2'-oxo-1,1',2',3-tetrahydrospiro[indene-2,3'-pyrrolo[2,3-b]pyridin]-5-yl)amino)ethyl)tetrahydro-2H-pyran-2-carboxamide 30.2k

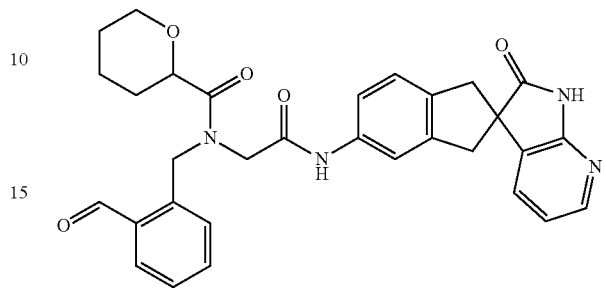

Synthesised according to General Route F (step 2) from 30.1k (30 mg, 0.051 mmol), p-toluene sulfonic acid monohydrate (10 mg, 0.052 mmol) in acetone (2 ml) to provide compound 30.2k (30 mg, quant.) as a yellow solid. UPLC-MS (short basic) rt 0.71 (539 [M+H]$^+$).

Example 64: N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)tetrahydro-2H-pyran-2-carboxamide 30K

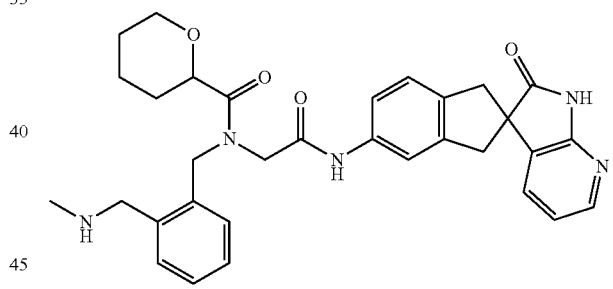

Synthesised according to General Route F (step 3) from 30.2k (30 mg, 0.051 mmol), methylamine hydrochloride (7.5 mg, 0.11 mmol), N,N-diisopropylethylamine (40 µl, 0.22 mmol) in dichloromethane (4 ml) to provide intermediate imine UPLC-MS (short basic) rt 0.73 (552 [M+H]$^+$), which was reduced with sodium borohydride (4.2 mg, 0.111 mmol) in methanol (4 ml) at RT for 3 h. Purified via flash silica chromatography (0-5% MeOH with ammonia in DCM) and SPE (STMAd, 2 g, MeOH then ammonia in MeOH) to provide compound 30K (5.4 mg, 17%) as a colourless solid. $^1$H NMR (CD$_3$OD, 400 MHz) δ 1.56 (m, 3H), 1.80 (br m, 2H), 1.92 (br m, 1H), 2.54 (2 s, 3H, rotamer), 3.02 (d, 2H), 3.49 (m, 3H), 3.65 (m, 1H), 3.94 (m, 3H), 4.35 (m, 3H), 4.99 (m, 1H), 6.85 (t, 1H), 7.10 (d, 1H), 7.20 (d, 1H), 7.33 (m, 6H), 8.05 (d, 1H). UPLC-MS (long basic) rt 1.62 (554 [M+H]$^+$), 95% pure.

265

N-(2-(Dimethoxymethyl)benzyl)-N-(2-oxo-2-((2'-oxo-1,1',2',3-tetrahydrospiro[indene-2,3'-pyrrolo[2,3-b]pyridin]-5-yl)amino)ethyl)cyclopentanecarboxamide 30.1l

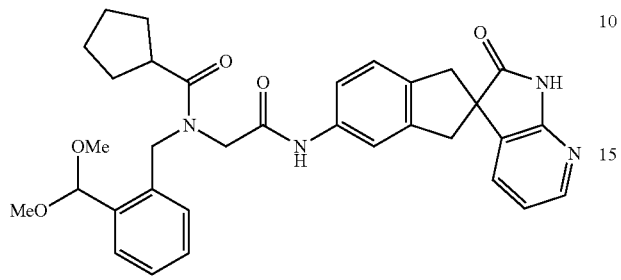

Synthesised according to General Route F (step 1 A) from Intermediate T (30 mg, 0.06 mmol) in dichloromethane (3 ml) with N,N-diisopropylethylamine (34 μl, 0.19 mmol), cyclopentanecarbonyl chloride (9.2 mg, 0.069 mmol) and purified via flash silica chromatography (4:1 EtOAc/heptane to 100% EtOAc) to provide compound 30.1l (30 mg, 88%) as a colourless glass. UPLC-MS (short basic) rt 0.87 (567 [M–H]⁻), 72% pure.

N-(2-Formylbenzyl)-N-(2-oxo-2-((2'-oxo-1,1',2',3-tetrahydrospiro[indene-2,3'-pyrrolo[2,3-b]pyridin]-5-yl)amino)ethyl)cyclopentanecarboxamide 30.2l

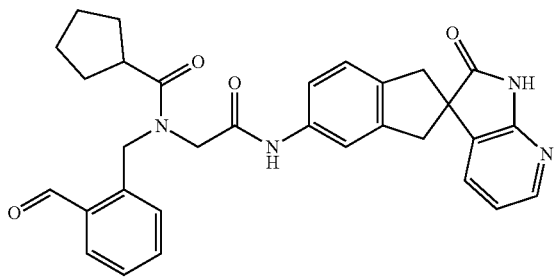 [SMILES: O=Cc1ccccc1CN(CC(=O)Nc1ccc2c(c1)CC1(C2)C(=O)Nc2ncccc21)C(=O)C1CCCC1]

266

Synthesised according to General Route F (step 2) from 30.1l (30 mg, 0.052 mmol), p-toluene sulfonic acid monohydrate (10 mg, 0.052 mmol) in acetone (3 ml), to provide compound 30.2l (27 mg, 99%) as a yellow solid. UPLC-MS (short basic) rt 0.78 (521 [M–H]⁻).

Example 65: N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)cyclopentanecarboxamide 30L

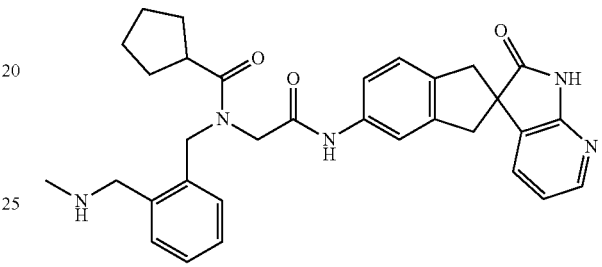

Synthesised according to General Route F (step 3) from 30.2l (27 mg, 0.052 mmol), methylamine hydrochloride (7.5 mg, 0.16 mmol), N,N-diisopropylethylamine (46 μl, 0.26 mmol) in dichloromethane (3 ml) to provide intermediate imine UPLC-MS (long basic) rt 1.91 (536 [M+H]⁺), which was reduced with sodium borohydride (3.5 mg, 0.093 mmol) in methanol (3 ml) at RT for 2 h. Purified via flash silica chromatography (0-4% MeOH with ammonia in DCM) and SPE (STMAd, 2 g, MeOH then ammonia in MeOH, then PE-AX, 2 g, MeOH) to provide compound 30L (2.8 mg, 11%) as a colourless solid. ¹H NMR (CD₃OD, 400 MHz) δ 1.63 (br m, 2H), 1.82 (br m, 4H), 1.95 (br m, 2H), 2.68 (2 s, 3H, rotamer), 2.94 (M, 1H), 3.05 (m, 2H), 3.50 (d, 2H), 4.00 (br m, 4H), 4.88 (m, 2H), 6.85 (t, 1H), 7.10 (d, 1H), 7.25 (m, 2H), 7.40 (m, 5H), 8.05 (d, 1H). UPLC-MS (long basic) rt 1.18 (538 [M+H]⁺), 93% pure.

Synthesis of Amine Intermediates U and V

SCHEME 31

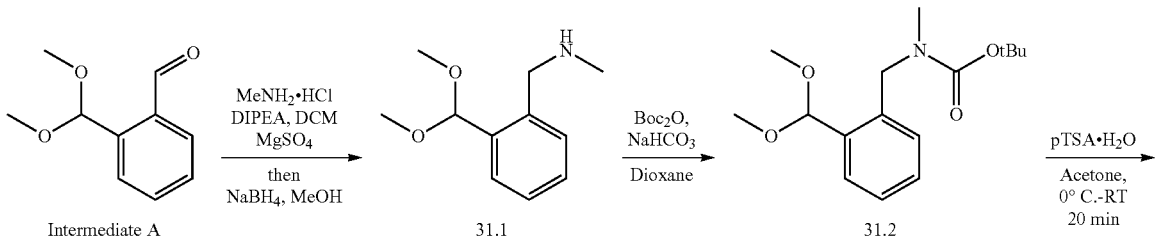

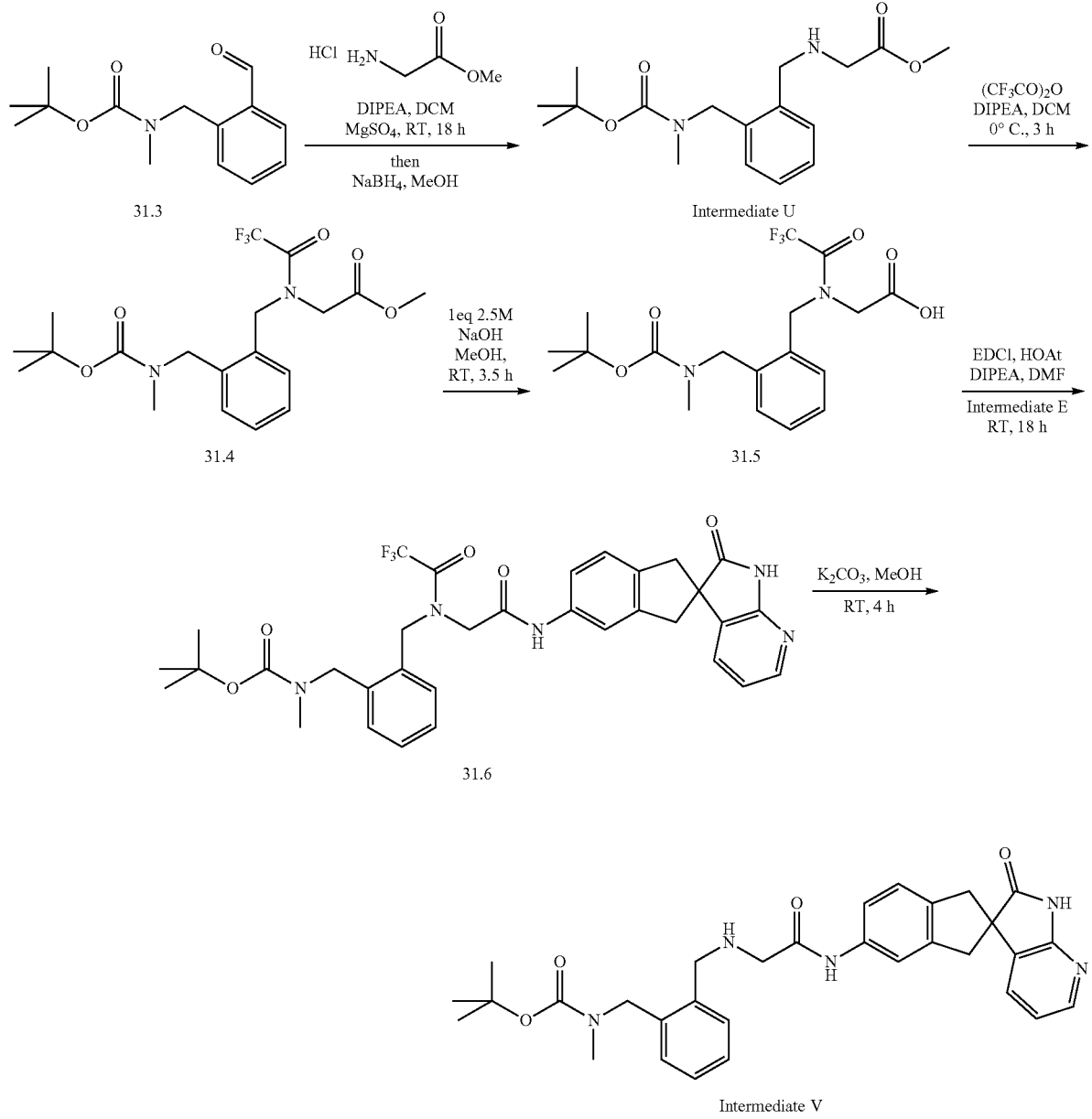

Intermediate U

Intermediate V 1-(2-(Dimethoxymethyl)phenyl)-N-methylmethanamine
31.1

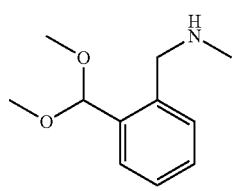

Intermediate A (8.0 g, 44.4 mmol) was dissolved in dichloromethane (110 ml) and N,N-diisopropylethylamine (40 ml, 222 mmol) was added followed by methylamine hydrochloride (9.04 g, 133.2 mmol) and stirred for 5 min at RT. Magnesium sulfate was added and the mixture was stirred at RT for 18 h. The mixture was filtered and washed with dichloromethane. The filtrate was washed twice with saturated sodium bicarbonate then the aqueous extracted twice with dichloromethane. The combined organic layers were dried over magnesium sulfate, filtered and evaporated to provide a colourless oil. This was dissolved in methanol (100 ml) under argon then cooled on water with a little ice. Sodium borohydride (2.01 g, 53.3 mmol) was added in several small portions over 20 min then the reaction was stirred at RT for 18 h. The reaction mixture was concentrated to about % volume then poured into saturated sodium bicarbonate and extracted three times with ethyl acetate. The organics were dried over magnesium sulfate, filtered and evaporated to provide compound 31.1 (8.14 g, ~70%, contains ethyl acetate) as a colourless oil. $^1$H NMR (CDCl$_3$, 400 MHz) δ 2.45 (s, 3H), 3.33 (s, 6H), 3.80 (s, 2H), 5.58 (s, 1H), 7.31 (m, 3H), 7.53 (dd, 1H) —contains ~30% ethyl acetate.

269 tert-Butyl 2-(dimethoxymethyl)benzyl(methyl)carbamate 31.2

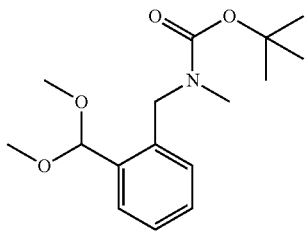 [SMILES: COC(OC)c1ccccc1CN(C)C(=O)OC(C)(C)C]

Compound 31.1 (8.14 g, ~30.0 mmol) was dissolved in 1,4-dioxane (100 ml) then saturated sodium bicarbonate (70 ml) was added followed by di-tert-butyl dicarbonate (7.85 g, 36.0 mmol) and the mixture was stirred rapidly at RT for 72 h. The reaction mixture was poured into saturated sodium bicarbonate and extracted three times with ethyl acetate. The organics were washed with brine, dried over magnesium sulfate, filtered and evaporated. The crude was purified via flash chromatography (250 ml silica, 2:1 to 1:2 heptane/ethyl acetate) to provide compound 31.2 (7.20 g, 81%) as a colourless gum. $^1$H NMR (CDCl$_3$, 300 MHz) δ 1.45 (s, 9H), 2.85 (m, 3H), 3.31 (s, 6H), 4.58 (s, 2H), 5.42 (s, 1H), 7.19 (dd, 1H), 7.29 (m, 2H), 7.54 (dd, 1H)—rotamers.

tert-Butyl 2-formylbenzyl(methyl)carbamate 31.3

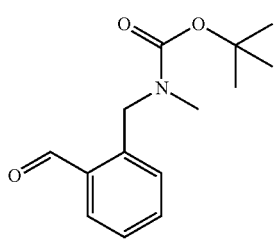 [SMILES: CN(Cc1ccccc1C=O)C(=O)OC(C)(C)C]

Compound 31.2 (0.43 g, 1.46 mmol) was dissolved in acetone (35 ml) then cooled on ice/water. p-Toluene sulfonic acid monohydrate (267 mg, 1.53 mmol) was added and the reaction stirred for 5 min before warming to RT for 15 min. The mixture was poured into saturated sodium bicarbonate and extracted three times with ethyl acetate. The combined organics were washed with brine, dried over magnesium sulfate, filtered and evaporated to provide compound 31.3 (0.35 g, 97%) as a colourless gum. $^1$H NMR (CDCl$_3$, 300 MHz) δ 1.41 (m, 9H), 2.90 (br s, 3H), 4.90 (s, 2H), 7.32 (d, 1H), 7.47 (t, 1H), 7.58 (t, 1H), 7.84 (d, 1H), 10.20 (s, 1H)—rotamers.

270

Methyl 2-((2-(((tert-butoxycarbonyl)(methyl)amino)methyl)benzyl)amino)acetate Intermediate U

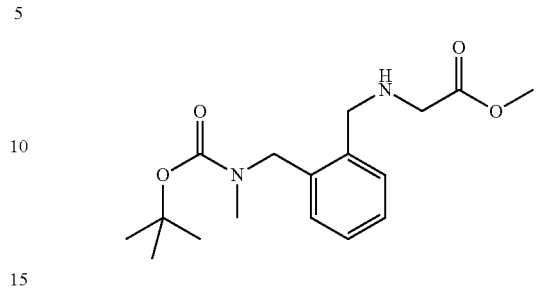

Compound 31.3 (0.35 g, 1.42 mmol) was dissolved in dichloromethane (12 ml) then N,N-diisopropylethylamine (0.76 ml, 4.38 mmol) and glycine methyl ester hydrochloride (365 mg, 2.9 mmol) were added followed by magnesium sulfate. The mixture was stirred at RT for 18 h. The mixture was poured into saturated sodium bicarbonate then the aqueous extracted three times with dichloromethane. The combined organic layers were dried over magnesium sulfate, filtered and evaporated. The residue was dissolved in methanol (8 ml) under argon then sodium borohydride (71 mg, 1.9 mmol) was added in portions over 2 min then the reaction was stirred at RT for 1 h. The reaction mixture was poured into saturated sodium bicarbonate and extracted three times with ethyl acetate. The combined organics were dried over magnesium sulfate, filtered and evaporated to provide Intermediate U (0.44 g, 94%) as a colourless gum. $^1$H NMR (CDCl$_3$, 300 MHz) δ 1.46 (m, 9H), 2.82 (br s, 3H), 3.71 (s, 3H), 4.58 (s, 2H), 7.18 (m, 2H), 7.30 (m, 2H)-rotamers. UPLC-MS (short base) 0.89 (323 [M+H]$^+$), Methyl 2-(N-(2-(((tert-butoxycarbonyl)(methyl)amino)methyl)benzyl)-2,2,2-trifluoroacetamido)acetate 31.4

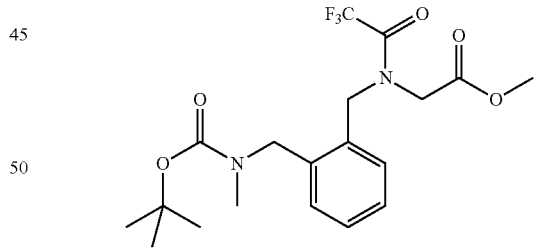

Intermediate U (0.44 g, 1.37 mmol) was dissolved in dichloromethane (12 ml) then N,N-diisopropylethylamine (0.6 ml, 3.42 mmol) was added and the mixture was cooled on ice/water. Trifluoroacetic anhydride (211 ml, 1.51 mmol) was added dropwise then the mixture was stirred on ice/water for 1.5 h. The mixture was poured into saturated sodium bicarbonate and extracted three times with dichloromethane. The organics were dried over magnesium sulfate, filtered and evaporated to provide compound 31.4 (595 mg, quant) as a colourless gum. UPLC-MS (short CSH, 2-50%) 1.46 (319 [M−Boc+H]$^+$).

2-(N-(2-(((tert-Butoxycarbonyl)(methyl)amino)methyl)benzyl)-2,2,2-trifluoroacetamido)acetic Acid 31.5

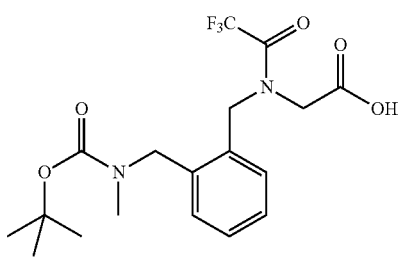 [SMILES: CN(Cc1ccccc1CN(CC(=O)O)C(=O)C(F)(F)F)C(=O)OC(C)(C)C]

Compound 31.4 (595 mg, 1.37 mmol) was dissolved in methanol (10 ml) and 2.5 M sodium hydroxide (0.55 ml, 1.37 mmol) was added and the reaction stirred at RT for 22 h. The mixture was poured into water and extracted three times with ethyl acetate. The organics were washed with brine. The aqueous was saturated with sodium chloride and extracted with ethyl acetate. The combined organics were dried over magnesium sulfate, filtered and evaporated to provide compound 31.5 (433 mg, 78%) as a colourless glass. Used directly. UPLC-MS (short CSH, 2-50%) 1.31 (305 [M−Boc+H]$^+$).

tert-Butyl methyl(2-((2,2,2-trifluoro-N-(2-oxo-2-((2'-oxo-1,1',2',3-tetrahydrospiro[indene-2,3'-pyrrolo[2,3-b]pyridin]-5-yl)amino)ethyl)acetamido)methyl)benzyl)carbamate 31.6

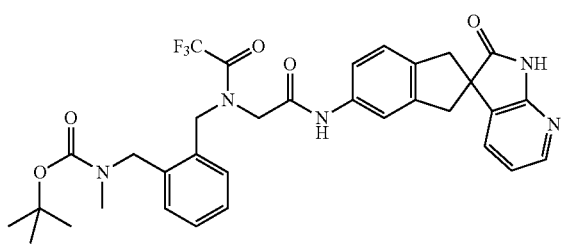 [SMILES: CN(Cc1ccccc1CN(CC(=O)Nc1ccc2c(c1)CC1(C2)C(=O)Nc2ncccc21)C(=O)C(F)(F)F)C(=O)OC(C)(C)C]

Compound 31.5 (45 mg, 0.11 mmol) was dissolved in N,N-dimethylformamide (2 ml) and N,N-diisopropylethylamine (48 µl, 0.27 mmol) was added followed by EDCl (28 mg, 0.13 mmol) and HOAt (18 mg, 0.13 mmol). Intermediate E (33 mg, 0.13 mmol) was added and the mixture stirred at RT for 76 h. The mixture was poured into saturated sodium bicarbonate and extracted three times with ethyl acetate. The organics were washed three times with water, dried over magnesium sulfate, filtered and evaporated. The residue was purified via flash chromatography (5 g SiO$_2$, 2:1 to 1:1 heptane/ethyl acetate) to provide compound 31.6 (42 mg, 59%) as a colourless glass. UPLC-MS (short CSH, 2-50%) 1.32 (538 [M−Boc+H]$^+$).

tert-Butyl methyl(2-(((2-oxo-2-((2'-oxo-1,1',2',3-tetrahydrospiro[indene-2,3'-pyrrolo[2,3-b]pyridin]-5-yl)amino)ethyl)amino)methyl)benzyl)carbamate Intermediate V

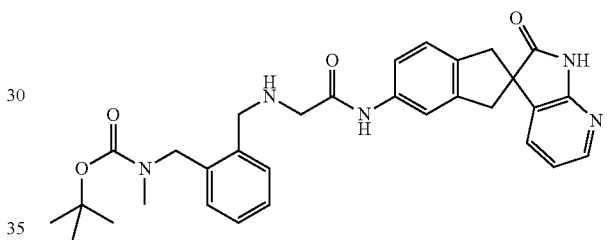

Compound 31.6 (42 mg, 0.064 mmol) was dissolved in methanol (1 ml) then potassium carbonate (11.4 mg, 0.075 mmol) was added in water (0.15 ml). The mixture stirred at RT for 4 h, with an extra 2 drops of water added at 1 h. The mixture was poured into saturated sodium bicarbonate and extracted three times with ethyl acetate. The organics were dried over magnesium sulfate, filtered and evaporated to provide compound Intermediate V (40 mg, Quant.) as a colourless glass. UPLC-MS (short CSH, 2-50%) 0.75 (542 [M+H]$^+$).

General Route G

SCHEME 32

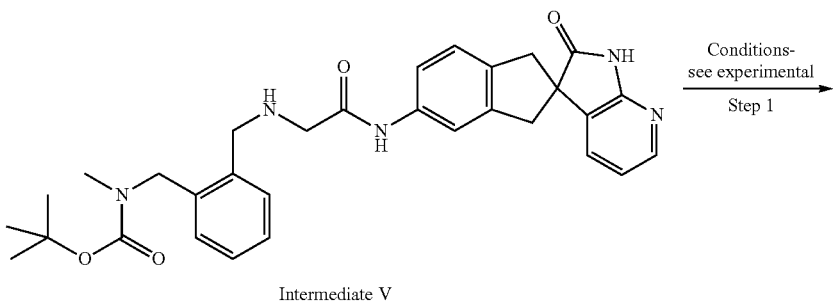

Intermediate V

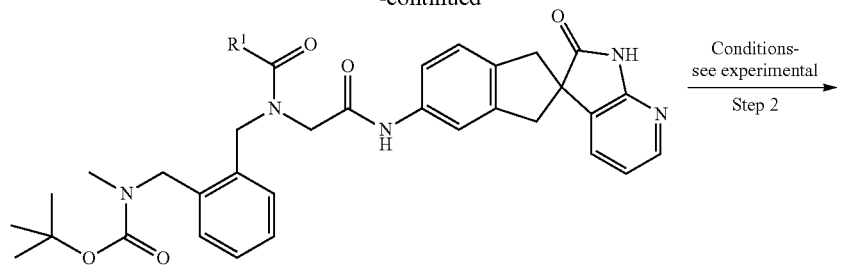

32.1a-z

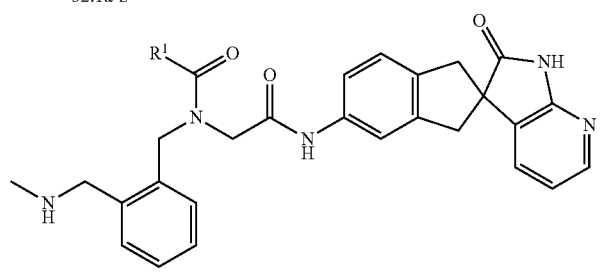

32A-Z

Step 1
A: Acid Chloride

Intermediate V was dissolved in dichloromethane under an argon atmosphere then N,N-diisopropylethylamine was added. Acid chloride R$^1$C(O)Cl was added and the mixture was stirred at room temperature for 18 h, after which time reaction was complete by UPLC-MS. The mixture was poured into saturated sodium bicarbonate. The aqueous layer was extracted three times with dichloromethane. The combined organic extracts were dried over magnesium sulfate, filtered, and the filtrate evaporated. The residue was purified via flash silica chromatography to provide compounds 32.1.

B: Carboxylic Acid

Intermediate V was dissolved in N,N-dimethylformamide followed by addition of N,N-diisopropylethylamine, carboxylic acid R$^1$COOH, EDCl.HCl and HOAt. The reaction was stirred at room temperature or 80° C. for 2-18 h depending on the acid. The mixture was diluted with ethyl acetate and washed with saturated sodium bicarbonate, three times with water, dried over sodium sulfate, filtered and evaporated. The crude residues were purified via flash silica chromatography to provide compounds 32.1.

C: Isocyanate

Intermediate V was dissolved in dichloromethane or 1,2-dichloroethane under an argon atmosphere. Isocyanate R$^1$C(O) was added and the mixture was stirred at room temperature for 18 h, after which time reaction was complete by UPLC-MS. The mixture was poured into saturated sodium bicarbonate. The aqueous layer was extracted three times with dichloromethane. The combined organic extracts were dried over magnesium sulfate, filtered, and the filtrate evaporated. The residue was purified via flash silica chromatography to provide compounds 32.1.

Step 2

A: Trifluoroacetic acid Compound 32.1 was dissolved in dichloromethane, trifluoroacetic acid was added and the mixture stirred at room temperature for 0.5-3 h. The mixture was poured into saturated sodium bicarbonate and extracted twice with dichloromethane then twice with ethyl acetate. The combined organics were dried over magnesium sulfate, filtered and evaporated. The crude residues were purified via flash silica chromatography, SPE or prep-HPLC.

B: Hydrochloric Acid

Compound 32.1 was dissolved in methanol/ethyl acetate then hydrochloric acid was added, and the mixture stirred at room temperature overnight. Volatiles were removed under vacuum and the crude material was purified directly by HPLC.

tert-Butyl methyl(2-((N-(2-oxo-2-((2'-oxo-1,1',2',3-tetrahydrospiro[indene-2,3'-pyrrolo[2,3-b]pyridin]-5-yl)amino)ethyl)oxetane-3-carboxamido)methyl)benzyl)carbamate 32.1a

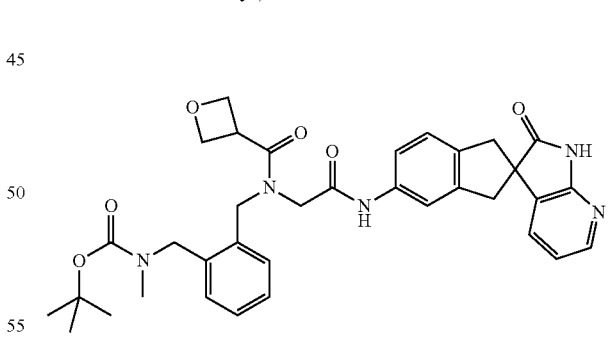

Synthesised according to General Route G (step 1B) from Intermediate V (40 mg, 0.064 mmol) in N,N-dimethylformamide (2 ml) with N,N-diisopropylethylamine (30 µl, 0.17 mmol), oxetane-3-carboxylic acid (8 mg, 0.077 mmol), EDCl.HCl (18 mg, 0.084 mmol), HOAt (12 mg, 0.084 mmol) and purified via flash silica chromatography (3:2 heptane/IPA) to provide compound 32.1a (12 mg, 30%) as a colourless glass. UPLC-MS (short CSH 2-50%) rt 1.12 (526 [M−Boc+H]$^+$).

Example 66: N-(2-((Methylamino)methyl)benzyl)-N-(2-oxo-2-((2'-oxo-1,1',2,3-tetrahydrospiro[indene-2,3'-pyrrolo[2,3-b]pyridin]-5-yl)amino)ethyl)oxetane-3-carboxamide 32A

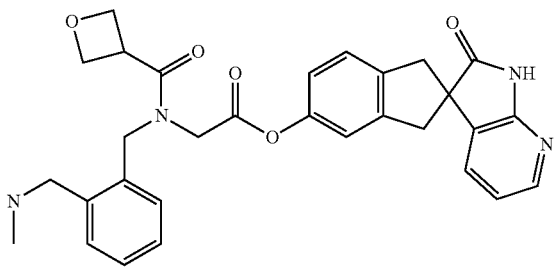 [SMILES: CNCc1ccccc1CN(CC(=O)Oc1ccc2c(c1)CC1(C2)C(=O)Nc2ncccc21)C(=O)C1COC1]

Synthesised according to General Route G (step 2A) from 32.1a (12 mg, 0.019 mmol), trifluoroacetic acid (0.16 ml) and dichloromethane (2 ml). Purified via SPE (2 g STMAd, methanol then ammonia in methanol) to provide compound 32A (3.2 mg, 32%) as a colourless solid. $^1$H NMR (CD$_3$OD, 300 MHz) δ 2.45 (m, 3H), 2.62 (s, 3H), 3.02 (s, 1H), 3.07 (s, 1H), 3.50 (dd, 2H), 3.80 (m, 2H), 4.20 (s, 2H), 4.92 (m, 2H), 6.85 (t, 1H), 7.10 (d, 1H), 7.19 (s, 2H), 7.30 (m, 3H), 7.40 (s, 2H), 8.03 (d, 1H), 8.76 (s, 1H). UPLC-MS (long basic) rt 1.28 (567 [M+H]$^+$), 92% pure.

tert-Butyl N-[[2-[[(3-methoxypyrrolidine-1-carbonyl)-[2-oxo-2-[(2-oxospiro[1H-pyrrolo[2,3-b]pyridine-3,2'-indane]-5'-yl)amino]ethyl]amino]methyl]phenyl]methyl]-N-methyl-carbamate 32.1b

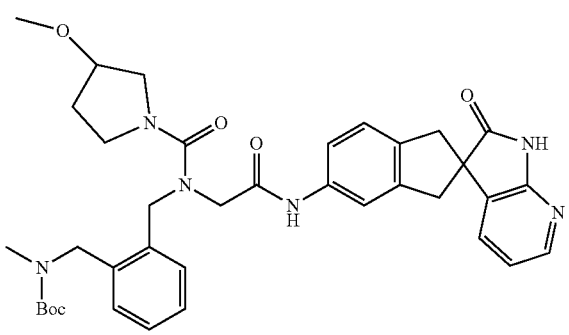 [SMILES: COC1CCN(C(=O)N(CC(=O)Nc2ccc3c(c2)CC2(C3)C(=O)Nc3ncccc32)Cc2ccccc2CN(C)C(=O)OC(C)(C)C)C1]

To a solution of Intermediate V (80 mg, 0.15 mmol) in tetrahydrofuran (2 mL) was added triethylamine (44 mg, 0.44 mmol) and triphosgene (43 mg, 0.14 mmol) at 0° C. The reaction mixture was stirred at 26° C. for 1 h. 3-Methoxypyrrolidine (22 mg, 0.16 mmol, HCl salt) was added into the mixture and the reaction mixture was stirred at 26° C. for 1 h. The reaction mixture was quenched by water (10 mL) and extracted with ethyl acetate (3×20 mL). The combined organic phases were washed with brine (3×20 mL) and dried over anhydrous sodium sulfate. After filtration and concentration, the residue was purified by prep-HPLC (column: Phenomenex Synergi C18 150×25 mm, 10 μm; mobile phase: [water (0.1% TFA)-acetonitrile]; B %: 42%-72%, 11 min). After lyophilisation, 32.1b (35 mg, 0.052 mmol, 35% yield) was obtained as colourless oil. LC-MS: rt 0.810 min, (669 [M+H]$^+$).

Example 67: 3-Methoxy-N-[[2-(methylaminomethyl)phenyl]methyl]-N-[2-oxo-2-[(2-oxospiro[1H-pyrrolo[2,3-b]pyridine-3,2'-indane]-5'-yl)amino]ethyl]pyrrolidine-1-carboxamide 32B

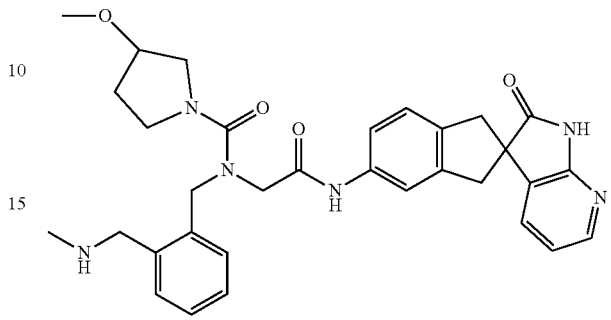

Synthesised according to General Route G (step 2A) from 32.1b (35 mg, 0.052 mmol) and trifluoroacetic acid (0.2 mL) in dichloromethane (1 mL) at 0° C. then at 20° C. for 0.5 h. The mixture was purified by prep-HPLC (column: Boston pH-lex 150×25 mm, 10 μm; mobile phase: [water (0.1% TFA)-acetonitrile]; B %: 20%-47%, 9 min). After lyophilisation, compound 32B was obtained as a yellow solid (3 mg, 7% yield, 99.7% purity, TFA salt). $^1$H NMR (CD$_3$OD, 400 MHz) δ 1.88-1.92 (m, 1H), 2.00-2.03 (m, 1H), 2.80 (s, 3H), 3.06 (d, 2H), 3.30-3.57 (m, 6H), 3.96 (s, 1H), 4.15 (d, 1H), 4.21-4.25 (m, 2H), 4.36-4.44 (m, 2H), 4.74-4.80 (m, 2H), 6.89 (dd, 1H), 7.14 (dd, 1H), 7.23 (d, 1H), 7.27-7.30 (m, 1H), 7.35-7.46 (m, 4H), 7.66 (d, 1H), 8.05 (dd, 1H). LC-MS: rt 2.551 min, (569 [M+H]$^+$), purity 99.7%.

Example 68: 1-(Acetyl)-N-[[2-(methylaminomethyl)phenyl]methyl]-N-[2-oxo-2-[(2-oxospiro[1H-pyrrolo[2,3-b]pyridine-3,2'-indane]-5'-yl)amino]ethyl]azetidine-3-carboxamide 32C

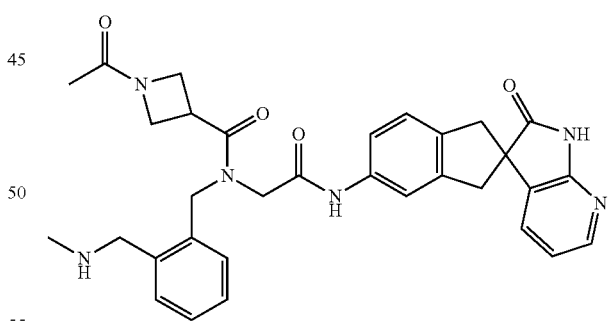

Synthesised according to General Route G (step 1B) from Intermediate V (60 mg) and 1-acetyl-azetidine-3-carboxylic acid. Step 2A purification was conducted by trituration with n-hexane to provide compound 32C as a yellow solid (20 mg, 95% purity). $^1$H NMR (DMSO-d$_6$, 400 MHz, T=80° C.) δ 1.75 (s, 3H), 2.51-2.52 (d, 3H), 3.10-3.13 (m, 2H), 3.37 (dd, 2H), 3.71-3.82 (m, 1H), 3.90-4.05 (m, 4H), 4.09 (s, 2H), 4.12-4.32 (m, 3H), 4.73 (s, 2H), 6.86 (dd, 1H), 7.15 (dd, 1H), 7.20 (d, 1H), 7.27-7.39 (m, 4H), 7.45 (dd, 1H), 7.48-7.56 (m, 1H), 8.06 (dd, 1H), 9.72-9.89 (m, 1H), 10.79 (br.s, 1H). LCMS: rt=2.005 min, (567 [M+H]$^+$), 95% purity.

Example 69: 1-Acetyl-N-[[2-(methylaminomethyl)phenyl]methyl]-N-[2-oxo-2-[(2-oxospiro[1H-pyrrolo[2,3-b]pyridine-3,2'-indane]-5'-yl)amino]ethyl]pyrrolidine-2-carboxamide 32D

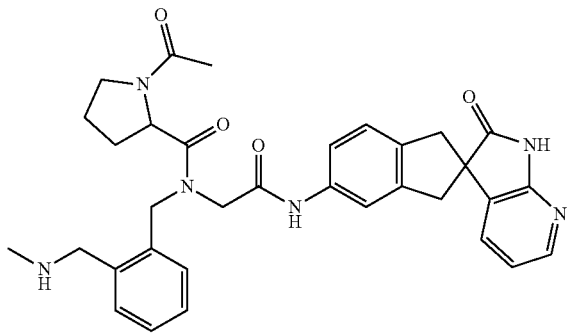 [SMILES: CNCc1ccccc1CN(CC(=O)Nc1ccc2c(c1)CC1(C2)C(=O)Nc2ncccc21)C(=O)C1CCCN1C(C)=O]

Compound 32D was synthesised according to General Route G (step 1B) from Intermediate V (60 mg) and 1-acetyl-pyrrolidine-2-carboxylic acid. The crude product from step 1B was purified by purified by prep-HPLC (column: Phenomenex Synergi C18 150×25 mm, 10 μm; mobile phase: [water (0.1% TFA)-acetonitrile]; B %: 35%-55%, 11 min). Step 2A was purified by trituration with n-hexane to provide compound 32D as a yellow solid (21 mg, 98.2% purity). $^1$H NMR (CD$_3$OD, 400 MHz) δ. 1.29 (d, 4H), 2.69 (s, 3H), 2.99 (d, 2H), 3.41 (dd, 2H), 4.19 (s, 2H), 4.71 (m, 4H), 6.80 (dd, 1H), 7.06 (dd, 1H), 7.14 (d, 1H), 7.22 (d, 1H), 7.31-7.38 (m, 5H), 7.96 (dd, 1H). LC-MS: rt 1.492 min, (578 [M+H]$^+$), purity 100.0%.

Methyl 1-(2-((tert-butoxycarbonyl)amino)acetyl)piperidine-4-carboxylate

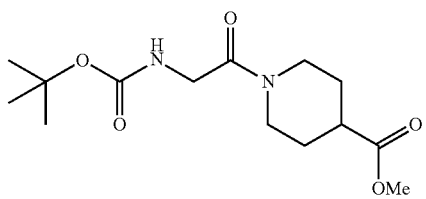 [SMILES: COC(=O)C1CCN(C(=O)CNC(=O)OC(C)(C)C)CC1]

To a solution of methyl piperidine-4-carboxylate (200 mg, 1.40 mmol) in N,N-dimethylformamide (4 ml) was added Boc-Gly-OH (245 mg, 1.40 mmol)), EDCl.HCl (349 mg, 1.82 mmol), HOAt (248 mg, 1.82 mmol) and N,N-diisopropylethylamine (0.73 ml, 4.19 mmol). The reaction mixture was stirred at room temperature overnight. The mixture was diluted with ethyl acetate then washed with saturated sodium bicarbonate, water and brine. The organics were dried over magnesium sulfate, filtered, evaporated and purified via SPE (5 g SiO$_2$ 50% ethyl acetate in heptane) to provide the desired product (99 mg, 24%). $^1$H NMR (CD$_3$OD, 300 MHz) δ 1.45 (s, 9H), 1.62-1.73 (m, 2H), 1.89-2.00 (m, 2H), 2.50-2.62 (m, 1H), 2.90 (t, 1H), 3.09 (t, 1H), 3.69 (d, 1H), 3.70 (s, 3H), 3.95 (d, 2H), 4.35 (d, 1H), 5.51 (s, NH); UPLC-MS 0.64 (201 [MH-Boc]*).

1-(2-((tert-Butoxycarbonyl)amino)acetyl)piperidine-4-carboxylic Acid

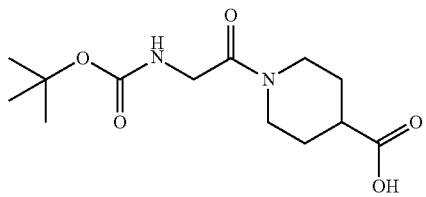 [SMILES: CC(C)(C)OC(=O)NCC(=O)N1CCC(C(=O)O)CC1]

Methyl 1-(2-((tert-butoxycarbonyl)amino)acetyl)piperidine-4-carboxylate (99 mg, 0.33 mmol) was dissolved in methanol (2 ml) and 2.5 M sodium hydroxide (0.2 ml, 0.49 mmol) was added and the reaction stirred at room temperature overnight. The mixture was acidified with 2M HCl and extracted three times with ethyl acetate. The organics were dried over magnesium sulfate, filtered and evaporated to provide the desired product as a colourless glass (46 mg, 49%). $^1$H NMR (CD$_3$OD, 300 MHz) δ 1.45 (s, 9H), 1.62-1.78 (m, 2H), 1.93-2.05 (m, 2H), 2.55-2.67 (m, 1H), 2.94 (td, 1H), 3.12 (td, 1H), 3.63-3.75 (m, 1H), 3.96 (d, 2H), 4.35 (dt, 2H), 5.55 (s, NH). UPLC-MS (short acid) 0.51 (187 [M−Boc+H]$^+$).

tert-Butyl 2-((1-(2-((tert-butoxycarbonyl)amino)acetyl)-N-(2-oxo-2-((2'-oxo-1,1',2',3-tetrahydrospiro[indene-2,3'-pyrrolo[2,3-b]pyridin]-5-yl)amino)ethyl) piperidine-4-carboxamido)methyl)benzyl (methyl)carbamate 32.1e

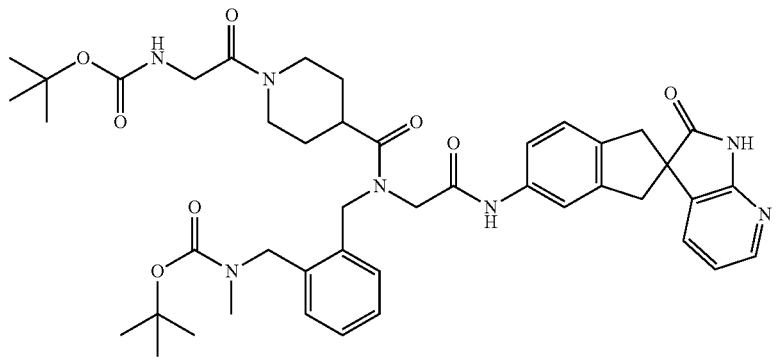 [SMILES: CN(Cc1ccccc1CN(CC(=O)Nc1ccc2c(c1)CC1(C2)C(=O)Nc2ncccc21)C(=O)C1CCN(C(=O)CNC(=O)OC(C)(C)C)CC1)C(=O)OC(C)(C)C]

Synthesised according to General Route G (step 1 B) from Intermediate V (52 mg, 0.096 mmol) in N,N-dimethylformamide (2 ml) with N,N-diisopropylethylamine (50 µl, 0.29 mmol), 1-(2-((tert-butoxycarbonyl)amino)acetyl)piperidine-4-carboxylic acid (28 mg, 0.096 mmol), EDCl.HCl (24 mg, 0.126 mmol), HOAt (17 mg, 0.126 mmol) and purified via flash silica chromatography (5 g SiO$_2$, ethyl acetate) to provide compound 32.1e as a colourless glass (42 mg, 74%). UPLC-MS (short CSH 2-50%) rt 1.08 (581 [M−Boc+H]$^+$).

Example 70: 1-(2-aminoacetyl)-N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)piperidine-4-carboxamide bis(2,2,2-trifluoroacetate) 32E

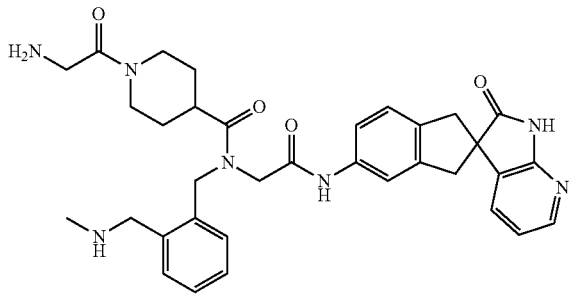 [SMILES: CNCc1ccccc1CN(CC(=O)Nc1ccc2c(c1)CC1(C2)C(=O)Nc2ncccc21)C(=O)C1CCN(C(=O)CN)CC1]

Synthesised according to General Route G (step 2B) from 32.1e (40 mg, 0.049 mmol) in methanol (0.6 ml) and ethyl acetate (0.6 ml) with hydrochloric acid 35% (110 µl). Purified by prep-HPLC (HP C18, ID 22 mm, length 150 mm, flow 16 ml/min: 5-60% acetonitrile-water/acetonitrile 0.1% TFA over 20 min) then freeze-dried to provide compound 32E as white solid (17 mg, 42%). $^1$H NMR (CD$_3$OD, 400 MHz) δ 1.75 (m, 2H), 1.92 (m, 2H), 2.82 (s, 3H), 3.12 (m, 3H), 2.98 (m, 1H), 3.01 (dd, 2H), 3.19 (m, 1H), 3.50 (dd, 2H), 3.80 (m, 1H), 3.96 (m, 2H), 4.32 (s, br, 2H), 4.48 (s, br, 2H), 4.56 (m, 1H), 4.84 (s, br, 2H), 6.91 (dd, 1H), 7.14 (m, 1H), 7.22 (s, br, 2H), 7.45 (m, 5H), 8.09 (dd, 1H); $^{19}$F NMR (CD$_3$OD, 400 MHz) δ −77.2. MS (567 [M+H]$^+$), 85% pure.

Methyl 1-(dimethylcarbamoyl)piperidine-4-carboxylate

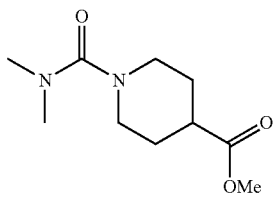

To a solution of methyl piperidine-4-carboxylate (200 mg, 1.40 mmol) in dichloromethane (4 ml) was added N,N-diisopropylethylamine (0.73 ml, 4.19 mmol) followed by dimethyl carbonyl chloride (0.13 ml, 1.40 mmol). The reaction mixture was stirred at room temperature overnight. The mixture was quenched with saturated sodium bicarbonate and extracted twice with dichloromethane. The organics were dried over magnesium sulfate, filtered, evaporated and purified via SPE (5 g SiO$_2$ 50% ethyl acetate in heptane) to provide methyl 1-(dimethylcarbamoyl)piperidine-4-carboxylate (50 mg, 17%). $^1$H NMR (CD$_3$OD, 300 MHz) δ 1.62-1.77 (m, 2H), 1.86-1.96 (m, 2H), 2.40-2.52 (m, 1H), 2.75-2.86 (m, 2H), 2.82 (m, 6H), 3.62 (dt, 2H), 3.69 (s, 3H); UPLC-MS (poor UV).

1-(Dimethylcarbamoyl)piperidine-4-carboxylic Acid

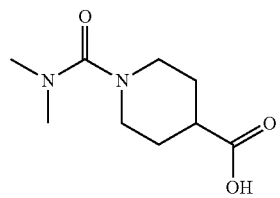

Methyl 1-(dimethylcarbamoyl)piperidine-4-carboxylate (50 mg, 0.23 mmol) was dissolved in methanol (2 ml) and 2.5 M sodium hydroxide (0.14 ml, 0.35 mmol) was added and the reaction stirred at room temperature overnight. The mixture was acidified with 2M HCl and extracted three times with ethyl acetate. The organics were dried over magnesium sulfate, filtered and evaporated to provide 1-(dimethylcarbamoyl)piperidine-4-carboxylic acid as a colourless glass (26 mg, 56%). $^1$H NMR (CD$_3$OD, 300 MHz) δ 1.63 (qd, 2H), 1.84-1.94 (m, 2H), 2.41-2.53 (m, 1H), 2.81 (s, 6H), 2.85 (td, 2H), 3.60 (dt, 2H); UPLC-MS (short acid) 0.38 (201 [MH]$^+$).

tert-Butyl 2-((1-(dimethylcarbamoyl)-N-(2-oxo-2-((2'-oxo-1,1',2',3-tetrahydrospiro[indene-2,3'-pyrrolo[2,3-b]pyridin]-5-yl)amino)ethyl) piperidine-4-carboxamido)methyl)benzyl(methyl)carbamate 32.1f

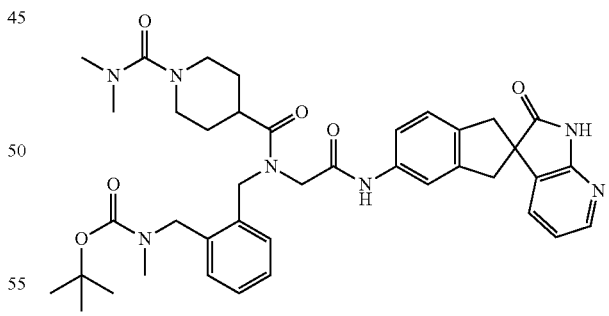

Synthesised according to General Route G (step 1 B) from Intermediate V (52 mg, 0.096 mmol) in N,N-dimethylformamide (1 ml) with N,N-diisopropylethylamine (50 µl, 0.29 mmol), 1-(dimethylcarbamoyl)piperidine-4-carboxylic acid (19 mg, 0.096 mmol), EDCl.HCl (24 mg, 0.126 mmol), HOAt (17 mg, 0.126 mmol) and purified via Biotage Isolera (5 g SiO$_2$, 0 to 5% methanol in ethyl acetate) to provide compound 32.1f as a colourless glass (35 mg, 49%). UPLC-MS (short acid) rt 0.80 (724 [MH]$^+$).

Example 71: N1,N1-dimethyl-N4-(2-((methylamino)methyl)benzyl)-N4-(2-oxo-2-((2'-oxo-1,1',2',3-tetrahydrospiro[indene-2,3'-pyrrolo[2,3-b]pyridin]-5-yl)amino)ethyl)piperidine-1,4-dicarboxamide 2,2,2-trifluoroacetate 32F

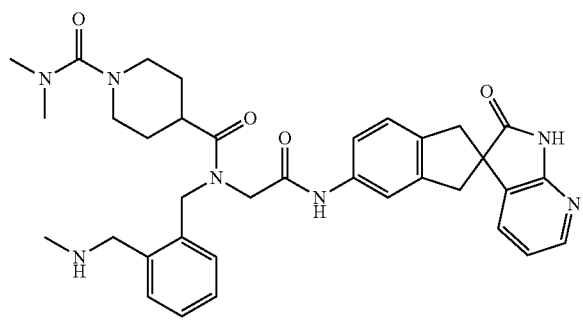 [SMILES: CNCc1ccccc1CN(CC(=O)Nc1ccc2c(c1)CC1(C2)C(=O)Nc2ncccc21)C(=O)C1CCN(C(=O)N(C)C)CC1]

Synthesised according to General Route G (step 2B) from compound 32.1f (16 mg, 0.026 mmol) in methanol (0.4 ml) and ethyl acetate (0.4 ml) with hydrochloric acid 35% (0.2 ml). Purified by prep-HPLC (HP C18, ID 22 mm, length 150 mm, flow 16 ml/min: 5-55% acetonitrile-water/acetonitrile 0.1% TFA over 20 min) then freeze-dried to provide compound 32F as white solid (12 mg, 62%). $^1$H NMR (CD$_3$OD, 400 MHz) δ 1.81 (m, 4H), 2.84 (m, 12H), 3.09 (m, 2H), 3.51 (m, 2H), 3.72 (m, 2H), 4.33 (s, br, 2H), 4.47 (s, br, 2H), 4.84 (m, 2H), 6.92 (dd, 1H), 7.16 (d, 2H), 7.22 (m, 2H), 7.45 (m, 5H), 8.08 (dd, 1H); $^{19}$F NMR (CD$_3$OD, 400 MHz) δ −77.3; MS (624 [M+H]$^+$), 98% pure.

Methyl 1-(methylsulfonyl)piperidine-4-carboxylate

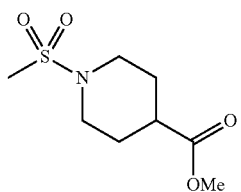

To a solution of methyl piperidine-4-carboxylate (200 mg, 1.40 mmol) in dichloromethane (4 ml) was added N,N-diisopropylethylamine (0.73 ml, 4.193 mmol) followed by methanesulfonyl chloride (0.11 ml, 1.40 mmol). The reaction mixture was stirred at room temperature overnight The mixture was quenched with saturated sodium bicarbonate and extracted twice with dichloromethane. The organics were dried over magnesium sulfate, filtered, evaporated and purified via SPE (5 g SiO$_2$ 50% ethyl acetate in heptane) to provide methyl 1-(methylsulfonyl)piperidine-4-carboxylate (67 mg, 22%). $^1$H NMR (CD$_3$OD, 300 MHz) δ 1.77-1.93 (m, 2H), 1.97-2.08 (m, 2H), 2.41-2.51 (m, 1H), 2.28 (s, 3H), 2.81-2.92 (m, 2H), 3.61-3.71 (m, 2H), 3.71 (s, 3H); UPLC-MS (poor UV).

1-(Methylsulfonyl)piperidine-4-carboxylic Acid

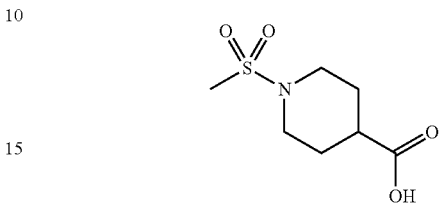

Methyl 1-(methylsulfonyl)piperidine-4-carboxylate (67 mg, 0.30 mmol) was dissolved in methanol (2 ml) and 2.5 M sodium hydroxide (0.18 ml, 0.45 mmol) was added and the reaction stirred at room temperature overnight. The mixture was acidified with 2M HCl and extracted three times with ethyl acetate. The organics were dried over magnesium sulfate, filtered and evaporated to provide 1-(methylsulfonyl)piperidine-4-carboxylic acid as a colourless glass (41 mg, 66%). $^1$H NMR (CD$_3$OD, 300 MHz) δ 1.72 (dq, 2H), 1.96-2.06 (m, 2H), 2.38-2.50 (m, 1H), 2.80 (s, 3H), 2.84 (td, 2H), 3.58-3.67 (m, 2H); UPLC-MS (short acid) (206 [M−H]$^+$).

tert-Butyl methyl(2-((1-(methylsulfonyl)-N-(2-oxo-2-((2'-oxo-1,1',2',3-tetrahydrospiro[indene-2,3'-pyrrolo[2,3-b]pyridin]-5-yl)amino)ethyl) piperidine-4-carboxamido)methyl)benzyl)carbamate 32.1g

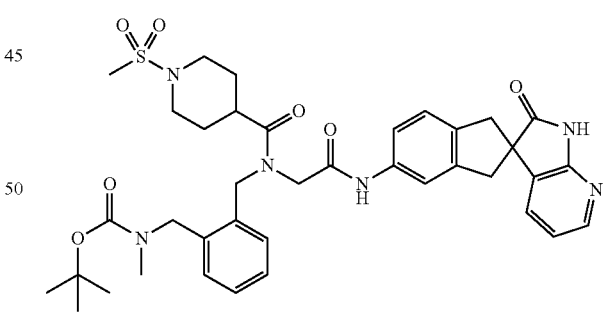

Synthesised according to General Route G (step 1B) from Intermediate V (52 mg, 0.096 mmol) in N,N-dimethylformamide (1 ml) with N,N-diisopropylethylamine (50 µl, 0.29 mmol), 1-(methylsulfonyl)piperidine-4-carboxylic acid (20 mg, 0.096 mmol), EDCl.HCl (24 mg, 0.13 mmol), HOAt (17 mg, 0.13 mmol) and purified via Biotage Isolera (5 g SiO$_2$, 0 to 5% methanol in ethyl acetate) to provide a mixture of 3:2 of compound 32.1g and starting material compound. The mixture was used in next step without further purification.

Example 72: N-(2-((methylamino)methyl)benzyl)-1-(methylsulfonyl)-N-(2-oxo-2-((2'-oxo-1,1',2',3-tetrahydrospiro[indene-2,3'-pyrrolo[2,3-b]pyridin]-5-yl)amino)ethyl)piperidine-4-carboxamide 2,2,2-trifluoroacetate 32G

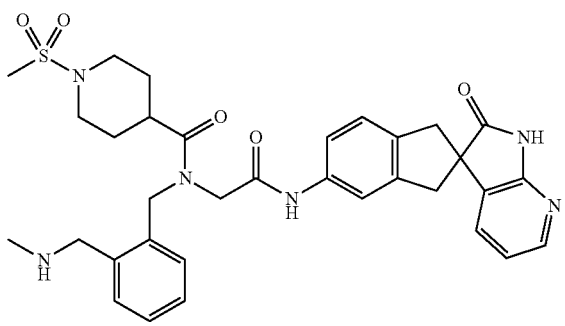 [SMILES: CNCc1ccccc1CN(CC(=O)Nc1ccc2c(c1)CC1(C2)C(=O)Nc2ncccc21)C(=O)C1CCN(S(C)(=O)=O)CC1]

Synthesised according to General Route G (step 2B) from compound 32.1g (16 mg, 0.022 mmol) in methanol (0.4 ml) and ethyl acetate (0.4 ml) with hydrochloric acid 35% (0.2 ml). Purified by prep-HPLC (HP C18, ID 22 mm, length 150 mm, flow 16 ml/min: 5-55% acetonitrile-water/acetonitrile 0.1% TFA over 20 min) then freeze-dried to provide compound 32G as white solid (8 mg, 51%). $^1$H NMR (CD$_3$OD, 400 MHz) δ 1.90 (m, 4H), 2.80 (m, 9H), 3.09 (m, 2H), 3.50 (m, 2H), 3.77 (m, 2H), 4.33 (s, br, 2H), 4.46 (s, br, 2H), 4.84 (m, 2H), 6.92 (dd, 1H), 7.15 (d, 1H), 7.22 (m, 2H), 7.45 (m, 5H), 8.08 (dd, 1H); $^{19}$F NMR (CD$_3$OD, 400 MHz) δ −77.3; MS (631 [M+H]$^+$), 97% pure.

Methyl 1-(isopropylcarbamoyl)piperidine-4-carboxylate

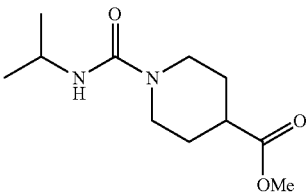 [SMILES: COC(=O)C1CCN(C(=O)NC(C)C)CC1]

To a solution of methyl piperidine-4-carboxylate (250 mg, 1.75 mmol) in dichloromethane (6 ml) was added isopropyl isocyanate (0.17 ml, 1.75 mmol). The reaction mixture was stirred at room temperature overnight. The mixture was quenched with saturated sodium bicarbonate and extracted twice with dichloromethane. The organics were dried over magnesium sulfate, filtered, evaporated and purified via SPE (5 g SiO$_2$ 50% ethyl acetate in heptane) to provide methyl 1-(isopropylcarbamoyl)piperidine-4-carboxylate (81 mg, 21%).

$^1$H NMR (CD$_3$OD, 300 MHz) δ 1.14 (d, 6H), 1.67 (td, 2H), 1.86-1.96 (m, 2H), 2.41-2.53 (m, 1H), 2.86 (ddd, 2H), 3.96 (s, 3H), 3.84 (dt, 2H), 3.96 (sextet, 1H), 4.14-4.26 (m, NH); UPLC-MS (short basic) 0.53 (229 [M−H]$^−$).

1-(Isopropylcarbamoyl)-4-methylpiperidine-4-carboxylic Acid

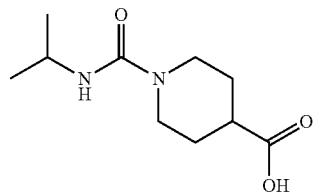

Methyl 1-(isopropylcarbamoyl)piperidine-4-carboxylate (82 mg, 0.36 mmol) was dissolved in methanol (2 ml), 2.5 M sodium hydroxide (0.22 ml, 0.54 mmol) was added, and the reaction stirred at room temperature overnight. The mixture was acidified with 2M HCl and extracted three times with ethyl acetate. The organics were dried over magnesium sulfate, filtered and evaporated to provide the desired product as a colourless glass (25 mg, 33%). $^1$H NMR (CD$_3$OD, 300 MHz) δ 1.11 (d, 6H), 1.55 (dq, 2H), 1.81-1.92 (m, 2H), 2.42-2.54 (m, 1H), 2.86 (ddd, 3H), 3.80-3.96 (m, 3H); UPLC-MS (short acid) 0.39 (213 [M−H]$^−$).

tert-Butyl 2-((1-(isopropylcarbamoyl)-N-(2-oxo-2-((2'-oxo-1,1',2',3-tetrahydrospiro[indene-2,3'-pyrrolo[2,3-b]pyridin]-5-yl)amino)ethyl) piperidine-4-carboxamido)methyl)benzyl(methyl)carbamate 32.1h

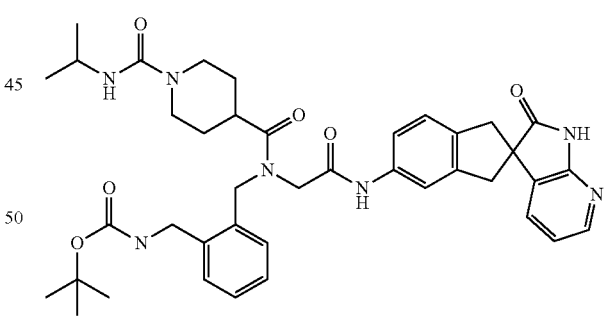

Synthesised according to General Route G (step 1B) from Intermediate V (52 mg, 0.096 mmol) in N,N-dimethylformamide (1 ml) with N,N-diisopropylethylamine (50 µl, 0.29 mmol), 1-(dimethylcarbamoyl)piperidine-4-carboxylic acid (21 mg, 0.096 mmol), EDCl.HCl (24 mg, 0.126 mmol), HOAt (17 mg, 0.126 mmol) and purified via biotage isolera (5 g SiO$_2$, 0 to 10% methanol in ethyl acetate) to provide compound 32.1h as a colourless glass (47 mg, 66%). UPLC-MS (short acid) rt 0.81 (738 [MH]$^+$).

Example 73: N1-isopropyl-N4-(2-((methylamino)methyl)benzyl)-N4-(2-oxo-2-((2'-oxo-1,1',2',3-tetrahydrospiro[indene-2,3'-pyrrolo[2,3-b]pyridin]-5-yl)amino)ethyl)piperidine-1,4-dicarboxamide 2,2,2-trifluoroacetate 32H

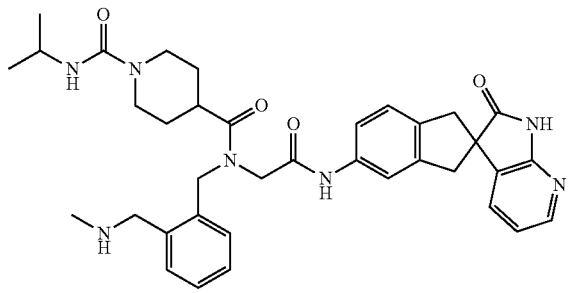 [SMILES: CNCc1ccccc1CN(CC(=O)Nc1ccc2c(c1)CC1(C2)C(=O)Nc2ncccc21)C(=O)C1CCN(C(=O)NC(C)C)CC1]

Synthesised according to General Route G (step 2 B) from compound 32.1h (16 mg, 0.021 mmol) in methanol (0.4 ml) and ethyl acetate (0.4 ml) with hydrochloric acid 35% (0.2 ml). Purified by prep-HPLC (HP C18, ID 22 mm, length 150 mm, flow 16 ml/min: 5-55% acetonitrile-water/acetonitrile 0.1% TFA over 20 min) then freeze-dried to provide compound 32H as white solid (9.1 mg, 58%). $^1$H NMR (CD$_3$OD, 400 MHz) δ 1.15 (d, 6H), 1.75 (m, 4H), 2.82 (m, 5H), 3.09 (m, 2H), 3.50 (m, 2H), 3.77 (m, 2H), 3.90 (hept, 1H), 4.09 (m, 2H), 4.33 (s, br, 2H), 4.47 (s, br, 2H), 4.83 (m, 2H), 6.92 (dd, 1H), 7.15 (d, 1H), 7.22 (m, 2H), 7.45 (m, 5H), 8.08 (dd, 1H); $^{19}$F NMR (CD$_3$OD, 400 MHz) δ −77.3; MS (638 [M+H]$^+$), 99% pure.

Methyl 1-acetylpyrrolidine-3-carboxylate

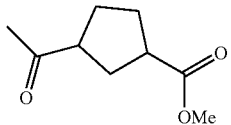

1-Acetylpyrrolidine-3-carboxylic acid hydrochloride (200 mg, 1.21 mmol) was dissolved in pyridine (2 ml) and acetic anhydride (0.14 ml, 2.32 mol) was added under argon and the mixture stirred was at room temperature for 5 h. The reaction mixture was poured into saturated sodium bicarbonate. The aqueous layer was extracted with dichloromethane, dried over sodium sulfate, filtered and evaporated to provide the desired compound as a colourless oil (190 mg, 92%). $^1$H NMR (CD$_3$OD, 300 MHz) δ 2.04, 2.05 (2 s, 3H), 2.20 (m, 2H), 3.11 (m, 1H), 3.46 (m, 1H), 3.60 (m, 3H), 3.72 (s, 3H). UPLC-MS (long basic) rt 0.66 (172 [M−H]$^−$).

1-Acetylpyrrolidine-3-carboxylic Acid

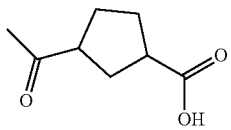

Methyl 1-acetylpyrrolidine-3-carboxylate (190 mg, 1.11 mmol) was dissolved in methanol (10 ml), 2.5 M sodium hydroxide (0.68 ml, 1.2 mmol) was added, and the reaction stirred at room temperature overnight. The mixture was poured into aqueous ammonium chloride and extracted three times with ethyl acetate. The organics were dried over magnesium sulfate, filtered and evaporated to provide the desired product as a colourless glass (20 mg, 12%).
$^1$H NMR (CD$_3$OD, 400 MHz) δ 2.07, 2.08 (2 s, 3H), 2.22 (m, 2H), 3.11-3.20 (m, 1H), 3.51 (m, 1H), 3.70 (m, 3H). UPLC-MS (short CSH, 2-20%) 0.47 (158 [MH]$^+$).

tert-Butyl 2-((1-acetyl-N-(2-oxo-2-((2'-oxo-1,1',2',3-tetrahydrospiro[indene-2,3'-pyrrolo[2,3-b]pyridin]-5-yl)amino)ethyl)pyrrolidine-3-carboxamido)methyl)benzyl(methyl)carbamate 32.1i

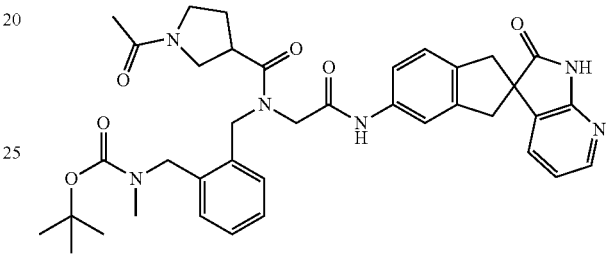

Synthesised according to General Route G (step 1 B) from Intermediate V (45 mg, 0.083 mmol) in N,N-dimethylformamide (2 ml) with N,N-diisopropylethylamine (44 μl, 0.28 mmol), 1-acetylpyrrolidine-3-carboxylic acid (20 mg, 0.127 mmol), EDCl.HCl (27 mg, 0.140 mmol), HOAt (19 mg, 0.140 mmol), and purified via flash silica chromatography (5 g SiO$_2$, ethyl acetate) to provide compound 32.1l as a colourless glass (42 mg, 74%). UPLC-MS (short CSH 2-50%) rt 1.08 (581 [M−Boc+H]$^+$).

Example 74: 1-acetyl-N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pyrrolidine-3-carboxamide 2,2,2-trifluoroacetate 32l

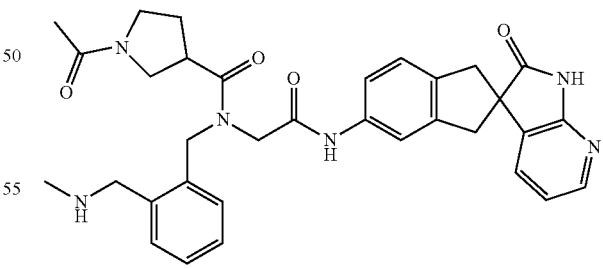

Synthesised according to General Route G (step 2 B) from compound 32.1l (16 mg, 0.023 mmol) in methanol (0.4 ml) and ethyl acetate (0.4 ml) with hydrochloric acid 35% (0.2 ml). Purified by prep-HPLC (HP C18, ID 22 mm, length 150 mm, flow 16 ml/min: 5-55% acetonitrile-water/acetonitrile 0.1% TFA over 20 min) and freeze-dried to provide compound 32l (10 mg, 65%) as a white solid. $^1$H NMR (CD$_3$OD, 400 MHz) δ 2.07, 2.08 (2 s, 3H), 2.27 (m, 2H), 2.82 (s, 3H), 3.08 (m, 2H), 3.52 (m, 5H), 3.75 (m, 2H), 4.52 (m, 5H), 4.85 (m, 1H), 5.03 (m, 1H), 6.92 (dd, 1H), 7.15 (d, 2H), 7.22 (m, 2H), 7.42 (m, 5H), 8.08 (dd, 1H). $^{19}$F NMR (CD$_3$OD, 400 MHz) δ −77.2. MS (581 [M+H]$^+$), 99% pure.

Example 75: N-[[2-(methylaminomethyl)phenyl]methyl]-N-[2-oxo-2-[(2-oxospiro[1H-pyrrolo[2,3-b]pyridine-3,2'-indane]-5'-yl)amino]ethyl]-1-(trifluoromethyl)cyclopropanecarboxamide 2,2,2-trifluoroacetate 32J

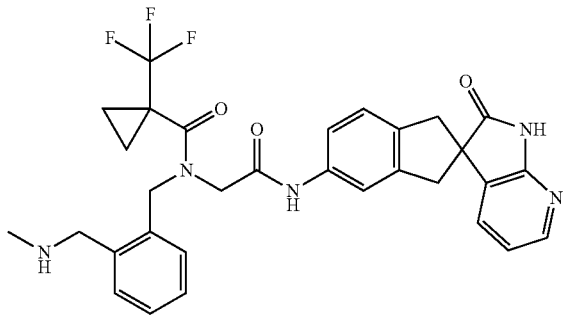 [SMILES: CNCc1ccccc1CN(CC(=O)Nc1ccc2c(c1)CC1(C2)C(=O)Nc2ncccc21)C(=O)C1(C(F)(F)F)CC1]

Compound 32J was synthesised according to General Route G from Intermediate V (70 mg). For step 1B, the condensation with 1-(trifluoromethyl)cyclopropane-1-carboxylic acid was conducted with HOAt, EDCl, and DIPEA at 80° C. The crude product was purified by prep-TLC (EA). For the step 2A, the deprotection was conducted with TFA. The purification was carried out by prep-HPLC (column: Boston pH-lex 150×25 mm, 10 μm; mobile phase: [water (0.1% TFA)-acetonitrile]; B %: 21%-51%, 10 min) and lyophilisation to provide compound 32J (16 mg, 51% yield) as a yellow solid. $^1$H NMR (CD$_3$OD, 400 MHz) δ. 1.29 (d, 4H), 2.69 (s, 3H), 2.99 (d, 2H), 3.41 (dd, 2H), 4.19 (s, 2H), 4.71 (m, 4H), 6.80 (dd, 1H), 7.06 (dd, 1H), 7.14 (d, 1H), 7.22 (d, 1H), 7.31-7.38 (m, 5H), 7.96 (dd, 1H). LC-MS: rt 1.492 min, (578 [M+H]$^+$), purity 100.0% tert-Butyl N-methyl-N-[[2-[[[2-oxo-2-[(2-oxospiro[1H-pyrrolo[2,3-b]pyridine-3,2'-indane]-5'-yl)amino]ethyl]-[1-(trifluoromethyl)cyclobutanecarbonyl]amino]methyl]phenyl]methyl]carbamate 32.1k

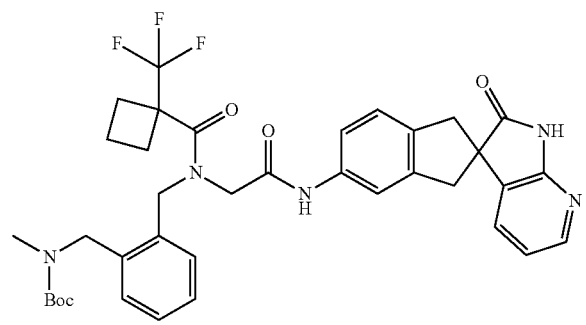 [SMILES: CN(Cc1ccccc1CN(CC(=O)Nc1ccc2c(c1)CC1(C2)C(=O)Nc2ncccc21)C(=O)C1(C(F)(F)F)CCC1)C(=O)OC(C)(C)C]

Compound 32.1k was prepared by a route analogous to General Route G step 1A: To a solution of compound 1-(trifluoromethyl)cyclobutanecarboxylic acid (28 mg, 0.16 mmol) in dichloromethane (2 mL) was added oxalyl chloride (15 mg, 0.12 mmol) and dimethyl formamide (6 mg, 0.82 mmol) at 0° C. The mixture was stirred at 0° C. for 1 h and concentrated in vacuum at 0° C. The residue was re-dissolved in dichloromethane (2 mL) and added to a solution of Intermediate V (50 mg, 0.82 mmol) and DIPEA (25 mg, 0.19 mmol) in dichloromethane (2 mL) at 0° C. The resulting mixture was stirred at 20° C. for another 3 h. The mixture was quenched by water (10 mL) and extracted with dichloromethane (3×10 mL). The organic phases were washed with brine (10 mL) and dried over anhydrous sodium sulfate. After filtration and concentration, the residue was purified by prep-TLC (petroleum ether ethyl aectate=0:1) to provide compound 32.1k as a yellow solid (40 mg, 55% yield). LC-MS: rt 0.882 min, (692 [M+H]$^+$), purity 78%.

Example 76: N-[[2-(methylaminomethyl)phenyl]methyl]-N-[2-oxo-2-[(2-oxospiro[1H-pyrrolo[2,3-b]pyridine-3,2'-indane]-5'-yl)amino]ethyl]-1-(trifluoromethyl)cyclobutanecarboxamide 2,2,2-trifluoroacetate 32K

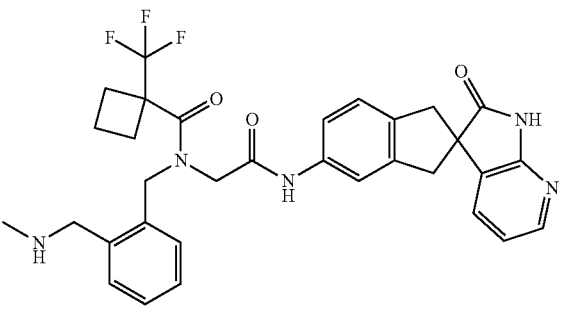 [SMILES: CNCc1ccccc1CN(CC(=O)Nc1ccc2c(c1)CC1(C2)C(=O)Nc2ncccc21)C(=O)C1(C(F)(F)F)CCC1]

To a solution of compound 32.1k (40 mg, 0.45 mmol) in dichloromethane (5 mL) was added trifluoroacetic acid (1 mL). The mixture was stirred at 20° C. for 1 hour. LCMS indicated the desired MS was detected. The mixture was concentrated to give a residue. The residue was purified by prep-HPLC (column: Boston pH-lex 150×25 mm, 10 μm; mobile phase: [water (0.1% TFA)-acetonitrile]; B %: 20%-50%, 10 min). After lyophilisation, compound 32K was obtained as a yellow solid (11 mg, 33% yield, 95.7% purity). $^1$H NMR (DMSO-d$_6$, 400 MHz) δ. 1.81-1.86 (m, 1H), 1.99-2.04 (m, 1H), 2.52 (m, 2H), 2.65 (s, 3H), 2.74-2.79 (m, 2H), 3.09 (dd, 2H), 3.35-3.40 (m, 2H), 4.04 (s, 2H), 4.18 (s, 2H), 4.74 (s, 2H), 6.86 (dd, 1H), 7.15-7.25 (m, 3H), 7.32 (dd, 1H), 7.37-7.54 (m, 4H), 8.06 (dd, 1H), 8.68 (br. s, 2H), 9.87 (br. s, 1H), 10.81 (s, 1H). LC-MS: rt 2.63 min, (592 [M+H]$^+$), purity 95.7%.

Example 77: 3-amino-N-[[2-(methylaminomethyl) phenyl]methyl]-N-[2-oxo-2-[(2-oxospiro[1H-pyrrolo [2,3-b]pyridine-3,2'-indane]-5'-yl)amino]ethyl]bicyclo[1.1.1]pentane-1-carboxamide bis(2,2,2-trifluoroacetate) 32L

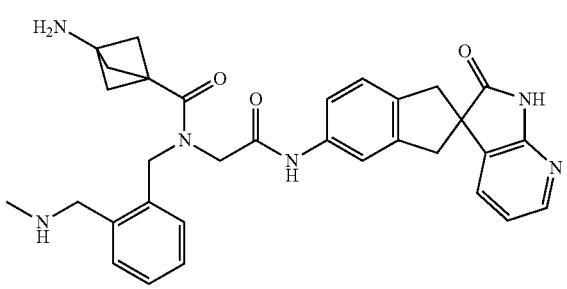 [SMILES: CNCc1ccccc1CN(CC(=O)Nc1ccc2c(c1)CC1(C2)C(=O)Nc2ncccc21)C(=O)C12CC(N)(C1)C2]

Compound 32L was synthesised according to General Route G (step 1B and step 2A) from Intermediate V (40 mg) and 3-amino-bicyclo[1.1.1]pentane-1-carboxylic acid. For the step 1B, the crude product was used directly. The purification of step 2A was conducted by prep-HPLC (column: Phenomenex Synergi C18 150×25 mm, 10 μm; mobile phase: [water (0.1% TFA)-acetonitrile]; B %: 5%-35%, 9 min) and lyophilisation to provide compound 32L as a white solid (40 mg, 70% yield).

Example 78: N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)bicyclo[1.1.1]pentane-1-carboxamide 2,2,2-trifluoroacetate 32M

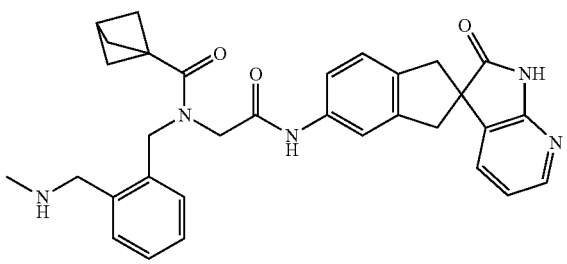 [SMILES: CNCc1ccccc1CN(CC(=O)Nc1ccc2c(c1)CC1(C2)C(=O)Nc2ncccc21)C(=O)C12CC(C1)C2]

Compound 32M was synthesised according to General Route G (step 1B and step 2A) from Intermediate V (40 mg) and bicyclo[1.1.1]pentane carboxylic acid. For the step 1B, the crude product was used directly. The purification of step 2A was conducted by prep-HPLC (column: Phenomenex Synergi C18 150×25 mm, 10 μm; mobile phase: [water (0.1% TFA)-acetonitrile]; B %: 15%-45%, 9 min) to provide compound 32M as a white solid (19 mg, 43% yield). $^1$H NMR (CD$_3$OD, 400 MHz) δ. 2.20 (s, 6H), 2.45 (s, 1H), 2.70 (s, 2H), 2.81 (s, 3H), 3.07 (dd, 2H), 3.46-3.51 (m, 2H), 4.33 (s, 2H), 4.47 (s, 2H), 4.79 (m, 2H), 6.89 (dd, 1H), 7.13-7.22 (m, 3H), 7.32 (s, 1H), 7.40-7.46 (m, 4H), 8.06 (dd, 1H). LC-MS: rt 1.432 min, (536 [M+H]$^+$), purity 98.6%.

tert-Butyl (2-((1-acetyl-N-(2-oxo-2-((2'-oxo-1,1',2', 3-tetrahydrospiro[indene-2,3'-pyrrolo[2,3-b]pyridin]-5-yl)amino)ethyl)piperidine-4-carboxamido)methyl) benzyl)(methyl)carbamate 32.1n

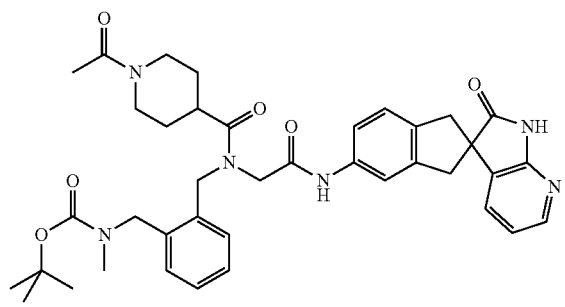 [SMILES: CC(=O)N1CCC(C(=O)N(CC(=O)Nc2ccc3c(c2)CC2(C3)C(=O)Nc3ncccc32)Cc2ccccc2CN(C)C(=O)OC(C)(C)C)CC1]

Synthesised according to General Route G (step 1 B) from Intermediate V (40 mg, 0.074 mmol) in N,N-dimethylformamide (1 ml) and dichloromethane (1 ml) with N,N-diisopropylethylamine (31 μl, 0.19 mmol), oxetane-3-carboxylic acid (15 mg, 0.089 mmol), EDCl.HCl (18 mg, 0.098 mmol), HOAt (12 mg, 0.098 mmol) and purified via flash silica chromatography (EtOAc 0-6% MeOH then dichloromethane 6-10% MeOH) to provide compound 32.1b (30 mg, 30%) as a colourless glass. $^1$H NMR (CDCl$_3$, 400 MHz) δ 1.56 (s, 9H), 1.80 (m, 2H), 2.05 (2 s, 3H), 2.82 (s, 3H), 3.05 (m, 4H), 3.60 (m, 3H), 4.10 (m, 2H), 4.46 (br s, 2H), 4.72 (m, 2H), 6.81 (dd, 1H), 7.04 (m, 2H), 7.15 (s, 3H), 7.30 (m, 2H), 7.50 (s, 1H), 7.92 (s, 1H), 8.10 (dd, 1H), 8.52 (m, 1H). UPLC-MS (short CSH 2-50%) rt 1.12 (695 [M+H]$^+$).

Example 79: 1-Acetyl-N-(2-((methylamino)methyl) benzyl)-N-(2-oxo-2-((2'-oxo-1,1',2',3-tetrahydrospiro [indene-2,3'-pyrrolo[2,3-b]pyridin]-5-yl)amino) ethyl)piperidine-4-carboxamide 32N

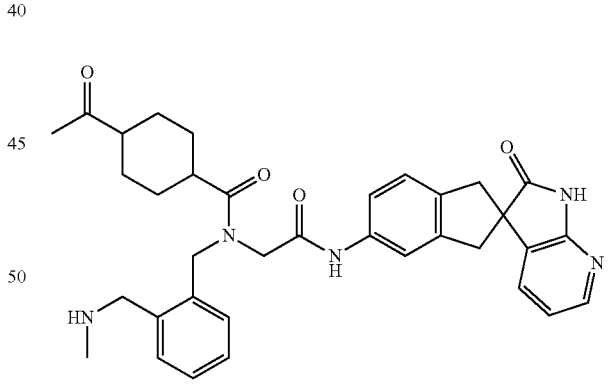

Synthesised according to General Route G (step 2AA) from 32.1b (30 mg, 0.043 mmol), trifluoroacetic acid (0.10 ml) and dichloromethane (2 ml) for 2.5 h, and purified via trituration (MeOH/diethyl ether) then azeotroped with methanol and toluene to provide compound 32N (11 mg, 43%) as a colourless solid. $^1$H NMR (CD$_3$OD, 300 MHz) δ 1.31 (m, 3H), 1.75 (m, 5H), 2.08, 2.09 (2 s, 3H), 2.46, 2.53 (2 s, 3H), 2.64 (m, 1H), 3.04 (m, 4H), 3.49 (m, 2H), 3.94 (m, 2H), 4.11 (m, 1H), 4.32 (m, 1H), 4.50 (m, 1H), 4.78 (m, 1H), 4.92 (s, 1H), 6.87 (dd, 1H), 7.12 (m, 3H), 7.32 (m, 4H), 7.52 (m, 1H), 8.03 (d, 1H). UPLC-MS (short CSH 2-50%) rt 1.28 (595 [M+H]$^+$), 94% pure.

291 tert-Butyl methyl(2-((N-(2-oxo-2-((2'-oxo-1,1',2',3-tetrahydrospiro[indene-2,3'-pyrrolo[2,3-b]pyridin]-5-yl)amino)ethyl)tetrahydrofuran-3-carboxamido)methyl)benzyl)carbamate 32.1o

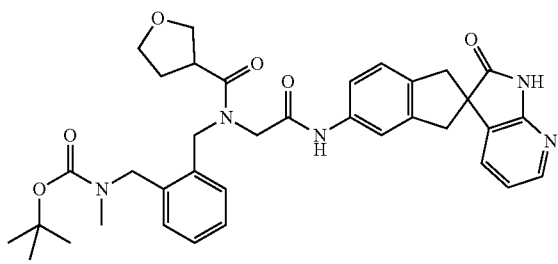 [SMILES: CN(Cc1ccccc1CN(CC(=O)Nc1ccc2c(c1)CC1(C2)C(=O)Nc2ncccc21)C(=O)C1CCOC1)C(=O)OC(C)(C)C]

Synthesised according to General Route G (step 1 B) from Intermediate V (33 mg, 0.061 mmol) in N,N-dimethylformamide (1 ml) and dichloromethane (2 ml) with N,N-diisopropylethylamine (24 µl, 0.15 mmol), 3-tetrahydrofuran carboxylic acid (8.5 mg, 0.073 mmol), EDCl.HCl (16 mg, 0.073 mmol), HOAt (12 mg, 0.073 mmol) and purified via flash silica chromatography (EtOAc) to provide compound 32.1o (21 mg, 54%) as a colourless glass. UPLC-MS (short CSH 2-50%) rt 1.14 (540 [M−Boc+H]$^+$).

Example 80: N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)tetrahydrofuran-3-carboxamide 32O

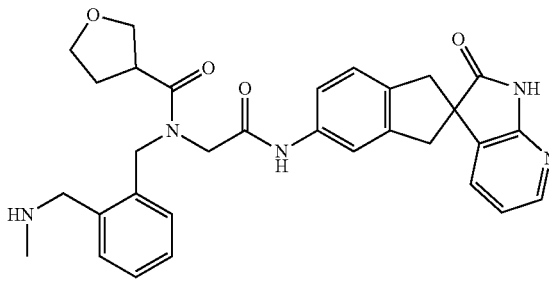

Synthesised according to General Route G (step 2AA) from 32.1o (21 mg, 0.033 mmol), trifluoroacetic acid (0.20 ml) and dichloromethane (2 ml) for 1 h, and purified via flash chromatography (silica, EtOAc 0-10% MeOH then dichloromethane 10-15% MeOH then dichloromethane 15-20% MeOH with ammonia) to provide compound 32O (5 mg, 28%) as a colourless solid. $^1$H NMR (CD$_3$OD, 300 MHz) δ 2.17 (m, 2H), 2.58 (s, 3H), 3.05 (d, 2H), 3.50 (m, 2H), 3.81 (m, 2H), 3.90 (m, 3H), 4.00 (m, 2H), 4.13 (s, 1H), 4.42 (dd, 1H), 4.90 (m, 2H), 6.88 (dd, 1H), 7.10 (d, 1H), 7.21 (m, 3H), 7.33 (m, 5H), 8.03 (d, 1H). UPLC-MS (short CSH 2-50%) rt 0.58 (540 [M+H]$^+$).

292 tert-Butyl methyl(2-((N-(2-oxo-2-((2'-oxo-1,1',2',3-tetrahydrospiro[indene-2,3'-pyrrolo[2,3-b]pyridin]-5-yl)amino)ethyl)pyrrolidine-1-carboxamido)methyl)benzyl)carbamate 32.1p

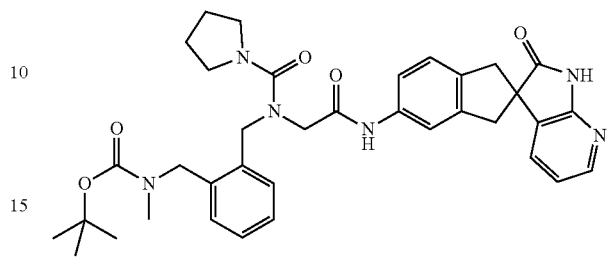

Synthesised according to General Route G (step 1A) from Intermediate V (33 mg, 0.061 mmol) in dichloromethane (2 ml) with N,N-diisopropylethylamine (24 µl, 0.15 mmol), pyrrolidine1-carbonyl chloride (10.5 mg, 0.079 mmol) at RT for 18 h, heated at 50° C. for 5 h then at RT for 12 days, and purified via flash silica chromatography (EtOAc 0-6% MeOH) to provide compound 32.1p (21 mg, 54%) as a colourless glass. UPLC-MS (short CSH 2-50%) rt 1.26 (639 [M+H]$^+$).

Example 81: N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)pyrrolidine-1-carboxamide 32P

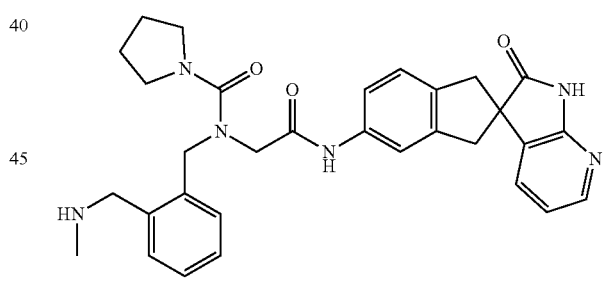

Synthesised according to General Route G (step 2A) from 32.1p (21 mg, 0.033 mmol), trifluoroacetic acid (0.20 ml) and dichloromethane (2 ml) for 1 h, and purified via flash chromatography (silica, EtOAc 0-10% MeOH then rir 10-15% MeOH then dichloromethane 15-20% MeOH with ammonia) to provide compound 32P (9 mg, 28%) as a colourless solid. $^1$H NMR (CD$_3$OD, 300 MHz) δ 1.84 (m, 4H), 2.57 (s, 3H), 3.04 (d, 2H), 3.42 (m, 4H), 3.50 (dd, 2H), 3.99 (s, 2H), 4.04 (s, 2H), 4.63 (s, 2H), 6.88 (dd, 1H), 7.11 (dd, 1H), 7.21 (d, 1H), 7.32 (m, 4H), 7.51 (m, 2H), 8.04 (dd, 1H). UPLC-MS (short CSH 2-50%) rt 0.67 (539 [M+H]$^+$), 98% purity.

293 tert-Butyl (2-((3-methoxy-3-methyl-1-(2-oxo-2-((2'-oxo-1,1',2',3-tetrahydrospiro[indene-2,3'-pyrrolo[2,3-b]pyridin]-5-yl)amino)ethyl)ureido)methyl)benzyl)(methyl)carbamate 32.1q

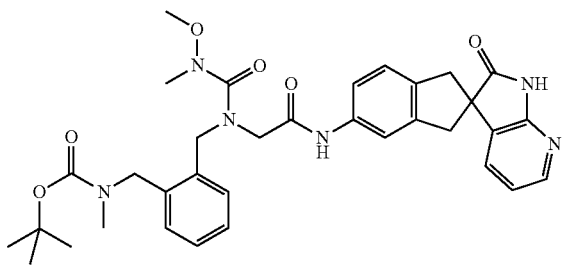 [SMILES: CON(C)C(=O)N(CC(=O)Nc1ccc2c(c1)CC1(C2)C(=O)Nc2ncccc21)Cc1ccccc1CN(C)C(=O)OC(C)(C)C]

Synthesised according to General Route G (step 1A) from Intermediate V (45 mg, 0.083 mmol) in dichloromethane (2 ml) with N,N-diisopropylethylamine (40 µl, 0.25 mmol), N-methoxy-N-methyl-1-carbamyl chloride (14 µl, 0.11 mmol) at RT for 18 h, and purified via flash silica chromatography (EtOAc) to provide compound 32.1q (40 mg, 78%) as a colourless glass. UPLC-MS (short CSH 2-50%) rt 1.26 (627 [M−H]$^-$), 95% pure.

Example 82: 2-(3-Methoxy-3-methyl-1-(2-((methylamino)methyl)benzyl)ureido)-N-(2'-oxo-1,1',2',3-tetrahydrospiro[indene-2,3'-pyrrolo[2,3-b]pyridin]-5-yl)acetamide 32Q

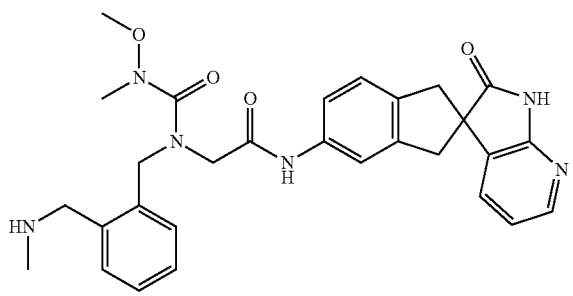 [SMILES: CNCc1ccccc1CN(CC(=O)Nc1ccc2c(c1)CC1(C2)C(=O)Nc2ncccc21)C(=O)N(C)OC]

Synthesised according to General Route G (step 2A) from 32.1q (40 mg, 0.064 mmol), trifluoroacetic acid (0.10 ml) and dichloromethane (2 ml) for 2.5 h, and purified via SPE (STMAd, 2 g, MeOH then MeOH with ammonia) to provide compound 32Q (20 mg, 59%) as a colourless solid. $^1$H NMR (CD$_3$OD, 300 MHz) δ 2.42, 2.44 (2 s, 3H), 3.05 (m, 5H), 3.48 (m, 2H), 3.55 (s, 3H), 3.76 (s, 2H), 4.02 (s, 2H), 4.77 (s, 2H), 6.87 (dd, 1H), 7.12 (dd, 1H), 7.20 (d, 1H), 7.32 (m, 5H), 7.50 (s, 1H), 8.04 (dd, 1H). UPLC-MS (short CSH 2-50%) rt 0.50 (529 [M+H]$^+$), 93% purity.

294 tert-Butyl (2-((3-cyclopentyl-1-(2-oxo-2-((2'-oxo-1,1',2',3-tetrahydrospiro[indene-2,3'-pyrrolo[2,3-b]pyridin]-5-yl)amino)ethyl)ureido)methyl)benzyl)(methyl)carbamate 32.1r

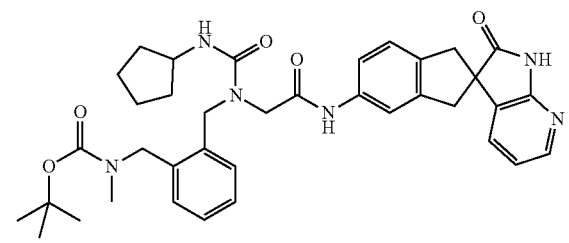 [SMILES: CN(Cc1ccccc1CN(CC(=O)Nc1ccc2c(c1)CC1(C2)C(=O)Nc2ncccc21)C(=O)NC1CCCC1)C(=O)OC(C)(C)C]

Synthesised according to General Route G (step 1C) from Intermediate V (45 mg, 0.083 mmol) in dichloromethane (1 ml) with cyclopentyl isocyanate (12 µl, 0.108 mmol) at RT for 18 h, and purified via flash silica chromatography (EtOAc) to provide compound 32.1r (34 mg, 63%) as a colourless glass. UPLC-MS (short CSH 2-50%) rt 1.33 (553 [M−Boc+H]$^+$), 99% pure.

Example 83: 2-(3-Cyclopentyl-1-(2-((methylamino)methyl)benzyl)ureido)-N-(2'-oxo-1,1',2',3-tetrahydrospiro[indene-2,3'-pyrrolo[2,3-b]pyridin]-5-yl)acetamide 32R

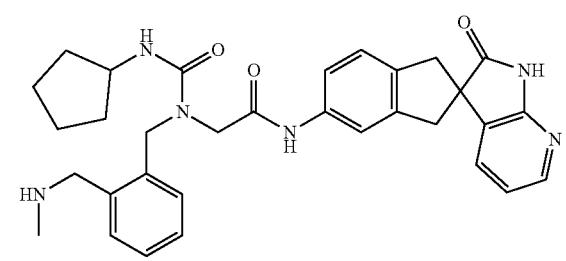 [SMILES: CNCc1ccccc1CN(CC(=O)Nc1ccc2c(c1)CC1(C2)C(=O)Nc2ncccc21)C(=O)NC1CCCC1]

Synthesised according to General Route G (step 2A) from 32.1r (34 mg, 0.052 mmol), trifluoroacetic acid (0.10 ml) and dichloromethane (2 ml) for 5 h, and purified via SPE (STMAd, 2 g, MeOH then MeOH with ammonia) to provide compound 32R (20 mg, 59%) as a colourless solid. $^1$H NMR (CD$_3$OD, 300 MHz) δ 1.52 (m, 6H), 1.89 (m, 2H), 2.44 (s, 3H), 3.04 (dd, 2H), 3.50 (dd, 2H), 3.74 (s, 2H), 4.04 (m, 1H), 4.08 (s, 2H), 4.69 (s, 2H), 6.87 (dd, 1H), 7.11 (dd, 1H), 7.28 (m, 6H), 7.47 (s, 1H), 8.02 (dd, 1H). UPLC-MS (short CSH 2-50%) rt 0.72 (553 [M+H]$^+$), 94% purity.

295 tert-Butyl (2-((3-isopropyl-1-(2-oxo-2-((2'-oxo-1,1',2',3-tetrahydrospiro[indene-2,3'-pyrrolo[2,3-b]pyridin]-5-yl)amino)ethyl)ureido)methyl)benzyl)(methyl)carbamate 32.1s

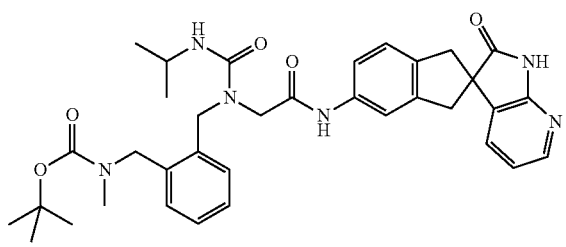 [SMILES: CC(C)NC(=O)N(CC(=O)Nc1ccc2c(c1)CC1(C2)C(=O)Nc2ncccc21)Cc1ccccc1CN(C)C(=O)OC(C)(C)C]

Synthesised according to General Route G (step 1C) from Intermediate V (45 mg, 0.083 mmol) in 1,2-dichloroethane (1 ml) with isopropyl isocyanate (11 μl, 0.108 mmol) at RT for 18 h, and purified via flash silica chromatography (EtOAc 0-5% MeOH) to provide compound 32.1s (39 mg, 75%) as a colourless glass. UPLC-MS (short CSH 2-50%) rt 1.21 (625 [M−H]⁻), 98% pure.

Example 84: 2-(3-Isopropyl-1-(2-((methylamino)methyl)benzyl)ureido)-N-(2'-oxo-1,1',2',3-tetrahydrospiro[indene-2,3'-pyrrolo[2,3-b]pyridin]-5-yl)acetamide 32S

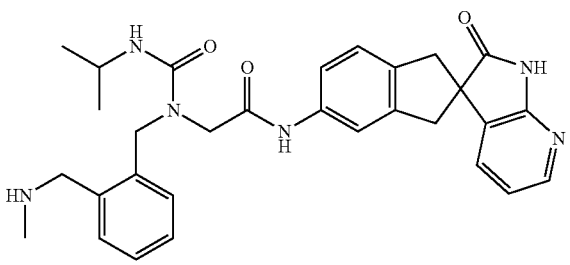 [SMILES: CNCc1ccccc1CN(CC(=O)Nc1ccc2c(c1)CC1(C2)C(=O)Nc2ncccc21)C(=O)NC(C)C]

Synthesised according to General Route G (step 2A) from 32.1s (39 mg, 0.062 mmol), trifluoroacetic acid (0.10 ml) and dichloromethane (2 ml) for 6 h, and purified via SPE (STMAd, 2 g, MeOH then MeOH with ammonia) to provide compound 32S (11 mg, 34%) as a colourless solid. $^1$H NMR (CD$_3$OD, 300 MHz) δ 1.11 (d, 6H), 2.44 (s, 3H), 3.04 (dd, 2H), 3.50 (dd, 2H), 3.73 (s, 2H), 3.92 (m, 1H), 4.08 (s, 2H), 4.69 (s, 2H), 6.88 (dd, 1H), 7.11 (dd, 1H), 7.25 (m, 6H), 7.48 (s, 1H), 8.02 (dd, 1H). UPLC-MS (short CSH 2-50%) rt 0.64 (527 [M+H]⁺), 94% purity.

296 tert-Butyl (2-((3,3-dimethyl-1-(2-oxo-2-((2'-oxo-1,1',2',3-tetrahydrospiro[indene-2,3'-pyrrolo[2,3-b]pyridin]-5-yl)amino)ethyl)ureido)methyl)benzyl)(methyl)carbamate 32.1t

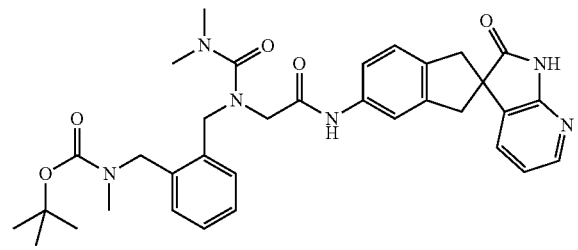 [SMILES: CN(C)C(=O)N(CC(=O)Nc1ccc2c(c1)CC1(C2)C(=O)Nc2ncccc21)Cc1ccccc1CN(C)C(=O)OC(C)(C)C]

Synthesised according to General Route G (step 1A) from Intermediate V (45 mg, 0.083 mmol) in 1,2-dichloroethane (1 ml) with N,N-diisopropylethylamine (40 μl, 0.25 mmol) and dimethyl carbamoyl chloride (10 μl, 0.108 mmol) at RT for 18 h then at 55° C. for 6.5 h then RT for 3 days, and purified via flash silica chromatography (EtOAc 0-5% MeOH) to provide compound 32.1t (38 mg, 75%) as a colourless glass. UPLC-MS (short CSH 2-50%) rt 1.17 (611 [M−H]⁻), 98% pure.

Example 85: 2-(3,3-Dimethyl-1-(2-((methylamino)methyl)benzyl)ureido)-N-(2'-oxo-1,1',2',3-tetrahydrospiro[indene-2,3'-pyrrolo[2,3-b]pyridin]-5-yl)acetamide 32T

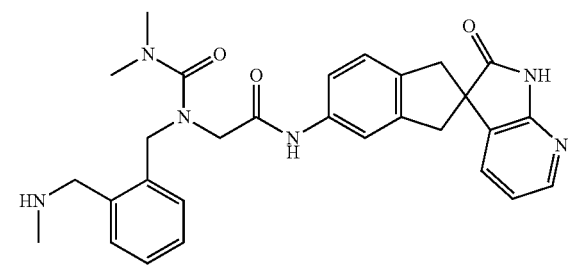 [SMILES: CNCc1ccccc1CN(CC(=O)Nc1ccc2c(c1)CC1(C2)C(=O)Nc2ncccc21)C(=O)N(C)C]

Synthesised according to General Route G (step 2A) from 32.1t (39 mg, 0.062 mmol), trifluoroacetic acid (0.10 ml) and dichloromethane (2 ml) for 6 h, and purified via SPE (STMAd, 2 g, MeOH then MeOH with ammonia) to provide compound 32T (18 mg, 57%) as a colourless solid. $^1$H NMR (CD$_3$OD, 300 MHz) δ 2.41 (s, 3H), 2.91 (s, 6H), 3.05 (dd, 2H), 3.50 (dd, 2H), 3.72 (s, 2H), 3.89 (s, 2H), 4.62 (s, 2H), 6.87 (dd, 1H), 7.12 (dd, 1H), 7.20 (d, 1H), 7.26 (m, 4H), 7.41 (m, 1H), 7.49 (s, 1H), 8.02 (dd, 1H). UPLC-MS (short CSH 2-50%) rt 0.63 (513 [M+H]⁺), 95% purity.

297 tert-Butyl methyl(2-((N-(2-oxo-2-((2'-oxo-1,1',2',3-tetrahydrospiro[indene-2,3'-pyrrolo[2,3-b]pyridin]-5-yl)amino)ethyl)morpholine-4-carboxamido)methyl)benzyl)carbamate 32.1 u

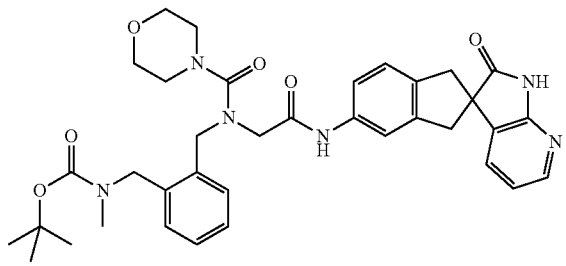 [SMILES: CN(Cc1ccccc1CN(CC(=O)Nc1ccc2c(c1)CC1(C2)C(=O)Nc2ncccc21)C(=O)N1CCOCC1)C(=O)OC(C)(C)C]

Synthesised according to General Route G (step 1A) from Intermediate V (45 mg, 0.083 mmol) in 1,2-dichloroethane (1 ml) with N,N-diisopropylethylamine (40 μl, 0.25 mmol) and morpholine-4-carbamyl chloride (13 μl, 0.108 mmol) at RT for 18 h, and purified via flash silica chromatography (EtOAc 0-6% MeOH) to provide compound 32.1u (40 mg, 74%) as a colourless glass. UPLC-MS (short CSH 2-50%) rt 1.19 (653 [M−H]⁻), 98% pure.

Example 86: N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)morpholine-4-carboxamide 32U

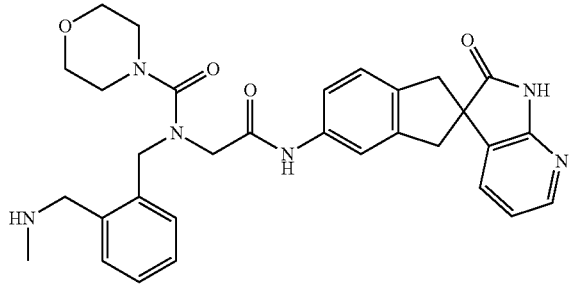 [SMILES: CNCc1ccccc1CN(CC(=O)Nc1ccc2c(c1)CC1(C2)C(=O)Nc2ncccc21)C(=O)N1CCOCC1]

Synthesised according to General Route G (step 2A) from 32.1u (40 mg, 0.061 mmol), trifluoroacetic acid (0.10 ml) and dichloromethane (2 ml) for 6 h, and purified via SPE (STMAd, 2 g, MeOH then MeOH with ammonia) to provide compound 32U (12 mg, 36%) as a colourless solid. ¹H NMR (CD₃OD, 300 MHz) δ 2.43 (s, 3H), 3.04 (dd, 2H), 3.35 (m, 4H), 3.50 (dd, 2H), 3.69 (m, 4H), 3.75 (s, 2H), 3.91 (s, 2H), 4.64 (s, 2H), 6.87 (dd, 1H), 7.11 (dd, 1H), 7.20 (d, 1H), 7.31 (m, 5H), 7.60 (s, 1H), 8.03 (dd, 1H). UPLC-MS (short CSH 2-50%) rt 0.60 (555 [M+H]⁺), 98% purity.

298 tert-Butyl methyl(2-((N-(2-oxo-2-((2'-oxo-1,1',2',3-tetrahydrospiro[indene-2,3'-pyrrolo[2,3-b]pyridin]-5-yl)amino)ethyl)piperidine-1-carboxamido)methyl)benzyl)carbamate 32.1v

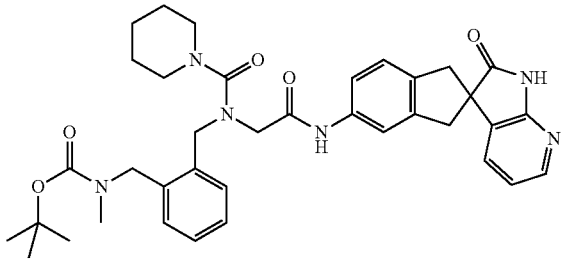 [SMILES: CN(Cc1ccccc1CN(CC(=O)Nc1ccc2c(c1)CC1(C2)C(=O)Nc2ncccc21)C(=O)N1CCCCC1)C(=O)OC(C)(C)C]

Synthesised according to General Route G (step 1A) from Intermediate V (45 mg, 0.083 mmol) in dichloromethane (1 ml) with N,N-diisopropylethylamine (40 μl, 0.25 mmol) and piperidine-1-carbamyl chloride (12 mg, 0.083 mmol) at RT for 4 days, and purified via normal phase chromatography (Zip sphere silica 5 g, 50-90% EtOAc in heptane) to provide compound 32.1v (32 mg, 59%) as a colourless glass. UPLC-MS (short CSH 2-95%) rt 0.96 (653 [M+H]⁺), 98% pure.

Example 87: N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)piperidine-1-carboxamide 32V

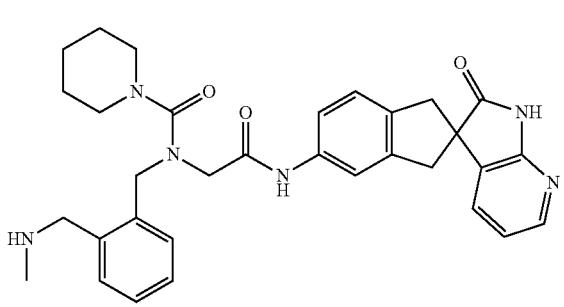

Synthesised according to General Route G (step 2A) from 32.1v (32 mg, 0.049 mmol), trifluoroacetic acid (0.10 ml) and dichloromethane (2 ml) for 3 h and purified via flash silica chromatography (EtOAc then dichloromethane 5% MeOH then dichloromethane 5% MeOH with ammonia) and SPE (SCX2 1 g, MeOH then ammonia in MeOH) to provide compound 32V (9 mg, 36%) as a colourless solid. ¹H NMR (CD₃OD, 300 MHz) δ 1.60 (m, 6H), 2.42 (s, 3H), 3.04 (dd, 2H), 3.30 (m, 4H), 3.50 (dd, 2H), 3.72 (s, 2H), 3.87 (s, 2H), 4.61 (s, 2H), 6.86 (dd, 1H), 7.11 (dd, 1H), 7.19 (d, 1H), 7.28 (m, 3H), 7.36 (m, 2H), 7.49 (s, 1H), 8.03 (dd, 1H). UPLC-MS (long CSH 2-95%) rt 1.16 (553 [M+H]⁺), 99% purity.

tert-butyl 4-((2-(((tert-butoxycarbonyl) (methyl) amino) methyl)benzyl)(2-oxo-2-((2'-oxo-1,1',2',3'-tetrahydrospiro[indene-2,3'-pyrrolo[2,3-b]pyridin]-5-yl)amino)ethyl)carbamoyl)piperidine-1-carboxylate 32.1w

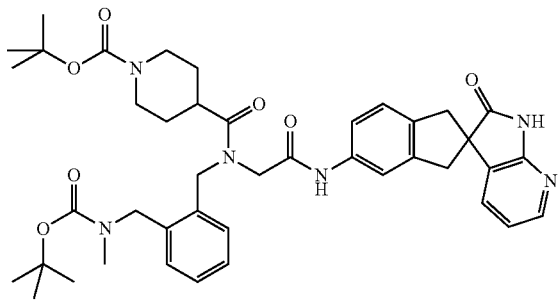 [SMILES: CN(Cc1ccccc1CN(CC(=O)Nc1ccc2c(c1)CC1(C2)C(=O)Nc2ncccc21)C(=O)C1CCN(C(=O)OC(C)(C)C)CC1)C(=O)OC(C)(C)C]

Synthesised according to General Route G (step 1 B) from Intermediate V (45 mg, 0.083 mmol) in N,N-dimethylformamide (1 ml) with N,N-diisopropylethylamine (40 µl, 0.25 mmol), N-Boc-isonipecotic acid (19 mg, 0.083 mmol), EDCl.HCl (21 mg, 0.108 mmol), HOAt (15 mg, 0.108 mmol) at RT for 4 days, and purified via normal phase chromatography (Zip sphere silica 5 g, 50-90% EtOAc in heptane) to provide compound 32.1w (37 mg, 59%) as a colourless glass. UPLC-MS (short CSH 2-95%) rt 0.98 (653 [M−2Boc+H]$^+$), 93% pure.

Example 88: N-(2-((Methylamino)methyl)benzyl)-N-(2-oxo-2-((2'-oxo-1,1',2',3'-tetrahydrospiro[indene-2,3'-pyrrolo[2,3-b]pyridin]-5-yl)amino)ethyl)piperidine-4-carboxamide 32W

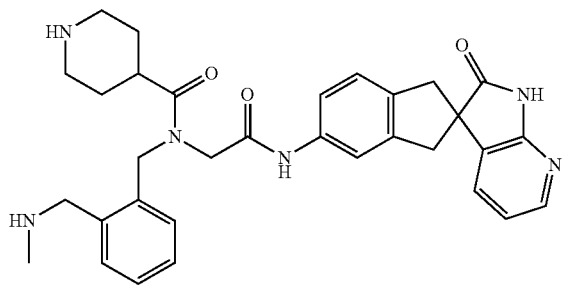

Synthesised according to General Route G (step 2A) from 32.1w (37 mg, 0.049 mmol), trifluoroacetic acid (0.10 ml) and dichloromethane (2 ml) for 3 h and purified via flash silica chromatography (EtOAc then dichloromethane 5-10% MeOH then dichloromethane 30% MeOH with ammonia) to provide compound 32W (6.4 mg, 24%) as a colourless solid. $^1$H NMR (CD$_3$OD, 400 MHz) δ 1.35 (m, 4H), 1.91 (m, 4H), 2.46, 2.54 (2 s, 3H), 2.87 (t, 1H), 3.05 (d, 2H), 3.47 (dd, 2H), 3.78, 3.93 (2 s, 2H), 4.12, 4.20, 4.32 (3 m, 2H), 4.77, 4.95 (2 s, 2H), 6.86 (dd, 1H), 7.10 (d, 1H), 7.29 (m, 6H), 7.53, 7.61, 7.70 (3 m, 1H), 8.04 (dd, 1H). UPLC-MS (long CSH 2-20%) rt 1.17 (553 [M+H]$^+$), 100% purity.

tert-Butyl 9-(chlorocarbonyl)-3,9-diazaspiro[5.5]undecane-3-carboxylate

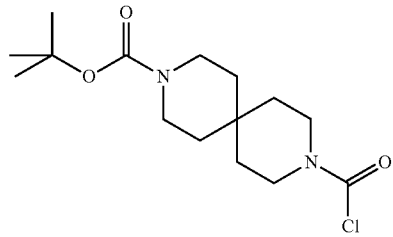 [SMILES: CC(C)(C)OC(=O)N1CCC2(CCN(C(=O)Cl)CC2)CC1]

Tert-butyl 3,9-diazaspiro[5.5]undecane-3-carboxylate (80 mg, 0.32 mmol) was dissolved in tetrahydrofuran (6 ml) under an argon atmosphere then triethylamine (69 µl, 0.49 mmol) was added and cooled on ice/water. Phosgene (36.5 mg, 0.13 mmol) was added and the mixture was stirred on ice/water for 10 min then RT for 21 h. Extra phosgene (15 mg, 0.05 mmol) was added and stirred at RT for 3 h. The mixture was poured into ice/water then extracted three times with ethyl acetate. The combined organic extracts were dried over sodium sulfate, filtered, and the filtrate evaporated to provide tert-butyl 9-(chlorocarbonyl)-3,9-diazaspiro[5.5]undecane-3-carboxylate (96 mg, quantitative) as a yellow oil. $^1$H NMR (CDCl$_3$, 300 MHz) δ 1.43 (s, 9H), 1.53 (m, 8H), 3.39 (m, 4H), 3.60 (m, 2H), 3.68 (m, 2H).

tert-Butyl 9-((2-(((tert-butoxycarbonyl)(methyl) amino)methyl)benzyl)(2-oxo-2-((2'-oxo-1,1',2',3'-tetrahydrospiro[indene-2,3'-pyrrolo[2,3-b]pyridin]-5-yl)amino)ethyl)carbamoyl)-3,9-diazaspiro[5.5] undecane-3-carboxylate 32.1x

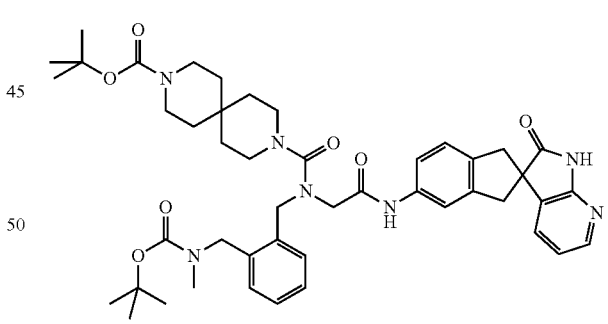

Synthesised according to General Route G (step 1A) from Intermediate V (45 mg, 0.083 mmol) in dichloromethane (1 ml) with N,N-diisopropylethylamine (40 µl, 0.25 mmol) and tert-butyl 9-(chlorocarbonyl)-3,9-diazaspiro[5.5]undecane-3-carboxylate (31.5 mg, 0.10 mmol) at RT for 18 h. A further portion of the acyl chloride (64 mg, 0.20 mmol) was added and stirred for 6 h, and purified via flash chromatography (silica 5 g, EtOAc) to provide compound 32.1x (32 mg, 47%) as a colourless glass. UPLC-MS (short CSH 2-50%) rt 1.52 (822 [M+H]$^+$), 87% pure.

Example 89: N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)-3,9-diazaspiro[5.5]undecane-3-carboxamide 32X

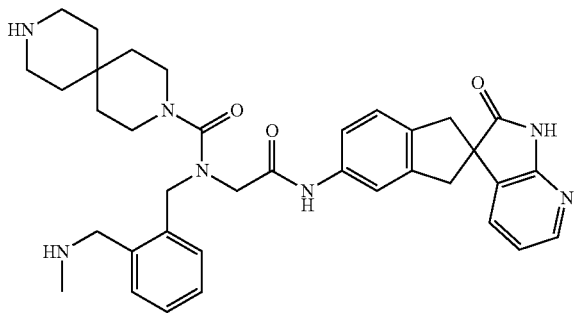 [SMILES: CNCc1ccccc1CN(CC(=O)Nc1ccc2c(c1)CC1(C2)C(=O)Nc2ncccc21)C(=O)N1CCC2(CCNCC2)CC1]

Synthesised according to General Route G (step 2A) from 32.1x (32 mg, 0.039 mmol), trifluoroacetic acid (0.10 ml) and dichloromethane (2 ml) for 4 h. No aqueous work-up, volatiles removed, co-evaporating with toluene, and purified via SPE (SCX2 500 mg, MeOH then MeOH with ammonia) to provide compound 32X (12 mg, 49%) as a colourless solid.

$^1$H NMR (CD$_3$OD, 300 MHz) δ 1.53 (m, 8H), 2.39 (s, 3H), 2.79 (m, 4H), 3.04 (dd, 2H), 3.33 (m, 4H), 3.50 (dd, 2H), 3.68 (s, 2H), 3.86 (s, 2H), 4.62 (s, 2H), 6.87 (dd, 1H), 7.11 (dd, 1H), 7.22 (d, 1H), 7.30 (m, 5H), 7.49 (s, 1H), 8.03 (dd, 1H). UPLC-MS (long CSH 2-95%) rt 0.46 (622 [M+H]$^+$), 95% purity.

tert-Butyl 2-(chlorocarbonyl)-2,8-diazaspiro[4.5]decane-8-carboxylate

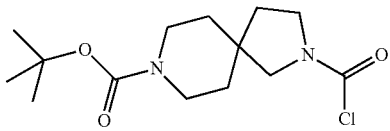 [SMILES: CC(C)(C)OC(=O)N1CCC2(CCN(C(=O)Cl)C2)CC1]

Tert-butyl 2,8-diazaspiro[4.5]decane-8-carboxylate (80 mg, 0.33 mmol) was dissolved in tetrahydrofuran (6 ml) under an argon atmosphere then triethylamine (68 µl, 0.49 mmol) was added and cooled on ice/water. Phosgene (38.5 mg, 0.13 mmol) was added and the mixture was stirred on ice/water for 10 min then RT for 3 h. The mixture was poured into ice/water then extracted three times with ethyl acetate. The combined organic extracts were dried over sodium sulfate, filtered, and the filtrate evaporated to provide tert-butyl 2-(chlorocarbonyl)-2,8-diazaspiro[4.5]decane-8-carboxylate (31 mg, 31%) as a yellow oil. $^1$H NMR (CDCl$_3$, 400 MHz) δ 1.45 (s, 9H), 1.53 (m, 4H), 1.83 (m, 2H), 3.28 (m, 2H), 3.37 (m, 2H), 3.44 (m, 2H), 3.49 (m, 2H), 3.59 (t, 1H), 3.68 (t, 1H).

tert-Butyl 2-((2-(((tert-butoxycarbonyl)(methyl)amino)methyl)benzyl) (2-oxo-2-((2'-oxo-1,1',2',3-tetrahydrospiro[indene-2,3'-pyrrolo[2,3-b]pyridin]-5-yl)amino)ethyl)carbamoyl)-2,8-diazaspiro[4.5]decane-8-carboxylate 32.1y

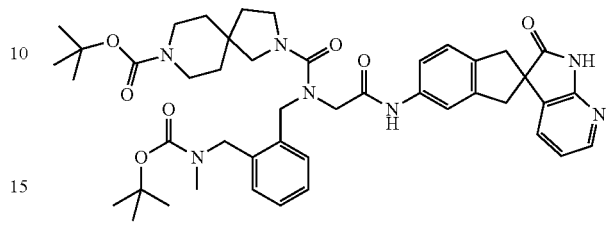

Synthesised according to General Route G (step 1A) from Intermediate V (45 mg, 0.083 mmol) in dichloromethane (1 ml) with N,N-diisopropylethylamine (40 µl, 0.25 mmol) and tert-butyl 2-(chlorocarbonyl)-2,8-diazaspiro[4.5]decane-8-carboxylate (30 mg, 0.10 mmol) at RT for 3 days, and purified via flash chromatography (silica 5 g, EtOAc 0-5% MeOH) to provide compound 32.1y (39 mg, 58%) as a colourless glass. UPLC-MS (short CSH 2-50%) rt 1.42 (808 [M+H]$^+$).

Example 90: N-(2-((Methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)-2,8-diazaspiro[4.5]decane-2-carboxamide 32Y

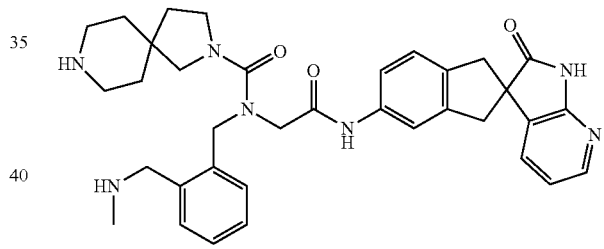

Synthesised according to General Route G (step 2A) from 32.1y (39 mg, 0.048 mmol), trifluoroacetic acid (0.10 ml) and dichloromethane (2 ml) for 6 h. No aqueous work-up, volatiles removed, co-evaporating with toluene, and purified via SPE (SCX2 500 mg, MeOH then MeOH with ammonia) and flash silica chromatography (dichloromethane 10-15% MeOH then dichloromethane 15-30% MeOH with ammonia) to provide compound 32Y (9 mg, 31%) as a colourless solid. $^1$H NMR (CD$_3$OD, 300 MHz) δ 1.51 (m, 4H), 1.73 (m, 2H), 2.40 (s, 3H), 2.79 (m, 4H), 3.05 (dd, 2H), 3.35 (s, 2H), 3.50 (m, 4H), 3.72 (s, 2H), 3.94 (s, 2H), 4.68 (s, 2H), 6.88 (dd, 1H), 7.11 (dd, 1H), 7.21 (d, 1H), 7.31 (m, 5H), 7.50 (s, 1H), 8.03 (dd, 1H). UPLC-MS (long CSH 2-95%) rt 0.46 (608 [M+H]$^+$), 94% purity.

SCHEME 33

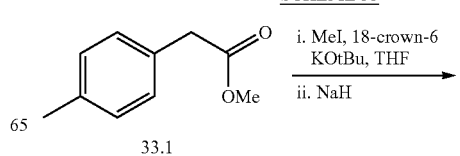

303

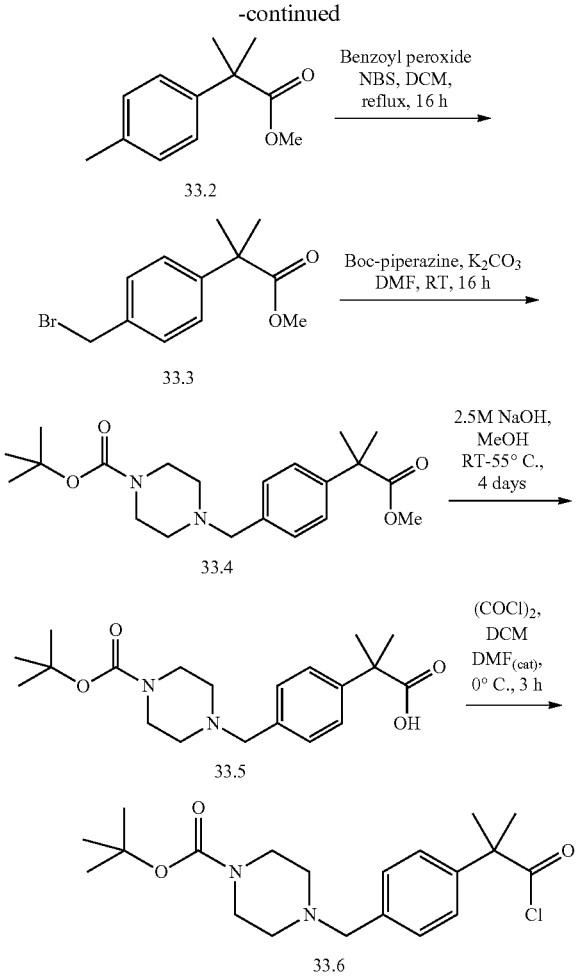

Methyl 2-methyl-2-(p-tolyl)propanoate 33.2

Methyl 4-methylphenyl acetate 33.1 (5 g, 30.4 mmol) was dissolved in dry tetrahydrofuran (150 ml) under argon. To this was added 18-crown-6 ether (2 g, 7.61 mmol), methyl iodide (5.68 ml, 91.3 mmol) followed by portionwise addition of potassium t-butoxide (10.25 g, 91.3 mmol) [caution—effervescence] and the mixture was stirred at RT for 18 h. To this mixture was added portionwise sodium hydride (60% in mineral oil, 3.65 g, 91.3 mmol) and the mixture stirred at RT for 22 h. The reaction was poured into ice/water with rapid stirring then extracted with ethyl acetate. The organic layer was washed with water, dried over magnesium sulfate, filtered and evaporated to provide compound 33.1 (4.02 g, 68%) as a yellow oil. $^1$H NMR (CDCl$_3$, 300 MHz) δ 1.55 (s, 6H), 2.32 (s, 3H), 3.60 (s, 3H), 7.10 (d, 2H), 7.22 (m, 2H).

304

Methyl 2-(4-(bromomethyl)phenyl)-2-methylpropanoate 33.3

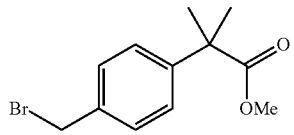

Compound 33.2 (3.6 g, 18.7 mmol) was dissolved in dry dichloromethane (40 ml) under argon. To this was added N-bromosuccinimide (3.99 g, 22.5 mmol) and benzoyl peroxide (75% in water, 266 mg, 0.82 mmol) then the mixture was stirred at reflux for 12 h. The mixture was filtered through a plug of silica and evaporated to provide compound 33.3 (4.35 g, 86%) as a yellow oil. $^1$H NMR (CDCl$_3$, 300 MHz) δ 1.60 (s, 6H), 3.65 (s, 3H), 4.47 (s, 2H), 7.32 (m, 4H).

tert-Butyl 4-(4-(1-methoxy-2-methyl-1-oxopropan-2-yl)benzyl)piperazine-1-carboxylate 33.4

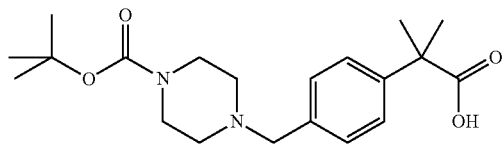 [SMILES: CC(C)(C)OC(=O)N1CCN(Cc2ccc(C(C)(C)C(=O)O)cc2)CC1]

1-Boc-piperazine (1.03 g, 5.53 mmol) was dissolved in dry N,N-dimethylformamide (25 ml) then potassium carbonate and compound 33.3 (1.5 g, 5.53 mmol) were added. The mixture was stirred at reflux for 16 h. The mixture was diluted with ethyl acetate and washed twice with water. The organic layer was dried over magnesium sulfate, filtered and evaporated. The residue was purified via flash silica chromatography (20-50% EtOAc in heptane) and then again (120 fold silica, 3:1 EtOAc/heptane with 2% MeOH; rf 0.6) to provide compound 33.4 (425 mg, 18%) as a colourless waxy solid. $^1$H NMR (CDCl$_3$, 300 MHz) δ 1.47 (s, 9H), 1.57 (s, 6H), 2.37 (m, 4H), 3.42 (m, 4H), 3.48 (s, 2H), 3.65 (s, 3H), 7.28 (m, 4H). UPLC (CSH 2-50%) 0.65 (321 [M−Boc+H]$^+$).

2-(4-((4-(tert-Butoxycarbonyl)piperazin-1-yl)methyl)phenyl)-2-methylpropanoic Acid 33.5

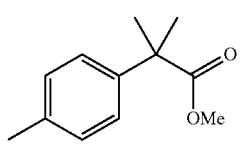

Compound 33.5 (100 mg, 0.238 mmol) was dissolved in dry methanol (3 ml) then 2.5 M sodium hydroxide (0.14 ml, 0.36 mmol) was added. The mixture was stirred at RT for 16 h. Extra 2.5 M sodium hydroxide (0.14 ml, 0.36 mmol) was added and the mixture heated at 55° C. for 3 days. The mixture was diluted with water, pH adjusted to 4 using 2M HCl then extracted twice with dichloromethane. The aqueous layer was saturated with sodium chloride then extracted three times with ethyl acetate; these organic layers were dried over magnesium sulfate, filtered and evaporated to provide compound 33.5 (100 mg, quantitative) as a colourless solid. UPLC (CSH 2-50%) 0.58 (307 [M−Boc+H]$^+$).

tert-Butyl 4-(4-(1-chloro-2-methyl-1-oxopropan-2-yl)benzyl)piperazine-1-carboxylate 33.6

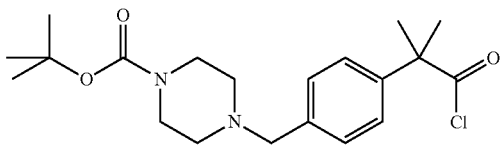 [SMILES: CC(C)(C)OC(=O)N1CCN(Cc2ccc(C(C)(C)C(=O)Cl)cc2)CC1]

Compound 33.5 (100 mg, 0.238 mmol) was dissolved in dry dichloromethane (3 ml), cooled on ice/water under argon. Oxalyl chloride (30 μl, 0.36 mmol) was added followed by 1 drop of N,N-dimethylformamide. The mixture was stirred on ice/water for 3 h. The reaction mixture was evaporated to provide compound 33.6 (110 mg, quantitative) as a colourless gum. UPLC in methanol (CSH 2-50%) 0.69 (321 [methyl ester M-Boc+H]$^+$).

tert-Butyl 4-(4-(1-((2-(((tert-butoxycarbonyl)(methyl)amino)methyl)benzyl)(2-oxo-2-((2'-oxo-1,1',2',3-tetrahydrospiro[indene-2,3'-pyrrolo[2,3-b]pyridin]-5-yl)amino)ethyl)amino)-2-methyl-1-oxopropan-2-yl)benzyl)piperazine-1-carboxylate 32.1z

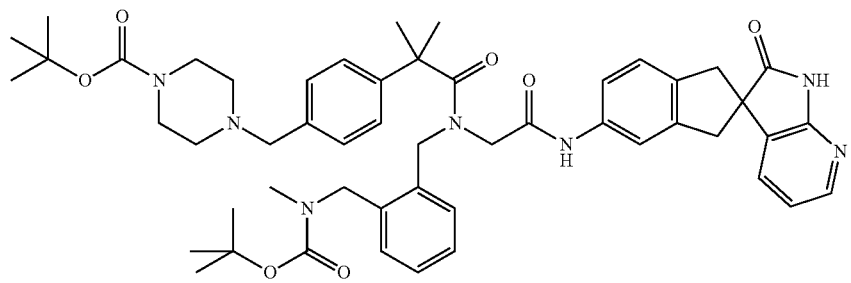 [SMILES: CN(Cc1ccccc1CN(CC(=O)Nc1ccc2c(c1)CC1(C2)C(=O)Nc2ncccc21)C(=O)C(C)(C)c1ccc(CN2CCN(C(=O)OC(C)(C)C)CC2)cc1)C(=O)OC(C)(C)C]

Synthesised according to General Route G (step 1A) from Intermediate V (45 mg, 0.083 mmol) in dichloromethane (2 ml) with N,N-diisopropylethylamine (45 μl, 0.29 mmol) and compound 33.6 (50 mg, 0.13 mmol) at RT for 18 h. Extra 33.6 (15 mg) was added and stirred at RT for 5 h, and purified via flash chromatography (silica 5 g, EtOAc 0-10% MeOH) then SPE (STMAd 2 g, MeOH, then 2-5% N-methylmorpholine in MeOH) to provide compound 32.1z (12 mg, 16%) as a colourless glass. UPLC-MS (short CSH 2-50%) rt 1.00 (886 [M+H]$^+$).

Example 91: 2-Methyl-N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)-2-(4-(piperazin-1-ylmethyl)phenyl)propanamide 32Z

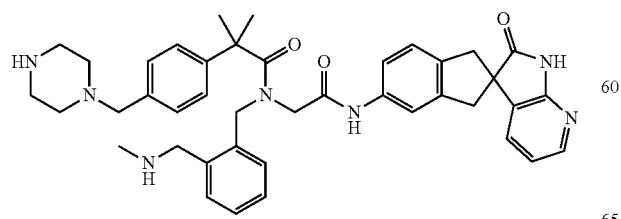

Synthesised according to General Route G (step 2A) from 32.1z (12 mg, 0.013 mmol), trifluoroacetic acid (0.10 ml) and dichloromethane (2 ml) for 4 h. No aqueous work-up, volatiles removed, co-evaporating with toluene to provide compound 32Z (5 mg, 42%) as a colourless solid (TFA salt). $^1$H NMR (CD$_3$OD, 300 MHz) δ 1.50, 1.51 (2 s, 6H), 2.30 (s, 5H), 2.73 (m, 3H), 2.83 (m, 2H), 3.12 (m, 3H), 3.20 (s, 1H), 3.40 (m, 2H), 3.48 (s, 2H), 4.12 (s, 1H), 4.35 (s, 1H), 4.75 (m, 1H), 4.90 (m, 2H), 6.92 (m, 1H), 7.13 (m, 6H), 7.31 (m, 6H), 8.06 (m, 1H). UPLC-MS (CSH 2-20%) rt 0.75 (686 [M+H]$^+$), 98% purity.

Synthesis of Intermediate W

SCHEME 34

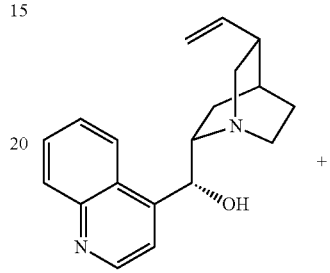

+

-continued

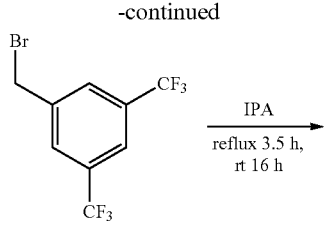

$\xrightarrow{\text{IPA}}$ reflux 3.5 h, rt 16 h

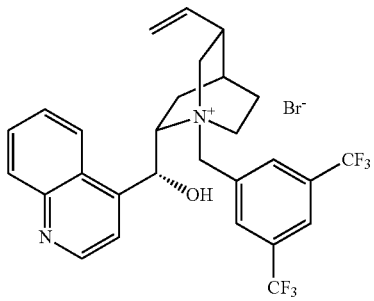

PTC*

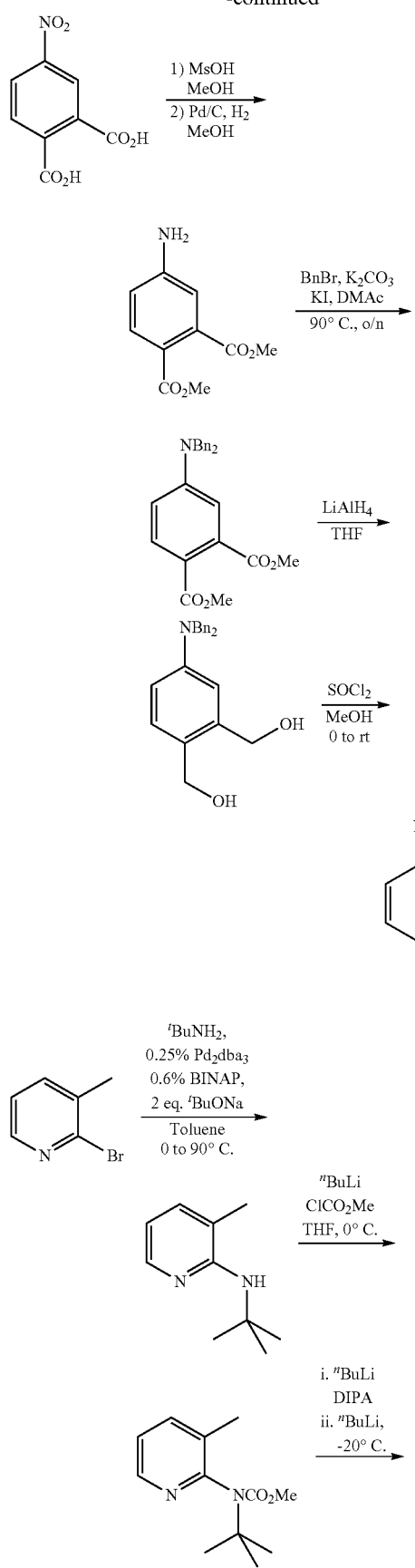
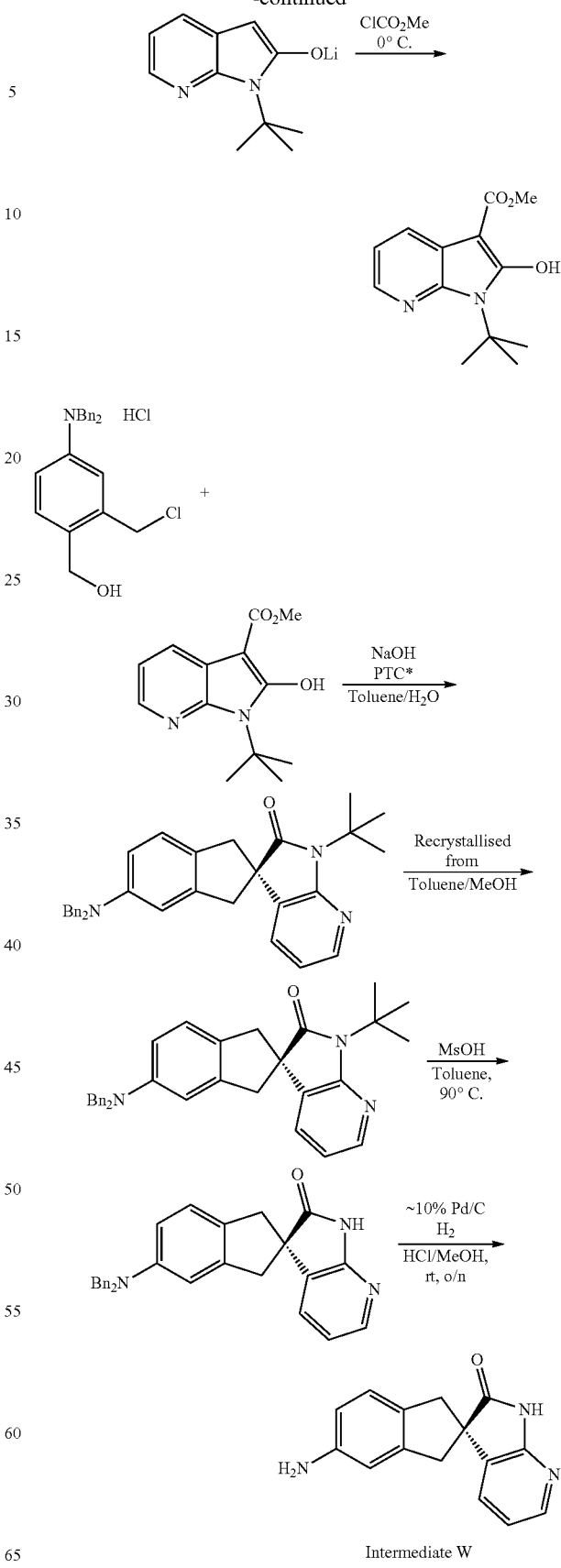
Intermediate W

(1S,2S,4S,5R)-1-(3,5-bis(trifluoromethyl)benyl)-2-((R)-hydroxy(quinolin-4-yl)methyl)-5-vinylquinuclidin-1-ium bromide ("PTC*")

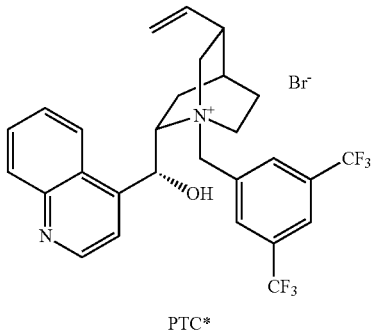 [SMILES: C=CC1C[N+]2(Cc3cc(C(F)(F)F)cc(C(F)(F)F)c3)CCC1CC2[C@H](O)c1ccnc2ccccc12 ; [Br-]]

PTC*

A solution of 3,5-bis(trifluoromethyl)benzyl bromide (5.00 g, 17.0 mmol) and cinchonidine (5.50 g, 17.8 mmol) in isopropyl alcohol (IPA) was heated at reflux for 3.5 h. After cooling to room temperature, the reaction mixture was slowly poured into diethyl ether (250 mL) with stirring. The precipitated solids were filtered and washed with diethyl ether (150 mL) and pentane (100 mL) to afford 8.60 g (84%) of the product. H NMR (CD$_3$OD, 400 MHz) δ 1.48 (m, 1H), 1.91 (m, 1H), 2.12 (m, 1H), 2.31 (m, 2H), 2.76 (s, br, 1H), 3.41 (t, 1H), 3.50 (dd, 1H), 3.71 (m, 1H), 4.02 (t, 1H), 4.58 (m, 1H), 5.03 (d, 1H), 5.19 (m, 2H), 5.37 (d, 1H), 5.71 (ddd, 1H), 6.67 (s, 1H), 7.98 (dddd, 2H), 8.15 (dd, 1H), 8.27 (s, 1H), 8.34 (d, 1H), 8.98 (d, 1H); $[\alpha]_D^{23}$=−139.5° (c 8.9, MeOH).

Dimethyl 4-aminophthalate

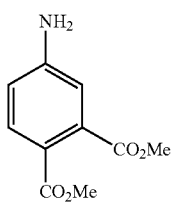

To a solution of 4-nitrophthalic acid (10.6 g, 50.2 mmol) in methanol (50 ml) was added methanesulfonic acid (7.2 g, 75.3 mmol). The reaction mixture was heated at reflux overnight. After cooling to room temperature, Pd/C (1 g in 5 ml of water) was added and the reaction mixture was stirred at 37° C. for 9 h. Ethyl acetate (50 ml) was then added and Pd/C was removed by filtration. Volatiles were removed under vacuum to dryness and the crude product was dissolved in ethyl acetate (~100 ml) and the organic phase was washed with water, dried over magnesium sulfate and filtered. Volatiles were removed under vacuum give 10.5 g (100%) of the desired product. This product was used directly in next step without further purification.

$^1$H NMR (CDCl$_3$, 400 MHz) δ 3.85 (s, 3H), 3.92 (s, 3H), 6.69 (d, 1H), 6.75 (s, 1H), 7.74 (d, 1H).

Dimethyl 4-(dibenzylamino)phthalate

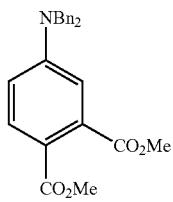

To a solution of dimethyl 4-aminobenzene-1,2-dicarboxylate (10.5 g, 50.2 mmol), potassium carbonate (22 g, 160.6 mmol) and anhydrous potassium iodide (1.70 g, 10.0 mmol) in N,N-dimethylacetamide (100 ml), was slowly added benzyl chloride (15.9 g, 125.5 mmol). The reaction mixture was heated at 90° C. overnight The reaction mixture was allowed to cool to room temperature, and then diluted with ethyl acetate (~500 ml). The organic layer was washed with brine and H$_2$O. The organic extract was dried over magnesium sulfate, filtered and volatiles were removed under vacuum to give 18.6 g (96%) of the desired product. This compound was used directly in the next step without further purification. $^1$H NMR (CDCl$_3$, 400 MHz) δ 7.76 (m, 1H), 7.36 (m, 7H), 7.21 (m, 3H), 6.83 (d, 1H), 6.74 (dd, 1H), 4.72 (s, 4H), 3.88 (s, 3H), 3.84 (s, 3H). LCMS (390.17 [M+H]$^+$).

(4-(Dibenzylamino)-1,2-phenylene)dimethanol

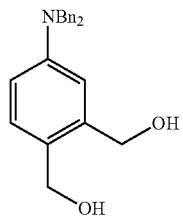

A solution of dimethyl 4-(dibenzylamino)benzene-1,2-dicarboxylate (16.00 g, 40.8 mmol) in tetrahydrofuran (200 ml) was added slowly to a solution of lithium aluminium hydride (3.1 g, 81.6 mmol) in tetrahydrofuran (300 ml) at P0C. The reaction mixture was stirred at P0C for 20 min then it was stirred at room temperature for 3 h. A solution of aqueous tetrahydrofuran (50 ml of water diluted with 50 ml of tetrahydrofuran) was then added slowly at 0° C. Next, 100 ml of a 15% sodium hydroxide solution was added. The reaction mixture was allowed to warm to room temperature, and then filtered through Celite. The mixture was concentrated and then extracted with ethyl acetate. The organic layer was washed with brine followed by aqueous ammonium chloride, dried over magnesium sulfate, filtered and evaporated to give 11.00 g (81%) of the desired product. This compound was used directly in the next step without further purification. $^1$H NMR (CD$_3$OD, 400 MHz) δ 4.54 (s, 2H), 4.61 (s, 2H), 4.67 (s, br, 4H), 6.61 (m, 1H), 6.90 (m, 1H), 7.12 (m, 1H), 7.26 (m, 10H).

311

(2-(Chloromethyl)-4-(dibenzylamino)phenyl)methanol Hydrochloride

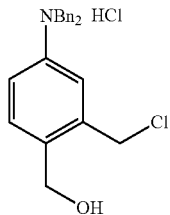

To a solution of thionyl chloride (7.1 ml, 96.3 mmol) in acetonitrile (20 ml) at 0° C. was added slowly (over 10 min) a solution 4-(dibenzylamino)benzene-1,2-diyl]dimethanol (10.7 g, 32.1 mmol) in acetonitrile (20 ml). The reaction mixture was stirred at room temperature for 1.5 h [note: a vigorous evolution of $HCl/SO_2$ gas was apparent]. Diethyl ether (140 ml) was added to the reaction mixture forming crystals after 10 min. Additional diethyl ether (50 ml) was added and the crystals were collected by filtration, transferred to a round-bottomed flask and stirred for 20 min in diethyl ether (80 ml). Crystals were then collected by filtration. This operation was repeated three times before the crystals were dried under vacuum to give 9.7 g (78%) of desired product. This compound was used directly in the next step without further purification. $^1$H NMR ($CDCl_3$. 400 MHz) δ 4.48 (s, 2H), 4.60 (s, 2H), 4.71 (s, br, 4H), 7.30 (m, 8H), 7.38 (s, 1H), 7.46 (m, 4H). LCMS (352.1 $[M+H]^+$)

N-(tert-Butyl)-3-methylpyridin-2-amine

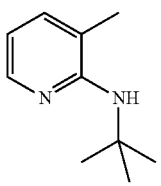

A mixture of 2-bromo-3-methyl pyridine (25.0 g, 145 mmol), $NaO^tBu$ (28.0 g, 291 mmol), $(Pd_2(dba)_3$ (0.30 g, 0.33 mmol), BINAP, (0.41 g, 0.66 mL) and $^tBuNH_2$ (31 ml, 290.66 mmol) in toluene (380 ml) was stirred at 85° C. overnight Water (~200 ml) was added to quench the reaction and the pH was adjusted pH ~4 by addition of 3M HCl. Diethyl ether (~300 ml) was added and the two layers were separated. The aqueous layer was extracted by diethyl ether and the combined organics were washed by brine, dried over magnesium sulfate, filtered and evaporated to give 21.9 g (92%) of the desired product. This compound was used directly in the next step without further purification. $^1$H NMR ($CDCl_3$. 400 MHz) δ 8.02 (d, 1H), 7.19 (d, 1H), 6.48 (dd, 1H), 4.01 (s, br, 1H), 2.05 (s, 3H), 1.52 (s, 9H). LCMS (165.14 $[M+H]^+$).

312

Methyl 1-(tert-butyl)-2-hydroxy-1H-pyrrolo[2,3-b]pyridine-3-carboxylate

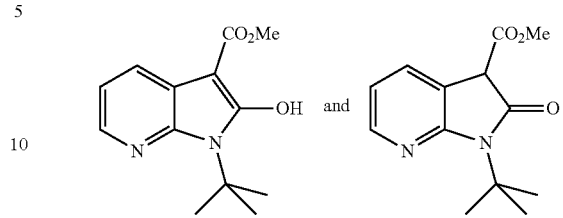

To a solution of N-tert-butyl-3-methylpyridin-2-amine (12.0 g, 73.1 mmol) in tetrahydrofuran (210 ml) at −30° C., was added slowly n-butyl lithium (35 ml, 80.4 mmol). After 15 min, methyl chloroformate (5.9 ml, 76.8 mmol) was added dropwise. After 5 min, the reaction mixture was warmed to room temperature and stirred for 1 h. The reaction mixture was cooled to −30° C. and n-butyl lithium (35 ml, 80.4 mmol) was added slowly. After 20 min at −30° C., diisopropylamine (14.0 ml, 102.3 mmol) was added followed directly by n-butyl lithium (35 ml, 80.4 mmol). The reaction mixture was stirred for ~15 min at −30° C. and then warmed to room temperature and stirred overnight The reaction mixture was cooled to −10° C. and methyl chloroformate (5.9 mL, 76.8 mmol) was added dropwise. The reaction mixture was warmed to room temperature and stirred for 1 h. 6M HCl (35 ml) was then added slowly to quench the reaction mixture. The tetrahydrofuran was evaporated to the minimum amount, water (~200 ml) was added and the product extracted by ethyl acetate. The combined extracts were washed by brine, dried over magnesium sulfate, filtered and evaporated to give 15.8 g (87%) of the desired product. This compound was used directly in the next step without further purification. $^1$H NMR ($CDCl_3$. 400 MHz) δ 1.80 (s, 2.7H), 1.93 (s, 6.3H), 3.82 (s, 0.9H), 3.98 (s, 2.1H), 6.95 (m, 0.3H), 7.09 (m, 0.7H), 7.53 (m, 0.3H), 7.91 (m, 0.7H), 8.16 (m, 0.7H), 8.24 (m, 0.3H) (spectra for the mixture of compounds). LCMS (249.12 $[M+H]^+$).

(R)-1'-(tert-Butyl)-5-(dibenzylamino)-1,3-dihydrospiro[indene-2,3'-pyrrolo[2,3-b]pyridin]-2'(1'H)-one

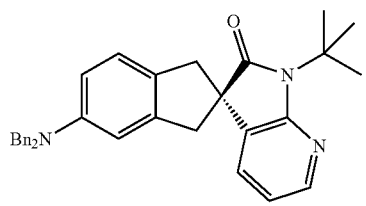

To a solution of sodium hydroxide (72 g) in water (60 ml) at room temperature was added toluene (130 ml) and [2-(chloromethyl)-4-(dibenzylamino)phenyl]methanol hydrochloride (4.7 g, 12.1 mmol). The reaction mixture was stirred at room temperature, while bubbling with argon, for 5 min. Methyl 1-tert-butyl-2-hydroxy-1H-pyrrolo[2,3-b]pyridine-3-carboxylate (3.0 g, 12.1 mmol) was added in 3 portions over 10 min. Argon continued to be bubbled through the stirring solution for 15 min and (9R)-1-[3,5-bis (trifluoromethyl)benzyl]cinchonan-1-ium-9-ol bromide (0.7 g, 1.2 mmol) was added in one portion at room temperature. This mixture was stirred at room temperature for 3 h under bubbling argon. Water (~300 ml) was added [note: exothermic reaction] and the mixture stirred for ~15 min while warming to room temperature. The two layers were separated, and the aqueous layer extracted by ethyl acetate. The combined extracts were washed with water, dried over magnesium sulfate, filtered and evaporated to give the crude product of ~90% purity, 83% ee. This product was dissolved in toluene (60 ml) at 60° C. Once totally dissolved, the mixture was warmed to room temperature and methanol (180 ml) was added. The mixture was stirred at room temperature for 16 h, and the resulting crystals were collected by filtration and washed with methanol to give the product (61%, 96% ee). The product was recrystallised using toluene (50 ml) and methanol (120 ml) to give 3.1 g (52%, >99% ee) of the product. $^1$H NMR (CDCl$_3$. 400 MHz) δ 8.14 (m, 1H), 7.30 (m, 10H), 7.05 (m, 2H), 6.78 (m, 1H), 6.67 (s, br, 2H), 4.67 (s, br, 4H), 3.48 (d, 2H), 2.87 (dd, 2H), 1.82 (s, 9H). LCMS (488.27 [M+H]$^+$). Chiral HPLC: PhenomenexeLux® 3p Cellulose-1 column; "hexane:isopropanol, 95:5; flow rate=1.0 ml/min; detection at 254 nm.

(R)-5-Amino-1,3-dihydrospiro[indene-2,3'-pyrrolo[2,3-b]pyridin]-2'(1$^1$H)-one Intermediate W

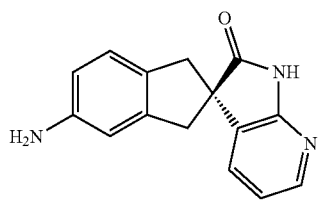 [SMILES: Nc1ccc2c(c1)C[C@@]1(C2)C(=O)Nc2ncccc21]

To a solution of (R)-1'-(tert-butyl)-5-(dibenzylamino)-1,3-dihydrospiro[indene-2,3'-pyrrolo[2,3-b]pyridin]-2'(1'H)-one (3.1 g, 6.36 mmol) in methanol (120 ml) was added methanesulfonic acid (11 ml) at room temperature. The mixture was stirred at reflux for 4 h. The methanol was removed under vacuum and water (~100 ml) was added to the mixture and pH adjusted to pH ~10 by adding a 50% aqueous solution of sodium hydroxide. The aqueous layer was extracted with ethyl acetate and the combined extracts were dried over magnesium sulfate, filtered and evaporated to give the crude product. The crude product was dissolved in methanol (~80 ml) and Pd/C (0.1 g) was added to the solution followed by concentrated HCl (7 ml). The mixture was stirred at room temperature under a balloon of H$_2$ overnight. Volatiles were removed to dryness and the crude material was then dissolved in dichloromethane. Water followed by saturated aqueous potassium carbonate was added to pH ~10. The mixture was extracted by dichloromethane, dried over magnesium sulfate, filtered and evaporated to give 1.2 g (77%) of the desired product. This compound was used directly in the next step without further purification. $^1$H NMR (CD$_3$OD, 400 MHz) δ 8.05 (dd, 1H), 7.14 (dd, 1H), 7.04 (d, 1H), 6.89 (dd, 1H), 6.71 (s, br, 1H), 6.67 (dd, 1H), 3.46 (dd, 2H), 2.96 (dd, 2H); LCMS (252.11 [M+H]$^+$); Chiral HPLC: Phenomenex® Lux 3p Cellulose-1 column; "hexane:isopropanol, 40:60; flow rate=0.5 mL/min; detection at 220 nm.

Synthesis of Intermediate X

SCHEME 35

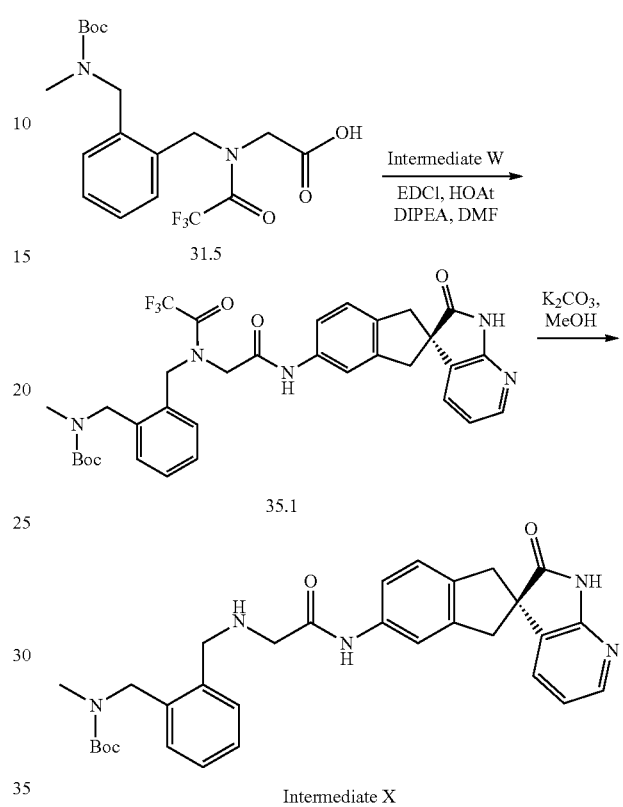

tert-Butyl N-methyl-N-[[2-[[[2-oxo-2-[[(3R)-2-oxospiro[1H-pyrrolo[2,3-b]pyridine-3,2'-indane]-5'-yl]amino]ethyl]-(2,2,2-trifluoroacetyl)amino]methyl]phenyl]methyl]carbamate 35.1

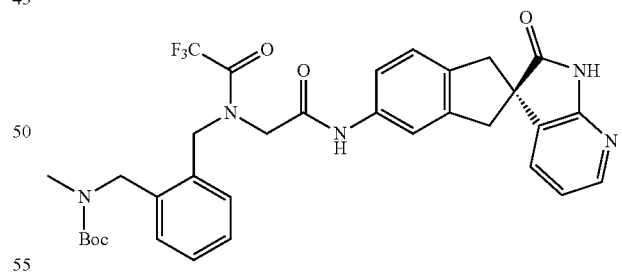

To a solution of compound 31.5 (4.50 g, 11.1 mmol) and Intermediate W (2.80 g, 11.1 mmol) in dimethyl formamide (20 mL) was added EDCl (2.56 g, 13.3 mmol), DIPEA (3.60 g, 27.8 mmol) and HOAt (1.82 g, 13.3 mmol). The mixture was stirred at 25° C. for 2 h. The mixture was quenched by addition of water (100 mL) and extracted with ethyl acetate (3×100 ml). The combined organic phases were washed with a 0.5 mol/L aqueous solution of hydrochloric acid (2×100 mL) than a saturated aqueous solution of sodium bicarbonate (100 mL). The organic phases were dried over sodium sulfate. After filtration and concentration, compound 35.1 was obtained as a yellow solid (6.1 g, 9.18 mmol, 83% yield, 96% purity). 1H NMR (CDCl3, 400 MHz) δ 1.44-1.47 (m, 9H), 2.82-2.91 (m, 3H), 3.04 (d, 2H), 3.57-3.63 (m, 2H), 4.02-4.12 (m, 2H), 4.44-4.49 (m, 2H), 4.85-4.88 (m, 2H), 6.83 (t, 1H), 7.07 (dd, 1H), 7.17-7.23 (m, 4H), 7.30-7.37 (m, 2H), 7.44-7.52 (m, 1H), 8.00 (br. s, 1H), 8.13 (d, 1H).

tert-Butyl N-methyl-N-[[2-[[[2-oxo-2-[[(3R)-2-oxospiro[1H-pyrrolo[2,3-b]pyridine-3,2'-indane]-5'-yl]amino]ethyl]amino]methyl]phenyl]methyl]carbamate Intermediate X

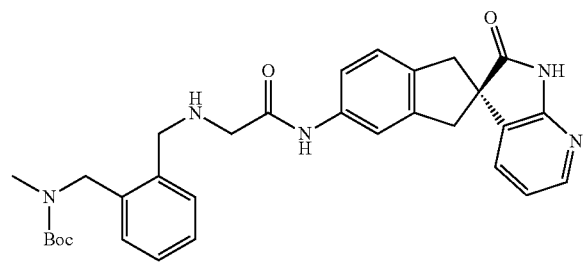 [SMILES: CN(Cc1ccccc1CNCC(=O)Nc1ccc2c(c1)C[C@@]1(C2)C(=O)Nc2ncccc21)C(=O)OC(C)(C)C]

To a solution of compound 35.1 (6.10 g, 9.57 mmol) in methanol (60 mL) and water (15 mL) was added potassium carbonate (2.64 g, 19.13 mmol). The mixture was stirred at 25° C. for 2 h. Methanol of the mixture was removed under vacuum. The residue was dissolved in ethyl acetate (200 mL) and washed with 0.5 mol/L aqueous solution of hydrochloric acid (2×100 mL). The organic phase was discarded. The aqueous phase was adjusted to pH=9 by saturated aqueous solution of sodium bicarbonate and then extracted with ethyl acetate (3×100 mL). The combined organic phases were dried over sodium sulfate. After filtration and concentration, Intermediate X (4.50 g, 86% yield) was obtained as a yellow solid. $^1$H NMR (CDCl$_3$, 400 MHz) δ 1.48 (s, 9H), 2.84 (s, 3H), 3.05 (dd, 2H), 3.47 (s, 2H), 3.64 (dd, 2H), 3.89 (s, 2H), 4.64 (s, 2H), 6.81 (dd, 1H), 7.07 (dd, 1H), 7.19-7.24 (m, 2H), 7.30-7.34 (m, 4H), 7.66 (s, 1H), 8.13 (dd, 1H), 8.49 (br. s, 1H), 9.26 (br. s, 1H).

General Route H

SCHEME 36

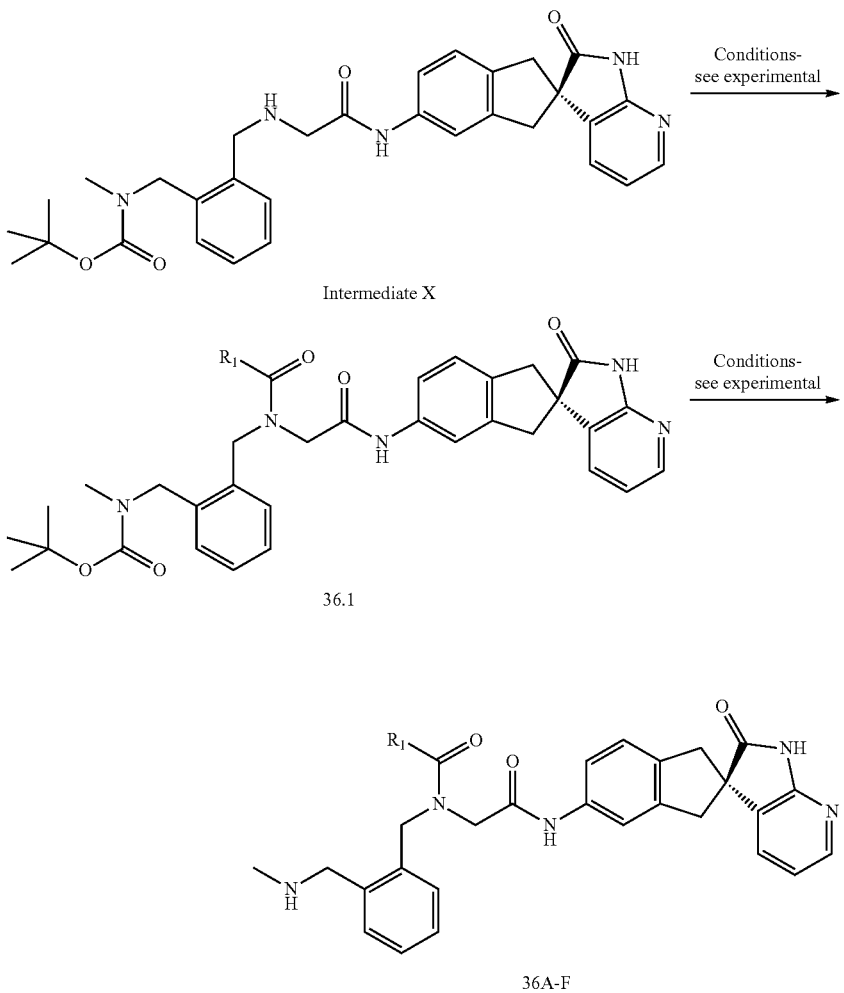

tert-Butyl N-[[2-[[adamantane-1-carbonyl-[2-oxo-2-[[(3R)-2-oxospiro[1H-pyrrolo[2,3-b]pyridine-3,2'-indane]5'-yl]amino]ethyl]amino]methyl]phenyl]methyl]-N-methyl-carbamate 36.1a

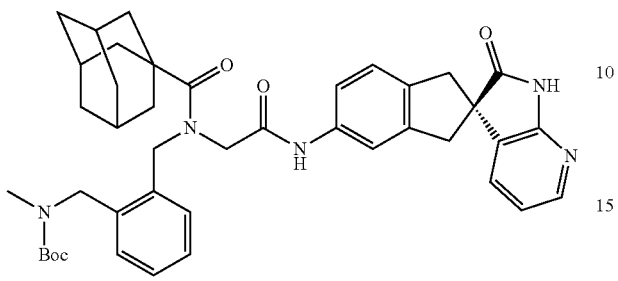

To a solution of adamantane-1-carboxylic acid (40 mg, 0.22 mmol) in thionyl chloride (5 mL) was added dimethyl formamide (1.62 mg, 0.22). The mixture was stirred at 80° C. for 3 h. The mixture was concentrated under vacuum and the residue dissolved with dichloromethane (1 mL). The solution was added to a solution of Intermediate X (50 mg, 0.92) and triethylamine (50 mg, 0.49 mmol) in dichloromethane (5 mL) slowly at 0° C. under nitrogen protection. The mixture was stirred at 25° C. for 1 h. The mixture was poured into water (20 mL) and then extracted with dichloromethane (3×20 mL). The combined organic phases were washed with brine (50 mL) and dried over sodium sulfate. After filtration and concentration, compound 36.1a (60 mg, 0.85 mmol, crude) was obtained as yellow solid. $^1$H NMR (CD$_3$OD, 400 MHz) δ 1.36 (s, 9H), 1.87 (s, 6H), 1.94 (s, 9H), 2.70 (s, 3H), 2.94-3.00 (m, 2H), 3.54-3.60 (m, 2H), 3.98-4.06 (m, 2H), 4.41 (s, 2H), 4.88 (s, 2H), 6.81-6.84 (m, 1H), 7.05-7.16 (m, 5H), 7.22-7.24 (m, 2H), 7.51 (s, 1H), 8.02 (d, 1H), 8.56 (br. s, 1H).

Example 92: N-[[2-(methylaminomethyl)phenyl]methyl]-N-[2-oxo-2-[[(3R)-2-oxospiro[1H-pyrrolo[2,3-b]pyridine-3,2'-indane]-5'-yl]amino]ethyl]adamantane-1-carboxamide 2,2,2-trifluoroacetate 36A

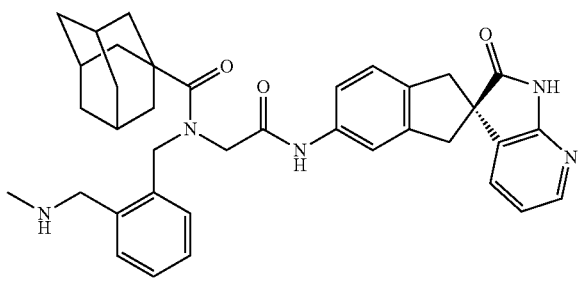 [SMILES: CNCc1ccccc1CN(CC(=O)Nc1ccc2c(c1)C[C@@]1(C2)C(=O)Nc2ncccc21)C(=O)C12CC3CC(CC(C3)C1)C2]

To a solution of compound 36.1a (60 mg, 0.85 mmol) in dichloromethane (5 mL) was added trifluoroacetic acid (1 mL). The mixture was stirred at 25° C. for 0.5 hr. LC-MS showed starting material was consumed completely and desired MS detected. The mixture was concentrated under vacuum and the residue was purified by prep-HPLC (column: Phenomenex Synergi C18 150×25 mm, 10 μm; mobile phase: [water (0.1% TFA)-acetonitrile]; B %: 22%-52%, 9 min). After lyophilisation, compound 36A was obtained as a white solid (15 mg, 0.24 mmol, 29% yield, 99% purity). $^1$H NMR (CD$_3$OD, 400 MHz) δ 1.77 (s, 6H), 2.03 (s, 9H), 2.81 (s, 3H), 3.10-3.30 (m, 2H), 3.48-3.54 (m, 2H), 4.32 (s, 2H), 4.69-4.74 (m, 4H), 6.89 (dd, 1H), 7.13 (dd, 1H), 7.24 (d, 1H), 7.40 (d, 1H), 7.42-7.48 (m, 5H), 8.05 (dd, 1H).

Ethyl 4,4-difluoro-1-methylcyclohexanecarboxylate

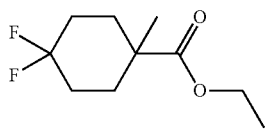

To a solution of diisopropylamine (354 mg, 3.51 mmol) in tetrahydrofuran (5 mL) was added n-BuLi (2.5 M, 1.40 mL) dropwise at −78° C. under nitrogen. The mixture was stirred at −78° C. for 1 h and ethyl 4,4-difluorocyclohexanecarboxylate (500 mg, 2.60 mmol) was added. The mixture was warmed to 0° C. and stirred for 30 min at which point it was re-cooled to −78° C. Methyl iodide (7.70 mL, 124 mmol) was added. The mixture was warmed to 15° C. and stirred at 15° C. for 12 h. The reaction mixture was quenched by saturated aqueous solution of ammonium chloride (50 mL), and then extraction with ethyl acetate (2×30 mL). The combined organic phases were washed with brine (20 mL) and dried over anhydrous sodium sulfate. After filtration and concentration, the residue was purified by silica gel column chromatography, diluted with petroleum ether ethyl acetate=100:1 to 80:1) to afford the product (400 mg, 75% yield) as yellow oil. $^1$H NMR (CDCl$_3$, 400 MHz) δ 1.22 (s, 3H), 1.27 (t, 3H), 1.53-1.56 (m, 2H), 1.74-1.91 (m, 2H), 1.93-2.03 (m, 2H), 2.16-2.21 (m, 2H), 4.18 (q, 2H).

4,4-Difluoro-1-methylcyclohexanecarboxylic Acid

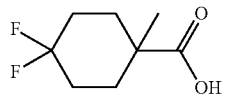

To a solution of ethyl 4,4-difluoro-1-methylcyclohexanecarboxylate (100 mg, 0.48 mmol) in tetrahydrofuran (2 mL), methanol (0.2 mL) and water (0.2 mL) was added sodium hydroxide (39 mg, 0.9 7 mmol). The mixture was stirred at 70° C. for 0.5 h. The reaction mixture was quenched by addition water 20 mL, and then added 1 mol/L aqueous solution of hydrochloric acid until pH=4 and extracted with ethyl acetate (2×30 mL). The combined organic phases were washed with brine (20 mL) and dried over anhydrous sodium sulfate. After filtration and concentration, the product (67 mg, 77% yield) was obtained as yellow solid. $^1$H NMR (CDCl$_3$, 400 MHz) δ 1.30 (s, 3H), 1.53-1.61 (m, 2H), 1.82-2.04 (m, 4H), 2.18-2.22 (m, 2H).

(R)-tert-Butyl 2-((4,4-difluoro-1-methyl-N-(2-oxo-2-((2'-oxo-1,1',2',3-tetrahydrospiro[indene-2,3'-pyrrolo[2,3-b]pyridin]-5-yl)amino)ethyl)cyclohexanecarboxamido)methyl)benzyl(methyl)carbamate 36.1b

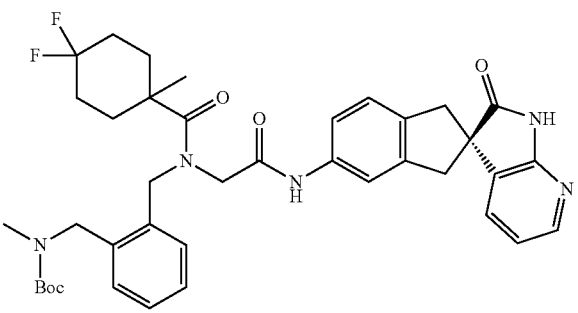 [SMILES: CN(Cc1ccccc1CN(CC(=O)Nc1ccc2c(c1)C[C@@]1(C2)C(=O)Nc2ncccc21)C(=O)C1(C)CCC(F)(F)CC1)C(=O)OC(C)(C)C]

To a solution of compound 3 (66 mg, 0.37 mmol) in dichloromethane (5 mL) was added thionyl chloride (200 μL 2.76 mmol) and dimethyl formamide (2.85 μL, 0.037 mmol). The mixture was stirred at 25° C. for 2 h and concentrated under reduced pressure to afford 72 mg of 4,4-difluoro-1-methyl-cyclohexanecarbonyl chloride as yellow oil. To a solution of Intermediate X (50 mg, 0.92 mmol) in dichloromethane (4 mL) was added triethylamine (111 mg, 1.10 mmol) and 4,4-difluoro-1-methyl-cyclohexanecarbonyl chloride (72 mg, 0.37 mmol). The mixture was stirred at 25° C. for 16 h. The reaction mixture was quenched by addition water 20 mL, and extraction with ethyl acetate (2×30 mL). The combined organic phases were washed with brine (20 mL) and dried over anhydrous sodium sulfate. After filtration and concentration, compound 36.1b was obtained as a yellow solid (64 mg, 99% yield). $^1$H NMR (CDCl$_3$, 400 MHz) δ 1.32 (s, 3H), 1.45 (s, 9H), 1.66-1.68 (m, 2H), 2.00-2.25 (m, 4H), 2.15-2.18 (m, 2H), 2.82 (s, 3H), 3.02-3.08 (dd, 2H), 3.62 (dd, 2H), 4.10-4.16 (m, 2H), 4.47 (s, 2H), 4.92 (br. s, 2H), 8.83 (dd, 1H), 7.08 (dd, 1H), 7.15-7.24 (m, 4H), 7.29-7.34 (m, 2H), 7.56 (s, 1H), 8.12-8.13 (m, 1H), 8.34 (br. s, 1H), 8.65 (br. s, 1H).

Example 93: (R)-4,4-difluoro-1-methyl-N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)cyclohexanecarboxamide 2,2,2-trifluoroacetate 36B

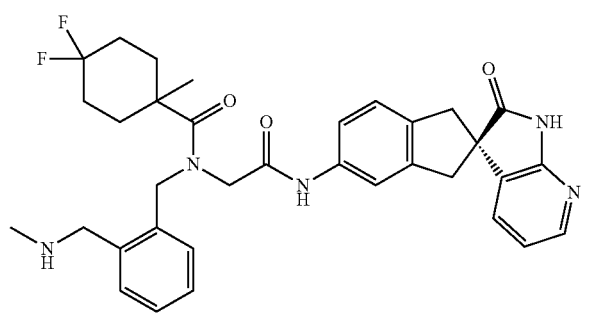 [SMILES: CNCc1ccccc1CN(CC(=O)Nc1ccc2c(c1)C[C@@]1(C2)C(=O)Nc2ncccc21)C(=O)C1(C)CCC(F)(F)CC1]

To a solution of compound 36.1b (64 mg, 0.91 mmol) in dichloromethane (5 mL) was added trifluoroacetic acid (0.5 mL, 6.75 mmol). The mixture was stirred at 25° C. for 0.5 h. The mixture was concentrated under reduced pressure to give a residue. The residue was purified by prep-HPLC (column: Phenomenex Synergi C18 150×25 mm, 10 μm; mobile phase: [water (0.1% TFA)-acetonitrile]; B %: 20%-50%, 9 min). After lyophilisation, compound 36B was obtained as a white solid (30 mg, 46% yield, 100% purity. $^1$H NMR (CD$_3$OD, 400 MHz) δ 1.36 (s, 3H), 1.55-1.65 (m, 2H), 1.86-2.00 (m, 4H), 2.23 (d, 2H), 2.81 (s, 3H), 3.10 (dd, 2H), 3.51 (dd, 2H), 4.33 (s, 2H), 4.51-4.80 (m, 4H), 6.90 (dd, 1H), 7.15 (dd, 1H), 7.24 (d, 1H), 7.35-7.46 (m, 5H), 7.53 (s, 1H), 8.06 (dd, 1H).

LC-MS: RT 0.905 min, (602 [M+H]$^+$), purity 100%.

tert-Butyl N-methyl-N-[[2-[[[2-oxo-2-[[(3R)-2-oxospiro[1H-pyrrolo[2,3-b]pyridine-3,2'-indane]-5'-yl]amino]ethyl]-[1-(trifluoromethyl)cyclopentanecarbonyl]amino]methyl]phenyl]methyl]carbamate 36.1c

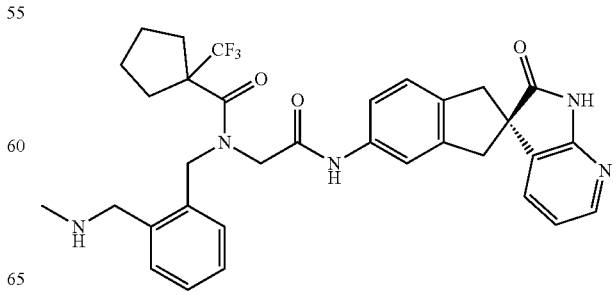

To a solution of 1-(trifluoromethyl)cyclopentane-1-carboxylic acid (50 mg, 0.27 mmol) in dichloromethane (5 mL) was added Ghosez's reagent (1-chloro-N,N,2-trimethyl-1-propenylamine) (44 mg, 0.33 mmol). The mixture was stirred at 20° C. for 2 h. The mixture was added into the solution of Intermediate X (50 mg, 0.92 mmol) and triethylamine (28 mg, 0.28 mmol) in dichloromethane (5 mL). The resulting mixture was stirred at 20° C. for 1 h. The mixture was quenched by addition water (20 mL) and extracted with dichloromethane (25 mL). The organic phase was dried over sodium sulfate. After filtration and concentration, compound 36.1c was obtained as a white solid (60 mg, 87% yield, 95% purity) and used without further purification. LC-MS: RT 0.917 min, (728 [M+Na]$^+$), purity 95.3%.

Example 94: N-[[2-(methylaminomethyl)phenyl]methyl]-N-[2-oxo-2-[[(3R)-2-oxospiro[1H-pyrrolo[2,3-b]pyridine-3,2'-indane]-5'-yl]amino]ethyl]-1-(trifluoromethyl)cyclopentanecarboxamide 2,2,2-trifluoroacetate 36C To a solution of compound 36.1c (60 mg, 0.85 mmol) in dichloromethane (5 mL) was added trifluoroacetic acid (0.5 mL). The mixture was stirred at 20° C. for 0.5 h. The mixture was concentrated and the residue was purified by prep-HPLC (column: Boston Prime C18 150×30 mm 5 µm; mobile phase: [water (0.1% TFA)-acetonitrile]; B %: 31%-51%, 8 min). After lyophilisation, compound 36C was obtained as a white solid (34 mg, 56% yield, 100% purity.

$^1$H NMR (CD$_3$OD, 400 MHz) δ 1.70-1.72 (m, 4H), 2.20-2.24 (m, 2H), 2.50-2.54 (m, 2H), 2.80 (s, 3H), 3.08 (dd, 2H), 3.51 (dd, 2H), 4.29 (s, 2H), 4.53 (br. s, 1H), 4.81 (m, 3H), 6.89-6.92 (m, 1H), 7.16-7.25 (m, 2H), 7.34-7.53 (m, 5H), 8.06 (dd, 1H).

LC-MS: RT 0.797 min, (606 [M+H]$^+$), purity 100%.

(R)-tert-Butyl 2-((2-fluoro-2-methyl-N-(2-oxo-2-((2'-oxo-1,1',2',3-tetrahydrospiro[indene-2,3'-pyrrolo[2,3-b]pyridin]-5-yl)amino)ethyl)propanamido)methyl) benzyl(methyl)carbamate 36.1 d

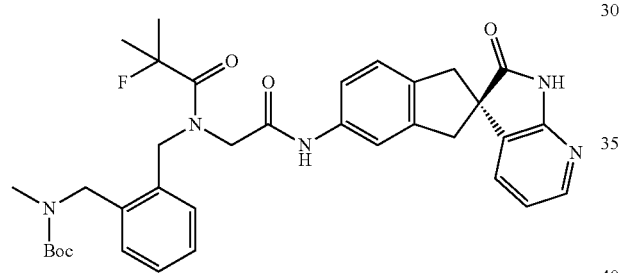

To a solution of 2-fluoro-2-methyl-propanoic acid (40 mg, 0.38 mmol) in dimethyl formamide (2 mL) was added DIEA (100 mg, 0.77 mmol), EDCl (85 mg, 0.44 mmol) and HOAt (60 mg, 0.44 mmol). Intermediate X (100 mg, 0.18 mmol) was added and the resulting mixture was stirred at 40° C. for 16 h. The reaction mixture was poured into water (50 mL), and then extraction with ethyl acetate (2×40 mL). The combined organic phases were washed with brine (20 mL) and dried over anhydrous sodium sulfate. After filtration and concentration, the crude product was purified by prep-HPLC (column: Luna C18 150×25, 5 µm; mobile phase: [water (0.1% TFA)-acetonitrile]; B %: 50%-70%, 8 min) to afford compound 36.1 d as a white solid (50 mg, 43% yield). $^1$H NMR (CDCl$_3$, 400 MHz) δ 1.37 (s, 9H), 1.62 (s, 3H), 1.67 (s, 3H), 2.72-2.74 (m, 3H), 2.97 (dd, 2H), 3.60-3.61 (m, 2H), 3.96-4.20 (m, 2H), 4.41 (s, 2H), 4.73-4.88 (m, 2H), 6.93 (dd, 1H), 7.12-7.13 (m, 4H), 7.23-7.27 (m, 3H), 7.53 (br. s, 1H), 7.91 (d, 1H), 8.32 (br. s, 1H), 11.39 (br. s, 1H).

Example 95: (R)-2-Fluoro-2-methyl-N-(2-((methylamino)methyl)benzyl)-N-(2-oxo-2-((2'-oxo-1,1',2',3-tetrahydrospiro[indene-2,3'-pyrrolo[2,3-b]pyridin]-5-yl)amino)ethyl)propanamide 2,2,2-trifluoroacetate 36D

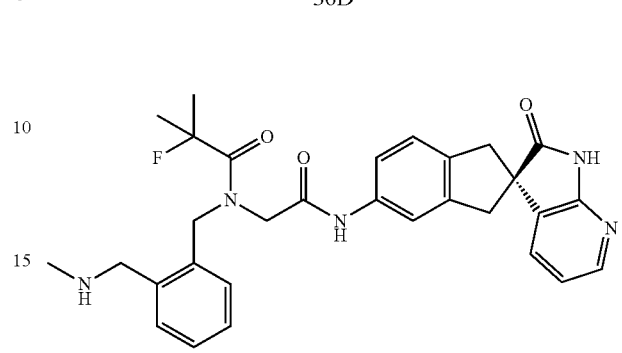

To a solution of compound 36.1 d (40 mg, 0.63 mmol) in dichloromethane (5 mL) was added TFA (0.5 mL). The mixture was stirred at 20° C. for 0.5 h. The mixture was concentrated under reduced pressure and the residue was purified by prep-HPLC (column: Phenomenex Synergi C18 150×25 mm, 10 µm; mobile phase: [water (0.1% TFA)-acetonitrile]; B %: 10%-40%, 10 min). After lyophilisation, compound 36D was obtained as a white solid (34 mg, 83% yield, 100% purity). $^1$H NMR (CD$_3$OD, 400 MHz) δ 1.67 (s, 3H), 1.72 (s, 3H), 2.83 (s, 3H), 3.08 (d, 2H), 3.52 (dd, 2H), 4.36 (s, 2H), 4.60-4.80 (m, 4H), 6.90-6.93 (m, 1H), 7.16-7.28 (m, 3H), 7.46-7.49 (m, 5H), 8.07 (d, 1H). LC-MS: RT=2.021 min, [M+H]$^+$ 530, 100% purity.

tert-Butyl N-methyl-N-[[2-[[[2-oxo-2-[[(3R)-2-oxospiro[1H-pyrrolo[2,3-b]pyridine-3,2'-indane]-5'-yl]amino]ethyl]-(3,3,3-trifluoro-2,2-dimethyl-propanoyl)amino]methyl]phenyl]methyl]carbon-ate 36.1e

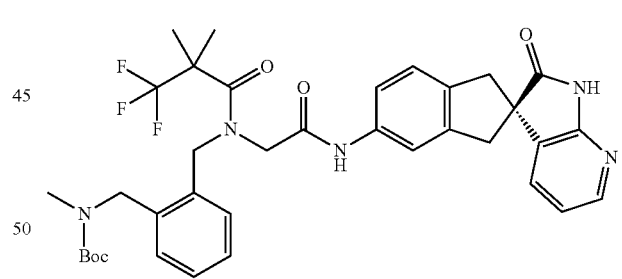

To a solution of 3,3,3-trifluoro-2,2-dimethyl-propanoic acid (70 mg, 0.45 mmol) in dichloromethane (1.5 mL) was added Ghosez's reagent (90 mg, 0.67 mmol) at 20° C. The result mixture was stirred at 20° C. for 2.5 h. The mixture was added to the solution of Intermediate X (40 mg, 0.74 mmol) and triethylamine (60 mg, 0.59 mmol) in dichloromethane (1.5 mL) at 0° C. The mixture was stirred at 20° C. for 2 h. The reaction mixture was poured into water (20 mL) and extracted with ethyl acetate (3×20 mL). The combined organic phases were washed with brine (2×20 mL) and dried over anhydrous sodium sulfate. After filtration and concentration, the residue was purified by silica gel column chromatography, eluting with petroleum etherethyl acetate=5:1 to 1:1, to provide compound 36.1e was obtained as an off-white solid (70 mg, 91% yield, 98% purity). $^1$H NMR (CDCl$_3$, 400 MHz) δ 1.42-1.49 (m, 9H), 1.54 (s, 6H), 2.83 (s, 3H), 3.05 (dd, 2H), 3.63 (dd, 2H), 4.12-4.16 (m, 2H), 4.46 (s, 2H), 4.93 (s, 2H), 6.83 (dd, 1H), 7.08 (dd, 1H), 7.13-7.25 (m, 4H), 7.30-7.37 (m, 2H), 7.55 (s, 1H), 8.11 (dd, 1H), 8.17 (br. s, 1H), 8.40 (br. s, 1H). LC-MS: RT=0.886 min, [M+Na]$^+$ 702, 98.16% purity.

Example 96: 3,3,3-trifluoro-2,2-dimethyl-N-[[2-(methylaminomethyl)phenyl]methyl]-N-[2-oxo-2-[[(3R)-2-oxospiro[1H-pyrrolo[2,3-b]pyridine-3,2'-indane]-5'-yl]amino]ethyl]propanamide 2,2,2-trifluoroacetate 36E

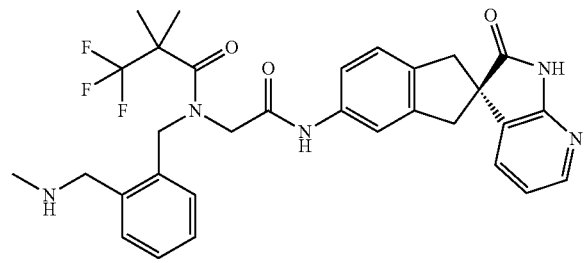 [SMILES: CNCc1ccccc1CN(CC(=O)Nc1ccc2c(c1)C[C@@]1(C2)C(=O)Nc2ncccc21)C(=O)C(C)(C)C(F)(F)F]

To a solution of compound 36.1e (65 mg, 0.96 mmol) in dichloromethane (2 mL) was added trifluoroacetic acid (0.4 mL) at 20° C. The mixture was stirred at 20° C. for 0.5 h. The mixture was concentrated under vacuum. The residue was purified by prep-HPLC (column: Phenomenex Synergi C18 150×25 mm, 10 μm; mobile phase: [water (0.1% TFA)-acetonitrile]; B %: 15%-45%, 9 min). After lyophilisation, compound 36E (was obtained as a white solid 36 mg, 54% yield, 100% purity. $^1$H NMR (CD$_3$OD, 400 MHz) δ 1.58 (s, 6H), 2.81 (s, 3H), 3.08 (d, 2H), 3.51 (dd, 2H), 4.31 (s, 2H), 4.42-4.60 (m, 2H), 4.90-5.03 (m, 2H), 6.90 (dd, 1H), 7.15 (dd, 1H), 7.24 (d, 1H), 7.33 (d, 1H), 7.39-7.53 (m, 5H), 8.06 (d, 1H). LC-MS rt=1.756 min, [M+H]$^+$ 580, 98.6% purity.

Benzyl 4,4,4-trifluoro-2,2-dimethylbutanoate

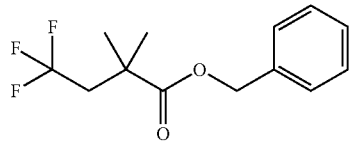 [SMILES: CC(C)(CC(F)(F)F)C(=O)OCc1ccccc1]

To a solution of diisopropylamine (624 mg, 6.17 mmol) in tetrahydrofuran (10 mL) was added n-BuLi (2.5 M, 2.5 mL) dropwise at −78° C. under nitrogen. The mixture was stirred at −78° C. for 1 h. Benzyl isobutyrate (1.00 g, 5.61 mmol) was added and stirring continued for 30 min at 0° C., when it was re-cooled to −78° C. 2,2,2-Trifluoroethyl trifluoromethanesulfonate (1.43 g, 6.17 mmol) was added. The resulting mixture was warmed to 15° C. and stirred for 12 h. The reaction mixture was quenched by addition aqueous solution of ammonium chloride (50 mL) and then extracted with ethyl acetate (2×50 mL). The combined organic phases were washed with brine (20 mL) and dried over anhydrous sodium sulfate. After filtration and concentration, the residue was purified by prep-HPLC (column: Phenomenex Synergi C18 150×25 mm, 10 μm; mobile phase: [water (0.1% TFA)-acetonitrile]; B %: 58%-88%, 9 min) to afford benzyl 4,4,4-trifluoro-2,2-dimethylbutanoate (160 mg, 11% yield) as colorless oil. 20 $^1$H NMR (CDCl$_3$, 400 MHz) δ 1.33 (d, 6H), 2.50 (q, 2H), 5.14 (s, 2H), 7.33-7.38 (m, 5H).

4,4,4-Trifluoro-2,2-dimethylbutanoic Acid

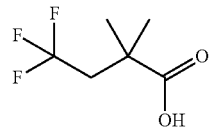

To a solution of benzyl 4,4,4-trifluoro-2,2-dimethylbutanoate (80 mg, 0.31 mmol) in methanol (4 mL) was added 10% Pd/C (10 mg). The mixture was degassed under vacuum and purged hydrogen for 3 times. The resulting suspension was stirred at 25° C. for 1 h under hydrogen balloon. The mixture was filtered and the filtrate concentrated under vacuum to afford compound 4,4,4-trifluoro-2,2-dimethylbutanoic acid (38 mg, 72.66% yield) as colorless oil.

$^1$H NMR (CDCl$_3$, 400 MHz) δ 1.36 (s, 6H), 2.50 (q, 2H).

tert-Butyl N-methyl-N-[[2-[[[2-oxo-2-[[(3R)-2-oxospiro[1H-pyrrolo[2,3-b]pyridine-3,2'-indane]-5'-yl]amino]ethyl]-(4,4,4-trifluoro-2,2-dimethyl-butanoyl)amino]methyl]phenyl]methyl] carbamate 36.1f

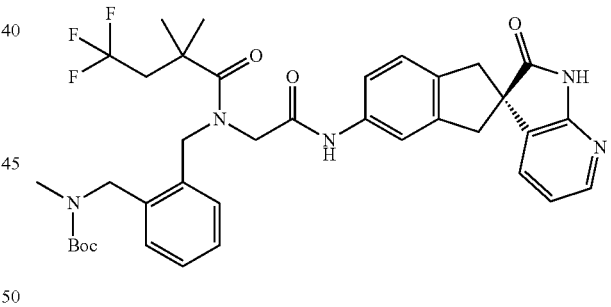

To a solution of compound 4,4,4-trifluoro-2,2-dimethylbutanoic acid (30 mg, 0.18 mmol) in dichloromethane (1 mL) was added Ghosez's reagent (35 mg, 0.26 mmol) at 20° C. The mixture was stirred at 20° C. for 2.5 h and added to a solution of Intermediate X (35 mg, 0.65 mmol) and triethylamine (52 mg, 0.52 mmol) in dichloromethane (1 mL) at 0° C. The resulting mixture was stirred at 20° C. for 1 h, poured into water (20 mL) and extracted with ethyl acetate (3×20 mL). The combined organic phases were washed with 0.1 M aqueous hydrochloric acid (20 mL) and saturated aqueous solution of sodium bicarbonate (30 mL), and dried over anhydrous sodium sulfate. After filtration and concentration, compound 36.1f was obtained as a yellow solid (40 mg, crude).

LCMS RT=0.979 min, [M+Na]$^+$=716

325

Example 97: 4,4,4-Trifluoro-2,2-dimethyl-N-[[2-(methylaminomethyl)phenyl]methyl]-N-[2-oxo-2-[[(3R)-2-oxospiro[1H-pyrrolo[2,3-b]pyridine-3,2'-indane]-5'-yl]amino]ethyl]butanamide 2,2,2-trifluoroacetate 36F

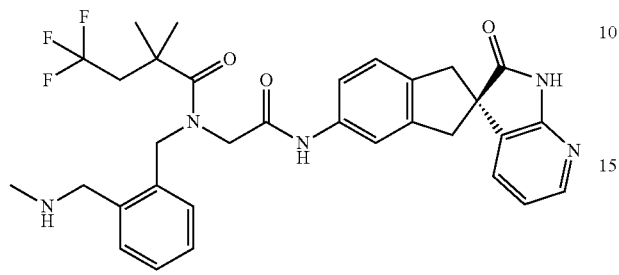

To a solution of compound 36.1f (40 mg, 0.58 mmol) in dichloromethane (1.5 mL) was added trifluoroacetic acid (0.2 mL) at 20° C. The mixture was stirred at 20° C. for 0.5 h and concentrated under vacuum. The residue was purified by prep-HPLC (column: Phenomenex luna C18 250×50 mm, 10 μm; mobile phase: [water (0.1% TFA)-acetonitrile]; B %: 23%-43%, 8 min) to provide compound 36F as a white solid (27.42 mg, 66.82% yield, 99.43% purity. 25 $^1$H NMR (CD$_3$OD, 400 MHz) δ 1.44 (s, 6H), 2.69 (q, 2H), 2.81 (s, 3H), 3.09 (d, 2H), 3.51 (dd, 2H), 4.32 (s, 2H), 4.38-4.56 (m, 1.5H), 4.77-4.83 (m, 2.5H), 6.87-6.94 (m, 1H), 7.13-7.21 (m, 1H), 7.24 (d, 1H), 7.32 (d, 1H), 7.37-7.52 (m, 5H), 8.06 (d, 1H). LC-MS RT=1.836 min, [M+H]$^+$ 594, 99.43% purity.

326

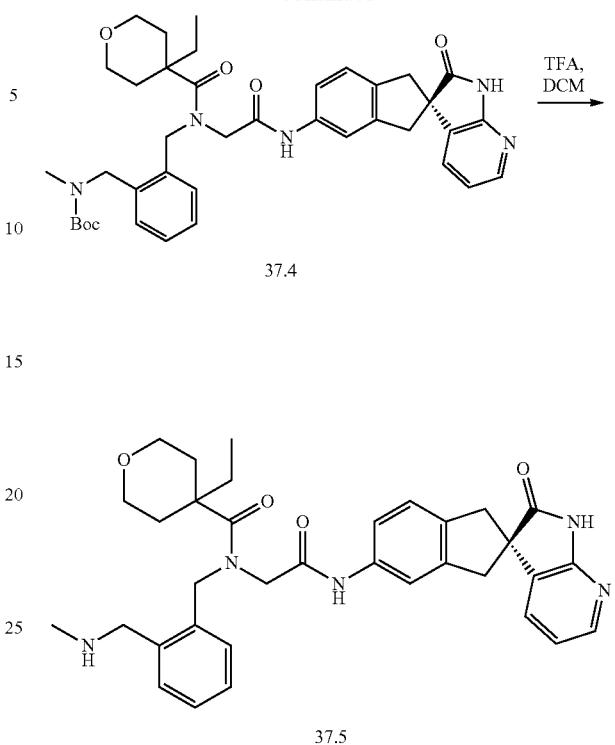

Ethyl 4-ethyltetrahydropyran-4-carboxylate 37.2

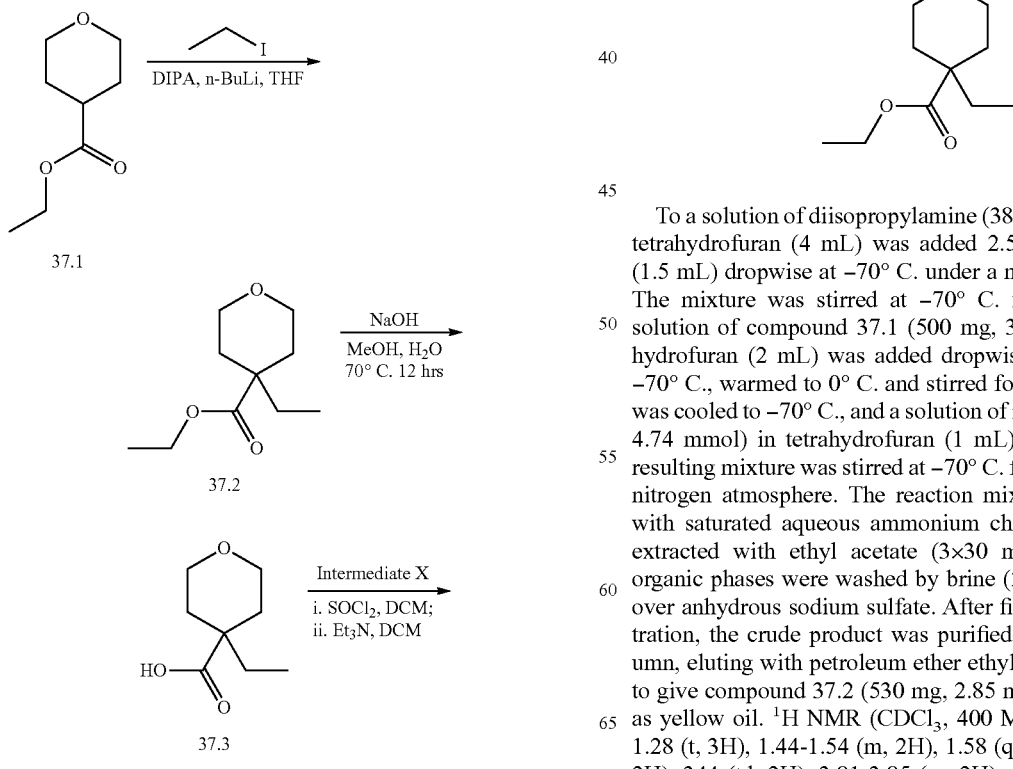

To a solution of diisopropylamine (380 mg, 3.76 mmol) in tetrahydrofuran (4 mL) was added 2.5 M n-butyl lithium (1.5 mL) dropwise at −70° C. under a nitrogen atmosphere. The mixture was stirred at −70° C. for 1 hour. Then a solution of compound 37.1 (500 mg, 3.16 mmol) in tetrahydrofuran (2 mL) was added dropwise to the mixture at −70° C., warmed to 0° C. and stirred for 0.5 h. The mixture was cooled to −70° C., and a solution of iodoethane (740 mg, 4.74 mmol) in tetrahydrofuran (1 mL) added slowly. The resulting mixture was stirred at −70° C. for another 2 h under nitrogen atmosphere. The reaction mixture was quenched with saturated aqueous ammonium chloride (30 mL) and extracted with ethyl acetate (3×30 mL). The combined organic phases were washed by brine (2×30 mL) and dried over anhydrous sodium sulfate. After filtration and concentration, the crude product was purified with silica gel column, eluting with petroleum ether ethyl acetate=1:0 to 50:1 to give compound 37.2 (530 mg, 2.85 mmol, 90.03% yield) as yellow oil. $^1$H NMR (CDCl$_3$, 400 MHz) δ 0.83 (t, 3H), 1.28 (t, 3H), 1.44-1.54 (m, 2H), 1.58 (q, 2H), 2.05-2.12 (m, 2H), 344 (td, 2H), 3.81-3.85 (m, 2H), 4.20 (q, 2H).

4-Ethyltetrahydropyran-4-carboxylic Acid 37.3

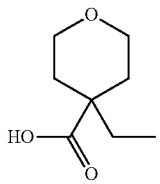

To a solution of compound 37.2 (250 mg, 1.34 mmol) in methanol (3 mL) was added a solution of sodium hydroxide (322 mg, 8.05 mmol) in water (1 mL) at 20° C. The mixture was heated to 70° C. and stirred for 12 h, poured into water (20 mL) and extracted with ethyl acetate (20 mL). The aqueous phase was retained, and the organic phase discarded. 1 M Hydrochloric acid was added to the aqueous phase until pH=4. The resulting mixture was extracted with ethyl acetate (3×20 mL). The combined organic phases were washed by brine (2×20 mL) and dried over anhydrous sodium sulfate. After filtration and concentration, compound 37.3 (150 mg, 71% yield) was obtained as a yellow solid. $^1$H NMR (CDCl$_3$, 400 MHz) δ 0.90 (t, 3H), 1.47-1.57 (m, 2H), 1.64 (q, 2H), 2.07 (d, 2H), 352 (td, 2H), 3.87 (dt, 2H).

tert-ButyN-[[2-[[(4-ethyltetrahydropyran-4-carbonyl)-[2-oxo-2-[[(3R)-2-oxospiro[1H-pyrrolo [2,3-b]pyridine-3,2'-indane]-5'-yl]amino]ethyl]amino]methyl] phenyl] methyl]-N-methyl-carbamate 37.4

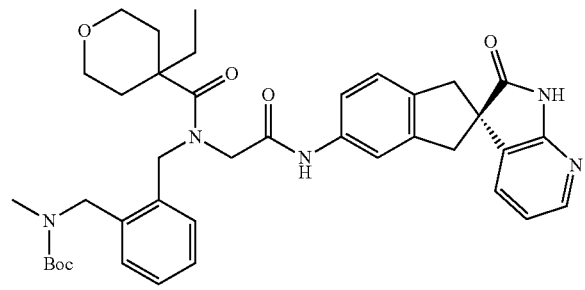 [SMILES: CCC1(C(=O)N(CC(=O)Nc2ccc3c(c2)C[C@@]2(C3)C(=O)Nc3ncccc32)Cc2ccccc2CN(C)C(=O)OC(C)(C)C)CCOCC1]

To a solution of compound 37.3 (50 mg, 0.32 mmol) and dimethylformamide (2.31 mg, 0.032 mmol) in dichloromethane (2 mL) was added thionyl chloride (376 mg, 3.20 mmol) at 20° C. The mixture was stirred at 20° C. for 1.5 h and concentrated in vacuo to give a residue. The residue was dissolved in dichloromethane (1.5 mL) and added to a solution of Intermediate X (65 mg) and triethylamine (97 mg, 0.96 mmol) in dichloromethane (2 mL) at 0° C. The mixture was stirred at 20° C. for 2 h, poured into water (10 mL) and extracted with ethyl acetate (3×20 mL). The combined organic phases were washed by 0.1 M hydrochloric acid (20 mL), saturated sodium bicarbonate (30 mL) and brine (2×30 mL) and dried over sodium sulfate. After filtration and concentration, the residue was purified by silica gel column chromatography, eluting with petroleum ether ethyl acetate=5:1 to 1:3 to give compound 37.4 (40 mg, 56.20 μmol, 47% yield, 95.8% purity) as a white solid. LCMS: RT=0.860 min, [M+H]=682, 95.795% purity.

Example 98: 4-Ethyl-N-[[2-(methylaminomethyl) phenyl]methyl]-N-[2-oxo-2-[[(3R)-2-oxospiro[1H-pyrrolo [2,3-b]pyridine-3,2'-indane]-5'-yl]amino] ethyl]tetrahydropyran-4-carboxamide 2,2,2 trifluoroacetate 37.5

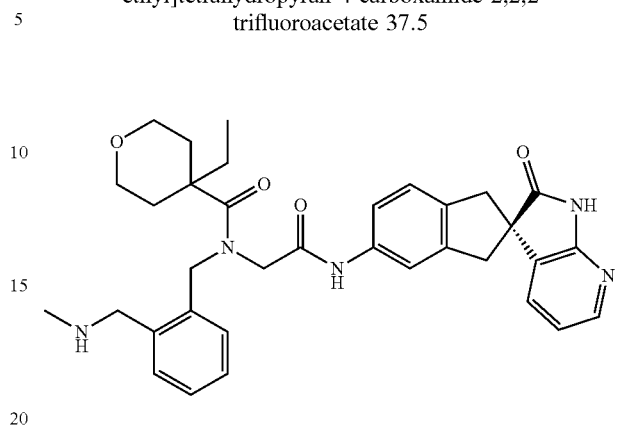

To a solution of compound 4 (40 mg, 58.67 μmol, 1 eq) in dichloromethane (1 mL) was added trifluoroacetic acid (0.2 mL) at 20° C. The mixture was stirred at 20° C. for 0.5 hours. LCMS showed starting material was consumed and desired mass detected. The reaction mixture was concentrated under vacuum to give a residue. The residue was purified by prep-HPLC (column: Phenomenex luna C18 250×50 mm, 10 μm; mobile phase: [water (0.1% trifluoroacetic acid)-acetonitrile]; B %: 24%-41%, 7 min) to give compound 37.5 (23.68 mg, 57% yield, 98.8% purity) as a white solid. $^1$H NMR (CD$_3$OD, 400 MHz) δ 0.85 (s, 3H), 1.48-1.60 (m, 2H), 1.73-1.86 (m, 2H), 2.19 (d, 2H), 2.82 (s, 3H), 3.09 (dd, 2H), 3.44-3.61 (m, 4H), 3.65-3.77 (m, 2H), 4.35 (s, 2H), 4.47-4.71 (m, 4H), 6.87-6.94 (m, 1H), 7.14-7.20 (m, 1H), 7.24 (d, 1H), 7.32-7.50 (m, 5H), 7.54 (s, 1H), 8.06 (dd, 1H). LC-MS: RT=1.650 min, [M+H]$^+$ 582.

SCHEME 38

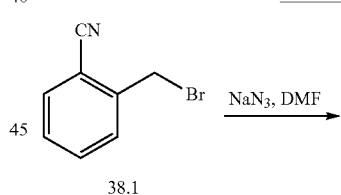

38.1

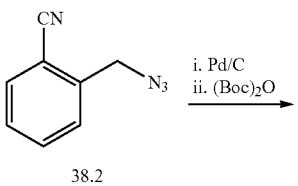

38.2

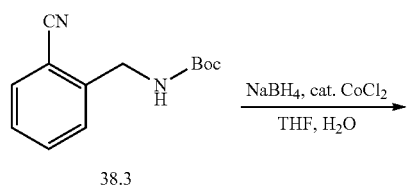

38.3

-continued

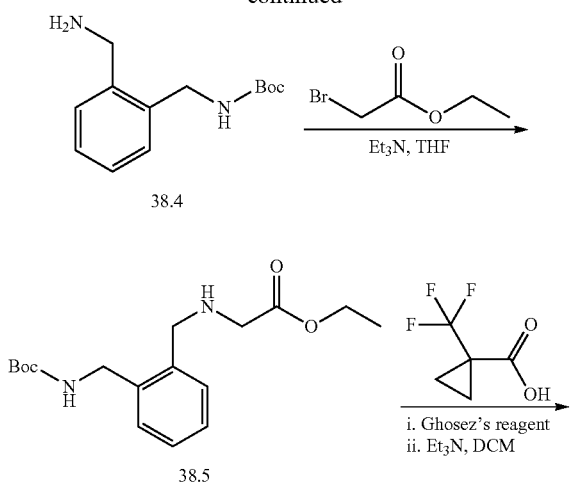

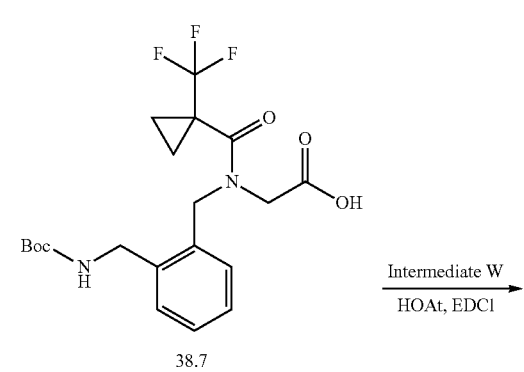

-continued

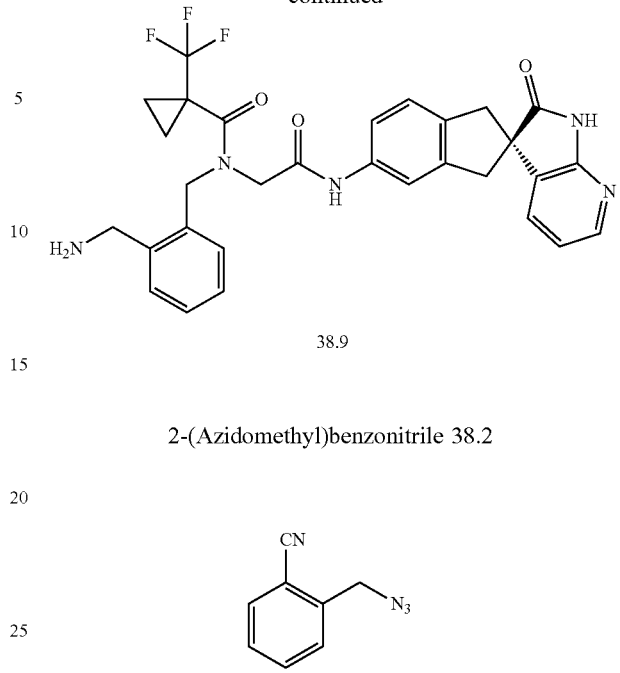

2-(Azidomethyl)benzonitrile 38.2

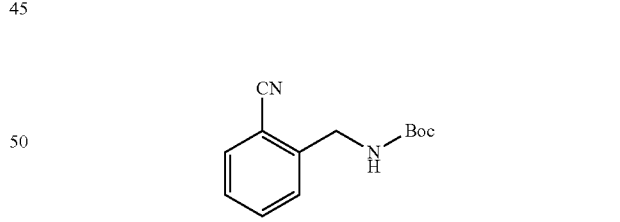

A mixture of 2-(bromomethyl)benzonitrile 38.1 (14.0 g, 71.4 mmol) in N,N-dimethylformamide (150 mL) was added sodium azide (7.90 g, 121 mmol). The mixture was stirred at 60° C. for 12 h, quenched by water (150 mL) and extracted with ethyl acetate (3×200 mL). The combined organic phases were washed with brine (3×200 mL) and dried with anhydrous sodium sulfate. After filtration, the solvent was concentrated under vacuum to approximately 20 mL and the mixture was diluted with isopropanol (100 mL). This procedure was repeated for 3 times. And the resulting mixture in 100 mL isopropanol was used directly for the next step. LCMS: RT=0.716 min, (159 [M+H]$^+$), 98.753% purity.

tert-Butyl N-[(2-cyanophenyl)methyl]carbamate 38.3

To the solution of compound 38.2 (11.2 g, 70.8 mmol) in isopropanol (100 mL) (vide supra) was added triethylamine (21.5 g, 212 mmol), di-tert-butyl dicarbonate (23.2 g, 106 mmol) and 10% Pd/C (1.0 g). The mixture was degassed under vacuum, purged three times with hydrogen and stirred under a balloon of hydrogen at 20° C. for 16 h. The reaction mixture was filtered and the filtrate was concentrated in vacuum. The residue was purified by silica gel column chromatography, eluting with petroleum ether ethyl acetate=25:1 to 15:1 to give compound 38.3 (4 g, 24.32% yield) as yellow oil. $^1$H NMR (CD$_3$OD, 400 MHz) δ 1.45 (s, 9H), 4.50 (d, 2H), 5.16 (br. s, 1H), 7.38 (td, 1H), 7.51-7.59 (m, 2H), 7.63 (d, 1H).

331 tert-Butyl N-[[2-(aminomethyl)phenyl]methyl]carbamate 38.4

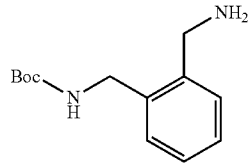 [SMILES: CC(C)(C)OC(=O)NCc1ccccc1CN]

To a solution of compound 38.3 (4.00 g, 17.2 mmol) in tetrahydrofuran (40 mL) was added the solution of cobaltous chloride (4.10 g, 17.2 mmol) in water (20 mL). Then sodium borohydride (1.30 g, 34.4 mmol) was added, the mixture stirred at 35° C. for 12 h, diluted with water (20 mL), and extracted with ethyl acetate (3×50 mL). The combined organic phases were washed with brine (3×50 mL) and dried with anhydrous sodium sulfate. After filtration and concentration, the residue was purified by reverse phase flash chromatography (ammonium hydroxide conditions) to give compound 38.4 (1.70 g, 43% yield) as yellow oil.

$^1$H NMR (CD$_3$OD, 400 MHz) δ 1.45 (s, 9H), 3.94 (s, 2H), 4.37 (d, 2H), 6.00 (br. s, 1H), 7.24-7.26 (m, 1H), 7.28-7.32 (m, 2H), 7.34-7.36 (m, 1H).

Ethyl 2-[[2-[(tert-butoxycarbonylamino)methyl]phenyl]methylamino]acetate 38.5

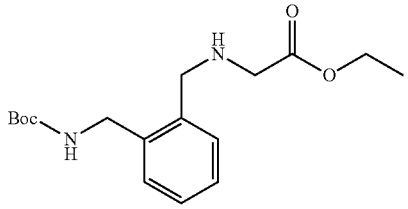 [SMILES: CCOC(=O)CNCc1ccccc1CNC(=O)OC(C)(C)C]

To a solution of compound 38.4 (500 mg, 2.12 mmol) in tetrahydrofuran (5 mL) was added triethylamine (642 mg, 6.35 mmol) and ethyl 2-bromoacetate (354 mg, 2.12 mmol). The mixture was stirred at 20° C. for 12 h, quenched with water (20 mL), and extracted with ethyl acetate (3×30 mL). The combined organic layers were washed with brine (3×30 mL) and dried with anhydrous sodium sulfate. After filtration and concentration, the residue was purified by silica gel column chromatography, eluting with petroleum ether ethyl acetate=30:1 to 10:1 to provide compound 38.5 (550 mg, 81% yield) as yellow oil. $^1$H NMR (CD$_3$OD, 400 MHz) δ 1.31 (t, 3H), 1.45 (s, 9H), 3.48 (s, 2H), 3.83 (s, 2H), 4.20 (q, 2H), 4.39 (d, 2H), 6.18 (br. s, 1H), 7.24-7.26 (m, 1H), 7.28-7.34 (m, 2H), 7.38-7.40 (m, 1H).

332

Ethyl 2-[[2-[(tert-butoxycarbonylamino)methyl]phenyl]methyl-[1-(trifluoromethyl) cyclopropanecarbonyl] amino]acetate 38.6

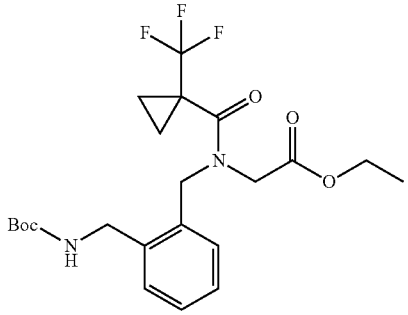 [SMILES: CCOC(=O)CN(Cc1ccccc1CNC(=O)OC(C)(C)C)C(=O)C1(C(F)(F)F)CC1]

To a solution of 1-(trifluoromethyl)cyclopropanecarboxylic acid (251 mg, 1.63 mmol) in dichloromethane (2 mL) was added Ghosez's reagent (280 mg, 2.09 mmol, 4.5 eq) at 20° C. The mixture was stirred at 20° C. for 2.5 h. The mixture was added to a solution of compound 38.5 (150 mg, 0.46 mmol) and triethylamine (376 mg, 3.72 mmol) in dichloromethane (2 mL) at 0° C. The resultant mixture was stirred at 20° C. for 0.5 h, poured into water (20 mL) and extracted with ethyl acetate (3×20 mL). The combined organic phases were washed by 0.1 M hydrochloric acid (20 mL), saturated aqueous solution of sodium bicarbonate (30 mL) and brine (2×20 mL), and dried over anhydrous sodium sulfate. After filtration and concentration, compound 38.6 (160 mg, 60% yield, 80% purity) was obtained as yellow oil.

$^1$H NMR (CDCl$_3$, 400 MHz) δ1.25-1.33 (m, 7H), 1.45 (s, 9H), 3.90-4.05 (m, 1H), 4.15-4.37 (m, 5H), 4.70-4.88 (m, 1H), 4.89-5.09 (m, 1H), 7.04-7.16 (m, 1H), 7.28-7.38 (m, 3H).

2-[[2-[(tert-Butoxycarbonylamino)methyl]phenyl]methyl-[1-(trifluoromethyl)cyclopropane carbonyl] amino] acetic acid 38.7

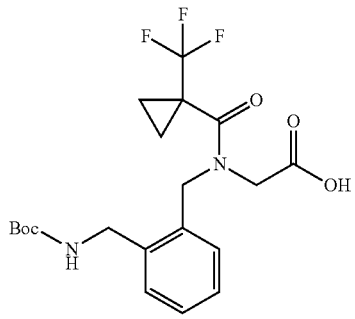 [SMILES: CC(C)(C)OC(=O)NCc1ccccc1CN(CC(=O)O)C(=O)C1(C(F)(F)F)CC1]

To a solution of compound 38.6 (160 mg, 0.28 mmol) in tetrahydrofuran (3 mL), methanol (1 mL) and water (1 mL) was added sodium hydroxide (56 mg, 1.40 mmol) at 20° C. The mixture was stirred at 20° C. for 2 h, poured into water (20 mL), extracted with ethyl acetate (20 mL), and the aqueous phase separated and saved. The aqueous phase was adjusted to pH 4 by adding 1 M hydrochloric acid. The resulting mixture was extracted with ethyl acetate (3×20 mL). The combined organic phases were washed by brine (2×20 mL) and dried over anhydrous sodium sulfate. After filtration and concentration, compound 38.7 was obtained as a yellow gum (110 mg, 0.24 mmol, 86% yield, 94% purity). ¹H NMR (CDCl₃, 400 MHz) δ1.29-1.35 (m, 4H), 1.46 (s, 9H), 3.96-4.05 (m, 1H), 4.20-4.36 (m, 3H), 4.75-4.85 (m, 1H), 4.93-5.02 (m, 1H), 7.07-7.14 (m, 1H), 7.28-7.36 (m, 3H). LCMS: RT=0.883 min, [M+Na]=453, 93.75% purity.

tert-Butyl N-[[2-[[[2-oxo-2-[(2-oxospiro[1H-pyrrolo[2,3-b]pyridine-3,2'-indane]-5'-yl)amino]ethyl]-[1-(trifluoromethyl)cyclopropanecarbonyl]amino]methyl]phenyl]methyl]carbamate 38.8

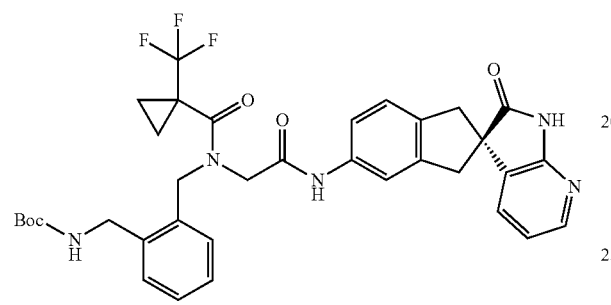

To a solution of compound 38.7 (50 mg, 0.12 mmol), EDCl (34 mg, 0.17 mmol) and HOAt (21 mg, 0.151 mmol) in dimethylformamide (1.5 mL) was added diisopropylethylamine (60 mg, 0.46 mmol) followed by Intermediate W (29 mg, 0.12 mmol) at 20° C. The mixture was stirred at 20° C. for 3 h, poured into water (20 mL) and extracted with ethyl acetate (3×20 mL). The combined organic phases were washed by brine (2×20 mL) and dried over anhydrous sodium sulfate. After filtration and concentration, compound 38.8 was obtained as a yellow solid (70 mg, 0.92 mmol, 79% yield, 87.4% purity). ¹H NMR (CDCl₃, 400 MHz) δ1.28-1.39 (m, 4H), 1.44 (s, 9H), 3.05 (dd, 2H), 3.62 (dd, 2H), 4.00-4.12 (m, 1H), 4.20-4.21 (m, 2.5H), 4.65-5.30 (m, 2.5H), 6.85 (dd, 1H), 7.10 (d, 1H), 7.16-7.25 (m, 3H), 7.28-7.37 (m, 3H), 7.44-7.55 (m, 1H), 8.13 (d, 1H), 8.18 (br s, 1H), 8.51 (br. s, 1H). LCMS RT=0.927 min, [M+Na]=686.

Example 99: N-[[2-(Aminomethyl)phenyl]methyl]-N-[2-oxo-2-[(2-oxospiro[1H-pyrrolo[2,3-b]pyridine-3,2'-indane]-5'-yl)amino]ethyl]-1-(trifluoromethyl)cyclopropylcarboxamide 2,2,2-trifluoroacetate 38.9

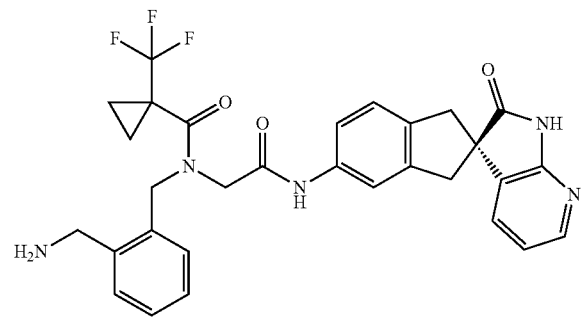 [SMILES: NCc1ccccc1CN(CC(=O)Nc1ccc2c(c1)C[C@@]1(C2)C(=O)Nc2ncccc21)C(=O)C1(C(F)(F)F)CC1]

To a solution of compound 38.8 (70 mg, 0.92 mmol) in dichloromethane (2 mL) was added trifluoroacetic acid (0.4 mL, 5.40 mmol) at 20° C. The mixture was stirred at 20° C. for 0.5 h and concentrated in vacuo to give a residue, which was purified by prep-HPLC (column: Boston Prime C18 150×30 mm, 5 μm; mobile phase: [water (0.1% TFA)-acetonitrile]; B %: 29%-46%, 7 min) to give 38.9 as a white solid (37 mg, 59% yield, 100% purity). ¹H NMR (CD₃OD, 400 MHz) δ 1.39 (s, 4H), 3.09 (d, 2H), 3.51 (dd, 2H), 4.22 (s, 2H), 4.50-4.64 (br. s, 2H), 4.80-4.83 (m, 2H), 6.87-6.94 (m, 1H), 7.16 (d, 1H), 7.22 (d, 1H), 7.31 (d, 1H), 7.36-7.50 (m, 5H), 8.06 (dd, 1H). LC-MS RT=1.700 min, [M+H]⁺ 564.

SCHEME 39

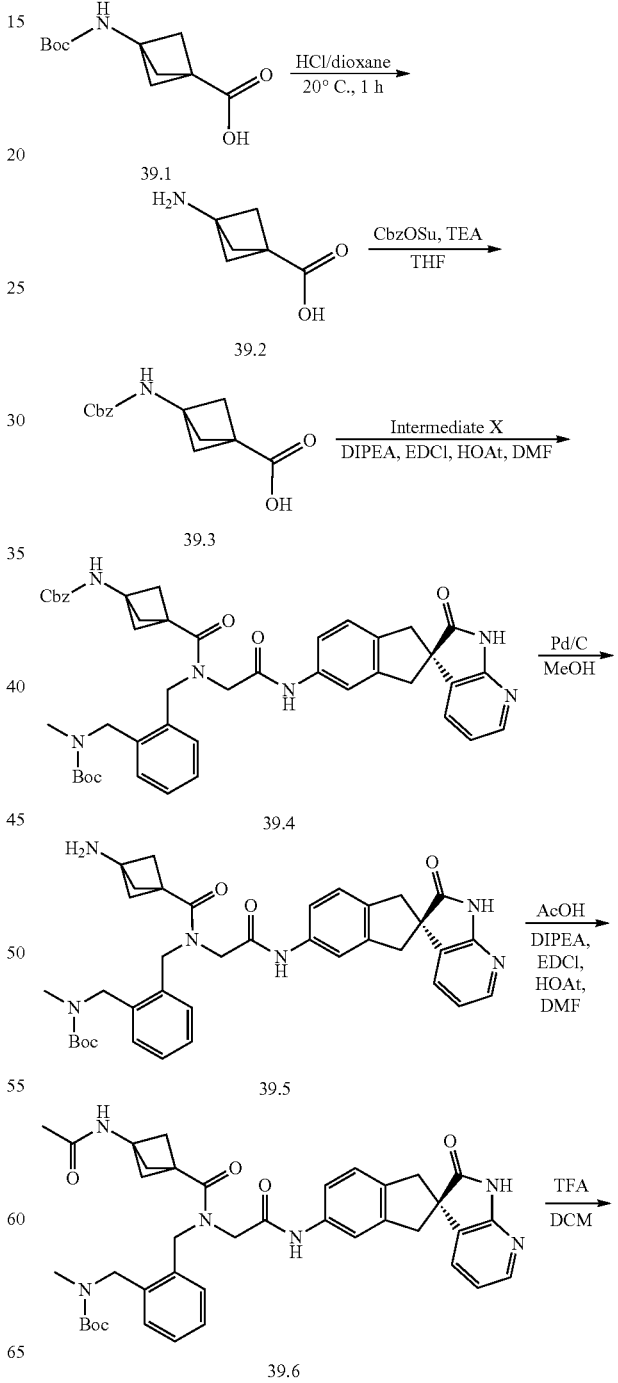

-continued

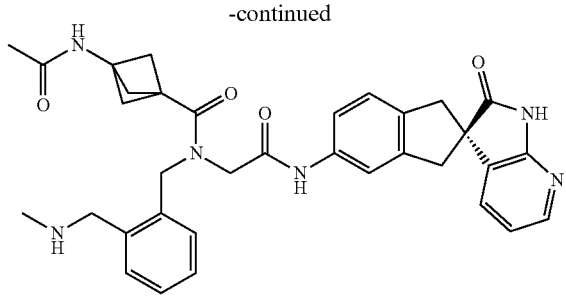

39.7

3-Aminobicyclo[1.1.1]pentane-1-carboxylic Acid 39.2

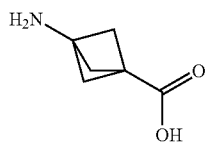

The solution of compound 39.1 (150 mg, 0.66 mmol) in 4M hydrochloric acid/dioxane (5 ML) was stirred at 20° C. for 1 h. The mixture was concentrated to give compound 39.2 (107 mg, 0.65 mmol, 99% yield, HCl salt) as a white solid.

$^1$H NMR (CD$_3$OD, 400 MHz) δ 2.34 (d, 6H).

3-(Benzyloxycarbonylamino)bicyclo[1.1.1]pentane-1-carboxylic Acid 39.3

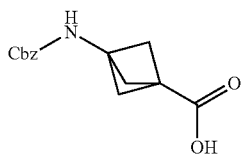 [SMILES: O=C(NC12CC(C(=O)O)(C1)C2)OCc1ccccc1]

To a solution of compound 39.2 (67 mg, 0.41 mmol, HCl salt) in tetrahydrofuran (5 mL) was added triethylamine (207 mg, 2.05 mmol) and N-(benzyloxycarbonyloxy)succinimide (122 mg, 0.49 mmol). The mixture was stirred at 20° C. for 2 h, quenched by adding water (20 mL) and extracted with ethyl acetate (2×25 mL). The combined organic phases were dried over sodium sulfate. After filtration and concentration, the residue was purified by silica gel column chromatography, eluting with petroleum ether/ethyl acetate=5:1-1:1 to provide compound 39.3 as a white solid (100 mg, 0.38 mmol, 93% yield). $^1$H NMR (CD$_3$OD, 400 MHz) δ 2.24 (s, 6H), 5.05 (s, 2H), 7.25-7.40 (m, 5H).

tert-Butyl N-[[2-[[[3-(benzyloxycarbonylamino)bicyclo[1.1.1]pentane-1-carbonyl]-[2-oxo-2-[[(3R)-2-oxospiro[1H-pyrrolo[2,3-b]pyridine-3,2'-indane]-5'-yl]amino]ethyl]amino]methyl]phenyl]methyl]-N-methyl-carbamate 39.4

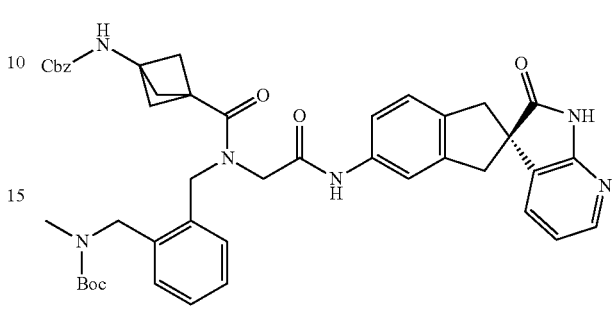

To a solution of Intermediate X (80 mg, 0.15 mmol) and compound 39.3 (46 mg, 0.18 mmol) in dimethyl formamide (3 mL) was added EDCl (57 mg, 0.29 mmol), HOAt (40 mg, 0.29 mmol) and DIEA (38 mg, 0.29 mmol). The mixture was stirred at 20° C. for 2 h, quenched by adding water (20 mL) and extracted with ethyl acetate (3×20 mL). The combined organic phases were washed with 0.5 M hydrochloric acid (2×20 mL), saturated aqueous solution of sodium bicarbonate (20 mL) and dried over sodium sulfate. After filtration and concentration, compound 39.4 was obtained as a white solid (80 mg, 59% yield, 86% purity).

$^1$H NMR (CDCl$_3$, 400 MHz) δ 1.45 (s, 9H), 2.33 (s, 6H), 2.82 (s, 3H), 3.04 (dd, 2H), 3.62 (dd, 2H), 4.06 (s, 2H), 4.45 (s, 2H), 4.81 (s, 2H), 5.04 (s, 2H), 6.80-6.83 (m, 1H), 7.06-7.08 (m, 2H), 7.18-7.23 (m, 3H), 7.30-7.33 (m, 6H), 7.54 (s, 1H), 8.13 (d, 1H), 8.69 (s, 1H), 8.92 (br. s, 1H). LCMS rt 0.970 (785 [M+H]$^+$).

tert-Butyl N-[[2-[[(3-aminobicyclo[1.1.1]pentane-1-carbonyl)-[2-oxo-2-[[(3R)-2-oxospiro[1H-pyrrolo[2,3-b]pyridine-3,2'-indane]-5'-yl]amino]ethyl]amino]methyl]phenyl]methyl]-N-methyl-carbamate 39.5

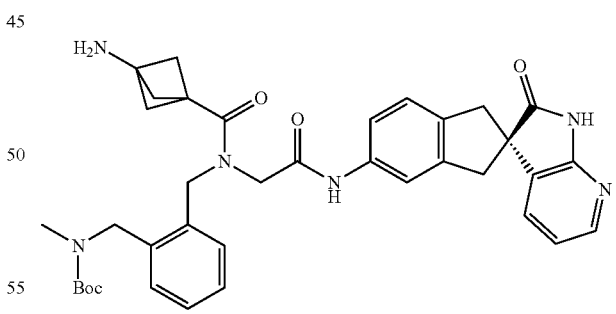

To a solution of compound 39.4 (80 mg, 0.10 mmol) in methanol (10 mL) was added 10% Pd/C (30 mg) under nitrogen atmosphere. The suspension was degassed under vacuum and purged with hydrogen for 3 times. The resulting mixture was stirred under hydrogen balloon at 20° C. for 2 h. The mixture was filtered through Celite and the filter liquid was concentrated to give compound 39.5 as a white solid (66 mg, 79% purity). $^1$H NMR (CD$_3$OD, 400 MHz) δ 1.45 (s, 9H), 2.12-2.28 (m, 6H), 2.82 (s, 3H), 3.08 (q, 2H), 3.52 (q, 2H), 4.17 (m, 2H), 4.46 (m, 2H), 4.71 (s, 2H), 6.87-6.91 (m, 1H), 7.20-7.37 (m, 7H), 7.54 (d, 1H), 8.05 (s, 1H). LCMS rt 0.708 (651 [M+H]⁺).

tert-Butyl N-[[2-[[(3-acetamidobicyclo[1.1.1]pentane-1-carbonyl)-[2-oxo-2-[[(3R)-2-oxospiro[1H-pyrrolo[2,3-b]pyridine-3,2'-indane]-5'-yl]amino]ethyl]amino]methyl]phenyl]methyl]-N-methyl-carbamate 39.6

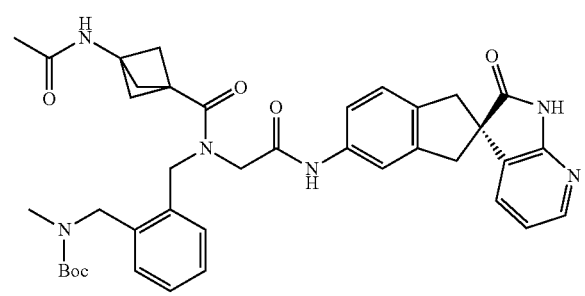 [SMILES: CC(=O)NC12CC(C(=O)N(CC(=O)Nc3ccc4c(c3)C[C@@]3(C4)C(=O)Nc4ncccc43)Cc3ccccc3CN(C)C(=O)OC(C)(C)C)(C1)C2]

To a solution of compound 39.5 (66 mg, 0.10 mmol) in dimethyl formamide (5 mL) was added acetic acid (12 mg, 0.20 mmol), EDCl (39 mg, 0.20 mmol), HOAt (28 mg, 0.20 mmol) and DIEA (26 mg, 0.20 mmol). The mixture was stirred at 20° C. for 2 h, quenched by adding water (20 mL) and extracted with ethyl acetate (3×20 mL). The combined organic phases were washed with 0.5 M hydrochloric acid (2×20 mL) and saturated aqueous sodium bicarbonate (20 mL) and dried over sodium sulfate. After filtration and concentration, compound 39.6 was obtained as yellow oil and used directly (70 mg, 71% purity).
LCMS rt 0.875 (693 [M+H]⁺).

Example 100: 3-Acetamido-N-[[2-(methylaminomethyl)phenyl]methyl]-N-[2-oxo-2-[[(3R)-2-oxospiro[1H-pyrrolo[2,3-b]pyridine-3,2'-indane]-5'-yl]amino]ethyl]bicyclo[1.1.1]pentane-1-carboxamide 2,2,2-trifluoroacetate 39.7

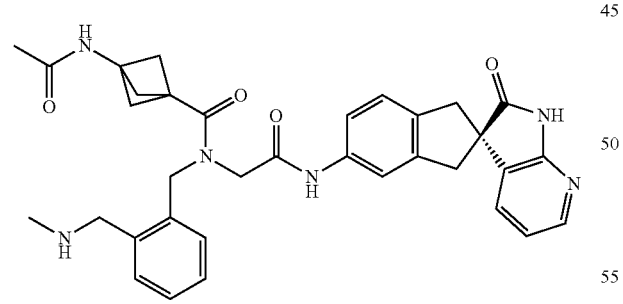

To a solution of compound 39.6 (70 mg, 0.10 mmol) in dichloromethane (5 mL) was added trifluoroacetic acid (0.5 mL). The mixture was stirred at 20° C. for 0.5 h, concentrated under vacuum and the residue purified by prep-HPLC (column: Phenomenex Synergi C18 150×25 mm, 10 μm; mobile phase: [water (0.1% TFA)-acetonitrile]; B %: 10%-40%, 9 min). After lyophilisation, compound 39.7 was obtained as a white solid (11 mg, 16% yield, 99.1% purity).
¹H NMR (CD₃OD, 400 MHz) δ 1.86 (s, 3H), 2.40 (s, 6H), 2.81 (s, 3H), 3.08 (d, 2H), 3.48 (dd, 2H), 4.34 (s, 2H), 4.44 (s, 2H), 4.90 (s, 2H), 6.91-6.93 (m, 1H), 7.16-7.21 (m, 3H), 7.34 (s, 1H), 7.40-7.46 (m, 4H), 8.06 (d, 1H). LCMS rt 0.719 (593 [M+H]⁺).

SCHEME 40

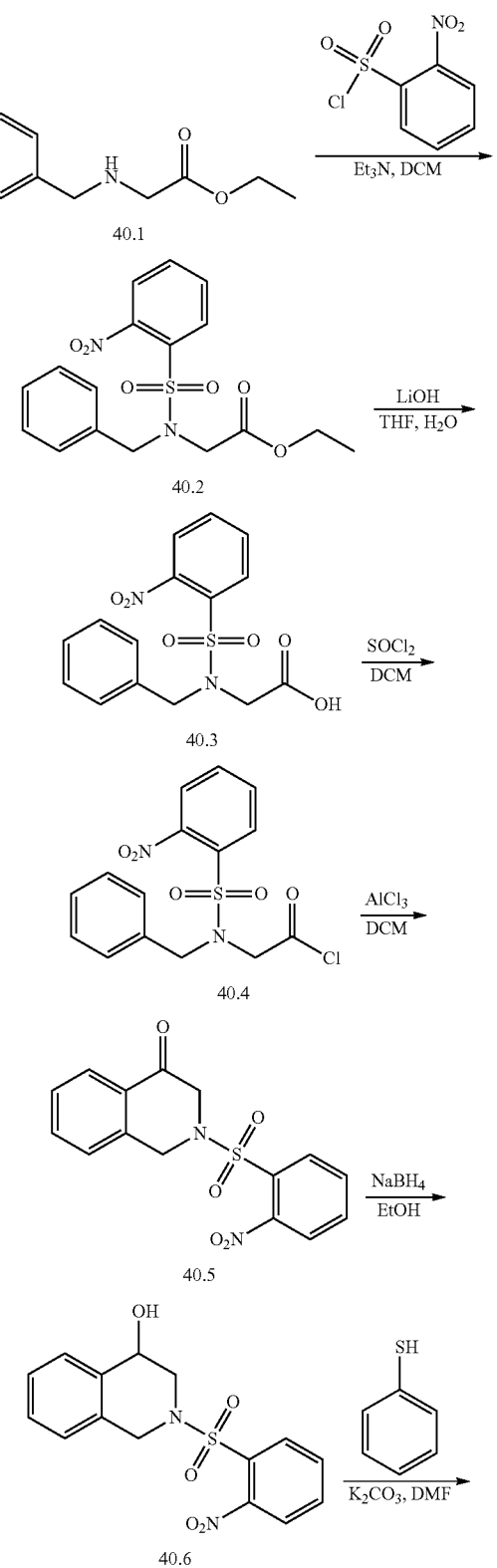

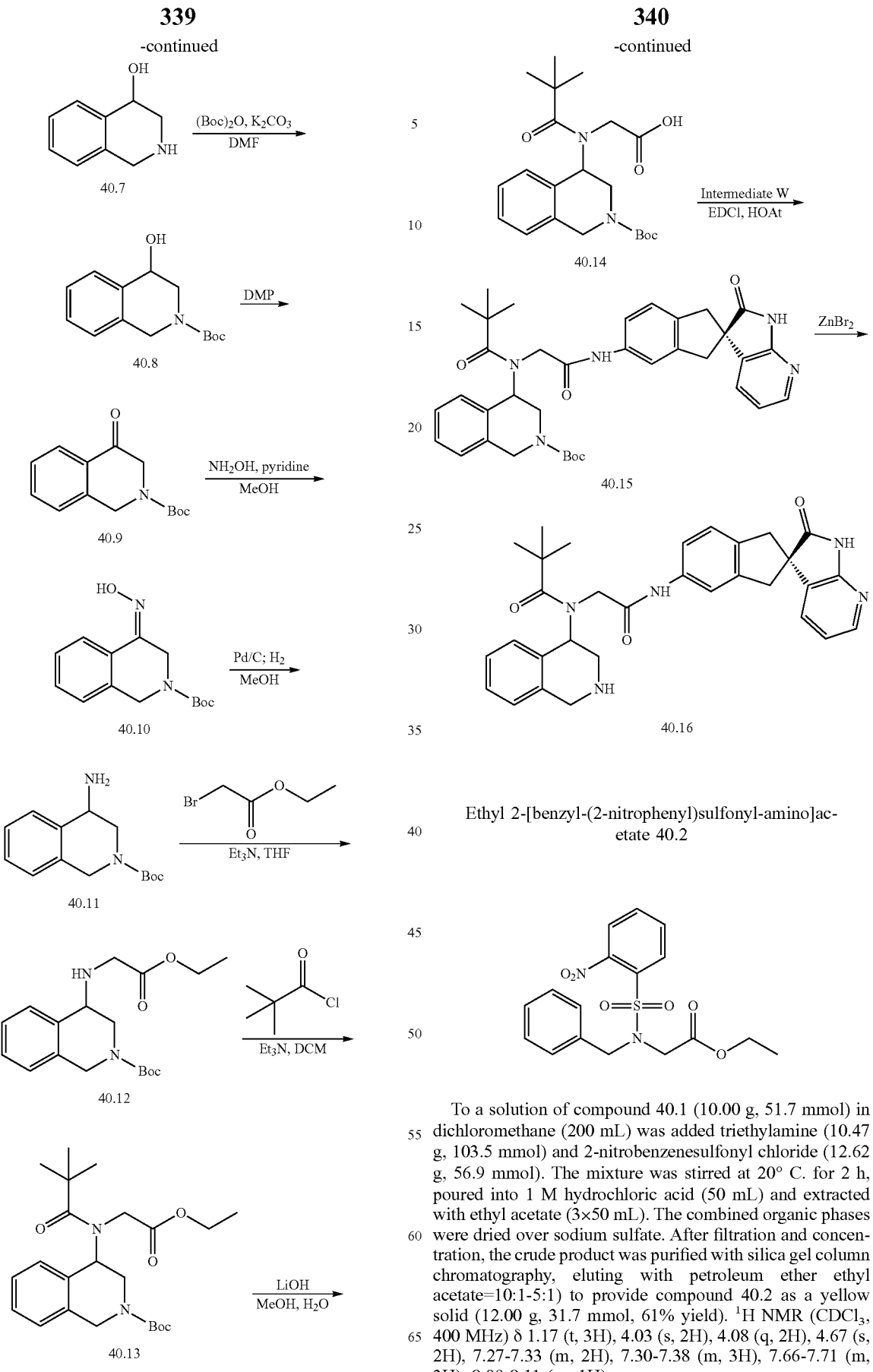

Ethyl 2-[benzyl-(2-nitrophenyl)sulfonyl-amino]acetate 40.2

To a solution of compound 40.1 (10.00 g, 51.7 mmol) in dichloromethane (200 mL) was added triethylamine (10.47 g, 103.5 mmol) and 2-nitrobenzenesulfonyl chloride (12.62 g, 56.9 mmol). The mixture was stirred at 20° C. for 2 h, poured into 1 M hydrochloric acid (50 mL) and extracted with ethyl acetate (3×50 mL). The combined organic phases were dried over sodium sulfate. After filtration and concentration, the crude product was purified with silica gel column chromatography, eluting with petroleum ether ethyl acetate=10:1-5:1) to provide compound 40.2 as a yellow solid (12.00 g, 31.7 mmol, 61% yield). $^1$H NMR (CDCl$_3$, 400 MHz) δ 1.17 (t, 3H), 4.03 (s, 2H), 4.08 (q, 2H), 4.67 (s, 2H), 7.27-7.33 (m, 2H), 7.30-7.38 (m, 3H), 7.66-7.71 (m, 3H), 8.09-8.11 (m, 1H).

2-[Benzyl-(2-nitrophenyl)sulfonyl-amino]acetic Acid 40.3

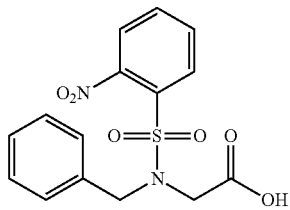 [SMILES: O=C(O)CN(Cc1ccccc1)S(=O)(=O)c1ccccc1[N+](=O)[O-]]

To a solution of compound 40.2 (11.00 g, 29.1 mmol) in tetrahydrofuran (100 mL) and water (15 mL) was added lithium hydroxide (6.10 g, 145 mmol). The mixture was stirred at 20° C. for 2 h, poured into 1 M hydrochloric acid (100 mL) and extracted with ethyl acetate (3×80 mL). The combined organic phases were dried over sodium sulfate. After filtration and concentration, compound 40.3 was obtained as yellow oil (10.00 g, 28.5 mmol, 98% yield).

$^1$H NMR (CDCl$_3$, 400 MHz) δ 4.08 (s, 2H), 4.65 (s, 2H), 7.23-7.25 (m, 2H), 7.31-7.33 (m, 3H), 7.68-7.72 (m, 3H), 8.06-8.08 (m, 2H).

2-[Benzyl-(2-nitrophenyl)sulfonyl-amino]acetyl Chloride 40.4

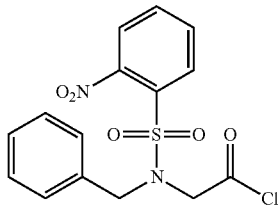 [SMILES: O=C(Cl)CN(Cc1ccccc1)S(=O)(=O)c1ccccc1[N+](=O)[O-]]

To a solution of compound 40.3 (10.0 g, 28.5 mmol) in dichloromethane (50 mL) was added thionyl chloride (30 mL). The mixture was stirred at 80° C. for 1 h and concentrated under vacuum to provide compound 40.4 as yellow oil.

2-(2-Nitrophenyl)sulfonyl-1,3-dihydroisoquinolin-4-one 40.5

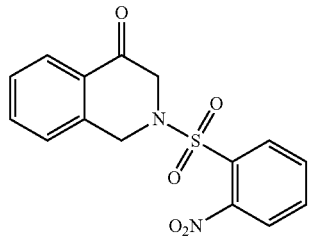 [SMILES: O=C1CN(S(=O)(=O)c2ccccc2[N+](=O)[O-])Cc2ccccc21]

To a solution of compound 40.4 (10.00 g, 27.1 mmol) in dichloromethane (150 mL) was added aluminium chloride (18.08 g, 135 mmol) at −40° C. The mixture was stirred at −20° C. for 1 h, poured into 1N hydrochloride acid (100 mL) and extracted with ethyl acetate (80 m L*3). The combined organic phases were dried over sodium sulfate. After filtration and concentration, the crude product was triturated with methanol (20 mL) to provide compound 40.5 as a yellow solid (8.00 g, 24.1 mmol, 89% yield). $^1$H NMR (DMSO-de, 400 MHz) δ 4.33 (s, 2H), 4.83 (s, 2H), 7.41 (t, 1H), 7.50 (d, 1H), 7.63 (t, 1H), 7.84-7.76 (m, 3H), 7.91 (dd, 1H). 8.06 (dd, 1H).

2-(2-Nitrophenyl)sulfonyl-3,4-dihydro-1H-isoquinolin-4-ol 40.6

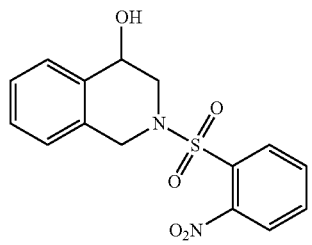 [SMILES: O=[N+]([O-])c1ccccc1S(=O)(=O)N1Cc2ccccc2C(O)C1]

To a solution of compound 40.5 (7.00 g, 21.1 mmol) in ethanol (100 mL) was added sodium borohydride (1.59 g, 42.1 mmol). The mixture was stirred at 25° C. for 3 h, concentrated under vacuum, and the residue dissolved with ethyl acetate (100 mL) and poured into water (50 mL). The organic phase was collected, and the aqueous phase was extracted with ethyl acetate (3×80 mL). The organic phases were combined and dried over sodium sulfate. After filtration and concentration, the crude product was purified with silica gel column, eluting with petroleum ether ethyl acetate=10:1-3:1, to provide compound 40.6 as a yellow solid (6.00 g, 17.9 mmol, 85% yield). $^1$H NMR (CDCl$_3$, 400 MHz) δ 2.30 (d, 1H), 3.53 (dd, 1H), 3.86 (dd, 1H), 4.41 (d, 1H), 4.80-4.77 (m, 2H), 7.15 (t, 1H), 7.27-7.32 (m, 2H), 7.49 (t, 1H), 7.67 (m, 1H), 7.74-7.72 (m, 2H), 8.15-8.13 (m, 1H).

tert-Butyl 4-hydroxy-3,4-dihydro-1H-isoquinoline-2-carboxylate 40.8

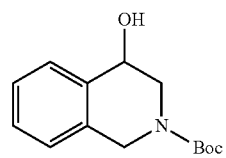

To a solution of compound 40.6 (4.00 g, 12.0 mmol) in dimethyl formamide (40 mL) was added potassium carbonate (2.48 g, 18.0 mmol) followed by benzenethiol (1.98 g, 18.0 mmol) at 20° C. The mixture was stirred at 20° C. for 4 h. TLC (petroleum ether ethyl acetate=1:1) showed starting material was consumed completely and provide compound 40.7. The reaction mixture was used directly for the next step without any further workup. To the reaction mixture was added additional potassium carbonate (1.11 g, 8.04 mmol) and di-tert-butyl dicarbonate (5.27 g, 24.1 mmol). The mixture was stirred at 20° C. for 1 h. TLC (petroleum ether ethyl acetate=2:1) detected a new spot and LCMS showed the starting material was consumed completely. The mixture was poured into water (10 mL) and extracted with ethyl acetate (3×20 mL). The combined organic phase was dried over sodium sulfate. After filtration and concentration, the crude product was purified with silica gel column, diluted with petroleum ether ethyl acetate=10: 1-5:1 to provide compound 40.8 as colourless oil (1.20 g, 4.81 mmol, 60% yield). $^1$H NMR (CDCl$_3$, 400 MHz) δ 1.51 (s, 9H), 3.60 (dd, 1H), 3.93 (dd, 1H), 4.43 (d, 1H), 4.80-4.76 (m, 2H), 7.40-7.16 (m, 1H), 7.30-7.28 (m, 2H), 7.48-7.46 (m, 1H.)

tert-Butyl
4-oxo-1,3-dihydroisoquinoline-2-carboxylate 40.9

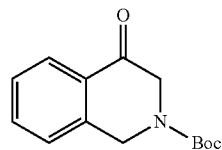 [SMILES: CC(C)(C)OC(=O)N1CC(=O)c2ccccc2C1]

To a solution of compound 40.8 (1.20 g, 4.81 mmol) in dichloromethane (20 mL) was added Dess—Martin Periodinane (DMP) (3.06 g, 7.22 mmol) and sodium bicarbonate (1.21 g, 14.4 mmol). The mixture was stirred at 20° C. for 1 h. The mixture was poured into saturate aqueous solution of sodium sulphite (10 mL) and extracted with ethyl acetate (3×20 mL). The combined organic phase was dried over sodium sulfate. After filtration and concentration, the crude product was purified with silica gel column, eluting with petroleum ether ethyl acetate=20:1-5:1 to provide compound 40.9 as colourless oil (800 mg, 2.62 mmol, 54% yield). $^1$H NMR (CDCl$_3$, 400 MHz) δ 1.46 (s, 9H), 4.34 (s, 2H), 4.78 (s, 2H), 7.31 (d, 1H), 7.41 (t, 1H), 7.58 (td, 1H), 8.07 (d, 1H).

tert-Butyl (4E)-4-hydroxyimino-1,3-dihydroisoquinoline-2-carboxylate 40.10

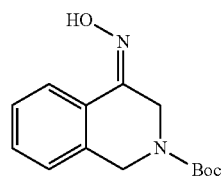 [SMILES: CC(C)(C)OC(=O)N1C/C(=N/O)c2ccccc2C1]

To a solution of compound 40.9 (800 mg, 3.24 mmol) in methanol (10 mL) was added hydroxylamine hydrochloride (450 mg, 6.47 mmol) and pyridine (1.28 g, 16.2 mmol). The mixture was stirred at 70° C. for 2 h, filtered and the filtrate concentrated under vacuum. The residue was purified with silica gel column, eluting with petroleum ether ethyl acetate=20:1 to provide compound 40.10 as a white solid (750 mg, 2.86 mmol, 88% yield). $^1$H NMR (CDCl$_3$, 400 MHz) δ 1.49 (s, 9H), 4.58 (s, 2H), 4.69 (s, 2H), 7.21 (d, 1H), 7.28 (t, 1H), 7.34 (td, 1H), 7.90 (d, 1H), 8.21 (br. s, 1H).

tert-Butyl
4-amino-3,4-dihydro-1H-isoquinoline-2-carboxylate
40.11

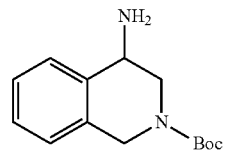 [SMILES: CC(C)(C)OC(=O)N1Cc2ccccc2C(N)C1]

To a solution of compound 40.10 (200 mg, 0.76 mmol) in isopropanol (1 mL) was added 10% Pd/C (100 mg). The mixture was degassed under vacuum, purged three times with hydrogen, and stirred at 25° C. for 16 h under a hydrogen balloon. The mixture was filtered, and the filtrate concentrated under vacuum to provide compound 40.11 (140 mg, crude) as colourless oil. $^1$H NMR (CD$_3$OD, 400 MHz) δ 1.49 (s, 9H), 3.63 (d, 2H), 3.96-3.97 (m, 1H), 4.49 (d, 1H), 4.71 (d, 1H), 7.15-7.34 (m, 1H), 7.22-7.41 (m, 2H), 7.42-7.44 (m, 1H).

tert-Butyl 4-[(2-ethoxy-2-oxo-ethyl)amino]-3,4-dihydro-1H-isoquinoline-2-carboxylate 40.12

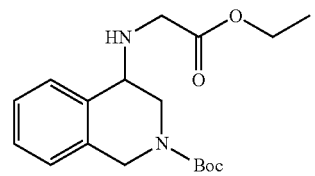 [SMILES: CCOC(=O)CNC1CN(C(=O)OC(C)(C)C)Cc2ccccc21]

To a solution of compound 40.11 (25 mg, 10 1 mmol) in tetrahydrofuran (2 mL) was added triethylamine (20 mg, 0.20 mmol) and ethyl 2-bromoacetate (18.mg, 0.11 mmol). The mixture was stirred at 40° C. for 48 h, concentrated under vacuum and the residue purified by silica gel column chromatography, eluting with petroleum ether ethyl acetate=20:1, to provide compound 40.12 as colourless oil (35 mg, crude). $^1$H NMR (CDCl$_3$, 400 MHz) δ 1.27 (t, 3H), 1.51 (s, 9H), 3.25 (d, 1H), 3.45-3.56 (m, 2H), 3.71-3.85 (m, 1H), 4.09-4.20 (m, 3H), 4.31-4.43 (m, 1H), 4.76-4.96 (m, 1H), 7.14 (d, 1H), 7.21-7.27 (m, 2H), 7.33-7.40 (m, 1H).

tert-Butyl 4-[2,2-dimethylpropanoyl-(2-ethoxy-2-oxo-ethyl)amino]-3,4-dihydro-1H-isoquinoline-2-carboxylate 40.13

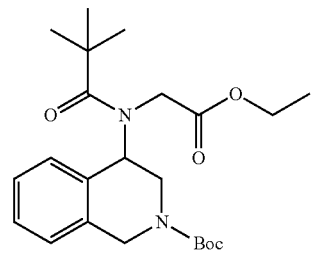 [SMILES: CCOC(=O)CN(C(=O)C(C)(C)C)C1CN(C(=O)OC(C)(C)C)Cc2ccccc21]

To a solution of compound 40.12 (35 mg, 0.10 mmol) in dichloromethane (1 mL) was added triethylamine (26 mg, 0.26 mmol) and 2,2-dimethylpropanoyl chloride (19 mg, 0.16 mmol). The mixture was stirred at 15° C. for 16 h and at 40° C. and for another 3 h. The mixture was concentrated under vacuum. The residue was purified by silica gel column chromatography, eluting with petroleum ether ethyl acetate=10:1, to provide compound 40.13 as yellow oil (35 mg, 88.4% purity). $^1$H NMR (CDCl$_3$, 400 MHz) δ 1.25 (t, 3H), 1.43 (s, 9H), 1.49 (s, 9H), 3.03 (t, 1H), 3.19 (d, 1H), 4.00 (d, 1H), 4.14 (q, 2H), 4.20-4.30 (m, 1H), 4.55-4.58 (m, 1H), 4.92-5.10 (m, 1H), 5.47-5.50 (m, 1H), 7.17 (d, 1H), 7.25-7.30 (m, 3H).

2-[(2-tert-Butoxycarbonyl-3,4-dihydro-1H-isoquinolin-4-yl)-(2,2-dimethylpropanoyl)amino]acetic Acid 40.14

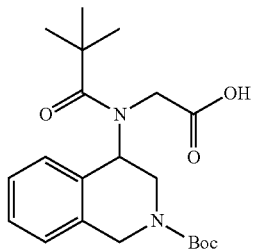 [SMILES: CC(C)(C)OC(=O)N1Cc2ccccc2C(N(CC(=O)O)C(=O)C(C)(C)C)C1]

To a solution of compound 40.13 (35 mg, 0.084 mmol) in methanol (1 mL) and water (0.5 mL) was added sodium hydroxide (10 mg, 0.25 mmol). The mixture was stirred at 40° C. for 1 h, poured into water (10 mL) and extracted with ethyl acetate (10 mL). The organic phase was discarded. The aqueous phase was acidified to pH=5-6 with 1M hydrochloric acid and then extracted with ethyl acetate (3×10 mL). The combined organic phases were dried over sodium sulfate. After filtration and concentration, compound 40.14 (30 mg, 83% yield, 90.9% purity) was obtained as colourless oil. LC-MS: rt 0.912 (MS=413 [M+Na]$^+$).

tert-Butyl 4-[2,2-dimethylpropanoyl-[2-oxo-2-[[(3R)-2-oxospiro[1H-pyrrolo[2,3-b]pyridine-3,2'-indane]-5'-yl]amino]ethyl]amino]-3,4-dihydro-1H-isoquinoline-2-carboxylate 40.15

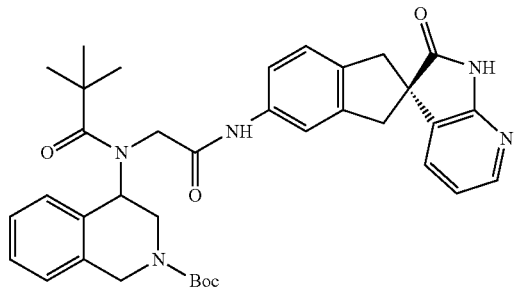 [SMILES: CC(C)(C)OC(=O)N1Cc2ccccc2C(N(CC(=O)Nc2ccc3c(c2)C[C@@]2(C3)C(=O)Nc3ncccc32)C(=O)C(C)(C)C)C1]

To a solution of compound 40.14 (20 mg, 0.051 mmol) in dimethyl formamide (1 mL) was added DIEA (20 mg, 0.15 mmol), EDCl (20 mg, 0.10 mmol) and HOAt (14 mg, 0.10 mmol). Intermediate W (19 mg, 0.077 mmol) was added and the resulting mixture was stirred for 16 h at 20° C. The mixture was poured into 0.5 M hydrochloric acid (10 mL) and extracted with ethyl acetate (3×10 mL). The combined organic phase was dried over sodium sulfate. After filtration and concentration, the crude compound 40.15 was obtained as yellow oil (40 mg, 80% yield, 63.8% purity). LC-MS: rt 0.967 (MS=624.4 [M+H]$^+$).

Example 101: 2,2-Dimethyl-N-[2-oxo-2-[(2-oxospiro[1H-pyrrolo[2,3-b]pyridine-3,2'-indane]-5'-yl)amino]ethyl]-N-(1,2,3,4-tetrahydroisoquinolin-4-yl)propanamide 2,2,2-trifluoroacetate 40.16

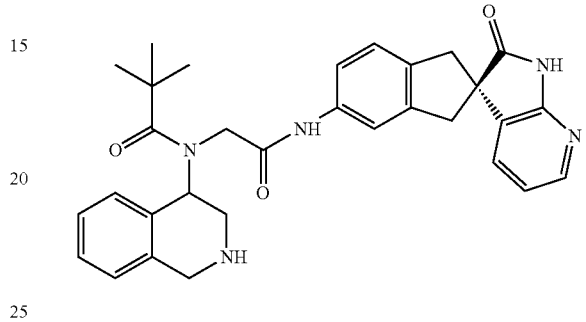

To a solution of compound 40.15 (40 mg, 0.064 mmol) in dichloromethane (1 mL) and methanol (0.1 mL) was added zinc bromide (217 mg, 0.96 mmol). The mixture was stirred at 20° C. for 1 h, poured into 5M aqueous sodium hydroxide (10 mL) and extracted with ethyl acetate (3×10 mL). The combined organic phases were dried over sodium sulfate. After filtration and concentration, the crude product was purified by prep-HPLC (column: Boston Prime C18 150×30 mm, 5 μm; mobile phase: [water (0.1% TFA)-acetonitrile]; B %: 27%-44%, 7 min) to provide compound 40.16 as a white solid (4 mg, 99.1% purity); $^1$H NMR (CDCl$_3$, 400 MHz) δ 1.37 (br. s, 9H), 3.11 (d, 2H), 3.49-3.56 (m, 2H), 3.65-3.94 (m, 2H), 4.83-3.94 (m, 2H), 4.80 (m, 3H), 6.87-6.90 (m, 1H), 7.14 (d, 1H), 7.24 (d, 1H), 7.31-7.60 (m, 6H), 8.06 (d, 1H).

SCHEME 41

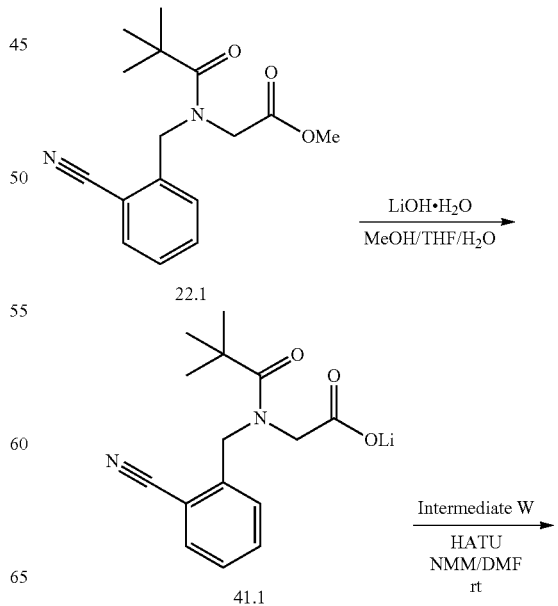

347

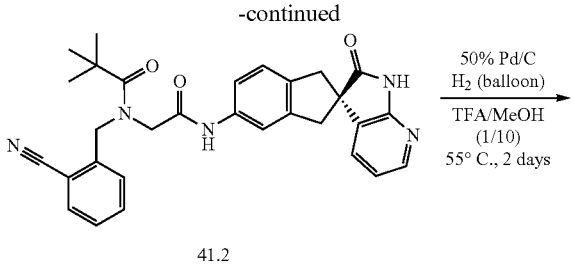

41.2

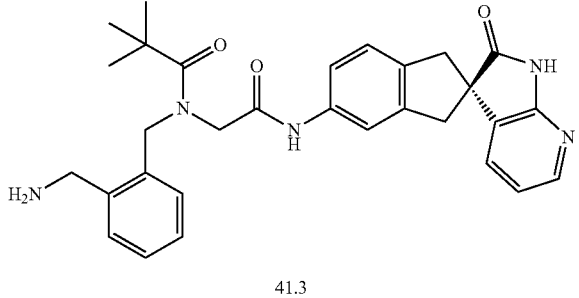

41.3

Lithium 2-(N-(2-cyanobenzyl)pivalamido)acetate
41.1

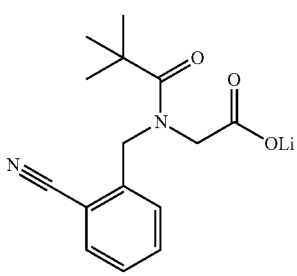

Compound 22.1 (91 mg, 0.31 mmol) was dissolved in a mixture of methanol (2 ml), tetrahydrofuran (2 ml) and water (1 ml) and lithium hydroxide monohydrate (40 mg, 0.91 mmol)) was added. The reaction mixture was stirred for 3 h before volatiles were removed and the crude product was directly purified via flash silica chromatography (100 ml $SiO_2$, 5-25% methanol/dichloromethane) to provide compound 41.1 as a colourless solid (73 mg, 84%). $^1$H NMR ($CD_3OD$, 400 MHz) δ 1.32 (s, 9H), 4.23 (br, 2H), 4.84 (br, 2H), 7.73 (m, br, 2H), 7.67 (m, br, 1H), 7.74 (m, br, 1H). LCMS (275 [M–Li+2H]$^+$).

348

(R)—N-(2-Cyanobenzyl)-N-(2-oxo-2-((2'-oxo-1,1', 2',3-tetrahydrospiro[indene-2,3'-pyrrolo[2,3-b]pyridin]-5-yl)amino)ethyl)pivalamide 41.2

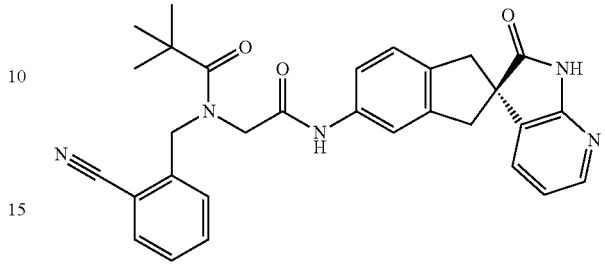

Compound 41.1 (59 mg, 0.21 mmol), Intermediate W (50 mg, 0.20 mmol) and HATU (83 mg, 0.22 mmol) were dissolved in dry N,N-dimethylformamide (2 ml). N-Methylmorpholine (0.1 ml, 9.3 mmol) was added and the mixture was stirred at room temperature for 15 min. The mixture was diluted with ethyl acetate and washed with brine, dried over magnesium sulfate, filtered, and the filtrate evaporated. The residue was purified via flash silica chromatography (5-25% dichloromethane/methanol) to provide compound 41.2 (82 mg, 84%) as a colourless glass. LCMS (508 [M+H]$^+$).

Example 102: (R)—N-(2-(Aminomethyl)benzyl)-N-(2-oxo-2-((2'-oxo-1,1',2',3-tetrahydrospiro[indene-2, 3'-pyrrolo[2,3-b]pyridin]-5-yl)amino)ethyl)pivalamide 2,2,2-trifluoroacetate 41.3

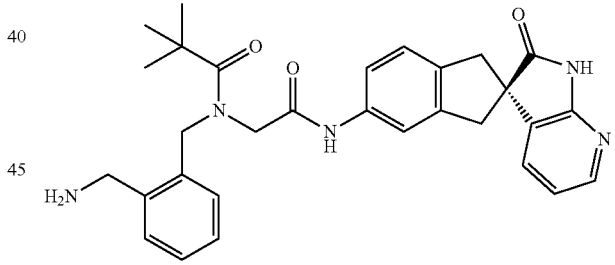

Compound 41.2 (16 mg, 0.03 mmol) was dissolved in trifluoroacetic acid (0.5 ml) and methanol (2 ml), and palladium-on-carbon (8 mg) was added. A balloon of hydrogen was fitted to the reaction flask and the reaction mixture was stirred at 55° C. under an atmosphere of hydrogen for 2 days. Ethyl acetate (~5 ml) was added to the mixture and the resulting suspension filtered. Volatiles were removed, and the crude material was purified via HPLC (HP C18, ID 22 mm, length 150 mm, flow 16 ml/min: 5-50% acetonitrile/water 0.1% TFA over 20 min) then freeze-dried to provide the compound 41.3 as white solid (8.2 mg, 51%).

$^1$H NMR ($CD_3OD$, 400 MHz) δ 1.34 (s, 9H), 3.10 (d, 2H), 3.53 (m, 2H), 4.26 (s, 2H), 4.44 (s, br, 2H), 4.85 (s, br, 2H), 6.92 (dd, 1H), 7.18 (dd, 1H), 7.25 (d, 1H), 7.36 (m, 1H), 7.45 (m, 4H), 7.52 (br, 1H), 8.08 (dd, 1H); $^{19}$F NMR ($CD_3OD$, 400 MHz) δ –77.3; LCMS (512 [M+H]$^+$), 98% pure.

349
Synthesis of Intermediate Y

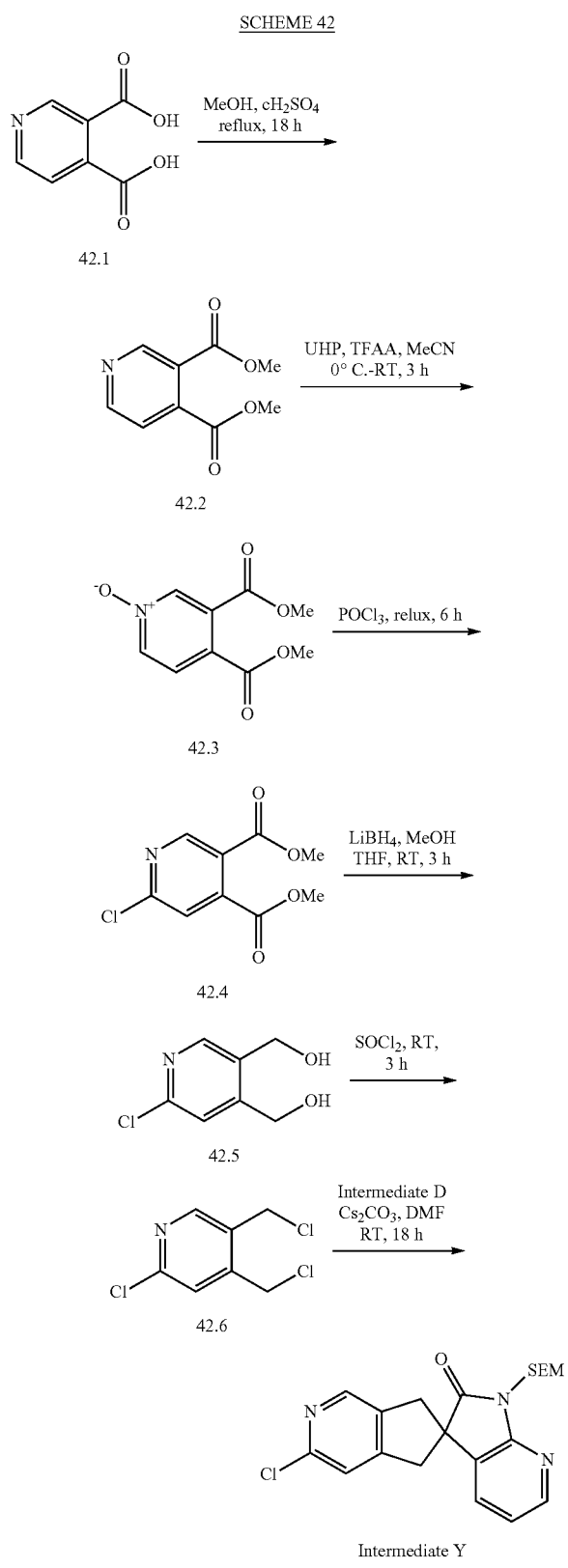

SCHEME 42

350
Dimethyl pyridine-3,4-dicarboxylate 42.2

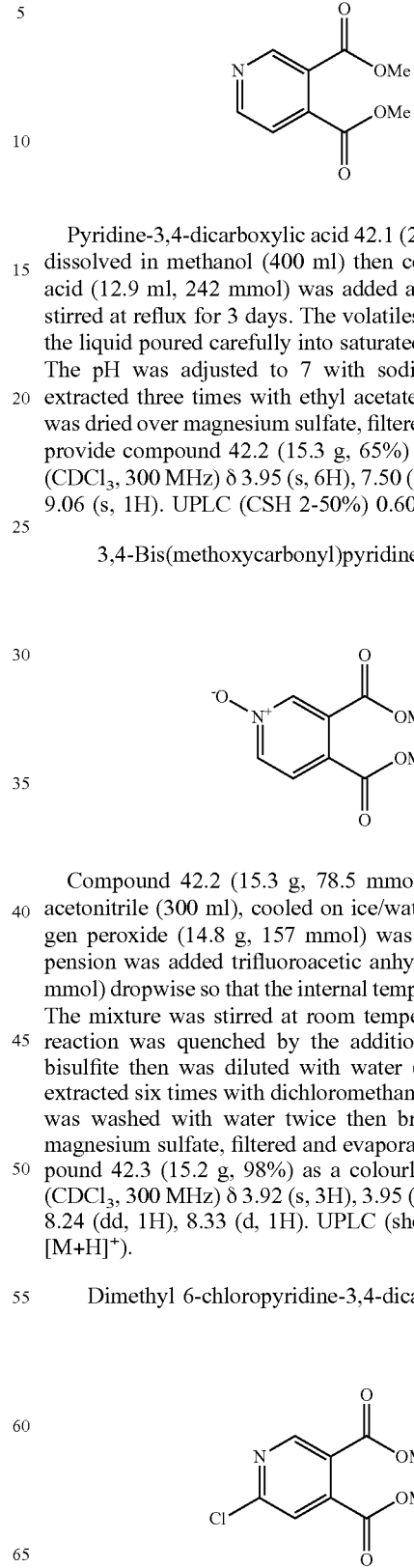

Pyridine-3,4-dicarboxylic acid 42.1 (20 g, 121 mmol) was dissolved in methanol (400 ml) then concentrated sulfuric acid (12.9 ml, 242 mmol) was added and the mixture was stirred at reflux for 3 days. The volatiles were removed and the liquid poured carefully into saturated sodium carbonate. The pH was adjusted to 7 with sodium carbonate then extracted three times with ethyl acetate. The organic layer was dried over magnesium sulfate, filtered and evaporated to provide compound 42.2 (15.3 g, 65%) as an oil. $^1$H NMR (CDCl$_3$, 300 MHz) δ 3.95 (s, 6H), 7.50 (d, 1H), 8.83 (d, 1H), 9.06 (s, 1H). UPLC (CSH 2-50%) 0.60 (196 [M+H]$^+$).

3,4-Bis(methoxycarbonyl)pyridine 1-oxide 42.3

Compound 42.2 (15.3 g, 78.5 mmol) was dissolved in acetonitrile (300 ml), cooled on ice/water then urea hydrogen peroxide (14.8 g, 157 mmol) was added. To the suspension was added trifluoroacetic anhydride (22.1 ml, 157 mmol) dropwise so that the internal temperature was <10° C. The mixture was stirred at room temperature for 3 h. The reaction was quenched by the addition of sodium metabisulfite then was diluted with water (800 ml). This was extracted six times with dichloromethane. The organic layer was washed with water twice then brine and dried over magnesium sulfate, filtered and evaporated to provide compound 42.3 (15.2 g, 98%) as a colourless solid. $^1$H NMR (CDCl$_3$, 300 MHz) δ 3.92 (s, 3H), 3.95 (s, 3H), 7.69 (d, 1H), 8.24 (dd, 1H), 8.33 (d, 1H). UPLC (short basic) 0.37 (212 [M+H]$^+$).

Dimethyl 6-chloropyridine-3,4-dicarboxylate 42.4

Compound 42.3 (15.2 g, 72.0 mmol) was suspended in phosphorus oxychloride (72 ml) then the mixture was stirred at reflux (105° C.) for 6 h and left at room temperature for 18 h. The volatiles were removed, the residue diluted with saturated sodium carbonate and extracted twice with ethyl acetate. The organic layer was dried over magnesium sulfate, filtered and evaporated. The residue was purified via flash silica chromatography (15-20% EtOAc in heptane) to provide compound 42.4 (4.56 g, 28%) as a brown oil. $^1$H NMR (CDCl$_3$, 400 MHz) δ 3.93 (s, 3H), 3.94 (s, 3H), 7.50 (s, 1H), 8.85 (s, 1H). UPLC (short basic) 0.72 (no m/z), 92%.

(6-Chloropyridine-3,4-diyl)dimethanol 42.5

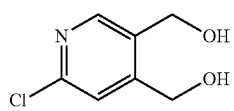

Compound 42.4 (4.56 g, 19.9 mmol) was dissolved in tetrahydrofuran (85 ml) and methanol (1.7 ml) and cooled on ice/water. Lithium borohydride (1.08 g, 49.6 mmol) was added then the mixture was stirred at room temperature for 3 h. The mixture was poured into saturated sodium bicarbonate and extracted four times with ethyl acetate. The organic layer was dried over sodium sulfate, filtered and evaporated. The residue was purified via flash silica chromatography (15-20% EtOAc in heptane) to provide compound 42.5 (3.1 g, 90%) as a yellow oil. $^1$H NMR (CD$_3$OD, 300 MHz) δ 4.61 (s, 2H), 4.74 (s, 2H), 7.56 (s, 1H), 8.26 (s, 1H). UPLC (short basic) 0.34 (174, 176 [M+H]$^+$), 91%.

2-Chloro-4,5-bis(chloromethyl)pyridine 42.6

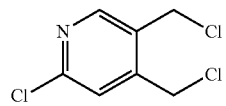 [SMILES: ClCc1cnc(Cl)cc1CCl]

Compound 42.5 (3.1 g, 17.9 mmol) was suspended in thionyl chloride (16 ml) then the mixture was stirred at RT for 3 h. The mixture was poured carefully into ice/water then neutralised with saturated sodium carbonate. This was extracted twice with ethyl acetate. The organic layer was dried over sodium sulfate, filtered and evaporated to provide compound 42.6 (2.53 g, 67%) as a yellow oil. $^1$H NMR (CDCl$_3$, 300 MHz) δ 4.68 (s, 4H), 7.45 (s, 1H), 8.37 (s, 1H).

3-Chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one Intermediate Y

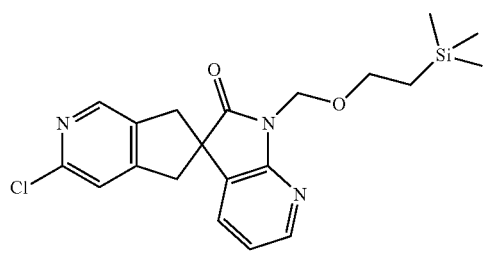 [SMILES: C[Si](C)(C)CCOCN1C(=O)C2(Cc3cnc(Cl)cc3C2)c2cccnc21]

Compound 42.6 (2.53 g, 12.0 mmol) and Intermediate D (3.17 g, 12.0 mmol) were dissolved in N,N-dimethylformamide (94 ml), caesium carbonate (13.7 g, 42.1 mmol) was added then the mixture was stirred at room temperature for 18 h. The mixture was filtered through Celite washing with ethyl acetate. The filtrate was washed three times with water and twice with brine, dried over magnesium sulfate, filtered and evaporated. The residue was purified via flash silica chromatography (8:2-7:3 heptane/EtOAc) and again (1:1 heptane/MTBE) to provide Intermediate Y (1.82 g, 38%) as a pale yellow oil. $^1$H NMR (CDCl$_3$, 300 MHz) δ −0.01 (s, 9H), 0.99 (m, 2H), 3.10 (dd, 2H), 3.62 (dd, 2H), 3.70 (m, 2H), 5.29 (s, 2H), 6.90 (dd, 1H), 7.10 (d, 1H), 7.29 (s, 1H), 8.24 (d, 1H), 8.31 (s, 1H). UPLC (short basic) 1.07 (402 [M+H]$^+$), 87%.

Synthesis of Intermediate Z

SCHEME 43

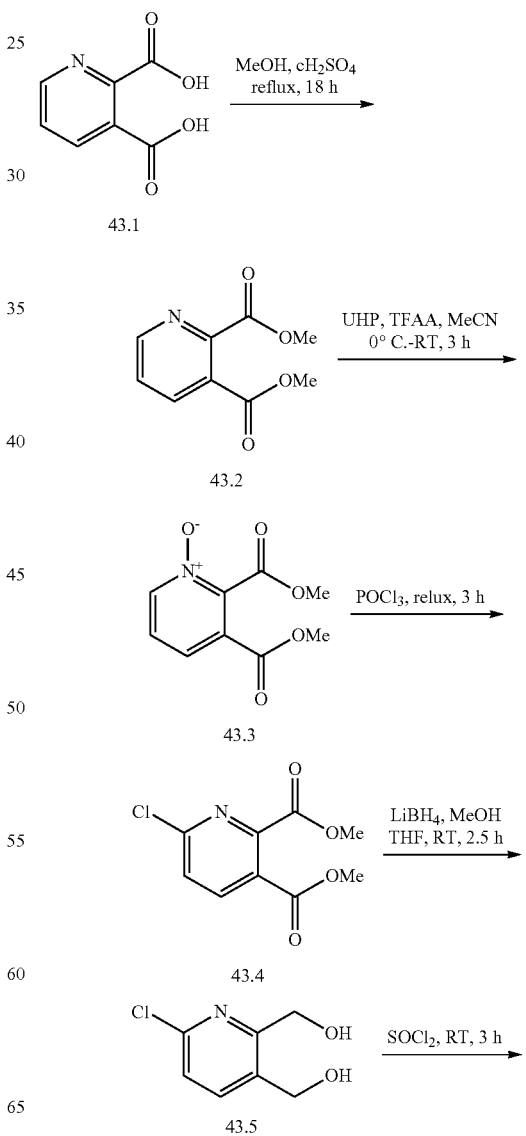

-continued

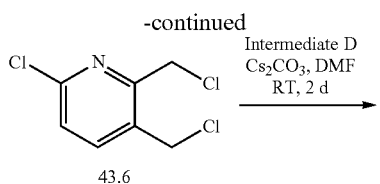

43.6

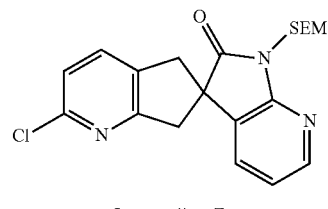

Intermediate Z

Dimethyl pyridine-2,3-dicarboxylate 43.2

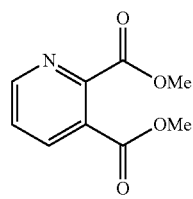 [SMILES: COC(=O)c1cccnc1C(=O)OC]

Pyridine-2,3-dicarboxylic acid 43.1 (20 g, 121 mmol) was dissolved in methanol (400 ml) then concentrated sulfuric acid (12.9 ml, 242 mmol) was added and the mixture was stirred at reflux for 18 h. The volatiles were removed, and the liquid poured carefully into saturated sodium carbonate. The pH was adjusted to 7 with sodium carbonate then extracted three times with ethyl acetate. The organic layer was dried over magnesium sulfate, filtered and evaporated to provide compound 43.2 (19.5 g, 83%) as an oil. $^1$H NMR (CDCl$_3$, 300 MHz) δ 3.96 (s, 3H), 4.04 (s, 3H), 7.50 (dd, 1H), 8.17 (d, 1H), 8.76 (d, 1H). UPLC (CSH 2-50%) 0.57 (196 [M+H]$^+$) 99%.

2,3-Bis(methoxycarbonyl)pyridine 1-oxide 43.3

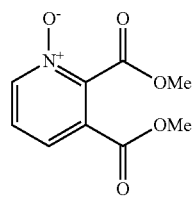 [SMILES: COC(=O)c1ccc[n+]([O-])c1C(=O)OC]

Compound 43.2 (19.5 g, 100 mmol) was dissolved in acetonitrile (385 ml), cooled on ice/water then urea hydrogen peroxide (18.8 g, 200 mmol) was added. To the suspension was added trifluoroacetic anhydride (28.2 ml, 200 mmol) dropwise so that the internal temperature was <10° C. The mixture was stirred at room temperature for 3 h. The reaction was quenched by the addition of sodium meta-bisulfite and diluted with water (800 ml). This was extracted six times with dichloromethane. The organic layer was washed with water twice then brine and dried over magnesium sulfate, filtered and evaporated. The residue was dissolved in dichloromethane and washed twice with water then brine, dried over magnesium sulfate, filtered and evaporated to provide compound 43.3 (11.6 g, 55%) as colourless solid. $^1$H NMR (CDCl$_3$, 300 MHz) δ 3.94 (s, 3H), 4.06 (s, 3H), 7.39 (dd, 1H), 7.86 (dd, 1H), 8.34 (d, 1H). UPLC (short basic) 0.36 (212 [M+H]$^+$) 99%.

Dimethyl 6-chloropyridine-2,3-dicarboxylate 43.4

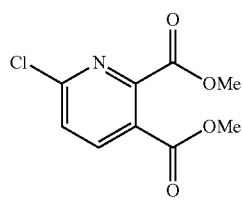 [SMILES: COC(=O)c1ccc(Cl)nc1C(=O)OC]

Compound 43.3 (11.6 g, 54.9 mmol) was suspended in phosphorus oxychloride (55 ml) then the mixture was stirred at reflux (105° C.) for 3 h. The volatiles were removed, the residue diluted with saturated sodium carbonate and extracted twice with ethyl acetate. The organic layer was dried over magnesium sulfate, filtered and evaporated. The residue was purified via flash silica chromatography (dichloromethane) to provide compound 43.4 (7.72 g, 62%) as a brown oil. $^1$H NMR (CDCl$_3$, 300 MHz) δ 3.93 (s, 3H), 3.99 (s, 3H), 7.51 (d, 1H), 8.16 (d, 1H). UPLC (short basic) 0.68 (no m/z), 99%.

(6-Chloropyridine-2,3-diyl)dimethanol 43.5

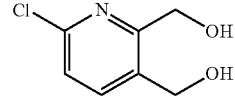 [SMILES: OCc1ccc(Cl)nc1CO]

Compound 43.4 (7.72 g, 33.8 mmol) was dissolved in tetrahydrofuran (144 ml) and methanol (2.8 ml) and cooled on ice/water. Lithium borohydride (1.84 g, 84.6 mmol) was added then the mixture was stirred at room temperature for 2.5 h. The mixture was poured into saturated sodium bicarbonate and extracted six times with ethyl acetate. The organic layer was dried over sodium sulfate, filtered and evaporated to provide compound 43.5 (5.54 g, 94%) as a yellow oil. $^1$H NMR (CD$_3$OD, 400 MHz) δ 4.68 (s, 2H), 4.71 (s, 2H), 7.35 (d, 1H), 7.85 (d, 1H). UPLC (short basic) 0.36 (174, 176 [M+H]$^+$), 93%.

6-Chloro-2,3-bis(chloromethyl)pyridine 43.6

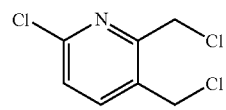

Compound 43.5 (5.54 g, 31.9 mmol) was suspended in thionyl chloride (78 ml) then the mixture was stirred at RT for 3 h. The mixture was poured carefully into ice/water then neutralised with saturated sodium carbonate. This was extracted twice with ethyl acetate. The organic layer was dried over sodium sulfate, filtered and evaporated to provide compound 43.6 (4.87 g, 73%) as a yellow oil. ¹H NMR (CDCl₃, 300 MHz) δ 4.72 (s, 2H), 4.75 (s, 2H), 7.33 (d, 1H), 7.72 (d, 1H).

2-Chloro-1'-((2-(trimethylsilyl)ethoxy)methyl)-5,7-dihydrospiro[cyclopenta[b]pyridine-6,3'-pyrrolo[2,3-b]pyridin]-2'(1'H)-one Intermediate Z

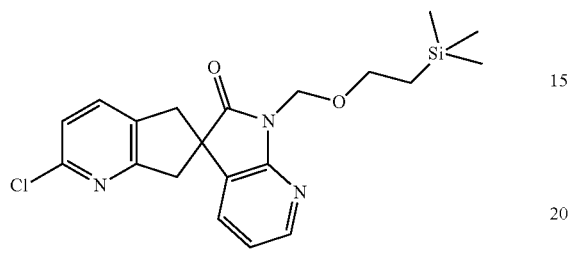

Compound 43.6 (4.87 g, 23.4 mmol) and Intermediate D (6.11 g, 23.1 mmol) were dissolved in N,N-dimethylformamide (180 ml), caesium carbonate (26.4 g, 81.0 mmol) was added then the mixture was stirred at RT for 2 days. The mixture was filtered through Celite washing with ethyl acetate. The filtrate was washed three times with water and twice with brine, dried over magnesium sulfate, filtered and evaporated. The residue was purified via flash silica chromatography (8:2-7:3 heptane/EtOAc) and again (1:1 heptane/MTBE) to provide Intermediate Z (2.35 g, 26%) as a pale yellow oil. ¹H NMR (CDCl₃, 300 MHz) δ -0.03 (s, 9H), 0.99 (m, 2H), 3.14 (dd, 2H), 3.61 (m, 2H), 3.71 (m, 2H), 5.29 (s, 2H), 6.91 (dd, 1H), 7.17 (dd, 1H), 7.22 (d, 1H), 7.54 (d, 1H), 8.24 (dd, 1H). UPLC (short basic) 1.09 (402 [M+H]⁺), 82%.

SCHEME 44

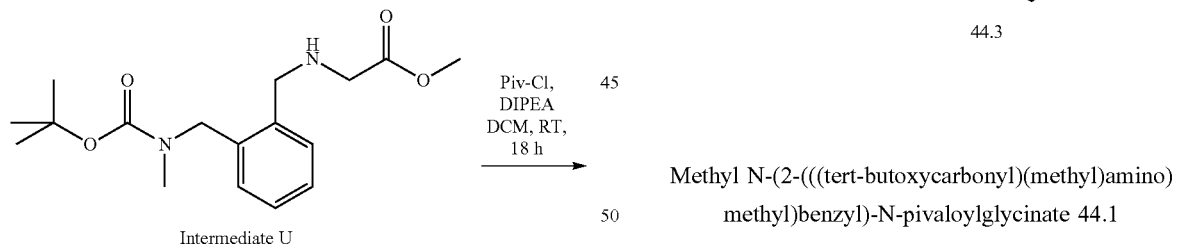

Intermediate U

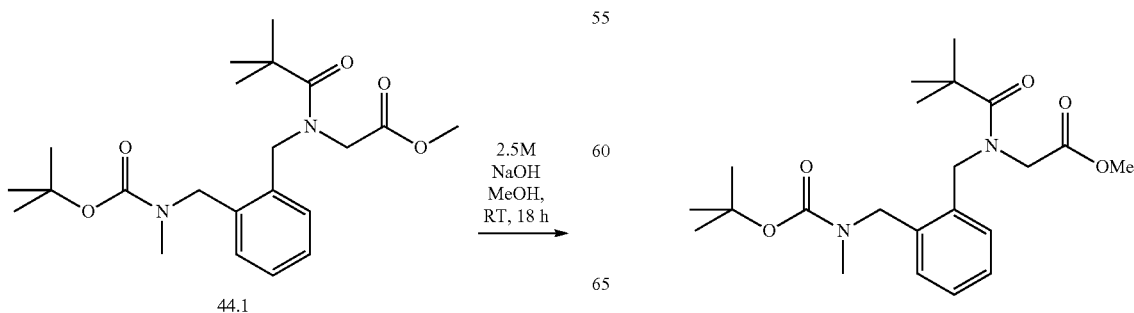

44.1

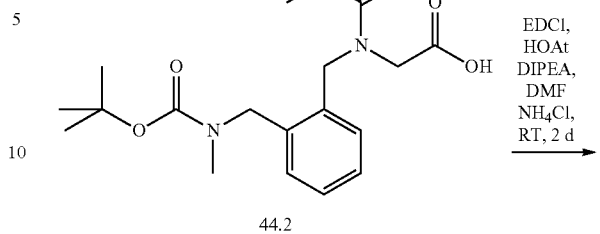

44.2

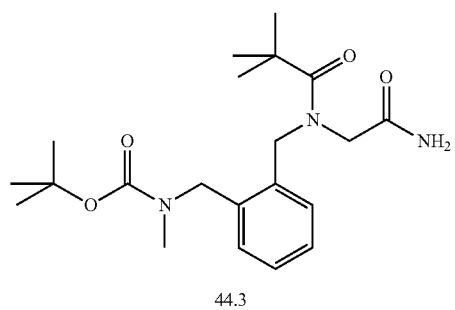

44.3

Methyl N-(2-(((tert-butoxycarbonyl)(methyl)amino)methyl)benzyl)-N-pivaloylglycinate 44.1

Intermediate U (670 mg, 2.08 mmol) was dissolved in dichloromethane (14 ml), N,N-diisopropylethylamine (1.1 ml, 6.24 mmol) was added followed by pivaloyl chloride (0.28 ml, 2.29 mmol) and the mixture was stirred at room temperature for 18 h. The mixture was washed twice with sodium bicarbonate. The organic layer was dried over magnesium sulfate, filtered and evaporated. The residue was purified via normal phase chromatography (80 g ZIP silica, heptane 1:0-8:2 ethyl acetate) to provide compound 44.1 (405 mg, 48%) as a colourless solid. $^1$H NMR (CDCl$_3$, 300 MHz) δ 1.28 (s, 9H), 1.47 (s, 9H), 2.77 (s, 3H), 3.72 (s, 3H), 3.94 (br s, 2H), 4.43 (s, 2H), 4.80 (s, 2H), 7.19 (m, 2H), 7.26 (m, 2H). UPLC (short basic) 1.03 (307 [M−Boc+H]$^+$) 96%.

N-(2-(((tert-Butoxycarbonyl)(methyl)amino)methyl) benzyl)-N-pivaloylglycine 44.2

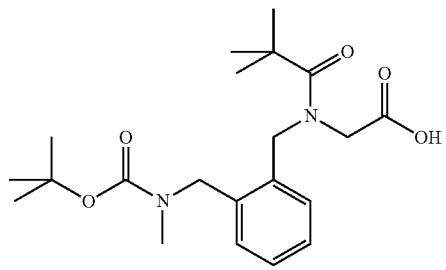 [SMILES: CN(Cc1ccccc1CN(CC(=O)O)C(=O)C(C)(C)C)C(=O)OC(C)(C)C]

Compound 44.1 (405 mg, 0.998 mmol) was dissolved in methanol (14 ml) then 2.5 M sodium hydroxide (0.6 ml, 1.50 mmol) was added and the mixture was stirred at room temperature for 18 h. The volatiles were removed then diluted with water and washed with dichloromethane. The aqueous was taken to pH 4 with 2M HCl and extracted three times with ethyl acetate. The organic layer was dried over magnesium sulfate, filtered and evaporated to provide compound 44.2 (303 mg, 77%) as a colourless solid. $^1$H NMR (CD$_3$OD, 300 MHz) δ 1.26 (s, 9H), 1.46 (s, 9H), 2.76 (s, 3H), 3.95 (m, 2H), 4.47 (s, 2H), 4.82 (m, 2H), 7.17 (m, 2H), 7.31 (m, 2H). UPLC (short basic) 0.58 (391 [M−H]$^−$) 99%.

tert-Butyl (2-((N-(2-amino-2-oxoethyl)pivalamido) methyl)benzyl)(methyl)carbamate 44.3

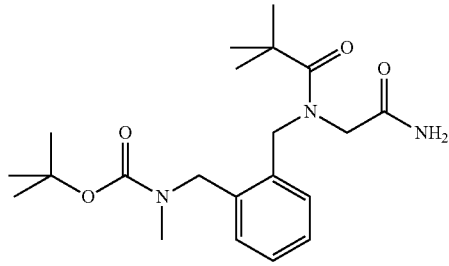 [SMILES: CN(Cc1ccccc1CN(CC(N)=O)C(=O)C(C)(C)C)C(=O)OC(C)(C)C]

Compound 44.2 (364 mg, 0.929 mmol) was dissolved in N,N-dimethylformamide (12 ml) then EDCl.HCl (232 mg, 1.21 mmol), HOAt (165 mg, 1.21 mmol), ammonium chloride (497 mg, 9.29 mmol) and N,N-diisopropylethylamine (2.1 ml, 12.1 mmol) were added and the mixture was stirred at RT for 18 h. Further EDCl.HCl (232 mg, 1.21 mmol), HOAt (165 mg, 1.21 mmol), ammonium chloride (497 mg, 9.29 mmol) and N,N-diisopropylethylamine (2.1 ml, 12.1 mmol) were added and the mixture was stirred at room temperature for 24 h. The mixture was poured into saturated sodium bicarbonate, then extracted twice with ethyl acetate. The organic layer was washed twice with sodium bicarbonate, water and brine, dried over magnesium sulfate, filtered and evaporated to provide compound 44.3 (248 mg, 68%) as a colourless solid. $^1$H NMR (CD$_3$OD, 300 MHz) δ 1.28 (s, 9H), 1.46 (s, 9H), 2.78 (s, 3H), 3.92 (s, 2H), 4.44 (s, 2H), 4.83 (s, 2H), 5.36 (br s, 1H), 6.17 (br s 1H), 7.11 (m, 1H), 7.17 (m, 1H), 7.28 (m, 2H). UPLC (short basic) 0.83 (390 [M−H]$^−$) 93%.

SCHEME 45

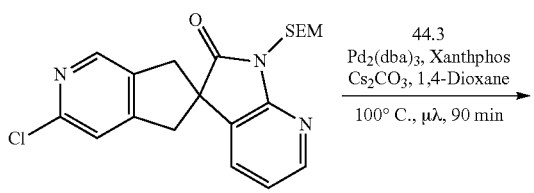

Intermediate Y

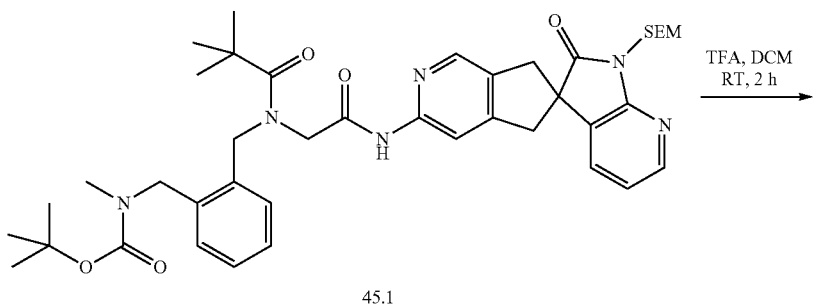

45.1

-continued

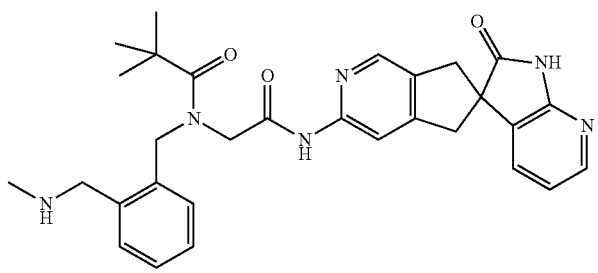

45.2 tert-Butyl methyl(2-((N-(2-oxo-2-((2'-oxo-1'-((2-(trimethylsilyl)ethoxy)methyl)-1',2',5,7-tetrahydrospiro[cyclopenta[c]pyridine-6,3'-pyrrolo[2,3-b]pyridin]-3-yl)amino)ethyl)pivalamido)methyl)benzyl)carbamate 45.1

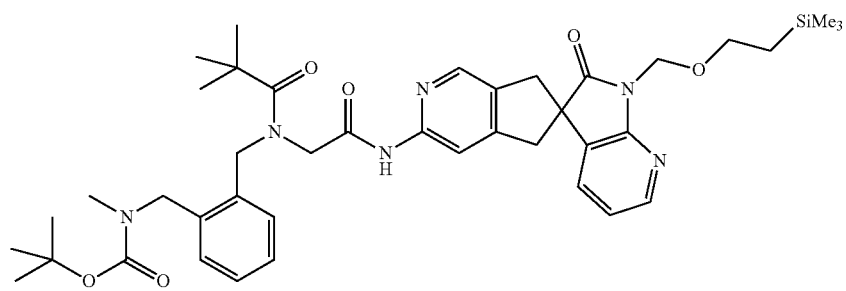 [SMILES: CN(Cc1ccccc1CN(CC(=O)Nc1cc2c(cn1)CC1(C2)C(=O)N(COCC[Si](C)(C)C)c2ncccc21)C(=O)C(C)(C)C)C(=O)OC(C)(C)C]

Compound 44.3 (127 mg, 0.317 mmol) and Intermediate Y (124 mg, 0.317 mmol) were dissolved in dry degassed 1,4-dioxane (5.5 ml) then caesium carbonate (516 mg, 1.58 mmol), Xanthphos (7.3 mg, 0.027 mmol) and tris(dibenzylideneacetone)dipalladium(0) (6 mg, 0.006 mmol) were added and the mixture was purged with argon for 1 min. The reaction vial was heated at 100° C. under microwave irradiation for 90 min. The mixture was poured into water then extracted twice with ethyl acetate. The organic layer was washed three times with water then brine, dried over magnesium sulfate, filtered and evaporated. The residue was purified via normal phase chromatography (10 g, ZIP silica, 20-50% EtOAc in heptane) to provide compound 45.1 (103 mg, 43%) as a colourless solid. $^1$H NMR (CD$_3$OD, 300 MHz) δ −0.01 (s, 9H), 0.99 (m, 2H), 1.33 (s, 9H), 1.44 (s, 9H), 2.79 (s, 3H), 3.05 (dd, 2H), 3.61 (dd, 2H), 3.71 (m, 2H), 4.08 (br s, 2H), 4.45 (s, 2H), 4.90 (s, 2H), 5.30 (s, 2H), 6.86 (dd, 1H), 7.07 (dd, 1H), 7.18 (m, 2H), 7.30 (m, 2H), 8.14 (s, 1H), 8.16 (s, 1H), 8.22 (dd, 1H), 8.51 (br s, 1H). UPLC (short basic) 1.24 (757 [M+H]$^+$) 95%.

Example 103: N-(2-((Methylamino)methyl)benzyl)-N-(2-oxo-2-((2'-oxo-1',2',5,7-tetrahydrospiro[cyclopenta[c] pyridine-6,3'-pyrrolo[2,3-b]pyridin]-3-yl)amino)ethyl)pivalamide 45.2

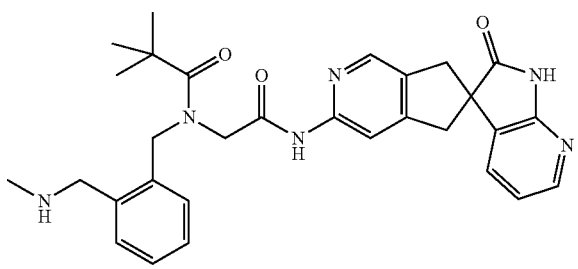 [SMILES: CNCc1ccccc1CN(CC(=O)Nc1cc2c(cn1)CC1(C2)C(=O)Nc2ncccc21)C(=O)C(C)(C)C]

Compound 45.1 (34 mg, 0.045 mmol) was dissolved in dichloromethane (3.2 ml) then trifluoroacetic acid (0.35 ml) was added and the mixture stirred at room temperature for 2 h. The mixture was poured into saturated sodium carbonate then extracted twice with dichloromethane. The organic layer was dried over magnesium sulfate, filtered and evaporated. The residue was purified via flash silica chromatography (2 g, EtOAc then 5% MeOH in dichloromethane, then 10% MeOH with ammonia in dichloromethane) followed by triturated in methanol to provide compound 45.2 (9.6 mg, 40%) as a colourless solid. ¹H NMR (DMSO-d6, 300 MHz) δ 1.15, 1.21 (2 s, 9H), 2.03, 2.17, 2.31 (3 s, 3H), 3.10 (m, 2H), 3.33 (m, 2H), 3.70 (s, 2H), 4.04 (m, 2H), 4.58 (m, 1H), 4.85 (br s, 2H), 6.85 (m, 1H), 7.25 (m, 5H), 8.00 (m, 3H), 10.25 (s, 1H), 10.90 (br s, 1H). UPLC (long acidic) 0.90 (527 [M+H]⁺) 94%.

added and the mixture was purged with argon for 1 min. The reaction vial was heated at 100° C. under microwave irradiation for 90 min. The mixture was poured into water then extracted twice with ethyl acetate. The organic layer was washed three times with water then brine, dried over magnesium sulfate, filtered and evaporated. The residue was

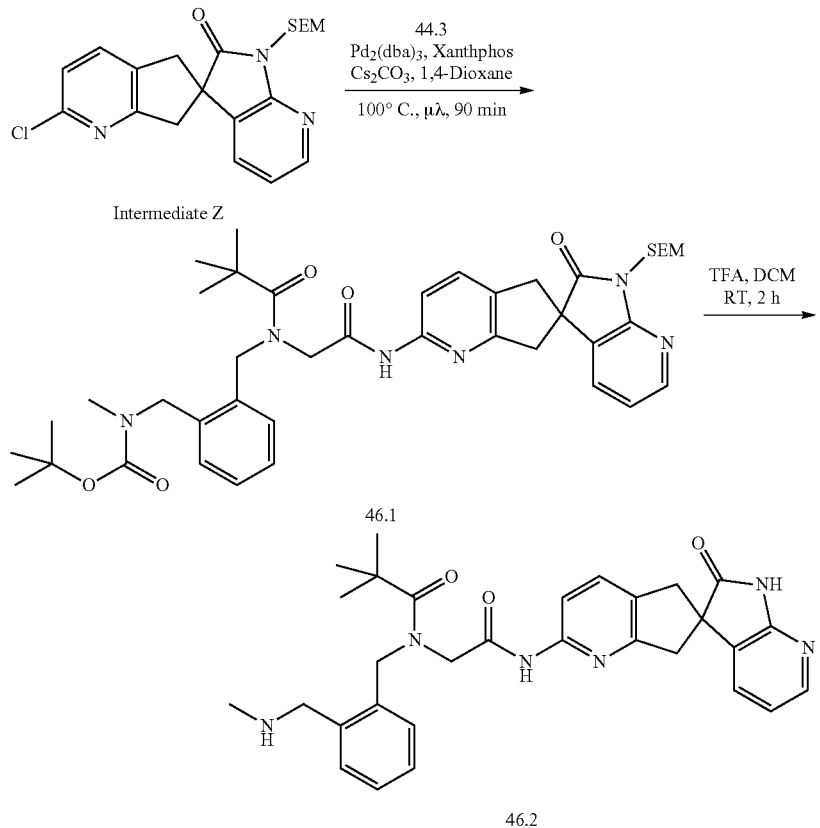

SCHEME 46 tert-Butyl methyl(2-((N-(2-oxo-2-((2'-oxo-1'-((2-(trimethylsilyl)ethoxy)methyl)-1',2',5,7-tetrahydrospiro[cyclopenta[b]pyridine-6,3'-pyrrolo[2,3-b]pyridin]-2-yl)amino)ethyl)pivalamido)methyl)benzyl)carbamate 46.1 purified via normal phase chromatography (10 g, ZIP silica, 20-40% EtOAc in heptane) to provide compound 46.1 (82 mg, 43%) as a colourless solid. ¹H NMR (CD₃OD, 300 MHz) δ −0.01 (s, 9H), 0.98 (m, 2H), 1.32 (s, 9H), 1.45 (s, 9H), 2.79 (s, 3H), 3.05 (d, 2H), 3.61 (t, 2H), 3.71 (m, 2H),

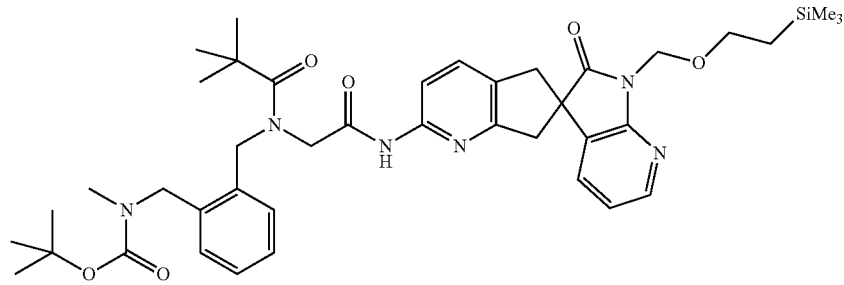 [SMILES: CN(Cc1ccccc1CN(CC(=O)Nc1ccc2c(n1)CC1(C2)C(=O)N(COCC[Si](C)(C)C)c2ncccc21)C(=O)C(C)(C)C)C(=O)OC(C)(C)C]

Intermediate Z (127 mg, 0.317 mmol) and compound 44.3 (124 mg, 0.317 mmol) were dissolved in dry degassed 1,4-dioxane (5.5 ml) then caesium carbonate (516 mg, 1.58 mmol), Xanthphos (7.3 mg, 0.027 mmol) and tris(dibenzylideneacetone)dipalladium(0) (6 mg, 0.006 mmol) were 4.08 (m, 2H), 4.46 (s, 2H), 4.90 (s, 2H), 5.30 (s, 2H), 6.89 (dd, 1H), 7.17 (m, 3H), 7.30 (m, 2H), 7.56 (d, 1H), 8.06 (d, 1H), 8.23 (d, 1H), 8.37 (br s, 1H). UPLC (short basic) 1.25 (757 [M+H]⁺) 95%.

Example 104: N-(2-((methylamino)methyl)benzyl)-N-(2-oxo-2-((2'-oxo-1',2',5,7-tetrahydrospiro[cyclopenta[b]pyridine-6,3'-pyrrolo[2,3-b]pyridin]-2-yl)amino)ethyl)pivalamide 46.2

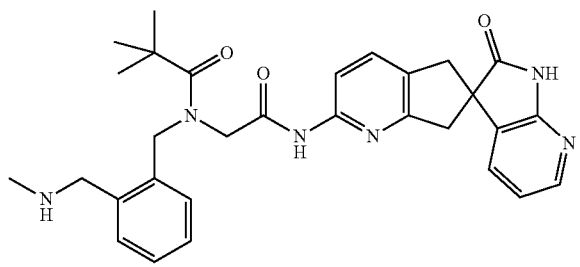 [SMILES: CNCc1ccccc1CN(CC(=O)Nc1ccc2c(n1)CC1(C2)C(=O)Nc2ncccc21)C(=O)C(C)(C)C]

Compound 46.1 (41 mg, 0.054 mmol) was dissolved in dichloromethane (3.6 ml) then trifluoroacetic acid (0.4 ml) was added and the mixture stirred at room temperature for 2 h. The mixture was poured into saturated sodium bicarbonate then extracted twice with dichloromethane. The organic layer was dried over magnesium sulfate, filtered and evaporated. The residue was purified via flash silica chromatography (2 g, EtOAc then 5% MeOH in dichloromethane, then 10% MeOH with ammonia in dichloromethane) followed by trituration in methanol to provide compound 46.2 (5 mg, 18%) as a colourless solid. $^1$H NMR (DMSO-de, 300 MHz) δ 1.15, 1.21 (2 s, 9H), 2.03, 2.17, 2.32 (3 s, 3H), 3.05 (m, 2H), 3.28 (dd, 2H), 3.46, 3.71 (2 s, 2H), 4.09 (m, 2H), 4.64 (s, 1H), 4.84 (m, 2H), 6.89 (m, 1H), 7.23 (m, 5H), 7.60 (m, 1H), 7.87 (m, 1H), 8.04, 8.11 (2 s, 1H), 10.27 (br s, 1H), 10.94 (br s 1H). UPLC (long acidic) 1.00 (527 [M+H]$^+$) 94%.

Synthesis of Intermediate AA

SCHEME 47

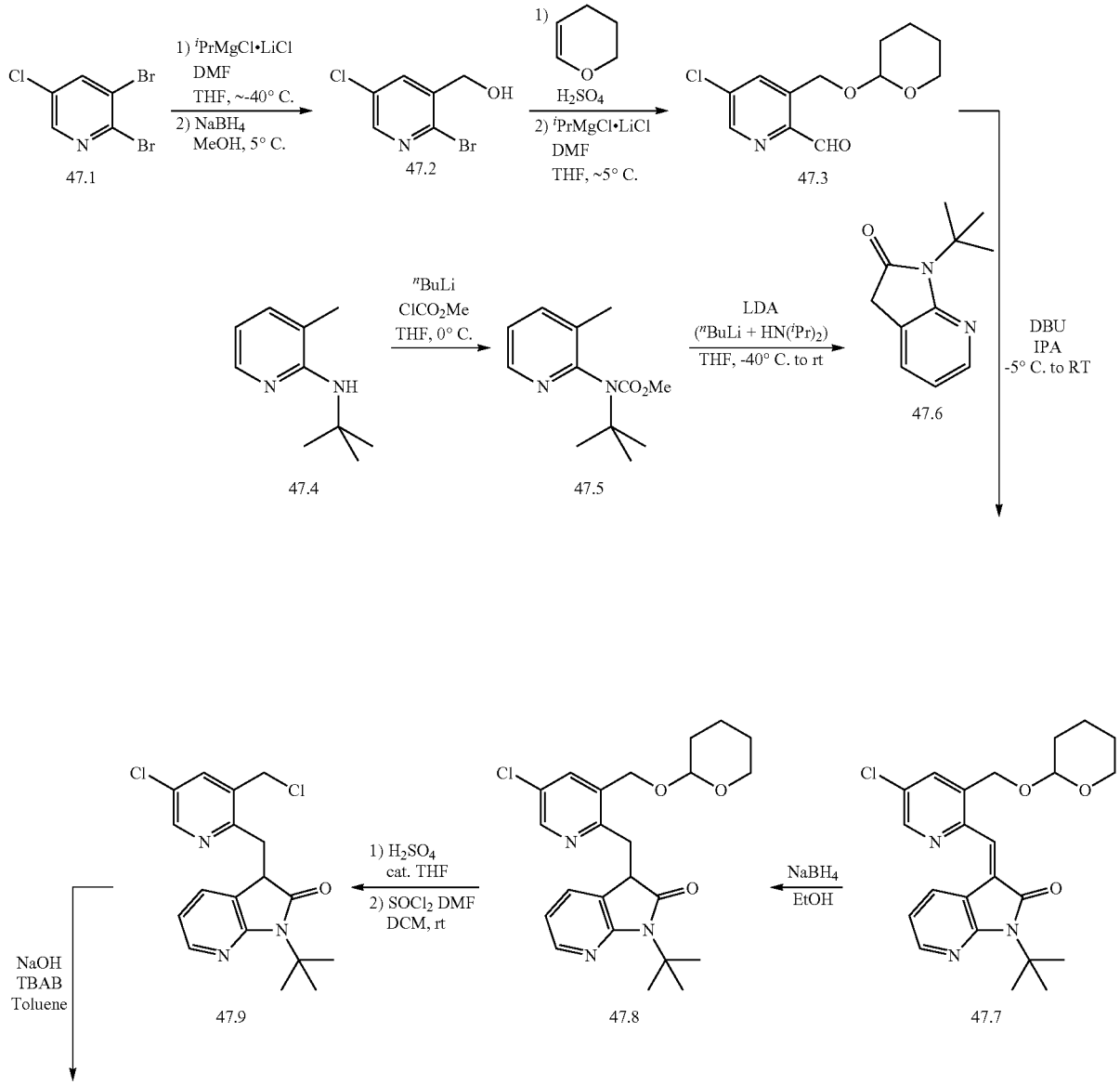

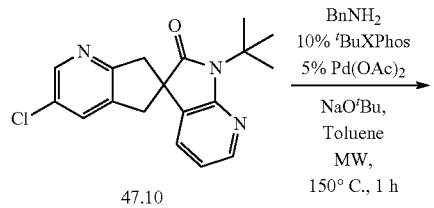 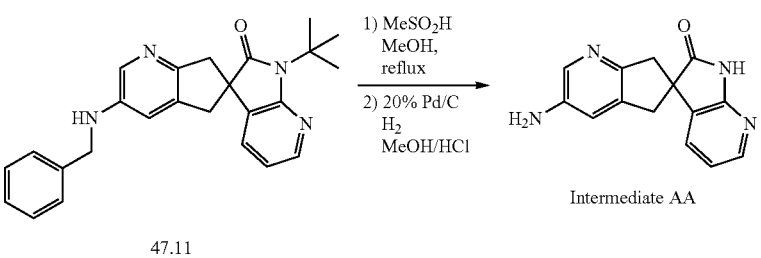

(2-Bromo-5-chloropyridin-3-yl)methanol 47.2

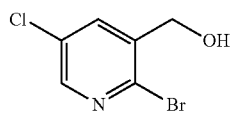

To a solution of compound 47.1 (10.0 g, 37.19 mmol) in THF (100 ml) was added slowly a solution of isopropylmagnesium chloride/lithium chloride (1.3 M in THF, 31 ml, 40.3 mmol) at −40° C. The solution was stirred for 30 min at −40° C. and DMF (8.5 ml, 111 mmol) was added. The resulting solution was warmed to room temperature and stirred for 30 min. The reaction was quenched with 1M HCl (70 ml) and diethyl ether (60 ml) was added. The organic layer was separated and washed with 5% aqueous NaHCO$_3$. The solvent was removed under vacuum. The resulting solids were dissolved in methanol (90 ml). The solution was cooled to 0° C. NaBH$_4$ (3.60 g, 95.2 mmol) was slowly added. The reaction mixture was stirred for 30 min, then quenched with water (30 ml). The resulting mixture was concentrated under vacuum to approximately 40 ml. The resulting suspension was stirred vigorously at room temperature for 1 h and the solids were collected by filtration and dried in a vacuum to give compound 47.2 (7.20 g, 88%) as a colourless solid. $^1$H NMR (CDCl$_3$, 400 MHz) δ 2.33 (t, 1H), 4.73 (d, 2H), 7.88 (d, 1H), 8.26 (d, 1H). LCMS (221.9 [M+H]$^+$).

5-Chloro-3-(((tetrahydro-2H-pyran-2-yl)oxy)methyl) picolinaldehyde 47.3

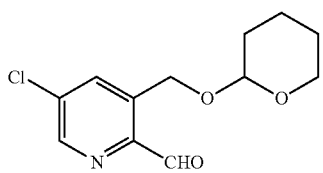 [SMILES: O=Cc1ncc(Cl)cc1COC1CCCCO1]

To a solution of compound 47.2 (7.30 g, 33.0 mmol) in tetrahydrofuran (30 mL) was added 3,4-dihydro-2H-pyran (3.30 g, 39.6 mmol) and concentrated sulfuric acid (185 mg) at room temperature. The solution mixture was stirred for 1 h, concentrated and purified directly via flash silica chromatography (5-10% ethyl acetate/petrol ether) to provide 2-bromo-5-chloro-3-(tetrahydropyran-2-yloxymethyl)pyridine (9.10 g, 90%) as a colourless oil. $^1$H NMR (CDCl$_3$, 400 MHz) δ 1.76 (m, 6H), 3.63 (m, 1H), 3.89 (m, 1H), 4.51 (m, 1H), 4.81 (m, 2H), 7.85 (s, 1H), 8.27 (s, 1H). LCMS (305.9 [M+H]$^+$).

To a solution of 2-bromo-5-chloro-3-(tetrahydropyran-2-yloxymethyl)pyridine (8.90 g, 34.9 mmol) in tetrahydrofuran (80 ml) was slowly added a solution of isopropylmagnesium chloride/lithium chloride (1.3 M in THF, 32.2 ml, 41.9 mmol) at 0° C. The resulting solution was stirred at 0° C. for 4 h. DMF (5 ml) was added slowly at 0° C. The resulting solution was stirred for another 1 h at 5° C. The reaction mixture was quenched by addition of diethyl ether, aqueous citric acid and water. The organic layer was separated and washed with brine. The organic layer was concentrated under vacuum to give compound 47.3 (6.90 g, 78%) as a colourless oil. $^1$H NMR (CDCl$_3$, 400 MHz) δ 1.70 (m, 6H), 3.58 (m, 1H), 3.88 (m, 1H), 4.80 (m, 1H), 5.01 (d, 1H), 5.25 (d, 1H), 8.20 (s, 1H), 8.65 (s, 1H), 10.13 (s, 1H). LCMS (256.1 [M+H]$^+$).

Methyl tert-butyl(3-methylpyridin-2-yl)carbamate 47.5

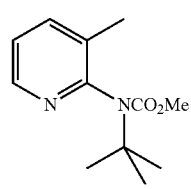

To a solution of compound 47.4 (4.30 g, 26.1 mmol) in tetrahydrofuran (40 ml) was added slowly n-butyllithium (2.2 M in THF, 13.0 ml, 28.7 mmol) at 0° C. The reaction was stirred at 0° C. for 1 h. Methyl chloroformate (2.1 ml, 27.4 mmol) was slowly added at 0° C. After 10 min at 0° C., the reaction mixture was then stirred at room temperature for 1.5 h. The reaction mixture was quenched by slow addition of aqueous ammonium chloride and water. The reaction mixture was extracted with ethyl acetate. The combined extracts were dried over MgSO$_4$, filtered and evaporated to give compound 47.5 (5.80 g, 100%). $^1$H NMR (CDCl$_3$, 400 MHz) δ 1.42 (s, 9H), 2.27 (s, 3H), 3.57 (s, 3H), 7.16 (dd, 1H), 7.57 (dd, 1H), 8.36 (dd, 1H). LCMS (223.1 [M+H]$^+$).

367

1-(tert-Butyl)-1H-pyrrolo[2,3-b]pyridin-2(3H)-one 47.6

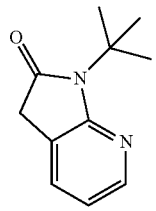

To a solution of compound 47.5 (5.40 g, 24.3 mmol) in tetrahydrofuran (30 ml) was slowly added LDA (1.0 M, 50 ml, freshly prepared from n-BuLi and diisopropylamine in THF) at −40° C. The reaction mixture was stirred at 10° C. for 4 h and quenched by addition of 2M HCl. The reaction mixture was extracted with ethyl acetate. The combined organic layers were washed with brine and concentrated. The residue was purified by silica gel column chromatography (10 to 30% EtOAc/petrol ether) to give compound 47.6 (2.60 g, 81%). 1H NMR (CDCl$_3$, 400 MHz) δ 1.80 (s, 9H), 3.46 (s, 2H), 6.89 (dd, 1H), 7.41 (m, 1H), 8.17 (m, 1H). LCMS (135.1 [M+H]$^+$).

(E)-1-(tert-Butyl)-3-((5-chloro-3-(((tetrahydro-2H-pyran-2-yl)oxy)methyl)pyridin-2-yl)methylene)indolin-2-one 47.7

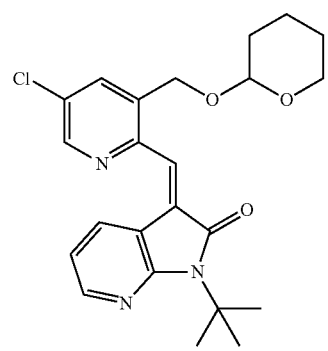 [SMILES: CC(C)(C)N1C(=O)/C(=C/c2ncc(Cl)cc2COC2CCCCO2)c2cccnc21]

To a solution of compound 47.3 (3.70 g, 14.5 mmol) and compound 47.6 (2.10 g, 15.2 mmol) in IPA (30 ml) was added DBU (0.10 g, 0.7 mmol) at 0° C. After stirring at 0° C. for 2 h, the reaction mixture was stirred at 10° C. for 3 h. Yellowish solids precipitated from the mixture. The suspension was stirred overnight at room temperature. The resulting suspension was warmed to 50° C. and stirred for an additional 4 h. After cooling to room temperature, water (35 ml) was added slowly. The suspension was filtered and washed with a mixture of IPA and water (1:1) and dried in a vacuum to give compound 47.7 (5.00 g 81% yield) as a yellow solid. LCMS (428.1 [M+H]$^+$).

368

1-(tert-Butyl)-3-((5-chloro-3-(((tetrahydro-2H-pyran-2-yl)oxy)methyl)pyridin-2-yl)methyl)indolin-2-one 47.8

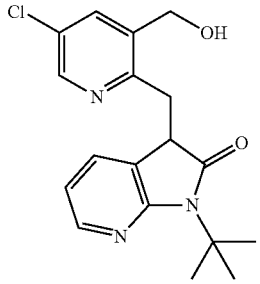 [SMILES: CC(C)(C)N1C(=O)C(Cc2ncc(Cl)cc2CO)c2cccnc21]

To a solution of compound 47.7 (5.00 g, 11.7 mmol) in ethanol (35 mL) was added NaBH$_4$ (0.70 g, 17.5 mmol) portion-wise. The resulting suspension was stirred at room temperature for 1 h. The reaction was quenched by adding water followed by slow addition of 6M HCl in IPA (5.0 ml, 30 mmol). The solution was stirred at 40° C. for 4 h. The reaction mixture was mixed with diethyl ether and saturated aqueous NaCl. The organic phase was separated and washed with water. The solution was concentrated under vacuum and the residue was triturated with hexane. The resulting suspension was stirred at room temperature for 20 min and collected by filtration to give compound 47.8 (3.70 g, 92% yield). LCMS (346.1 [M+H]$^+$).

1-(tert-Butyl)-3-((5-chloro-3-(chloromethyl)pyridin-2-yl)methyl)indolin-2-one 47.9

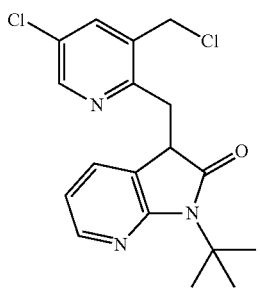 [SMILES: CC(C)(C)N1C(=O)C(Cc2ncc(Cl)cc2CCl)c2cccnc21]

To a solution of compound 47.8 (3.30 g, 9.60 mmol) in dichloromethane (20 ml) was added was added DMF (5 drops) and thionyl chloride (0.9 ml, 11.4 mmol) at −5° C. The mixture was stirred for 45 min at −5° C. followed by addition of aqueous NaCl. The organic layer was separated and washed with brine. The solvent was removed and the residue was dissolved in heptane. The solution was stirred for 30 min and the product was precipitated. The suspension was cooled to 0° C. and filtered to give compound 47.9 (2.90 g, 85% yield) as an off-white solid. $^1$H NMR (CDCl$_3$, 400 MHz) δ 1.75 (s, 9H), 3.32 (dd, 1H), 3.66 (dd, 1H), 4.06 (m, 1H), 4.58 (m, 2H), 6.78 (dd, 1H), 7.19 (m, 1H), 7.65 (d, 1H), 8.13 (m, 1H), 8.36 (d, 1H).
LCMS (364.1 [M+H]$^+$).

369

1'-(tert-Butyl)-3-chloro-5,7-dihydrospiro[cyclopenta[b]pyridine-6,3'-pyrrolo[2,3-b]pyridin]-2'(1'H)-one 47.10

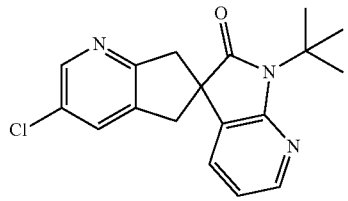 [SMILES: CC(C)(C)N1C(=O)C2(Cc3cc(Cl)cnc3C2)c2cccnc21]

To a solution of compound 47.9 (2.80 g, 7.70 mmol) in toluene (50 mL) was added tetrabutylammonium bromide (0.30 g, 0.90 mmol) at room temperature followed by aqueous 0.3 M NaOH solution (10 ml). The resulting reaction mixture was stirred at room temperature overnight. Water was added to the reaction mixture and the mixture was extracted by ethyl acetate. The combined extracts were washed by brine, dried over MgSO$_4$, filtered and evaporated. The residue was purified by silica gel column chromatography (10 to 30% EtOAc/petrol ether) to give compound 47.10 (2.00 g, 79%). $^1$H NMR (CDCl$_3$, 400 MHz) δ 1.83 (s, 9H), 3.09 (dd, 2H), 3.61 (dd, 2H), 6.83 (dd, 1H), 7.10 (d, 1H), 7.56 (s, 1H), 8.19 (d, 1H), 8.42 (s, 1H). LCMS (328.1 [M+H]$^+$).

3-(Benzylamino)-1'-(tert-butyl)-5,7-dihydrospiro[cyclopenta[b]pyridine-6,3'-pyrrolo[2,3-b]pyridin]-2'(1'H)-one 47.11

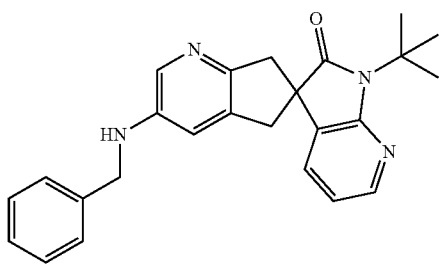 [SMILES: CC(C)(C)N1C(=O)C2(Cc3cc(NCc4ccccc4)cnc3C2)c2cccnc21]

Compound 47.10 (1.50 g, 4.60 mmol), benzylamine (1.2 ml, 11.1 mmol), palladium acetate (90 mg, 0.40 mmol), 2-di-tert-butylphosphino-2',4',6'-triisopropylbiphenyl (tBuXPhos) (335 mg, 0.80 mmol) and sodium tert-butoxide (1.10 g, 11.1 mmol) were dissolved in dry toluene (12 ml). The mixture was stirred at 150° C. under microwave irradiation for 1 h. Ethyl acetate and aqueous ammonium chloride were added. The organic extract was washed twice with brine, dried over magnesium sulfate, filtered and the filtrate evaporated. The residue was purified by silica gel column chromatography (10 to 30% EtOAc/petrol ether) to give the compound 47.11 (1.20 g, 65%). $^1$H NMR (CDCl$_3$, 400 MHz) δ 1.83 (s, 9H), 2.96 (dd, 2H), 3.52 (dd, 2H), 4.12 (br, 1H), 4.36 (br, 2H), 6.81 (m, 2H), 7.09 (dd, 1H), 7.34 (m, 5H), 7.94 (d, 1H), 8.16 (dd, 1H). LCMS (399.2 [M+H]$^+$).

370

3-Amino-5,7-dihydrospiro[cyclopenta[b]pyridine-6,3'-pyrrolo[2,3-b]pyridin]-2'(1'H)-one Intermediate AA

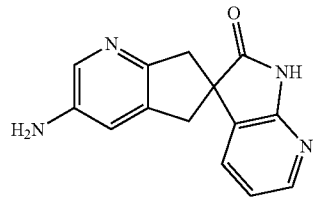 [SMILES: Nc1cnc2c(c1)CC1(C2)C(=O)Nc2ncccc21]

To a solution of compound 47.11 (1.10 g, 2.70 mmol) in methanol (30 ml) was added methanesulfonic acid (7 ml) at room temperature. The mixture was stirred at reflux for 48 h. Volatiles were removed under vacuum and water (~100 ml) was added to the mixture and the pH adjusted to pH ~10 by adding 50% aqueous sodium hydroxide. The aqueous layer was extracted with ethyl acetate and the combined extracts were dried over magnesium sulfate, filtered and evaporated to give the crude product. The crude product was dissolved in methanol (25 ml) and Pd/C (65 mg) was added to the solution followed by concentrated hydrochloric acid (2 ml). The mixture was stirred at 55° C. under a balloon of H$_2$ overnight. Volatiles were removed and the crude material was then dissolved in dichloromethane. Water and saturated K$_2$CO$_3$ were added to pH ~10. The mixture was extracted by dichloromethane, dried over MgSO$_4$, filtered and evaporated. The residue was purified by silica gel column chromatography (5-10% methanol/dichloromethane) to give Intermediate AA (325 mg, 47%) as a colourless solid. LCMS (253.1 [M+H]$^+$).

SCHEME 48

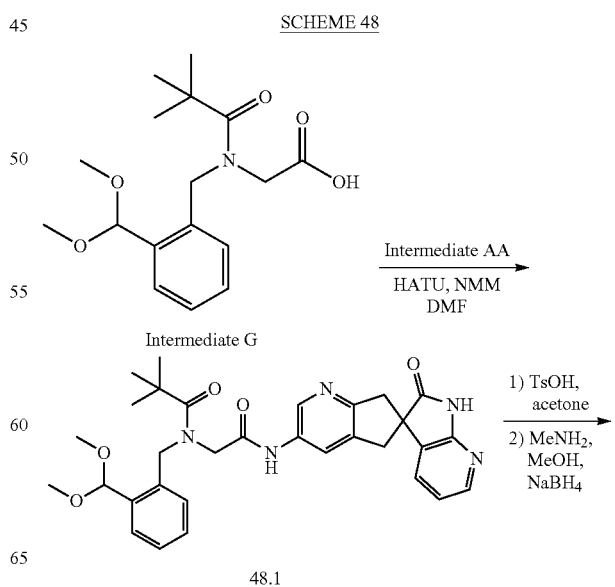

48.1

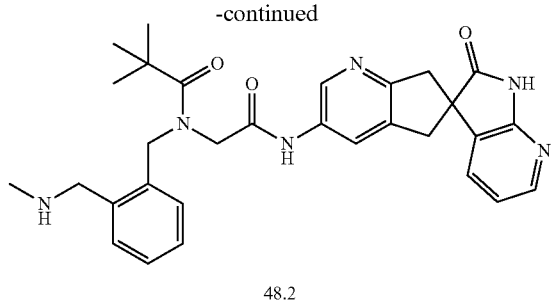

48.2

N-(2-(Dimethoxymethyl)benzyl)-N-(2-oxo-2-((2'-oxo-1',2,5,7-tetrahydrospiro[cyclopenta[b]pyridine-6,3'-pyrrolo[2,3-b]pyridin]-3-yl)amino)ethyl)pivalamide 48.1

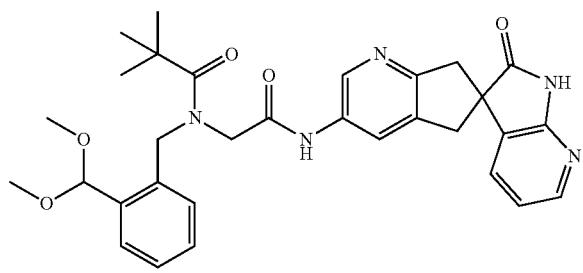 [SMILES: COC(OC)c1ccccc1CN(CC(=O)Nc1cnc2c(c1)CC1(C2)C(=O)Nc2ncccc21)C(=O)C(C)(C)C]

Intermediate G (36 mg, 0.11 mmol), Intermediate AA (29 mg, 0.11 mmol) and HATU (52 mg, 0.14 mmol) were dissolved in dry N,N-dimethylformamide (1 ml). N-Methylmorpholine (0.1 ml, 9.3 mmol) was added and the mixture was stirred at room temperature for 10 min. The mixture was diluted with ethyl acetate and washed with brine, dried over magnesium sulfate, filtered, and the filtrate evaporated. The residue was purified via flash silica chromatography (80% EtOAc/petrol ether then 5-25% dichloromethane/methanol) to provide compound 48.1 (54 mg, 88%) as a colourless glass. LCMS (558.3 [M+H]$^+$).

Example 105: N-(2-((methylamino)methyl)benzyl)-N-(2-oxo-2-((2'-oxo-1',2',5,7-tetrahydrospiro[cyclopenta[b] pyridine-6,3'-pyrrolo[2,3-b]pyridin]-3-yl)amino)ethyl)pivalamide 2,2,2-trifluoroacetate 48.2

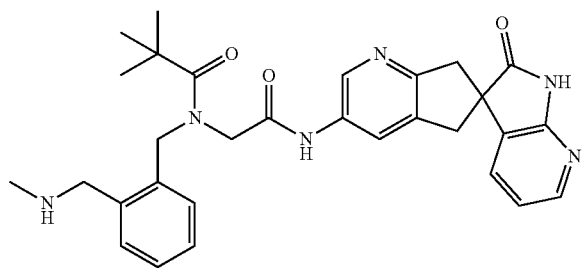 [SMILES: CNCc1ccccc1CN(CC(=O)Nc1cnc2c(c1)CC1(C2)C(=O)Nc2ncccc21)C(=O)C(C)(C)C]

Compound 48.1 (54 mg, 0.097 mmol) was dissolved in acetone (1.5 ml) and p-toluenesulfonic acid monohydrate (23 mg, 0.14 mmol) was added. The mixture was stirred at room temperature for 1 h. The mixture was poured into saturated sodium bicarbonate. The aqueous layer was extracted three times with ethyl acetate. The combined organic extracts were washed with brine, dried over sodium sulfate, filtered and the filtrate evaporated to provide the crude compound which was dissolved in methanol (1.2 ml). Methylamine (6.4 µL, 0.15 mmol) was added. The reaction mixture was stirred at room temperature for 15 min. Sodium borohydride (7.5 mg, 0.2 mmol) was added to the mixture at room temperature and the reaction mixture was stirred for 45 min. The mixture was filtered and purified directly via HPLC (HP C18, ID 22 mm, length 150 mm, flow 16 ml/min: 5-55% MeCN water/acetonitrile 0.1% TFA over 20 min) then freeze-dried to provide compound 48.2 (28 mg, 53%) as white solid. $^1$H NMR (CD$_3$OD, 400 MHz) δ 1.34 (s, 9H), 2.85 (s, 3H), 3.30 (dd, 2H), 3.54 (dd, 2H), 4.34 (br, 2H), 4.51 (br, 2H), 4.88 (br, 2H), 6.99 (dd, 1H), 7.42 (m, 5H), 8.03 (m, 1H), 8.13 (dd 1H), 8.60 (m, 1H); $^{19}$F NMR (CD$_3$OD, 400 MHz) δ −76.9; LCMS (527.3 [M+H]$^+$), 100% pure.

Biological Assays

The following assays can be used to measure the effects of the compounds of the present invention.

cAMP/Agonist-Antagonist Competition Assays in Cell Lines

Compounds were assessed for their ability to inhibit ligand-induced elevations of cAMP, using the Perkin Elmer LANCE cAMP assay using commercially-available cells expressing a specific receptor of interest using the following general procedure:

Compound Preparation

Compounds were prepared in dimethyl sulfoxide (DMSO—99.9% pure) (Sigma Aldrich, Cat #: D4540) added to powder stocks to produce a 20 mM solution (100% DMSO) that was sonicated at 37° C. for 10 minutes to fully dissolve the compounds. The 20 mM stocks were diluted further in DMSO to produce a 2 mM solution that was sonicated at 37° C. for 10 minutes. 2 mM stocks were dissolved in assay/stimulation buffer to produce a 400 µM solution that was sonicated at 37° C. for 10 minutes for all cAMP assays. All stocks were stored at −20° C. Then serial dilution (Dilution factor 10) was performed to achieve the desire experimental concentrations.

Assay Protocol

Competition assays were performed according to the manufactures instructions using LANCE® TR-FRET cAMP assay kit (Perkin Elmer, Cat #: AD0264). Serial dilutions (3 µl/well) of the molecules were plated in a 384-well OptiPlate (Perkin Elmer, Cat #: 6007299) in duplicates. Appropriate controls (100% stimulation: Forskolin and 0% stimulation: Vehicle control) (6 µl/well) were included in each plate for data normalization. Following the compound addition, 6 µl of G-protein coupled receptor overexpressing cells/Alexa Fluor antibody solution (1:100 dilution) was added in each well at a desired density of 2500 cells/well. The overexpressing cell lines were purchased from DiscoveRx, Birmingham, UK. After spinning the plate at 1000 rpm for 1 minute and vortexing briefly, the cells were pre-incubated with the compounds for 30 minutes at room temperature (covered). Then 3 µl of the equivalent peptide ligand (EC$_{50}$ dose) was added to all the wells except vehicle and forskolin controls. The plate were then spun down at 1000 rpm for 1 minute and once finished they were vortexed briefly and covered. Cells were stimulated in the presence of the ligands for 15 minutes at room temperature. After stimulation 12 µl of detection mix (Europium-Chelate streptavidin/biotinylated cAMP tracer solution) was added to all wells and incubated for 60 minutes at room temperature. The plate was then read on the Enspire multimode Plate reader (Perkin Elmer), at; 320/340 nm excitation and 615/665 nm emission was recorded.

Assay/Stimulation Buffer (30 mL)—pH 7.4
  28 mL Hank's Balanced salt solution (+MgCl$_2$, +CaCl$_2$)—(Thermo Fisher Cat #:14170112)
  150 µl HEPES (1M)—(Thermo Fisher Cat #:15630080)
  400 µl Stabilizer (DTPA) Purified BSA (7.5%)—(Perkin Elmer, Cat #: CR84-100)
  60 µl IBMX (250 mM)—(Sigma Aldrich, Cat #: 15879)

Specific cAMP/Agonist-Antagonist Competition Assays

The following specific assays were run using the procedure above

AM$_2$ Receptor Inhibition

The ability of a compound to inhibit the AM induced cAMP activation in AM$_2$ receptor-expressing cells (1321N1 cells transfected with CALCRL+RAMP3, sourced from DiscoverX catalogue number 95-0169C6) was assessed using the protocol above. The activity of compounds in this assay are set out in Tables 5 and 6.

AM$_1$ Receptor Inhibition

The ability of a compound to inhibit AM induced activation of AM$_1$ receptor-expressing cells (CHO-K1 cells transfected with CALCRL+RAMP2, sourced from DiscoverX catalogue number 93-0270C2) was assessed using the general protocol above.

Compounds tested in this assay generally exhibited a pIC$_{50}$ in the range of 5 to 5.7.

AMY$_3$ Receptor Inhibition

The ability of a compound to inhibit AMY induced activation of AMY$_3$R-expressing cells (1321N1 cells transfected with CALCR+RAMP-3 sourced from DiscoverX, catalogue number 95-0166C6) was assessed using the general protocol above.

Compounds tested in this assay generally exhibited a pIC$_{50}$ in the range of 3.5 to 6.6.

Cell Viability Assays

Cell viability assays were performed according to the manufacturer's instructions using RealTime-Glo™ MT Cell Viability Assay kit (Promega, Cat #: G9712). These assays demonstrated the test compounds' (3 µM) ability to inhibit cell survival and growth by between 40% and 70%.

All cell lines used were purchased from ATCC Virginia, USA (Table 2). Cells were seeded at a desired density in complete growth media into white clear-bottom 96-well plates (Corning, Cat #: 3610). Plates were incubated for 15 mins at room temperature (to ensure even settling of the cells) before incubated overnight at 37° C. in 5% CO$_2$. The next day the viability assay kit reagents (enzyme and substrate) were equilibrated in a 37° C. water bath alongside suboptimal growth media (assay buffer) for 10-15 mins. A reagent solution was then made containing 1:1000 of each reagent in the suboptimal growth media of each cell line (vortex well prior to use). The complete growth media was then removed from the wells and replaced with 100 µl of the reagent solution. Plates were then incubated at 37° C. in 5% CO$_2$ for at least 1 hour before reading untreated baseline. Reagents were replaced every 3 days the wells were washed once with PBS and fresh reagents were added as above for longer duration of treatments. After reading the baseline, the wells were treated with the appropriate concentration of test molecules the plates were centrifuged at 110×g for 1 min to ensure wells with even compound distribution, then incubated at 37° C. in 5% CO$_2$. Plates were treated once-daily (for 9 days) after luminescence measurements were taken using Enspire multimode Plate reader (Perkin Elmer).

TABLE 2

Cell Lines and corresponding complete growth media, suboptimal media and seeding density

| Cell Line | Complete Growth Media | Suboptimal Media | Seeding Density (per well) |
| --- | --- | --- | --- |
| MDA-MB-231 | RPMI + 10% FBS (Sigma) | RPMI + 1% FBS (Sigma) | 2,000 |
| 178-2 BMA | DMEM + 10% FBS (Gibco) + 0.01M HEPES | DMEM + 2% FBS (Gibco) + 0.01M HEPES | 2,000 |
| ASPC-1 | RPMI + 15% FBS (Gibco) | RPMI + 5% FBS (Gibco) | 2,000 |
| BxPC-3 | RPMI + 10% FBS (Gibco) | RPMI + 5% FBS (Gibco) | 2,000 |
| Capan-2 | McCoy's + 10% FBS (Sigma) | McCoy's + 5% FBS (Sigma) | 2,000 |
| CFPAC-1 | DMEM + 10% FBS (Gibco) | DMEM + 5% FBS (Gibco) | 2,000 |
| HPAF-II | RPMI + 10% FBS (Gibco) | RPMI + 5% FBS (Gibco) | 2,000 |
| Panc10.05 | RPMI + 15% FBS (Gibco) | RPMI + 5% FBS (Gibco) | 2,000 |
| SW1990 | DMEM + 10% FBS (Gibco) | DMEM + 1% FBS (Gibco) | 2,000 |

In-Vivo Effects

The in-vivo efficacy of a compound can be assessed using the following xenograft mouse model Tumour Inoculation All cell lines used in the in-vivo experiments were purchased from ATCC Virginia, USA (Table 3). Cells were cultured in complete growth media in T500 TripleFlasks (Thermo Fisher, Cat #: 132913). When 80-90% confluency was reached, cells were detached from the flasks using TrypLE Express Enzyme dissociation buffer (Thermo Fisher, Cat #: 12605).

Cells were counted using Countess II Automated Cell Counter and then were centrifuged at 110×g for 5 mins. The pellet was re-suspended in the appropriate volume of ice cold PBS (depending on the cell number). To ensure tumour inoculation, cells (500 µL) were mixed with 500 µL of ice cold matrigel (Corning, Cat #: 354234) using chilled pipette tips (pipette slowly to ensure uniform mixing and prevent air bubbles forming in matrigel). Matrigel/cell suspension and syringes were kept on ice before injection into mice. 100 µL of cell suspension (5×10$^6$ cells in 50% PBS+50% Matrigel) was injected subcutaneously into 27-week old female Balb/c nude mice for each experiment (10 treatment group and 10 vehicle control group).

TABLE 3

Cell lines and corresponding complete growth media

| Cell Line | Complete Growth Media |
| --- | --- |
| MDA-MB-231 | RPMI + 10% FBS (Sigma) |
| Capan-2 | McCoy's + 10% FBS (Sigma) |
| CFPAC-1 | DMEM + 10% FBS (Gibco) |
| HPAF-II | RPMI + 10% FBS (Gibco) |
| Panc10.05 | RPMI + 15% FBS (Gibco) |

Compound Preparation

Powder-form compounds were diluted in 100% DMSO (Sigma Aldrich, Cat #: D4540) according to the following formula:

$$\text{Volume of } DMSO = 0.06 \times \frac{\text{Mass of compound (mg)}}{8 \text{ mg/ml}}.$$

The compounds were then sonicated at 37° C. for 10 mins. Then the appropriate volume of solvent (Table 4) was added to yield 6% DMSO/94% solvent solution according to the following formula:

$$\text{Volume of solvent} = 0.94 \times \frac{\text{Mass of compound (mg)}}{8 \text{ mg/mL}}.$$

The compounds were then sonicated at 37° C. for 10 mins.

TABLE 4

Recipe for compound solvent

| Reagent | Ratio |
| --- | --- |
| Kolliphor HS15 | 1 (weight in g) |
| Kollisolv PCGE400 | 3 (volume in mL) |
| PBS | 6 (volume in mL) |

In-Vivo Treatment with Test Compounds

Before treatment each compound vial was diluted with equal part solvent resulting in 4 mg/mL compound in 3% DMSO and then sonicated at 37° C. for 10 mins. Mice were treated daily intraperitoneally with 100 µL of treatment (20 mg/kg) or vehicle control. Tumour size and mouse weights were measured once a week. The compounds that have been tested in this assay (at a dose of 20 mg/kg i.p once daily) inhibited tumour growth in a range of 60-80% compared with control.

Biological Data

The compounds shown in Table 5 and Table 6 exhibited the following activity in the $AM_2$ LANCE cAMP assay described above.

TABLE 5

| Example/ (Compound # ) | $AM_2$ $pIC_{50}$ |
| --- | --- |
| Example 1 (5A) | 9.02 |
| Example 2 (5B) | 8.77 |
| Example 3 (5C) | 6.49 |
| Example 4 (5D) | 7.22 |
| Example 5 (5E) | 7.01 |
| Example 6 (5F) | 6.29 |
| Example 7 (5G) | 6.90 |
| Example 8 (5H) | 6.78 |
| Example 9 (5I) | 6.62 |
| Example 10 (6A) | 7.04 |

TABLE 5-continued

| Example/ (Compound # ) | $AM_2$ $pIC_{50}$ |
| --- | --- |
| Example 11 (6B) | 6.40 |
| Example 12 (6C) | 6.73 |
| Example 13 (6D) | 7.48 |
| Example 14 (7A) | 9.07 |
| Example 15 (7A_S) | 6.88 |
| Example 16 (7A_R) | 9.13 |
| Example 17 (7B) | 7.91 |
| Example 18 (7C) | 7.48 |
| Example 19 (7D) | 7.05 |
| Example 20 (7E) | 6.98 |
| Example 21 (7F) | 8.87 |
| Example 22 (9A) | 8.28 |
| Example 23 (9B) | 7.88 |
| Example 24 (9C) | 7.46 |
| Example 25 (9D) | 7.12 |
| Example 26 (23A) | 8.10 |
| Example 27 (23B) | 7.52 |
| Example 28 (23.1c) | 6.31 |
| Example 29 (23C) | 7.54 |
| Example 30 (23D) | 7.53 |
| Example 31 (23E) | 7.02 |
| Example 32 (23F) | 7.01 |
| Example 33 (23G) | 6.91 |
| Example 34 (23H) | 7.91 |
| Example 35 (23I) | 7.74 |
| Example 36 (23J) | 7.03 |
| Example 37 (23K) | 6.84 |
| Example 38 (23L) | 8.16 |
| Example 39 (23M) | 7.81 |
| Example 40 (23N) | 8.13 |
| Example 41 (23O) | 7.00 |
| Example 42 (23P) | 6.87 |
| Example 43 (23Q) | 7.01 |
| Example 44 (24A) | 7.13 |
| Example 45 (25A) | 6.61 |
| Example 46 (25B) | 8.55 |
| Example 47 (25C) | 7.81 |
| Example 48 (25D) | 8.40 |

TABLE 5-continued

| Example/ (Compound #) | AM₂ pIC₅₀ |
|---|---|
| Example 49 (25E) | 7.99 |
| Example 50 (25F) | 7.13 |
| Example 51 (25G) | 7.07 |
| Example 52 (25H) | 7.33 |
| Example 53 (25I) | 7.92 |
| Example 54 (30A) | 8.45 |
| Example 55 (30B) | 8.01 |
| Example 56 (30C) | 6.82 |
| Example 57 (30D) | 6.57 |
| Example 58 (30E) | 7.82 |
| Example 59 (30F) | 8.03 |
| Example 60 (30G) | 8.15 |
| Example 61 (30H) | 6.66 |
| Example 62 (30I) | 7.37 |
| Example 63 (30J) | 7.27 |
| Example 64 (30K) | 7.07 |
| Example 65 (30L) | 8.55 |
| Example 66 (32A) | 7.28 |

TABLE 6

| Example/ (Compound #) | AM₂ pIC₅₀ | Example/ (Compound #) | AM₂ pIC₅₀ |
|---|---|---|---|
| Example 67 (32B) | 7.19 | Example 68 (32C) | 7.48 |
| Example 69 (32D) | 6.89 | Example 70 (32E) | 7.35 |
| Example 71 (32F) | 8.61 | Example 72 (32G) | 7.39 |
| Example 73 (32H) | 8.08 | Example 74 (32I) | 7.81 |
| Example 75 (32J) | 8.44 | Example 76 (32K) | 8.87 |
| Example 77 (32L) | 7.35 | Example 78 (32M) | 8.26 |
| Example 79 (32N) | 7.65 | Example 80 (32O) | 7.83 |
| Example 81 (32P) | 8.13 | Example 82 (32Q) | 6.58 |
| Example 83 (32R) | 7.37 | Example 84 (32S) | 7.28 |
| Example 85 (32T) | 6.63 | Example 86 (32U) | 6.75 |
| Example 87 (32V) | 7.36 | Example 88 (32W) | 6.83 |
| Example 89 (32X) | 7.06 | Example 90 (32Y) | 6.3 |
| Example 91 (32Z) | 7.62 | Example 92 (36A) | 7.1 |
| Example 93 (36B) | 7.78 | Example 94 (36C) | 7.75 |
| Example 95 (36D) | 7.54 | Example 96 (36E) | 7.31 |
| Example 97 (36F) | 7.22 | Example 98 (37.5) | 7.67 |

TABLE 6-continued

| Example/ (Compound #) | AM₂ pIC₅₀ | Example/ (Compound #) | AM₂ pIC₅₀ |
|---|---|---|---|
| Example 99 (38.9) | 6.61 | Example 100 (39.7) | 6.51 |
| Example 101 (40.16) | 7.4 | Example 102 (41.3) | 8.14 |
| Example 103 (45.2) | 7.62 | Example 104 (46.2) | 6.82 |
| Example 105 (48.2) | 7.3 | | |

OTHER EMBODIMENTS

Also disclosed are the following numbered clauses:

P1. A compound of formula (I), or a pharmaceutically acceptable salt thereof

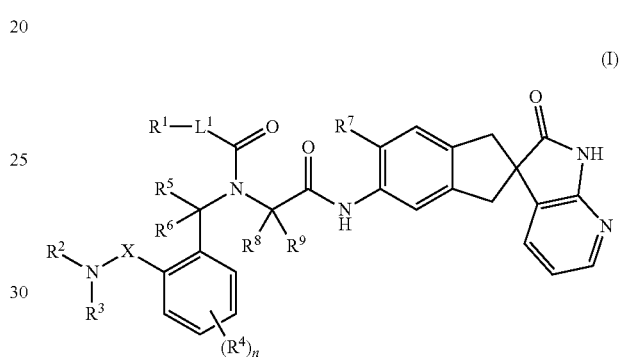

wherein
$L^1$ is a bond, —O—, or —N($R^{10}$)—;
$R^1$ is selected from: H, $C_{1-6}$ alkyl, $C_{2-6}$ alkenyl, $C_{2-6}$ alkynyl, $C_{1-6}$ haloalkyl, $C_3$a cycloalkyl, $C_{3-6}$ a cycloalkyl-$C_{1-4}$ alkyl, 4 to 7 membered heterocyclyl, 4 to 7 membered heterocyclyl-$C_{1-4}$ alkyl, $C_{6-10}$ aryl, $C_{6-10}$ aryl-$C_{1-4}$ alkyl, 5 to 10 membered heteroaryl, and 5 to 10 membered heteroaryl-$C_{1-4}$ alkyl;

and wherein $R^1$ is optionally substituted by one or more substituents independently selected from: halo, $C_{1-4}$ alkyl, $C_{1-4}$ haloalkyl, —$OR^{A1}$, —$NR^{A1}R^{B1}$, —$S(O)_xR^{A1}$ (wherein x is 0, 1 or 2), —$C(O)R^{A1}$, —$OC(O)R^{A1}$, —$C(O)OR^{A1}$, —$NR^{A1}C(O)R^{B1}$, —$C(O)NR^{A1}R^{B1}$, —$NR^{A1}SO_2R^{B1}$, —$SO_2NR^{A1}R^{B1}$, =O, —CN and $R^{17}$;

$R^{17}$ is independently selected from: $C_{3-6}$ cycloalkyl, $C_{3-6}$ cycloalkyl-$C_{1-4}$ alkyl, 4 to 7 membered heterocyclyl, 4 to 7 membered heterocyclyl-$C_{1-4}$ alkyl, phenyl, phenyl-$C_{1-4}$ alkyl, 5 to 10 membered heteroaryl, and 5 to 10 membered heteroaryl-$C_{1-4}$ alkyl, wherein $R^{17}$ is optionally substituted one or more substituents independently selected from: halo, $C_{1-4}$ alkyl, $C_{1-4}$ haloalkyl, —$OR^{A6}$, —$NR^{A6}R^{B6}$, —$S(O)_xR^{A6}$ (wherein x is 0, 1 or 2), —$C(O)R^{A6}$, —$OC(O)R^{A6}$, —$C(O)OR^{A6}$, —$NR^{A6}C(O)R^{B6}$, —$C(O)NR^{A6}R^{B6}$, —$NR^{A6}SO_2R^{B6}$, —$SO_2NR^{A6}R^{B6}$, =O and —CN;

X is —($CR^AR^B)_p$—;
$R^2$ and $R^3$ are each independently selected from: H, —C(=$NR^{A9}$)N($R^{A9}$)₂, —C(=$NR^{A9}$)$R^{A7}$, —C(=NCN)N($R^{A9}$)₂, $C_{1-4}$ alkyl, $C_{2-6}$ alkenyl, $C_{2-6}$ alkynyl, $C_{1-4}$ haloalkyl, —$OR^{A10}$, $C_{3-6}$ cycloalkyl, $C_{3-6}$ cycloalkyl-$C_{1-6}$ alkyl-, 4 to 7 membered heterocyclyl, 4 to 7 membered heterocyclyl-C1 alkyl-, $C_{6-10}$ aryl-$C_{1-6}$ alkyl-, 5 to 10 membered heteroaryl-$C_{1-6}$ alkyl-, $C_{2-4}$ alkyl substituted by —$NR^{11}R^{12}$ and $C_{2-6}$ alkyl substituted by —OR$^{13}$, wherein R$^{11}$, R$^{12}$ and R$^{13}$ are independently selected from H, C$_{1-4}$ alkyl and C$_{1-4}$ haloalkyl, or R$^{11}$ and R$^{12}$ together with the nitrogen to which they are attached form a 4 to 6 membered heterocyclyl, R$^{A7}$ and each R$^{A9}$ is independently selected from H, C$_{1-6}$ alkyl, C$_{1-6}$ haloalkyl and C$_{3-6}$ cycloalkyl, or any —N(R$^{A9}$)$_2$ within a substituent may form a 4 to 6 membered heterocyclyl;

and wherein R$^2$ and R$^3$ are independently optionally further substituted by one or more substituents independently selected from: halo, C$_{1-4}$ alkyl, C$_{1-4}$ haloalkyl, C$_{3-6}$ cycloalkyl, —OR$^{A2}$, —NR$^{A2}$R$^{B2}$, —S(O)$_x$R$^{A2}$, wherein x is 0, 1 or 2, —C(O)R$^{A2}$, —OC(O)R$^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, =O and —CN; or R$^2$ and R$^3$ together with the nitrogen atom to which they are attached form a 4 to 7 membered heterocyclyl, or imidazolyl, wherein said 4 to 7 membered heterocyclyl or imidazolyl formed by R$^2$ and R$^3$ is optionally further substituted by one or more substituents selected from halo, C$_{1-4}$ alkyl, C$_{1-4}$ haloalkyl, C$_{3-6}$ cycloalkyl, —OR$^{A3}$, —NR$^{A3}$R$^{B3}$, —S(O)$_x$R$^{A3}$ (wherein x is 0, 1 or 2), —C(O)R$^{A3}$, —C(O)OR$^{A3}$, =O, —CN, C$_{1-6}$ alkyl substituted by —NR$^{A3}$R$^{B3}$ and C$_{1-6}$ alkyl substituted by —OR$^{A3}$; or the group R$^2$N(R$^3$)X— and the phenyl ring carbon atom adjacent to X together form a group of the formula:

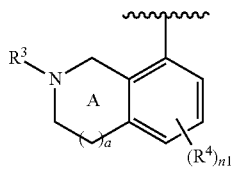

wherein

⌇⌇⌇ indicates the point of attachment to the C(R$^5$R$^6$) group in formula (I);

a is an integer 0, 1 or 2;

n1 is an integer 0, 1, 2 or 3 and, when present, R$^4$ is located on the phenyl ring; and wherein Ring A is optionally substituted by one or more substituents selected from halo, C$_{1-4}$ alkyl, C$_{1-4}$ haloalkyl, —OR$^{A3}$, —NR$^{A3}$R$^{B3}$ and =O;

R$^4$ is independently selected from: halo, C$_{1-4}$ alkyl, C$_{1-4}$ haloalkyl, —OR$^{A4}$, —NR$^{A4}$R$^{B4}$, —S(O)$_x$R$^{A4}$ (wherein x is 0, 1 or 2) and —CN;

R$^5$, R$^6$, R$^8$ and R$^9$ are independently selected from: H, C$_{1-6}$ alkyl and C$_{1-6}$ haloalkyl, wherein the C$_{1-6}$ alkyl is optionally substituted by —OR$^{A5}$, —NR$^{A5}$R$^{B5}$, —S(O)$_x$R$^{A5}$ (wherein x is 0, 1 or 2), or R$^5$ and R$^6$ together with the carbon to which they are attached form a C$_{3-6}$ cycloalkyl or 4 to 7 membered heterocyclyl, or R$^8$ and R$^9$ together with the carbon to which they are attached form a C$_{3-6}$ cycloalkyl or 4 to 7 membered heterocyclyl;

R$^7$ is selected from: H, halo, C$_{1-6}$ alkyl and C$_{1-6}$ haloalkyl;

R$^A$ and R$^B$ are each independently selected from: H, halo, C$_{1-6}$ alkyl and C$_{1-6}$ haloalkyl, or R$^A$ and R$^B$ together with the carbon to which they are attached form a C$_{3-6}$ cycloalkyl or 4 to 7 membered heterocyclyl, or R$^A$ and R$^B$ attached to the same carbon atom in X form =NR$^B$ or =NOR$^{A8}$;

R$^{10}$ is selected from: H, C$_{1-6}$ alkyl and C$_{1-6}$ haloalkyl;

R$^{A1}$, R$^{B1}$, R$^{A2}$, R$^{B2}$, R$^{A3}$, R$^{B3}$, R$^{A4}$, R$^{B4}$, R$^{A5}$, R$^{B5}$, R$^{A6}$, R$^{B6}$, R$^{A8}$ and R$^{A10}$ are each independently selected from: H, C$_{1-4}$ alkyl and C$_{1-4}$ haloalkyl, or wherein any —NR$^{A1}$R$^{B1}$, —NR$^{A2}$R$^{B2}$ or —NR$^{A3}$R$^{B3}$ within a substituent may form a 4 to 6 membered heterocyclyl;

n is an integer selected from 0, 1, 2, 3 or 4; and p is an integer selected from 0, 1, 2 or 3.

P2. The compound of P1 wherein L$^1$ is a bond or —O—.

P3. The compound of P1 or P2, wherein R$^8$ and R$^9$ are independently selected from: H and C$_{1-3}$ alkyl.

P4. The compound of any of clauses P1 to P3, wherein R$^5$ and R$^6$ are independently selected from: H and C$_{1-3}$ alkyl; or R$^5$ and R$^6$ together with the carbon to which they are attached form cyclopropyl, cyclobutyl or oxetanyl.

P5. The compound of any of clauses P1 to P4, wherein R$^4$ is independently selected from: halo, C$_{1-4}$ alkyl, C$_{1-4}$ haloalkyl, —OR$^{A4}$ and —NR$^{A4}$R$^{B4}$; and n is 1 or 2.

P6. The compound of any of clauses P1 to P4, wherein R$^4$ is independently selected from halo (for example fluoro); and n is 1 or 2.

P7. The compound of any of clauses P1 to P6, wherein R$^7$ is hydrogen.

P8. The compound of any of clauses P1 to P6, wherein R$^7$ is selected from: halo, C$_{1-4}$ alkyl and C$_{1-4}$ haloalkyl (for example R$^7$ is C$_{1-4}$ alkyl).

P9. The compound of any of clauses P1 to P8, wherein p is 0.

P10. The compound of any of clauses P1 to P8, wherein p is 1 or 2 (for example p is 1).

P11. The compound of any of clauses P1 to P8, wherein p is 1 or 2 and X is selected from: —CH$_2$—, —CH$_2$CH$_2$—, —CHR$^A$—, *—CH$_2$CHR$^A$—, *—CHR$^A$CH$_2$—, —CR$^A$R—, *—CH$_2$CR$^A$R$^B$—, *—CR$^A$R$^B$CH$_2$—, —C(=NR$^{A8}$)—, —C(=NOR$^{A8}$)—, *—C(=NR$^{A8}$)CH$_2$—, *—C(=NOR$^{A8}$)CH$_2$—

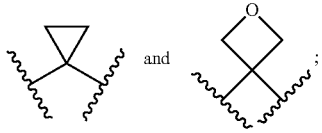

wherein R$^A$ and R$^B$ are each independently C$_{1-3}$alkyl;

R$^{A8}$ is H or C$_{1-4}$ alkyl; and

* shows the point of attachment to NR$^2$R$^3$.

P12. The compound of any of clauses P1 to P8, wherein p is 1 and X is —CH$_2$— or —CH(CH$_3$)—.

P13. The compound of any of clauses P1 to P12, wherein R$^2$ and R$^3$ are each independently selected from: H, C$_{1-6}$ alkyl, C$_{2-6}$ alkenyl, C$_{2-6}$ alkynyl, C$_{1-6}$ haloalkyl, C$_{3-6}$ cycloalkyl, C$_{3-6}$ cycloalkyl-C$_{1-3}$ alkyl-, 4 to 6 membered heterocyclyl, 4 to 6 membered heterocyclyl-C$_{1-3}$ alkyl-, phenyl-C$_{1-3}$ alkyl-, 5 or 6 membered heteroaryl-C$_{1-3}$ alkyl-, C$_{2-6}$ alkyl substituted by —NR$^{11}$R$^{12}$ and C$_{2-6}$ alkyl substituted by —OR$^{13}$, wherein R$^{11}$, R$^{12}$ and R$^{13}$ are independently selected from H, C$_{1-4}$ alkyl and C$_{1-4}$ haloalkyl, or R$^{11}$ and R$^{12}$ together with the nitrogen to which they are attached form a 4 to 6 membered heterocyclyl;

and wherein R$^2$ and R$^3$ are independently optionally further substituted by one or more substituents independently selected from: halo, C$_{1-4}$ alkyl, C$_{1-4}$ haloalkyl, C$_{3-6}$ cycloalkyl, —OR$^{A2}$, —NR$^{A2}$R$^{B2}$, —S(O)$_x$R$^{A2}$, wherein x is 0, 1 or 2, —C(O)R$^{A2}$, —OC(O)R$^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, =O and —CN; or R$^2$ and R$^3$ together with the nitrogen atom to which they are attached form a 4 to 7 membered saturated heterocyclyl containing one ring nitrogen atom and optionally one additional ring nitrogen atom, and wherein said heterocyclyl is optionally substituted by one or more substituents selected from halo, C$_{1-4}$ alkyl, C$_{1-4}$ haloalkyl, C$_{3-6}$ cycloalkyl, —OR$^{A3}$, —NR$^{A3}$R$^{B3}$, —S(O)$_x$R$^{A3}$, wherein x is 0, 1 or 2, =O, —CN, C$_{2-6}$ alkyl substituted by —NR$^{A3}$R$^{B3}$ and C$_{2-6}$ alkyl substituted by —OR$^{A3}$.

P14. The compound of any of clauses P1 to P12, wherein R$^2$ and R$^3$ are each independently selected from: H, C$_{1-4}$ alkyl, C$_{1-4}$ fluoroalkyl, C$_{3-6}$ cycloalkyl, C$_{3-6}$ cycloalkyl-C$_{1-3}$ alkyl-, C$_{2-3}$ alkyl substituted by —NR$^{11}$R$^{12}$ and C$_{2-3}$ alkyl substituted by —OR$^{13}$, wherein R$^{11}$, R$^{12}$ and R$^{13}$ are independently selected from H, C$_{1-4}$ alkyl and C$_{1-4}$ haloalkyl;

or R$^2$ and R$^3$ together with the nitrogen atom to which they are attached form a heterocyclyl selected from azetidinyl, pyrrolidinyl, piperidinyl, piperazinyl, homopiperidinyl and homopiperazinyl, wherein the heterocyclyl formed by R$^2$ and R$^3$ is optionally substituted by one or more (for example 1, 2 or 3) substituents independently selected from: halo, =O, C$_{1-4}$ alkyl, C$_{1-4}$ haloalkyl and —NR$^{A2}$R$^{B2}$.

P15. The compound of any of clauses P1 to P12, wherein R$^2$ and R$^3$ are each independently selected from: H, C$_{1-3}$ alkyl, C$_{1-3}$ fluoroalkyl, cyclopropyl, cyclobutyl, cyclopropyl-C$_{1-2}$ alkyl-, cyclobutyl-C$_{1-2}$ alkyl-, 2-hydroxyethyl, 2-methoxyethyl, 2-aminoethyl, 2-(methylamino)ethyl, 2-(dimethylamino)ethyl, 3-aminopropyl, 3-(methylamino)propyl and 3-(dimethylamino)propyl; or R$^2$ and R$^3$ together with the nitrogen atom to which they are attached form a heterocyclyl selected from azetidinyl, pyrrolidinyl, piperidinyl and piperazinyl, wherein the heterocyclyl formed by R$^2$ and R$^3$ is optionally substituted by one or more (for example 1, 2 or 3) substituents independently selected from: fluoro and C$_{1-4}$ alkyl.

P16. The compound of any of clauses P1 to P12, wherein R$^2$ is H or C$_{1-4}$ alkyl; and R$^3$ is selected from: H, —C(=NH)NH$_2$, —C(=NR$^{A9}$)NH$_2$, —C(=NH)NHR$^{A9}$, —C(=NH)N(R$^{A9}$)$_2$, —C(=NR$^{A9}$)NHR$^{A9}$, —C(=NR$^{A9}$)N(R$^{A9}$)$_2$, —C(=NH)R$^{A9}$, —C(=NR$^{A9}$)R$^{A7}$, —C(=NCN)NH$_2$, —C(=NCN)NHR$^{A9}$, —C(=NCN)N(R$^{A9}$)$_2$, C$_{1-4}$ alkyl, C$_{2-4}$ alkenyl, C$_{2-4}$ alkynyl, C$_{1-4}$ haloalkyl, —OR$^{A10}$, C$_{3-6}$ cycloalkyl, C$_{3-6}$ cycloalkyl-C$_{1-3}$ alkyl-, 4 to 7 membered heterocyclyl, 4 to 7 membered heterocyclyl-C$_{1-3}$ alkyl-, phenyl-C$_{1-3}$ alkyl-, 5 or 6 membered heteroaryl-C$_{1-3}$ alkyl-, C$_{2-4}$ alkyl substituted by —NR$^{11}$R$^{12}$ and C$_{2-4}$ alkyl substituted by —OR$^{13}$, wherein R$^{11}$, R$^{12}$ and R$^{13}$ are independently selected from: H, C$_{1-4}$ alkyl and C$_{1-4}$ haloalkyl, or R$^{11}$ and R$^{12}$ together with the nitrogen to which they are attached form a 4 to 6 membered heterocyclyl, and wherein each R$^{A9}$ and R$^{A7}$ is independently C$_{1-4}$ alkyl; and wherein R$^3$ is optionally further substituted by one or more substituents (for example 1, 2 or 3) independently selected from: halo, C$_{1-4}$ alkyl, C$_{1-4}$ haloalkyl, C$_{3-6}$ cycloalkyl, —OR$^{A2}$, —NR$^{A2}$R$^{B2}$, —S(O)$_x$R$^{A2}$, wherein x is 0, 1 or 2, —C(O)R$^{A2}$, —OC(O)R$^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{A2}$, =O and —CN.

P17. The compound of any of clauses P1 to P12, wherein: R$^2$ is H or C$_{1-4}$ alkyl; and R$^3$ is selected from —C(=NH)NH$_2$, —C(=NR$^{A9}$)NH$_2$, —C(=NH)NHR$^{A9}$, —C(=NH)N(R$^{A9}$)$_2$, —C(=NR$^{A9}$)NHR$^{A9}$, —C(=NR$^{A9}$)N(R$^{A9}$)$_2$, —C(=NH)R$^{A7}$, —C(=NR$^{A9}$)R$^{A7}$, —C(=NCN)NH$_2$, —C(=NCN)NHR$^{A9}$, —C(=NCN)N(R$^{A9}$)$_2$; wherein R$^{A7}$ and each R$^{A9}$ are independently selected from C$_{1-4}$ alkyl P18. The compound of any of clauses P1 to P12, wherein:
R$^2$ is H and R$^3$ is selected from: methyl, ethyl, isopropyl, 2-fluoroethyl, 2-methoxyethyl, 2-hydroxyethyl, cyclopropyl and cyclobutyl; or R$^2$ and R$^3$ are both methyl; or R$^2$ and R$^3$ together with the nitrogen to which they are attached form a heterocyclyl selected from: azetidinyl, pyrrolidinyl, piperidinyl and piperazinyl, which heterocyclyl is optionally substituted by one or two fluoro substituents.

P19. The compound of any of clauses P1 to P12, wherein the group:

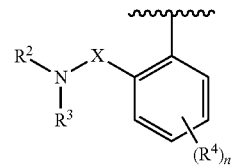

forms a group of the formula:

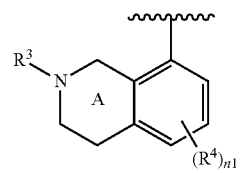

wherein:
n1 is an integer 0, 1 or 2 and, when present, R$^4$ is located on the phenyl ring; and Ring A is optionally substituted by one or more (for example 1, 2 or 3) substituents selected from: halo, C$_{1-4}$ alkyl, C$_{1-4}$ haloalkyl and =O.

P20. The compound of any of clauses P1 to P19, wherein R$^1$ is selected from: C$_{1-6}$ alkyl, C$_{1-6}$ haloalkyl, C$_{3-4}$ cycloalkyl, 4 to 7 membered heterocyclyl, phenyl and 5 to 10 membered heteroaryl;

and wherein R$^1$ is optionally substituted by one or more substituents selected from: halo, C$_{1-4}$ alkyl, C$_{1-4}$ haloalkyl, C$_{3-6}$ cycloalkyl, —OR$^{A1}$, —NR$^{A1}$R$^{B1}$, —S(O)$_x$R$^{A1}$ (wherein x is 0, 1 or 2), =O and —CN.

P21. The compound of any of clauses P1 to P19, wherein R$^1$ is a group of the formula:

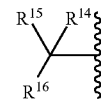

wherein
R$^{14}$, R$^{15}$ and R$^{16}$ are each independently selected from: halo, —OR$^{A1}$, —NR$^{A1}$R$^{B1}$, C$_{1-4}$ alkyl, C$_{2-4}$ alkenyl, C$_{2-4}$ alkynyl, C$_{1-4}$ haloalkyl, C$_{3-6}$ cycloalkyl, 4 to 7 membered heterocyclyl, 4 to 7 membered heterocyclyl-$C_{1-2}$ alkyl, phenyl, phenyl-$C_{1-2}$ alkyl, 5 or 6 membered heteroaryl, and 5 or 6 membered heteroaryl-$C_{1-2}$ alkyl;

or $R^{14}$ and $R^{15}$ together with the carbon atom to which they are attached form a $C_{3-6}$ cycloalkyl or 4 to 7 membered heterocyclyl;

and wherein the $C_{1-4}$ alkyl, $C_{2-4}$ alkenyl, $C_{2-4}$ alkynyl, $C_{1-4}$ haloalkyl, $C_{3-6}$ cycloalkyl, 4 to 7 membered heterocyclyl, 4 to 7 membered heterocyclyl-$C_{1-2}$ alkyl, phenyl, phenyl-$C_{1-2}$ alkyl, 5 or 6 membered heteroaryl, or 5 or 6 membered heteroaryl-$C_{1-2}$ alkyl groups represented by any of $R^{14}$, $R^{15}$ and $R^{16}$, or the $C_{3-6}$ cycloalkyl or 4 to 7 membered heterocyclyl formed by $R^{14}$ and $R^{15}$ together with the carbon atom to which they are attached are each optionally substituted by one or more substituents selected from: halo, $C_{1-4}$ alkyl, $C_{1-4}$ haloalkyl, $C_3$ cycloalkyl, $-OR^{41}$, $-NR^{41}R^{B1}$, $-S(O)_xR^{41}$ (wherein x is 0, 1 or 2), $=O$ and $-CN$.

P22. The compound of any of clauses P1 to P19, wherein $R^1$ is selected from: methyl, ethyl, isopropyl, tert-butyl, hydroxymethyl, 2-hydroxyethyl, methoxymethyl, 2-methoxyethyl, cyclopropyl, cyclobutyl, cyclopentyl, oxetanyl, tetrahydrofuranyl, tetrahydropyranyl, phenyl, thiazolyl, pyridyl,

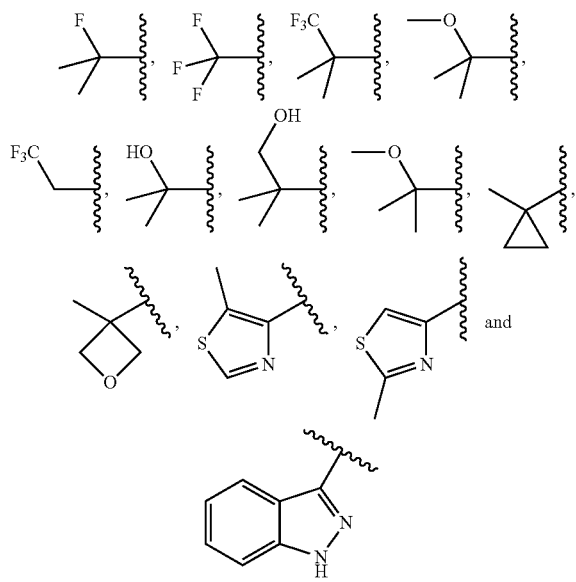

P23. The compound of any of clauses P1 to P19, wherein $R^1$ is tert-butyl.

P24. The compound of any of clauses P1 to P23, wherein the group of the formula:

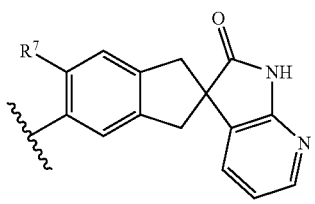

in the compounds of the formula (I) is of the formula:

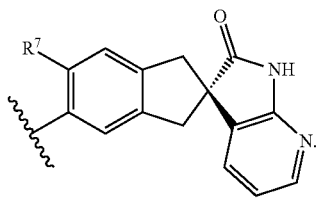

P25. A compound according to P1 selected from Table 1 in the description, or a pharmaceutically acceptable salt thereof.

P26. A pharmaceutical composition comprising a compound of any of clauses P1 to P25, or a pharmaceutically acceptable salt thereof, and a pharmaceutically acceptable excipient.

P27. A compound of any of clauses P1 to P25, or a pharmaceutically acceptable salt thereof, for use as a medicament.

P28. A compound of any of clauses P1 to P25, or a pharmaceutically acceptable salt thereof, for use in the treatment of a disease or medical condition mediated by adrenomedullin receptor subtype 2 receptors ($AM_2$).

P29. A compound of any of clauses P1 to P25, or a pharmaceutically acceptable salt thereof, for use in the treatment of a proliferative disease, particularly a cancer.

P30. The compound for the use of P29, for use in the treatment of a cancer selected from pancreatic cancer, colorectal cancer, breast cancer, lung cancer and a bone cancer.

P31. The compound for the use of P29 or P30, wherein the compound is administered to a subject with elevated expression of AM, $AM_2$, CLR, and/or RAMP3 compared to controls, for example wherein the subject has elevated expression levels of AM or $AM_2$ in a serum sample.

P32. A method of treating a disease or medical condition mediated by $AM_2$ in a subject in need thereof, the method comprising administering to the subject an effective amount of a compound of any of clauses P1 to P25, or a pharmaceutically acceptable salt thereof.

P33. A compound for the use of any of clauses 29 to 31 or the method of P32, wherein the compound is administered in combination with one or more additional anti-cancer agent and/or radiotherapy.

P34. A compound of the formula (VII), or a salt thereof:

(VII)

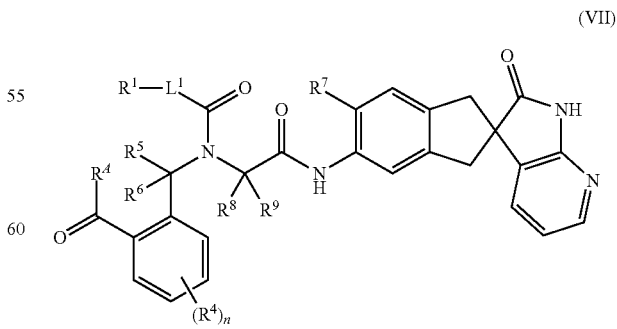

wherein $R^1$, $R^4$, $R^4$, $R^5$, $R^6$, $R^7$, $R^8$, $R^9$, $L^1$ and n are as defined in P1.

P35. A compound of the formula (VIII), or a salt thereof:

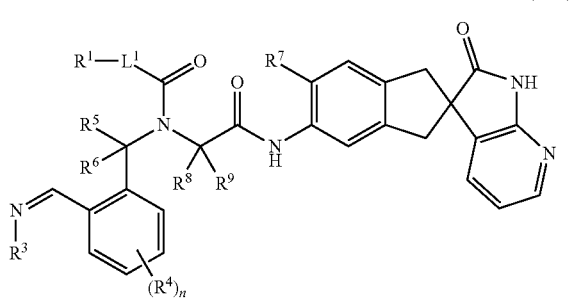

(VIII)

wherein $R^1$, $R^3$, $R^4$, $R^5$, $R^6$, $R^7$, $R^8$, $R^9$, $L^1$ and n are as defined in P1.

P36. A compound of the formula (IX), or a salt thereof:

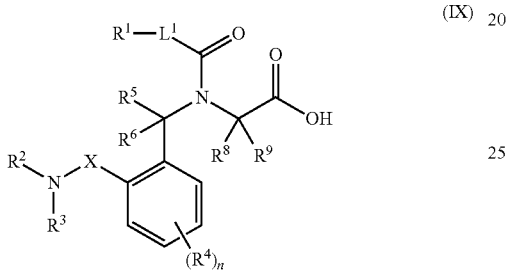

(IX)

wherein $R^1$, $R^2$, $R^3$, $R^4$, $R^5$, $R^6$, $R^8$, $R^9$, $L^1$ and n are as defined in P1.

P37. A compound of the formula (XI), or a salt thereof:

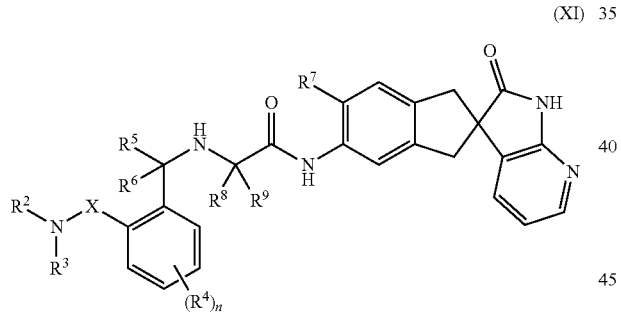

(XI)

wherein $R^2$, $R^3$, $R^4$, $R^5$, $R^6$, $R^7$, $R^8$, $R^9$, X and n are as defined in P1.

The invention claimed is:

1. A compound of formula (I), or a pharmaceutically acceptable salt thereof:

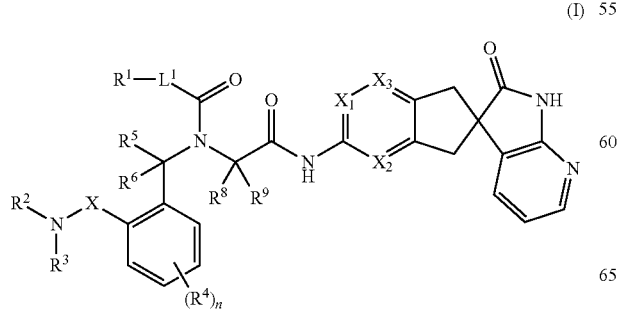

(I)

wherein
$X_1$ is N or $CR^7$;
$X_2$ and $X_3$ are each independently N or CH, provided that no more than one of $X_1$, $X_2$ and $X_3$ is N;
$L^1$ is a bond, —O—, or —N($R^{10}$)—;
$R^1$ is selected from: H, $C_{1-6}$ alkyl, $C_{2-6}$ alkenyl, $C_{2-6}$ alkynyl, $C_{1-6}$ haloalkyl, $C_{3-12}$ cycloalkyl, $C_{3-12}$ cycloalkyl-$C_{1-4}$ alkyl, $C_{3-12}$ cycloalkenyl, $C_{3-12}$ cycloalkenyl-$C_{1-4}$ alkyl, 4 to 12 membered heterocyclyl, 4 to 12 membered heterocyclyl-$C_{1-4}$ alkyl, $C_{6-10}$ aryl, $C_{6-10}$ aryl-$C_{1-4}$ alkyl, 5 to 10 membered heteroaryl, and 5 to 10 membered heteroaryl-$C_{1-4}$ alkyl;
and wherein $R^1$ is optionally substituted by one or more substituents independently selected from: halo, $C_{1-4}$ alkyl, —$C_{1-4}$ alkyl-$OR^{A1}$, —$C_{1-4}$ alkyl-$NR^{A1}R^{B1}$, —$C_{1-4}$alkyl-C(O)$R^{A1}$, —$C_{1-4}$ alkyl-C(O)$NR^{A1}R^{B1}$, —$C_{1-4}$ alkyl-$NR^{A1}$C(O)$R^{B1}$, —$C_{1-4}$ alkyl-S(O)$_2$$NR^{A1}R^{B1}$, —$C_{1-4}$ alkyl-$NR^{A1}$S(O)$_2$$R^{B1}$, —$C_{1-4}$ alkyl-C(O)$OR^{A1}$, —$C_{1-4}$ alkyl-OC(O)$R^{A1}$, —$C_{1-4}$ alkyl-S(O)$_x$$R^{A1}$ (wherein x is 0, 1 or 2), $C_{1-4}$ haloalkyl, —$OR^{A1}$, —$NR^{A1}R^{B1}$, —$SR^{A1}$, —S(O)$R^{A1}$, —S(O)$_2R^{18}$, —C(O)$R^{18}$, —OC(O)$R^{A1}$, —C(O)$OR^{A1}$, —$NR^{A1}$C(O)$R^{18}$, —C(O)$NR^{A1}R^{18}$, —$NR^{A1}$SO$_2R^{B1}$, —SO$_2$$NR^{A1}R^{18}$, =O, —CN and $R^{17}$;
$R^{17}$ is independently selected from: $C_{3-6}$ cycloalkyl, $C_{3-6}$ cycloalkyl-$C_{1-4}$ alkyl, 4 to 7 membered heterocyclyl, 4 to 7 membered heterocyclyl-$C_{1-4}$ alkyl, phenyl, phenyl-$C_{1-4}$ alkyl, 5 to 10 membered heteroaryl, and 5 to 10 membered heteroaryl-$C_{1-4}$ alkyl;
$R^{18}$ is independently selected from H, $C_{1-6}$ alkyl, $C_{1-6}$ haloalkyl, $C_{3-6}$ cycloalkyl, $C_{3-6}$ cycloalkyl-$C_{1-4}$ alkyl, 4 to 7 membered heterocyclyl, 4 to 7 membered heterocyclyl-$C_{1-4}$ alkyl, $C_{6-10}$ aryl, $C_{6-10}$ aryl-$C_{1-4}$ alkyl, 5 to 10 membered heteroaryl, and 5 to 10 membered heteroaryl-$C_{1-4}$ alkyl,
or any $NR^{A1}R^{18}$ group in $R^1$ forms a 4 to 7 membered heterocyclyl;
wherein $R^{17}$ and $R^{18}$ are each independently optionally substituted by one or more substituents independently selected from: halo, $C_{1-4}$ alkyl, $C_{1-4}$ haloalkyl, —$OR^{A6}$, —$NR^{A6}R^{B6}$, —S(O)$_x$$R^{A6}$ (wherein x is 0, 1 or 2), —C(O)$R^{A6}$, —OC(O)$R^{A6}$, —C(O)$OR^{A6}$, —$NR^{A6}$C(O)$R^{B6}$, —C(O)$NR^{A6}R^{B6}$, —$NR^{A6}$SO$_2R^{B6}$, —SO$_2$$NR^{A6}R^{B6}$, =O and —CN;
X is —(CR$^A$R$^B$)$_p$—;
$R^2$ and $R^3$ are each independently selected from: H, —C(=$NR^{A9}$)N($R^{A9}$)$_2$, —C(=$NR^{A9}$)$R^{A7}$, —C(=NCN)N($R^{A9}$)$_2$, $C_{1-6}$ alkyl, $C_{2-6}$ alkenyl, $C_{2-6}$ alkynyl, $C_{1-6}$ haloalkyl, —$OR^{A10}$, $C_{3-8}$ cycloalkyl, $C_{3-8}$ cycloalkyl-$C_{1-6}$ alkyl-, 4 to 7 membered heterocyclyl, 4 to 7 membered heterocyclyl-$C_{1-6}$ alkyl-, $C_{6-10}$ aryl-$C_{1-6}$ alkyl-, 5 to 10 membered heteroaryl-$C_{1-6}$ alkyl-, $C_{2-6}$ alkyl substituted by —$NR^{11}R^{12}$ and $C_{2-6}$ alkyl substituted by —$OR^{13}$, wherein $R^{11}$, $R^{12}$ and $R^{13}$ are independently selected from H, $C_{1-4}$ alkyl and $C_{1-4}$ haloalkyl, or $R^{11}$ and $R^{12}$ together with the nitrogen to which they are attached form a 4 to 6 membered heterocyclyl,
$R^{A7}$ and each $R^{A9}$ is independently selected from H, $C_{1-6}$ alkyl, $C_{1-6}$ haloalkyl and $C_{3-6}$ cycloalkyl, or any —N($R^{A9}$)$_2$ within a substituent may form a 4 to 6 membered heterocyclyl;
and wherein $R^2$ and $R^3$ are independently optionally further substituted by one or more substituents independently selected from: halo, $C_{1-4}$ alkyl, $C_{1-4}$ haloalkyl, $C_{3-6}$ cycloalkyl, —$OR^{A2}$, —$NR^{A2}R^{B2}$, —S(O)$_x$$R^{A2}$ (wherein x is 0, 1 or 2), —C(O)$R^{A2}$, —OC(O)$R^{A2}$, —C(O)OR$^{A2}$, —NR$^{A2}$C(O)R$^{B2}$, —C(O)NR$^{A2}$R$^{B2}$, —NR$^{A2}$SO$_2$R$^{B2}$, SO$_2$NR$^{A2}$R$^{B2}$, =O and —CN;

or

R$^2$ and R$^3$ together with the nitrogen atom to which they are attached form a 4 to 7 membered heterocyclyl, or imidazolyl, wherein said 4 to 7 membered heterocyclyl or imidazolyl formed by R$^2$ and R$^3$ is optionally further substituted by one or more substituents selected from halo, C$_{1-4}$ alkyl, C$_{1-4}$ haloalkyl, C$_{3-6}$ cycloalkyl, —OR$^{A3}$, —NR$^{A3}$R$^{B3}$, —S(O)$_x$R$^{A3}$ (wherein x is 0, 1 or 2), —C(O)R$^{A3}$, —C(O)OR$^{A3}$, =O, —CN, C$_{1-6}$ alkyl substituted by —NR$^{A3}$R$^{B3}$ and C$_{1-6}$ alkyl substituted by —OR$^{A3}$;

or the group R$^2$N(R$^3$)X— and the phenyl ring carbon atom adjacent to X together form a group of the formula:

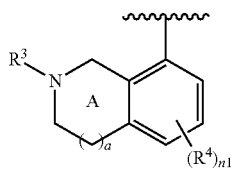

wherein

∼∼∼ indicates the point of attachment to the C(R$^5$R$^6$) group in formula (I);

a is an integer 0, 1 or 2;

n1 is an integer 0, 1, 2 or 3 and, when present, R$^4$ is located on the phenyl ring; and wherein Ring A is optionally substituted by one or more substituents selected from halo, C$_{1-4}$ alkyl, C$_{1-4}$ haloalkyl, —OR$^{A3}$, —NR$^{A3}$R$^{B3}$ and O;

or the group R$^2$N(R$^3$)X— and R$^6$ together with the atoms to which they are attached form a group of the formula:

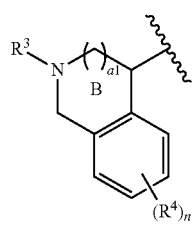

wherein

∼∼∼ indicates the point of attachment to the —N(C(O)L$^1$R$^1$)— group in formula (I);

a1 is an integer 0, 1 or 2; when present, R$^4$ is located on the phenyl ring; and wherein Ring B is optionally substituted by one or more substituents selected from halo, C$_{1-4}$ alkyl and C$_{1-4}$ haloalkyl;

R$^4$ is independently selected from: halo, C$_{1-4}$ alkyl, C$_{1-4}$ haloalkyl, —OR$^{A4}$, —NR$^{A4}$R$^{B4}$, —S(O)$_x$R$^{A4}$ (wherein x is 0, 1 or 2) and —CN;

R$^5$, R$^6$, R$^8$ and R$^9$ are independently selected from: H, C$_{1-6}$ alkyl and C$_{1-6}$ haloalkyl, wherein the C$_{1-6}$ alkyl is optionally substituted by —OR$^{A5}$, —NR$^{A5}$R$^{B5}$, —S(O)$_x$R$^{A5}$ (wherein x is 0, 1 or 2), or R$^5$ and R$^6$ together with the carbon to which they are attached form a C$_{3-6}$ cycloalkyl or 4 to 7 membered heterocyclyl, or R$^8$ and R$^9$ together with the carbon to which they are attached form a C$_{3-6}$ cycloalkyl or 4 to 7 membered heterocyclyl;

R$^7$ is selected from: H, halo, C$_{1-6}$ alkyl and C$_{1-6}$ haloalkyl;

R$^A$ and R$^B$ are each independently selected from: H, halo, C$_{1-6}$ alkyl and C$_{1-6}$ haloalkyl, or R$^A$ and R$^B$ together with the carbon to which they are attached form a C$_{3-6}$ cycloalkyl or 4 to 7 membered heterocyclyl, or R$^A$ and R$^B$ attached to the same carbon atom in X form =NR$^{A8}$ or =NOR$^{A8}$;

R$^{10}$ is selected from: H, C$_{1-6}$ alkyl, C$_{1-6}$ haloalkyl and —OR$^{A12}$;

R$^{A1}$, R$^{B1}$, R$^{A2}$, R$^{B2}$, R$^{A3}$, R$^{B3}$, R$^{A4}$, R$^{B4}$, RAS, R$^{B5}$, R$^{A6}$, R$^{B6}$, R$^{A8}$, R$^{A1O}$ and R$^{A12}$ are each independently selected from: H, C$_{1-4}$ alkyl and C$_{1-4}$ haloalkyl, or wherein any —NR$^{A1}$R$^{B1}$, —NR$^{A2}$R$^{B2}$ or —NR$^{A3}$R$^{B3}$ within a substituent may form a 4 to 6 membered heterocyclyl;

n is an integer selected from 0, 1, 2, 3 or 4; and p is an integer selected from 0, 1, 2 or 3.

2. The compound of claim 1, wherein L$^1$ is a bond.

3. The compound of claim 1, wherein n is 0.

4. The compound of claim 1, wherein X$_1$ is CR$^7$ and R$^7$ is H.

5. The compound of claim 1, wherein X$_1$ is CR$^7$ and R$^7$ is selected from: halo, C$_{1-4}$ alkyl and C$_{1-4}$ haloalkyl.

6. The compound of claim 1, wherein R$^2$ is H and R$^3$ is selected from: methyl, ethyl, isopropyl, 2-fluoroethyl, 2-methoxyethyl, 2-hydroxyethyl, cyclopropyl and cyclobutyl, or R$^2$ and R$^3$ are both methyl, or R$^2$ and R$^3$ together with the nitrogen to which they are attached form a heterocyclyl selected from: azetidinyl, pyrrolidinyl, piperidinyl and piperazinyl, which heterocyclyl is optionally substituted by one fluoro substituent.

7. The compound of claim 1, wherein the group —NR$^2$R$^3$ is selected from —NH$_2$, —NH(Me), —NH(Et), —N(Me)$_2$, —NH(cyclopropyl), —NH(CH$_2$CH$_2$F), —NH(CH$_2$CH$_2$OH), —NH(CH$_2$CH$_2$OMe), azetidin-1-yl and pyrrolidin-1-yl.

8. The compound of claim 1, wherein the group —NR$^2$R$^3$ is —NH(Me).

9. The compound of claim 1, wherein X is selected from —CH$_2$—, —CH(CH$_3$)— and —CH$_2$CH$_2$—.

10. The compound of claim 1, wherein X is —CH$_2$—.

11. The compound of claim 1, wherein R$^1$ is selected from C$_{1-6}$ alkyl, C$_{2-6}$ alkenyl, C$_{2-6}$ alkynyl, C$_{1-6}$ haloalkyl, C$_{3-6}$ cycloalkyl, C$_{3-6}$ cycloalkyl-C$_{1-4}$ alkyl, 4 to 7 membered heterocyclyl, 4 to 7 membered heterocyclyl-C$_{1-4}$ alkyl, phenyl, phenyl-C$_{1-4}$ alkyl, 5 to 10 membered heteroaryl, and 5 to 10 membered heteroaryl-C$_{1-4}$ alkyl;

and wherein R$^1$ is optionally substituted by one or more substituents independently selected from: halo, C$_{1-4}$ alkyl, C$_{1-4}$ haloalkyl, —OR$^{A1}$, —NR$^{A1}$R$^{B1}$, —S(O)$_x$R$^{A1}$ (wherein x is 0, 1 or 2), —C(O)R$^{A1}$, —OC(O)R$^{A1}$, —C(O)OR$^{A1}$, —NR$^{A1}$C(O)R$^{B1}$, —C(O)NR$^{A1}$R$^{B1}$, —NR$^{A1}$SO$_2$R$^{B1}$, —SO$_2$NR$^{A1}$R$^{B1}$, =O, —CN and R$^{17}$;

R$^{17}$ is independently selected from: C$_{3-6}$ cycloalkyl, 4 to 7 membered heterocyclyl, 4 to 7 membered heterocyclyl-C$_{1-3}$ alkyl, phenyl, phenyl-C$_{1-4}$ alkyl, 5 to 10 membered heteroaryl, and 5 to 10 membered heteroaryl-C$_{1-4}$ alkyl;

wherein R$^{17}$ is optionally substituted one or more substituents independently selected from: halo, C$_{1-4}$ alkyl, C$_{1-4}$ haloalkyl, —OR$^{A6}$, —NR$^{A6}$R$^{B6}$, —S(O)$_x$R$^{A6}$ (wherein x is 0, 1 or 2), —C(O)R$^{A6}$, —OC(O)R$^{A6}$, —C(O)OR$^{A6}$, —NR$^{A6}$C(O)R$^{B6}$, —C(O)NR$^{A6}$R$^{B6}$, —NR$^{A6}$SO$_2$R$^{B6}$, —SO$_2$NR$^{A6}$R$^{B6}$, =O and —CN.

12. The compound of any of claim 1, wherein R$^1$ is selected from: methyl, ethyl, propyl, isopropyl,

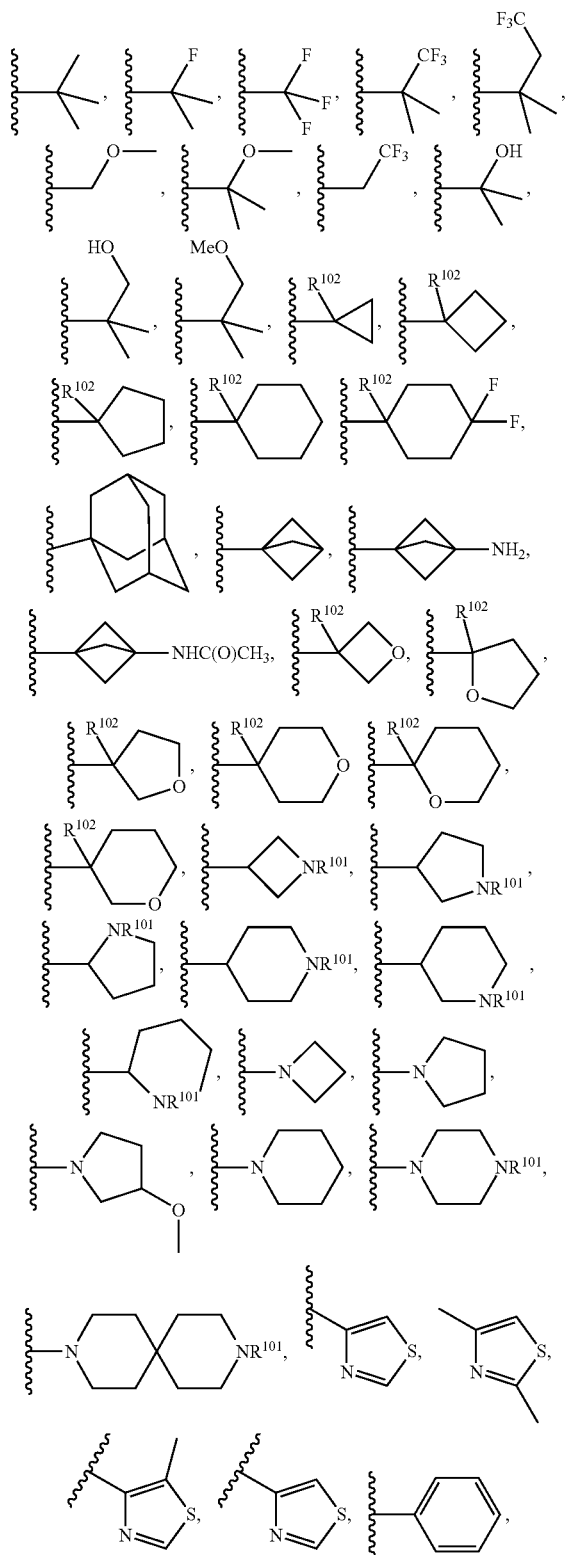

wherein

R$^{101}$ is independently selected from: H, C$_{1-4}$ alkyl, C$_{1-4}$ haloalkyl, —C$_{2-4}$ alkyl-OR$^{A1}$, —C$_{2-4}$ alkyl-NR$^{A1}$R$^{B1}$, —C$_{1-4}$ alkyl-C(O)NR$^{A1}$R$^{B1}$, —C$_{1-4}$ alkyl-NR$^{A1}$C(O)R$^{B1}$, —C$_{1-4}$ alkyl-C(O)OR$^{A1}$, —C$_{1-4}$ alkyl-OC(O)R$^{A1}$, —S(O)$_2$R$^{18B}$, —C(O)R$^{18B}$, —C(O)NR$^{A1}$R$^{18B}$, and R$^{17F}$;

R$^{17F}$ is selected from C$_{3-6}$ cycloalkyl, C$_{3-6}$ cycloalkyl-C$_{1-3}$ alkyl-, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, morpholinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_{1-3}$ alkyl-;

R$^{18B}$ is selected from C$_{1-4}$ alkyl, C$_{1-4}$ haloalkyl, C$_{3-6}$ cycloalkyl, C$_{3-6}$ cycloalkyl-C$_{1-3}$ alkyl, azetidinyl, pyrrolidinyl, piperidinyl, piperazinyl, morpholinyl, azetidinyl-C$_{1-3}$ alkyl-, pyrrolidinyl-C$_{1-3}$ alkyl-, piperidinyl-C$_{1-3}$ alkyl-, piperazinyl-C$_{1-3}$ alkyl-, phenyl, phenyl-C$_{1-3}$ alkyl-, pyrazolyl, pyridyl, pyrimidyl, pyrazinyl, pyridazinyl, pyrazolyl-C$_{1-3}$ alkyl-, pyridyl-C$_{1-3}$ alkyl-, pyrimidyl-C$_{1-3}$ alkyl-, pyrazinyl-C$_{1-3}$ alkyl- and pyridazinyl-C$_{1-3}$ alkyl-;

wherein R$^{17F}$ and R$^{18B}$ are each independently optionally substituted one or more substituents independently selected from: halo, C$_{1-4}$ alkyl, C$_{1-4}$ haloalkyl, —OR$^{A6}$, —NR$^{A6}$R$^{B6}$, —C(O)R$^{A6}$, —C(O)OR$^{A6}$ and —C(O)NR$^{A6}$R$^{B6}$; and R$^{102}$ is selected from H, C$_{1-3}$ alkyl and C$_{1-3}$ haloalkyl.

13. The compound of claim 1, wherein R$^1$ is tert-butyl.

14. The compound of claim 1, wherein the group of the formula:

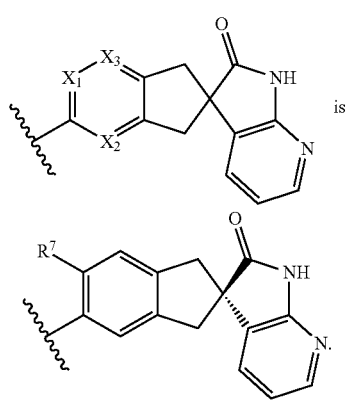

is

15. The compound of claim 1 selected from any of:
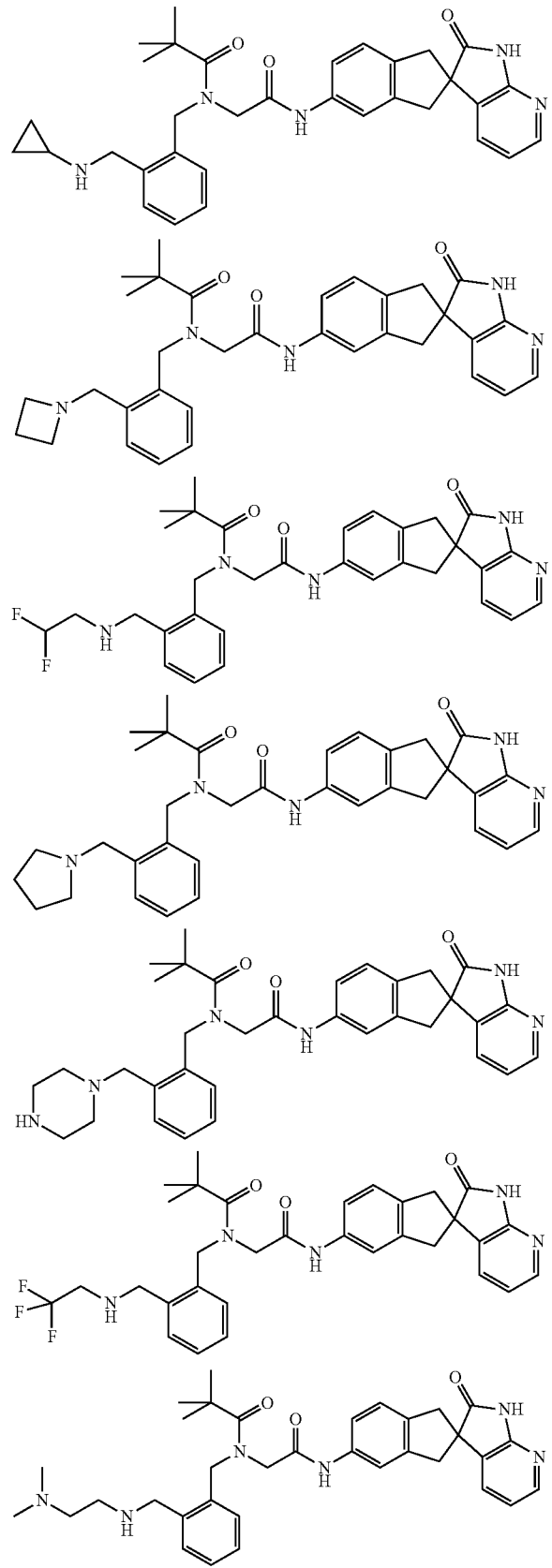
-continued
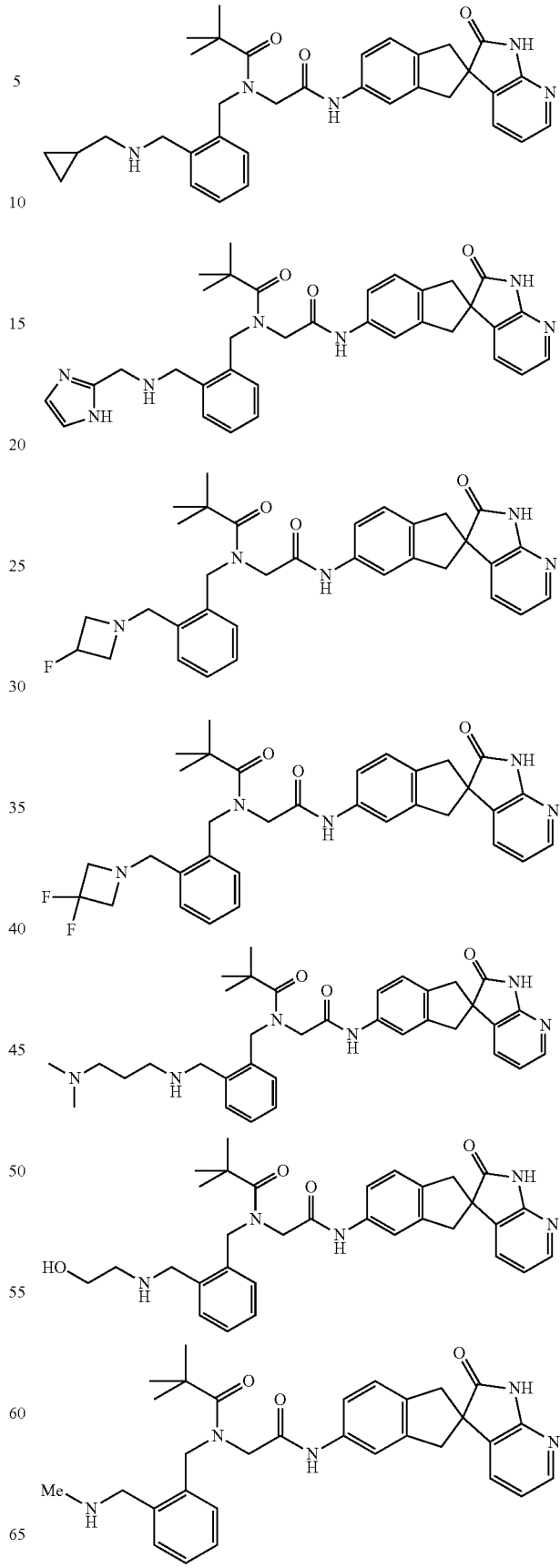

393
-continued
394
-continued
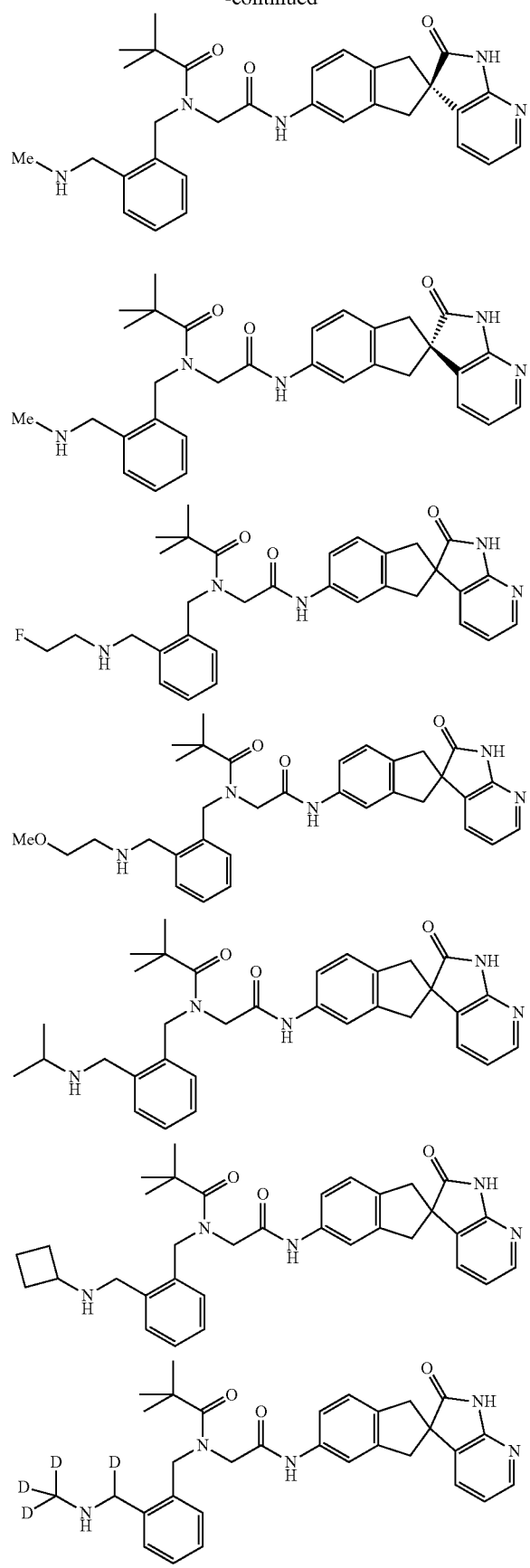
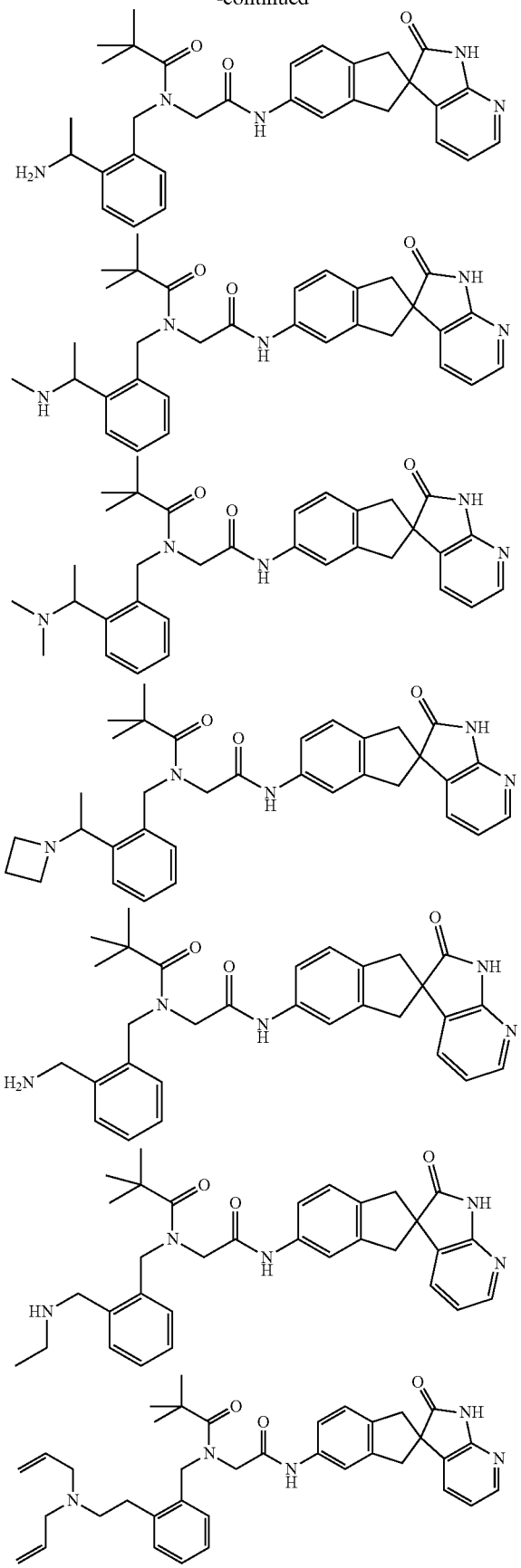

395
-continued
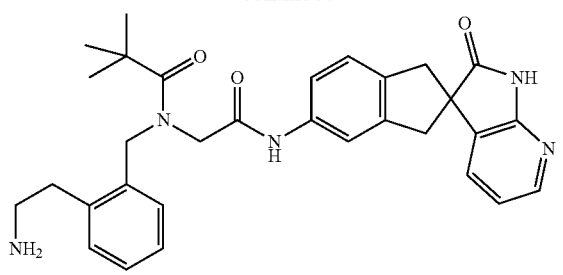
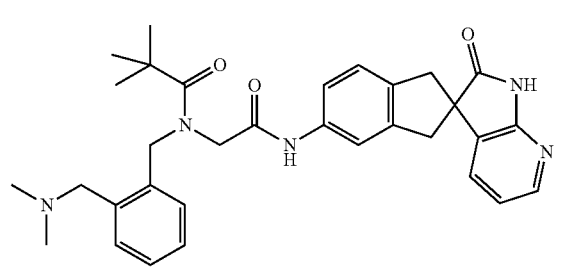
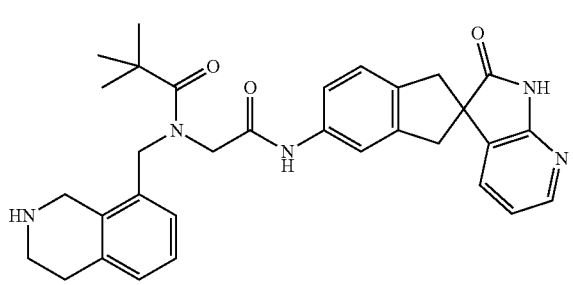
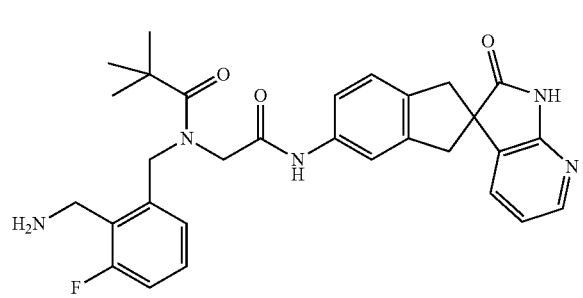
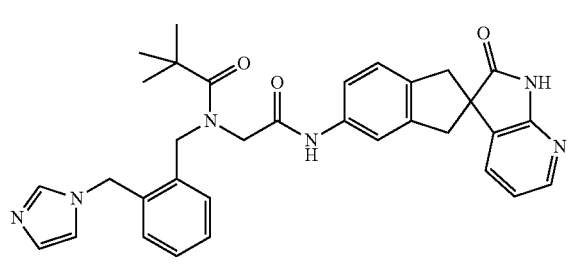
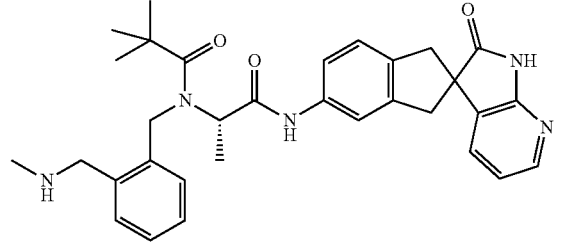
396
-continued
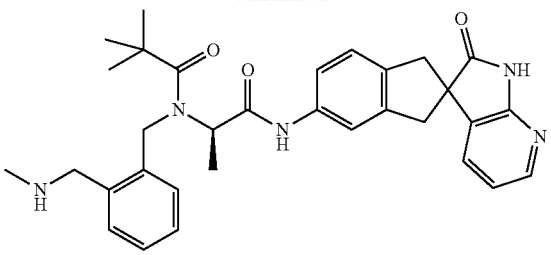
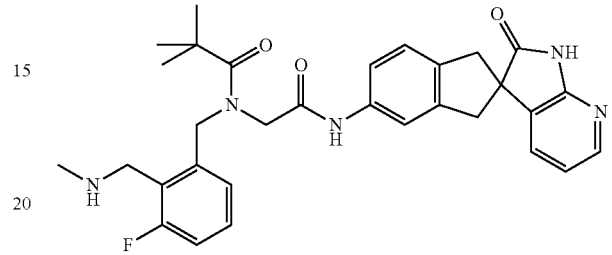
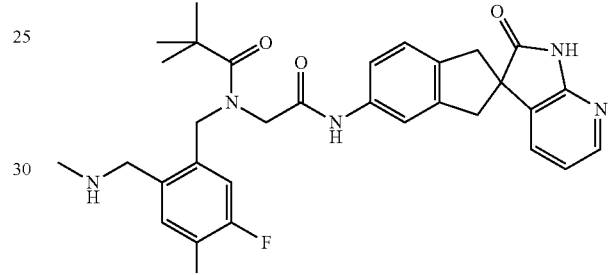
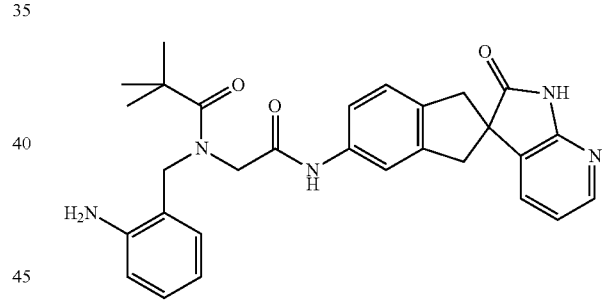
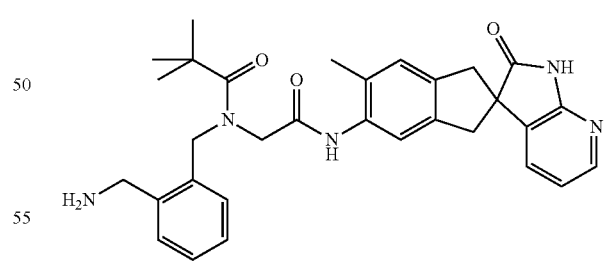
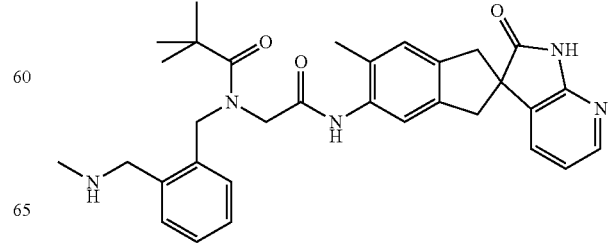

397
-continued
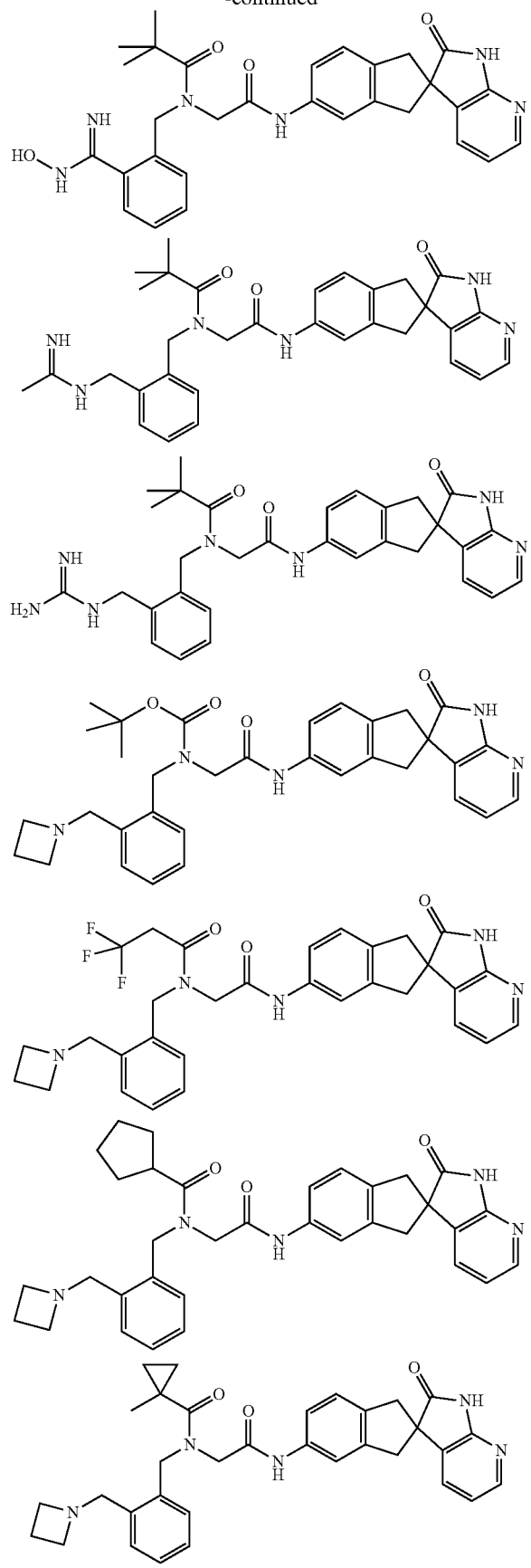
398
-continued
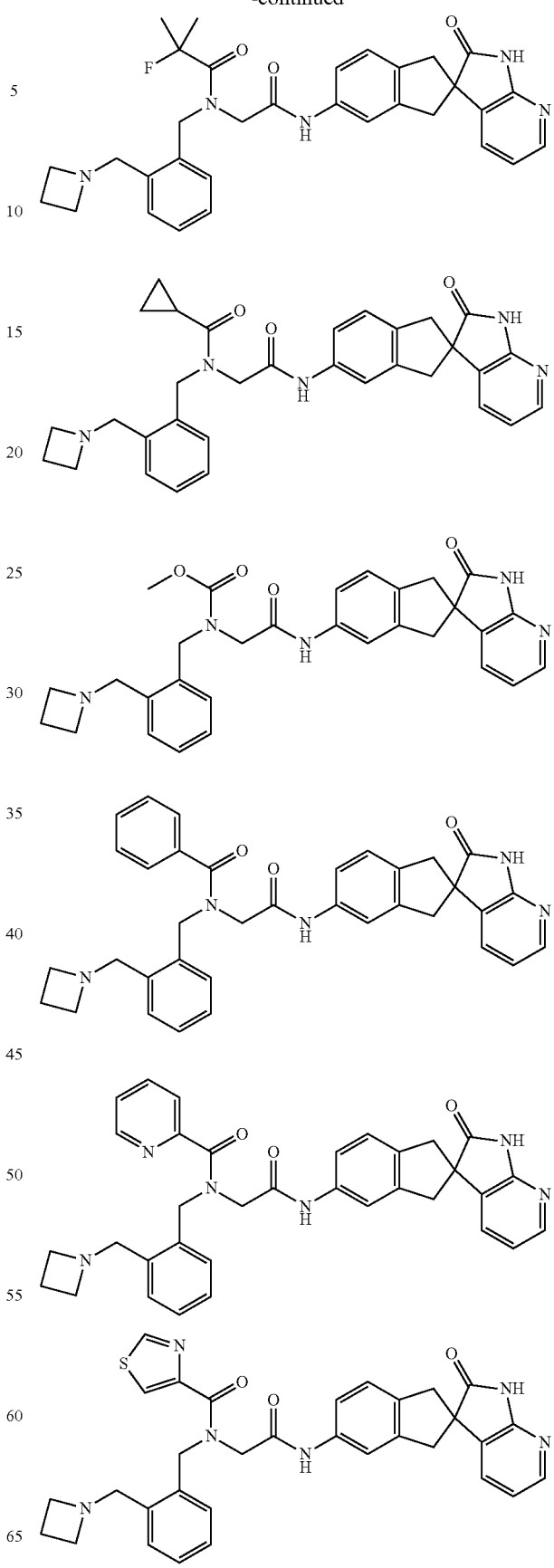

399
-continued
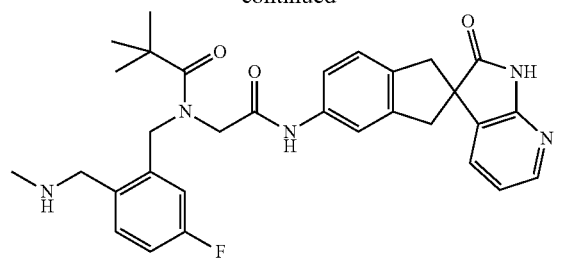
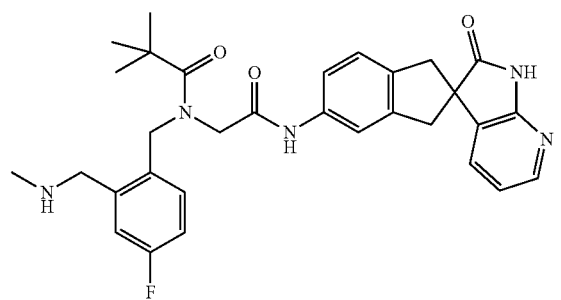
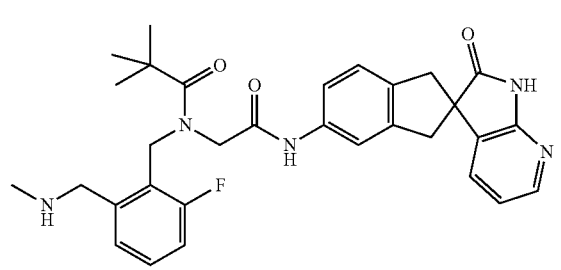
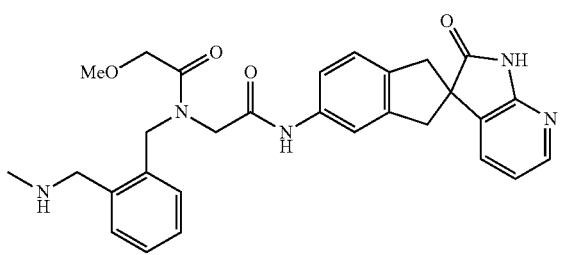
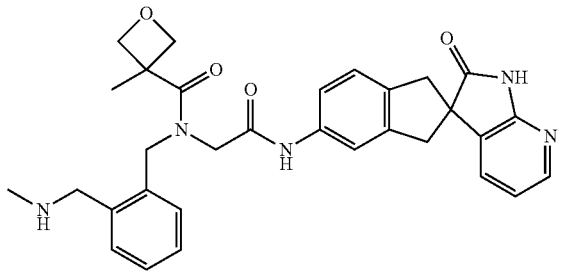
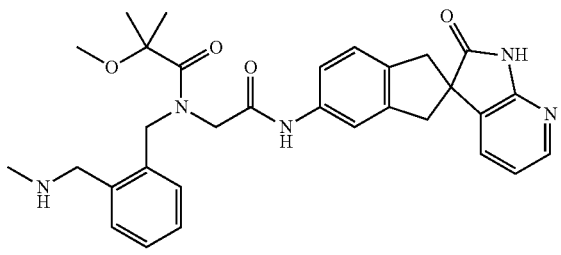
400
-continued
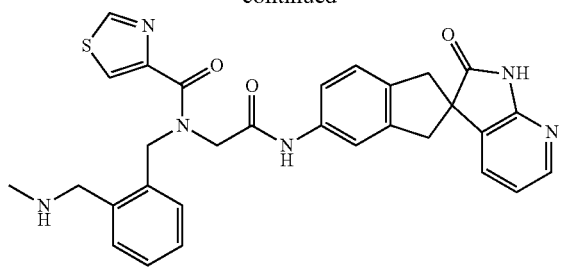
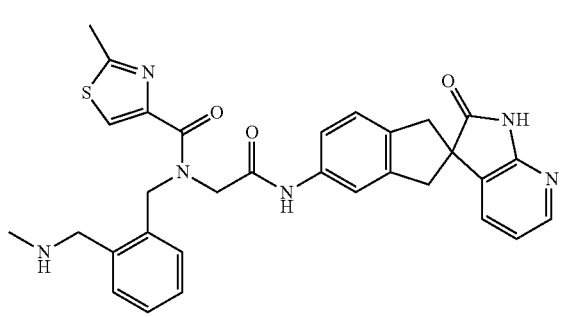
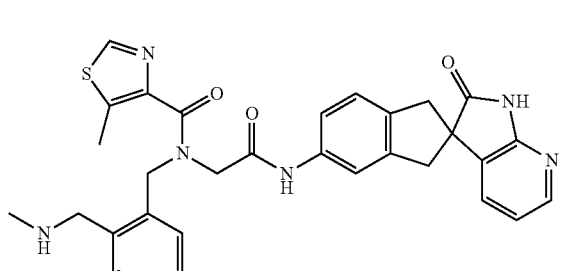
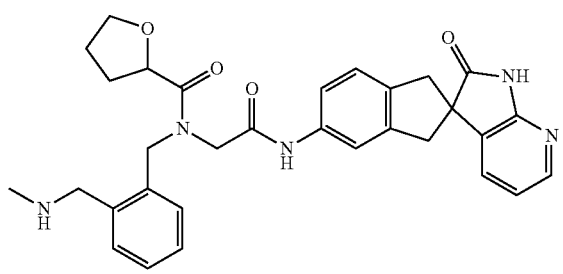
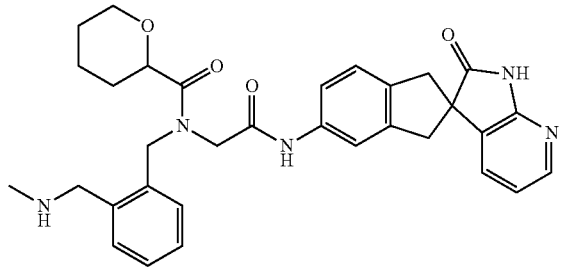
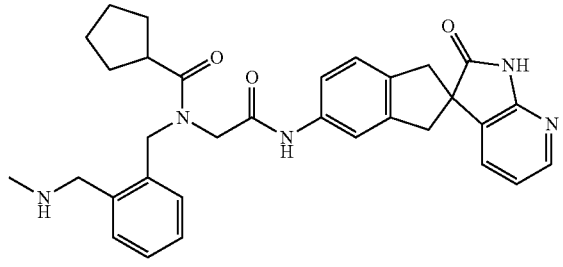

401
-continued
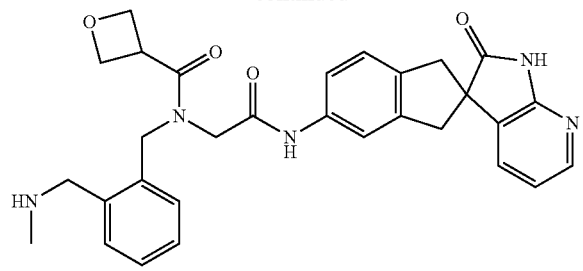
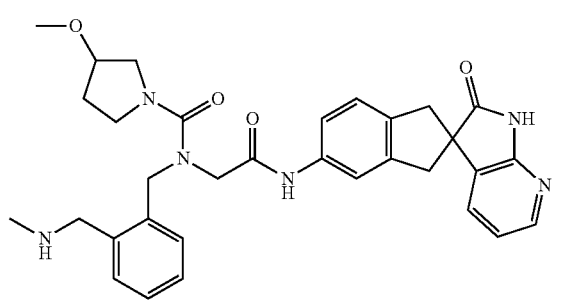
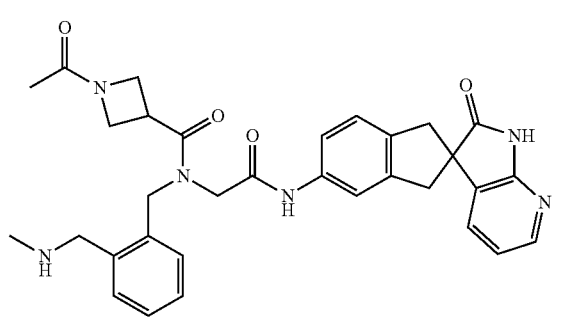
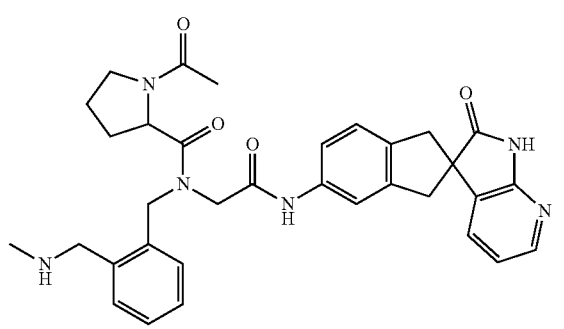
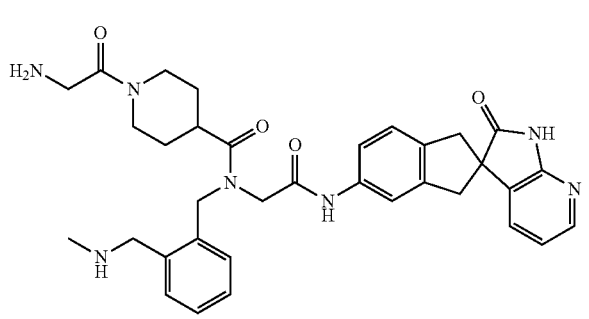
402
-continued
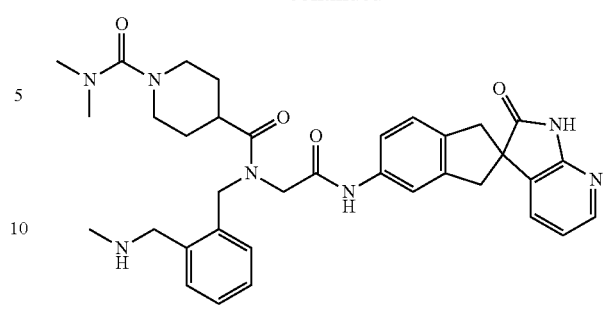
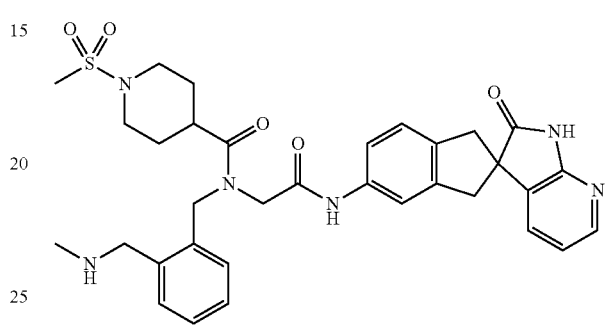
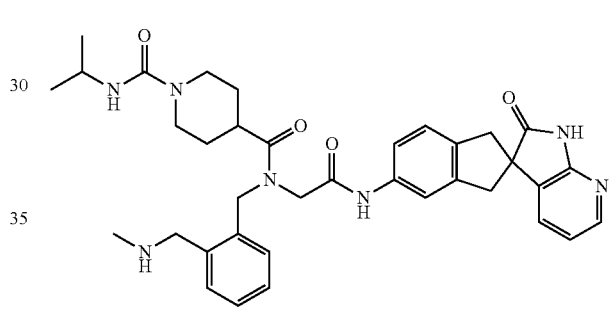
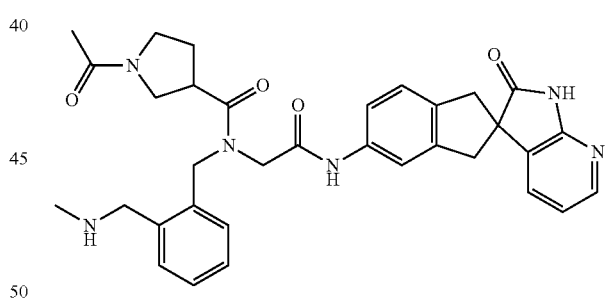

403
-continued
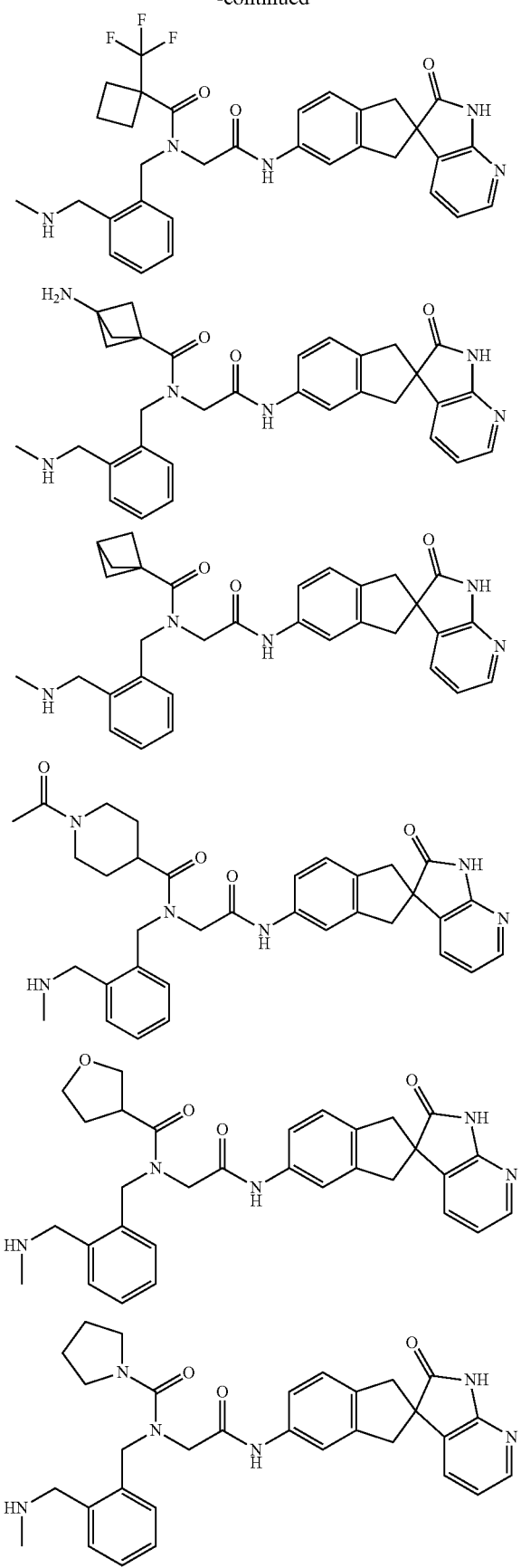
404
-continued
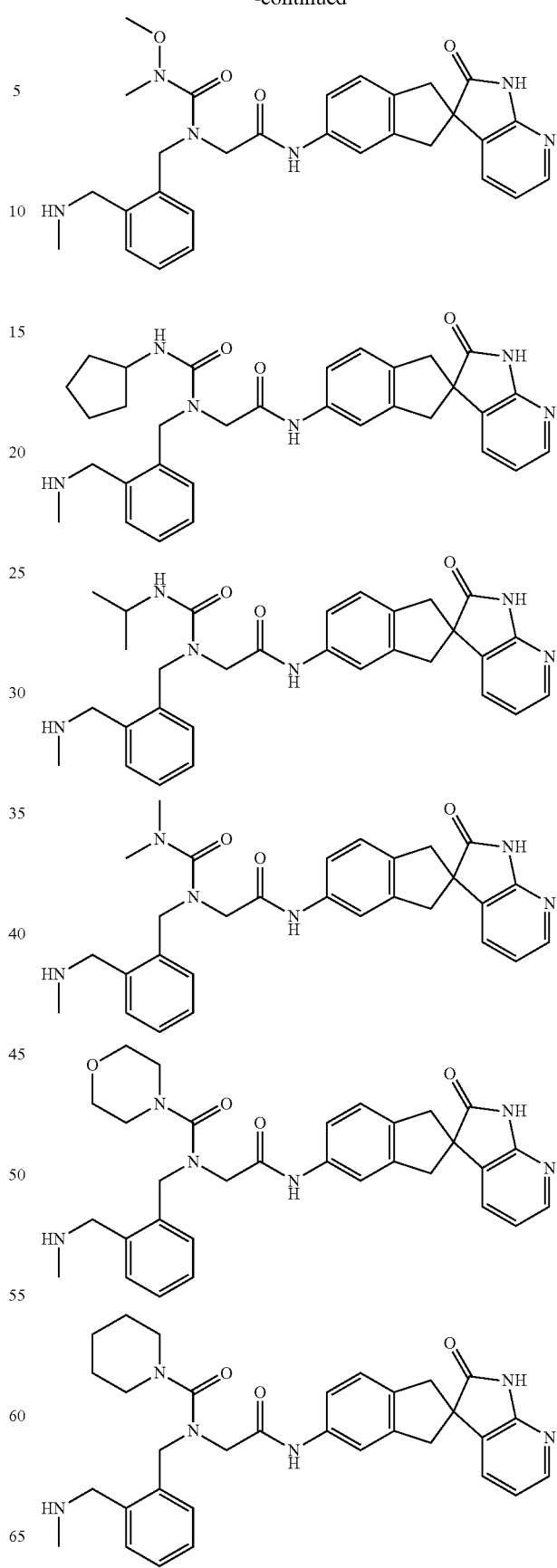

405
-continued
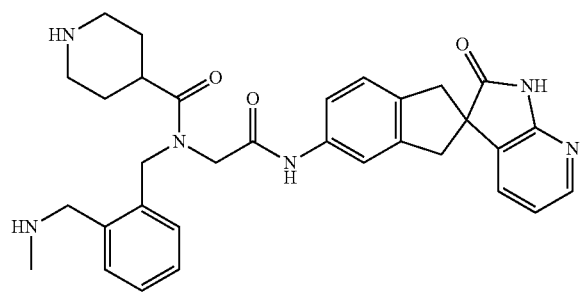
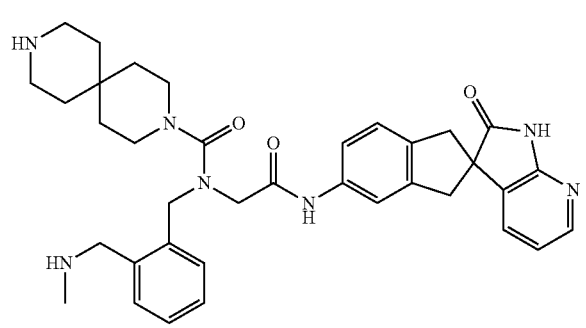
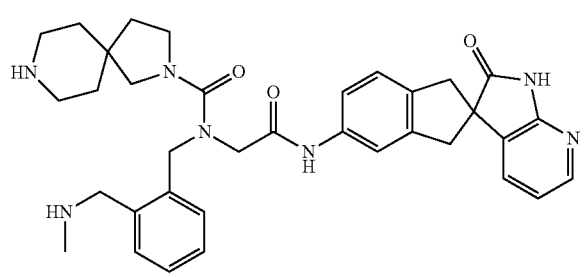
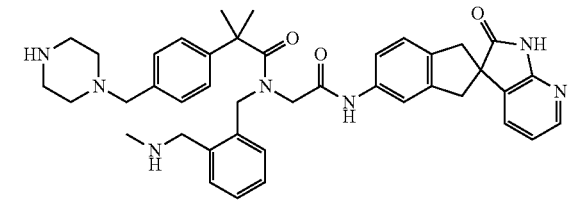
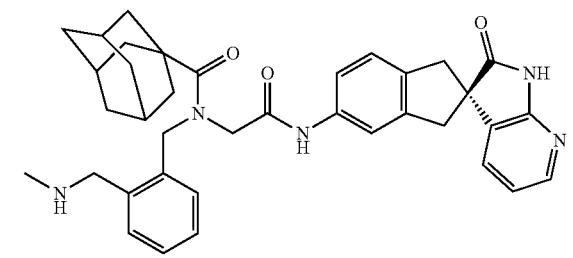
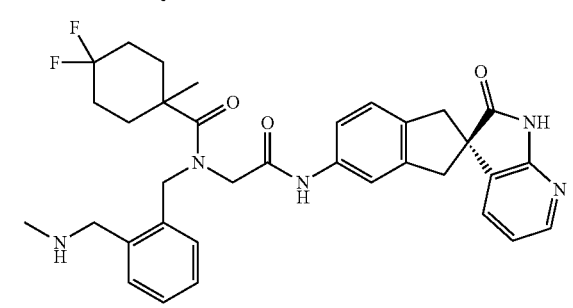
406
-continued
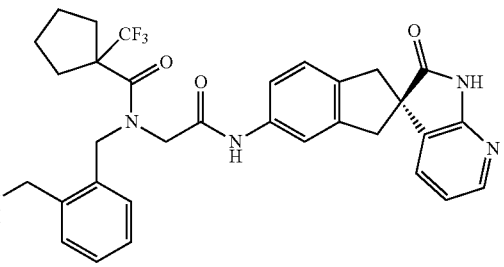
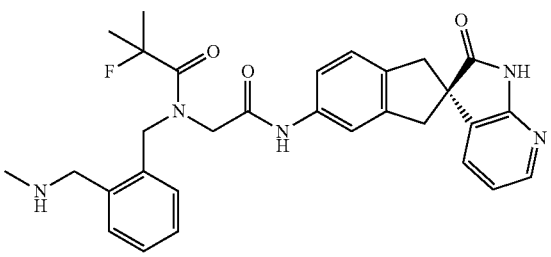
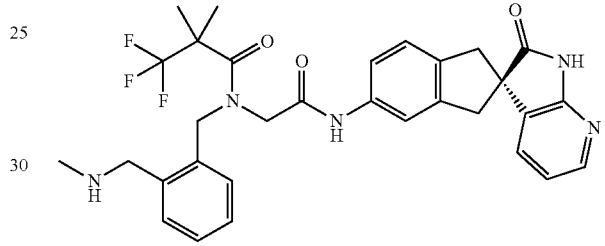
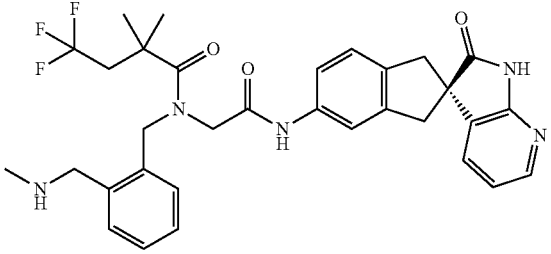
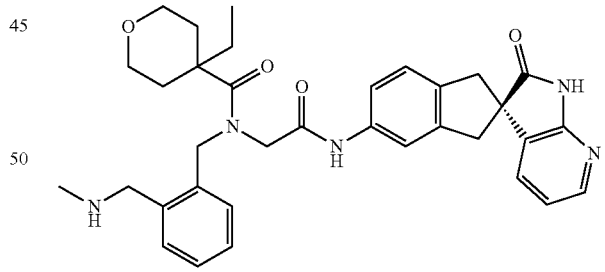
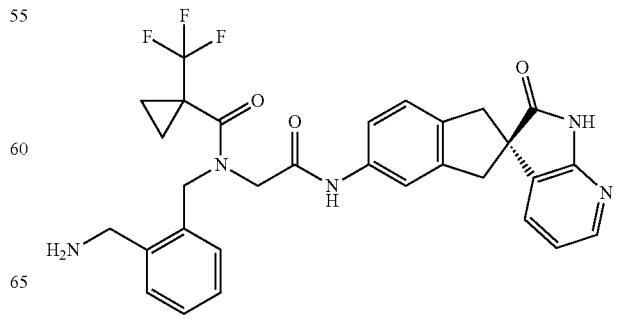

407
-continued

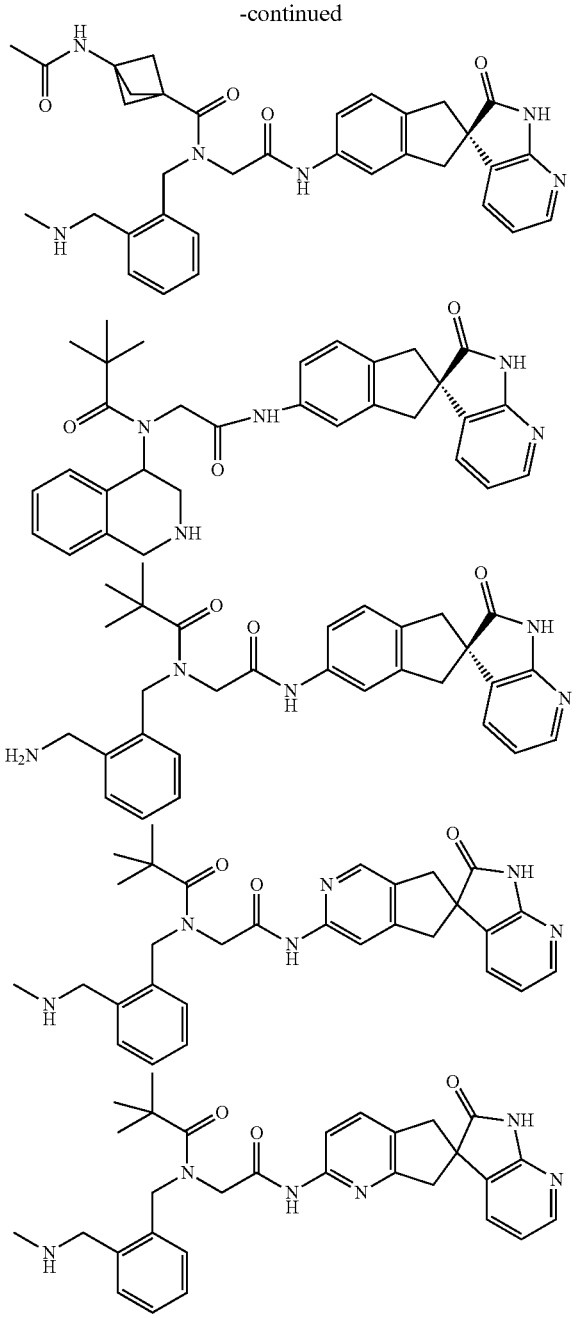

408
-continued

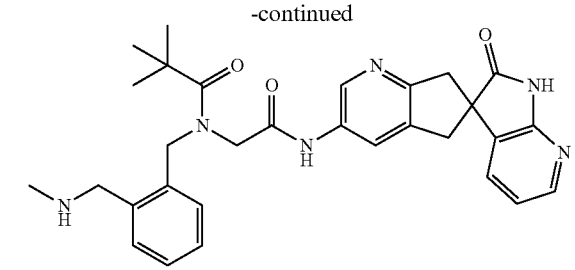

or a pharmaceutically acceptable salt thereof.

16. A pharmaceutical composition comprising a compound of claim 1, or a pharmaceutically acceptable salt thereof, and a pharmaceutically acceptable excipient.

17. A method of treating a cancer in a subject in need thereof, the method comprising administering to the subject an effective amount of a compound of claim 1, or a pharmaceutically acceptable salt thereof.

18. The method of claim 17, wherein the compound is administered in combination with one or more additional anti-cancer agent and/or radiotherapy.

19. The method of claim 17, wherein the compound is administered to a subject with elevated expression of AM, $AM_2$, CLR, and/or RAMP3 compared to controls.

20. The compound of claim 1, wherein $R^5$, $R^6$, $R^8$ and $R^9$ are independently selected from H and $C_{1-3}$ alkyl.

21. The compound of claim 1, wherein the compound of formula (I) is of the formula (XIa), or a pharmaceutically acceptable salt thereof:

(XIa)

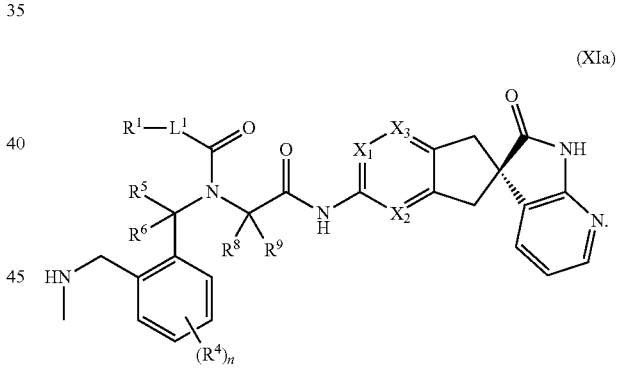

* * * * *